(12) United States Patent
Dubow et al.

(10) Patent No.: US 11,602,512 B1
(45) Date of Patent: *Mar. 14, 2023

(54) MODIFIED RELEASE GAMMA-HYDROXYBUTYRATE FORMULATIONS HAVING IMPROVED PHARMACOKINETICS

(71) Applicant: Flamel Ireland Limited, Dublin (IE)

(72) Inventors: Jordan Dubow, Lyons (FR); Hervé Guillard, Villeurbanne (FR); Claire Mégret, Lyons (FR); Jean-François Dubuisson, Lyons (FR)

(73) Assignee: Flamel Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/497,381

(22) Filed: Oct. 8, 2021

Related U.S. Application Data

(63) Continuation-in-part of application No. 17/178,117, filed on Feb. 17, 2021, which is a continuation-in-part of application No. 16/527,633, filed on Jul. 31, 2019, now Pat. No. 11,065,224, which is a continuation of application No. 16/281,235, filed on Feb. 21, 2019, now Pat. No. 10,736,866, which is a continuation of application No. 15/655,924, filed on Jul. 21, 2017, now Pat. No. 10,272,062.

(60) Provisional application No. 62/474,330, filed on Mar. 21, 2017, provisional application No. 62/399,413, filed on Sep. 25, 2016, provisional application No. 62/365,812, filed on Jul. 22, 2016.

(51) Int. Cl.
*A61K 31/22* (2006.01)
*A61K 9/16* (2006.01)
*A61K 9/50* (2006.01)
*A61K 31/19* (2006.01)
*A61K 9/14* (2006.01)

(52) U.S. Cl.
CPC .............. *A61K 31/22* (2013.01); *A61K 9/14* (2013.01); *A61K 9/1676* (2013.01); *A61K 9/5015* (2013.01); *A61K 9/5026* (2013.01); *A61K 9/5042* (2013.01); *A61K 9/5078* (2013.01); *A61K 9/5084* (2013.01); *A61K 31/19* (2013.01)

(58) Field of Classification Search
None
See application file for complete search history.

(56) References Cited

U.S. PATENT DOCUMENTS

| | | |
|---|---|---|
| 3,051,619 A | 8/1962 | Marie et al. |
| 3,419,588 A | 12/1968 | De et al. |
| 4,221,778 A | 9/1980 | Raghunathan |
| 4,374,441 A | 2/1983 | Carter et al. |
| 4,393,236 A | 7/1983 | Klosa |
| 4,510,128 A | 4/1985 | Khanna |
| 4,524,217 A | 6/1985 | Davenport et al. |
| 4,687,662 A | 8/1987 | Schobel |
| 4,738,985 A | 4/1988 | Kluger et al. |
| 4,916,161 A | 4/1990 | Patell |
| 4,939,949 A | 7/1990 | Langenberg |
| 4,976,351 A | 12/1990 | Mangini et al. |
| 4,983,632 A | 1/1991 | Gessa et al. |
| 5,294,430 A | 3/1994 | Borch et al. |
| 5,326,856 A | 7/1994 | Coughlin et al. |
| 5,364,842 A | 11/1994 | Justice et al. |
| 5,380,937 A | 1/1995 | Koehler et al. |
| 5,415,870 A | 5/1995 | Gergely et al. |
| 5,424,218 A | 6/1995 | Miljanich et al. |
| 5,426,120 A | 6/1995 | Crepaldi et al. |
| 5,449,761 A | 9/1995 | Belinka, Jr. et al. |
| 5,527,885 A | 6/1996 | Coughlin et al. |
| 5,578,288 A | 11/1996 | Belinka, Jr. et al. |
| 5,578,484 A | 11/1996 | Horoszewicz |
| 5,585,468 A | 12/1996 | Coughlin et al. |
| 5,587,454 A | 12/1996 | Justice et al. |
| 5,593,656 A | 1/1997 | Belinka, Jr. et al. |
| 5,594,030 A | 1/1997 | Conte et al. |
| 5,753,708 A | 5/1998 | Koehler et al. |
| 5,758,095 A | 5/1998 | Albaum et al. |
| 5,763,202 A | 6/1998 | Horoszewicz |
| 5,795,864 A | 8/1998 | Amstutz et al. |
| 5,833,599 A | 11/1998 | Schrier et al. |
| 5,840,331 A | 11/1998 | Van Cauter et al. |
| 5,845,255 A | 12/1998 | Mayaud |
| 5,891,849 A | 4/1999 | Amstutz et al. |
| 5,955,106 A | 9/1999 | Moeckel et al. |
| 5,990,162 A | 11/1999 | Scharf |
| 6,014,631 A | 1/2000 | Teagarden et al. |
| 6,022,562 A | 2/2000 | Autant et al. |

(Continued)

FOREIGN PATENT DOCUMENTS

| | | |
|---|---|---|
| AR | 062556 A1 | 11/2008 |
| AR | 063201 A1 | 1/2009 |

(Continued)

OTHER PUBLICATIONS

Dornbierer et al., "Nocturnal Gamma-Hydroxybutyrate Reduces Cortisol-Awakening Response and Morning Kynurenine Pathway Metabolites in Healthy Volunteers" International Journal of Neuropsychopharmacology (2019) 22(10): 631-639 (Year: 2019).*
Non-Final Office Action for U.S. Appl. No. 17/497,366 dated Apr. 27, 2022, 24 pages.

(Continued)

*Primary Examiner* — Aradhana Sasan
(74) *Attorney, Agent, or Firm* — Polsinelli PC

(57) ABSTRACT

Modified release formulations of gamma-hydroxybutyrate having improved dissolution and pharmacokinetic properties are provided, and therapeutic uses thereof.

11 Claims, 80 Drawing Sheets

(56) References Cited

U.S. PATENT DOCUMENTS

| | | |
|---|---|---|
| 6,054,429 A | 4/2000 | Bowersox et al. |
| 6,067,524 A | 5/2000 | Byerly et al. |
| 6,103,292 A | 8/2000 | Del Vecchio |
| 6,112,182 A | 8/2000 | Akers et al. |
| 6,184,205 B1 | 2/2001 | Sparks et al. |
| 6,255,307 B1 | 7/2001 | Cox et al. |
| 6,317,719 B1 | 11/2001 | Schrier et al. |
| 6,322,819 B1 | 11/2001 | Burnside et al. |
| 6,356,873 B1 | 3/2002 | Teagarden et al. |
| 6,361,938 B1 | 3/2002 | O'Mahony et al. |
| 6,384,020 B1 | 5/2002 | Flanner et al. |
| 6,432,920 B1 | 8/2002 | Sparks et al. |
| 6,436,430 B1 | 8/2002 | Mulye |
| 6,436,998 B1 | 8/2002 | Cacciaglia et al. |
| 6,461,197 B2 | 10/2002 | Crane, Jr. et al. |
| 6,472,431 B2 | 10/2002 | Cook et al. |
| 6,472,432 B1 | 10/2002 | Perricone |
| 6,495,598 B1 | 12/2002 | Yoneda et al. |
| 6,565,872 B2 | 5/2003 | Wu et al. |
| 6,599,905 B2 | 7/2003 | Cox et al. |
| 6,638,522 B1 | 10/2003 | Mulye |
| 6,699,973 B1 | 3/2004 | O'Mahony et al. |
| 6,703,362 B1 | 3/2004 | Alvarez et al. |
| 6,780,889 B2 | 8/2004 | Cook et al. |
| 6,803,464 B2 | 10/2004 | Edney et al. |
| 6,913,768 B2 | 7/2005 | Couch et al. |
| 7,015,200 B2 | 3/2006 | Mamelak et al. |
| 7,072,840 B1 | 7/2006 | Mayaud |
| 7,135,457 B1 | 11/2006 | Alvarez et al. |
| 7,238,367 B2 | 7/2007 | Tardi et al. |
| 7,262,219 B2 | 8/2007 | Cook et al. |
| 7,268,109 B2 | 9/2007 | Ellis et al. |
| 7,524,812 B2 | 4/2009 | Ellis et al. |
| 7,566,766 B2 | 7/2009 | O'Mahony et al. |
| 7,568,822 B2 | 8/2009 | Ibrahim |
| 7,572,605 B2 | 8/2009 | Mamelak et al. |
| 7,668,730 B2 | 2/2010 | Reardan et al. |
| 7,683,024 B2 | 3/2010 | Chan et al. |
| 7,709,445 B2 | 5/2010 | Soula et al. |
| 7,744,921 B2 | 6/2010 | Tardi et al. |
| 7,765,106 B2 | 7/2010 | Reardan et al. |
| 7,765,107 B2 | 7/2010 | Reardan et al. |
| 7,797,171 B2 | 9/2010 | Reardan et al. |
| 7,833,973 B2 | 11/2010 | Ellis et al. |
| 7,842,676 B2 | 11/2010 | Janoff et al. |
| 7,850,090 B2 | 12/2010 | Ollendick |
| 7,851,506 B2 | 12/2010 | Cook et al. |
| 7,879,362 B2 | 2/2011 | Castan et al. |
| 7,895,059 B2 | 2/2011 | Reardan et al. |
| 7,906,145 B2 | 3/2011 | Castan et al. |
| 7,956,030 B2 | 6/2011 | Ellis et al. |
| 7,977,307 B2 | 7/2011 | Ellis et al. |
| 8,022,279 B2 | 9/2011 | Mayer et al. |
| 8,062,667 B2 | 11/2011 | Mehta et al. |
| 8,084,045 B2 | 12/2011 | Pouliquen et al. |
| 8,092,828 B2 | 1/2012 | Louie et al. |
| 8,101,209 B2 | 1/2012 | Legrand et al. |
| 8,193,211 B2 | 6/2012 | Liang et al. |
| 8,202,537 B2 | 6/2012 | Mehta et al. |
| 8,202,542 B1 | 6/2012 | Mehta et al. |
| 8,263,125 B2 | 9/2012 | Vaya et al. |
| 8,263,650 B2 | 9/2012 | Cook et al. |
| 8,268,774 B2 | 9/2012 | Ellis et al. |
| 8,287,848 B2 | 10/2012 | Mehta et al. |
| 8,287,903 B2 | 10/2012 | Mehta et al. |
| 8,324,275 B2 | 12/2012 | Cook et al. |
| 8,337,890 B2 | 12/2012 | Mehta et al. |
| 8,431,806 B2 | 4/2013 | Mayer et al. |
| 8,445,023 B2 | 5/2013 | Guimberteau et al. |
| 8,457,988 B1 | 6/2013 | Reardan et al. |
| 8,461,197 B2 | 6/2013 | Tung |
| 8,461,203 B2 | 6/2013 | Cook et al. |
| 8,465,765 B2 | 6/2013 | Mehta et al. |
| 8,486,924 B2 | 7/2013 | Ansell et al. |
| 8,491,935 B2 | 7/2013 | Mehta et al. |
| 8,507,003 B2 | 8/2013 | Jorda et al. |
| 8,512,688 B2 | 8/2013 | Mehta et al. |
| 8,513,198 B2 | 8/2013 | Ellis et al. |
| 8,518,437 B2 | 8/2013 | Tardi et al. |
| 8,529,954 B2 | 9/2013 | Lebon et al. |
| 8,563,033 B1 | 10/2013 | Mehta et al. |
| 8,589,182 B1 | 11/2013 | Reardan et al. |
| 8,591,922 B1 | 11/2013 | Allphin et al. |
| 8,597,684 B2 | 12/2013 | Mehta et al. |
| 8,598,191 B2 | 12/2013 | Liang et al. |
| 8,609,651 B2 | 12/2013 | Jamieson et al. |
| 8,623,409 B1 | 1/2014 | Mehta et al. |
| 8,652,523 B2 | 2/2014 | Guimberteau et al. |
| 8,652,529 B2 | 2/2014 | Guimberteau et al. |
| 8,653,033 B2 | 2/2014 | Ellis et al. |
| 8,679,540 B2 | 3/2014 | Bonnet-Gonnet et al. |
| 8,680,228 B2 | 3/2014 | Guo et al. |
| 8,707,348 B2 | 4/2014 | Sakhartov et al. |
| 8,716,279 B2 | 5/2014 | Jamieson et al. |
| 8,731,963 B1 | 5/2014 | Reardan et al. |
| 8,734,850 B2 | 5/2014 | Castan et al. |
| 8,747,902 B2 | 6/2014 | Mehta et al. |
| 8,759,394 B2 | 6/2014 | Tung et al. |
| 8,765,178 B2 | 7/2014 | Parikh et al. |
| 8,765,680 B2 | 7/2014 | Ellis et al. |
| 8,771,735 B2 | 7/2014 | Rourke et al. |
| 8,772,306 B1 | 7/2014 | Eller |
| 8,778,301 B2 | 7/2014 | Mamelak et al. |
| 8,778,390 B2 | 7/2014 | Mehta et al. |
| 8,778,398 B2 | 7/2014 | Rourke et al. |
| 8,790,700 B2 | 7/2014 | Mehta et al. |
| 8,821,935 B2 | 9/2014 | Guimberteau et al. |
| 8,859,619 B2 | 10/2014 | Cook et al. |
| 8,883,217 B2 | 11/2014 | Mehta et al. |
| 8,901,173 B2 | 12/2014 | Allphin et al. |
| 8,916,202 B2 | 12/2014 | Lebon et al. |
| 8,952,029 B2 | 2/2015 | Eller |
| 8,952,062 B2 | 2/2015 | Cook et al. |
| 8,956,649 B2 | 2/2015 | Mehta et al. |
| 8,999,386 B2 | 4/2015 | Tu et al. |
| 8,999,392 B2 | 4/2015 | Suplie et al. |
| 9,023,400 B2 | 5/2015 | Guimberteau et al. |
| 9,040,083 B2 | 5/2015 | Mehta et al. |
| 9,050,302 B2 | 6/2015 | Eller |
| 9,132,107 B2 | 9/2015 | Allphin et al. |
| 9,180,100 B2 | 11/2015 | Tu et al. |
| 9,180,104 B2 | 11/2015 | Nelson et al. |
| 9,198,864 B2 | 12/2015 | Mehta et al. |
| 9,226,910 B2 | 1/2016 | Khayrallah et al. |
| 9,271,931 B2 | 3/2016 | Tardi et al. |
| 9,295,642 B2 | 3/2016 | Tu et al. |
| 9,359,290 B2 | 6/2016 | Khayrallah et al. |
| 9,408,823 B2 | 8/2016 | Nelson et al. |
| 9,427,429 B2 | 8/2016 | Gray |
| 9,486,426 B2 | 11/2016 | Eller |
| 9,522,191 B2 | 12/2016 | Mehta et al. |
| 9,539,330 B2 | 1/2017 | Cook et al. |
| 9,545,399 B2 | 1/2017 | Tu et al. |
| 9,549,989 B2 | 1/2017 | Mehta et al. |
| 9,555,017 B2 | 1/2017 | Allphin et al. |
| 9,561,179 B2 | 2/2017 | Castan et al. |
| 9,585,863 B2 | 3/2017 | Khayrallah et al. |
| 9,649,291 B2 | 5/2017 | Khayrallah et al. |
| 9,675,703 B2 | 6/2017 | Mehta et al. |
| 9,675,704 B2 | 6/2017 | Mehta et al. |
| 9,707,270 B2 | 7/2017 | Ellis et al. |
| 9,770,514 B2 | 9/2017 | Ghebre-Sellassie et al. |
| 9,795,567 B2 | 10/2017 | Rourke et al. |
| 9,801,852 B2 | 10/2017 | Allphin |
| 9,814,684 B2 | 11/2017 | Castan et al. |
| 9,844,544 B2 | 12/2017 | Tu et al. |
| 9,844,545 B2 | 12/2017 | Tu et al. |
| RE46,686 E | 1/2018 | Bonnet-Gonnet et al. |
| 9,867,797 B2 | 1/2018 | Nelson et al. |
| 9,920,311 B2 | 3/2018 | Abribat |
| 9,943,488 B2 | 4/2018 | Suplie et al. |
| 10,004,693 B2 | 6/2018 | Castan et al. |
| 10,028,912 B2 | 7/2018 | Cabral-Lilly et al. |
| 10,052,289 B2 | 8/2018 | Meyrueix et al. |

(56) References Cited

U.S. PATENT DOCUMENTS

| | | |
|---|---|---|
| 10,058,507 B2 | 8/2018 | Tardi et al. |
| RE47,084 E | 10/2018 | Castan et al. |
| 10,086,087 B2 | 10/2018 | Mehta et al. |
| 10,092,511 B2 | 10/2018 | Castan et al. |
| 10,105,341 B2 | 10/2018 | Khayrallah et al. |
| 10,172,958 B2 | 1/2019 | Mehta et al. |
| 10,174,302 B1 | 1/2019 | Friedrich et al. |
| 10,183,939 B2 | 1/2019 | Bingham et al. |
| 10,195,151 B2 | 2/2019 | Allphin et al. |
| 10,195,168 B2 | 2/2019 | Allphin et al. |
| 10,213,400 B2 | 2/2019 | Eller |
| 10,259,780 B2 | 4/2019 | Khayrallah et al. |
| 10,272,062 B2 | 4/2019 | Megret et al. |
| 10,307,463 B2 | 6/2019 | Ellis et al. |
| 10,398,662 B1 | 9/2019 | Allphin et al. |
| 10,457,627 B2 | 10/2019 | Xiang et al. |
| 10,501,401 B2 | 12/2019 | Xiang et al. |
| 10,507,203 B2 | 12/2019 | Tu et al. |
| 10,512,609 B2 | 12/2019 | Allphin et al. |
| 10,618,886 B1 | 4/2020 | Xiang et al. |
| 10,640,451 B2 | 5/2020 | Xiang et al. |
| 10,640,476 B2 | 5/2020 | Xiang et al. |
| 10,668,163 B2 | 6/2020 | Mehta et al. |
| 10,675,258 B2 | 6/2020 | Allphin et al. |
| 10,683,262 B2 | 6/2020 | Xiang et al. |
| 10,710,958 B2 | 7/2020 | Hurley et al. |
| 10,730,853 B2 | 8/2020 | Xiang et al. |
| 10,736,866 B2 | 8/2020 | Megret et al. |
| 10,758,488 B2 | 9/2020 | Allphin et al. |
| 10,774,031 B2 | 9/2020 | Xiang et al. |
| 10,813,885 B1 | 10/2020 | Allphin et al. |
| 10,829,443 B2 | 11/2020 | Nelson et al. |
| 10,836,714 B2 | 11/2020 | Xiang et al. |
| 10,857,143 B2 | 12/2020 | Tu et al. |
| 10,858,394 B2 | 12/2020 | Xiang et al. |
| 10,864,181 B2 | 12/2020 | Eller |
| 10,882,832 B2 | 1/2021 | Xiang et al. |
| 10,889,572 B2 | 1/2021 | Xiang et al. |
| 10,903,276 B2 | 1/2021 | Chan et al. |
| 10,905,775 B2 | 2/2021 | Mayer et al. |
| 10,912,754 B2 | 2/2021 | Carter et al. |
| 10,925,844 B2 | 2/2021 | Grassot et al. |
| 10,933,143 B2 | 3/2021 | Mehta et al. |
| 10,940,133 B1 | 3/2021 | Zomorodi |
| 10,941,107 B2 | 3/2021 | Xiang et al. |
| 10,952,986 B2 * | 3/2021 | Megret .................. A61P 43/00 |
| 10,959,956 B2 | 3/2021 | Allphin et al. |
| 10,959,976 B2 | 3/2021 | Carter et al. |
| 10,966,931 B2 | 4/2021 | Allphin et al. |
| 10,968,202 B2 | 4/2021 | Xiang et al. |
| 10,973,795 B2 | 4/2021 | Megret et al. |
| 10,987,310 B2 | 4/2021 | Allphin et al. |
| 11,000,498 B2 * | 5/2021 | Megret ................ A61K 9/1676 |
| 11,033,530 B2 | 6/2021 | Allphin |
| 11,046,946 B2 | 6/2021 | Abribat |
| 11,072,579 B2 | 7/2021 | Khayrallah et al. |
| 11,077,079 B1 | 8/2021 | Allphin et al. |
| 11,090,269 B1 | 8/2021 | Allphin et al. |
| 11,147,782 B1 | 10/2021 | Allphin et al. |
| 11,207,270 B2 | 12/2021 | Allphin et al. |
| 11,364,215 B1 | 6/2022 | Allphin et al. |
| 11,400,052 B2 | 8/2022 | Walsh et al. |
| 11,400,065 B2 | 8/2022 | Grassot et al. |
| 2002/0077334 A1 | 6/2002 | Cook et al. |
| 2003/0091632 A1 | 5/2003 | Campbell et al. |
| 2003/0180249 A1 | 9/2003 | Khanna et al. |
| 2004/0092455 A1 | 5/2004 | Mamelak et al. |
| 2005/0031688 A1 | 2/2005 | Ayala |
| 2005/0037077 A1 | 2/2005 | Legrand et al. |
| 2005/0113366 A1 | 5/2005 | Bourguignon et al. |
| 2005/0142192 A1 | 6/2005 | Benjamin et al. |
| 2005/0158384 A1 | 7/2005 | Couch et al. |
| 2005/0181050 A1 | 8/2005 | Hirsh et al. |
| 2005/0239838 A1 | 10/2005 | Edgar et al. |
| 2005/0244496 A1 | 11/2005 | Campbell et al. |
| 2006/0018933 A1 | 1/2006 | Vaya et al. |
| 2006/0024365 A1 | 2/2006 | Vaya et al. |
| 2006/0069040 A1 | 3/2006 | Mamelak |
| 2006/0078614 A1 | 4/2006 | Venkatesh |
| 2006/0182805 A1 | 8/2006 | Pfeiffer et al. |
| 2006/0204575 A1 | 9/2006 | Feng et al. |
| 2006/0210630 A1 * | 9/2006 | Liang .................. A61K 9/5031 424/468 |
| 2006/0228410 A1 | 10/2006 | Dumont et al. |
| 2007/0270491 A1 | 11/2007 | Cook et al. |
| 2008/0003267 A1 | 1/2008 | Spencer et al. |
| 2008/0004329 A1 | 1/2008 | Jamieson et al. |
| 2008/0020039 A1 | 1/2008 | Parikh et al. |
| 2008/0069871 A1 | 3/2008 | Vaughn et al. |
| 2008/0085304 A1 | 4/2008 | Baichwal et al. |
| 2008/0118571 A1 | 5/2008 | Lee et al. |
| 2008/0146549 A1 | 6/2008 | Coleman |
| 2008/0226564 A1 | 9/2008 | Weers et al. |
| 2008/0292700 A1 | 11/2008 | Nghiem et al. |
| 2008/0293698 A1 | 11/2008 | Johnson |
| 2009/0137565 A1 | 5/2009 | Frucht |
| 2009/0155357 A1 | 6/2009 | Muhuri |
| 2009/0220611 A1 | 9/2009 | Dargelas et al. |
| 2009/0317355 A1 | 12/2009 | Roth et al. |
| 2010/0112056 A1 | 5/2010 | Rourke et al. |
| 2010/0159001 A1 | 6/2010 | Cardinal et al. |
| 2010/0160363 A1 | 6/2010 | Cardinal et al. |
| 2010/0172989 A1 | 7/2010 | Roth et al. |
| 2010/0266701 A1 | 10/2010 | Guimberteau et al. |
| 2011/0034727 A1 | 2/2011 | Luchi et al. |
| 2011/0039929 A1 | 2/2011 | Cook et al. |
| 2011/0091537 A1 | 4/2011 | Castan et al. |
| 2011/0111027 A1 | 5/2011 | Rourke et al. |
| 2011/0119085 A1 | 5/2011 | Reardan et al. |
| 2011/0213004 A1 | 9/2011 | Kim et al. |
| 2011/0213298 A1 | 9/2011 | Pinnisi |
| 2011/0223241 A1 | 9/2011 | Tardi et al. |
| 2011/0293729 A1 | 12/2011 | Lebon et al. |
| 2012/0020833 A1 | 1/2012 | Cook et al. |
| 2012/0076865 A1 | 3/2012 | Allphin et al. |
| 2012/0148672 A1 | 6/2012 | Mehta et al. |
| 2012/0164228 A1 | 6/2012 | Suplie et al. |
| 2012/0202879 A1 | 8/2012 | Cook et al. |
| 2012/0202880 A1 | 8/2012 | Cook et al. |
| 2012/0207843 A1 | 8/2012 | Lebon et al. |
| 2013/0012565 A1 | 1/2013 | Tung et al. |
| 2013/0064814 A1 | 3/2013 | Gray |
| 2013/0143965 A1 | 6/2013 | Cook et al. |
| 2013/0230587 A1 | 9/2013 | Pilgaonkar et al. |
| 2013/0267595 A1 | 10/2013 | Cook et al. |
| 2013/0273159 A1 | 10/2013 | Howard et al. |
| 2013/0337078 A1 | 12/2013 | Mayer et al. |
| 2014/0004202 A1 | 1/2014 | Suplie et al. |
| 2014/0037745 A1 | 2/2014 | Liang et al. |
| 2014/0072624 A1 | 3/2014 | Jung et al. |
| 2014/0093578 A1 | 4/2014 | Mehta et al. |
| 2014/0127306 A1 | 5/2014 | Mehta et al. |
| 2014/0141090 A1 | 5/2014 | Wilson |
| 2014/0171506 A1 | 6/2014 | Allphin et al. |
| 2014/0188504 A1 | 7/2014 | Reardan et al. |
| 2014/0207480 A1 | 7/2014 | Reardan et al. |
| 2014/0207481 A1 | 7/2014 | Reardan et al. |
| 2014/0231300 A1 | 8/2014 | Mogna |
| 2014/0256709 A1 | 9/2014 | Glozman |
| 2014/0271896 A1 | 9/2014 | Abu Shmeis et al. |
| 2014/0275244 A1 | 9/2014 | Khayrallah et al. |
| 2014/0294916 A1 | 10/2014 | Tu et al. |
| 2014/0296830 A1 | 10/2014 | Gibson et al. |
| 2014/0316796 A1 | 10/2014 | Cox |
| 2014/0348917 A1 | 11/2014 | Rourke et al. |
| 2014/0371153 A1 | 12/2014 | Ellis et al. |
| 2015/0005334 A1 | 1/2015 | Shah et al. |
| 2015/0018414 A1 | 1/2015 | Khayrallah et al. |
| 2015/0073052 A1 | 3/2015 | Cook et al. |
| 2015/0182469 A1 | 7/2015 | Mehta et al. |
| 2015/0328168 A1 | 11/2015 | Daviaud-Venet et al. |
| 2016/0058704 A1 | 3/2016 | Tardi et al. |
| 2016/0068463 A1 | 3/2016 | Peoples et al. |
| 2016/0143854 A1 | 5/2016 | Tu et al. |

(56) References Cited

U.S. PATENT DOCUMENTS

| | | |
|---|---|---|
| 2016/0154947 A1 | 6/2016 | Reardan et al. |
| 2016/0180058 A1 | 6/2016 | Reardan et al. |
| 2016/0228379 A1 | 8/2016 | Kumar et al. |
| 2016/0271070 A1 | 9/2016 | Singh et al. |
| 2016/0310478 A1 | 10/2016 | Mehta et al. |
| 2016/0326086 A1 | 11/2016 | Tung et al. |
| 2016/0338966 A1 | 11/2016 | Guimberteau et al. |
| 2016/0346200 A1 | 12/2016 | Sommer et al. |
| 2016/0346216 A1 | 12/2016 | Chen |
| 2017/0042873 A1 | 2/2017 | Mehta et al. |
| 2017/0042874 A1 | 2/2017 | Mehta et al. |
| 2017/0119627 A1 | 5/2017 | Bhargava et al. |
| 2017/0224825 A1 | 8/2017 | Cook et al. |
| 2017/0319566 A1 | 11/2017 | Tu et al. |
| 2017/0340519 A9 | 11/2017 | Bhargava et al. |
| 2018/0000954 A1 | 1/2018 | Mehta et al. |
| 2018/0008539 A1 | 1/2018 | Singh et al. |
| 2018/0021284 A1 | 1/2018 | Megret et al. |
| 2018/0042855 A1 | 2/2018 | Rourke et al. |
| 2018/0193277 A1 | 7/2018 | Suplie et al. |
| 2018/0200221 A1 | 7/2018 | Nelson et al. |
| 2018/0228822 A1 | 8/2018 | Krouse et al. |
| 2018/0263936 A1 | 9/2018 | Allphin et al. |
| 2018/0280357 A1 | 10/2018 | Maricich |
| 2018/0318222 A1 | 11/2018 | Allphin et al. |
| 2018/0346900 A1 | 12/2018 | Abribat |
| 2019/0015389 A1 | 1/2019 | Mehta et al. |
| 2019/0099395 A1 | 4/2019 | Khayrallah et al. |
| 2019/0151460 A1 | 5/2019 | Mehta et al. |
| 2019/0169589 A1 | 6/2019 | Friedrich et al. |
| 2019/0183806 A1 | 6/2019 | Guillard |
| 2019/0183836 A1 | 6/2019 | Megret et al. |
| 2019/0194120 A1 | 6/2019 | Xiang et al. |
| 2019/0218168 A1 | 7/2019 | Xiang et al. |
| 2019/0269640 A1 | 9/2019 | Megret et al. |
| 2019/0269641 A1 | 9/2019 | Megret et al. |
| 2019/0274990 A1 | 9/2019 | Megret et al. |
| 2019/0282532 A1 | 9/2019 | Megret et al. |
| 2019/0328882 A1 | 10/2019 | Cook et al. |
| 2020/0085748 A1 | 3/2020 | Allphin et al. |
| 2020/0113840 A1 | 4/2020 | Allphin et al. |
| 2020/0113853 A1 | 4/2020 | Allphin et al. |
| 2020/0163926 A1 | 5/2020 | Nelson et al. |
| 2020/0163943 A1 | 5/2020 | Maricich et al. |
| 2020/0197347 A1 | 6/2020 | Megret et al. |
| 2020/0197377 A1 | 6/2020 | Maricich |
| 2020/0239416 A1 | 7/2020 | Xiang et al. |
| 2020/0261489 A1 | 8/2020 | Dimitrova et al. |
| 2020/0276142 A1* | 9/2020 | Grassot ............... A61K 9/0053 |
| 2020/0290955 A1 | 9/2020 | Hurley et al. |
| 2020/0330393 A1 | 10/2020 | Walsh et al. |
| 2020/0338029 A1 | 10/2020 | Allphin et al. |
| 2020/0360293 A1 | 11/2020 | Guillard |
| 2020/0360319 A1 | 11/2020 | Grassot et al. |
| 2020/0368187 A1 | 11/2020 | Grassot et al. |
| 2020/0369599 A1 | 11/2020 | Xiang et al. |
| 2020/0375995 A1 | 12/2020 | Sudhakar et al. |
| 2020/0385367 A1 | 12/2020 | Richardson et al. |
| 2021/0015744 A1 | 1/2021 | Jain et al. |
| 2021/0015745 A1 | 1/2021 | Jain et al. |
| 2021/0020317 A1 | 1/2021 | Lillaney et al. |
| 2021/0032199 A1 | 2/2021 | Xiang et al. |
| 2021/0038588 A1 | 2/2021 | Tu et al. |
| 2021/0038734 A1 | 2/2021 | Mehta et al. |
| 2021/0047367 A1 | 2/2021 | Xiang et al. |
| 2021/0053912 A1 | 2/2021 | Hurley |
| 2021/0061791 A1 | 3/2021 | Xiang et al. |
| 2021/0069105 A1 | 3/2021 | Jain et al. |
| 2021/0069136 A1 | 3/2021 | Jain et al. |
| 2021/0077450 A1 | 3/2021 | Khayrallah et al. |
| 2021/0087177 A1 | 3/2021 | Xiang et al. |
| 2021/0093575 A1 | 4/2021 | Rourke et al. |
| 2021/0093603 A1 | 4/2021 | Hurley |
| 2021/0093623 A1 | 4/2021 | Tu et al. |
| 2021/0094925 A1 | 4/2021 | Xiang et al. |
| 2021/0121423 A1 | 4/2021 | Allphin et al. |
| 2021/0128502 A1 | 5/2021 | Eller |
| 2021/0162055 A1 | 6/2021 | Mehta et al. |
| 2021/0186907 A1 | 6/2021 | Skobieranda |
| 2021/0187004 A1 | 6/2021 | McMahon et al. |
| 2021/0205227 A1 | 7/2021 | Allphin et al. |
| 2021/0205257 A1 | 7/2021 | Carter et al. |
| 2021/0212970 A1 | 7/2021 | Eller |
| 2021/0213007 A1 | 7/2021 | Tu et al. |
| 2021/0244670 A1 | 8/2021 | Allphin et al. |
| 2021/0267928 A1* | 9/2021 | Megret ............... A61K 31/22 |
| 2021/0361601 A1 | 11/2021 | Skobieranda |
| 2022/0016066 A1 | 1/2022 | Megret et al. |

FOREIGN PATENT DOCUMENTS

| | | |
|---|---|---|
| AR | 109376 A1 | 11/2018 |
| AR | 112403 A1 | 10/2019 |
| AT | 536867 T | 12/2011 |
| AU | 775523 B2 | 8/2004 |
| AU | 2007269896 A1 | 1/2008 |
| AU | 2006214454 B2 | 5/2011 |
| AU | 2007290589 B2 | 4/2012 |
| AU | 2011359405 A1 | 8/2013 |
| AU | 2011232408 B2 | 7/2015 |
| AU | 2007227569 B9 | 4/2016 |
| AU | 2010352575 C1 | 11/2016 |
| AU | 2013359114 B2 | 1/2017 |
| AU | 2013302657 B2 | 8/2018 |
| AU | 2014248849 B2 | 8/2018 |
| AU | 2014223373 B2 | 12/2018 |
| AU | 2014240988 B9 | 1/2019 |
| AU | 2017202955 B2 | 1/2019 |
| AU | 2017300845 A1 | 1/2019 |
| AU | 2017324855 A1 | 3/2019 |
| AU | 2018278332 A1 | 1/2020 |
| AU | 2018287145 A1 | 2/2020 |
| AU | 2018309068 A8 | 2/2020 |
| AU | 2015314007 B2 | 3/2020 |
| AU | 2018312328 A1 | 3/2020 |
| AU | 2017406159 B2 | 5/2020 |
| AU | 2018375183 A1 | 6/2020 |
| AU | 2018389797 A1 | 6/2020 |
| AU | 2018388577 A1 | 7/2020 |
| AU | 2019206950 A1 | 8/2020 |
| AU | 2016328150 B2 | 10/2020 |
| AU | 2019252790 A1 | 10/2020 |
| AU | 2019383389 A1 | 5/2021 |
| AU | 2019283096 A1 | 7/2021 |
| AU | 2019420189 A1 | 7/2021 |
| AU | 2020231916 A1 | 8/2021 |
| BR | 9916063 A | 1/2002 |
| BR | PI0607003 A2 | 7/2009 |
| BR | PI0713801 A2 | 11/2012 |
| BR | PI0714907 A2 | 8/2014 |
| BR | 112015014007 A2 | 7/2017 |
| BR | 112015021403 A2 | 7/2017 |
| BR | 112013020537 A2 | 9/2017 |
| BR | 112019000848 A2 | 4/2019 |
| BR | 112019004479 A2 | 7/2019 |
| BR | 112015021012 A8 | 11/2019 |
| BR | 112015003120 A2 | 12/2019 |
| BR | 112019020464 A2 | 4/2020 |
| BR | 112019025286 A2 | 6/2020 |
| BR | 112020002289 A2 | 7/2020 |
| BR | 112019027479 A2 | 9/2020 |
| BR | 112020010976 A2 | 11/2020 |
| BR | 112020012417 A2 | 11/2020 |
| BR | 112020020865 A2 | 1/2021 |
| BR | 112020014189 A2 | 2/2021 |
| BR | 112012028035 B1 | 5/2021 |
| BR | PI0709606 B8 | 5/2021 |
| BR | 112021006027 A2 | 6/2021 |
| CA | 2217902 A1 | 1/1999 |
| CA | 2112663 C | 4/2002 |
| CA | 2510289 A1 | 7/2004 |
| CA | 2597910 A1 | 8/2006 |
| CA | 2654383 A1 | 1/2008 |
| CA | 2662197 A1 | 3/2008 |

(56) References Cited

FOREIGN PATENT DOCUMENTS

| | | |
|---|---|---|
| CA | 2423358 C | 5/2011 |
| CA | 2786819 A1 | 7/2011 |
| CA | 2880456 A1 | 2/2014 |
| CA | 2904045 A1 | 10/2014 |
| CA | 2917702 A1 | 1/2015 |
| CA | 2645855 C | 2/2015 |
| CA | 2540895 C | 8/2016 |
| CA | 2999367 A1 | 3/2017 |
| CA | 2798178 C | 6/2017 |
| CA | 2894876 C | 8/2017 |
| CA | 2740146 C | 11/2017 |
| CA | 3028878 A1 | 1/2018 |
| CA | 3036068 A1 | 3/2018 |
| CA | 3036071 A1 | 3/2018 |
| CA | 3039045 A1 | 4/2018 |
| CA | 2794171 C | 7/2018 |
| CA | 3056316 A1 | 9/2018 |
| CA | 2930900 C | 10/2018 |
| CA | 3058216 A1 | 10/2018 |
| CA | 3065522 A1 | 12/2018 |
| CA | 3068100 A1 | 12/2018 |
| CA | 3071544 A1 | 2/2019 |
| CA | 3071779 A1 | 2/2019 |
| CA | 2825991 C | 3/2019 |
| CA | 3083499 A1 | 6/2019 |
| CA | 3084120 A1 | 6/2019 |
| CA | 3085941 A1 | 6/2019 |
| CA | 3086153 A1 | 6/2019 |
| CA | 3097737 A1 | 6/2019 |
| CA | 3087912 A1 | 7/2019 |
| CA | 3095335 A1 | 10/2019 |
| CA | 2902948 C | 12/2019 |
| CA | 3102650 A1 | 12/2019 |
| CA | 3115122 A1 | 5/2020 |
| CN | 1236813 C | 1/2006 |
| CN | 101132780 A | 2/2008 |
| CN | 101478952 A | 7/2009 |
| CN | 101400343 B | 1/2012 |
| CN | 101528261 B | 7/2012 |
| CN | 102905688 A | 1/2013 |
| CN | 102946869 A | 2/2013 |
| CN | 102958930 A | 3/2013 |
| CN | 103209966 A | 7/2013 |
| CN | 103209967 A | 7/2013 |
| CN | 102488652 B | 6/2014 |
| CN | 105073106 A | 11/2015 |
| CN | 105188677 A | 12/2015 |
| CN | 102917697 B | 1/2016 |
| CN | 102946869 B | 8/2016 |
| CN | 105848650 A | 8/2016 |
| CN | 105025892 B | 3/2018 |
| CN | 109789096 A | 5/2019 |
| CN | 109906078 A | 6/2019 |
| CN | 105873576 B | 7/2019 |
| CN | 109996540 A | 7/2019 |
| CN | 110049966 A | 7/2019 |
| CN | 110638804 A | 1/2020 |
| CN | 110638805 A | 1/2020 |
| CN | 110709386 A | 1/2020 |
| CN | 111094238 A | 5/2020 |
| CN | 111132663 A | 5/2020 |
| CN | 111201014 A | 5/2020 |
| CN | 111278807 A | 6/2020 |
| CN | 111315878 A | 6/2020 |
| CN | 111317730 A | 6/2020 |
| CN | 111356699 A | 6/2020 |
| CN | 111511355 A | 8/2020 |
| CN | 111770914 A | 10/2020 |
| CN | 111818937 A | 10/2020 |
| CN | 111836798 A | 10/2020 |
| CN | 106866733 B | 11/2020 |
| CN | 112004520 A | 11/2020 |
| CN | 112004802 A | 11/2020 |
| CN | 112135812 A | 12/2020 |
| CN | 112236149 A | 1/2021 |
| CN | 112566902 A | 3/2021 |
| CN | 108283000 B | 4/2021 |
| CN | 106866784 B | 5/2021 |
| CN | 107108588 B | 6/2021 |
| CN | 113061089 A | 7/2021 |
| CO | 2020001873 A2 | 4/2020 |
| DE | 60129122 T2 | 10/2007 |
| DK | 1278721 T3 | 10/2007 |
| DK | 2018160 T3 | 2/2012 |
| DK | 2428205 T3 | 10/2012 |
| DK | 2931268 T3 | 2/2018 |
| DK | 2961399 T3 | 2/2018 |
| DK | 2884961 T3 | 4/2019 |
| DK | 2675438 T3 | 5/2019 |
| DK | 2768484 T3 | 10/2019 |
| DK | 3335708 T3 | 2/2020 |
| DK | 3021838 T3 | 8/2020 |
| DK | 3335709 T3 | 10/2020 |
| EP | 0203768 A2 | 12/1986 |
| EP | 0235408 A1 | 9/1987 |
| EP | 0344704 A1 | 12/1989 |
| EP | 0616804 A1 | 9/1994 |
| EP | 0635265 A1 | 1/1995 |
| EP | 0709087 B1 | 12/1999 |
| EP | 0635265 B1 | 2/2000 |
| EP | 1140061 A2 | 10/2001 |
| EP | 1140061 B1 | 5/2003 |
| EP | 1316309 A1 | 6/2003 |
| EP | 1278721 B1 | 6/2007 |
| EP | 1853230 A2 | 11/2007 |
| EP | 2032125 A2 | 3/2009 |
| EP | 2056877 A2 | 5/2009 |
| EP | 2068933 A2 | 6/2009 |
| EP | 2018160 B | 12/2011 |
| EP | 1135150 B1 | 10/2012 |
| EP | 2428205 B1 | 10/2012 |
| EP | 2549987 A4 | 1/2015 |
| EP | 2968151 B1 | 4/2017 |
| EP | 2451486 B1 | 5/2017 |
| EP | 2760911 B1 | 11/2017 |
| EP | 2931268 B1 | 11/2017 |
| EP | 2961399 B1 | 11/2017 |
| EP | 1434572 B1 | 12/2017 |
| EP | 3353145 A1 | 8/2018 |
| EP | 2341910 B1 | 9/2018 |
| EP | 3418383 A1 | 12/2018 |
| EP | 2884961 B1 | 3/2019 |
| EP | 2675438 B1 | 4/2019 |
| EP | 3470067 A1 | 4/2019 |
| EP | 3487483 A1 | 5/2019 |
| EP | 2768484 B1 | 7/2019 |
| EP | 3353145 A4 | 7/2019 |
| EP | 3523275 A1 | 8/2019 |
| EP | 3572071 A1 | 11/2019 |
| EP | 3335708 B1 | 12/2019 |
| EP | 3595648 A1 | 1/2020 |
| EP | 3509581 A4 | 4/2020 |
| EP | 3642340 A1 | 4/2020 |
| EP | 3021838 B1 | 5/2020 |
| EP | 3509582 A4 | 5/2020 |
| EP | 3661484 A1 | 6/2020 |
| EP | 2566462 B1 | 7/2020 |
| EP | 3335709 B1 | 8/2020 |
| EP | 3695833 A1 | 8/2020 |
| EP | 3716997 A1 | 10/2020 |
| EP | 3727348 A1 | 10/2020 |
| EP | 3601235 A4 | 11/2020 |
| EP | 3737353 A1 | 11/2020 |
| EP | 3737665 A1 | 11/2020 |
| EP | 3740188 A1 | 11/2020 |
| EP | 3740189 A1 | 11/2020 |
| EP | 3668837 A4 | 12/2020 |
| EP | 3679051 A4 | 12/2020 |
| EP | 3773608 A1 | 2/2021 |
| EP | 3630072 A4 | 3/2021 |
| EP | 3661911 A4 | 4/2021 |
| EP | 3799867 A1 | 4/2021 |
| EP | 3802501 A1 | 4/2021 |
| ES | 2378573 T3 | 4/2012 |

(56) References Cited

FOREIGN PATENT DOCUMENTS

| | | |
|---|---|---|
| ES | 2396039 T3 | 2/2013 |
| ES | 2717469 T3 | 6/2019 |
| ES | 2721900 T3 | 8/2019 |
| GB | 922029 A | 3/1963 |
| GB | 2295390 A | 5/1996 |
| HK | 1156518 A | 6/2012 |
| HK | 1181639 A | 11/2013 |
| HK | 1201039 A1 | 8/2015 |
| HK | 1215181 A1 | 8/2016 |
| HK | 1215539 A1 | 9/2016 |
| HK | 1219236 A1 | 3/2017 |
| HK | 1256965 A1 | 10/2019 |
| HK | 1257965 A1 | 11/2019 |
| HK | 40002726 A | 3/2020 |
| HK | 40003964 A | 4/2020 |
| HK | 40009279 A | 6/2020 |
| HK | 40014757 A | 8/2020 |
| HK | 40027633 A | 1/2021 |
| HK | 40029219 A | 2/2021 |
| HK | 40029594 A | 2/2021 |
| HK | 40029856 A | 2/2021 |
| HK | 40031621 A | 3/2021 |
| HK | 40031646 A | 3/2021 |
| HK | 1182964 B | 4/2021 |
| HK | 1257033 B | 4/2021 |
| HK | 40033315 A | 4/2021 |
| HK | 40035049 A | 5/2021 |
| HK | 40038018 A | 6/2021 |
| ID | 201703439 A | 4/2017 |
| ID | 201906443 A | 8/2019 |
| ID | 201906490 A | 8/2019 |
| ID | 201907562 A | 10/2019 |
| IL | 143580 A | 5/2007 |
| IL | 194042 A | 6/2014 |
| IL | 239355 A | 5/2017 |
| IL | 222012 A | 11/2017 |
| IL | 222161 A | 11/2017 |
| IL | 227734 A | 8/2018 |
| IL | 236847 A | 5/2019 |
| IL | 240874 A | 6/2019 |
| IL | 241533 A | 2/2020 |
| IL | 275312 | 7/2020 |
| IL | 275444 | 8/2020 |
| IL | 265193 A | 4/2021 |
| IN | 200706499 P1 | 9/2007 |
| IN | 216331 B | 3/2008 |
| IN | 222233 B | 8/2008 |
| IN | 200808703 P1 | 5/2009 |
| IN | 200900401 P4 | 6/2009 |
| IN | 200901567 P1 | 6/2009 |
| IN | 201209462 P1 | 1/2016 |
| IN | 201505205 P4 | 7/2016 |
| IN | 201917009658 A | 6/2019 |
| IN | 201917013067 A | 6/2019 |
| IN | 201917017276 A | 8/2019 |
| IN | 342246 B | 7/2020 |
| IN | 342829 B | 7/2020 |
| IN | 202017008027 A | 8/2020 |
| IN | 202017008237 A | 10/2020 |
| IN | 202017045975 A | 2/2021 |
| IN | 361207 B | 3/2021 |
| JP | S5742651 A | 3/1982 |
| JP | S6212715 A | 1/1987 |
| JP | H0449212 A | 2/1992 |
| JP | H05508422 A | 11/1993 |
| JP | H06508839 A | 10/1994 |
| JP | H0753365 A | 2/1995 |
| JP | H08511257 A | 11/1996 |
| JP | H09104620 A | 4/1997 |
| JP | H10505604 A | 6/1998 |
| JP | 2001513552 A | 9/2001 |
| JP | 2002531515 A | 9/2002 |
| JP | 2004514732 A | 5/2004 |
| JP | 2006524207 A | 10/2006 |
| JP | 2007521231 A | 8/2007 |
| JP | 2007532689 A | 11/2007 |
| JP | 2008512386 A | 4/2008 |
| JP | 2008519847 A | 6/2008 |
| JP | 2008520633 A | 6/2008 |
| JP | 2008528571 A | 7/2008 |
| JP | 2009526825 A | 7/2009 |
| JP | 2009532331 A | 9/2009 |
| JP | 2011500865 A | 1/2011 |
| JP | 2012507532 A | 3/2012 |
| JP | 2012508784 A | 4/2012 |
| JP | 2013522373 A | 6/2013 |
| JP | 2014505094 A | 2/2014 |
| JP | 5479086 B2 | 4/2014 |
| JP | 5816091 B2 | 11/2015 |
| JP | 2016503002 A | 2/2016 |
| JP | 5925766 B2 | 5/2016 |
| JP | 5968300 B2 | 8/2016 |
| JP | 6215347 B2 | 10/2017 |
| JP | 6433440 B2 | 12/2018 |
| JP | 6516720 B2 | 5/2019 |
| JP | 6529495 B2 | 6/2019 |
| JP | 2019163298 A | 9/2019 |
| JP | 6683886 B2 | 4/2020 |
| JP | 2020100670 A | 7/2020 |
| JP | 6781150 B2 | 11/2020 |
| JP | 6824315 B2 | 2/2021 |
| JP | 6830671 B2 | 2/2021 |
| JP | 2021506752 A | 2/2021 |
| JP | 2021506984 A | 2/2021 |
| KR | 100602725 B1 | 7/2006 |
| KR | 20070104471 A | 10/2007 |
| KR | 20090031598 A | 3/2009 |
| KR | 20090043603 A | 5/2009 |
| KR | 101495146 B1 | 2/2015 |
| KR | 20150129695 A | 11/2015 |
| KR | 20160030955 A | 3/2016 |
| KR | 20160032127 A | 3/2016 |
| KR | 20180058738 A | 6/2018 |
| KR | 20190065311 A | 6/2019 |
| KR | 20190072561 A | 6/2019 |
| KR | 20190104510 A | 9/2019 |
| KR | 20190134711 A | 12/2019 |
| KR | 20200016889 A | 2/2020 |
| KR | 20200030065 A | 3/2020 |
| KR | 20200045489 A | 5/2020 |
| KR | 20200116102 A | 10/2020 |
| KR | 20200119234 A | 10/2020 |
| KR | 20200121780 A | 10/2020 |
| KR | 2180343 B1 | 11/2020 |
| KR | 2192554 B1 | 12/2020 |
| KR | 20210008478 A | 1/2021 |
| KR | 2239042 B1 | 4/2021 |
| KR | 20210094513 A | 7/2021 |
| MA | 29319 B1 | 3/2008 |
| MX | PA01005884 A | 4/2002 |
| MX | 233001 B | 12/2005 |
| MX | 2007009923 A | 3/2008 |
| MX | 2008015083 A | 12/2008 |
| MX | 2009002310 A | 9/2009 |
| MX | 2015011242 A | 5/2016 |
| MX | 340591 B | 7/2016 |
| MX | 366681 B | 7/2019 |
| MX | 2019002606 A | 9/2019 |
| MX | 372447 B | 3/2020 |
| MX | 377251 B | 11/2020 |
| MX | 381381 B | 4/2021 |
| MY | 118612 A | 12/2004 |
| NO | 20073854 L | 11/2007 |
| NO | 326479 B1 | 12/2008 |
| NO | 20085158 L | 1/2009 |
| NO | 20091211 L | 5/2009 |
| NZ | 512287 A | 12/2002 |
| NZ | 556562 A | 8/2010 |
| NZ | 572481 A | 3/2011 |
| NZ | 575744 A | 10/2011 |
| NZ | 595388 A | 12/2011 |
| OA | 14824 A | 1/2011 |
| PH | 12019500493 A1 | 5/2019 |
| PH | 12019500494 A1 | 6/2019 |

(56) References Cited

FOREIGN PATENT DOCUMENTS

| | | | |
|---|---|---|---|
| PH | 12019500751 A1 | 8/2019 |
| PH | 12019502723 A1 | 7/2020 |
| PL | 192864 B1 | 12/2006 |
| PT | 1278721 E | 7/2007 |
| PT | 2931268 T | 2/2018 |
| PT | 2961399 T | 2/2018 |
| PT | 2768484 T | 10/2019 |
| PT | 3335708 T | 3/2020 |
| PT | 3021838 T | 9/2020 |
| PT | 3335709 T | 10/2020 |
| RS | 57077 B1 | 6/2018 |
| RU | 2210360 C1 | 8/2003 |
| RU | 2257917 C2 | 8/2005 |
| RU | 2435569 C2 | 12/2011 |
| RU | 2673239 C2 | 11/2018 |
| RU | 2725886 C1 | 7/2020 |
| RU | 2019110127 A | 10/2020 |
| RU | 2020101972 A | 7/2021 |
| SG | 136196 A1 | 11/2007 |
| SG | 11201504637 B | 10/2017 |
| SG | 11201505029 B | 11/2017 |
| SG | 11201901996 A1 | 4/2019 |
| SG | 11201901998 A1 | 4/2019 |
| SG | 11201903076 A1 | 5/2019 |
| SG | 11201911470 A1 | 12/2019 |
| SG | 11201912625 A1 | 1/2020 |
| SG | 11202000817 A1 | 2/2020 |
| SG | 11202000952 A1 | 2/2020 |
| SG | 11201507121 B | 5/2020 |
| SG | 11202004965 A1 | 6/2020 |
| SG | 11202006575 A1 | 8/2020 |
| TW | 513416 B | 12/2002 |
| TW | 200812649 A | 3/2008 |
| TW | 200815045 A | 4/2008 |
| TW | 200824693 A | 6/2008 |
| TW | I619492 B | 4/2018 |
| TW | 201831174 A | 9/2018 |
| TW | 201836596 A | 10/2018 |
| TW | 201840544 A | 11/2018 |
| TW | I639425 B | 11/2018 |
| TW | 201909904 A | 3/2019 |
| TW | 201919605 A | 6/2019 |
| TW | 201932448 A | 8/2019 |
| TW | I681770 B | 1/2020 |
| TW | 202014186 A | 4/2020 |
| TW | 202019880 A | 6/2020 |
| TW | I707677 B | 10/2020 |
| TW | I710552 B | 11/2020 |
| TW | I716458 B | 1/2021 |
| TW | I727362 B | 5/2021 |
| UY | 30442 A1 | 1/2008 |
| UY | 30561 A1 | 3/2008 |
| VN | 65599 A | 9/2019 |
| VN | 66223 A | 10/2019 |
| VN | 66257 A | 10/2019 |
| VN | 76195 A | 3/2021 |
| WO | 9428880 A1 | 12/1994 |
| WO | 9640105 A1 | 12/1996 |
| WO | 9909972 A1 | 3/1999 |
| WO | 0033862 A1 | 6/2000 |
| WO | 0038672 A2 | 7/2000 |
| WO | 0119361 A2 | 3/2001 |
| WO | 0224715 A2 | 3/2002 |
| WO | 0245684 A2 | 6/2002 |
| WO | 2004093884 A2 | 11/2004 |
| WO | 2005016318 A1 | 2/2005 |
| WO | 2005030174 A1 | 4/2005 |
| WO | 2005055983 A2 | 6/2005 |
| WO | 2005099671 A2 | 10/2005 |
| WO | 2006029155 A2 | 3/2006 |
| WO | 2006053186 A2 | 5/2006 |
| WO | 2006080029 A1 | 8/2006 |
| WO | 2006088814 A3 | 2/2007 |
| WO | 2007053698 A2 | 5/2007 |
| WO | 2007103200 A2 | 9/2007 |
| WO | 2007109104 A3 | 12/2007 |
| WO | 2008033351 A2 | 3/2008 |
| WO | 2008027395 A3 | 4/2008 |
| WO | 2008042218 A1 | 4/2008 |
| WO | 2008005240 A3 | 5/2008 |
| WO | 2008086804 A2 | 7/2008 |
| WO | 2008027357 A9 | 4/2009 |
| WO | 2009056550 A2 | 5/2009 |
| WO | 2009092818 A1 | 7/2009 |
| WO | 2009104080 A2 | 8/2009 |
| WO | 2010042759 A2 | 4/2010 |
| WO | 2010053691 A1 | 5/2010 |
| WO | 2010055260 A1 | 5/2010 |
| WO | 2010124046 A1 | 10/2010 |
| WO | 2011119839 A1 | 9/2011 |
| WO | 2011127252 A2 | 10/2011 |
| WO | 2011135461 A2 | 11/2011 |
| WO | 2011139271 A1 | 11/2011 |
| WO | 2011140310 A2 | 11/2011 |
| WO | 2012028688 A1 | 3/2012 |
| WO | 2012085656 A2 | 6/2012 |
| WO | 2012107652 A1 | 8/2012 |
| WO | 2012112140 A1 | 8/2012 |
| WO | 2012112492 A1 | 8/2012 |
| WO | 2012114342 A1 | 8/2012 |
| WO | 2013119231 A1 | 8/2013 |
| WO | 2014028610 A1 | 2/2014 |
| WO | 2014078014 A2 | 5/2014 |
| WO | 2014093791 A1 | 6/2014 |
| WO | 2014134380 A1 | 9/2014 |
| WO | 2014159340 A1 | 10/2014 |
| WO | 2015006685 A1 | 1/2015 |
| WO | 2015010014 A1 | 1/2015 |
| WO | 2015076821 A1 | 5/2015 |
| WO | 2015120006 A1 | 8/2015 |
| WO | 2015120110 A2 | 8/2015 |
| WO | 2015166473 A1 | 11/2015 |
| WO | 2016087952 A1 | 6/2016 |
| WO | 2016178132 A1 | 11/2016 |
| WO | 2017049470 A1 | 3/2017 |
| WO | 2017050259 A1 | 3/2017 |
| WO | 2017147375 A1 | 8/2017 |
| WO | 2017182851 A1 | 10/2017 |
| WO | 2018015563 A1 | 1/2018 |
| WO | 2018048862 A1 | 3/2018 |
| WO | 2018048871 A1 | 3/2018 |
| WO | 2018067971 A1 | 4/2018 |
| WO | 2018167303 A1 | 9/2018 |
| WO | 2018176343 A1 | 10/2018 |
| WO | 2018222954 A1 | 12/2018 |
| WO | 2018234492 A1 | 12/2018 |
| WO | 2019027941 A1 | 2/2019 |
| WO | 2019033330 A1 | 2/2019 |
| WO | 2019041361 A1 | 3/2019 |
| WO | 2019109018 A1 | 6/2019 |
| WO | 2019123269 A1 | 6/2019 |
| WO | 2019126214 A1 | 6/2019 |
| WO | 2019126215 A1 | 6/2019 |
| WO | 2019126218 A1 | 6/2019 |
| WO | 2019137381 A1 | 7/2019 |
| WO | 2019028340 A9 | 8/2019 |
| WO | 2019126216 A8 | 10/2019 |
| WO | 2019200251 A1 | 10/2019 |
| WO | 2019232724 A1 | 12/2019 |
| WO | 2019233447 A1 | 12/2019 |
| WO | 2020019247 A1 | 1/2020 |
| WO | 2020020189 A1 | 1/2020 |
| WO | 2020062251 A1 | 4/2020 |
| WO | 2020106735 A1 | 5/2020 |
| WO | 2020118165 A1 | 6/2020 |
| WO | 2020143198 A1 | 7/2020 |
| WO | 2020178695 A1 | 9/2020 |
| WO | 2021078988 A1 | 4/2021 |
| WO | 2021127461 A1 | 6/2021 |
| WO | 2021133778 A1 | 7/2021 |
| WO | 2021168403 A1 | 8/2021 |

(56) References Cited

FOREIGN PATENT DOCUMENTS

| ZA | 200104585 B | 6/2002 |
|---|---|---|
| ZA | 202000676 B | 1/2021 |

OTHER PUBLICATIONS

Pai M.P., et al., "Drug Dosing Based on Weight and Body Surface Area: Mathematical Assumptions and Limitations in Obese Adults," Pharmacotherapy, Sep. 2012, vol. 32, No. 9, pp. 856-868.
Chen., et al., "Pharmacokinetics, Relative Bioavailability and Food Effect of JZP-258 and Sodium Oxybate: Results of two Phase 1, Open-Label, randomised crossover studies in healthy volunteers," Sleep Medicine, Abstracts, 2019, vol. 64, pp. S65-S66.
Erowid, "Gamma-hydroxybutyrnte (GHB) Basic Synthesis Procedure," Retrieved from the internet URL: http://www.erowid.org/chemicals/ghb/ghb_synthesis.shtml (as downloaded on Aug. 8, 2013) 2 pages.
Fides, "Solutions of 4-hydrox-ybutyric acid salts for injection," Chern Abstract ES302338. Laboratorio M. Cuatecases, S.A., 2011. 1 page.
Jazz Pharmaceuticals, Inc., "XYREM® (sodium oxybate) oral solution Prescribing Information," XYREM® US Package Insert available at http://pp.jazzpliamia.com/pi/xyem.en.USPI.pdf (downloaded Sep. 12, 2017, 32 pages.
Jha M.K., "Modified Release Formulations to Achieve the Quality Target Product Profile (QTPP)," IJPSR, 2012, vol. 3, No. 8, pp. 2376-2386.
Leu-Semenescu., et al., "Benefits and risk of sodium oxybate in idiopathic hypersomnia versus narcolepsy type 1: a chart review," Sleep Medicine, Jan. 2016, vol. 17, pp. 38-44.
Morrison, Robert T., et al., "Organic Chemistry", Chapter 20: "Functional Derivatives of Carboxylic Acids," 3rd Edition, 1973, pp. 658-700.
Office Action for Argentina Patent Application No. 20170102053, dated Nov. 9, 2021, 5 Pages.
Office Action for Japanese Patent Application No. 2020055505, dated Oct. 28, 2021, 11 Pages.
Office Action for Canadian Patent Application No. 3084120, dated Aug. 26, 2021, 5 Pages.
Office Action for Chinese Patent Application No. 201880082447.4, dated Oct. 12, 2021, 20 Pages.
Rujivipat., et al., "Improved Drug Delivery to the Lower Intestinal Tract with Tablets Compression-Coated with Enteric/Nonenteric Polymer Powder Blends," European Journal of Pharmaceutics and Biopharmaceutics, 2010, vol. 76, pp. 486-492.
Scammell T.E., "Narcolepsy," The New England Journal of Medicine, Dec. 31, 2015, vol. 373, No. 27, pp. 2654-2662.
Vogel., et al., "Toxicologic/transport properties of NCS-382, a y-hydroxybutyrate (GHB) receptor ligand, in neuronal and epithelial cells: Therapeutic implications for SSADH deficiency, a GABA metabolic disorder," Toxicol in Vitro, 2018, vol. 46, pp. 203-212.
A Double-Blind, Placebo-Controlled Study Demonstrates Sodium Oxybate is Effective for the Treatment of Excessive Daytime Sleepiness in Narcolepsy, Xyrem International Study Group, Journal of Clinical Sleep Medicine, 2005, vol. 1(4), pp. 391-397.
Abad V.C., et al., "New Developments in the Management of Narcolepsy," Nature and Science of Sleep, 2017, vol. 9, pp. 39-57.
Abanades S., et al., "Relative Abuse Liability of y-Hydroxybutyric Acid, Flunitrazepam, and Ethanol in Club Drug Users," Journal of Clinical Psychopharmacology, 2007, vol. 27 (6), pp. 625-638.
Abanades S., et al., "y-Hydroxybutyrate (GHB) in Humans, Pharmacodynamics and Pharmacokinetics," Annals New York Academy of Sciences, 2006, vol. 1074, pp. 559-576.
"Activase," Physicians Desk Reference, 50th Edition, 1996, pp. 312, 1058-1061.
Ahmed S.M., et al., "Narcolepsy and Influenza Vaccination-Induced Autoimmunity," Annals of Translational Medicine, 2017, vol. 5(1), pp. 1-4.

Ahmed S.M., et al., "The Safety of Adjuvanted Vaccines Revisited: Vaccine-Induced Narcolepsy," The Israel Medical Association Journal, 2016, vol. 18, pp. 216-220.
Akala E.O., "Effect of Packaging on Stability of Drugs and Drug Products," Pharmaceutical Manufacturing Handbook Regulations and Quality, 2008, pp. 641-686.
Akifuddin S.K., et al., "Preparation, Characterization and In-Vitro Evaluation of Microcapsules for Controlled Release of Diltiazem Hydrochloride by Ionotropic Gelation Technique," Journal of Applied Pharmaceutical Science, Apr. 2013, vol. 3 (4), pp. 35-42.
Aldrete J.A., et al., "Does Magnesium Produce Anesthesia Evaluation of Its Effects on the Cardiovascular and Neurologic Systems," Anesthesia and Analgesia, 1968, vol. 47 (4), pp. 428-433.
Alshaikh M.K., et al., "Sodium Oxybate for Narcolepsy with Cataplexy: Systematic Review and Meta-Analysis," Journal of Clinical Sleep Medicine, 2012, vol. 8 (4), pp. 451-458.
"Amberlite IRN78 Resin, Nuclear Grade Strong Base Anion Resin," The Dow Chemical Company, Product Data Sheet, Form No. 177-02230-0311, Rev. 0, 3 pages.
Anand V., et al., "Ion-Exchange Resins: Carrying Drug Delivery Forward," Drug Discovery Today 2001, Sep. 17, 2001, vol. 6 (17), pp. 905-914.
Anonymous, "The Engineering Toolbox," Retrieved from internet URL: https://www.engineeringtoolbox.com/relative-humidity-production-processd_511.html, 2003, 3 pages.
Arena C., et al., "Absorption of Sodium y-Hydroxybutyrate and Its Prodrug y-Butyrolactone: Relationship between In Vitro Transport and In Vivo Absorption," Journal of Pharmaceutical Sciences, 1980, vol. 69 (3), pp. 356-358.
Baldrick P., "Pharmaceutical Excipient Development: The Need for Preclinical Guidance," Regulatory Toxicology and Pharmacology, Oct. 2000, vol. 32 (2), pp. 210-218.
Barateau L., et al., "Hypersomnolence, Hypersomnia, and Mood Disorders," Current Psychiatry Reports, 2017, vol. 19, pp. 1-11.
Barateau L., et al., "Management of Narcolepsy," Current Treatment Options in Neurology, 2016, vol. 18, pp. 1-13.
Bayram A.K., et al., "Efficiency of a Combination of Pharmacological Treatment and Nondrug Interventions in Childhood Narcolepsy," Neuropediatrics, 2016, vol. 47 (6), pp. 380-387.
Bedard M.A., et al., "Nocturnal y-Hydroxybutyrate—Effect on Periodic Leg Movements and Sleep Organization of Narcoleptic Patients," Clinical Neuropharmacology, Feb. 1989, vol. 12 (1), pp. 29-36.
Berthier M., et al., "Possible Involvement of a Gamma-Hydroxybutyric Acid Receptor in Startle Disease," Acta Paediatr, 1994, vol. 83, pp. 678-680.
Bhattacharya I., et al., "Feasibility of D-Glucuronate to Enhance y-Hydroxybutyric Acid Metabolism During y-Hydroxybutyric Acid Toxicity: Pharmacokinetic and Pharmacodynamic Studies," Biopharmaceutics & Drug Disposition, 2007, vol. 28, pp. 1-11.
Bhattacharya I., et al., "Potential y-Hydroxybutyric acid (GHB) Drug Interactions Through Blood-Brain Barrier Transport Inhibition: A Pharmacokinetic Simulation-Based Evaluation," Journal of Pharmacokinetics and Pharmacodynamics, 2006, vol. 33 (5), pp. 657-681.
Biospace: "Flamel Technologies Announces Positive Results of A Second Clinical Trial with Micropump® Sodium Dxybate," BioSpace, Published on: Dec. 22, 2014, 6 Pages.
Black J., et al., "Medical Comorbidity in Narcolepsy: Findings from the Burden of Narcolepsy Disease (BOND) Study," Sleep Medicine, 2017, vol. 33, pp. 13-18.
Black J., et al., "The Nightly Use of Sodium Oxybate Is Associated with a Reduction in Noctural Sleep Disruption: A Double-Blind, Placebo-Controlled Study in Patients with Narcolepsy," Journal of Clinical Sleep Medicine, 2010, vol. 6 (6), pp. 596-602.
Black S.W., et al., "Challenges in the Development of Therapeutics for Narcolepsy," Prog NeurobioL, 2017, vol. 152, pp. 89-113.
Bodmeier R., "Tableting of Coated Pellets," European Journal of Pharmaceutics and Biopharmaceutics, 1997, vol. 43 (1), pp. 1-8.
Bogan R., et al., "Evaluation of Quality of Life in Patients With Narcolepsy Treated with Sodium Oxybate: Use of the 36-Item Short-Form Health Survey in a Clinical Trial," Neurology and Therapy, 2016, vol. 5, pp. 203-213.

(56) References Cited

OTHER PUBLICATIONS

Borgen L., et al., "Xyrem (sodium oxybate): A Study of Dose Proportionality in Healthy Human Subjects," Journal of Clinical Pharmacology, 2000, vol. 40, p. 1053.

Borgen L.A., et al., "The Influence of Gender and Food on the Pharmacokinetics of Sodium Oxybate Oral Solution in Healthy Subjects," Journal of Clinical Pharmacology, 2003, vol. 43, pp. 59-65.

Borgen L.A., et al., "The Pharmacokinetics of Sodium Oxybate Oral Solution following Acute and Chronic Administration to Narcoleptic Patients," Journal of Clinical Pharmacology, 2004, vol. 44, pp. 253 257.

Boscolo-Berto R., et al., "Narcolepsy and Effectiveness of Gamma-Hydroxybutyrate (GHB): A Systematic Review and Meta-analysis of Randomized Controlled Trials," Sleep Medicine Reviews, 2012, vol. 16, pp. 431-443.

Bowker M.J., et al., "Preparation of Water-Soluble Compounds Through Salt Formulation," Edited by Wermuth C. G., The Practice of Medicinal Chemistry, Academic Press, Third Edition, Chapter 37, 2008, pp. 749-766.

Brailsford A.D., et al., "Increases in Serum Growth Hormone Concentrations Associated with GHB Administration," Journal of Analytical Toxicology, 2017, vol. 41, pp. 54-59.

Brenneisen R., et al., "Pharmacokinetics and Excretion of Gamma-Hydroxybutyrate (GHB) in Healthy Subjects," Journal of Analytical Toxicology, 2004, vol. 28, pp. 625-630.

Broughton R., et al., "Effects of Nocturnal Gamma-Hydroxybutyrate on Spell/Waking Patterns in Narcolepsy-Cataplexy," The Canadian Journal of Neurological Sciences, Feb. 1980, vol. 7 (1), pp. 23-31.

Broughton R., et al., "Gamma-Hydroxy-Butyrate in the Treatment of Narcolepsy: A Preliminary Report," Narcolepsy, Spectrum Publications, Inc, N.Y., 1976, pp. 659-667.

Broughton R., et al., "The Treatment of Narcolepsy-Cataplexy with Nocturnal Gamma-Hydroxybutyrate," The Canadian Journal of Neurological Sciences, 1979, vol. 6 (1), pp. 1-6.

Caballero F., et al., "Characterization of Alginate Beads Loaded With Ibuprofen Lysine Salt and Optimization of the Preparation Method," International Journal of Pharmaceutics, 2014, vol. 460 (1), pp. 181-188.

Calik M.W., "Update on the Treatment of Narcolepsy: Clinical Efficacy of Pitolisant," Nature and Science of Sleep, 2017, vol. 9, pp. 127-133.

Carlier L., et al., "Gamma-Hydroxybutyrate (GHB), An Unusual Cause of High Anion Gap Metabolic Acidosis," Canadian Journal of Emergency Medicine | Journal Canadian De La Medecine D'urgence, 2018, vol. 20, pp. S2-S5.

Carter L.P., et al., "Behavioural Analyses of GHB: Receptor Mechanisms," Pharmacology & Therapeutics, 2009, vol. 121 (1), pp. 100-114.

Carter L.P., et al., "Cognitive, Psychomotor, and Subjective Effects of Sodium Oxybate and Triazolam in Healthy Volunteers," Psychopharmacology (Berl), 2009, vol. 206 (1), pp. 141-154.

Chang R.K., et al., "Polymethacrylates," Handbook of Pharmaceutical Excipients, 2006, Fifth Edition, Pharmaceutical Press, London, pp. 553-560.

Chem Abstract, ES302338, SciFinder, 1964, 1 page.

Ciolino L.A., et al., "The Chemical Interconversion of GHB and GBL: Forensic Issues and Implications," Journal of Forensic Sciences, 2001, vol. 46 (6), pp. 1315-1323.

Code of Federal Regulations (C.F.R.), Title 21 "Food and Drugs," Part 211 "Current Good Manufacturing Practice for finished Pharmaceuticals," Stability testing, vol. 4, Revised as of Apr. 1, 2019, 3 pages.

Consolo S., et al., "Mediation by the Corticostriatal Input of the In Vivo Increase in Rat Striatal Acetylcholine Content Induced by 2-Chloroadenosine," Biochemical Pharmacology, 1983, vol. 32 (19), pp. 2993-2996.

Goyanes A., et al., "Gastrointestinal Release Behaviour of Modified-Release Drug Products: Dynamic Dissolution Testing of Mesalazine Formulations," International Journal of Pharmaceutics, 2015, vol. 484, No. 1-2, pp. 103-108, Retrieved from the Internet: URL: https://discovery.ucl.ac.uk/id/eprint/1462647/3/Basit.1462647_5-ASA.pdf.

Office Action for European Patent Application No. 17742441.3, dated Mar. 11, 2022, 7 Pages.

Office Action for Japanese Patent Application No. 2020055505, dated Feb. 21, 2022, 11 Pages.

"Pharma Excipients," EUDRAGIT® L 100-55, Description, Additional Information, Mar. 2022, 2 pages, Retrieved from the internet URL: https://www.pharmaexcipients.com/product/eudragit-l-100-55/.

Examination Report No. 1 for Australian Patent Application No. 2017300845 dated May 17, 2022, 6 Pages.

Kothare S.V., et al., "Pharmacotherapy of Narcolepsy: Focus on Sodium Oxybate," Clinical Medicine Insights: Therapeutics, 2010, vol. 2, pp. 37-52.

Non-Final Office Action for U.S. Appl. No. 17/666,192 dated May 19, 2022, 17 pages.

Non-Final Office Action for U.S. Appl. No. 17/666,205 dated May 13, 2022, 8 pages.

Haller C., et al., "GHB Urine Concentrations After Single-Dose Administrationin Humans," Journal of Analytical Toxicology, 2006, vol. 30, pp. 360-364.

Haque T., et al., "Model Dependent and Independent Approaches to Compare in Vito Release Profiles From Ethylcellulose and Eudragit L100 Based Matrix Tablets," Dhaka University Journal of Pharmaceutical Sciences, 2009, vol. 8 (1), pp. 89-98.

Hasenbos M.A.W.M., et al., "Anaesthesia for Bullectomy, A Technique With Spontaneous Ventilation and Extradural Blockade," Anaesthesia, 1985, vol. 40 (10), pp. 977-980.

Heide A.V.D., et al., "Core Body and Skin Temperature in Type 1 Narcolepsy in Daily Life; Effects of Sodium Oxybate and Prediction of Sleep Attacks," Sleep, 2016, vol. 39 (11), pp. 1941-1949.

Helrich M., et al., "Correlation of Blood Levels of 4-Hydroxybutyrate with State of Consciousness," Anesthesiology, 1964, vol. 25 (6), pp. 771-775.

Hennessy S.A., et al., "The Reactivity of Gamma-Hydroxybutyric acid (GHB) and Gamma-Butyrolactone (GBL) in Mcoholic Solutions," Journal of Forensic Sciences, 2004, vol. 49 (6), pp. 1-10.

"Hib-Imune," Physicians Desk Reference, 41st Edition, 1987, pp. 1095-1096.

"HibVAX," Physicians Desk Reference, 41st Edition, 1987, p. 870.

Hoes M.J.A.J.M., et al., "Gamma-Hydroxybutyric Acid (*) as Hypnotic, Clinical and Pharmacokinetic Evaluation of Gamma Hydroxybutyric Acid as Hypnotic in Man," L'Encephale: Revue de psychiatry clinique biologique et therapeutique, 1980, vol. 6 (1), pp. 93-99.

International Preliminary Report on Patentability for International Application No. PCT/EP2017/068552, dated Jan. 31, 2019, 9 pages.

International Search Report and Written Opinion for International Application No. PCT/B2018/060278, dated Apr. 15, 2019, 8 pages.

International Search Report and Written Opinion for International Application No. PCT/EP2017/068552, dated Sep. 15, 2017, 10 pages.

International Search Report and Written Opinion for International Application No. PCT/IB2020/051726, dated May 18, 2020, 13 pages.

Jazz Pharmaceuticals., "Jazz Pharmaceuticals Announces Positive Top-line Results from Phase 3 Study of JZP-258 in Adult Narcolepsy Patients with Cataplexy and Excessive Daytime Sleepiness," Retrieved from URL: https://investor.jazzpharma.com/node/16206/pdf, Mar. 26, 2019, 2 pages.

Jennum P., et al., "Morbidity of Childhood Onset Narcolepsy: A Controlled National Study," Sleep Medicine, 2017, vol. 29, pp. 13-17.

Johnson M.W., et al., "Comparative Abuse Liability of GHB and Ethanol in Humans," Experimental and Clinical Psychopharmacology, 2013, vol. 21 (2), pp. 112-123.

Jones A.W., et al., "Concentration-Time Profiles of Gamma-Hydroxybutyrate in Blood After Recreational Doses are Best Described by Zero-Order Rather Than First-Order Kinetics," Journal of Analytical Toxicology, 2009, vol. 33, pp. 332-335.

(56) References Cited

OTHER PUBLICATIONS

Kallweit U., et al., "Pharmacological Management of Narcolepsy with and without Cataplexy," Expert Opinionon Pharmacotherapy, 2017, vol. 18 (8) pp. 809-817.

Keating G.M., "Sodium Oxybate: A Review of Its Use in Alcohol Withdrawal Syndrome and in the Maintenance of Abstinence in Alcohol Dependence," Clinical Drug Investigation, 2014, vol. 34, pp. 63-80.

Khatami R., et al., "The European Narcolepsy Network (EU-NN) database," Journal of Sleep Research, 2016, vol. 25, pp. 356-364.

Khediri F., et al., "Efficacy of Diosmectite (Smecta) in the Treatment of Acute Watery Diarrhea in Adults: A Multicenter, Randomized, Double-Blind, Placebo-Controlled, Parallel Group Study," Hindawi Publishing Corporation, Gastroenterology Research and Practice, 2011, vol. 2011, Article ID 783196, 9 pages.

Kollb-Sielecka M., et al., "The European Medicines Agency Review of Pitolisant for Treatment of Narcolepsy: Summary of the Scientific Assessment by the Committee for Medicinal Products for Human Use," Sleep Medicine, 2017, vol. 33, pp. 125-129.

Kornum B.R., et al., "Narcolepsy," Nature Reviews/Disease Primers, Feb. 9, 2017, vol. 3, pp. 1-19.

Kovalska P., et al., "Higher Body Mass Index in Narcolepsy with Cataplexy: Lifelong Experience", Sleep Medicine, 2017, vol. 32, 1 page.

Kovalska P., et al., "Narcolepsy with Cataplexy in Patients Aged Over 60 years: A Case-Control Study," Sleep Medicine, 2016, vol. 26, pp. 79-84.

Krahn L.E., "Understanding the Needs of Older Patients with Narcolepsy," Sleep Medicine, 2016, vol. 26, 3 pages.

Kristoffersen L., et al., "Determination of Safety Margins for Whole Blood Concentrations of Alcohol and Nineteen Drugs in Driving Under the Influence Cases," Forensic Science International, 2016, vol. 259, pp. 119-126.

Laborit H., "Gamma-Hydroxybutyrate, Succinic Semialdehyde and Sleep," Laboratoire d'Eutonologie, 1973, pp. 257-274.

Ladinsky H., et al., "Mode of Action of Gamma-Butyrolactone on the Central Cholinergic System," Naunyn-Schmiedeberg's, Arch Pharmacol, 1983, vol. 322 (1), pp. 42-48.

Lam W.K., et al., "Monocarboxylate Transporter-Mediated Transport of y-Hydroxybutyric Acid in Human Intestinal Caco-2 Cells," Drug Metabolism and Disposition, 2010, vol. 38 (3), pp. 441-447.

Lammers G.J., et al., "Gamma-Hydroxybutyrate and Narcolepsy: A Double-Blind Placebo-Controlled Study," Sleep, 1993, vol. 16 (3), pp. 216-220.

Lapierre, et al., "The Effect of Gamma-Hydroxybutyrate: A Double-Blind Study of Normal Subjects," Sleep Research, 1988, vol. 17 (99), 6 pages.

Lapierre O., et al., "The Effect of Gamma-Hydroxybutyrate on Nocturnal and Diurnal Sleep of Normal Subjects: Further Considerations on REM Sleep-Triggering Mechanisms," Sleep, 1990, vol. 13 (1), pp. 24-30.

Lecendreux M., et al., "Narcolepsy Type 1 Is Associated with a Systemic Increase and Activation of Regulatory T Cells and with a Systemic Activation of Global T Cells," PLoS ONE, Jan. 20, 2017, pp. 1-14.

Lee C.R., "Evidence for the Beta-Oxidation of Orally Administered 4-Hydroxybutyrate in Humans," Biochemical Medicine, 1977, vol. 17 (3), pp. 284-291.

Lernmark A., "Environmental Factors in the Etiology of Type 1 Diabetes, Eliac Disease and Narcolepsy," Pediatric Diabetes, Jul. 2016, vol. 17 (22), pp. 65-72.

Lettieri J., et al., "Improved Pharmacological Activity via Pro-Drug Modification: Comparative Pharmacokinetics of Sodium Gamma-hydroxybutyrate and Gamma-butyrolactone," Research Communications in Chemical Pathology and Pharmacology, Oct. 1, 1978, vol. 22 (1), pp. 107-118.

Liakoni E., et al., "Presentations to an Urban Emergency Department in Switzerland Due to Acute Y-hydroxybutyrate Toxicity," Scandinavian Journal of Trauma, Resuscitation and Emergency Medicine, 2016, vol. 24 (107), pp. 1-9.

Liechti M.E., et al., "Pharmacokinetics and Pharmacodynamics of y-Hydroxybutyrate in Healthy Subjects," British Journal of Clinical Pharmacology, 2016, vol. 81, pp. 980-988.

Lin R.Y., et al., "Human Monocarboxylate Transporter 2 (MCT2) Is a High Affinity Pyruvate Transporter," The Journal of Biological Chemistry, Oct. 30, 1998, vol. 273 (44), pp. 28959-28965.

Lingford-Hughes A., et al., "Improving GHB Withdrawal with Baclofen: Study Protocol for a Feasibility Study for a Randomized Controlled Trial," Trials, 2016, vol. 17, pp. 1-11.

Linselle M., et al., "Can Drugs Induce or Aggravate Sleep Apneas? A Case Non Case Study in Vigibase the WHO Pharmacovigilance Database," Fundamental & Clinical Pharmacology, 2017, vol. 31 (3), pp. 359-366.

Lubrano E., et al., "Fibromyalgia in Patients with Irritable Bowel Syndrome. An Association with the Severity of the Intestinal Disorder," International Journal of Colorectal Disease, 2001, vol. 16 (4), pp. 211-215.

Luhn O., "Using Excipients In Powder Formulations," Pharmaceutical Technology Europe, Retrieved from URL: https://www.pharmtech.com/view/using-excipients-powder-formulations, Jan. 7, 2011, vol. 23 (1), 2 pages.

Lusina M., et al., "Stability Study of Losartan/hydrochlorothiazide Tablets," International Journal of Pharmaceutics, 2005, vol. 291 (1-2), pp. 127-137.

Mahore J.G., et al., "Ion Exchange Resins: Pharmaceutical Applications and Recent Advancement," International Journal of Pharmaceutical Sciences Review and Research, Mar.-Apr. 2010, vol. 1 (2), pp. 8-13.

Maitre M., et al., "Mechanisms for the Specific Properties of y-Hydroxybutyrate in Brain," Medicinal Research Reviews, 2016, vol. 36, pp. 1-25.

Mamelak M., et al., "A Pilot Study on the Effects of Sodium Oxybate on Sleep Architecture and Daytime Alertness in Narcolepsy," Sleep, 2004, vol. 27 (7), pp. 1327-1334.

Mamelak M., et al., "Sleep-Inducing Effects of Gammahydroxybutyrate," The Lancet, Aug. 11, 1973, vol. 302 (7824), pp. 328-329.

Mamelak M., et al., "The Effects of y-Hydroxybutyrate on Sleep," Biological Psychiatry, 1977, vol. 12 (2), pp. 273-288.

FDA: "Impurities in New Drug Products," Guidance for Industry Q3B(R2), Aug. 2006, Revision 3, 18 pages, Retrieved from the Internet: https://www.fda.gov/media/71733/download.

Final Office Action for U.S. Appl. No. 16/984,645, dated Mar. 4, 2022, 51 pages.

Tittarelli R., et al., "Ultra-High-Performance Liquid Chromatography Tandem Mass Spectrometry Determination of GHB, GHB-Glucuronide in Plasma and Cerebrospinal Fluid of Narcoleptic Patients under Sodium Oxybate Treatment," Forensic Science International, 2017, vol. 274, pp. 70-74.

"Transcript of a Markman Hearing," In the Case of *Jazz Pharmaceuticals, Inc.*, Plaintiff, v. *Roxane Laboratories, Inc.*, Defendant (United States District Court for the District of New Jersey, Civil 106108 ES), Apr. 26, 2012, 231 pages.

Tunnicliff G., "Sites of Action of Gamma-Hydroxybutyrate (GHB)—A Neuroactive Drug with Abuse Potential," Clinical Toxicology, 1997, vol. 35 (6), pp. 581-590.

Turnberg L.A., "Abnormalities in Intestinal Electrolyte Transport in Congenital Chloridorrhoea," Gut, 1971, vol. 12 (7), pp. 544-551.

United States Pharmacopeial Convention, Inc.: The National Formulary, 23/NF18, Jan. 1, 1995, p. 2205.

U.S. Department of Health and Human Services., et al., "Dissolution Testing of Immediate Release Solid Oral Dosage Forms," Food and Drug Administration, CDER, Aug. 1997, 18 pages.

U.S. Department of Health and Human Services., et al., "Extended Release Oral Dosage Forms: Development, Evaluation, and Application of In Vitro/In Vivo Correlations," Food and Drug Administration, CDER, Sep. 1997, 28 pages.

Van A.G., et al., "Placentatransfer of 4-Hydroxybutyric Acid in Man," Anaesthesiology and Intensive Care Medicine, 1978, vol. 110, pp. 55-64.

Van Ginneken C.A.M., et al., "Linear and Nonlinear Kinetics of Drug Elimination. I. Kinetics on the Basis of a Single Capacity-Limited Pathway of Elimination with or Without Simultaneous

(56) References Cited

OTHER PUBLICATIONS

Supply-Limited Elimination," Journal of Pharmacokinetics and Biopharmaceutics, 1974, vol. 2 (5), pp. 395-415.

Vickers M.D., "Gammahydroxybutyric Acid," International Anesthesiology Clinics, 1969, vol. 7 (1), pp. 75-89.

Wade A., et al., "Malic Acid," The Handbook of Pharmaceutical Excipients, Second Edition, 1994, pp. 285-286, 633.

Walden M., et al., "The Effect of Ethanol on the Release of Opioids 30 from Oral Sustained-Release Preparations," Drug Development and Industrial Pharmacy, 2007, vol. 33 (10), pp. 1101-1111.

Wang Q., et al., "Characterization of Monocarboxylate Transport in Human Kidney HK-2 Cells," Molecular Pharmaceutics, 2006, vol. 3 (6), pp. 675-685.

Wang Q., et al., "Flavonoids Modulate Monocarboxylate Transporter-1-Mediated Transport of y-Hydroxybutyrate In Vitro and In Vivo," Drug Metabolism and Disposition, 2007, vol. 35 (2), pp. 201-208.

Wang Q., et al., "Monocarboxylate Transporter (MOT) Mediates the Transport of y-Hydroxybutyrate in Human Kidney HK-2 cells," Pharmaceutical Research, 2007, vol. 24 (6), pp. 1067-1078.

Wang Q., et al., "Pharmacokinetic Interaction between the Flavonoid Luteolin and y-Hydroxybutyrate in Rats Potential Involvement of Monocarboxylate Transporters," The American Association of Pharmaceutical Scientists, 2008, vol. 10(1), pp. 47-55.

Wang Q., et al., "The Role of Monocarboxylate Transporter 2 and 4 in the Transport of y-Hydroxybutyric Acid in Mammalian Cells," Drug Metabolism and Disposition, 2007, vol. 35 (8), pp. 1393-1399.

Wang Q., et al., "Transport of y-Hydroxybutyrate in Rat Kidney Membrane Vesicles: Role of Monocarboxylate Transporters," Journal of Pharmacology and Experimental Therapeutics, 2006, vol. 318 (2), pp. 751-761.

World Health Organization, "Annex 7: Multisource (Generic) Pharmaceutical Products: Guidelines on Registration Requirements to Establish Interchangeability," WHO Expert Committee on Specifications for Pharmaceutical Preparations, Fortieth Report, Retrieved from URL: http://apps.who.int/prequal/infogeneral/documents/TRS937/WHOTRS937_eng.pdf#page=359, 2006, pp. 347-390.

World Health Organization (WHO), "Guidelines on Packaging for Pharmaceutical Products," WHO Technical Report Series, Annexure 9, 2002, pp. 119-156.

Xyrem: "Mean Oxybate Plasma Concentration in Healthy Volunteers," retrieved from URL: https://www.xyremhcp.com/xyrem-pharmacokinetics-adults, downloaded in Jul. 2021, 10 Pages.

Xyrem (Sodium Oxybate)., "Highlights of Prescribing Information and Full Prescribing Information," Jazz Pharmaceuticals Inc, Apr. 2015, 31 pages.

Yamada Y., et al., "Effect of Butyrolactone and Gamma-Hydroxybutyrate on the EEG and Sleep Cycle in Man," Electroencephalography and Clinical Neurophysiology, 1967, vol. 22 (6), pp. 558-562.

Zheng J., "Formulation and Analytical Development for Low-Dose Oral Drug Products," John Wiley & Sons Inc, Hoboken, New Jersey, Table 4.1, 2009, 28 pages.

Final Office Action for U.S. Appl. No. 17/484,916 dated Feb. 15, 2022, 47 Pages.

Non-Final Office Action for U.S. Appl. No. 17/322,299 dated Mar. 15, 2022, 37 pages.

Mamelak M., et al., "Treatment of Narcolepsy and Sleep Apnea with Gammahydroxybutyrate: A Clinical and Polysomnographic Case Study," Sleep, 1981, vol. 4 (1), pp. 105-111.

Mamelak M., et al., "Treatment of Narcolepsy with y-Hydroxybutyrate. A Review of Clinical and Sleep Laboratory Findings," Sleep, 1986, vol. 9 (1), pp. 285-289.

Mamelak M., "Gamma-hydroxybutyrate: An Endogenous Regulator of Energy Metabolism," Neuroscience and Biobehavioral Reviews, 1989, vol. 13 (4), pp. 187-198.

Maresova P., et al., "Treatment Cost of Narcolepsy with Cataplexy in Central Europe," Therapeutics and Clinical Risk Management, 2016, vol. 12, pp. 1709-1715.

Markman Opinion, filed Sep. 14, 2012, In the Case of *Jazz Pharmaceuticals, Inc.*, Plaintiff, v. *Roxane Laboratories, Inc.*, Defendant (United States District Court for the District of New Jersey, Civil 10-6108 ES, 43 pages.

Martinez-Orozco F.J., et al., "Comorbidity of Narcolepsy Type 1 With Autoimmune Diseases and Other Immunopathological Disorders: A Case-Control Study," Journal of Clinical Medicine Research, 2016, vol. 8 (7), pp. 495-505.

Mason P.E., et al., "Gamma Hydroxybutyric Acid (GHB) Intoxication," Academic Emergency Medicine, 2002, vol. 9 (7), pp. 730-739.

Mazarr-Proo S., et al., "Distribution of GHB in Tissues and Fluids Following a Fatal Overdose," Journal of Analytical Toxicology, 2005, vol. 29 (5), pp. 398-400.

Medicines for Children, "Oral Rehydration Salts," Leaflet information by Neonatal and Paediatric Pharmacists Group (NPPG), Retrieved from URL: https://www.medicinesforchildren.org.uk/oral-rehydration-salts, published Jul. 25, 2013, 3 pages.

Mesmer, et al., "Determination of Gamma-Hydroxybutyrate (GHB) and Gamma-Butyrolactone (GBL) by HPLC/UV-VIS Spectrophotometry and HPLC/Thermospray Mass Spectrometry," Journal of Forensic Sciences, 1998, vol. 43 (3), pp. 489-492.

Moldofsky H., "A Chronobiologic Theory of Fibromyalgia," Journal of Musculoskeletal Pain, 1993, vol. 1 (1), pp. 49-59.

Moldofsky H., et al., "Muskuloskeletal Symptoms and Non-REM Sleep Disturbance in Patients with 'Fibrositis Syndrome' and Healthy Subjects," Psychosomatic Medicine, Jul.-Aug. 1975, vol. 37 (4), pp. 341-351.

Moresco M., et al., "Pharmacogenetics and Treatment Response in Narcolepsy Type 1: Relevance of the Polymorphisms of the Drug Transporter Gene ABCB1," Clinical Neuropharmacology, 2016, vol. 39 (1), pp. 18-23.

Morgenthaler T.I., "Practice Parameters for the Treatment of Narcolepsy and other Hypersomnias of Central Origin," Sleep, 2007, vol. 30 (12), 16 pages.

Morris M.E., et al., "Overview of the Proton-coupled MCT (SLC16A) Family of Transporters: Characterization, Function and Role in the Transport of the Drug of Abuse Y-Hydroxybutyric Acid," The American Association of Pharmaceutical Scientists, 2008, vol. 10 (2), pp. 311-321.

Morris M.E., et al., "Renal Clearance of y-Hydroxybutyric Acid in Rats: Increasing Renal Elimination as a Detoxification Strategy," Journal of Pharmacology and Experimental Therapeutics, 2005, vol. 313 (3), pp. 1194-1202.

Morrison R.T., et al., "Organic Chemistry," 3rd Edition, 1973, pp. 672-677.

Morse B.L., et al., "Effects of Monocarboxylate Transporter Inhibition on the Oral Toxicokinetics/Toxicodynamics of y-Hydroxybutyrate and y-Butyrolactone," The Journal of Pharmacology and Experimental Therapeutics, 2013, vol. 345, pp. 102-110.

Mellore A., et al., "Narcolepsy and Influenza Vaccination—the Inappropriate Awakening of Immunity," Annals of Translational Medicine, 2016, vol. 4 (29), pp. 1-6.

Nema S., et al., "Excipients and Their Use in Injectable Products," PDA Journal of Pharmaceutical Science and Technology, Jul.-Aug. 1997, vol. 51 (4), pp. 166-171.

Neuman A., "GHB's Path to Legitimacy: An Administrative and Legislative History of Xyrem," Harvard Law School, Class of 2005, Food and Drug Law, Winter Term 2004, Professor Peter Barton Hutt, Apr. 2004, pp. 1-39.

Non Final Office Action for U.S. Appl. No. 16/223,940, dated Apr. 15, 2020, 22 pages.

Non-Final Office Action for U.S. Appl. No. 15/655,924, dated May 3, 2018, 15 pages.

Non-Final Office action for U.S. Appl. No. 16/281,235, dated Jan. 24, 2020, 13 pages.

Non-Final Office Action for U.S. Appl. No. 16/419,516, dated Jul. 9, 2020, 11 pages.

Non-Final Office Action for U.S. Appl. No. 16/420,321, dated Aug. 26, 2020, 21 pages.

Non-Final Office Action for U.S. Appl. No. 16/431,219, dated Aug. 26, 2020, 14 pages.

(56) References Cited

OTHER PUBLICATIONS

Non-Final Office Action for U.S. Appl. No. 16/527,633, dated Feb. 18, 2021, 21 pages.
Non-Final Office Action for U.S. Appl. No. 16/984,645, dated Jul. 7, 2021, 22 pages.
Non-Final Office Action for U.S. Appl. No. 16/984,645, dated Nov. 23, 2020, 18 pages.
Non-Final Office Action for U.S. Appl. No. 16/987,510, dated Dec. 1, 2020, 11 pages.
Non-Final Office Action for U.S. Appl. No. 16/987,515, dated Dec. 24, 2020, 19 pages.
Non-Final Office Action for U.S. Appl. No. 17/322,299, dated Jul. 21, 2021, 18 pages.
Notice of Allowance for Japanese Application No. 2019-503463, dated Feb. 28, 2020, 6 pages.
Notice of Allowance for U.S. Appl. No. 16/419,616, dated Dec. 10, 2020, 8 pages.
Notice of Allowance for U.S. Appl. No. 16/420,321, dated Dec. 15, 2020, 8 pages.
Notification of Issue for U.S. Appl. No. 16/281,235, dated Aug. 11, 2020, filed May 29, 2000, 1 Page.
Office Action for Canada Application No. 3,028,878, dated Feb. 18, 2020, 3 pages.
Office Action for Japanese Patent Application No. 2020-055505, dated Mar. 12, 2020, 9 Pages.
Ohta K.M., et al., "Development of a Simple Method for the Preparation of a Silica Gel Based Controlled Delivery System With a High Drug Content," European Journal of Pharmaceutical Sciences, 2005, vol. 26 (1), pp. 87-96.
Okun M.S., et al., "GHB: An Important Pharmacologic and Clinical Update," Journal of Pharmaceutical Sciences, 2001, vol. 4 (2), pp. 167-175.
Ondo W.G., et al., "Sodium Oxybate for Excessive Daytime Sleepiness in Parkinson's Disease: An Open-Lable Polysomnographic Study," Arch Neural, Oct. 2008, vol. 65 (10), pp. 1337-1340.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES).
Outlaw W.M., et al., "Dyspepsia and its Overlap with Irritable Bowel Syndrome," Current Gastroenterology Reports, 2006, vol. 8 (4), pp. 266-272.
Palatini P., et al., "Dose Dependent Absorption and Elimination of Gamma-Hydroxybutyric Acid in Healthy Volunteers," European Journal of Clinical Pharmacology, 1993, vol. 45 (4), pp. 353-356.
Palatini P., et al., "Dose-Dependent Absorption and Elimination of Gamma-Hydroxybutyric Acid in Healthy Volunteers," European Journal of Clinical Pharmacology, 1993, vol. 45, pp. 353-356.
Pardi D., et al., "γ-Hydroxybutyrate/Sodium Oxybate; Neurobiology, and Impact on Sleep and Wakefulness," Central Nervous System Drugs, 2006, vol. 20 (12), pp. 993-1018.
Parmar A., et al., "Clinical Characteristics of Cataplectic Attacks in Type 1 Narcolepsy," Current Neurology and Neuroscience Reports, 2020, vol. 20 (38), 9 pages.
Patil P., et al., "A Review on Ionotropic Gelation Method: Novel Approach for Controlled Gastroretentive Gelispheres," International Journal of Pharmacy and Pharmaceutical Sciences, 2012, vol. 4, Suppl. 4, pp. 27-32.
"Phospholine Iodide," Physicians Desk Reference, 50th Edition, 1996, p. 2784.
Puguan J.M.C., et al., "Diffusion Characteristics of Different Molecular Weight Solutes in Ca-Alginate Gel Beads," Colloids and Surfaces A: Physicochemical and Engineering Aspects, 2015, vol. 469, pp. 158-165.
Raybon J.J., et al., "Pharmacokinetics and Pharmacodynamics of γ-Hydroxybutyric Acid during Tolerance in Rats: Effects on Extracellular Dopamine," The Journal of Pharmacology and Experimental Therapeutics, 2007, vol. 320 (3), pp. 1252-1260.
Raymond C.R., "Polymethacrylates," Handbook of Pharmaceutical Excipients, Fifth Edition, Pharmaceutical Press, London, 2006, pp. 553-560.
Ritzhaupt A., et al., "The Characterization of Butyrate Transport across Pig and Human Colonic Luminal Membrane," Journal of Physiology, 1998, vol. 507 (3), pp. 819-830.
Roth R.H., et al., "γ-Butyrolactone and γ-Hydroxybutyric Acid-I, Distribution and Metabolism," Biochemical Pharmacology, 1966, vol. 15 (9), pp. 1333-1348.
Roth R.H., et al., "γ-Butyrolactone and γ-Hydroxybutyric Acid-II, The Pharmacologically Active Form," International Journal of Neuropharmacology, 1966, vol. 5 (6), pp. 421-428.
Roth T., et al., "Effect of Sodium Oxybate on Disrupted Night Time Sleep in Patients with Narcolepsy," Journal of Sleep Research, 2017, vol. 26, pp. 407-414.
Roxane Laboratories Inc., "Answer, Affirmative Defenses and Counterclaims to Plaintiff's Complaint," dated Jun. 1, 2011, 12 pages.
Roxane Laboratories Inc.,"Answer, Affirmative Defenses and Counterclaims to Plaintiff's Complaint," dated Mar. 9, 2011, 13 pages.
Roxane Laboratories Inc., "Answer, Affirmative Defenses and Counterclaims to Plaintiff's Complaint," dated Nov. 9, 2012, 18 pages.
Roxane Laboratories Inc., "Answer, Affirmative Defenses and Counterclaims to Plaintiff's Complaint," dated Dec. 29, 2010, 21 pages.
Roxane Laboratories Inc., "Answer and Affirmative Defenses to Plaintiff's Complaint," dated Jan. 4, 2013, 8 pages.
Roxane Laboratories Inc., "Intitial Invalidity and Noninfringement Contentions Pursuant to Local Patent Rule 3.6," dated Apr. 14, 2011, 23 pages.
Rubbens J., et al., "Gastric and Duodenal Ethanol Concentrations after Intake of Alcoholic Beverages in Postprandial Conditions," Molecular Pharmaceutics, 2017, vol. 14 (12), pp. 4202-4208.
Russell I.J., et al., "Sodium Oxybate Relieves Pain and Improves Function in Fibromyalgia Syndrome," Arthritis & Rheumatism, Jan. 2009, vol. 60 (1), pp. 299-309.
Russell J., et al., "Sodium Oxybate Reduces Pain, Fatigue, and Sleep Disturbance and Improves Functionality in Fibromyalgia: Results from a 14-week, Randomized, Double-Blind, Placebo-Controlled Study," Pain, 2011, vol. 152 (5), pp. 1007-1017.
Russell J., et al., "Sodium Oxybate Relieves Pain and Improves Function in Fibromyalgia Syndrome. A Randomized, Double-Blind, Placebo-Controlled, Multicenter Clinical Trial," Arthritis & Rheumatism, 2009, vol. 60 (1), pp. 299-309.
Scammell T.E., "Narcolepsy," The New England Journal of Medicine, vol. 373 (27), Dec. 31, 2015, 9 pages.
Scharf M.B., et al., "Effect of Gamma-Hydroxybutyrate on Pain, Fatigue, and the Alpha Sleep Anomaly in Patients with Fibromyalgia Preliminary Report," 1998, Journal of Rheumatology, 1998, vol. 25 (10), pp. 1986-1990.
Scharf M.B., et al., "GHB-New Hope for Narcoleptics?," Biol Psychiatry, 1989, vol. 26 (4), pp. 329-330.
Scharf M.B., et al., "Pharmacokinetics of Gammahydroxybutyrate (GHB) in Narcoleptic Patients," Sleep, 1998, vol. 21 (5), pp. 507-514.
Scharf M.B., et al., "The Effects of Sodium Oxybate on Clinical Symptoms and Sleep Patterns in Patients with Fibromyalgia," Journal of Rheumatology, May 2003, vol. 30 (5) pp. 1070-1074.
Scharf M.B., "The Effects and Effectiveness of γ-Hydroxybutyrate in Patients with Narcolepsy," Journal of Clinical Psychiatry, Jun. 1985, vol. 46 (6), pp. 222-225.
Schie M.K.M.V., et al., "Improved Vigilance after Sodium Oxybate Treatment in Narcolepsy: A Comparison between In-Field and In-Laboratory Measurements," Journal of Sleep Research, 2016, vol. 25, pp. 486-496.
Scrima L., et al., "Effect of Gamma-Hydroxybutyrate on a Patient with Obstructive Sleep Apnea," Sleep Research, 1987, vol. 16, p. 137.
Scrima L., et al., "Effect of High Altitude on a Patient with Obstructive Sleep Apnea," Sleep Research, 1987, vol. 16, p. 427.
Scrima L., et al., "Efficacy of Gamma-Hydroxybutyrate Versus Placebo in Treating Narcolepsy—Cataplexy: Double-Blind Subjective Measures," Biological Psychiatry, 1989, vol. 26 (4), pp. 331-343.
Scrima L., et al., "Gamma-Hydroxybutyrate Effects on Cataplexy and Sleep Attacks in Narcoleptics," Sleep Research, 1987, vol. 16, p. 134.

(56) References Cited

OTHER PUBLICATIONS

Scrima L., et al., "Narcolepsy," The New England Journal of Medicine, Jan. 24, 1991, vol. 324 (4), pp. 270-272.
Scrima L., et al., "The Effects of y-Hydroxybutyrate on the Sleep of Narcolepsy Patients: A Double-Blind Study," Sleep, 1990, vol. 13 (6), pp. 479-490.
Second Office Action for Canadian Patent Application No. 3028878, dated Apr. 1, 2021, 4 Pages.
Second Office Action for Chinese Patent Application No. 201780057633, dated Jun. 30, 2021, 12 Pages.
Seno M., et al., "The Rheological Behaviour of Suspensions of Ion-exchange Resin Particles," Bulletin of the Chemical Society of Japan, Apr. 1966, vol. 39 (4), pp. 776-778.
Series F., et al., "Effects of Enhancing Slow-Wave Sleep by Gamma-Hydroxybutyrate on Obstructive Sleep Apnea," The American Review of Respiratory Disease, Jun. 1992, vol. 145 (6), pp. 1378-1383.
Shah V.P., et al., "In Vitro Dissolution Profile Comparison—Statistics and Analysis of the Similarity Factor, f2," Pharmaceutical Research, 1998, vol. 15 (6), pp. 889-896.
Singh I., et al., "Ion Exchange Resins: Drug Delivery and Therapeutic Applications," Fabad Journal of Pharmaceutical Sciences, 2007, vol. 32, pp. 91-100.
Snead O.C., et al., "Ontogeny of y-Hydroxybutyric Acid. I. Regional Concentration in Developing Rat, Monkey and Human Brain," Brain Research, 1981, vol. 227 (4), pp. 579-589.
Snead O.C., "y-Hydroxybutyrate Model of Generalized Absence Seizures: Further Characterization and Comparison with Other Absence Models," Epilepsia, 1988, vol. 29 (4), pp. 361-368.
Srikanth M.V., et al., "Ion-Exchange Resins as Controlled Drug Delivery Carriers," Journal of Scientific Research, 2010, vol. 2 (3), pp. 597-611.
Stock G., "Increase in Brain Dopamine After Axotomy or Treatment With Gamma Hydroxybutyric Acid Due to Elimination of the Nerve Impulse Flow," Naunyn-Schmiedeberg's Arch. Pharmacol, 1973, vol. 278 (4), pp. 347-361.
Strand M.C., et al., "Driving Under the Influence of Non-Alcohol Drugs—An Update. Part II: Experimental Studies," Forensic Science Review, 2016, vol. 28 (2), pp. 100-101.
Strong A.J., "y-Hydroxybutyric Acid and Intracranial Pressure," The Lancet, Jun. 9, 1984, vol. 1 (8389), p. 1304.
Suner S., et al., "Pediatric Gamma Hydroxybutyrate Intoxication," Academic Emergency Medicine, 1997, vol. 4 (11), pp. 1041-1045.
Susta M., et al., "Emotion Stimulus Processing in Narcolepsy with Cataplexy," Journal of Sleep Research, 2017, vol. 26, pp. 30-37.
Takahara J., et al., "Stimulatory Effects of Gamma-Hydroxybutyric Acid on Growth Hormone and Prolactin Release in Humans," Journal of Clinical Endocrinology & Metabolism, 1977, vol. 44 (5), pp. 1014-1017.
Takka S., et al., "Evaluation of Chitosan/Alginate Beads Using Experimental Design: Formulation and in Vitro Characterization," AAPS Pharm Sci Tech, Mar. 2010, vol. 11 (1), pp. 460-466.
"Taxotere," Physicians Desk Reference, 51st Edition, 1997, pp. 2204-2207.
Thai D., et al., "GHB and Ethanol Effects and Interactions in Humans," Journal of Clinical Psychopharmacology, 2006, vol. 26 (5), pp. 524-529.
Thorpy M., et al., "Reducing the Clinical and Socioeconomic Burden of Narcolepsy by Earlier Diagnosis and Effective Treatment," Sleep Medicine Clinics, 2017, vol. 12 (1), pp. 61-71.
Thorpy M.J., "Recently Approved and Upcoming Treatments for Narcolepsy," CNS Drugs, 2020, vol. 34, pp. 9-27.
Cook S.I., et al., "Review Article: Short Chain Fatty Acids in Health and Disease," Alimentary Pharmacology & Therapeutics, 1998, vol. 12, pp. 499-507.
Cremaschi R.C., et al., "Narcolepsy Type 1 and Type 2—A 10-Year Follow-up: Body Mass Index and Comorbidities," Sleep Medicine, 2017, vol. 32, pp. 285-286.
Dauvilliers Y., et al., "Narcolepsy with Cataplexy," The Lancet, 2007, vol. 369, pp. 499-511.
Dauvilliers Y., et al., "Vitamin D Deficiency in Type 1 Narcolepsy: A Reappraisal," Sleep Medicine, 2017, vol. 29, pp. 1-6.
Davis G.R., et al., "Active Chloride Secretion in the Normal Human Jejunum," Journal of Clinical Investigation, Dec. 1980, vol. 66 (6), pp. 1326-1333.
Donjacour C.E.H.M., et al., "Sodium Oxybate Increases Prolactin Secretion in Narcolepsy Patients and Healthy Controls," European Journal of Endocrinology, 2011, vol. 164, pp. 363-370.
Drakatos P., et al., "Sleep-Stage Sequencing of Sleep-Onset REM Periods in MSLT Predicts Treatment Response n Patients with Narcolepsy," Journal of Sleep Research, 2016, vol. 25, pp. 203-210.
Dye T.J., et al., "Epidemiology and Pathophysiology of Childhood Narcolepsy," Paediatric Respiratory Reviews, 2018, vol. 25, pp. 14-18.
FDA Guideline, Revised Guidance for Industry on Bioavailability and Bioequivalence Studies for Orally Administered Drug Products—General Considerations; Availability, Federal Register, Mar. 19, 2003, vol. 68 (53), 1 page.
Felmlee M.A., et al., "Concentration-Effect Relationships for the Drug of Abuse y-Hydroxybutyric Acid," The Journal of Pharmacology and Experimental Therapeutics, 2010, vol. 333 (3), pp. 764-771.
Felmlee M.A., et al., "Mechanistic Toxicokinetic Model for y-Hydroxybutyric Acid: Inhibition of Active Renal Reabsorption as a Potential Therapeutic Strategy," The American Association of Pharmaceutical Scientists, 2010, vol. 12(3), pp. 407-416.
Ferrara S.D., et al., "Pharmacokinetics of y-Hydroxybutyric Acid in Alcohol Dependent Patients After Single and Repeated Oral Doses," British Journal of Clinical Pharmacology, 1992, vol. 34, pp. 231-235.
Ferrara S.D., et al., "Therapeutic Gamma-Hydroxybutyric Acid Monitoring in Plasma and Urine by Gas Chromatographymass Spectrometry," Journal of Pharmaceutical & Biomedical Analysis, 1993, vol. 11 (6), pp. 483-487.
Ferris T.J., et al., "Synthesis, Characterisation and Detection of Gamma-Hydroxybutyrate Salts," Forensic Science International, 2012, vol. 216, pp. 158-162.
Final Office Action for U.S. Appl. No. 16/223,940, dated Sep. 10, 2020, 22 pages.
Final Office Action for U.S. Appl. No. 16/281,235, dated Apr. 15, 2020, 6 pages.
Final Office Action for U.S. Appl. No. 16/419,516, dated Feb. 24, 2021, 13 pages.
Final Office Action for U.S. Appl. No. 16/419,616, dated Aug. 19, 2020, 13 pages.
Final Office Action for U.S. Appl. No. 16/419,616, dated Nov. 24, 2020, 10 pages.
Final Office Action for U.S. Appl. No. 16/420,321, dated Nov. 24, 2020, 11 pages.
Final Office Action for U.S. Appl. No. 16/431,219, dated Feb. 24, 2021, 11 pages.
Final Office Action for U.S. Appl. No. 16/984,645, dated Feb. 24, 2021, 20 pages.
Final Office Action for U.S. Appl. No. 16/987,515, dated Apr. 21, 2021, 78 pages.
First Office Action for Brazilian Patent Application No. 112019000848.9, dated Jun. 29, 2021, 5 Pages.
First Office Action for Chinese Patent Application No. 201780057633, dated Oct. 21, 2020, 14 Pages.
First Office Action for European Patent Application No. 18842651.4, dated May 18, 2021, 5 Pages.
Flamel: "Flamel's Drug Delivery Platforms," publication date: Jun. 2015, pp. 1-43.
Flores N.M., et al., "The Humanistic and Economic Burden of Narcolepsy," Journal of Clinical Sleep Medicine, 2016, vol. 12 (3), pp. 401-407.
Food and Drug Administration (FDA), U.S. Department of Health and Human Services, Center for Drug Evaluation and Research (CDER), Center for Biologies Evaluation and Research (CBER), "Guidance for Industry Container Closure Systems for Packaging Human Drugs and Biologies, Chemistry, Manufacturing, And Controls Documentation," May 1999, 56 pages.

(56) References Cited

OTHER PUBLICATIONS

"Food and Drug Administration, HHS," 21 C.F.R., Part 184, 1998, pp. 441-535.
Franco P., et al., "High Bicarbonate Levels in Narcoleptic Children," Journal of Sleep Research, 2016, vol. 25, pp. 194-202.
Frucht S.J., et al., "A Pilot Tolerability and Efficacy Trial of Sodium Oxybate in Ethanol-Responsive Movement Disorders," Movement Disorders, 2005, vol. 20 (10), pp. 1330-1337.
Frucht S.J., et al., "A Single-Blind, Open-Label Trial of Sodium Oxybate for Myoclonus and Essential Tremor," Neurology, 2005, vol. 65 (12), pp. 1967-1970.
Fuller D.E., et al., "The Xyrem Risk Management Program," Drug Safety, 2004, vol. 27 (5), pp. 293-306.
Fung H., et al., "Pharmacokinetics of 1,4-Butanediol in Rats: Bioactivation to y-Hydroxybutyric Acid, Interaction with Ethanol, and Oral Bioavailability," The American Association of Pharmaceutical Scientists, 2008, vol. 10 (1), pp. 56-69.
Gadroen K., et al., "Patterns of Spontaneous Reports on Narcolepsy following Administration of Pandemic Influenza Vaccine; A Case Series of Individual Case Safety Reports in Eudravigilance," Vaccine, 2016, vol. 34, pp. 4892-4897.
Gallimberti L., et al., "Clinical Efficacy of Gamma-Hydroxybutyric Acid in Treatment of Opiate Withdrawal," Eur Arch Psychiatry Clin Neurosci, 1994, vol. 244 (3), pp. 113-114.
Gallimberti L., et al., "Gamma-Hydroxybutyric Acid for Treatment of Opiate Withdrawal Syndrome," Neuropsychopharmacology, 1993, vol. 9 (1), pp. 77-81.
Gallimberti L., "Gamma-hydroxybutyric Acid for Treatment of Alcohol Withdrawal Syndrome," The Lancet, Sep. 30, 1989, vol. 2 (8666), pp. 787-789.
Gallimberti L., "Gamma-Hydroxybutyric Acid in the Treatment of Alcohol Dependence: A Double Blind Study," Alcoholism: Clinical and Experimental Research, Jul./Aug. 1992, vol. 16 (4), pp. 673-676.
Gennaro A.R., "Oral Solid Dosage Forms," 20th Edition, Chapter 45, The Science and Practice of Pharmacy, 2000, pp. 858-893.
Gennaro A.R., "Remington: The Science and Practice of Pharmacy," 20th Edition, 2000, pp. 860-863.
George C.F.P., et al., "A 2-week, Polysomnographic, Safety Study of Sodium Oxybate in Obstructive Sleep Apnea Syndrome," Sleep Breath, 2011, vol. 15, pp. 13-20.
Gerra G., et al., "Flumazenil Effects on Growth Hormone Response to Gamma-Hydroxybutyric Acid," International Clinical Psychopharmacology, 1994, vol. 9, pp. 211-215.
Gessa G.L., et al., "Gamma-Hydroxybutyric acid (GHB) for Treatment of Ethanol Dependence," European Neuropsychopharmacology, 1993, vol. 3 (3), pp. 224-225.
Gessa G.L., et al., "Gamma-Hydroxybutyric Acid in the Treatment of Alcohol Dependence," Clinical Neuropharmacology, 1992, vol. 15, Suppl. 1, Pt. A, pp. 303A-304A.
Gill R.K., et al., "Expression and Membrane Localization of MCT Isoforms along the Length of the Human Intestine," American Journal of Physiology—Cell Physiology, 2005, vol. 289, pp. C846-C852.
Grenier V., et al., "Enzymatic Assay for GHB Determination in Forensic Matrices," Journal of Analytical Toxicology, 2012, vol. 36, pp. 523-528.
Grove-White I.G., et al., "Critical Flicker Frequency after Small Doses of Methohexitone, Diazepam and Sodium 4-Hydroxybutyrate," British Journal of Anaesthesia, Feb. 1971, vol. 43 (2), pp. 110-112.
Grove-White I.G., et al., "Effect of Methohexitone, Diazepam and Sodium 4-Hydroxybutyrate on Short-Term Memory," British Journal of Anaesthesia, Feb. 1971, vol. 43 (2), pp. 113-116.
Chemical Book, CAS DataBase List, Ethyl cellulose, downloaded in Oct. 2021, 5 Pages, (Year: 2021).
Fallingborg J., "Intraluminal pH of the Human Gastrointestinal Tract," Danish Medical Bulletin, Jun. 1999, vol. 46 (3), pp. 183-196.
Final Office Action for U.S. Appl. No. 17/322,299, dated Oct. 25, 2021, 28 pages.
Jefferies, Flamel Technologies SA publication, https://www.jefferies.com/CMSFiles/Jefferies.com/files/Flamel.pdf, May 1, 2015, 1 Page.
Martin John., "Capsule Endoscopy: How Long Does it Take to Pass," Pill Cam, https://www.topdoctors.eo.uk/medical-articles/capsule-endoscopy-how-long-does-it-take-to-pass, Oct. 5, 2019, 4 Pages.
Momenzadeh S., et al., "Evaluation of in Vivo Transfection Efficiency of Eudragit Coated Nanoparticles of Chitosan-DNA: A pH-sensitive System Prepared for Oral DNA Delivery," Iran Red Crescent Med J, Apr. 2015, vol. 17, No. 4, DOI: 10.5812/ircmj.16761, 7 Pages.
Non Final Office Action for U.S. Appl. No. 16/804,966, dated Dec. 10, 2021, 13 pages.
Non Final Office Action for U.S. Appl. No. 17/484,916, dated Nov. 10, 2021, 34 pages.
Notice of Allowance for U.S. Appl. No. 15/655,924, dated Feb. 7, 2019, 8 pages.
Notice of Allowance for U.S. Appl. No. 15/655,924, dated Dec. 11, 2018, 6 pages.
Notice of Allowance for U.S. Appl. No. 15/655,924, dated Nov. 13, 2018, 11 pages.
Notice of Allowance for U.S. Appl. No. 16/281,235, dated May 1, 2020, 8 pages.
Notice of Allowance for U.S. Appl. No. 16/281,235, dated Jun. 26, 2020, 8 pages.
Noticeof Allowance for U.S. Appl. No. 16/419,516, dated Mar. 10, 2021, 8 pages.
Notice of Allowance for U.S. Appl. No. 16/527,633, dated Jun. 9, 2021, 11 pages.
Notice of Allowance for U.S. Appl. No. 16/987,510, dated Jan. 13, 2021, 8 pages.
Thorpy M.J., "Update on Therapy for Narcolepsy" Current Treatment Options in Neurology, 2015, 17(20), pp. 1-12.
Office Action for Chinese Patent Application No. 201880082447.4, dated May 23, 2022, 13 Pages.
Final Office Action for U.S. Appl. No. 17/666,205 dated Jun. 29, 2022, 15 Pages.
Non Final Office Action for U.S. Appl. No. 17/497,366 dated Aug. 1, 2022, 33 pages.
Office Action for Canadian Patent Application No. 3,084,120 dated Jul. 25, 2022, 3 pages.
Anonymous., "How Much Protein Is In Your Cup of Milk?", Retrieved from Internet URL: https://milklife.com/articles/nutrition/how-much-protein-your-cup-milk, Retrieved on Aug. 30, 2022, 2 pages.
Black J., et al., "Sodium Oxybate Improves Excessive Daytime Sleepiness in Narcolepsy," Sleep, Jul. 2006, vol. 29, No. 7, pp. 939-946.
Guiraud J., et al., "Treating Alcohol Dependence with an Abuse and Misuse Deterrent Formulation of Sodium Oxybate: Results of a Randomised, Double-Blind, Placebo-Controlled Study," European Neuropsychopharmacology, vol. 52, Retrieved from Internet URL: www.elsevier.com/locate/euroneuro, accepted on Jun. 7, 2021, pp. 18-30.
Jazz Pharmaceuticals, Inc., "XYREM® (Sodium Oxybate) Oral Solution, CIII," Highlights of Prescribing Information, Revised, Sep. 2020, 35 pages.
Jazz Pharmaceuticals, Inc., "XYWAV® (Calcium, Magnesium, Potassium, and Sodium Oxybates) Oral Solution, CIII," Highlights of Prescribing Information, Aug. 2021, 40 pages.
Maruyama T., et al., "The Pathogenesis of Narcolepsy, Current Treatments and Prospective Therapeutic Targets," Expert Opinion on Orphan Drugs, 2016, vol. 4, No. 1, pp. 63-82.
Notice of Allowance and Fee(s) due for U.S. Appl. No. 17/497,366 dated Sep. 20, 2022, 10 pages.
Office Action for Australian Application No. 2017300845, dated Nov. 2, 2022, 3 pages.
Office Action for Brazilian Application No. 1120201112417 dated Sep. 1, 2022, 5 pages.
Office Action for Canadian Application No. 3,126,493 dated Aug. 23, 2022, 6 pages.
Office Action for European Application No. 18842651.4 dated Aug. 2, 2022, 5 pages.

(56) References Cited

OTHER PUBLICATIONS

Office Action for Japanese Application No. 2020-529210, dated Oct. 27, 2022, 7 pages.
Office Action for U.S. Appl. No. 17/497,393, dated Oct. 20, 2022, 18 pages.
Office Action for U.S. Appl. No. 17/530,096, dated Nov. 22, 2022, 20 pages.
Office Action for U.S. Appl. No. 17/666,192 dated Sep. 6, 2022, 15 pages.
Office Action for U.S. Appl. No. 17/666,201 dated Aug. 26, 2022, 18 pages.
Thorpy M.J., "Update on Therapy for Narcolepsy," Current Treatment Options in Neurology, vol. 17, No. 20, May 2015, pp. 20-32.
U.S. Department of Health and Human Services., "Guidance for Industry, Food-Effect Bioavailability and Fed Bioequivalence Studies," Food and Drug Administration, Center for Drug Evaluation and Research, Dec. 2002, BP, 12 pages.

\* cited by examiner

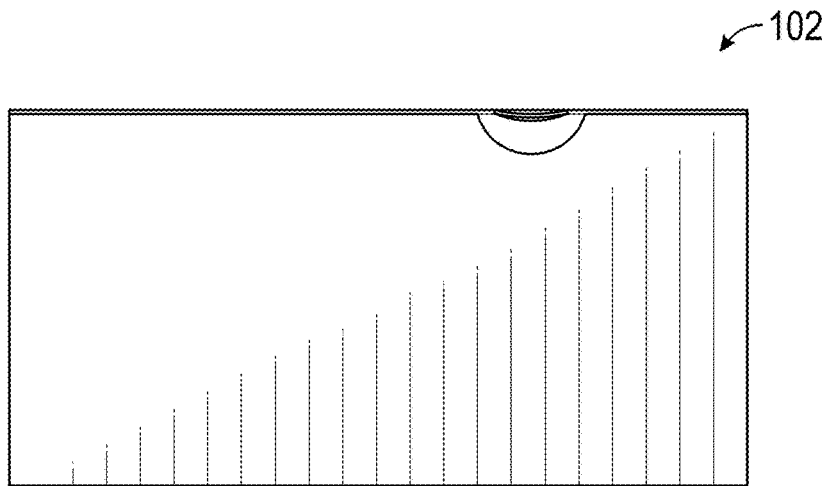
FIG. 92
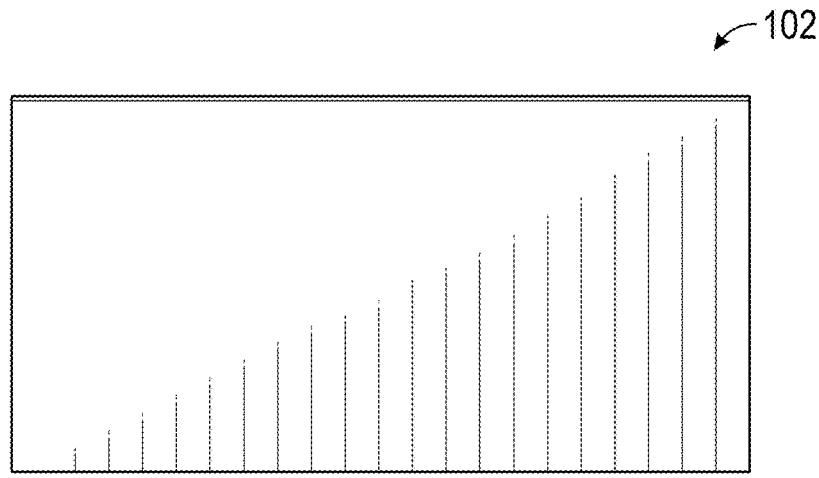
FIG. 93
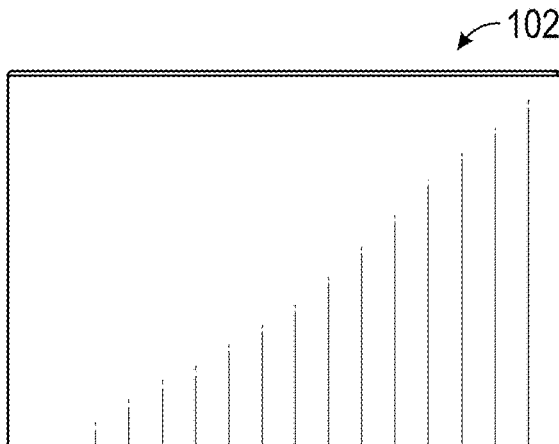 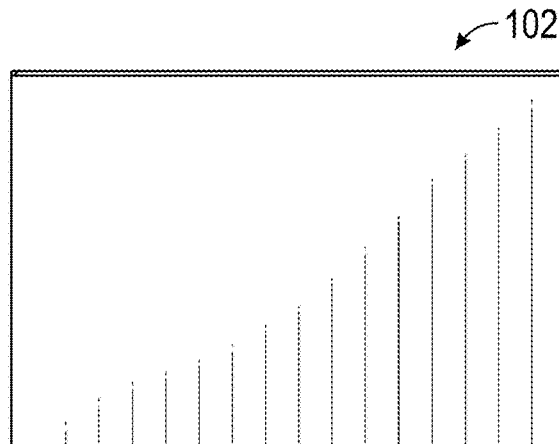
FIG. 94  FIG. 95

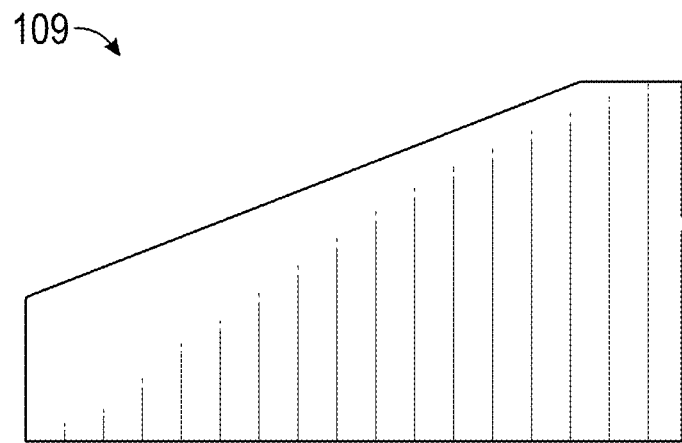
FIG. 102
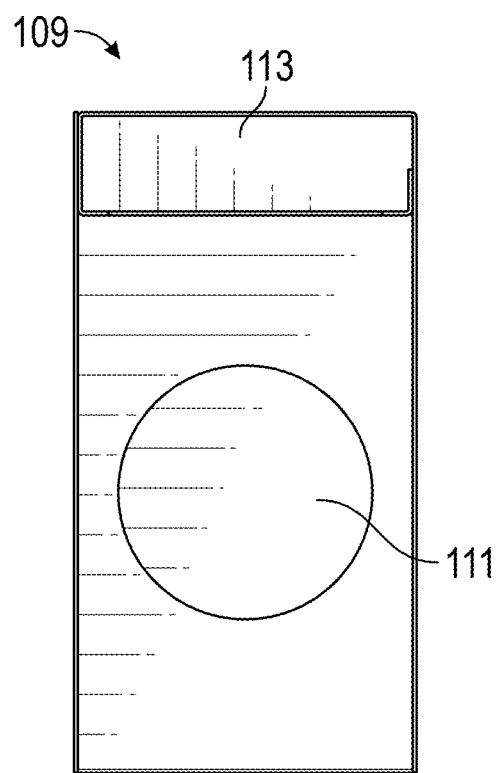 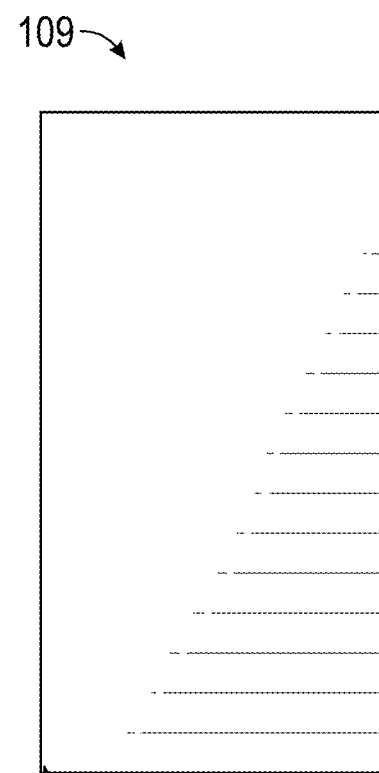
FIG. 103     FIG. 104

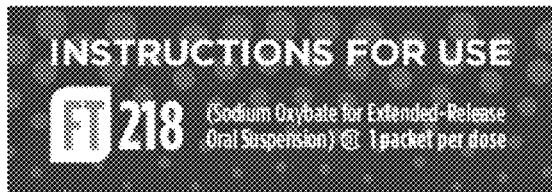

INSTRUCTIONS FOR USE
FT218 (Sodium Oxybate for Extended-Release Oral Suspension) — 1 packet per dose This "Instructions for Use" contains information on how to take FT218. Make sure that you read, understand, and follow the Instructions for Use before taking FT218 and each time you get a refill. There may be new information.

This information does not take the place of talking to your doctor about your medical condition or your treatment. If you have questions, please speak with your doctor.

Important information when taking FT218

- Take only one nightly dose packet per day at bedtime.
- Avoid getting out of your bed after taking FT218.
- Medications that cause sleepiness should not be used while taking FT218.
- DO NOT take FT218 if pregnant or nursing.
- DO NOT use FT218 with alcohol.
- DO NOT drive or operate heavy machinery within 6 hours of taking FT218.

How should I store FT218?

- Store FT218 and all medicines out of the reach of children.
- Store FT218 at room temperature, between 59°F–86°F (15°C–30°C).
- Keep FT218 away from fire.
- Store FT218 in a clean and dry place.

Before using a new FT218 kit

- Check the tamper-evident seal on the carton lid to make sure it is not missing or broken.
  - DO NOT use the FT218 kit if the tamper-evident seal is missing or broken.
- Check the expiration date (EXP) on the FT218 kit.
  - DO NOT use the FT218 kit after the expiration date (EXP) on the label has passed.
- Open the FT218 kit by tearing the tamper-evident seal with your hands or by using a pair of scissors.

FT218 Kit

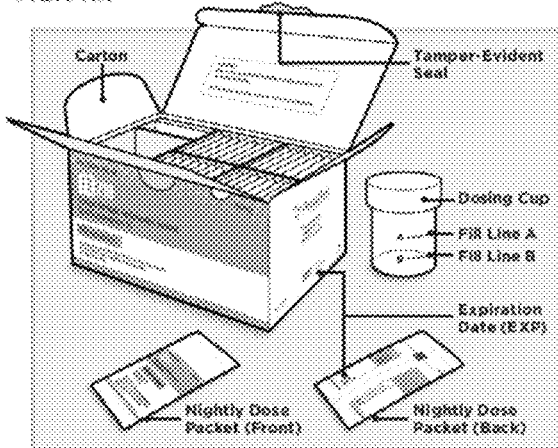

Additional supplies needed

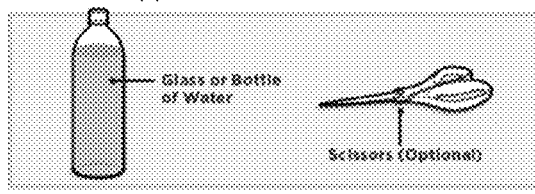

- Clean the dosing cup by rinsing it with water and letting it dry before each use.
- DO NOT use a measuring device other than the dosing cup that comes in your FT218 kit to measure and take a dose of FT218.
- Check the expiration date (EXP) on the nightly dose packet label. DO NOT use the FT218 nightly dose packet after the expiration date has passed.

IMPORTANT: Make sure to prep FT218 at bedside.

Gather the following supplies and place them on a flat surface at your bedside:

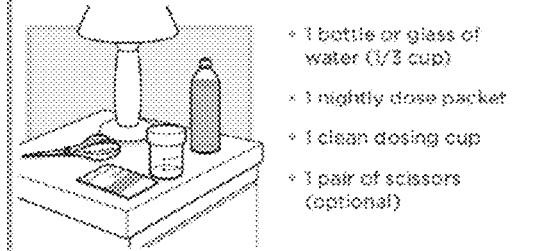

- 1 bottle or glass of water (1/3 cup)
- 1 nightly dose packet
- 1 clean dosing cup
- 1 pair of scissors (optional)

Page 1 ▶

FIG. 133B

MODIFIED RELEASE GAMMA-HYDROXYBUTYRATE FORMULATIONS HAVING IMPROVED PHARMACOKINETICS

CROSS-REFERENCE TO RELATED APPLICATIONS

This application is a continuation-in-part of U.S. application Ser. No. 17/178,117, filed Feb. 17, 2021, which is a continuation-in-part of U.S. application Ser. No. 16/527,633, filed Jul. 31, 2019, now U.S. Pat. No. 11,065,224, which is a continuation of U.S. application Ser. No. 16/281,235, filed Feb. 21, 2019, now U.S. Pat. No. 10,736,866, which is a continuation of U.S. application Ser. No. 15/655,924, filed Jul. 21, 2017, now U.S. Pat. No. 10,272,062, which claims priority to U.S. Provisional Application No. 62/365,812, filed Jul. 22, 2016, U.S. Provisional Application No. 62/399,413, filed Sep. 25, 2016, and U.S. Provisional Application No. 62/474,330, filed Mar. 21, 2017.

FIELD OF THE INVENTION

The present invention relates to modified release formulations of gamma-hydroxybutyrate having improved pharmacokinetic (PK) properties, and to therapeutic uses thereof.

BACKGROUND

Narcolepsy is a devastating disabling condition. The cardinal symptoms are excessive daytime sleepiness (EDS), cataplexy (a sudden loss of muscle tone triggered by strong emotions, seen in approximately 60% of patients), hypnogogic hallucination (HH), sleep paralysis (SP), and disturbed nocturnal sleep (DNS). Other than EDS, DNS is the most common symptom seen among narcolepsy patients.

The diagnosis of narcolepsy rests in part on clinical grounds. When narcolepsy is suspected, it is standard practice to administer an overnight polysomnogram (PSG) followed by a multiple sleep latency test (MSLT) to document the rapid eye movement (REM) abnormality that characterizes the disorder. On the MSLT a mean sleep latency less than or equal to 8 minutes and two or more sleep onset REM periods (SOREMPs) are required to confirm a diagnosis of Type 1 or Type 2 narcolepsy. It is also possible, but infrequently preferred, that narcolepsy be diagnosed by measuring hypocretin in the cerebrospinal fluid (CSF) in cases where the PSG and/or MSLT is not completed. For these cases, a hypocretin concentration of less than 110 pg/nL confirms a narcolepsy Type 1 diagnosis.

One of the major treatments for narcolepsy is sodium oxybate, a neuroactive agent with a variety of Central Nervous System (CNS) pharmacological properties. The species is present endogenously in many tissues, where it acts as a neurotransmitter on a gamma-hydroxybutyrate (GHB) receptor (GHBR), and possesses neuromodulatory properties with significant effects on dopamine and Gamma-Aminobutyric Acid (GABA). Studies have suggested that sodium oxybate improves Rapid Eye Movement Sleep (REM sleep, REMS) of narcoleptics in contrast to antidepressant drugs.

Sodium oxybate is also known as sodium 4-hydroxybutanoate, or gamma-hydroxybutyric acid sodium salt, and has the following chemical structure:

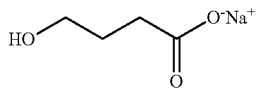

Sodium oxybate is marketed commercially in the United States as Xyrem®. The product is formulated as an immediate release liquid solution that is taken once immediately before bed, and a second time approximately 2.5 to 4 hours later, in equal doses. Sleep-onset can be dramatic and fast, and patients are advised to be sitting in bed when consuming the dose. The most commonly reported side effects are confusion, depressive syndrome, incontinence and sleep-walking.

When initiating treatment with sodium oxybate, careful titration up to an adequate level is essential both to obtain positive results and avoid adverse effects. The recommended starting dose is 4.5 g divided into 2 equal doses of 2.25 g, the first taken at bedtime and the second taken 2.5 to 4 hours later. The starting dosage can be decreased to 3.0 g/day or increased to as high as 9.0 g/day in increments of 1.5 g/day (0.75 g per dose). Two weeks are recommended between dosage adjustments to optimize reduction of daytime symptoms and minimize side effects. The ideal dose will provide an effective eight hours of sleep but, at the end of eight hours, very little of the drug will remain in the patient's bloodstream to affect the patient's wakefulness.

The requirement to take Xyrem® twice each night is a substantial inconvenience to narcolepsy patients. The patient must typically set an alarm to take the second dose, which can interrupt ongoing productive sleep. Several efforts have been made to provide a once-nightly modified release dosage form of sodium oxybate, but none has yet received approval from the United States Food and Drug Administration ("FDA") or proven effective in the clinic.

One of the biggest drawbacks of these once-nightly formulations is the reduction in bioavailability that occurs when sodium oxybate is formulated in a modified release dosage form, as measured by the blood concentration/time area under the curve ("AUC"). U.S. 2012/0076865 A1 by Allphin et al. ("Allphin"), for example, conducted two separate crossover bioavailability trials involving three separate modified release formulations and an immediate release solution, and reported the following bioavailability results:

| | $\lambda\_z$ (1 hr) | $T_{12}$ (hr) | Tmax (hr)$^a$ | Cmax (ug/ml) | AUClast (hr* ug/ml) | AUCinf (hr* ug/ml) |
|---|---|---|---|---|---|---|
| Summary of PK Parameters for Treatments A, B, C | | | | | | |
| Treatment A | | | | | | |
| N | 29 | 29 | 29 | 29 | 29 | 29 |
| Mean | 1.22 | 0.6 | 4.50 (0.5, 4.75) | 130.79 | 350.84 | 351.2 |
| SD | 0.27 | 0.13 | | 31.52 | 116.74 | 116.74 |
| CV % | 21.93 | 22.61 | | 24.1 | 33.27 | 33.24 |
| Mean | 1.19 | 0.58 | | 127.3 | 333.33 | 333.72 |
| Treatment B | | | | | | |
| N | 18 | 18 | 19 | 19 | 19 | 18 |
| Mean | 0.62 | 1.22 | 2.00 (1.50, 5.00) | 41.78 | 188.23 | 196.25 |
| SD | 0.16 | 0.40 | | 18.40 | 103.60 | 102.50 |
| CV % | 26.44 | 32.58 | | 44.03 | 5504 | 52.23 |
| Mean | 0.59 | 1.17 | | 38.46 | 163.80 | 173.33 |

-continued

| | $\lambda\_z$ (1 hr) | $T_{12}$ (hr) | Tmax (hr)$^a$ | Cmax (ug/ml) | AUClast (hr* ug/ml) | AUCinf (hr* ug/ml) |
|---|---|---|---|---|---|---|
| Treatment C | | | | | | |
| N | 19 | 19 | 19 | 19 | 19 | 19 |
| Mean | 0.74 | 0.99 | 2.50 (1.00, 5.00) | 50.49 | 221.64 | 222.60 |
| SD | 0.16 | 0.23 | | 15.83 | 106.85 | 106 80 |
| CV % | 22.25 | 22.93 | | 31.35 | 48.21 | 47.98 |
| Mean | 0.72 | 0.96 | | 48.10 | 200.08 | 201.12 |
| Summary of OK Parameters for Treatments A, D, E | | | | | | |
| Treatment A | | | | | | |
| N | 30 | 30 | 30 | 30 | 30 | 30 |
| Mean | 1.08 | 0.71 | 4.50 (0.50, 5.50) | 114.59 | 301.28 | 301.59 |
| SD | 0.31 | 0.27 | | 27.91 | 100.85 | 100.87 |
| CV% | 29.00 | 37.90 | | 24.36 | 33.47 | 33.45 |
| Mean | 1.03 | 0.67 | | 111.20 | 285.47 | 285.79 |
| Treatment D | | | | | | |
| N | 30 | 30 | 30 | 30 | 30 | 30 |
| Mean | 0.46 | 1.63 | 0.75 (0.50, 2.50) | 25.10 | 64.44 | 65.58 |
| SD | 0.14 | 0.47 | | 7.33 | 20.36 | 20.26 |
| CV % | 30.27 | 29.00 | | 29.20 | 31.60 | 30.90 |
| Mean | 0.44 | 1.56 | | 24.10 | 61.31 | 62.55 |
| Treatment E | | | | | | |
| N | 30 | 30 | 30 | 30 | 30 | 30 |
| Mean | 0.59 | 1.36 | 1.00 (0.50, 5.00) | 59.52 | 242.30 | 243.80 |
| SD | 0.20 | 0.64 | | 17.72 | 117.15 | 116.79 |
| CV % | 34.57 | 46.91 | | 29.77 | 48.35 | 47.91 |
| Mean | 0.55 | 1.25 | | 56.89 | 216.33 | 218.12 |

Treatment A: Two 3 g IR doses administered four hours apart
Treatment B: One 6 g CR dose administered at time zero (no IR component)
Treatment C: One 6 g CR dose administered at time zero (no IR component)
Treatment D: One 4 g dose including IR and CR fractions administered at time zero
Treatment E: One 8 g dose including IR and CR fractions administered at time zero As can be seen, mean $AUC_{inf}$, which measures the total exposure of the body to sodium oxybate for a given dose, was significantly less for the doses having a modified release component when compared to the immediate release doses. Mean $AUC_{inf}$ for Treatment B, which included the exact same dose of sodium oxybate as Treatment A, was only 56% of the mean $AUC_{inf}$ for Treatment A; mean $AUC_{inf}$ for Treatment C, which also included the same dose of sodium oxybate as Treatment A, was only 63% of the mean $AUC_{inf}$ for Treatment A; mean $AUC_{inf}$ for Treatment E was only 81% of the mean $AUC_{inf}$ of Treatment A, even though Treatment E dosed 2 g more of sodium oxybate than Treatment A, which, compared to same dose, represented only 61% of the mean $AUC_{inf}$ of Treatment A. Mean $AUC_{inf}$ for Treatment D was only 22% of the mean $AUC_{inf}$ of Treatment A, although Treatment D dosed 2 g less of sodium oxybate than Treatment A, which, compared to same dose, represented only 33% of the mean $AUC_{inf}$ of Treatment A. As shown in FIGS. 12 and 14 of U.S. 2012/0076865 A1, Allphin's formulations also suffered from an excess of sodium oxybate remaining in the bloodstream at 8 hours.

U.S. Pat. No. 8,193,211 to Liang et al. ("Liang") reports even lower bioavailability from his once-nightly formulations. Liang developed several enterically coated delayed release formulations of sodium oxybate, and tested these formulations in dogs alongside an immediate release formulation to compare the relative pharmacokinetics (PK) of these formulations. The results of Liang's testing are reported below:

| | Mean GHB Concentrations (ug/mL) | | | |
|---|---|---|---|---|
| | Period | | | |
| Time Point (Hr) | 1 DR1-w/Acid | 2 DR1-No Acid | 3 IR | 4 DR2 |
| 0 | 0.00 | 0.00 | 0.00 | 0.00 |
| 0.5 | 0.00 | 0.00 | 116.04 | 0.00 |
| 1 | 0.00 | 4.76 | 248.27 | 1.53 |
| 2 | 4.99 | 11.62 | 195.51 | 32.52 |
| 3 | 26.31 | 31.88 | 117.56 | 100.99 |
| 4 | 35.14 | 38.26 | 47.21 | 100.57 |
| 5 | 29.18 | 34.77 | 8.74 | 54.99 |
| 6 | 21.09 | 27.83 | 0.00 | 23.42 |
| 7 | 11.25 | 9.13 | 0.00 | 7.52 |
| 8 | 8.67 | 2.53 | 0.00 | 0.34 |
| 10 | 1.43 | 3.03 | 0.00 | 0.00 |
| 12 | 0.98 | 0.67 | 0.00 | 0.00 |
| 14 | 0.43 | 0.00 | 0.00 | 0.00 |
| Tmax (Hr) | 4.2 | 5.2 | 1.2 | 3.7 |
| Cmax (ug/mL) | 38.77 | 58.44 | 249.5 | 112.7 |
| AUClast | 134.3 | 162.6 | 601.0 | 318.4 |
| Rel BA | 22% | 27% | 100% | 53% |

DR1-w/Acid: Two 1 g DR capsules administered at time zero
DR1-No Acid: Two 1 g DR capsules administered at time zero
IR: Two 1 g IR capsules administered at time zero
DR2: Two 1 g DR capsules administered at time zero As can be seen, by encapsulating the sodium oxybate in an enteric/delayed release coating, Liang decreased the AUC of the sodium oxybate significantly. One of the formulations, DR1-w/ Acid, had a relative bioavailability of only 22% compared to the immediate release dosage form. DR2 had the greatest relative bioavailability, but still only 53% compared to the immediate release dosage form. One can easily calculate that any of the envisioned combinations of immediate release (IR) components and delayed release (DR) components as described in col. 5 lines 3 to 28 of U.S. Pat. No. 8,193,211 will not give a relative bioavailability greater than 78%.

All of these formulations are inconvenient for at least two reasons: (1) the low relative bioavailability necessitates an increase in the dose compared to current IR treatments which already require a large dose (4.5 to 9 g a day), and (2) when provided in the form of pills, a patient must swallow around 4 to 9 pills per dose, which is a serious inconvenience for the patient and potential drawback for patient compliance.

Various other techniques are known for formulating modified release dosage forms including, for example, the techniques described in U.S. Pat. No. 8,101,209 to Legrand et al. ("Legrand"). Legrand provides a system ensuring that the active ingredient is released with certainty from the modified release dosage form by means of a dual mechanism of "time-dependent" and "pH-dependent" release. Legrand did not describe any dosage forms for delivering sodium oxybate or other forms of gamma-hydroxybutyrate.

Another drawback of Xyrem® is the high level of the daily dose, generally 7.5 g or 9 g of sodium oxybate taken daily over long periods of time. This represents a very high sodium intake which is not recommended in persons with high blood pressure, risk of cardiovascular disease, stroke or coronary heart disease (See WHO. Guideline: Sodium intake for adults and children. Geneva, World Health Organization (WHO), 2012.).

Accordingly, one object of the present invention is to provide modified release formulations of gamma-hydroxybutyrate that are administered only once at bed-time with improved dissolution and pharmacokinetic profiles.

Another object of the present invention is to provide modified release formulations of gamma-hydroxybutyrate that optimize the bioavailability of the gamma-hydroxybutyrate, and roughly approximate the bioavailability of an equal dose of an immediate release liquid solution of sodium oxybate administered twice nightly.

Still another object of the present invention is to provide once-nightly modified release formulations of gamma-hydroxybutyrate that roughly approximate or exceed the bioavailability of an equal dose of an immediate release solution of sodium oxybate administered twice nightly, across the entire therapeutic range of sodium oxybate doses.

Yet another object of the present invention is to provide modified release formulations of gamma-hydroxybutyrate which, 8 hours after administration, produce very little residual drug content in the bloodstream of most patients but still similar to the one observed after administration of an equal dose of an immediate release liquid solution of sodium oxybate administered twice nightly.

Yet another object of the present invention is to improve the therapeutic effectiveness and safety profile of gamma-hydroxybutyrate based on novel dissolution and pharmacokinetic profiles.

Yet another object of the present invention is to provide modified release formulations of gamma-hydroxybutyrate that yield a similar pharmacokinetic profile compared to an immediate release liquid solution of sodium oxybate administered twice nightly while potentially giving a reduced dose.

Yet another object of the present invention is to provide modified release formulations of gamma-hydroxybutyrate that allow once daily administration and reduced dose compared to the commercial treatment Xyrem®.

Yet another object of the present invention is to provide a convenient dosage form of gamma-hydroxybutyrate that may be easily swallowed.

Yet another object of the present invention is to provide modified release formulations of gamma-hydroxybutyrate that are administered only once at bed-time with improved dissolution and pharmacokinetic profiles and reduced sodium content compared to an immediate release liquid solution of sodium oxybate administered twice nightly.

SUMMARY OF INVENTION

As the prior art demonstrates, it is extremely difficult to find a modified release formulation of gamma-hydroxybutyrate which, when administered only once nightly, has a comparable bioavailability to an immediate release liquid solution of sodium oxybate administered twice nightly. Even if such a formulation could be found, it probably still would not be satisfactory because the dose of gamma-hydroxybutyrate differs among individuals, and the size of the dose affects the amount of drug absorbed through the GI tract. I.e., even if the prior art formulations achieved comparable bioavailability at one dose—which they do not—they would not be comparable at other doses.

The inventors have discovered a novel relationship between the in vitro release profile of gamma-hydroxybutyrate modified release formulations and in vivo absorption which permits, for the first time, a modified release formulation of gamma-hydroxybutyrate that approximates the bioavailability of a twice-nightly equipotent immediate release liquid solution of sodium oxybate, and that does so across a range of therapeutic doses. In particular, the inventors have discovered that a modified release formulation of gamma-hydroxybutyrate that rapidly releases half of its gamma-hydroxybutyrate in 0.1N hydrochloric acid dissolution medium, and rapidly releases the other half of its gamma-hydroxybutyrate in phosphate buffer pH 6.8 dissolution medium, approximates or exceeds the in vivo bioavailability of an equipotent immediate release liquid solution of sodium oxybate administered twice nightly. This can be seen by comparing the formulations of Examples 1 and 4, which satisfy the dissolution requirements of the present invention and achieve the necessary bioavailability for a commercial formulation, with the Comparative formulation of Example 7, which exhibited a dissolution profile similar to prior art dissolution profiles, and did not achieve the necessary bioavailability for a commercial formulation.

This phenomenon is observed especially with higher doses of gamma-hydroxybutyrate. For example, the inventors have discovered that a modified release composition of gamma-hydroxybutyrate according to the invention administered once approximately two hours after a standardized evening meal at the dose equivalent to 7.5 g of sodium oxybate results in a similar pharmacokinetic profile as an immediate release liquid solution of sodium oxybate given in two separate equal doses of 4.5 g of sodium oxybate each administered at $t_0$ and $t_{4h}$.

The modified release formulations of gamma-hydroxybutyrate preferably have both immediate release and modified release portions. The release of gamma-hydroxybutyrate from the immediate release portion is practically uninhibited, and occurs almost immediately in 0.1N hydrochloric acid dissolution medium. In contrast, while the modified release portion also preferably releases its gamma-hydroxybutyrate almost immediately when fully triggered, the release is not triggered until a predetermined lag-time or the drug is subjected to a suitable dissolution medium such as a phosphate buffer pH 6.8 dissolution medium. Without wishing to be bound by any theory, it is believed that this rapid release in two dissolution media compresses the blood concentration vs. time curve in vivo, resulting in a relative bioavailability of gamma-hydroxybutyrate comparable to or greater than an equipotent dose of an immediate-release liquid solution of sodium oxybate administered twice nightly. In a first embodiment, provided herein is a method of treating cataplexy or excessive daytime sleepiness (EDS) in a patient with narcolepsy, the method comprising: orally administering a dosage of a composition comprising gamma-hydroxybutyrate once per night, wherein the patient experiences fewer adverse reactions as compared to a second patient administered twice-nightly gamma-hydroxybutyrate treatment.

In a second embodiment, provided herein is a method comprising: orally administering a dosage of a composition comprising gamma-hydroxybutyrate once per night, wherein the patient experiences no adverse reactions.

In a third embodiment, provided herein is a method comprising: orally administering a dosage of a composition comprising gamma-hydroxybutyrate once per night, wherein the patient experiences less or no obtundation as compared to the twice-nightly gamma-hydroxybutyrate treatment.

In a fourth embodiment, provided herein is a method comprising: orally administering a dosage of a composition comprising gamma-hydroxybutyrate once per night, wherein the patient experiences less or no clinically significant respiratory depression as compared to the twice-nightly gamma-hydroxybutyrate treatment.

In a fifth embodiment, provided herein is a method comprising: orally administering a dosage of a composition comprising gamma-hydroxybutyrate once per night, wherein the patient does not have profound CNS depression or severe difficulty breathing at doses of 4.5 g to 9 g gamma-hydroxybutyrate per night.

In a sixth embodiment, provided herein is a method comprising: orally administering a dosage of a composition comprising gamma-hydroxybutyrate once per night, wherein the patient does not have a clinically significant worsening of respiratory function as measured by apnea/hypopnea index and pulse oximetry at doses of 4.5 g to 9 g gamma-hydroxybutyrate per night.

In a seventh embodiment, provided herein is a method comprising: orally administering a dosage of a composition comprising gamma-hydroxybutyrate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

In an eighth embodiment, provided herein is a method comprising: orally administering a dosage of a composition comprising gamma-hydroxybutyrate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

In a ninth embodiment, provided herein is a method comprising: orally administering a dosage of a composition comprising gamma-hydroxybutyrate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

In a tenth embodiment, provided herein is a method comprising: orally administering a dosage of a composition comprising gamma-hydroxybutyrate once per night, wherein a peak plasma concentration ($C_{max}$) following administration of one dose is lower than a twice-nightly gamma-hydroxybutyrate treatment. In some aspects, the $C_{max}$ following administration of one 6 g dose is about 65.8 mcg/mL. In other aspects, there is a steady decrease in concentration following a time to peak plasma concentration ($T_{max}$) approximately two hours after dosing. In additional aspects, the $T_{max}$ is about 1.51 hours.

In an eleventh embodiment, provided herein is a method comprising: orally administering a dosage of a composition comprising gamma-hydroxybutyrate once per night, wherein the dosage of the composition initially administered comprises 4.5 g gamma-hydroxybutyrate. In some aspects, the method further comprises increasing the dosage by 1.5 g per night at weekly intervals to an effective dosage range of 6 g to 9 g per night.

In a twelfth embodiment, provided herein is a method comprising: orally administering a dosage of a composition comprising gamma-hydroxybutyrate once per night, wherein the composition is a powder for oral suspension. In some aspects, the composition comprises immediate-release and controlled-release granules comprising gamma-hydroxybutyrate and may further comprise microcrystalline cellulose spheres, povidone K30, hydrogenated vegetable oil, methacrylic acid copolymer, malic acid, xanthan gum, hydroxyethyl cellulose, carrageenan, and/or magnesium stearate.

In a thirteenth embodiment, provided herein is a method comprising: providing the composition in a nightly dose packet of 4.5 g, 6 g, 7.5, g, or 9 g gamma-hydroxybutyrate, wherein the composition is a powder for oral suspension; and orally administering a dosage of a composition comprising gamma-hydroxybutyrate once per night.

In a fourteenth embodiment, provided herein is a method comprising: providing the composition in a nightly dose packet of 4.5 g, 6 g, 7.5, g, or 9 g gamma-hydroxybutyrate, wherein the composition is a powder for oral suspension; preparing the dosage by suspending the composition from the dose packet in water; and orally administering a dosage of a composition comprising gamma-hydroxybutyrate once per night. In some aspects, the dosage is suspended in approximately 50 mL of water.

In a fifteenth embodiment, provided herein is a method comprising: orally administering a dosage of a composition comprising gamma-hydroxybutyrate once per night, wherein the dosage is administered without regard for meals.

In a sixteenth embodiment, provided herein is a method comprising: orally administering a dosage of a composition comprising gamma-hydroxybutyrate once per night, wherein the patient is in bed prior to orally administering the dosage. In some aspects, the patient lays down immediately after administering the dosage.

In a seventeenth embodiment, provided herein is a method comprising: orally administering a dosage of a composition comprising gamma-hydroxybutyrate once per night, wherein the patient falls asleep within 5 minutes to 15 minutes after administering the dosage.

In an eighteenth embodiment, provided herein is a method comprising: orally administering a dosage of a composition comprising gamma-hydroxybutyrate once per night and administering single dose of divalproex sodium ER. In some aspects, the dose of divalproex sodium ER is about 1250 mg.

In a nineteenth embodiment, provided herein is a method comprising: orally administering a dosage of a composition comprising gamma-hydroxybutyrate once per night, wherein the patient is an adult.

In a twentieth embodiment, provided herein is a method of treating cataplexy or excessive daytime sleepiness (EDS) in a patient with narcolepsy, the method comprising: orally administering a dosage of a composition comprising gamma-hydroxybutyrate once per night, wherein the patient experiences less obtundation as compared to a twice-nightly gamma-hydroxybutyrate treatment.

In a twenty first embodiment, provided herein is a method comprising: orally administering a dosage of a composition comprising gamma-hydroxybutyrate once per night, wherein the patient experiences no obtundation.

In a twenty second embodiment, provided herein is a method comprising: orally administering a dosage of a composition comprising gamma-hydroxybutyrate once per night, wherein the patient experiences less or no clinically significant respiratory depression as compared to the twice-nightly gamma-hydroxybutyrate treatment.

In a twenty third embodiment, provided herein is a method comprising: orally administering a dosage of a composition comprising gamma-hydroxybutyrate once per night, wherein the patient does not have profound CNS depression or severe difficulty breathing at doses of 4.5 g to 9 g gamma-hydroxybutyrate per night.

In a twenty fourth embodiment, provided herein is a method comprising: orally administering a dosage of a composition comprising gamma-hydroxybutyrate once per night, wherein the patient does not have a clinically significant worsening of respiratory function as measured by apnea/hypopnea index and pulse oximetry at doses of 4.5 g to 9 g gamma-hydroxybutyrate per night.

In a twenty fifth embodiment, provided herein is a method comprising: orally administering a dosage of a composition comprising gamma-hydroxybutyrate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

In a twenty sixth embodiment, provided herein is a method comprising: orally administering a dosage of a composition comprising gamma-hydroxybutyrate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

In a twenty seventh embodiment, provided herein is a method comprising: orally administering a dosage of a composition comprising gamma-hydroxybutyrate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

In a twenty ninth embodiment, provided herein is a method of treating cataplexy or excessive daytime sleepiness (EDS) in a patient with narcolepsy, the method comprising: orally administering a dosage of a composition comprising gamma-hydroxybutyrate once per night, wherein the patient experiences less respiratory depression as compared to a twice-nightly gamma-hydroxybutyrate treatment.

In a thirtieth embodiment, provided herein is a method comprising: orally administering a dosage of a composition comprising gamma-hydroxybutyrate once per night, wherein the patient experiences no clinically significant respiratory depression.

In a thirty first embodiment, provided herein is a method comprising: orally administering a dosage of a composition comprising gamma-hydroxybutyrate once per night, wherein the patient experiences less or no obtundation as compared to the twice-nightly gamma-hydroxybutyrate treatment.

In a thirty second embodiment, provided herein is a method comprising: orally administering a dosage of a composition comprising gamma-hydroxybutyrate once per night, wherein the patient does not have profound CNS depression or severe difficulty breathing at doses of 4.5 g to 9 g gamma-hydroxybutyrate per night.

In a thirty third embodiment, provided herein is a method comprising: orally administering a dosage of a composition comprising gamma-hydroxybutyrate once per night, wherein the patient does not have a clinically significant worsening of respiratory function as measured by apnea/hypopnea index and pulse oximetry at doses of 4.5 g to 9 g gamma-hydroxybutyrate per night.

In a thirty fourth embodiment, provided herein is a method comprising: orally administering a dosage of a composition comprising gamma-hydroxybutyrate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

In a thirty fifth embodiment, provided herein is a method comprising: orally administering a dosage of a composition comprising gamma-hydroxybutyrate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

In a thirty sixth embodiment, provided herein is a method comprising: orally administering a dosage of a composition comprising gamma-hydroxybutyrate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

In a thirty seventh embodiment, provided herein is a modified release formulation of gamma-hydroxybutyrate comprising immediate release and modified release portions, wherein the modified release formulation is suitable for administration only once nightly, without obtundation and clinically significant respiratory depression occurring in adult patients treated with twice-nightly gamma-hydroxybutyrate.

In a thirty eighth embodiment, provided herein is a modified release formulation of gamma-hydroxybutyrate comprising immediate release and modified release portions, wherein the modified release formulation is suitable for administration only once nightly, with reduced side effects of obtundation and clinically significant respiratory depression occurring in adult patients treated with twice-nightly gamma-hydroxybutyrate.

In a thirty ninth embodiment, provided herein is a modified release formulation of gamma-hydroxybutyrate comprising immediate release and modified release portions, wherein the immediate release portion comprises gamma-hydroxybutyrate, and the modified release portion comprises gamma-hydroxybutyrate coated with a coating comprising: a polymer carrying free carboxylic groups, and a hydrophobic compound having a melting point equal or greater than 40° C.

In a fortieth embodiment, provided herein is a modified release formulation of gamma-hydroxybutyrate comprising immediate release and modified release portions, wherein the formulation yields a plasma concentration versus time curve when administered at a dose of 4.5 g, 6.0 g or 7.5 g approximately two hours after a standardized evening meal substantially as depicted in FIG. 12 or FIG. 13 for the corresponding dose.

In a forty fourth embodiment, provided herein is a modified release formulation of gamma-hydroxybutyrate comprising immediate release and modified release portions, wherein the formulation yields a plasma concentration versus time curve when administered at a dose of 4.5 g approximately two hours after a standardized evening meal substantially as depicted in FIG. 22.

In a forty fifth embodiment, provided herein is a modified release formulation of gamma-hydroxybutyrate comprising immediate release and modified release portions, wherein the formulation yields a dissolution profile substantially as depicted in FIG. 7 and FIG. 8.

In a forty sixth embodiment, provided herein is a modified release formulation of gamma-hydroxybutyrate comprising immediate release and modified release portions, wherein the formulation yields a dissolution profile substantially as depicted in FIG. 20 and FIG. 21.

In a forty seventh embodiment, provided herein is a modified release formulation of gamma-hydroxybutyrate comprising immediate release and modified release portions, wherein the modified release portion yields a dissolution profile substantially as depicted in FIG. 3 or FIG. 16.

In a forty eighth embodiment, provided herein is a modified release formulation of gamma-hydroxybutyrate comprising immediate release and modified release portions, wherein the formulation yields a dissolution profile between the minimum and maximum values depicted in FIG. 25 and FIG. 26.

In a forty ninth embodiment, provided herein is a modified release formulation of gamma-hydroxybutyrate comprising immediate release and modified release portions, wherein the formulation yields a dissolution profile between the minimum and maximum values depicted in FIG. 27 and FIG. 28.

In a fiftieth embodiment, provided herein is a modified release formulation of gamma-hydroxybutyrate comprising immediate release and modified release portions, wherein the formulation yields a dissolution profile substantially as shown in any one of FIGS. 29 through 89.

In a fifty first embodiment, provided herein is a modified release formulation of gamma-hydroxybutyrate comprising immediate release and modified release portions, wherein the formulation yields a plasma concentration versus time curve when administered at a dose of 4.5 g, 7.5 g or 9.0 g approximately two hours after a standardized evening meal substantially as depicted in FIG. 90 for the corresponding dose.

In a fifty second embodiment, provided herein is a modified release formulation of gamma-hydroxybutyrate comprising immediate release and modified release portions, wherein the formulation yields a dissolution profile between the minimum and maximum values depicted in FIG. 26 and FIG. 28.

In a fifty third embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 4.5 g dose achieves a mean $C_{8h}$ of from 4.7 to 9.0 microgram/mL.

In a fifty fourth embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 4.5 g dose achieves a mean $C_{8h}$ of from 3.5 to 4.7 microgram/mL.

In a fifty fifth embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 6.0 g dose achieves a mean $C_{8h}$ of from 6.3 to 16.7 microgram/mL.

In a fifty sixth embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 6.0 g dose achieves a mean $C_{8h}$ of from 7.3 to 15.4 microgram/mL.

In a fifty seventh embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 7.5 g dose achieves a mean $C_{8h}$ of from 13.0 to 40.3 microgram/mL.

In a fifty eighth embodiment, provided herein is a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 7.5 g dose achieves a mean $C_{8h}$ of from 24.7 to 37.2 microgram/mL.

In a fifty ninth embodiment, provided herein is a modified release formulation of gamma-hydroxybutyrate comprising immediate release and modified release portions, wherein the formulation is defined based on the time required to reach maximum blood concentration of gamma-hydroxybutyrate to a patient, and further achieves a median $T_{max}$ of 1.25 to 3.25 hours when administered once approximately two hours after a standardized evening meal.

In a sixtieth embodiment, provided herein is a modified release formulation of gamma-hydroxybutyrate comprising immediate release and modified release portions, wherein the formulation is defined based on the time required to reach maximum blood concentration of gamma-hydroxybutyrate to a patient, and further achieves a median $T_{max}$ of 0.5 to 3.25 hours when administered once approximately two hours after a standardized evening meal.

In a sixty first embodiment, provided herein is a modified release formulation of gamma-hydroxybutyrate comprising immediate release and modified release portions, wherein the formulation produces a residual drug content in the bloodstream similar to one observed after administration of an equal dose of an immediate release liquid solution of gamma-hydroxybutyrate administered twice nightly.

In a sixty second embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation is suitable for administration once-daily, and further wherein the formulation is resistant to alcohol-induced dose dumping.

In a sixty third embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

In a sixty fourth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

In a sixty fifth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

In a sixty sixth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

In a sixty seventh embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

In a sixty eighth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion provides a modified release profile, and the release rate when measured using a first in vitro dissolution test in the absence of ethanol and the release rate when using a second vitro dissolution test in the presence of about 5% to about 20% ethanol (v/v) are substantially the same, wherein, other than the absence or presence ethanol, the first in vitro dissolution test and the second in vitro dissolution test are the same.

In a sixty ninth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm, and further wherein ethanol concentrations from about 5% to about 20% does not change the dissolution profile.

In a seventieth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

In a seventy first embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a relative bioavailability (RBA) of greater than 80% when compared to an equal dose of an immediate release liquid solution of gamma-hydroxybutyrate administered at $t_0$ and $t_{4h}$ in equally divided doses, when administered approximately two hours after a standardized evening meal.

In a seventy second embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 1.25 to 3.25 hours when administered once approximately two hours after a standardized evening meal.

In a seventy third embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 0.5 to 3.25 hours when administered once approximately two hours after a standardized evening meal.

In a seventy fourth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of about 1.25, 1.5, 1.75, 2, 2.25, 2.5, 2.75, 3, or 3.25 hours when administered once approximately two hours after a standardized evening meal.

In a seventy fifth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $AUC_{inf}$ of greater than 300 hr·microgram/mL when administered once approximately two hours after a standardized evening meal. In some aspects, the mean $AUC_{inf}$ is greater than 340 hr·microgram/mL, 375 hr·microgram/mL, or greater than 400 hr·microgram/mL.

In a seventy sixth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $C_{max}$ of greater than 70 microgram/mL when administered once approximately two hours after a standardized evening meal.

In a seventy seventh embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a mean $AUC_{inf}$ of greater than 80% of the mean $AUC_{inf}$ provided by an equal dose of immediate release liquid solution of gamma-hydroxybutyrate administered at $t_0$ and $t_{4h}$ in equally divided doses approximately two hours after a standardized evening meal, and a mean $C_{8h}$ less than 95% of the mean $C_{8h}$ provided by an equal dose of immediate release liquid solution of gamma-hydroxybutyrate administered at $t_0$ and $t_{4h}$ in equally divided doses approximately two hours after a standardized evening meal.

In a seventy eighth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 4.7 to 9.0 microgram/mL when administered once approximately two hours after a standardized evening meal.

In a seventy ninth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 3.5 to 4.7 microgram/mL when administered once approximately two hours after a standardized evening meal.

In an eightieth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 6.3 to 16.7 microgram/mL when administered once approximately two hours after a standardized evening meal.

In an eighty first embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 7.3 to 15.4 microgram/mL when administered once approximately two hours after a standardized evening meal.

In an eighty second embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 13.0 to 40.3 microgram/mL when administered once approximately two hours after a standardized evening meal.

In an eighty third embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 24.7 to 37.2 microgram/mL when administered once approximately two hours after a standardized evening meal.

In an eighty fourth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C.

In an eighty fifth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the weight ratio of the hydrophobic compound to the polymer carrying free carboxylic groups is from 0.4 to 4.

In an eighty sixth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the pharmaceutically acceptable salt of gamma-hydroxybutyrate comprises a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some aspects, the pharmaceutically acceptable salt of gamma-hydroxybutyrate is a calcium salt of gamma-hydroxybutyric acid.

In an eighty seventh embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising microcrystalline cellulose. In some aspects, the microcrystalline cellulose is present at about 10% w/w-15% w/w.

In an eighty eighth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising a layer of hydroxypropyl cellulose.

In an eighty ninth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups has a pH-dependent solubility.

In a ninetieth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups is selected from the group consisting of (meth)acrylic acid/alkyl (meth)acrylate copolymers, methacrylic acid and methylmethacrylate copolymers, methacrylic acid and ethyl acrylate copolymers, methacrylic acid copolymers type A, B or C, cellulose derivatives carrying free carboxylic groups, preferably cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate, and mixtures thereof.

In a ninety first embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups comprises a methacrylic acid copolymer. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In additional aspects, the methacrylic acid copolymer comprises poly(methacrylic acid, ethyl acrylate) 1:1.

In a ninety second embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the coating is from 10 to 50% of the weight of the modified release portion.

In a ninety third embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising an immediate release portion comprising a pharmaceutically acceptable salt of gamma-hydroxybutyrate. In some aspects, the formulation further comprises xanthan gum, carrageenan gum, gellan gum, guar gum, sodium alginate, calcium alginate, agar, sodium carboxymethyl cellulose, microcrystalline cellulose, hydroxyethyl cellulose, hydroxypropylmethyl cellulose, or mixtures thereof. In at least one aspect, the formulation comprises guar gum. For example, the guar gum is present at 1% to 15% by weight of the formulation.

In a ninety fourth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation is a dry particulate formulation or a powdered formulation.

In a ninety fifth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation comprises 4.5 g, 6.0 g, 7.5 g, or 9.0 g of gamma-hydroxybutyrate.

In a ninety sixth embodiment, provided herein is a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation is suitable to be orally administered once-nightly.

In a ninety seventh embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C.

In a ninety eighth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the weight ratio of the hydrophobic compound to the methacrylic acid copolymer is from 0.4 to 4.

In a ninety ninth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the ratio of gamma-hydroxybutyrate in the immediate release portion and the modified release portion is from 10/90 to 65/35.

In a one hundredth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the pharmaceutically acceptable salt of gamma-hydroxybutyrate is selected from a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some aspects, the pharmaceutically acceptable salt of gamma-hydroxybutyrate is a calcium salt of gamma-hydroxybutyric acid.

In a one hundred and first embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the microparticles further comprise a layer of hydroxypropyl cellulose.

In a one hundred and second embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the methacrylic acid copolymer is selected from the group consisting of (meth)acrylic acid/alkyl (meth) acrylate copolymers, methacrylic acid and methylmethacrylate copolymers, methacrylic acid and ethyl acrylate copolymers, methacrylic acid copolymers type A, B or C, and mixtures thereof. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In at least one aspect, the methacrylic acid copolymers comprise poly (methacrylic acid, ethyl acrylate) 1:1.

In a one hundred and third embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the coating is from 10 to 50% of the weight of the microparticles.

In a one hundred and fourth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., further comprising xanthan gum, carrageenan gum, gellan gum, guar gum, sodium alginate, calcium alginate, agar, sodium carboxymethyl cellulose, microcrystalline cellulose, hydroxyethyl cellulose, hydroxypropylmethyl cellulose, or mixtures thereof. In some aspects, the formulation comprises guar gum. In at least one aspect, the guar gum is present at 1% to 15% by weight of the formulation.

In a one hundred and fifth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation is a dry particulate formulation or a powdered formulation.

In a one hundred and sixth embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation comprises 4.5 g, 6.0 g, 7.5 g, or 9.0 g of the pharmaceutically acceptable salt of gamma-hydroxybutyrate.

In a one hundred and seventh embodiment, provided herein is a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation is suitable to be orally administered once-daily. In some aspects, the formulation is suitable to be orally administered once-nightly.

In a one hundred and eighth embodiment, provided herein is a formulation comprising: a modified release portion comprising: microparticles comprising a pharmaceutically acceptable salt of gamma-hydroxybutyrate; and at least one coating on the microparticles comprising a methacrylic acid copolymer.

In a one hundred and ninth embodiment, provided herein is a formulation comprising: a modified release portion comprising: microparticles comprising a pharmaceutically acceptable salt of gamma-hydroxybutyrate; and at least one coating on the microparticles comprising a methacrylic acid copolymer, wherein the pharmaceutically acceptable salt of gamma-hydroxybutyrate is selected from a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some aspects, the pharmaceutically acceptable salt of gamma-hydroxybutyrate is a calcium salt of gamma-hydroxybutyric acid.

In a one hundred and tenth embodiment, provided herein is a formulation comprising: a modified release portion comprising: microparticles comprising a pharmaceutically acceptable salt of gamma-hydroxybutyrate; and at least one coating on the microparticles comprising a methacrylic acid copolymer, wherein the microparticles further comprise a layer of hydroxypropyl cellulose.

In a one hundred and eleventh embodiment, provided herein is a formulation comprising: a modified release portion comprising: microparticles comprising a pharmaceutically acceptable salt of gamma-hydroxybutyrate; and at least one coating on the microparticles comprising a methacrylic acid copolymer, wherein the methacrylic acid copolymer is selected from the group consisting of (meth)acrylic acid/alkyl (meth)acrylate copolymers, methacrylic acid and methylmethacrylate copolymers, methacrylic acid and ethyl acrylate copolymers, methacrylic acid copolymers type A, B or C, and mixtures thereof. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In at least one aspect, the methacrylic acid copolymers comprise poly (methacrylic acid, ethyl acrylate) 1:1.

In a one hundred and twelfth embodiment, provided herein is a formulation comprising: a modified release portion comprising: microparticles comprising a pharmaceutically acceptable salt of gamma-hydroxybutyrate; and at least one coating on the microparticles comprising a methacrylic acid copolymer, wherein the coating is from 10 to 50% of the weight of the microparticles.

In a one hundred and thirteenth embodiment, provided herein is a method of treating cataplexy in narcolepsy or excessive daytime sleepiness ("EDS") in narcolepsy, the method comprising administering a formulation of gamma-hydroxybutyrate once-daily.

In a one hundred and fourteenth embodiment, provided herein is a method of treating cataplexy in narcolepsy or excessive daytime sleepiness ("EDS") in narcolepsy, the method comprising administering a formulation of gamma-hydroxybutyrate once-nightly.

In a one hundred and fifteenth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation is suitable for administration once-daily.

In a one hundred and sixteenth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm.

In a one hundred and seventeenth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In a one hundred and eighteenth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm.

In a one hundred and nineteenth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

In a one hundred and twentieth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a one hundred and twenty first embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

In a one hundred and twenty second embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a relative bioavailability (RBA) of greater than 80% when compared to an equal dose of an immediate release liquid solution of gamma-hydroxybutyrate administered at $t_0$ and $t_{4h}$ in equally divided doses, when administered approximately two hours after a standardized evening meal.

In a one hundred and twenty third embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 1.25 to 3.25 hours when administered once approximately two hours after a standardized evening meal.

In a one hundred and twenty fourth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 0.5 to 3.25 hours when administered once approximately two hours after a standardized evening meal.

In a one hundred and twenty fifth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of about 1.25, 1.5, 1.75, 2, 2.25, 2.5, 2.75, 3, or 3.25 hours when administered once approximately two hours after a standardized evening meal.

In a one hundred and twenty sixth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $AUC_{inf}$ of greater than 300 hr·microgram/mL when administered once approximately two hours after a standardized evening meal. In some aspects, the mean $AUC_{inf}$ is greater than 340 hr·microgram/mL, greater than 375 hr·microgram/mL, or greater than 400 hr·microgram/mL.

In a one hundred and twenty seventh embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $C_{max}$ of greater than 70 microgram/mL when administered once approximately two hours after a standardized evening meal.

In a one hundred and twenty eighth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a mean $AUC_{inf}$ of greater than 80% of the mean $AUC_{inf}$ provided by an equal dose of immediate release liquid solution of gamma-hydroxybutyrate administered at $t_0$ and $t_{4h}$ in equally divided doses approximately two hours after a standardized evening meal, and a mean $C_{8h}$ less than 95% of the mean $C_{8h}$ provided by an equal dose of immediate release liquid solution of gamma-hydroxybutyrate administered at t0 and t4h in equally divided doses approximately two hours after a standardized evening meal.

In a one hundred and twenty ninth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 4.7 to 9.0 microgram/mL when administered once approximately two hours after a standardized evening meal.

In a one hundred and thirtieth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 3.5 to 4.7 microgram/mL when administered once approximately two hours after a standardized evening meal.

In a one hundred and thirty first embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 6.3 to 16.7 microgram/mL when administered once approximately two hours after a standardized evening meal.

In a one hundred and thirty second embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 7.3 to 15.4 microgram/mL when administered once approximately two hours after a standardized evening meal.

In a one hundred and thirty third embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 13.0 to 40.3 microgram/mL when administered once approximately two hours after a standardized evening meal.

In a one hundred and thirty fourth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 24.7 to 37.2 microgram/mL when administered once approximately two hours after a standardized evening meal.

In a one hundred and thirty fifth embodiment, provided herein is a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the composition produces a residual drug content in the bloodstream similar to one observed after administration of an equal dose of an immediate release liquid solution of gamma-hydroxybutyrate administered twice nightly.

In a one hundred and thirty sixth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, and wherein the formulation is suitable for administration once-daily.

In a one hundred and thirty seventh embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a mean AUCinf of greater than 80% of the mean AUCinf provided by an equal dose of immediate release liquid solution of gamma-hydroxybutyrate administered at t0 and t4h in equally divided doses approximately two hours after a standardized evening meal. In some aspects, a 7.5 g dose of the formulation achieves a mean AUCinf of greater than 340 hr·microgram/mL, greater than 375 hr·microgram/mL, or greater than 400 hr·microgram/mL.

In a one hundred and thirty eighth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median Tmax of 1.25 to 3.25 hours when administered once approximately two hours after a standardized evening meal.

In a one hundred and thirty ninth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median Tmax of 0.5 to 3.25 hours when administered once approximately two hours after a standardized evening meal.

In a one hundred and fortieth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median Tmax of about 1.25, 1.5, 1.75, 2, 2.25, 2.5, 2.75, 3, or 3.25 hours when administered once approximately two hours after a standardized evening meal.

In a one hundred and forty first embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose of the formulation achieves a mean Cmax of greater than 70 microgram/mL when administered once approximately two hours after a standardized evening meal.

In a one hundred and forty second embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 4.5 g dose achieves a mean C8h of from 4.7 to 9.0 microgram/mL when administered once approximately two hours after a standardized evening meal.

In a one hundred and forty third embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 4.5 g dose achieves a mean C8h of from 3.5 to 4.7 microgram/mL when administered once approximately two hours after a standardized evening meal.

In a one hundred and forty fourth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 6.0 g dose achieves a mean C8h of from 6.3 to 16.7 microgram/mL when administered once approximately two hours after a standardized evening meal.

In a one hundred and forty fifth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 6.0 g dose achieves a mean C8h of from 7.3 to 15.4 microgram/mL when administered once approximately two hours after a standardized evening meal.

In a one hundred and forty sixth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose achieves a mean C8h of from 13.0 to 40.3 microgram/mL when administered once approximately two hours after a standardized evening meal.

In a one hundred and forty seventh embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose achieves a mean C8h of from 24.7 to 37.2 microgram/mL when administered once approximately two hours after a standardized evening meal.

In a one hundred and forty eighth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein the 7.5 g dose of the formulation achieves a mean C8h from 50% to 130% of the mean C8h provided by an equal dose of an immediate release liquid solution of gamma-hydroxybutyrate administered at t0 and t4h in equally divided doses approximately two hours after a standardized evening meal. In some aspects, the mean C8h achieved by the formulation is from 60% to 90% of the mean C8h provided by the immediate release liquid solution of gamma-hydroxybutyrate.

In a one hundred and forty ninth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a relative bioavailability (RBA) of greater than 80% when compared to an equal dose of an immediate release liquid solution of gamma-hydroxybutyrate administered at t0 and t4h in equally divided doses, when administered approximately two hours after a standardized evening meal.

In a one hundred and fiftieth embodiment, provided herein is a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein the dose is a 4.5 g, 6 g, 7.5 g, or 9 g dose of the formulation.

In a one hundred and fifty first embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers.

In a one hundred and fifty second embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising ethylcellulose or microcrystalline cellulose.

In a one hundred and fifty third embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising cellulose derivatives carrying free carboxylic groups.

In a one hundred and fifty fourth embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate, and mixtures thereof.

In a one hundred and fifty fifth embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers comprising Eudragit™ L100, or Eudragit™ L100-55, or Eudragit™ S100.

In a one hundred and fifty sixth embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, wherein the coating comprises ethyl acrylate.

In a one hundred and fifty seventh embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers comprising poly (methacrylic acid, methyl methacrylate) 1:1, poly (methacrylic acid, ethyl acrylate) 1:1, or poly (methacrylic acid, methyl methacrylate).

In a one hundred and fifty eighth embodiment, provided herein is a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, wherein the coating comprises a polymer that is selected from methylmethacrylate polymers having a pH-dependent solubility.

In a one hundred and fifty ninth embodiment, provided herein is a pharmaceutical formulation comprising: particles of gamma-hydroxybutyrate comprising a core and a coating deposited on the core; and immediate release particles that release at least 80% or 90% of its gamma-hydroxybutyrate at 3 hours, 2 hours, 1 hour, 0.5 hours, or 0.25 hours, wherein the coating inhibits the release of gamma-hydroxybutyrate, and wherein the coating comprises a polymer that is selected from methylmethacrylate polymers.

Formulations that achieve this improved bioavailability can be described using several different pharmacokinetic and in vitro dissolution parameters. In a one hundred and sixtieth embodiment, the invention provides a modified release formulation of gamma-hydroxybutyrate, preferably comprising immediate release and modified release portions, wherein a 7.5 g dose of the formulation has been shown to achieve a mean AUCinf of greater than 340 hr×microgram/mL.

In a one hundred and sixty first embodiment, the invention provides a modified release formulation of gamma-hydroxybutyrate, preferably comprising immediate release and modified release portions, wherein a 7.5 g dose of the formulation has been shown to achieve a mean AUCinf of greater than 340 hr×microgram/mL, and a mean C8h that is from 50% to 130% of the mean C8h provided by an equal dose of an immediate release liquid solution of sodium oxybate administered at t0 and t4h in equally divided doses approximately two hours after a standardized evening meal.

In a one hundred and sixty second embodiment, the invention provides a modified release formulation of gamma-hydroxybutyrate, preferably comprising immediate release and modified release portions, wherein the formulation releases (a) at least 80% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In a one hundred and sixty third embodiment, the invention provides a modified release formulation of gamma-hydroxybutyrate, comprising immediate release and modified release portions, wherein (a) the formulation releases at least 80% of its gamma-hydroxybutyrate at 3 hours, when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a one hundred and sixty fourth embodiment, the invention provides a modified release formulation of gamma-hydroxybutyrate, comprising immediate release and modified release portions, wherein (a) the formulation releases at least 80% of its gamma-hydroxybutyrate at 3 hours, when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases 10% to 65%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60% of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a one hundred and sixty fifth embodiment, the invention provides a modified release formulation of gamma-hydroxybutyrate, comprising immediate release and modified release portions, wherein (a) a 7.5 g dose of the formulation has been shown to achieve a mean AUCinf of greater than 340 hr×microgram/mL, and a mean C8h that is from 50% to 130%, of the mean C8h provided by an equal dose of an immediate release liquid solution of sodium oxybate administered at t0 and t4h in equally divided doses approximately two hours after a standardized evening meal, and (b) the formulation releases (i) at least 80% or 90% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, and (ii) from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a one hundred and sixty sixth embodiment, the invention provides a modified release formulation of gamma-hydroxybutyrate comprising immediate release and modified release portions, wherein: (a) said immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (b) said modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; and (c) said modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm.

In a one hundred and sixty seventh embodiment, the invention provides a modified release formulation of gamma-hydroxybutyrate comprising immediate release and modified release portions, wherein: (a) said immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (b) said modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (c) said modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm; and (d) said modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a one hundred and sixty eighth embodiment, the invention provides a modified release formulation of gamma-hydroxybutyrate, preferably comprising immediate release and modified release portions, wherein 4.5 g, 6 g, 7.5 g, and 9 g doses of the formulation have been shown to achieve a relative bioavailability (RBA) of greater than 80% when compared to an equal dose of an immediate release liquid solution of sodium oxybate administered at t0 and t4h in equally divided doses, when administered approximately two hours after a standardized evening meal.

In a one hundred and sixty ninth embodiment, the invention provides a modified release formulation of gamma-hydroxybutyrate, preferably comprising immediate release and modified release portions, wherein 4.5 g and 9 g doses of the formulation have been shown to achieve a relative bioavailability (RBA) of greater than 80% when compared to an equal dose of an immediate release liquid solution of sodium oxybate administered at t0 and t4h in equally divided doses, when administered approximately two hours after a standardized evening meal.

In a one hundred and seventieth embodiment, the invention provides a modified release formulation of gamma-hydroxybutyrate, preferably comprising immediate release and modified release portions, that yields a plasma concentration versus time curve when administered once nightly at a strength of 4.5 g, 6.0 g or 7.5 g approximately two hours after a standardized evening meal substantially as depicted in FIG. 12 or FIG. 13 for the corresponding strength.

In a one hundred and seventy first embodiment, the invention provides a modified release formulation of gamma-hydroxybutyrate, preferably comprising immediate release and modified release portions, that yields a plasma concentration versus time curve when administered once nightly at a strength of 4.5 g approximately two hours after a standardized evening meal substantially as depicted in FIG. 22.

In a one hundred and seventy second embodiment, the invention provides a modified release formulation of gamma-hydroxybutyrate, preferably comprising immediate release and modified release portions, that yields a dissolution profile substantially as depicted in FIG. 7 and FIG. 8.

In a one hundred and seventy second embodiment, the invention provides a modified release formulation of gamma-hydroxybutyrate, preferably comprising immediate release and modified release portions, that yields a dissolution profile substantially as depicted in FIG. 20 and FIG. 21.

In a one hundred and seventy third embodiment, the invention provides a modified release formulation of gamma-hydroxybutyrate comprising immediate release and modified release portions, wherein said modified release portion yields a dissolution profile substantially as depicted in FIG. 3 or FIG. 16.

In a one hundred and seventy fourth embodiment, the invention provides a modified release formulation of gamma-hydroxybutyrate, comprising immediate release and modified release portions that yields a dissolution profile between the minimum and maximum values depicted in FIG. 25 and FIG. 26.

In a one hundred and seventy fifth embodiment, the invention provides a modified release formulation of gamma-hydroxybutyrate, comprising immediate release and modified release portions that yields a dissolution profile between the minimum and maximum values depicted in FIG. 27 and FIG. 28.

In a one hundred and seventy sixth embodiment, the invention provides a modified release formulation of gamma-hydroxybutyrate yielding a dissolution profile substantially as shown in any one of FIGS. 29 through 89.

In a one hundred and seventy seventh embodiment, the present invention provides a modified release formulation of gamma-hydroxybutyrate, preferably comprising immediate release and modified release portions, that yields a plasma concentration versus time curve when administered once nightly at a strength of 4.5 g, 7.5 g or 9.0 g approximately two hours after a standardized evening meal substantially as depicted in FIG. 90 for the corresponding strength.

In a one hundred and seventy eighth embodiment, the present invention provides a modified release formulation of gamma-hydroxybutyrate, preferably comprising immediate release and modified release portions that yields a dissolution profile between the minimum and maximum values depicted in FIG. 26 and FIG. 28.

In a one hundred and seventy ninth embodiment, the present invention provides a pharmaceutical composition storage and administration system comprising: at least seven nightly dose packets, each nightly dose packet operable to contain a single once daily dosage of a composition comprising gamma-hydroxybutyrate; one or more packet containers, each packet container operable to receive up to seven nightly dose packets; a mixing cup comprising a lid, a first fill line, and a second fill line; a mixing cup receptacle comprising a cup retaining portion operable to receive the mixing cup; and a carton operable to removably receive the one or more packet containers with up to seven packets in each container and the mixing cup receptacle with the mixing cup.

In a one hundred and eightieth embodiment, the present invention provides a pharmaceutical composition storage and administration system, wherein each nightly dose packet contains a once daily dosage of 4.5 g, 6 g, 7.5, g, or 9 g gamma-hydroxybutyrate.

In a one hundred and eighty first embodiment, the present invention provides a pharmaceutical composition storage and administration system, wherein the carton is operable to removably receive one packet container with seven nightly dose packets and the mixing cup receptacle with the mixing cup to provide a 7-day supply of the composition.

In a one hundred and eighty second embodiment, the present invention provides a pharmaceutical composition storage and administration system, wherein the mixing cup receptacle further comprises a packet portion operable to receive up to two nightly dose packets. In some aspects, the carton is operable to removable receive four packet containers, each with seven nightly dose packets, and the mixing cup receptacle with the mixing cup to provide a 30-day supply of the composition.

In a one hundred and eighty third embodiment, the present invention provides a pharmaceutical composition storage and administration system, wherein the first fill line measures about 50 mL and the second fill line measures about 25 mL.

In a one hundred and eighty fourth embodiment, the present invention provides a pharmaceutical composition storage and administration system, wherein the mixing cup comprises a bottom and a wall having an inner side operable to intersect with the bottom. In some aspects, the intersection of the inner side of the wall and the bottom is rounded to limit adhesion to the mixing cup. In other aspects, the intersection is not 90 degrees.

In a one hundred and eighty fifth embodiment, the present invention provides a method of preparing and administering a pharmaceutical composition to a patient, the method comprising: providing a pharmaceutical composition storage and administration system; removing the lid of the mixing cup and filling the mixing cup with water up to the first fill line; opening one nightly dose packet; emptying the composition from the nightly dose packet into the mixing cup filled with water; replacing the lid of the mixing cup; shaking the mixing cup to form a first suspension of the composition in the water; and administering the first suspension to the patient.

In a one hundred and eighty sixth embodiment, the present invention provides a method of preparing and administering a pharmaceutical composition to a patient, the method further comprising: removing the lid of the mixing cup and filling the mixing cup with water up to the second fill line; replacing the lid of the mixing cup; shaking the mixing cup to form a second suspension of any residual composition in the water; and administering the second suspension to the patient.

In a one hundred and eighty seventh embodiment, the present invention provides a once-daily modified release formulation of gamma-hydroxybutyrate, wherein the formulation decreases the number of cataplexy attacks (NCA), compared to a dosing regimen consisting of administering the twice-nightly gamma-hydroxybutyrate treatment.

In a one hundred and eighty eighth embodiment, the present invention provides a once-daily modified release formulation of gamma-hydroxybutyrate, wherein the formulation produces less confusion, less depressive syndrome, less incontinence, less nausea, or less sleepwalking, compared to a dosing regimen consisting of administering the twice-nightly gamma-hydroxybutyrate treatment.

In a one hundred and eighty ninth embodiment, the present invention provides a once-daily modified release formulation of gamma-hydroxybutyrate, wherein the formulation decreases PSG transitions from N/2 to N/3 and REM sleep to wake and N1 sleep, compared to a dosing regimen consisting of administering the twice-nightly gamma-hydroxybutyrate treatment.

In a one hundred and ninetieth embodiment, the present invention provides a once-daily modified release formulation of gamma-hydroxybutyrate, wherein the formulation decreases the number of arousals or wakenings obtained from a polysomnogram, compared to a dosing regimen consisting of administering the twice-nightly gamma-hydroxybutyrate treatment.

In a one hundred and ninety first embodiment, the present invention provides a once-daily modified release formulation of gamma-hydroxybutyrate, wherein the formulation decreases daytime sleepiness when measured by the Maintenance of Wakefulness Test based on EEG measures of wakefulness, compared to a dosing regimen consisting of administering the twice-nightly gamma-hydroxybutyrate treatment.

In a one hundred and ninety second embodiment, the present invention provides a once-daily modified release formulation of gamma-hydroxybutyrate, wherein the formulation decreases the hypnagogic hallucinations or sleep paralysis symptoms in Type 1 narcolepsy patients, compared to a dosing regimen consisting of administering the twice-nightly gamma-hydroxybutyrate treatment.

In a one hundred and ninety third embodiment, the present invention provides a once-daily modified release formulation of gamma-hydroxybutyrate, wherein the formulation increases the mean sleep latency compared to a dosing regimen consisting of administering the twice-nightly gamma-hydroxybutyrate treatment.

In a one hundred and ninety fourth embodiment, the present invention provides a once-daily modified release formulation of gamma-hydroxybutyrate, wherein the formulation decreases excessive daytime sleepiness (EDS) as measured by patient report via the Epworth Sleepiness Scale (ESS), compared to a dosing regimen consisting of administering the twice-nightly gamma-hydroxybutyrate treatment.

In a one hundred and ninety fifth embodiment, the present invention provides a once-daily modified release formulation of gamma-hydroxybutyrate, wherein the formulation improves a Clinical Global Impression (CGI) rating of sleepiness, compared to a dosing regimen consisting of administering the twice-nightly gamma-hydroxybutyrate treatment.

In a one hundred and ninety sixth embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in the number of cataplexy attacks (NCA), compared to a patient with a dosing regimen consisting of administering the twice-nightly gamma-hydroxybutyrate treatment.

In a one hundred and ninety seventh embodiment, the present invention provides a method of treating cataplexy or excessive daytime sleepiness (EDS) in a patient with narcolepsy by orally administering a dosage of a composition comprising gamma-hydroxybutyrate once per night, wherein the patient has less confusion, less depressive syndrome, less incontinence, less nausea, or less sleepwalking, compared to a patient with a dosing regimen consisting of administering the twice-nightly gamma-hydroxybutyrate treatment.

In a one hundred and ninety eighth embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in PSG transitions from N/2 to N/3 and REM sleep to wake and N1 sleep, compared to a patient with a dosing regimen consisting of administering the twice-nightly gamma-hydroxybutyrate treatment.

In a one hundred and ninety ninth embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in the number of arousals or wakenings obtained from a polysomnogram, compared to a patient with a dosing regimen consisting of administering the twice-nightly gamma-hydroxybutyrate treatment.

In a two hundredth embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in hypnagogic hallucinations or sleep paralysis symptoms in Type 1 narcolepsy patients, compared to a patient with a dosing regimen consisting of administering the twice-nightly gamma-hydroxybutyrate treatment.

In a two hundred and first embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in daytime sleepiness when measured by the Maintenance of Wakefulness Test based on EEG measures of wakefulness, compared to a patient administered the twice-nightly gamma-hydroxybutyrate treatment.

In a two hundred and second embodiment, the present invention provides a method of treating cataplexy or excessive daytime sleepiness (EDS) in a patient with narcolepsy by orally administering a dosage of a composition comprising gamma-hydroxybutyrate once per night, wherein the patient has a decrease in excessive daytime sleepiness (EDS) as measured by patient report via the Epworth Sleepiness Scale (ESS), compared to a patient administered the twice-nightly gamma-hydroxybutyrate treatment.

In a two hundred and third embodiment, the present invention provides a method of treating cataplexy or excessive daytime sleepiness (EDS) in a patient with narcolepsy by orally administering a dosage of a composition comprising gamma-hydroxybutyrate once per night, wherein the patient has an increase in mean sleep latency compared to a patient administered the twice-nightly gamma-hydroxybutyrate treatment.

In a two hundred and fourth embodiment, the present invention provides a method of treating cataplexy or excessive daytime sleepiness (EDS) in a patient with narcolepsy by orally administering a dosage of a composition comprising gamma-hydroxybutyrate once per night, wherein the patient improves the Clinical Global Impression-Improvement (CGI) rating of sleepiness, compared to a patient administered the twice-nightly gamma-hydroxybutyrate treatment.

In a two hundred and fifth embodiment, the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a plasma GHB concentration maintained throughout the night, and gradual decline of the GHB concentration to lowest levels by 8 to 10 hours after dosing.

In a two hundred and sixth embodiment, the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a pharmacokinetic profile that supports once nightly dosing, and eliminates the need for the patient having to wake up in the middle of the night to take a second dose.

In a two hundred and seventh embodiment, the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a pharmacokinetic profile that supports once nightly dosing and a full 8 hours of consolidated nocturnal sleep.

In a two hundred and eighth embodiment, the present invention provides a method of treating cataplexy or excessive daytime sleepiness (EDS) in a child or adolescent patient with narcolepsy comprising: orally administering a dosage of a composition comprising gamma-hydroxybutyrate once per night, wherein the child or adolescent patient dosage is not calculated based on weight of the patient.

Still further embodiments relate to methods of using the formulations of the present invention to treat narcolepsy and associated disorders and symptoms, and to physical aspects of the formulations of the present invention. Additional principal embodiments and sub-embodiments thereto will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE FIGURES

The patent or application file contains at least one drawing executed in color. Copies of this patent or patent application publication with color drawing(s) will be provided by the Office upon request and payment of the necessary fee.

Figure 25:
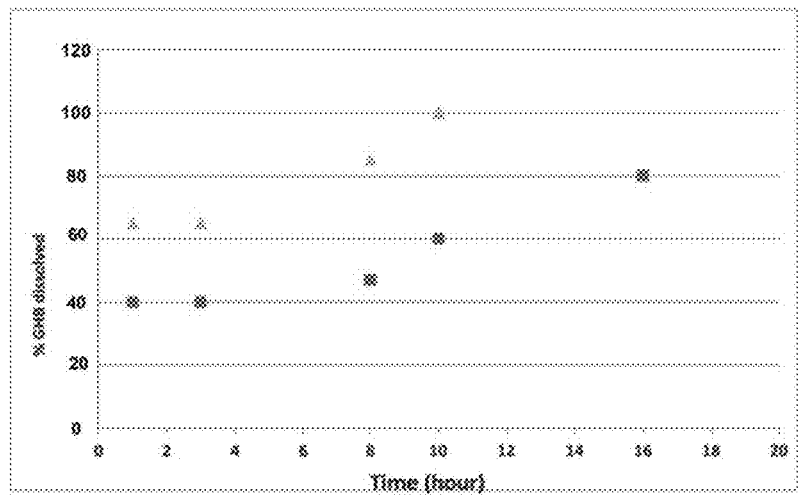

FIG. 25 plots the Min (■) and Max (▲) values of a preferred dissolution profile in 0.1N HCl of finished composition according to the invention.

Figure 26:
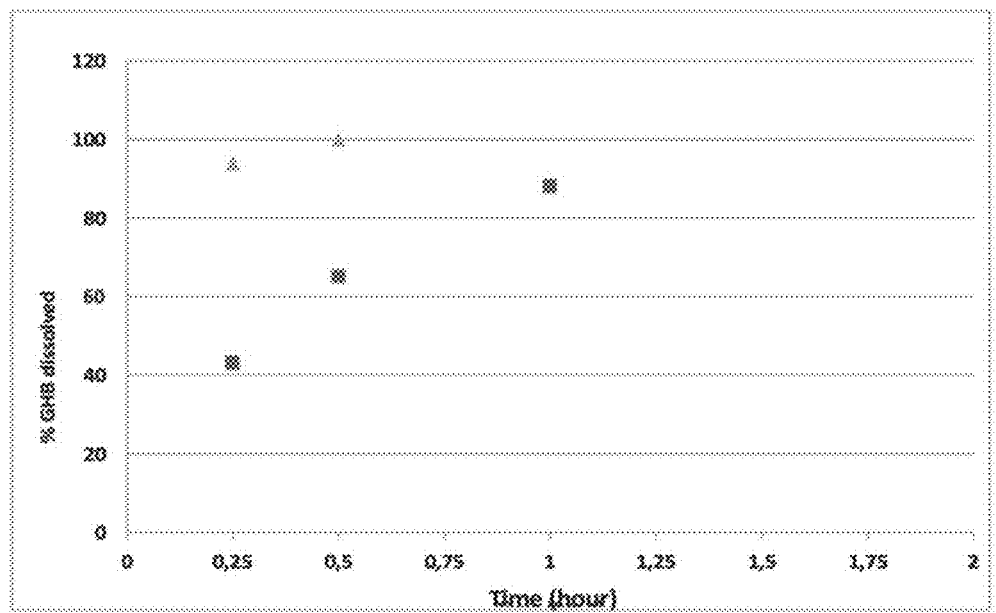

FIG. 26 plots the Min (■) and Max (▲) values of a preferred dissolution profile in phosphate buffer pH 6.8 of finished composition according to the invention.

Figure 27:
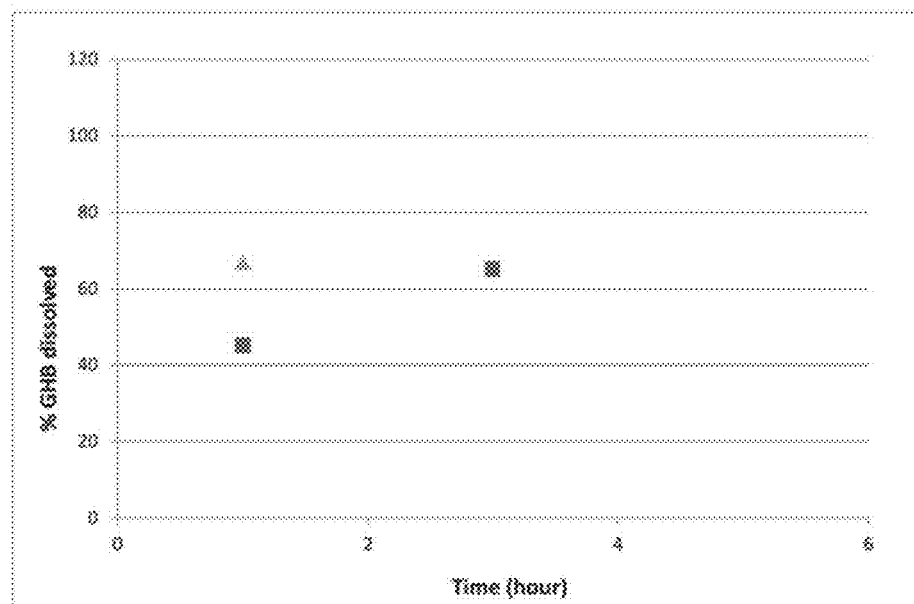

FIG. 27 plots the Min (■) and Max (▲) values of another preferred dissolution profile in phosphate buffer pH 6.8 of finished composition according to the invention.

Figure 28:
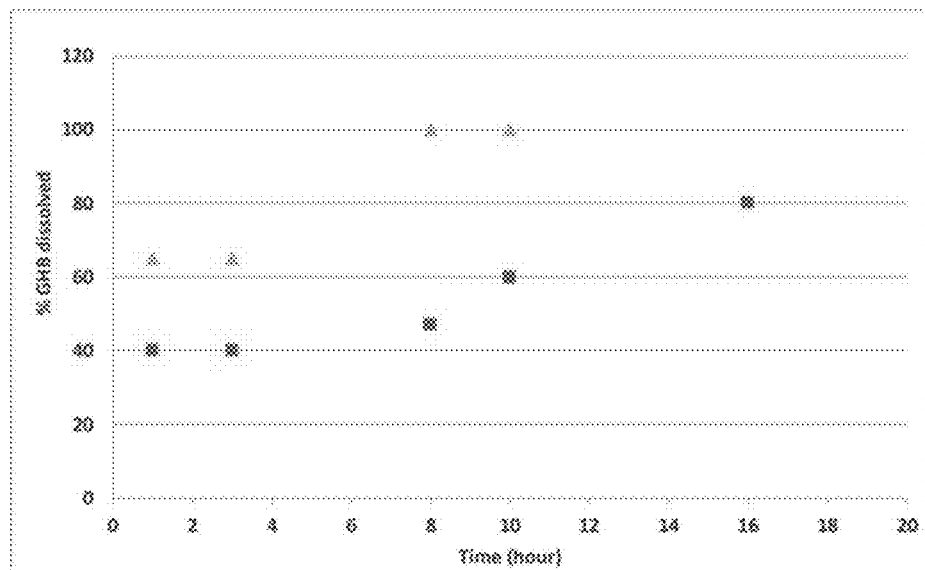

FIG. 28 plots the Min (■) and Max (▲) values of another preferred dissolution profile in 0.1N HCl of finished composition according to the invention.

Figure 29:
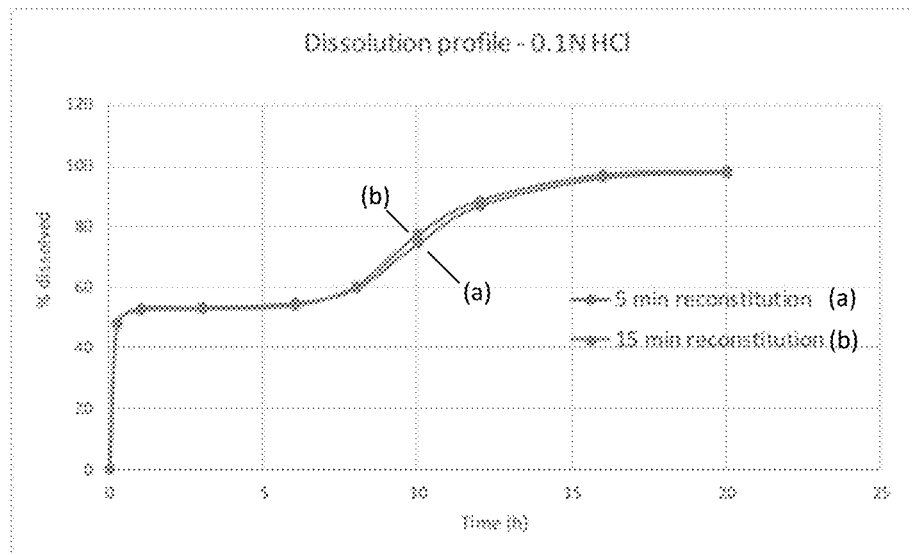

FIG. 29 depicts a dissolution profile determined in 0.1N HCl using a USP apparatus 2 for the formulation of Example 9.1 5 minutes and 15 minutes after reconstitution in water.

Figure 30:
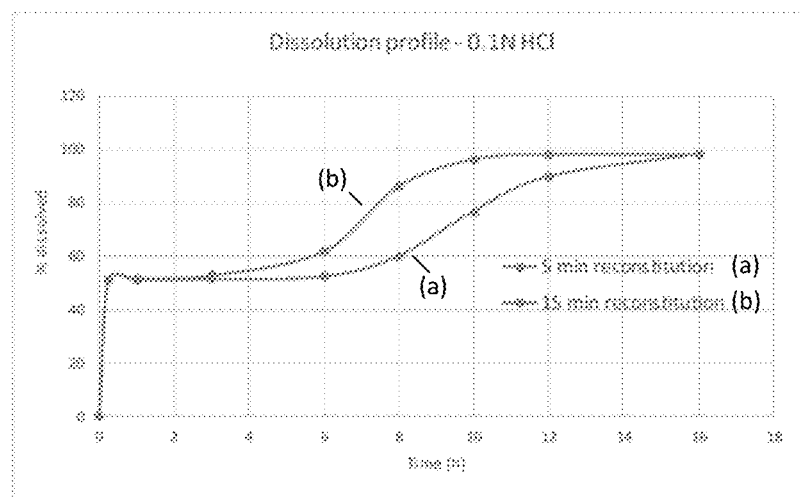

FIG. 30 depicts a dissolution profile determined in 0.1N HCl using a USP apparatus 2 for the formulation of Example 9.2 5 minutes and 15 minutes after reconstitution in water.

Figure 31:
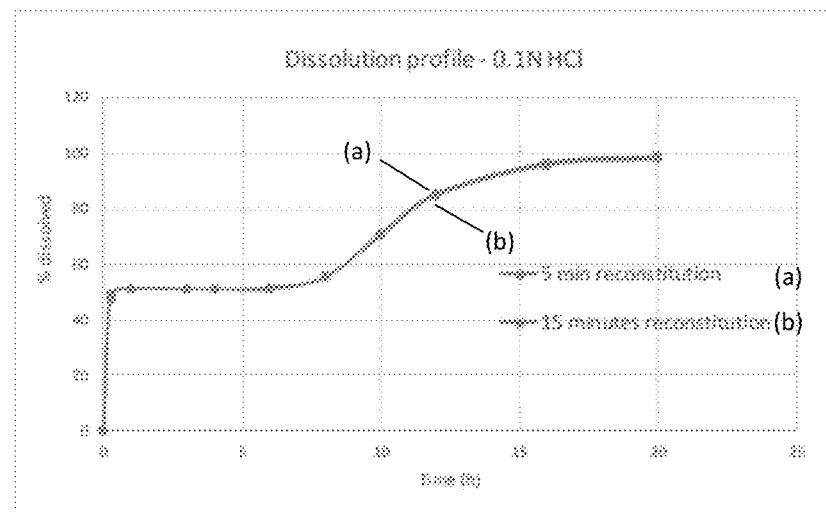

FIG. 31 depicts a dissolution profile determined in 0.1N HCl using a USP apparatus 2 for the formulation of Example 9.3 5 minutes and 15 minutes after reconstitution in water.

Figure 32:
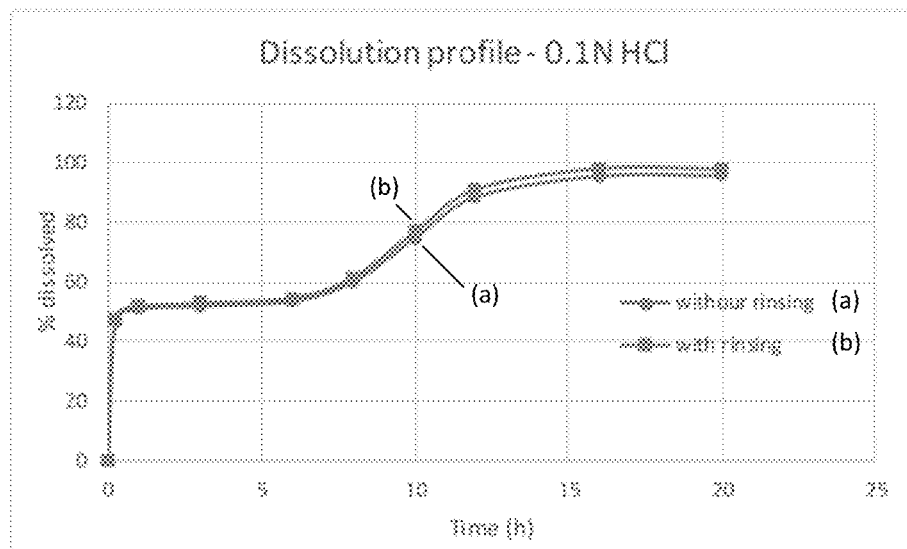

FIG. 32 depicts the dissolution profile determined in 0.1N HCl using a USP apparatus 2 of a 9 g dose of the formulation of Example 10 with and without rinsing.

Figure 33:
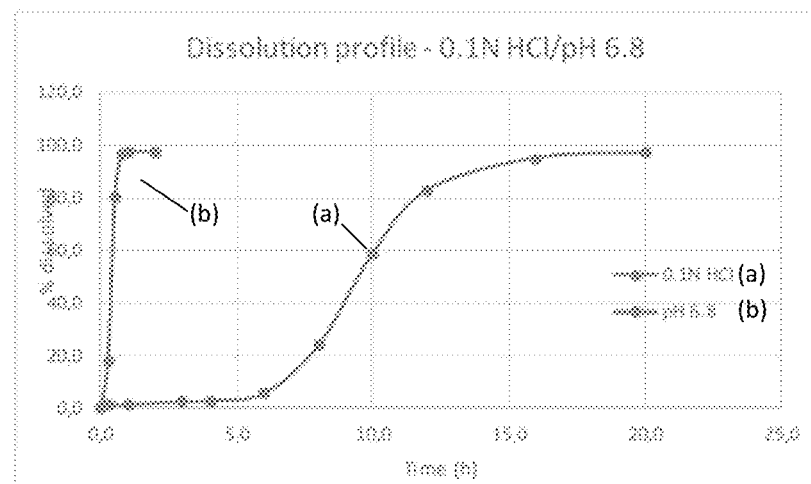

FIG. 33 depicts the dissolution profile of the MR portion of the formulation of Example 11a in 900 ml of 0.1N HCl and pH 6.8 phosphate buffer (0.05M monobasic potassium phosphate solution—pH adjusted to 6.8 with 5N NaOH) using a USP apparatus 2.

Figure 34:
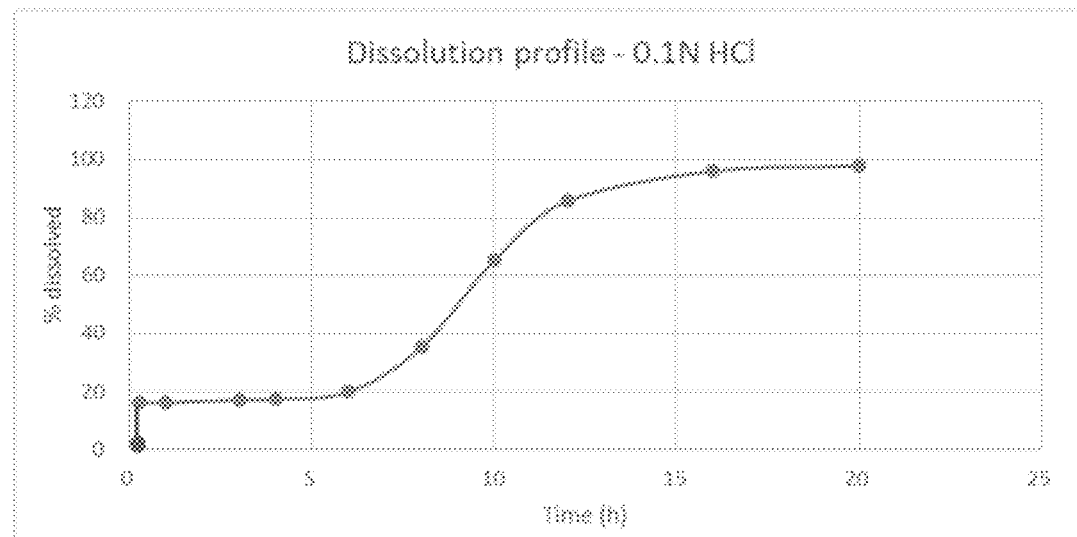

FIG. 34 depicts the dissolution profile of the formulation of Example 11a in 900 ml of 0.1N HCl using a USP apparatus 2.

Figure 35:
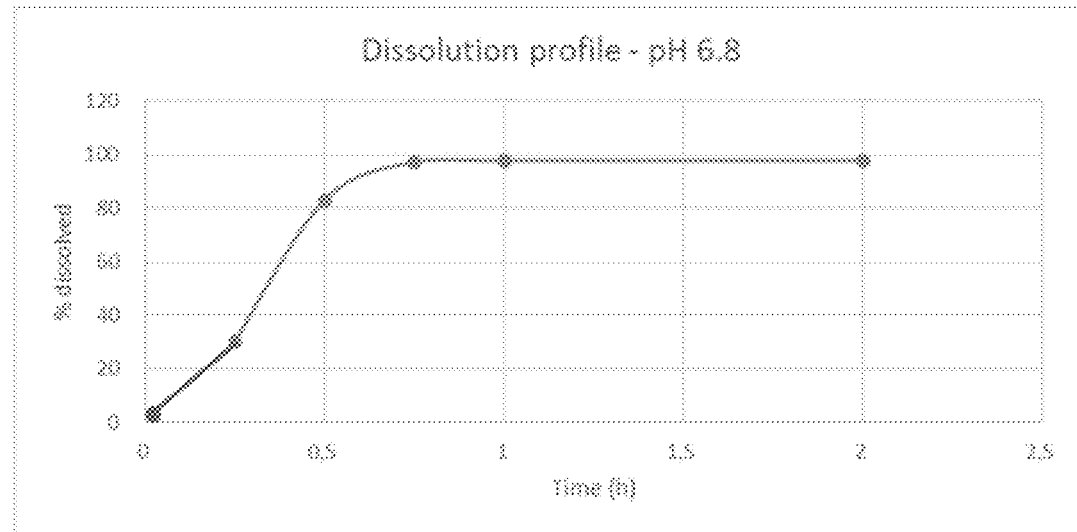

FIG. 35 depicts the dissolution profile of the formulation of Example 11a in pH6.8 phosphate buffer (0.05M monobasic potassium phosphate solution—pH adjusted to 6.8 with 5N NaOH) using a USP apparatus 2.

Figure 36:
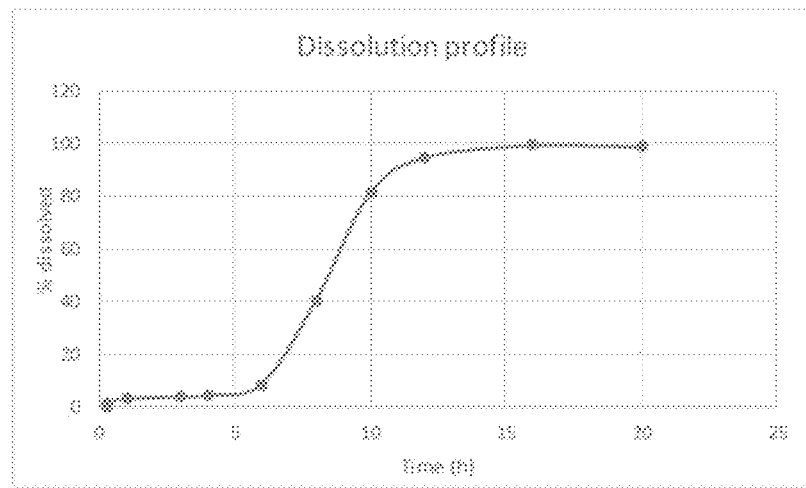

FIG. 36 depicts the dissolution profile of the MR portion of the formulation of Example 11b in 900 ml of 0.1N HCl using a USP apparatus 2.

Figure 37:
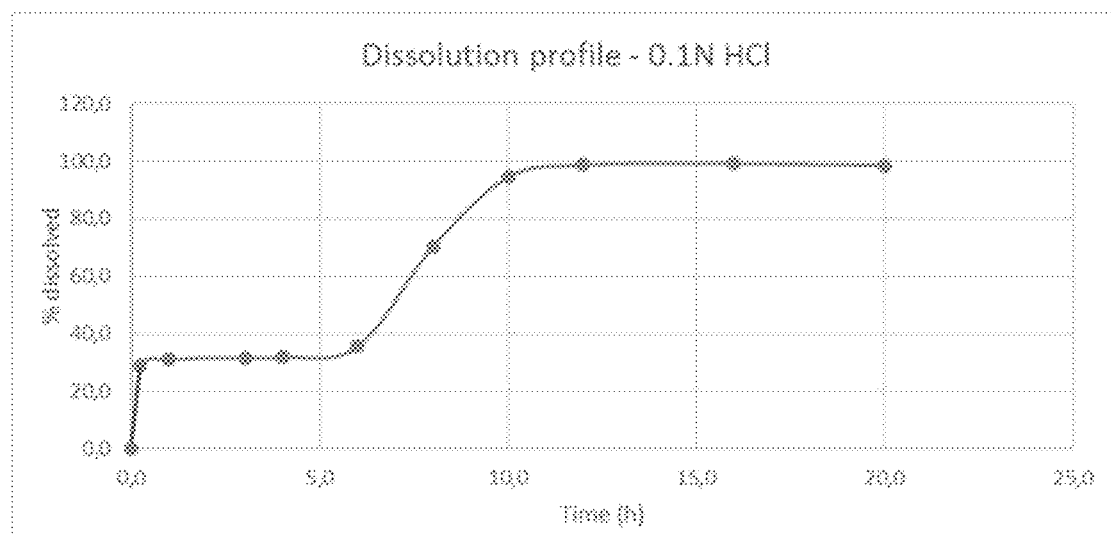

FIG. 37 depicts the dissolution profile of the formulation of Example 11b in 900 ml of 0.1N HCl using a USP apparatus 2.

Figure 38:
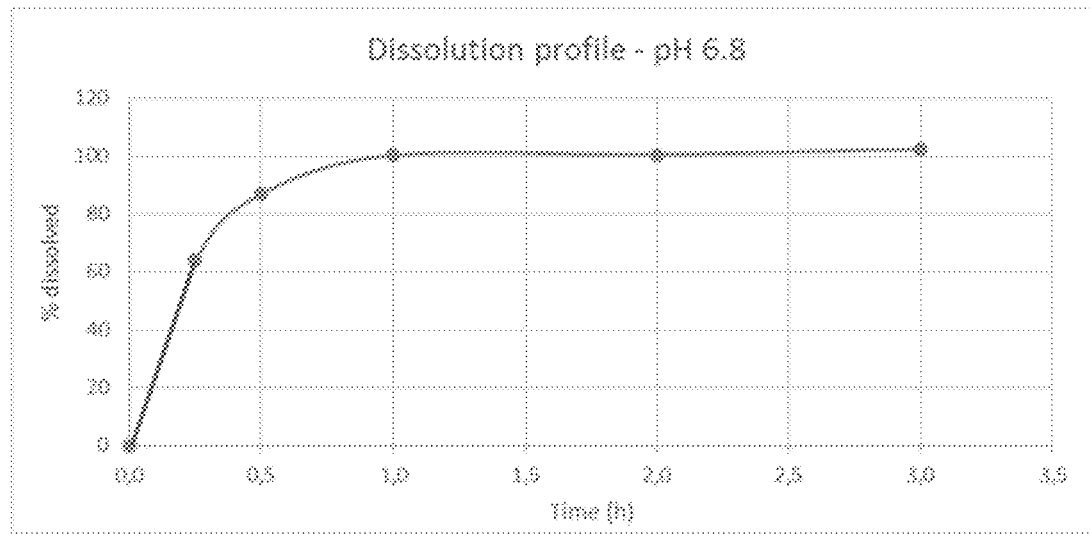

FIG. 38 depicts the dissolution profile of the formulation of Example 11b in pH6.8 phosphate buffer (0.05M monobasic potassium phosphate solution—pH adjusted to 6.8 with 5N NaOH) using a USP apparatus 2.

Figure 39:
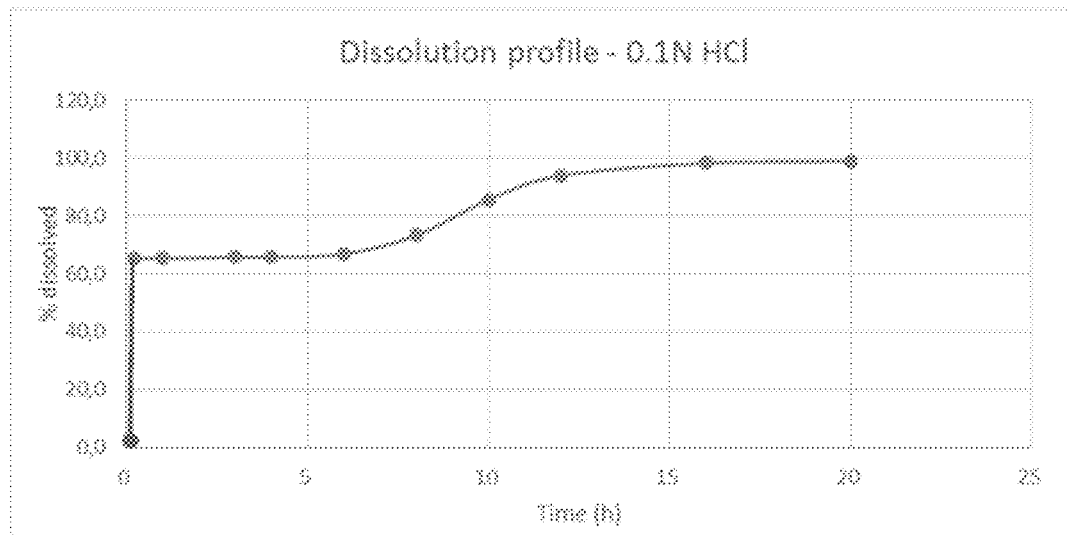

FIG. 39 depicts the dissolution profile of the formulation of Example 11c in 900 ml of 0.1N HCl using a USP apparatus 2.

Figure 40:
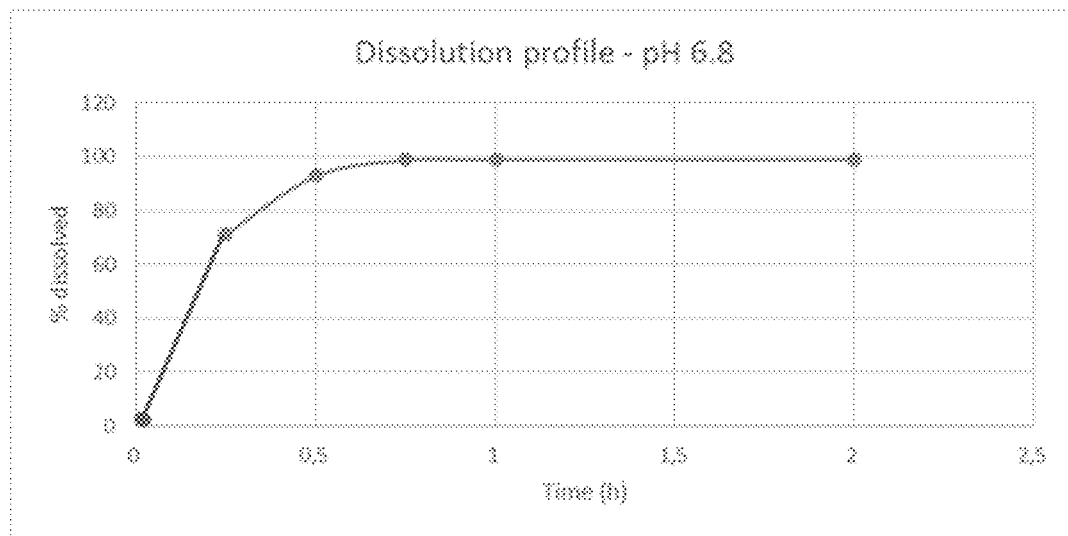

FIG. 40 depicts the dissolution profile of the formulation of Example 11c in pH6.8 phosphate buffer (0.05M monobasic potassium phosphate solution—pH adjusted to 6.8 with 5N NaOH) using a USP apparatus 2.

Figure 41:
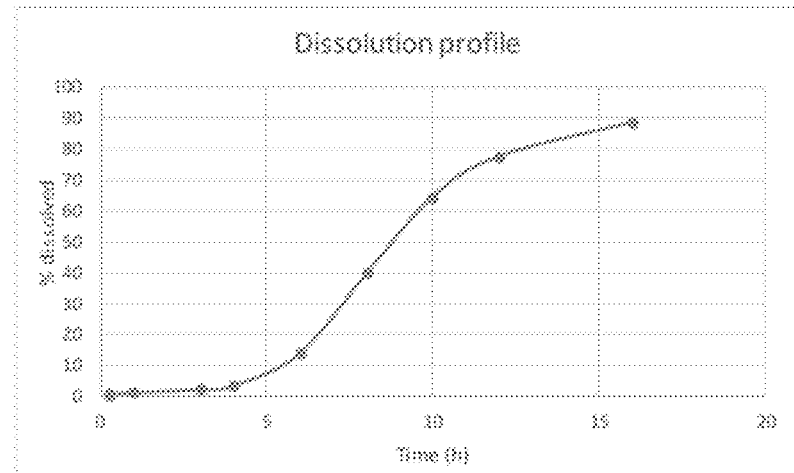

FIG. 41 depicts the dissolution profile of the MR portion of the formulation of Example 12a in 900 ml of 0.1N HCl using a USP apparatus 2.

Figure 42:
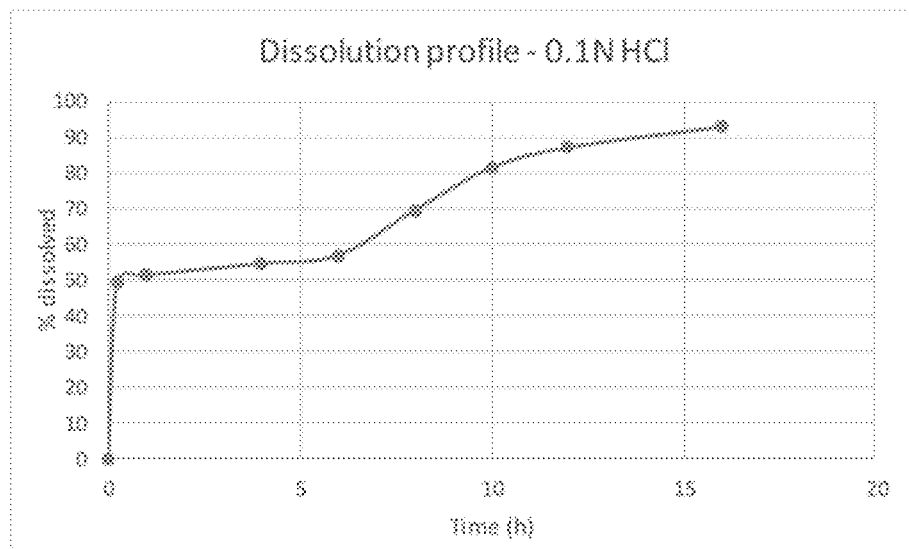

FIG. 42 depicts the dissolution profile of the formulation of Example 12a using a USP apparatus 2 in 0.1N HCl.

Figure 43:
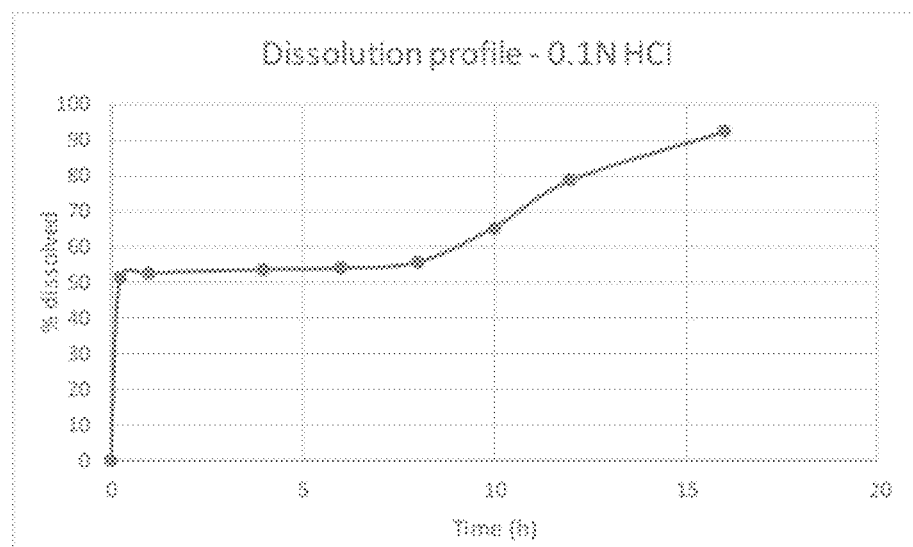

FIG. 43 depicts the dissolution profile of the formulation of Example 12b in 900 ml of 0.1N HCl using a USP apparatus 2.

Figure 44:
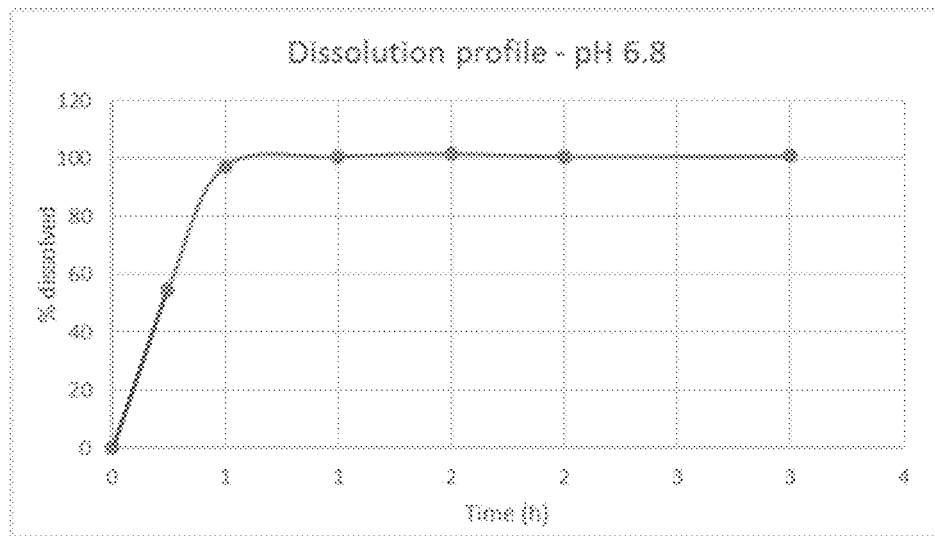

FIG. 44 depicts the dissolution profile of the formulation of Example 12b in pH6.8 phosphate buffer (0.05M monobasic potassium phosphate solution—pH adjusted to 6.8 with 5N NaOH) using a USP apparatus 2.

Figure 45:
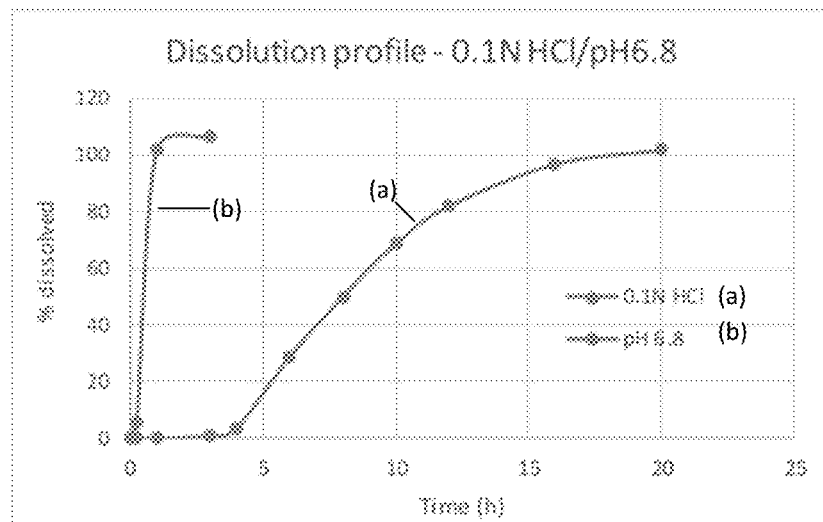

FIG. 45 depicts the dissolution profile of the MR portion of the formulation of Example 13 in 900 ml of 0.1N HCl and pH 6.8 phosphate buffer (0.05M monobasic potassium phosphate solution—pH adjusted to 6.8 with 5N NaOH) using a USP apparatus 2.

Figure 46:
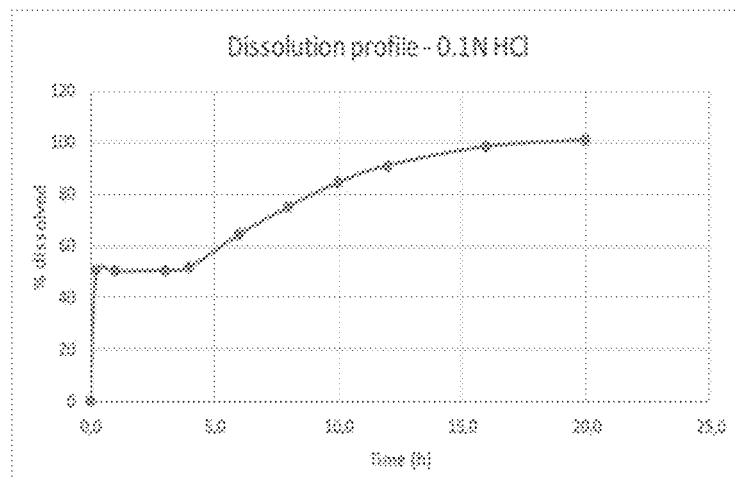

FIG. 46 depicts the dissolution profile of the formulation of Example 13 in 900 ml of 0.1N HCl using a USP apparatus 2.

Figure 47:
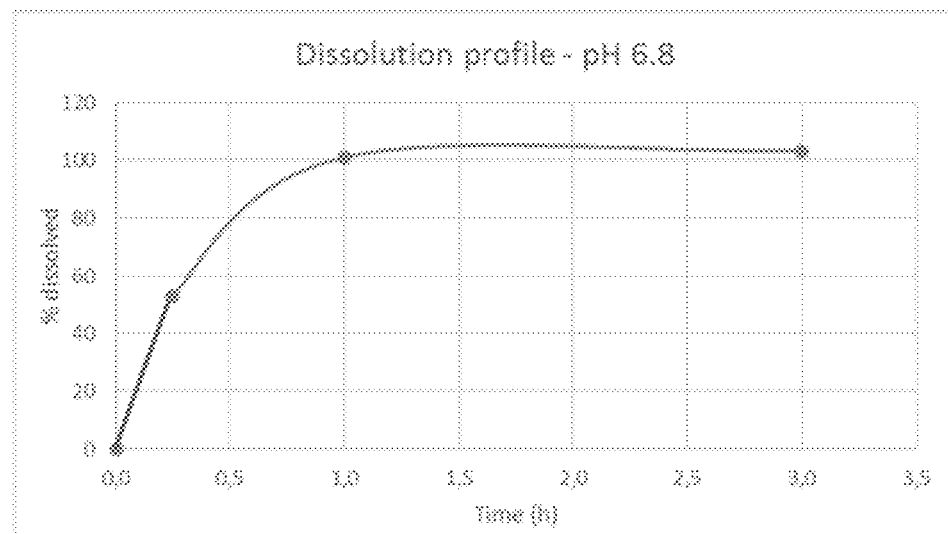

FIG. 47 depicts the dissolution profile of the formulation of Example 13 in pH6.8 phosphate buffer (0.05M monobasic potassium phosphate solution—pH adjusted to 6.8 with 5N NaOH) using a USP apparatus 2.

Figure 48:
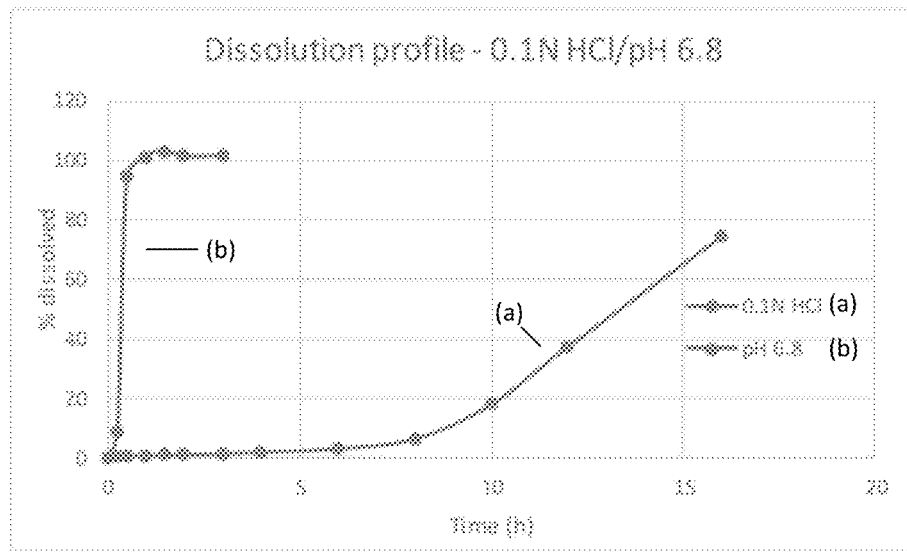

FIG. 48 depicts the dissolution profile of the MR portion of the formulation of Example 14 in 900 ml of 0.1N HCl and pH 6.8 phosphate buffer (0.05M monobasic potassium phosphate solution—pH adjusted to 6.8 with 5N NaOH) using a USP apparatus 2.

Figure 49:
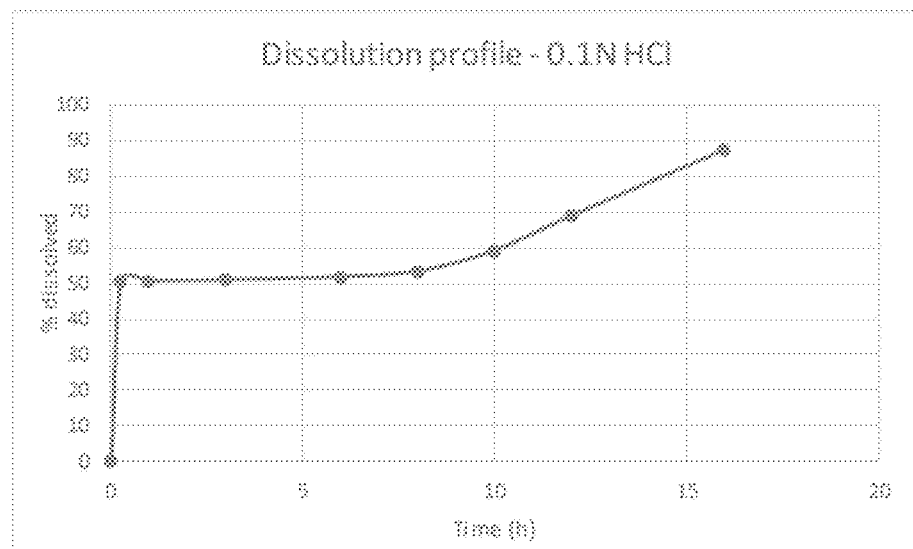

FIG. 49 depicts the dissolution profile of the formulation of Example 14 in 900 ml of 0.1N HCl using a USP apparatus 2.

Figure 50:
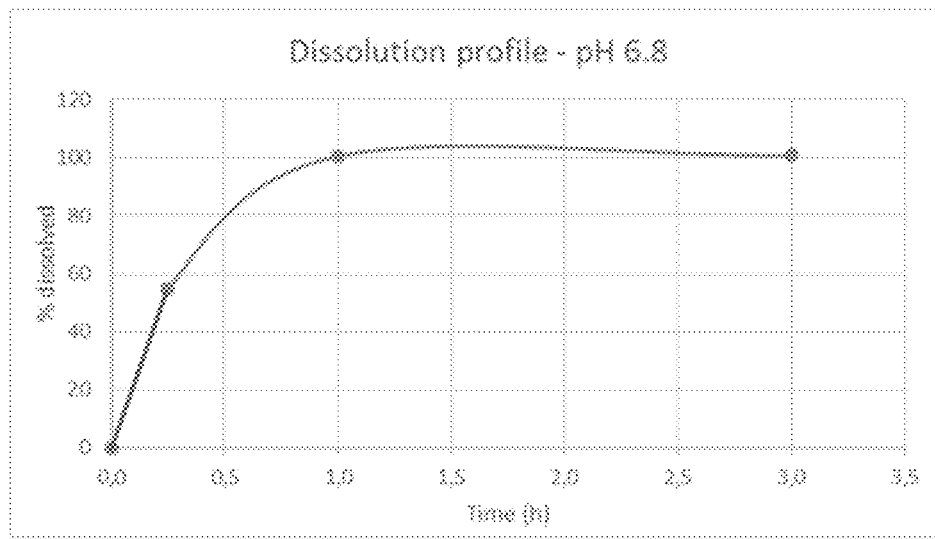

FIG. 50 depicts the dissolution profile of the formulation of Example 14 in pH6.8 phosphate buffer (0.05M monobasic potassium phosphate solution—pH adjusted to 6.8 with 5N NaOH) using a USP apparatus 2.

Figure 51:
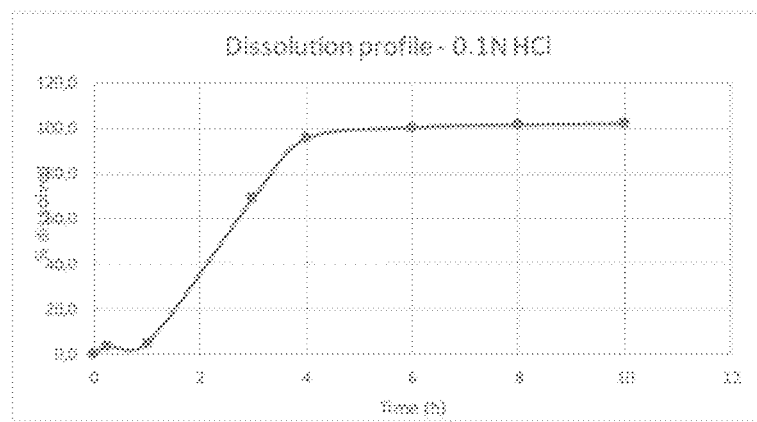

FIG. 51 depicts the dissolution profile of the MR portion of the formulation of Example 15a (coating weight 35%) in 900 ml of 0.1N HCl using a USP apparatus 2.

Figure 52:
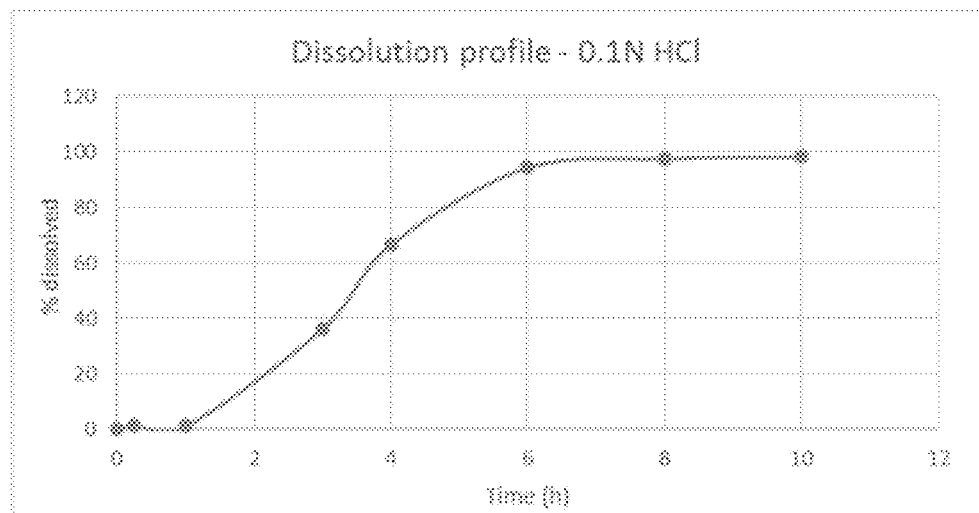

FIG. 52 depicts the dissolution profile of the MR portion of the formulation of Example 15a (coating weight 50%) in 900 ml of 0.1N HCl using a USP apparatus 2.

Figure 53:
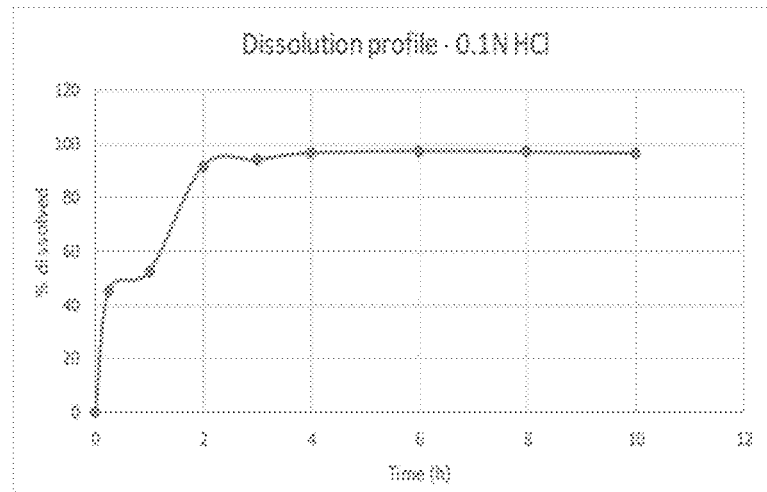

FIG. 53 depicts the dissolution profile of the formulation of Example 15a in 900 ml of 0.1N HCl using a USP apparatus 2.

Figure 54:
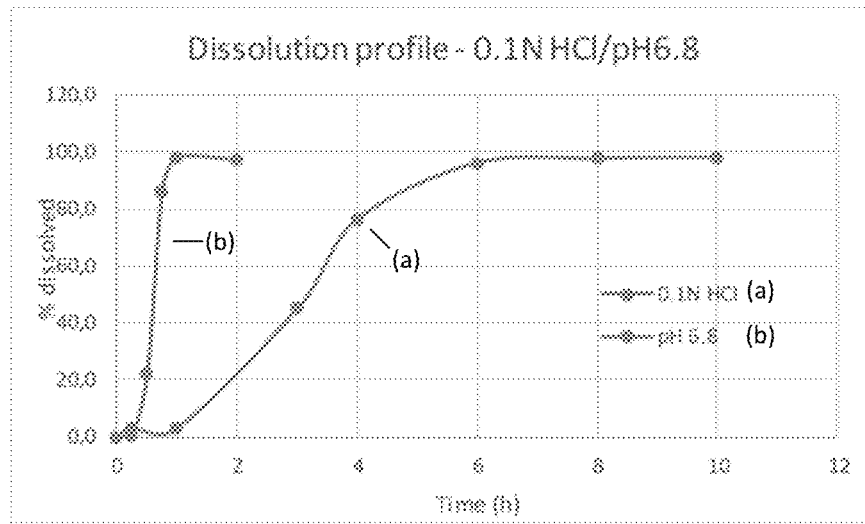

FIG. 54 depicts the dissolution profile of the MR portion of the formulation of Example 15b in 900 ml of 0.1N HCl and pH 6.8 phosphate buffer (0.05M monobasic potassium phosphate solution—pH adjusted to 6.8 with 5N NaOH) using a USP apparatus 2.

Figure 55:
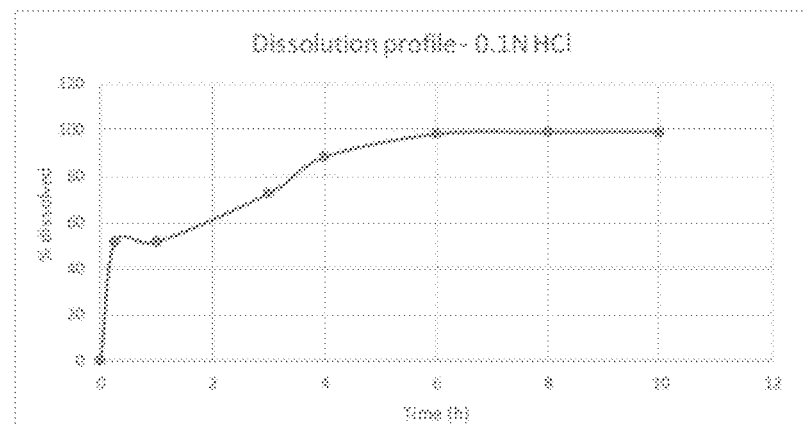

FIG. 55 depicts the dissolution profile of the formulation of Example 15b in 900 ml of 0.1N HCl using a USP apparatus 2.

Figure 56:
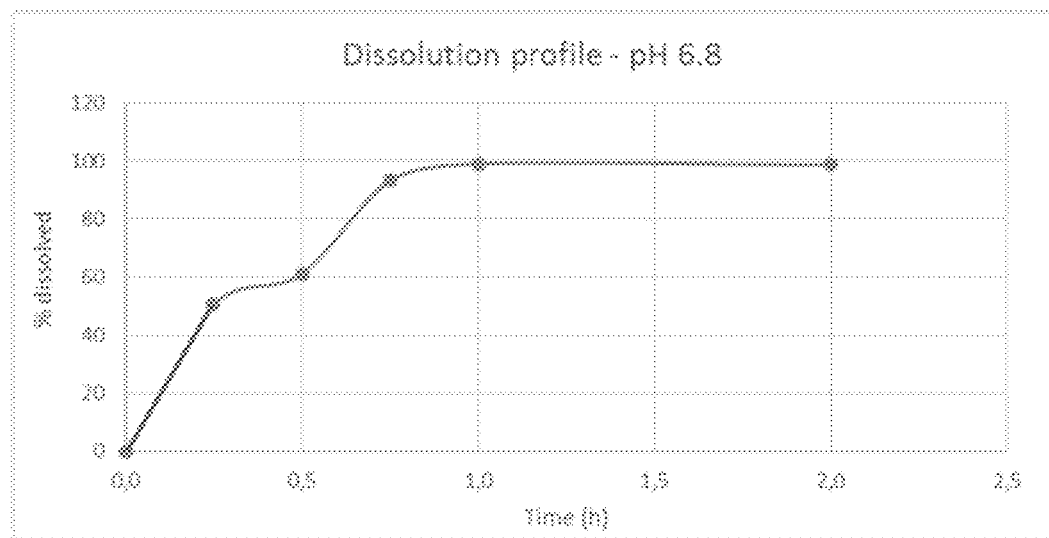

FIG. 56 depicts the dissolution profile of the formulation of Example 15b in pH6.8 phosphate buffer (0.05M monobasic potassium phosphate solution—pH adjusted to 6.8 with 5N NaOH) using a USP apparatus 2.

Figure 57:
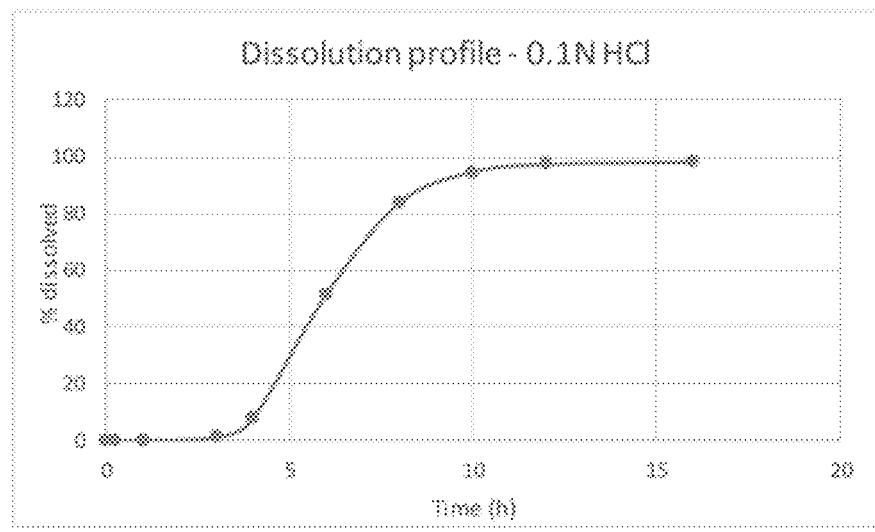

FIG. 57 depicts the dissolution profile of the MR portion of the formulation of Example 15c in 900 ml of 0.1N HCl using a USP apparatus 2.

Figure 58:
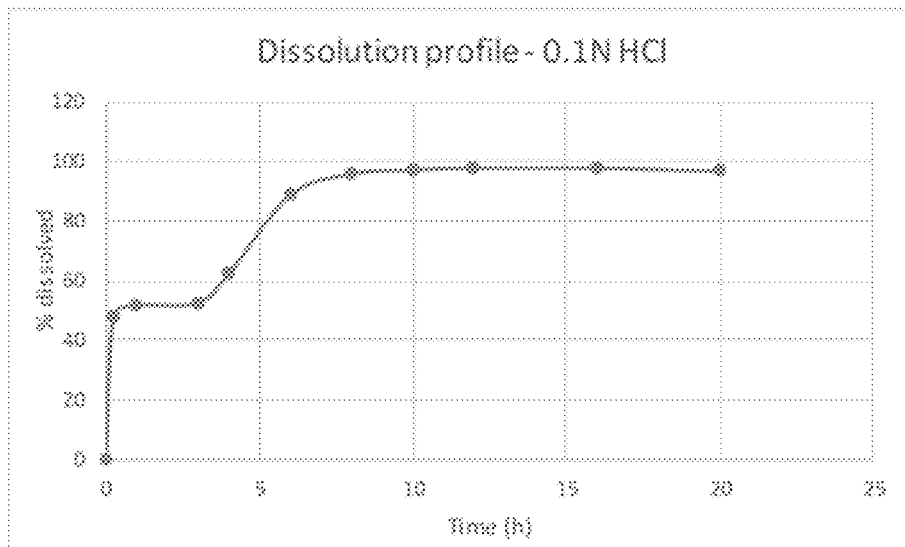

FIG. 58 depicts the dissolution profile of the formulation of Example 15c in 900 ml of 0.1N HCl using a USP apparatus 2.

Figure 59:
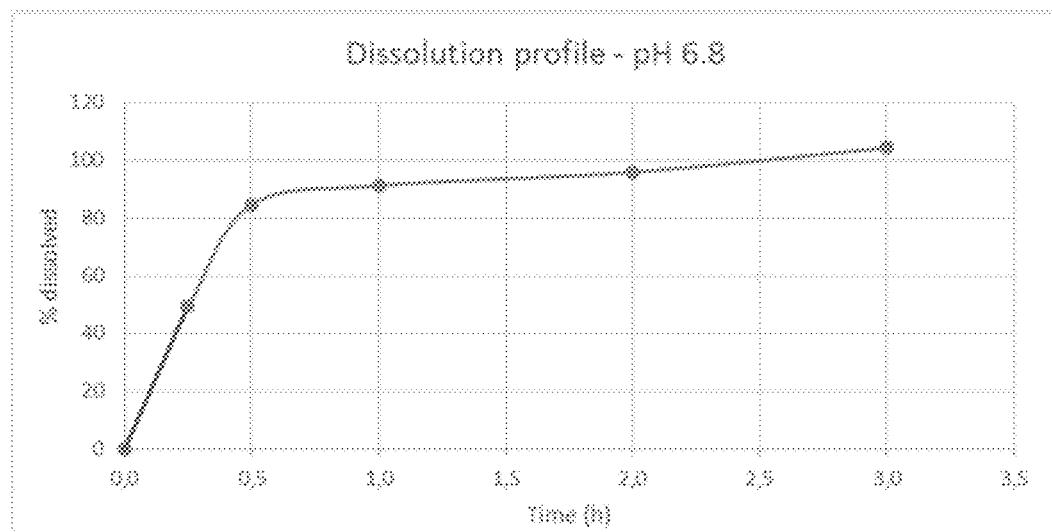

FIG. 59 depicts the dissolution profile of the formulation of Example 15c in pH6.8 phosphate buffer (0.05M monobasic potassium phosphate solution—pH adjusted to 6.8 with 5N NaOH) using a USP apparatus 2.

Figure 60:
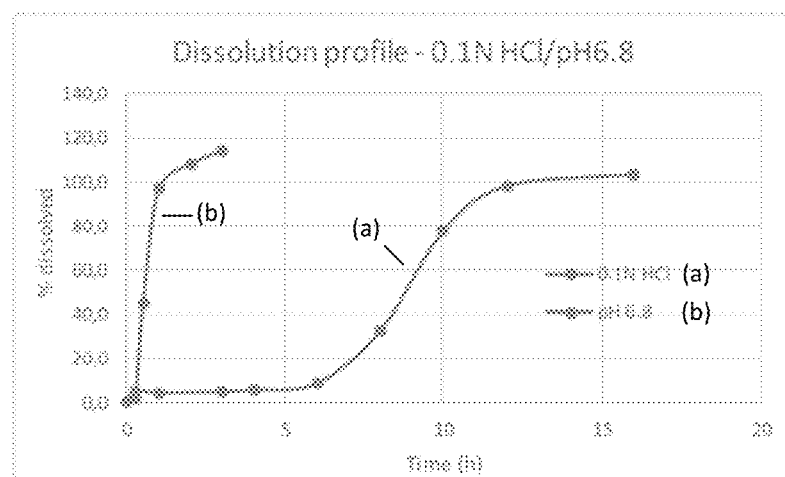

FIG. 60 depicts the dissolution profile of the MR portion of the formulation of Example 15d in 900 ml of 0.1N HCl and pH 6.8 phosphate buffer (0.05M monobasic potassium phosphate solution—pH adjusted to 6.8 with 5N NaOH) using a USP apparatus 2.

Figure 61:
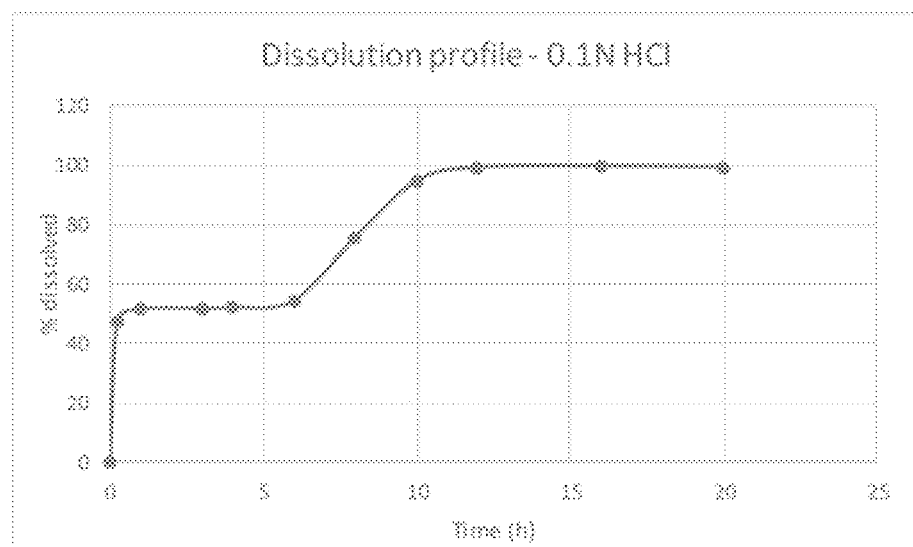

FIG. 61 depicts the dissolution profile of the formulation of Example 15d in 900 ml of 0.1N HCl using a USP apparatus 2.

Figure 62:
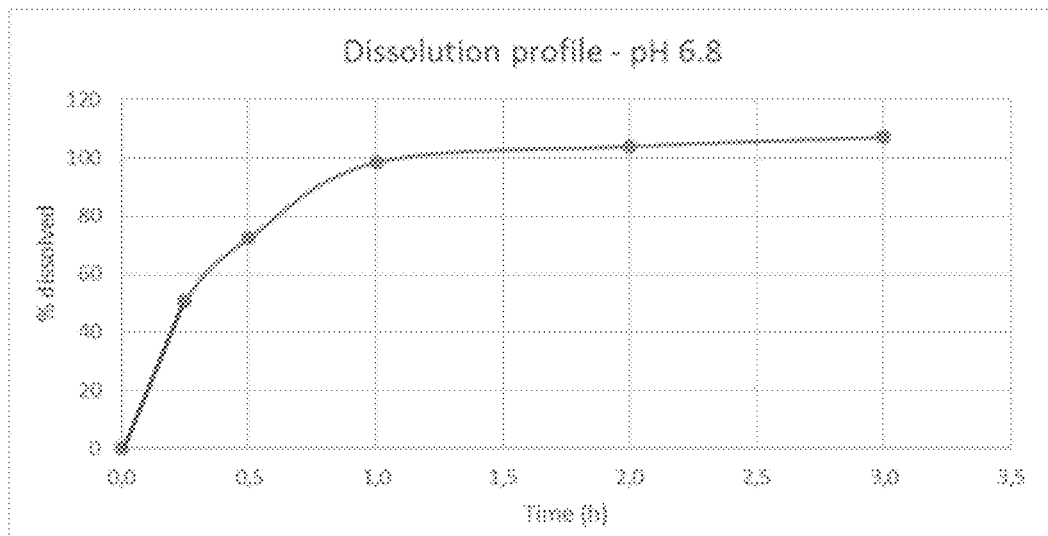

FIG. 62 depicts the dissolution profile of the formulation of Example 15d in pH6.8 phosphate buffer (0.05M monobasic potassium phosphate solution—pH adjusted to 6.8 with 5N NaOH) using a USP apparatus 2.

Figure 63:
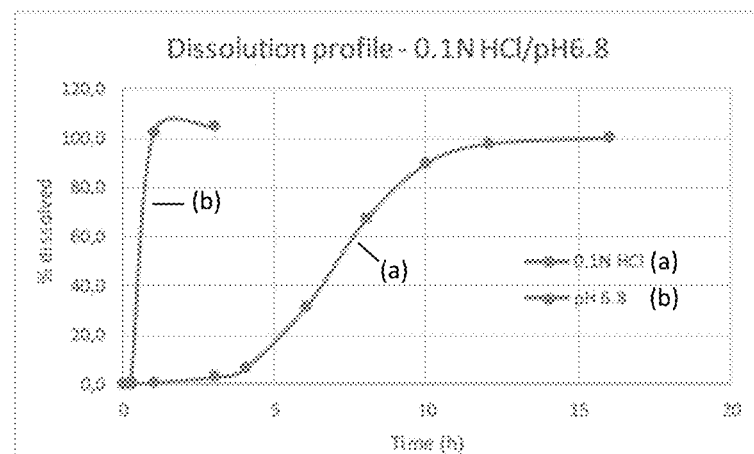

FIG. 63 depicts the dissolution profile of the MR portion of the formulation of Example 16a in 900 ml of 0.1N HCl and pH 6.8 phosphate buffer (0.05M monobasic potassium phosphate solution—pH adjusted to 6.8 with 5N NaOH) using a USP apparatus 2.

Figure 64:
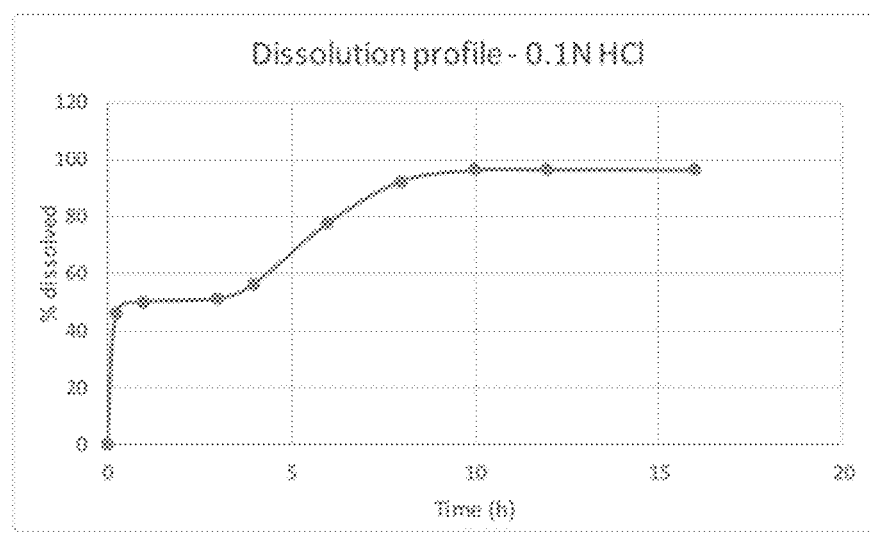

FIG. 64 depicts the dissolution profile of the formulation of Example 16a in 900 ml of 0.1N HCl using a USP apparatus 2.

Figure 65:
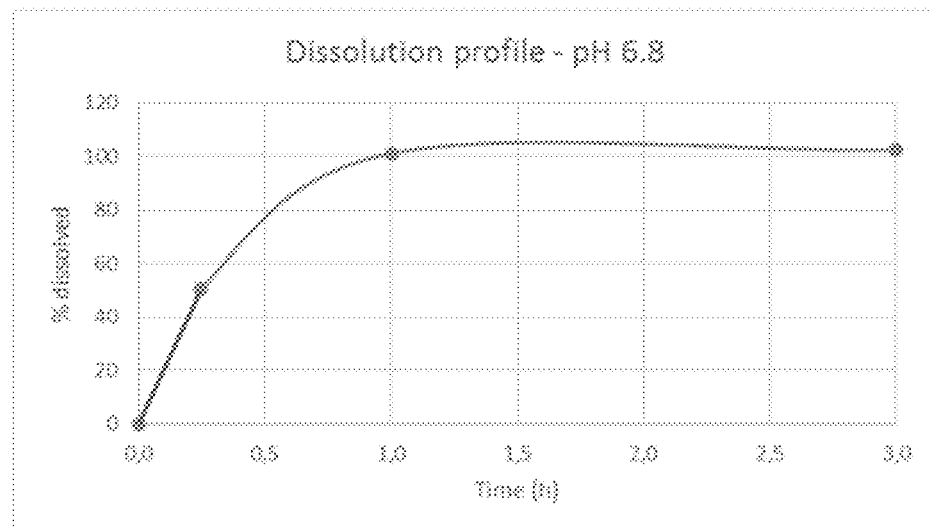

FIG. 65 depicts the dissolution profile of the formulation of Example 16a in pH6.8 phosphate buffer (0.05M monobasic potassium phosphate solution—pH adjusted to 6.8 with 5N NaOH) using a USP apparatus 2.

Figure 66:
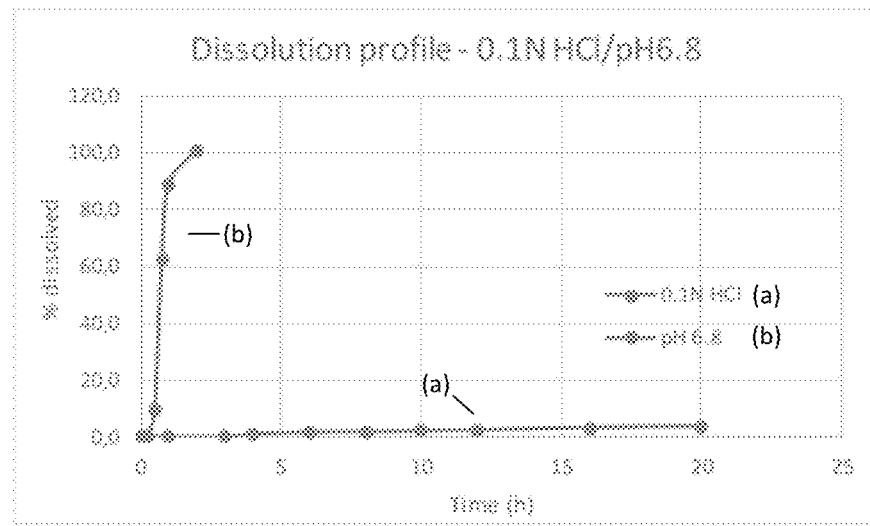

FIG. 66 depicts the dissolution profile of the MR portion of the formulation of Example 16b in 900 ml of 0.1N HCl and pH 6.8 phosphate buffer (0.05M monobasic potassium phosphate solution—pH adjusted to 6.8 with 5N NaOH) using a USP apparatus 2.

Figure 67:
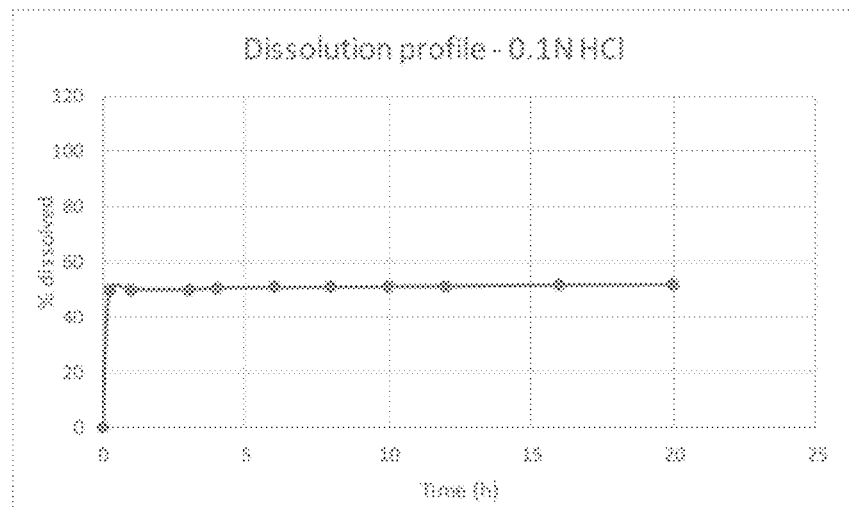

FIG. 67 depicts the dissolution profile of the formulation of Example 16b in 900 ml of 0.1N HCl using a USP apparatus 2.

Figure 68:
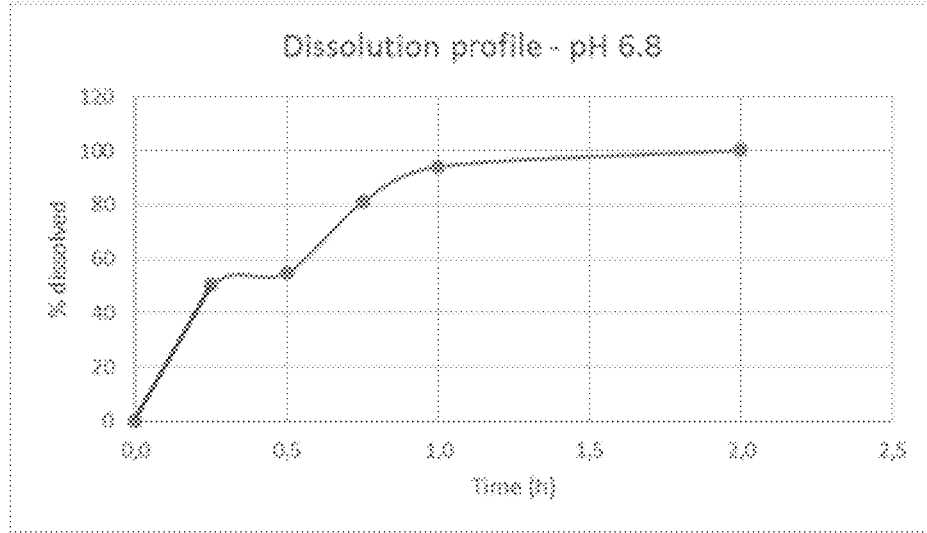

FIG. 68 depicts the dissolution profile of the formulation of Example 16b in pH6.8 phosphate buffer (0.05M monobasic potassium phosphate solution—pH adjusted to 6.8 with 5N NaOH) using a USP apparatus 2.

Figure 69:
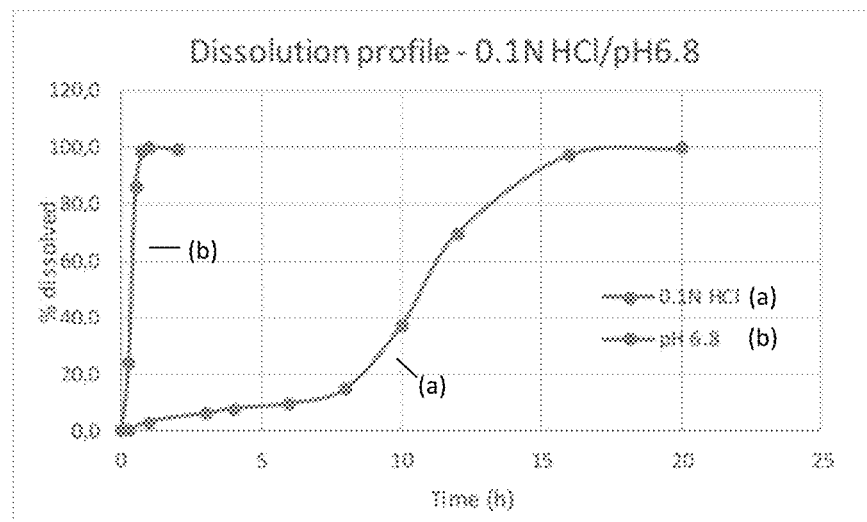

FIG. 69 depicts the dissolution profile of the MR portion of the formulation of Example 16c in 900 ml of 0.1N HCl and pH 6.8 phosphate buffer (0.05M monobasic potassium phosphate solution—pH adjusted to 6.8 with 5N NaOH) using a USP apparatus 2.

Figure 70:
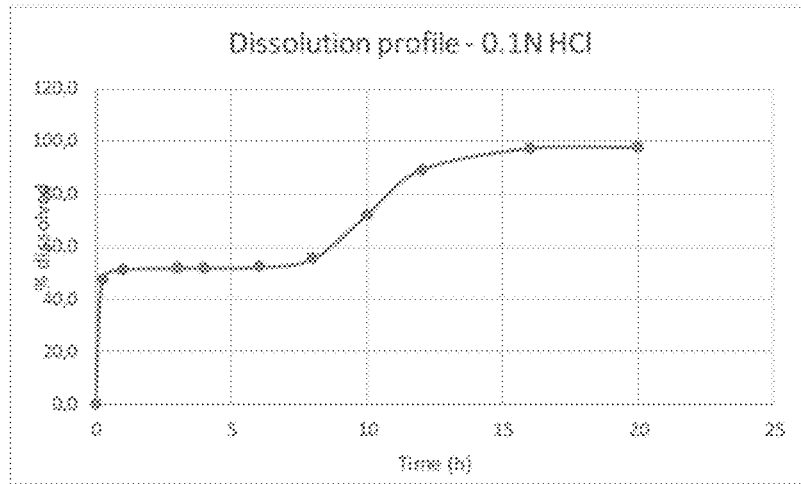

FIG. 70 depicts the dissolution profile of the formulation of Example 16c in 900 ml of 0.1N HCl using a USP apparatus 2.

Figure 71:
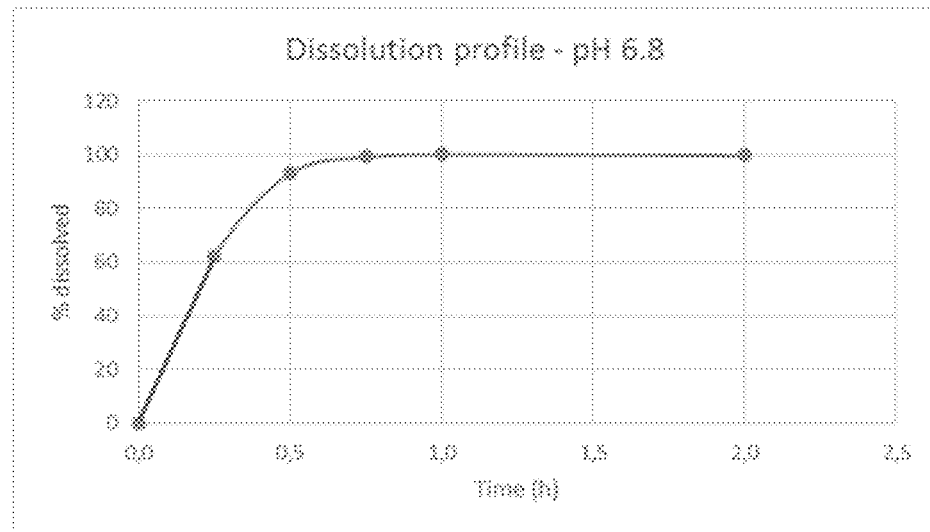

FIG. 71 depicts the dissolution profile of the formulation of Example 16c in pH6.8 phosphate buffer (0.05M monobasic potassium phosphate solution—pH adjusted to 6.8 with 5N NaOH) using a USP apparatus 2.

Figure 72:
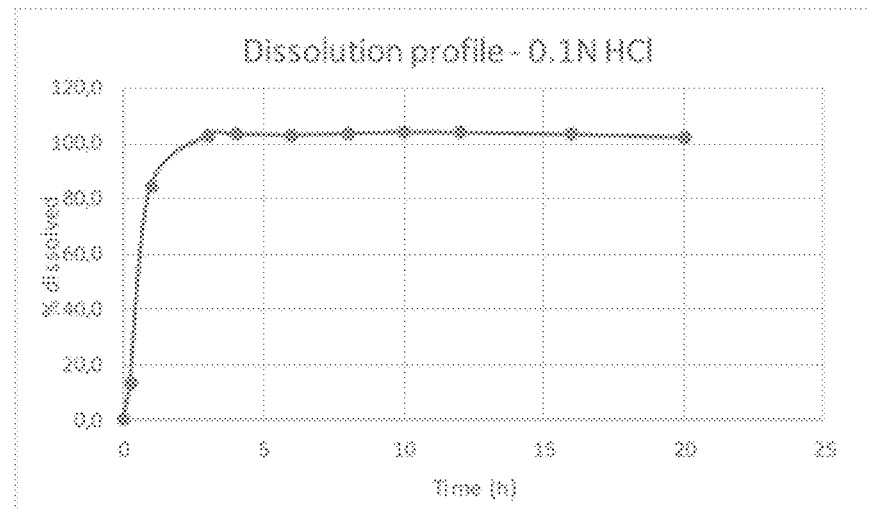

FIG. 72 depicts the dissolution profile of the MR portion of the formulation of Example 16d in 900 ml of 0.1N HCl using a USP apparatus 2.

Figure 73:
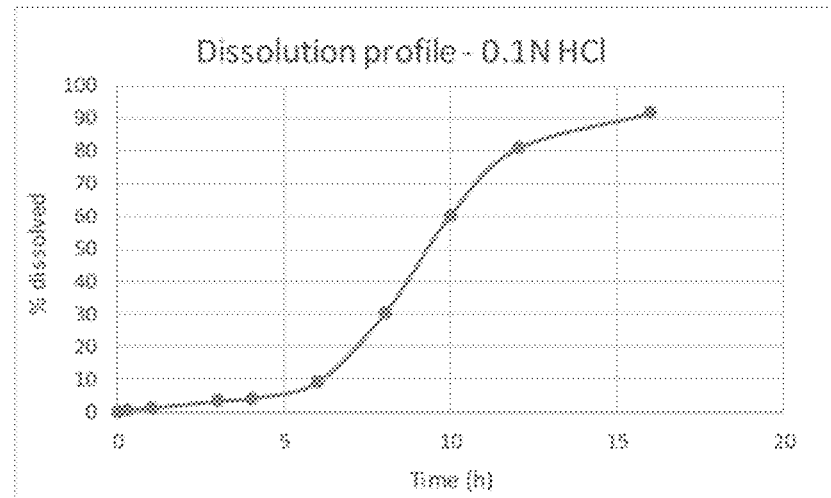

FIG. 73 depicts the dissolution profile of the MR portion of the formulation of Example 17a in 900 ml of 0.1N HCl using a USP apparatus 2.

Figure 74:
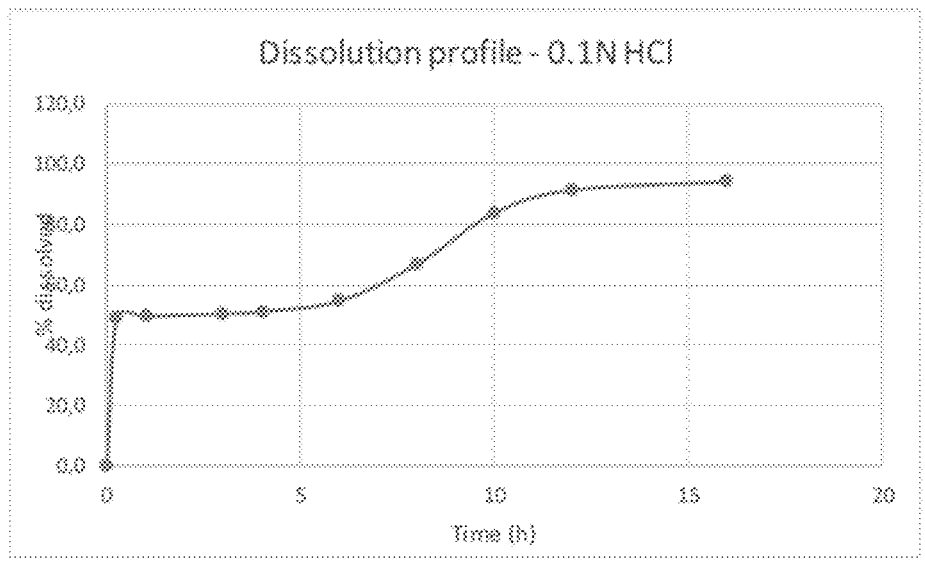

FIG. 74 depicts the dissolution profile of the formulation of Example 17a in 900 ml of 0.1N HCl using a USP apparatus 2.

Figure 75:
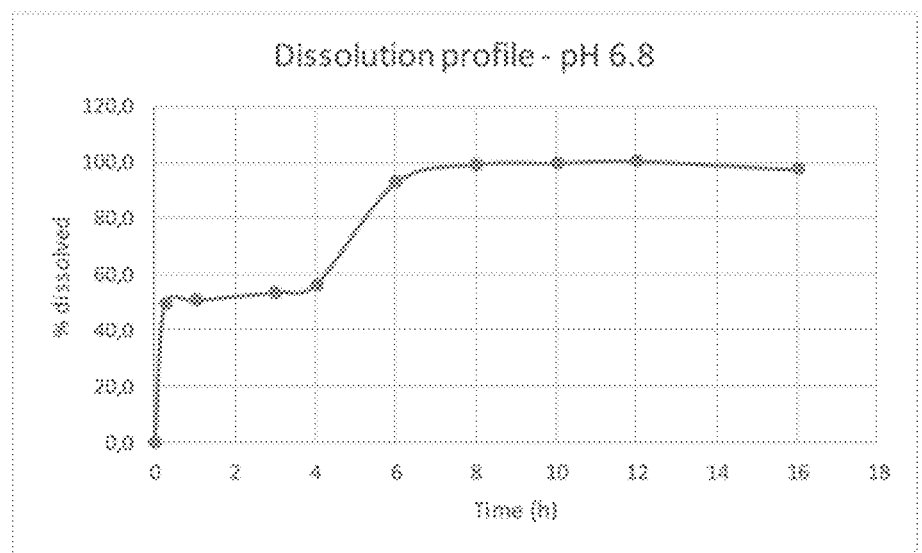

FIG. 75 depicts the dissolution profile of the formulation of Example 17a in pH6.8 phosphate buffer (0.05M monobasic potassium phosphate solution—pH adjusted to 6.8 with 5N NaOH) using a USP apparatus 2.

Figure 76:
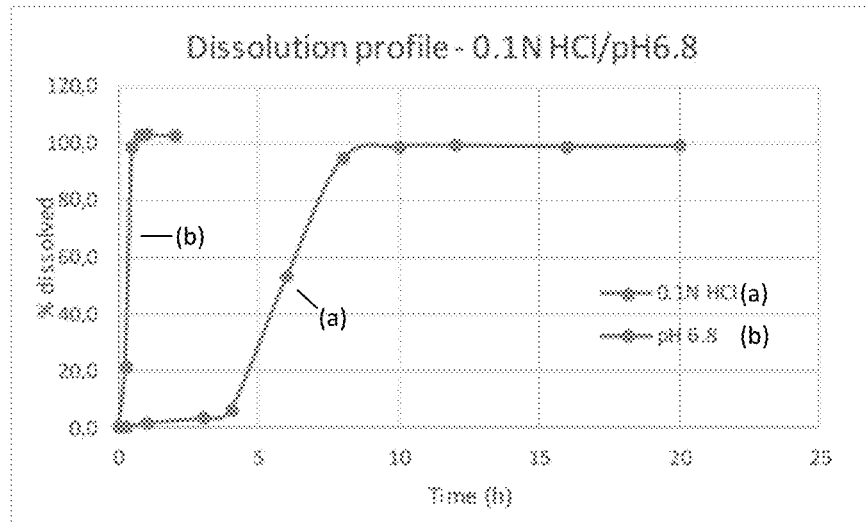

FIG. 76 depicts the dissolution profile of the MR portion of the formulation of Example 17b in 900 ml of 0.1N HCl and pH 6.8 phosphate buffer (0.05M monobasic potassium phosphate solution—pH adjusted to 6.8 with 5N NaOH) using a USP apparatus 2.

Figure 77:
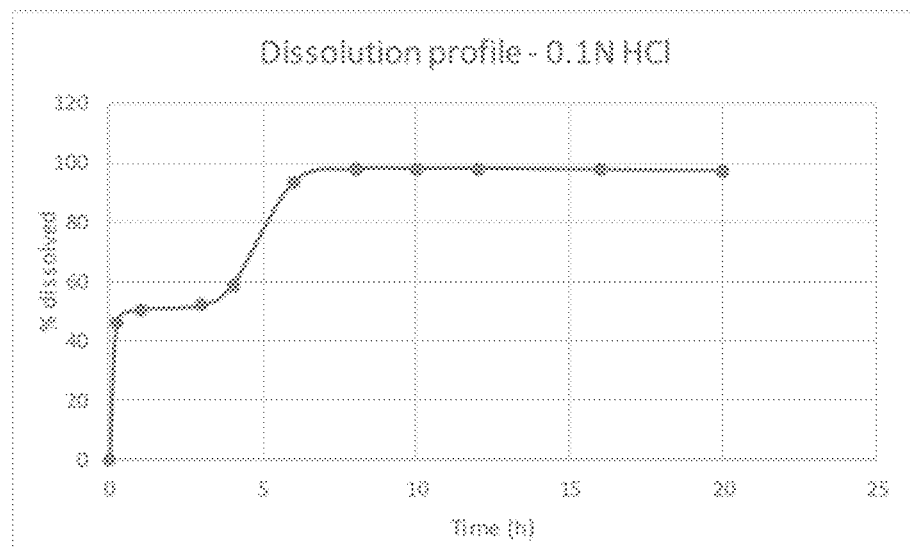

FIG. 77 depicts the dissolution profile of the formulation of Example 17b in 900 ml of 0.1N HCl using a USP apparatus 2.

Figure 78:
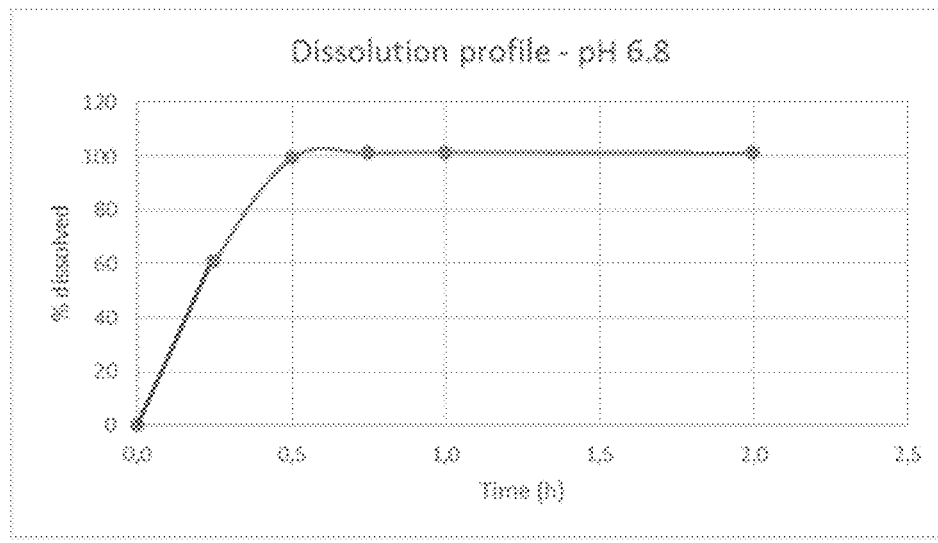

FIG. 78 depicts the dissolution profile of the formulation of Example 17b in pH6.8 phosphate buffer (0.05M monobasic potassium phosphate solution—pH adjusted to 6.8 with 5N NaOH) using a USP apparatus 2.

Figure 79:
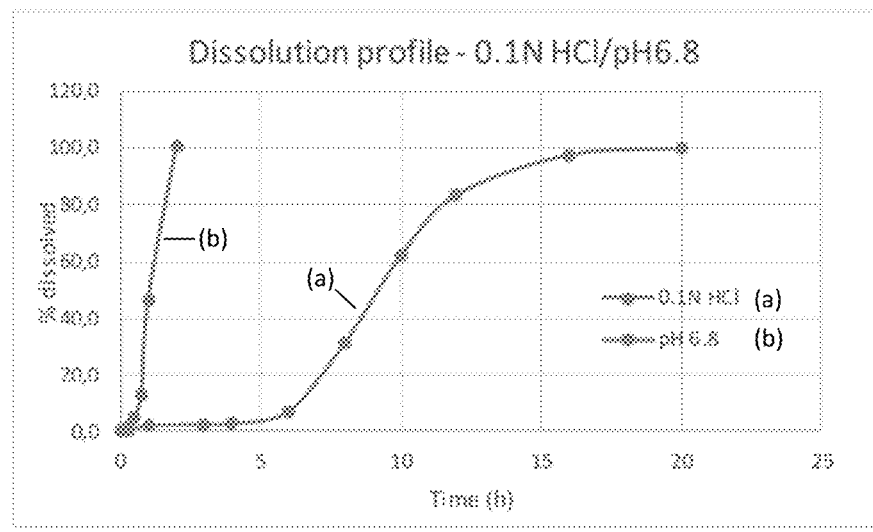

FIG. 79 depicts the dissolution profile of the MR portion of the formulation of Example 17c in 900 ml of 0.1N HCl and pH 6.8 phosphate buffer (0.05M monobasic potassium phosphate solution—pH adjusted to 6.8 with 5N NaOH) using a USP apparatus 2.

Figure 80:
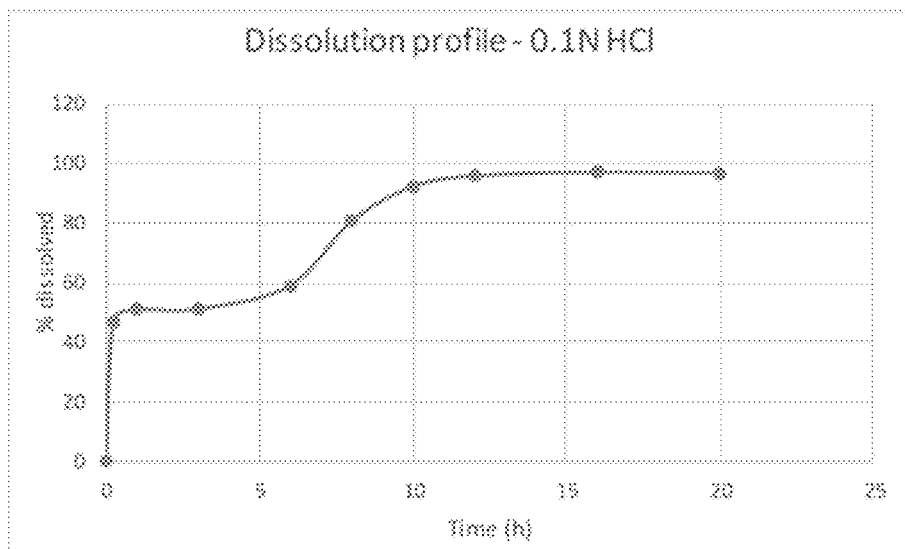

FIG. 80 depicts the dissolution profile of the formulation of Example 17c in 900 ml of 0.1N HCl using a USP apparatus 2.

Figure 81:
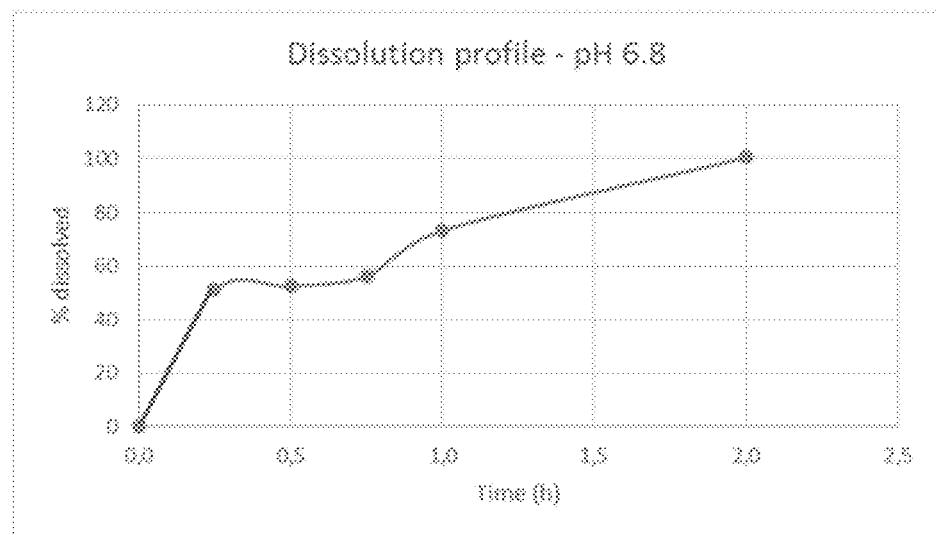

FIG. 81 depicts the dissolution profile of the formulation of Example 17c in pH6.8 phosphate buffer (0.05M monobasic potassium phosphate solution—pH adjusted to 6.8 with 5N NaOH) using a USP apparatus 2.

Figure 82:
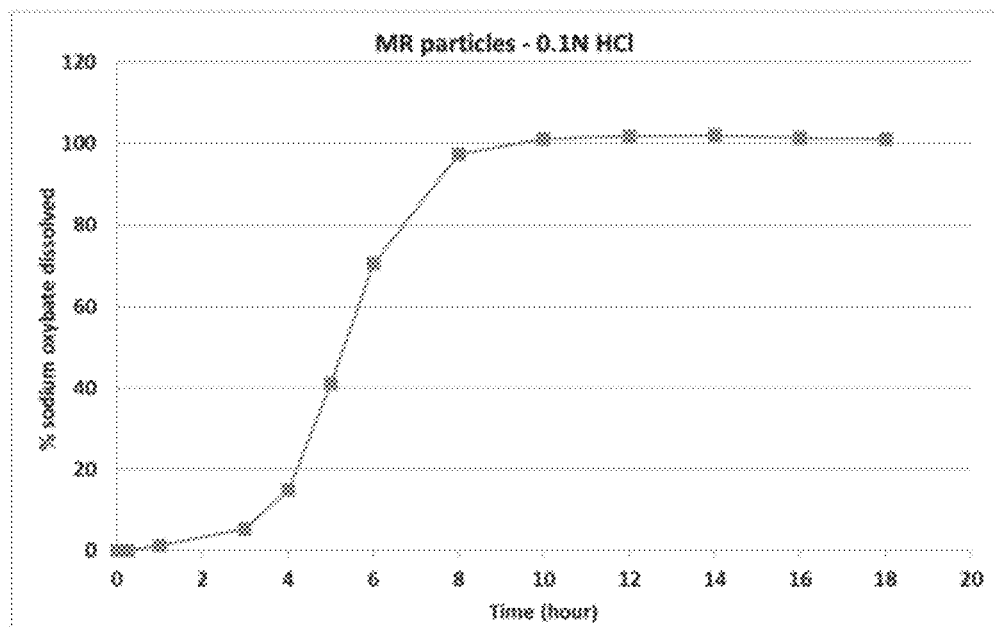

FIG. 82 depicts a preferred dissolution profile of sodium oxybate MR microparticles in 900 ml 0.1N HCl using a USP apparatus 2 at 75 rpm.

Figure 83:
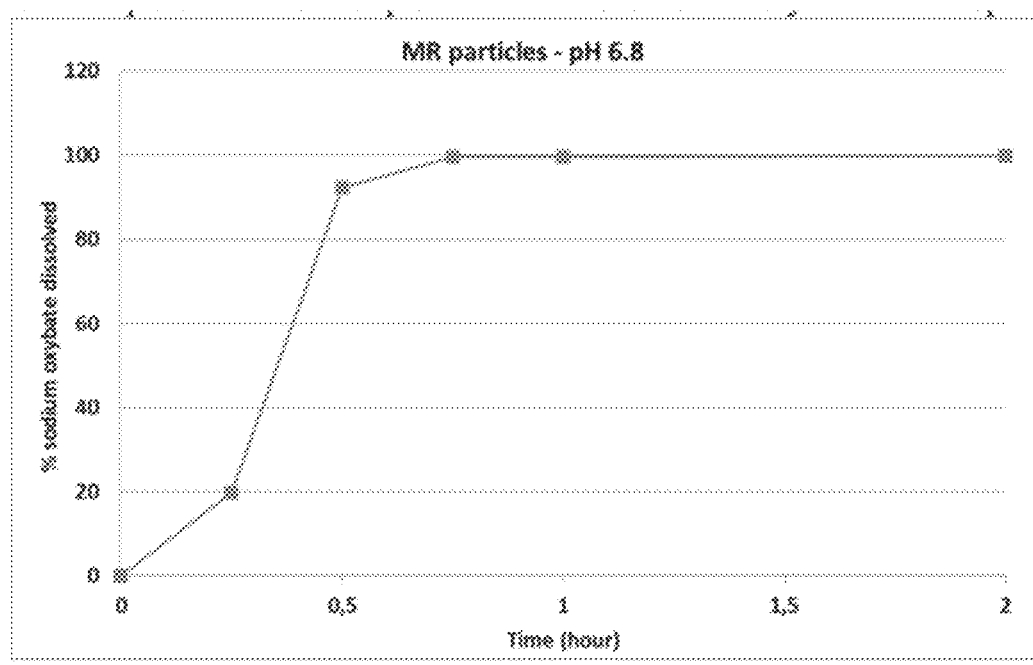

FIG. 83 depicts a preferred dissolution profile of sodium oxybate MR microparticles in 900 ml pH 6.8 phosphate buffer (0.05M monobasic potassium phosphate solution—pH adjusted to 6.8 with 5N NaOH) using a USP apparatus 2 at 75 rpm.

Figure 84:
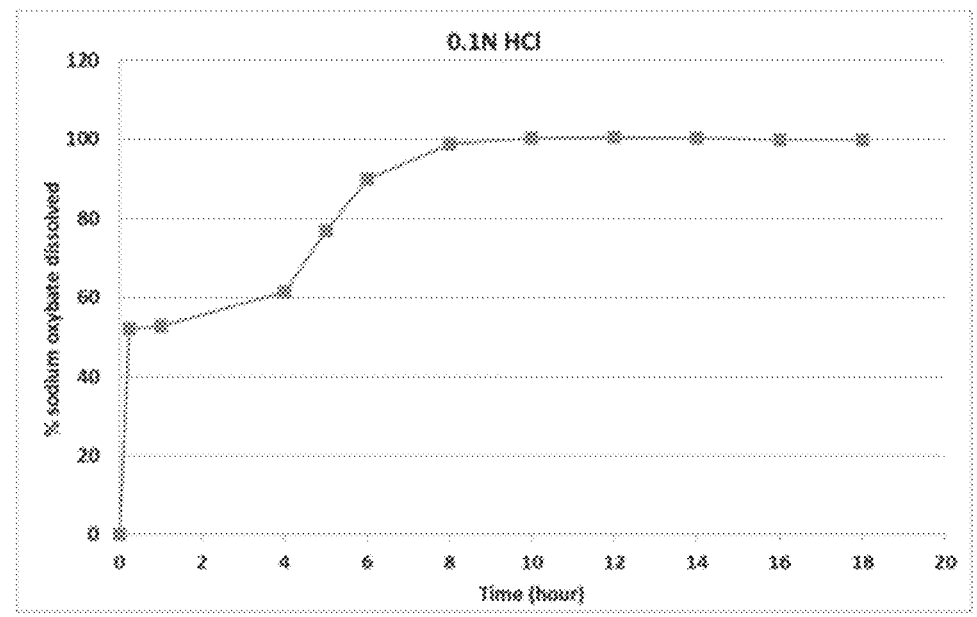

FIG. 84 depicts a preferred dissolution profile of a sodium oxybate finished formulation comprising IR and MR microparticles in 900 ml 0.1N HCl using a USP apparatus 2 at 75 rpm.

Figure 85:
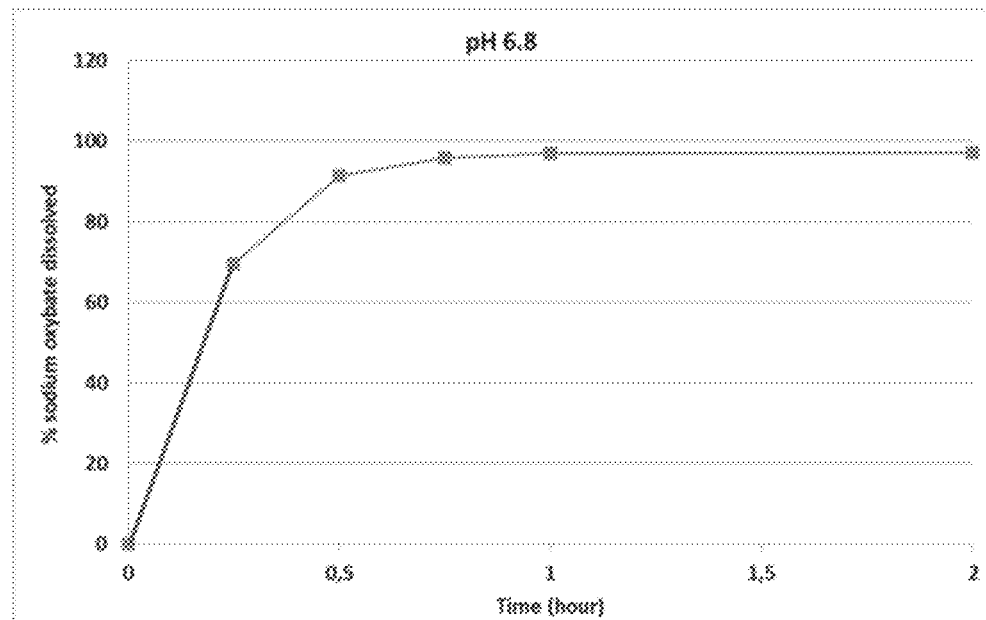

FIG. 85 depicts a preferred dissolution profile of a sodium oxybate finished formulation comprising IR and MR microparticles in 900 ml pH 6.8 phosphate buffer (0.05M monobasic potassium phosphate solution—pH adjusted to 6.8 with 5N NaOH) using a USP apparatus 2 at 75 rpm.

Figure 86:
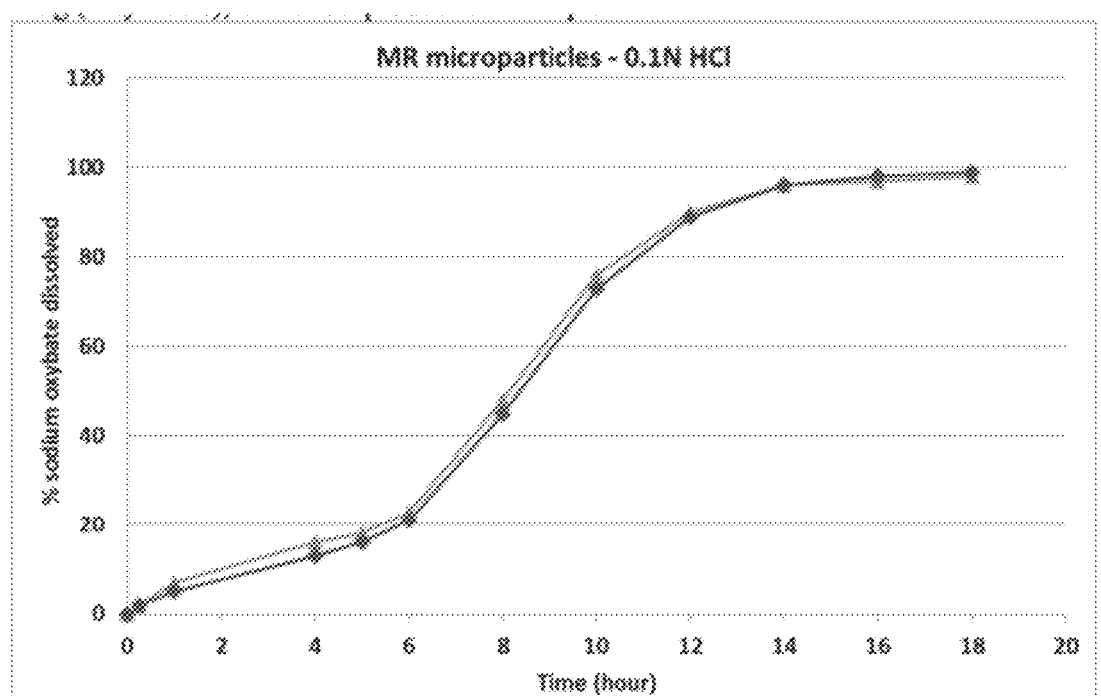

FIG. 86 is a dissolution profile in 0.1N HCl of two separate batches of the sodium oxybate MR microparticles present in the finished composition of Example 18.

Figure 87:
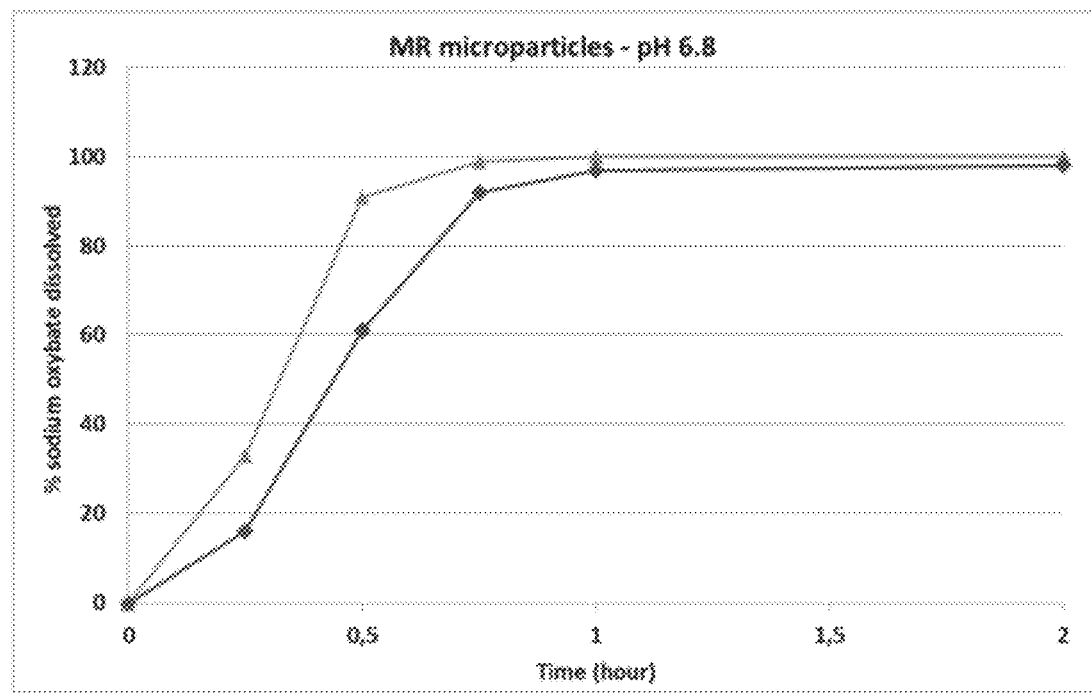

FIG. 87 is a dissolution profile in phosphate buffer pH 6.8 of two separate batches of the sodium oxybate MR microparticles present in the finished composition of Example 18.

Figure 88:
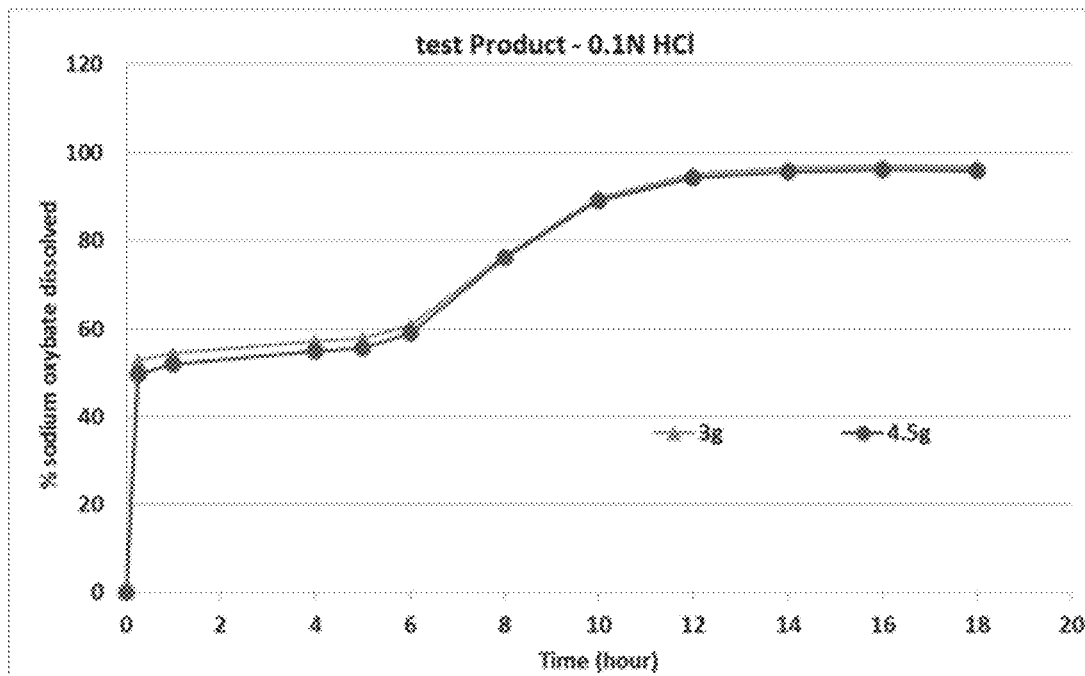

FIG. 88 is a dissolution profile in 0.1N HCl of two unit doses of 3 g (▲ symbols) and 4.5 g (• symbols) of the finished composition of Example 18.

Figure 89:
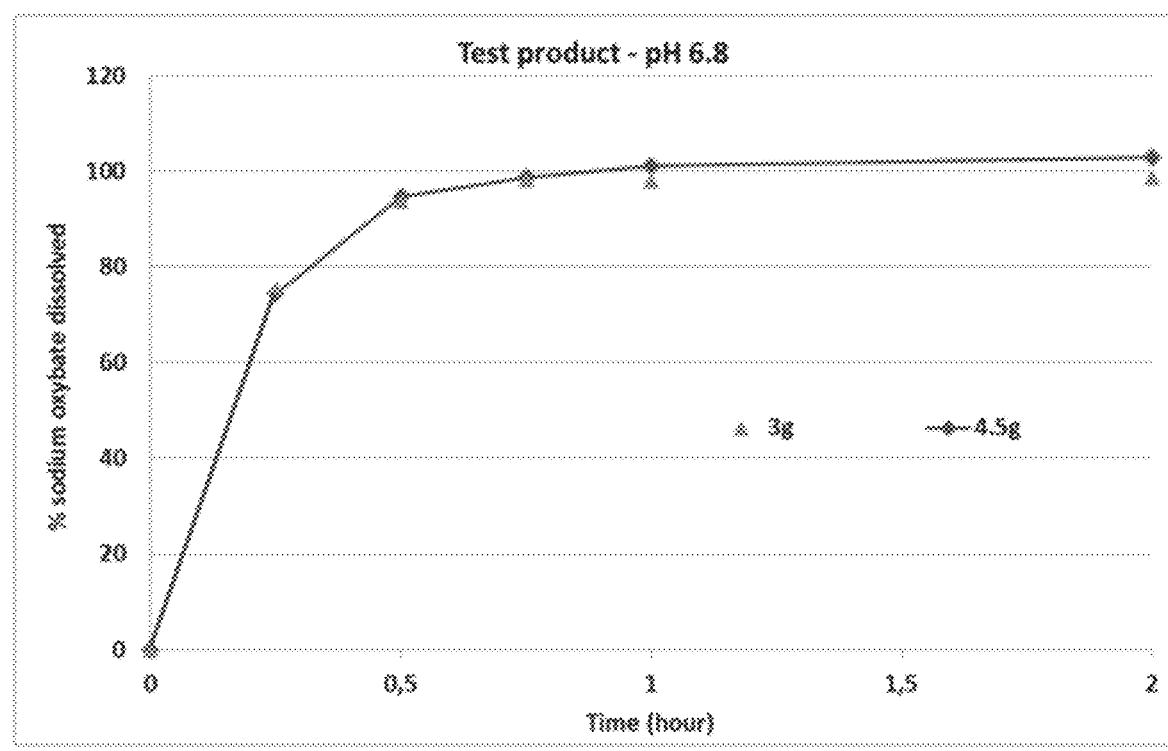

FIG. 89 is a dissolution profile in phosphate buffer pH 6.8 of two unit doses of 3 g (▲ symbols) and 4.5 g (• symbols) of the finished composition of Example 18.

Figure 90:
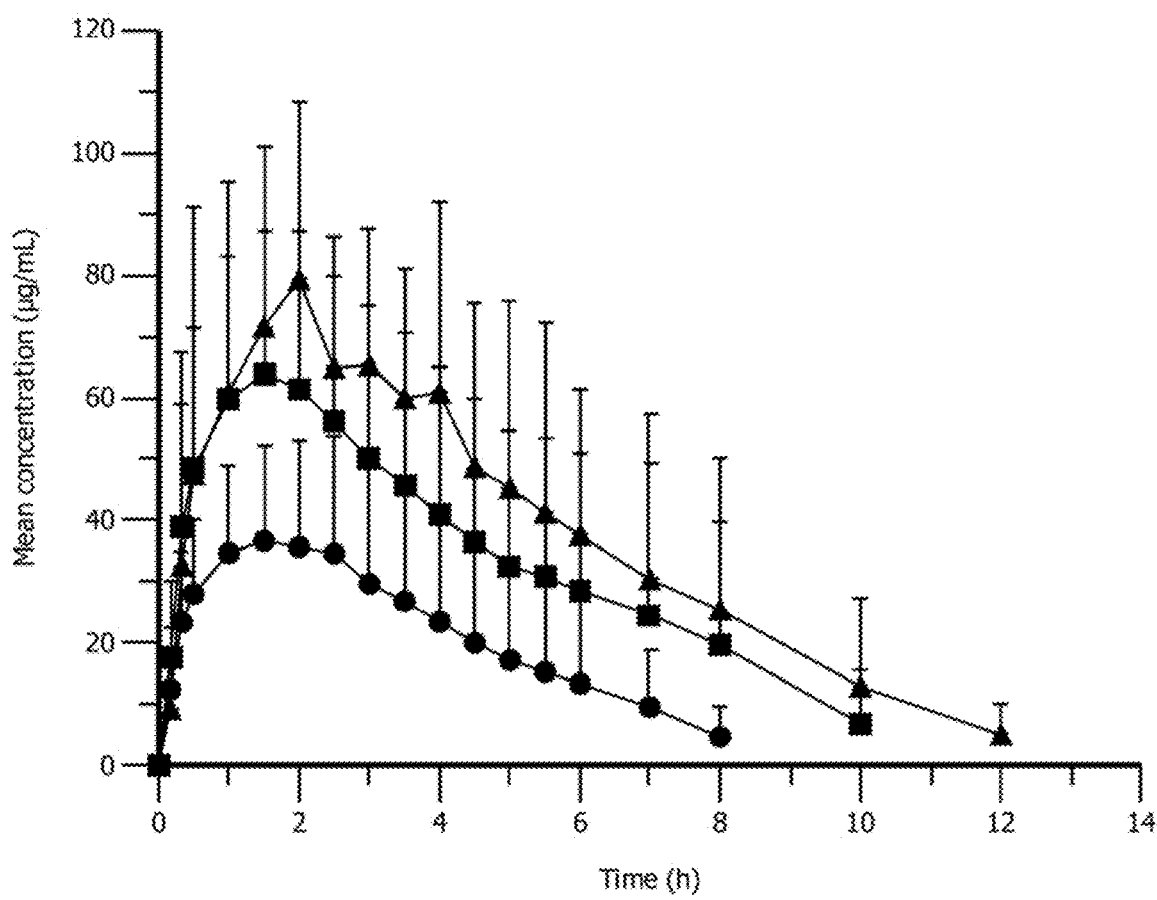

FIG. 90 plots mean plasma gamma-hydroxybutyrate concentrations (microgram/mL)+SD—time profiles after a single oral administration of 4.5 g (• symbols), 7.5 g (■ symbols) and 9 g (▲ symbols) of the finished composition of Example 18.

Figure 91:
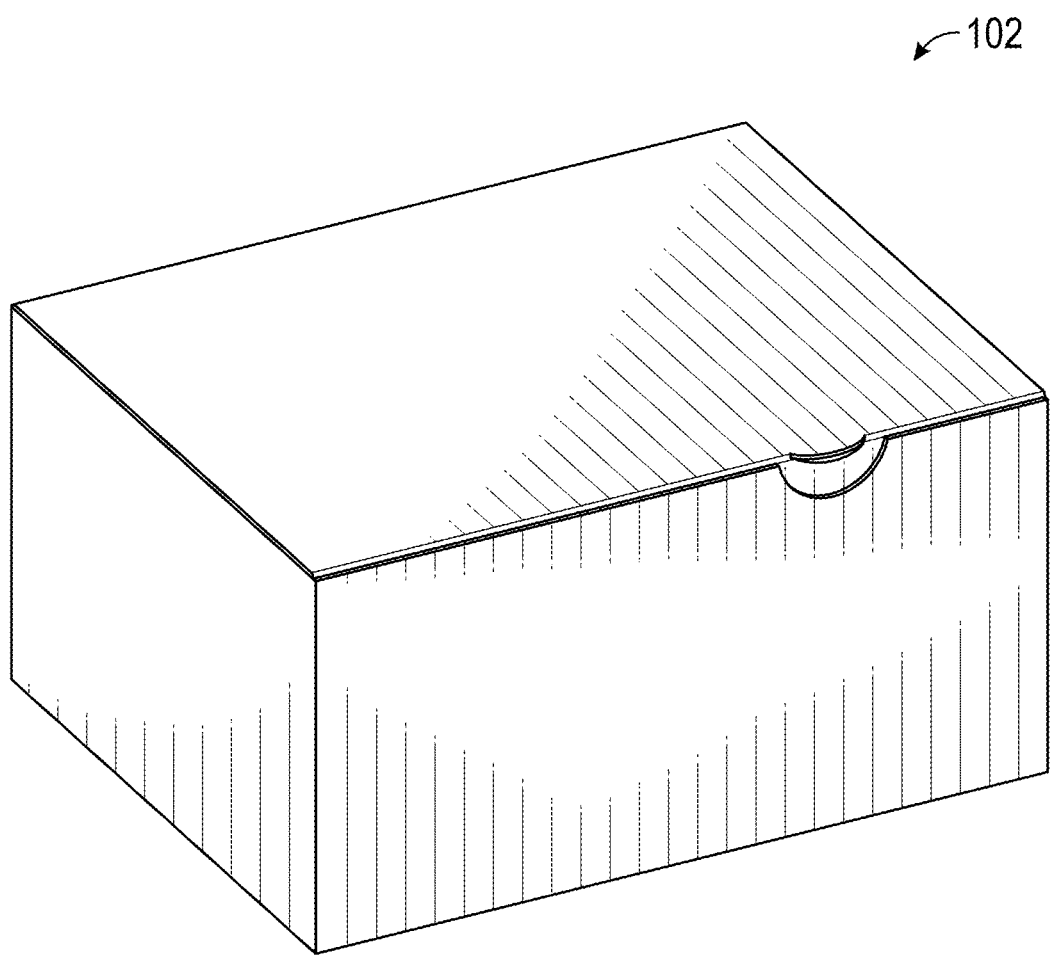

FIG. 91 is a top isometric view of a closed 30-day supply carton in one example.

Figure 96:
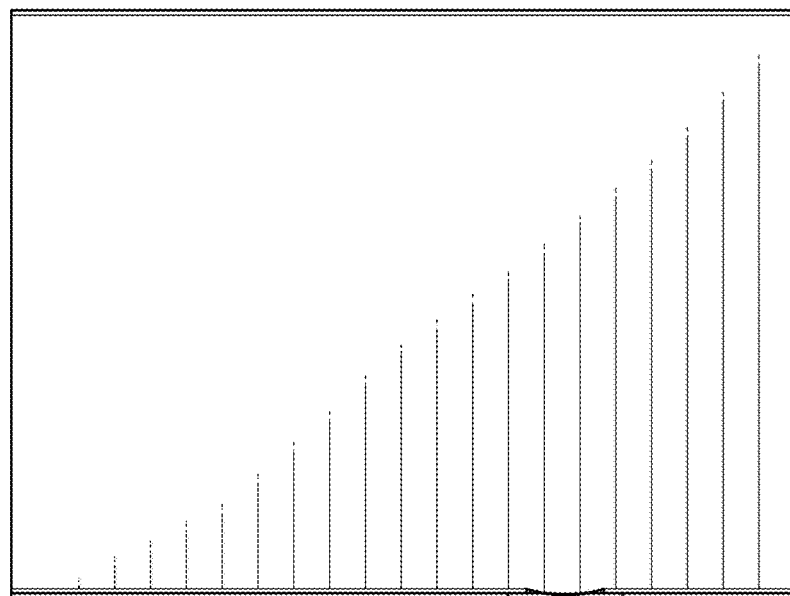

FIG. 92 is a front elevational view of FIG. 91;

FIG. 93 is a rear elevational view of FIG. 91;

FIG. 94 is a right side elevational view of FIG. 91;

FIG. 95 is a left side elevational view of FIG. 91;

FIG. 96 is a top plan view of FIG. 91.

Figure 97:
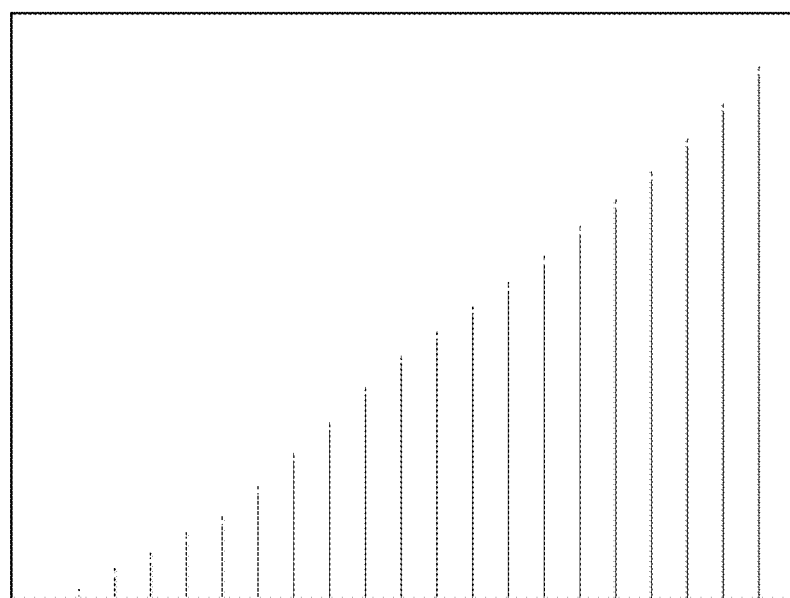

FIG. 97 is a bottom plan view of FIG. 91.

Figure 98:
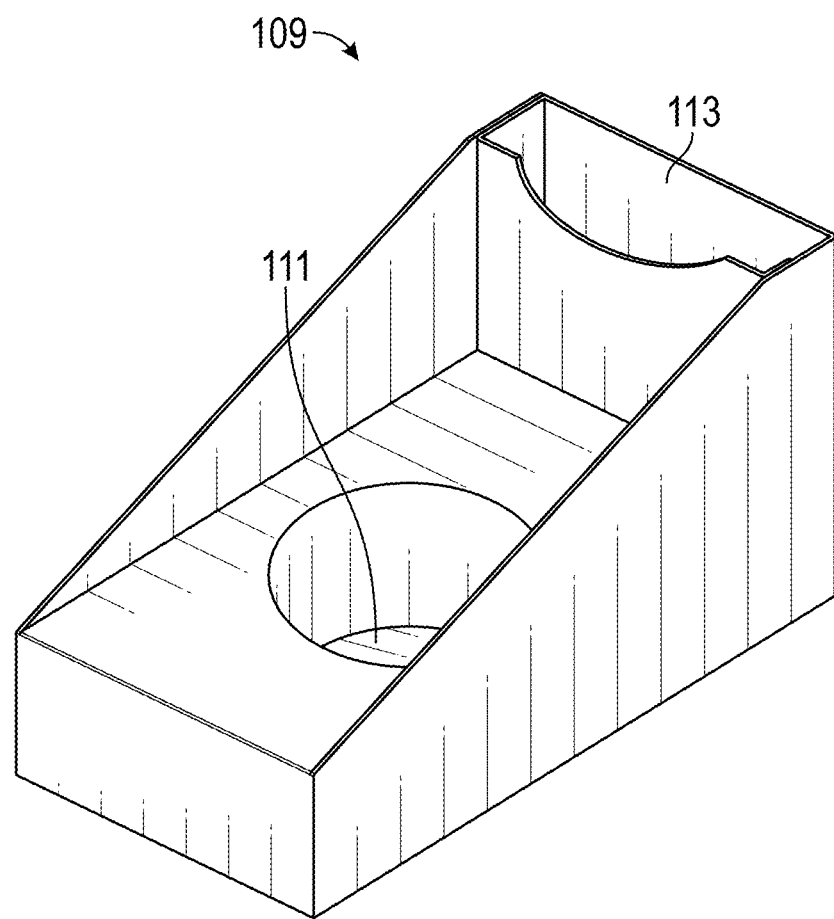

FIG. 98 is a top isometric view of a mixing cup receptacle insert in one example.

Figure 99:
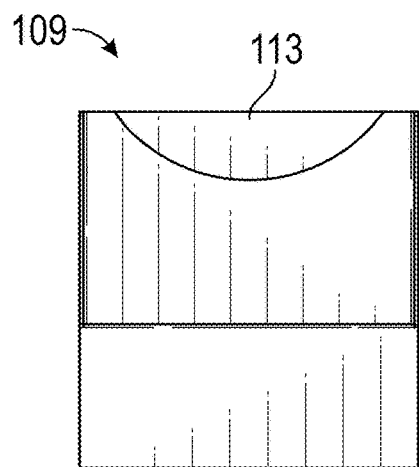
Figure 100:
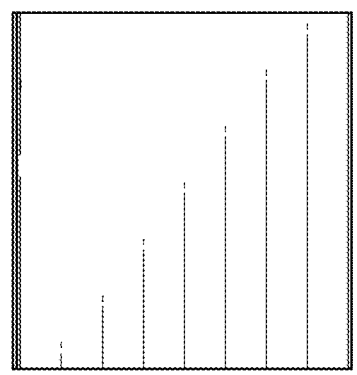
Figure 101:
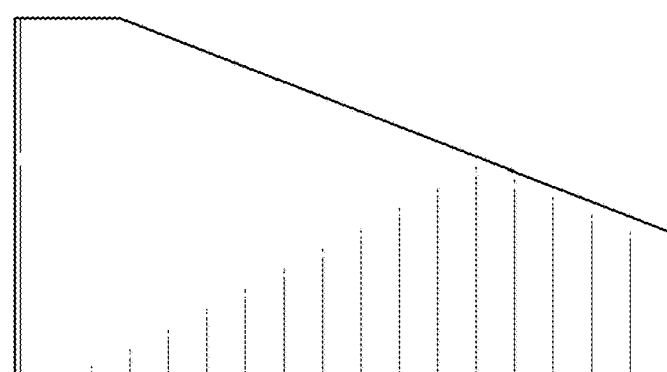

FIG. 99 is a front elevational view of FIG. 98;

FIG. 100 is a rear elevational view of FIG. 98;

FIG. 101 is a right side elevational view of FIG. 98;

FIG. 102 is a left side elevational view of FIG. 98;

FIG. 103 is a top plan view of FIG. 98.

FIG. 104 is a bottom plan view of FIG. 98.

Figure 105:
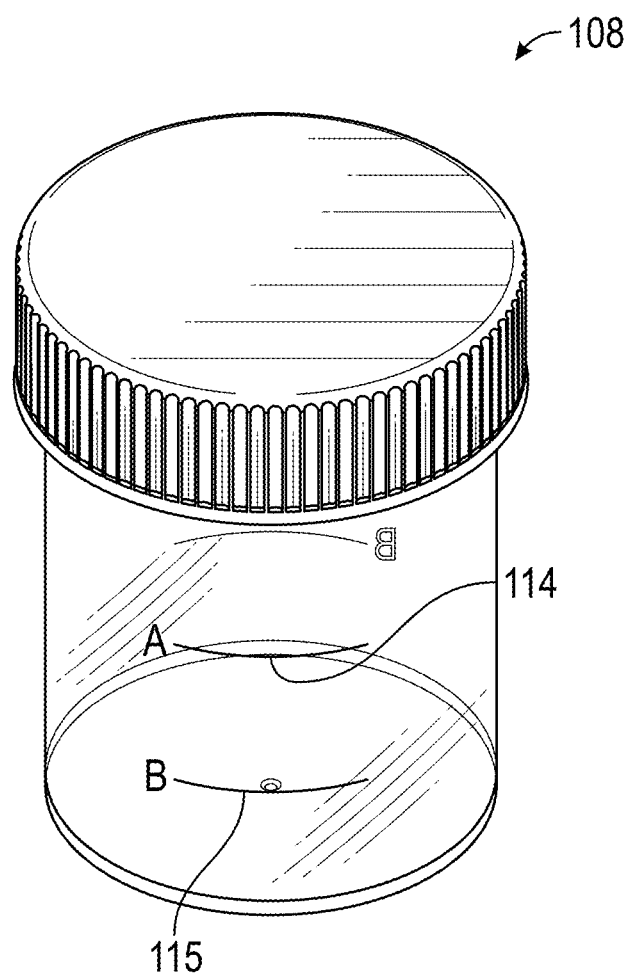

FIG. 105 is a top isometric view of a mixing cup in one example.

Figure 106:
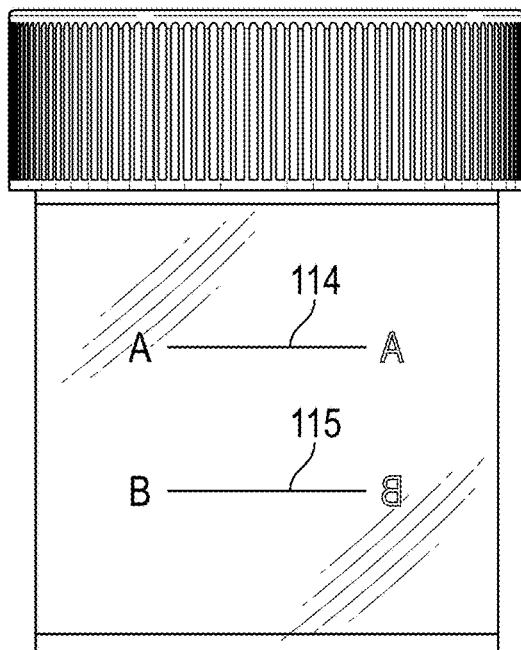
Figure 107:
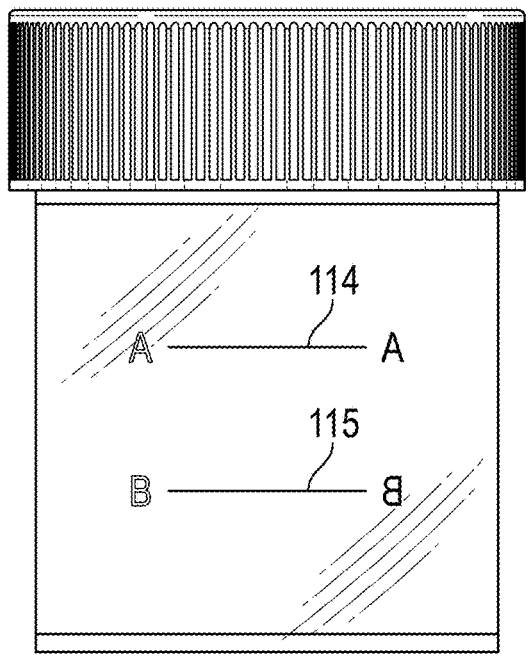
Figure 108:
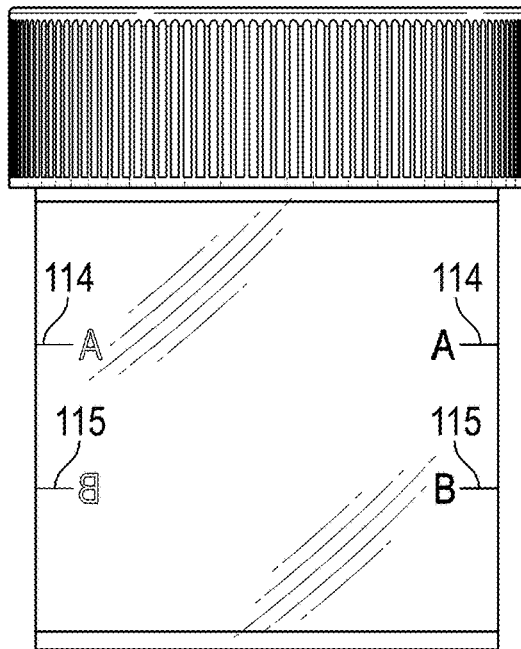
Figure 109:
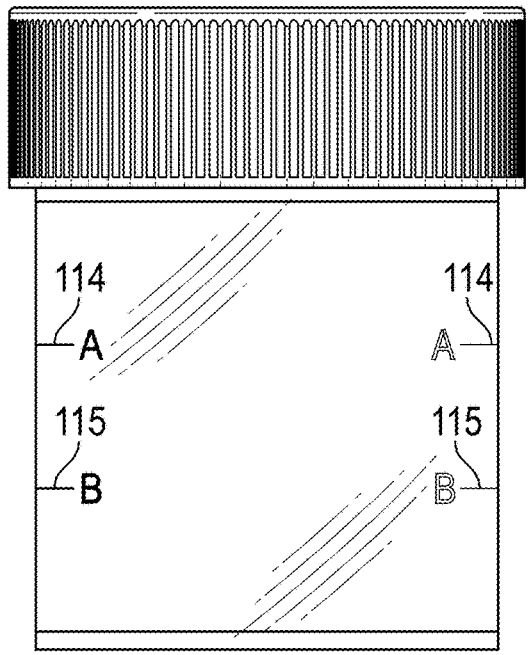
Figure 110:
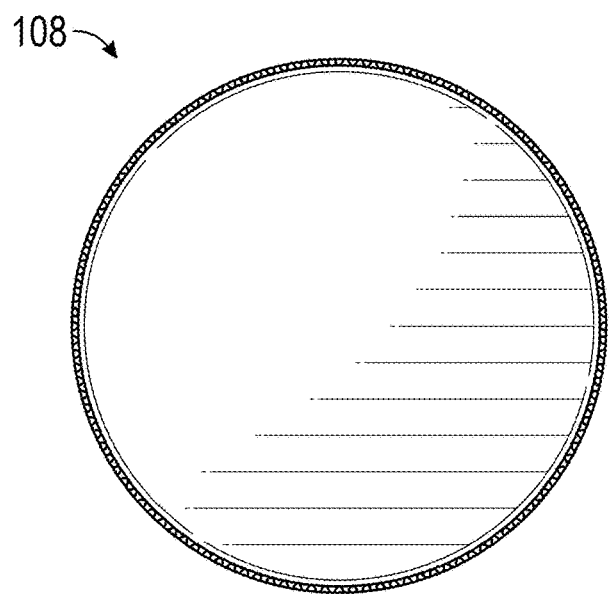

FIG. 106 is a front elevational view of FIG. 105;

FIG. 107 is a rear elevational view of FIG. 105;

FIG. 108 is a right side elevational view of FIG. 105;

FIG. 109 is a left side elevational view of FIG. 105;

FIG. 110 is a top plan view of FIG. 105.

Figure 111:
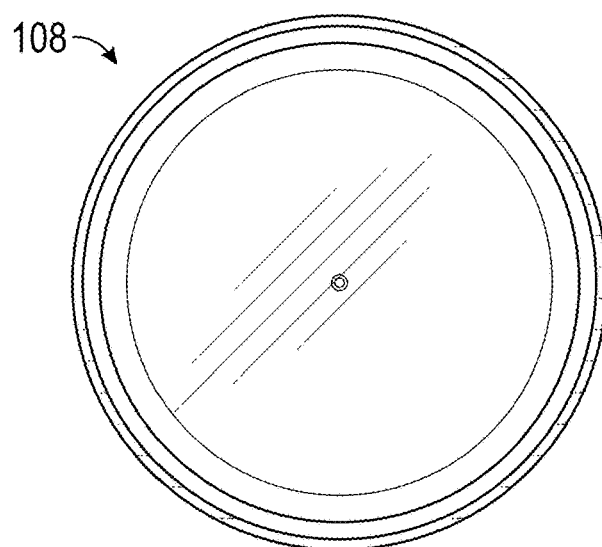

FIG. 111 is a bottom plan view of FIG. 105.

Figure 112:
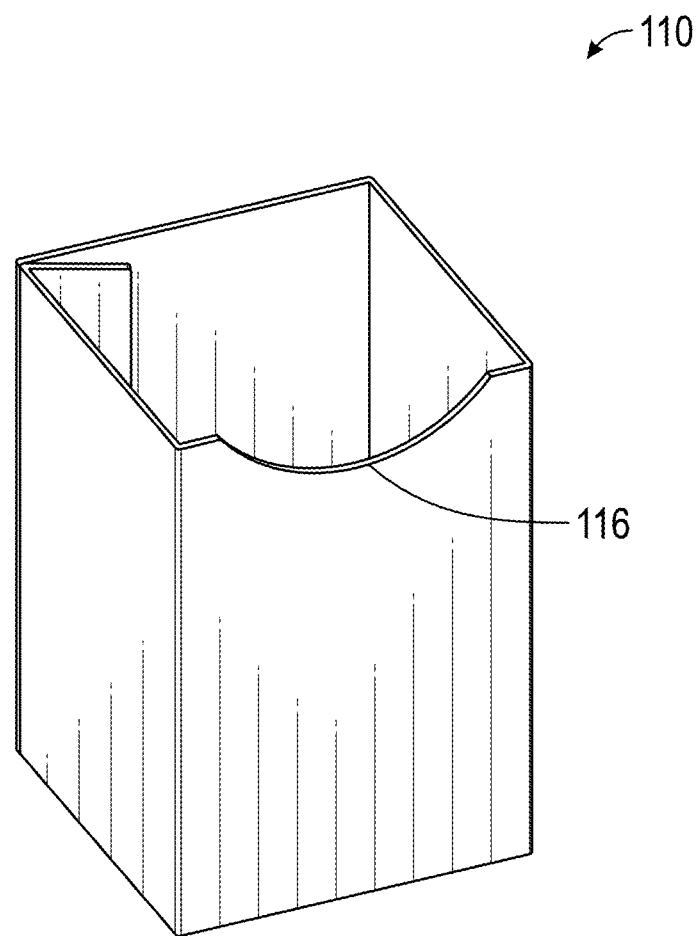

FIG. 112 is a top isometric view of a once-nightly dose packet container in one example.

Figure 113:
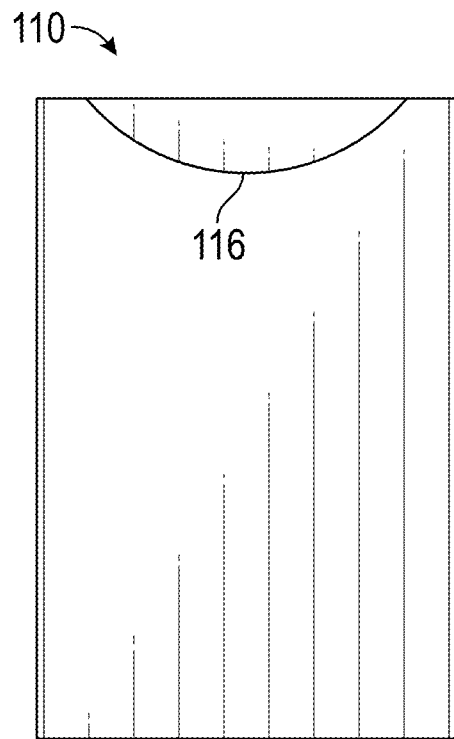
Figure 114:
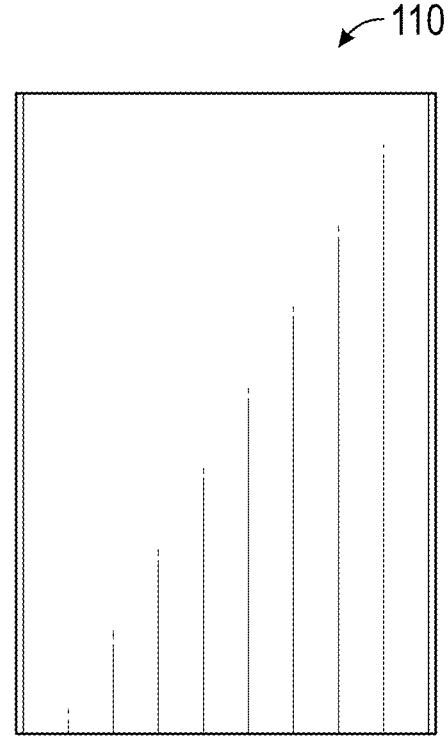
Figure 115:
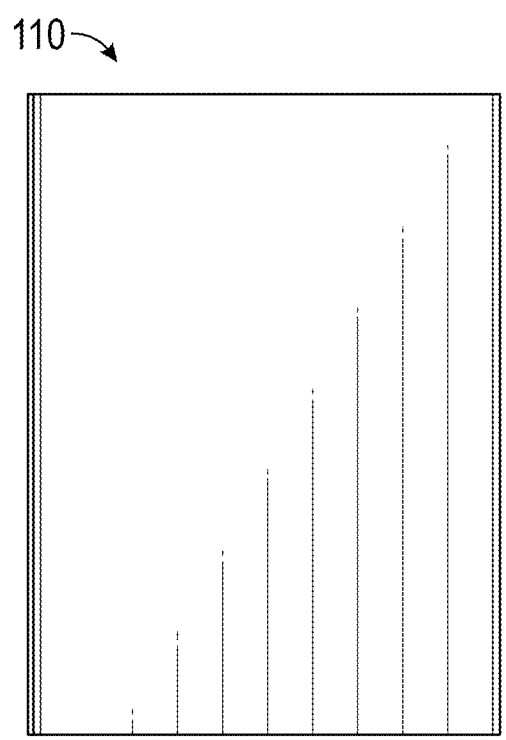
Figure 116:
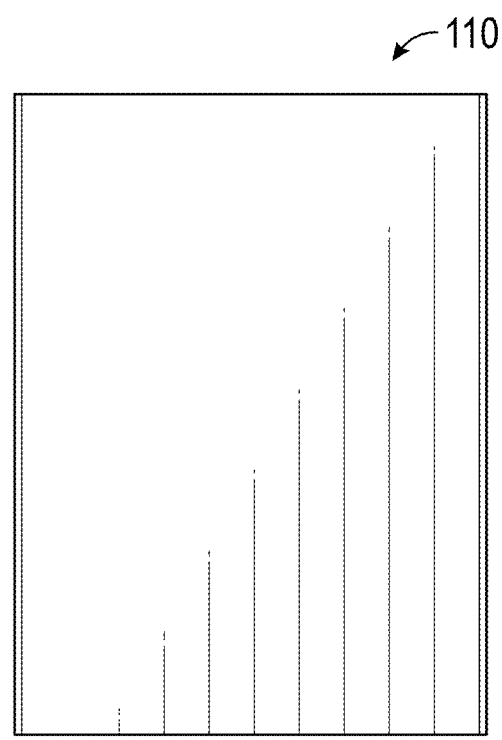
Figure 117:
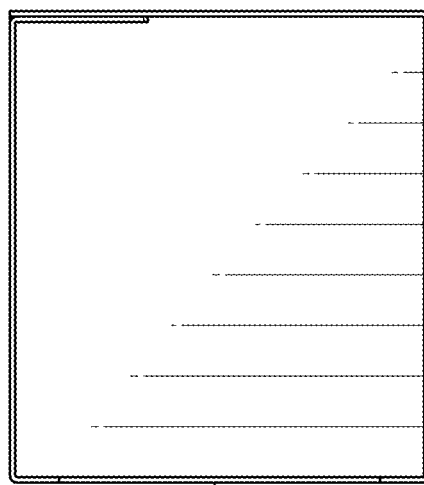

FIG. 113 is a front elevational view of FIG. 112;

FIG. 114 is a rear elevational view of FIG. 112;

FIG. 115 is a right side elevational view of FIG. 112;

FIG. 116 is a left side elevational view of FIG. 112;

FIG. 117 is a top plan view of FIG. 112.

Figure 118:
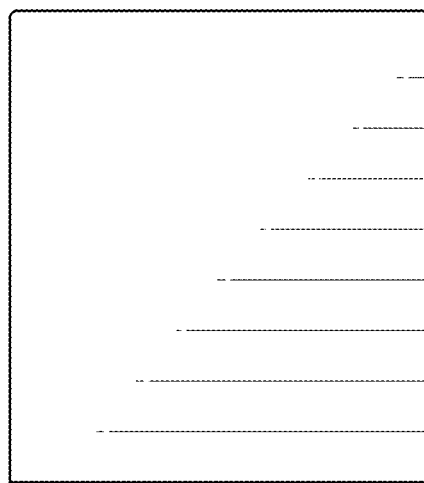

FIG. 118 is a bottom plan view of FIG. 112.

Figure 119:
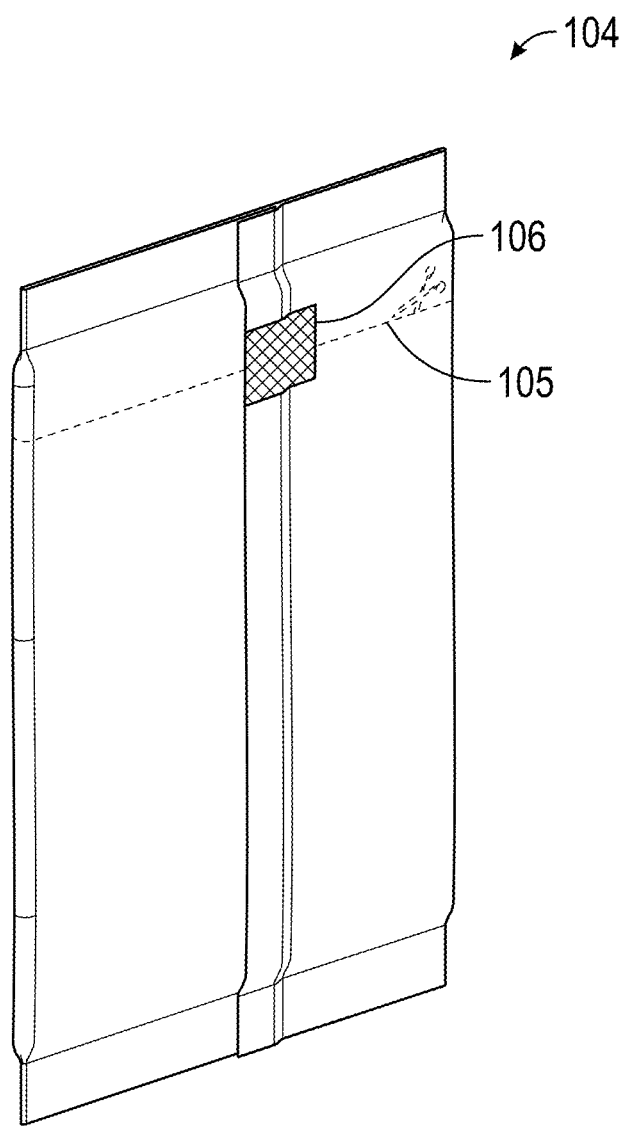

FIG. 119 is a top isometric view of a once-nightly dose packet in one example.

Figure 120:
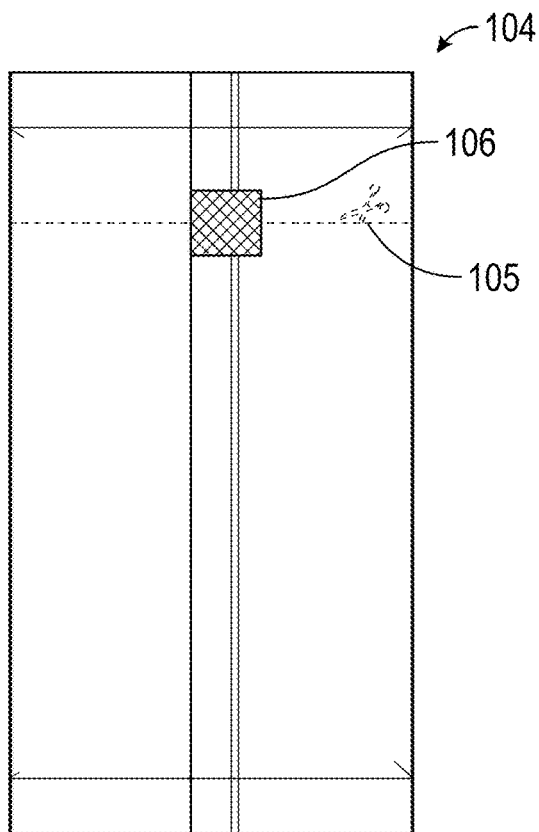
Figure 121:
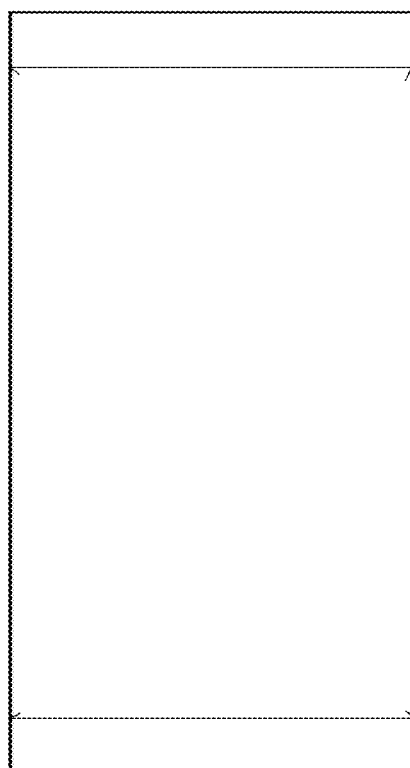
Figure 122:
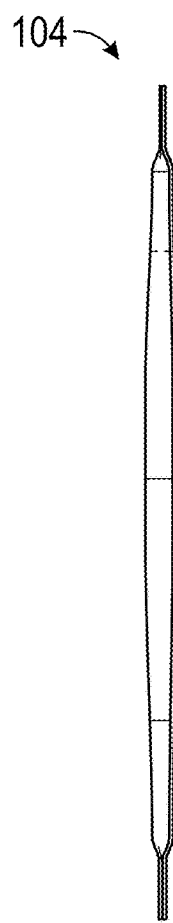
Figure 123:
Figure 124:
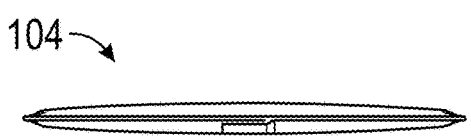

FIG. 120 is a front elevational view of FIG. 119;

FIG. 121 is a rear elevational view of FIG. 119;

FIG. 122 is a right side elevational view of FIG. 119;

FIG. 123 is a left side elevational view of FIG. 119;

FIG. 124 is a top plan view of FIG. 119.

Figure 125:
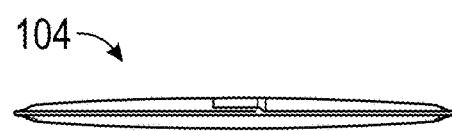

FIG. 125 is a bottom plan view of FIG. 119.

Figure 126:
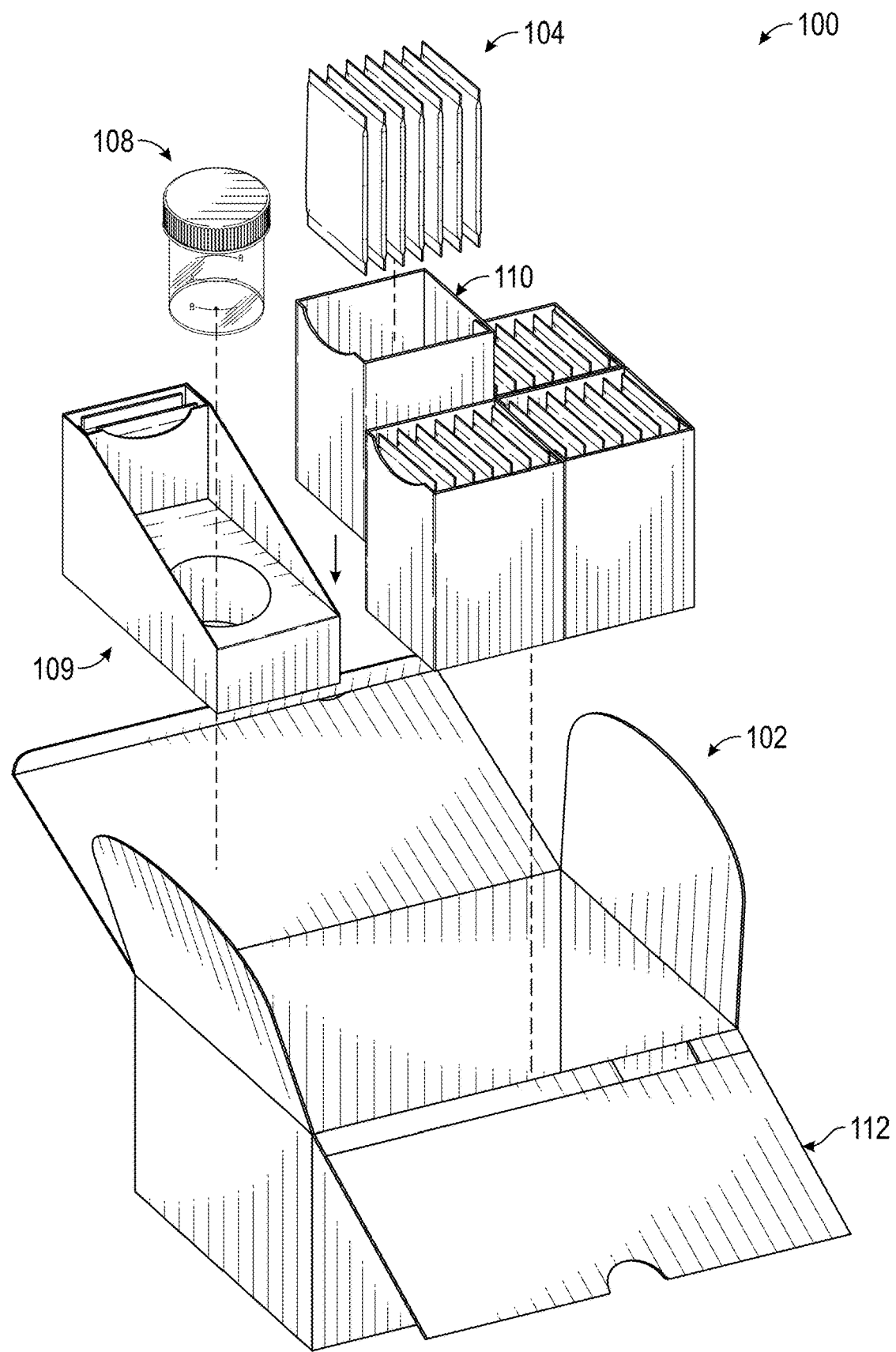

FIG. 126 is an exploded top isometric view of an open 30-day supply carton with 30 once-nightly dose packets, a mixing cup, and respective containers and receptacle, in one example.

Figure 127:
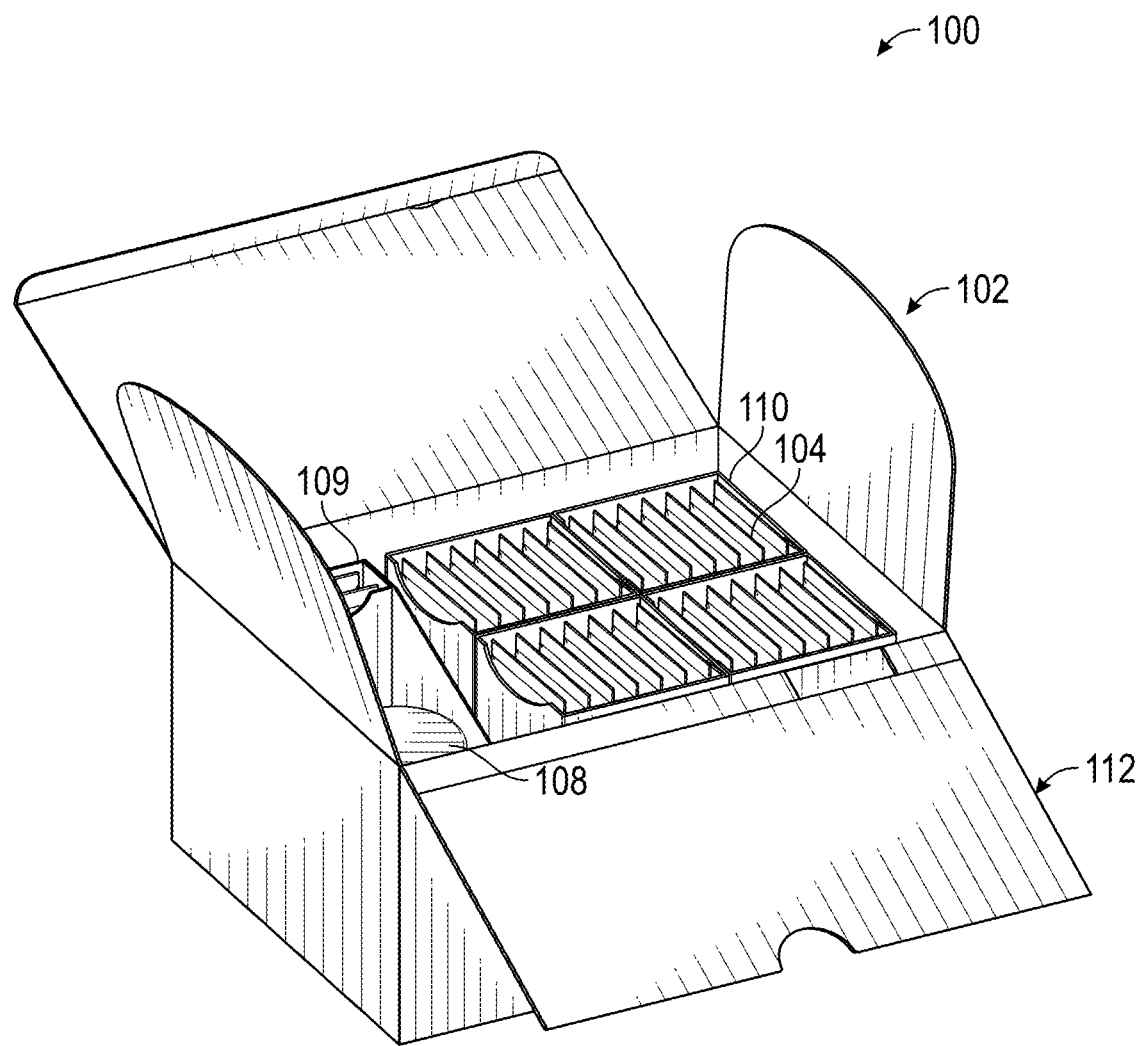

FIG. 127 is a top isometric view of an open 30-day supply carton with 30 once-nightly dose packets, a mixing cup, and respective containers and receptacle, in one example.

Figure 128:
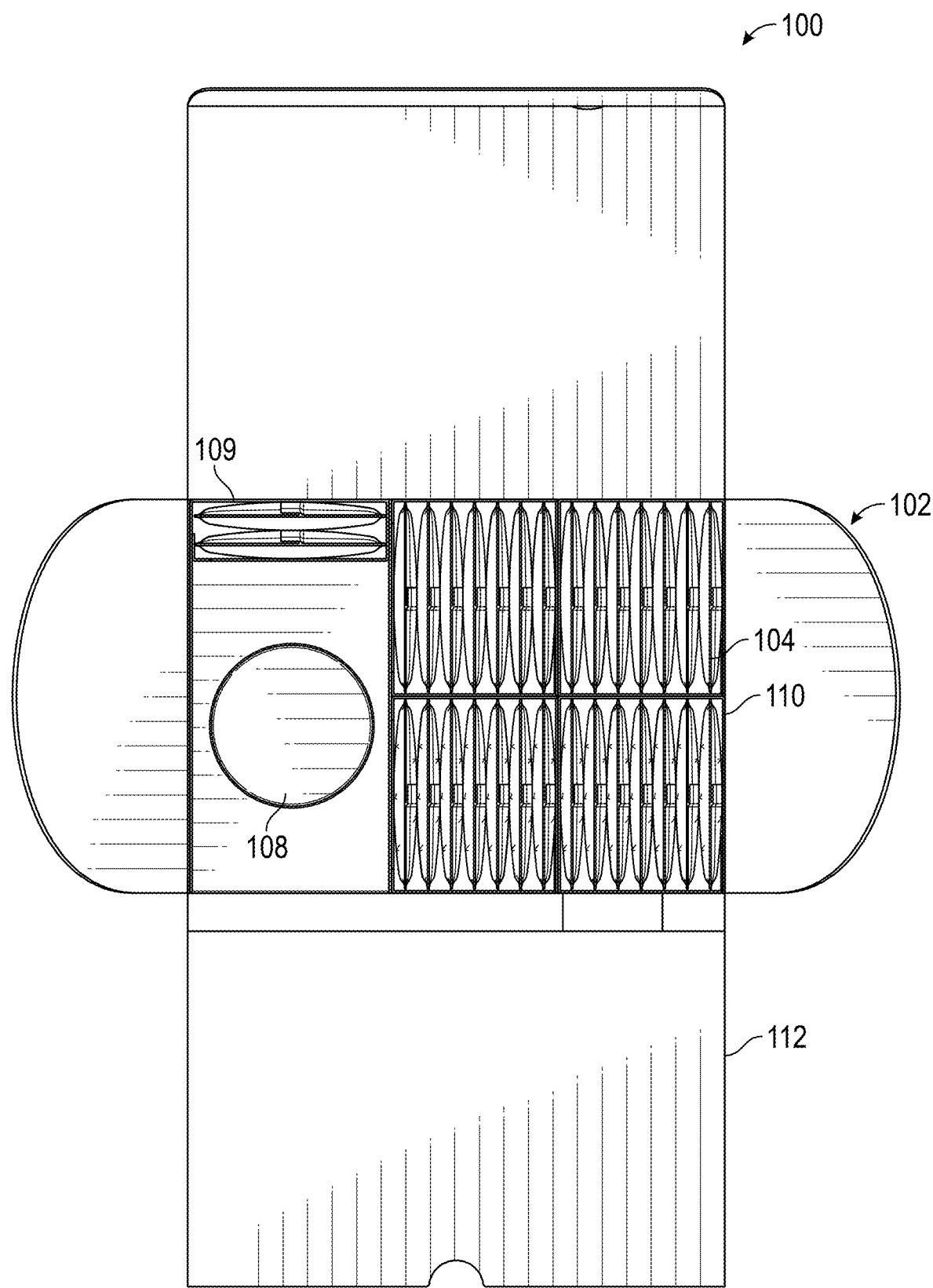

FIG. 128 is a top plan view of FIG. 127.

Figure 129:
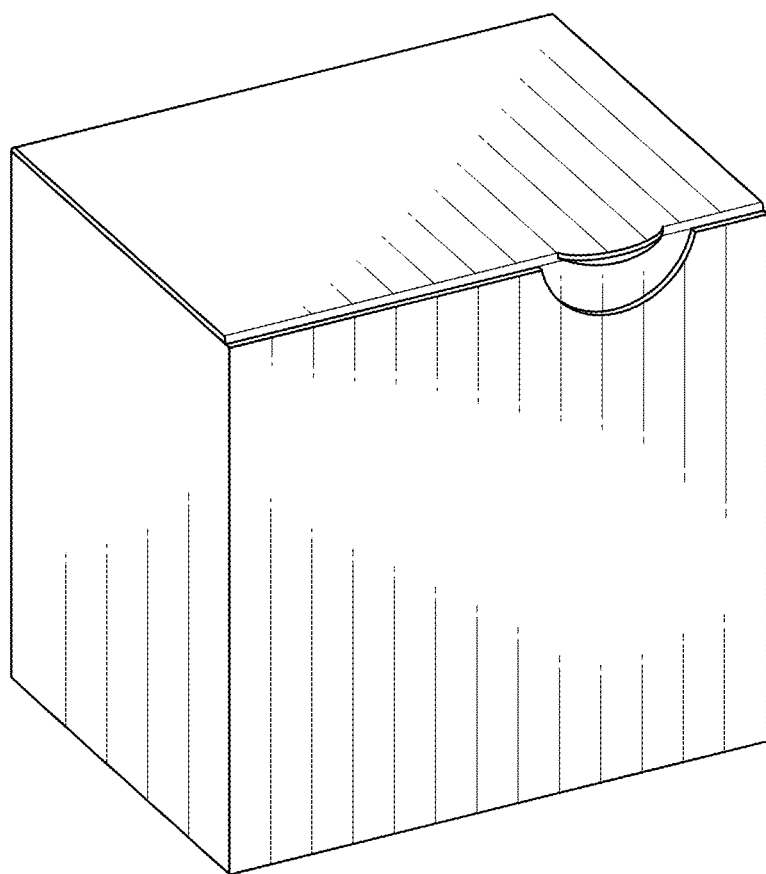

FIG. 129 is a top isometric view of a closed 7-day supply carton in one example.

Figure 130:
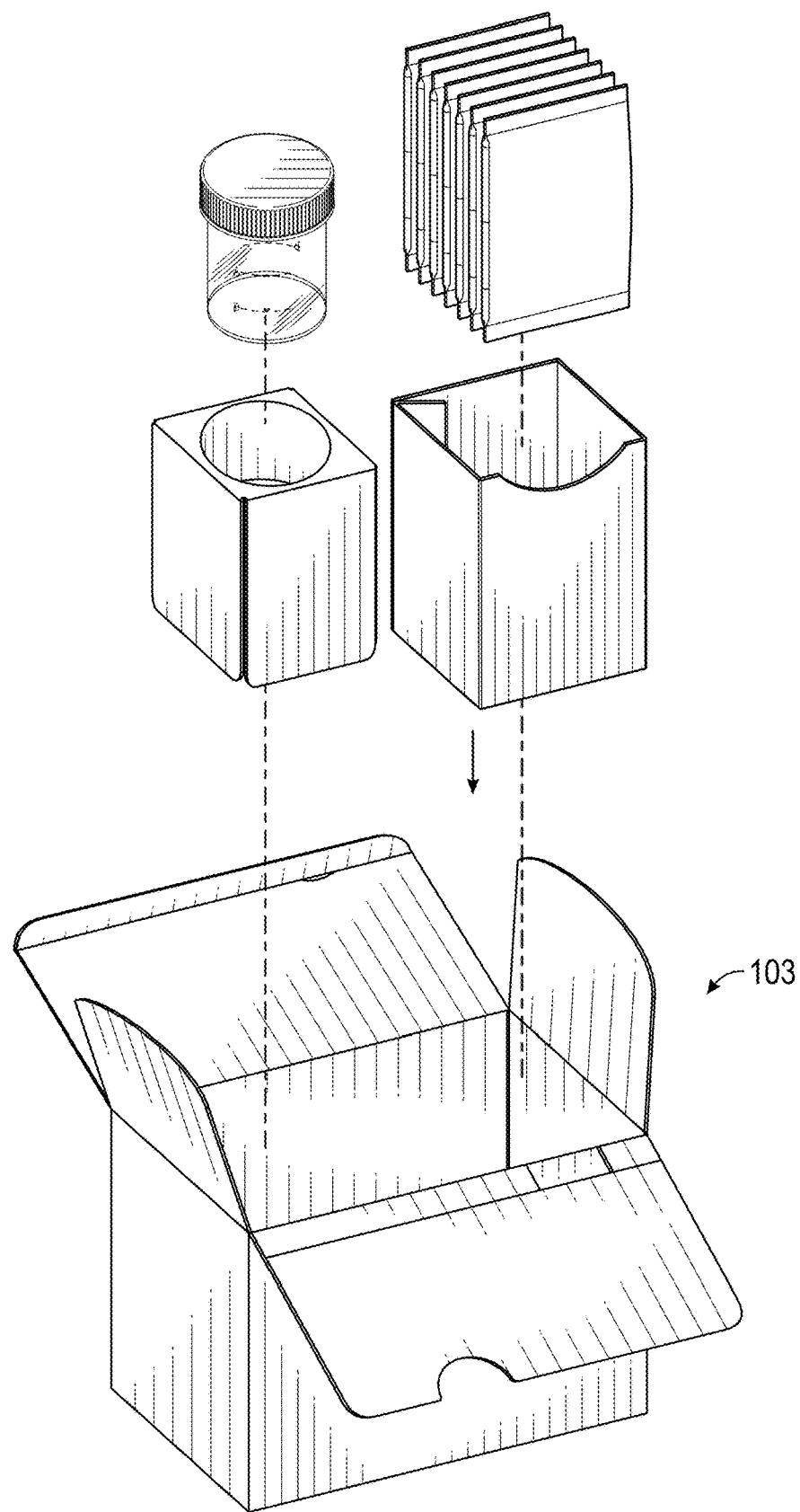

FIG. 130 is an exploded top isometric view of an open 7-day supply carton with 7 once-nightly dose packets, a mixing cup, and respective container and receptacle, in one example.

Figure 131:
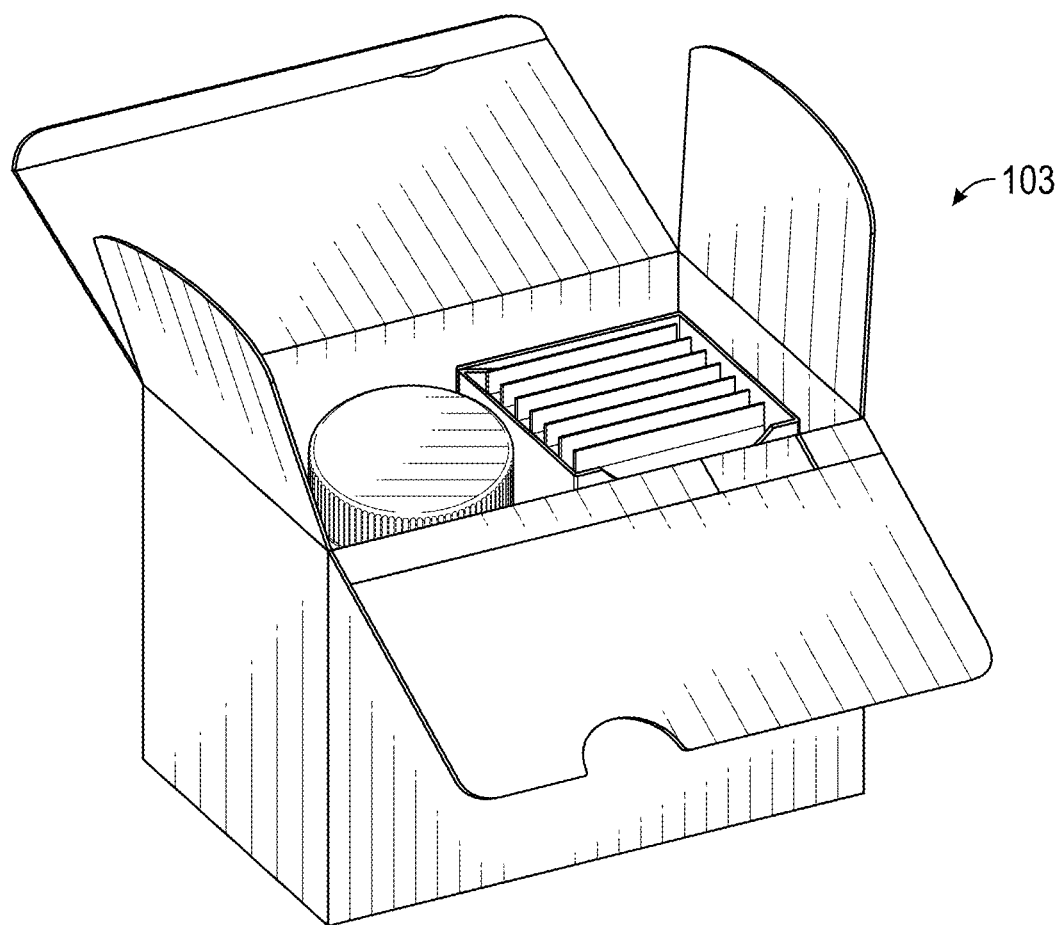

FIG. 131 is a top isometric view of an open 7-day supply carton with 7 once-nightly dose packets, a mixing cup, and respective container and receptacle, in one example.

Figure 132:
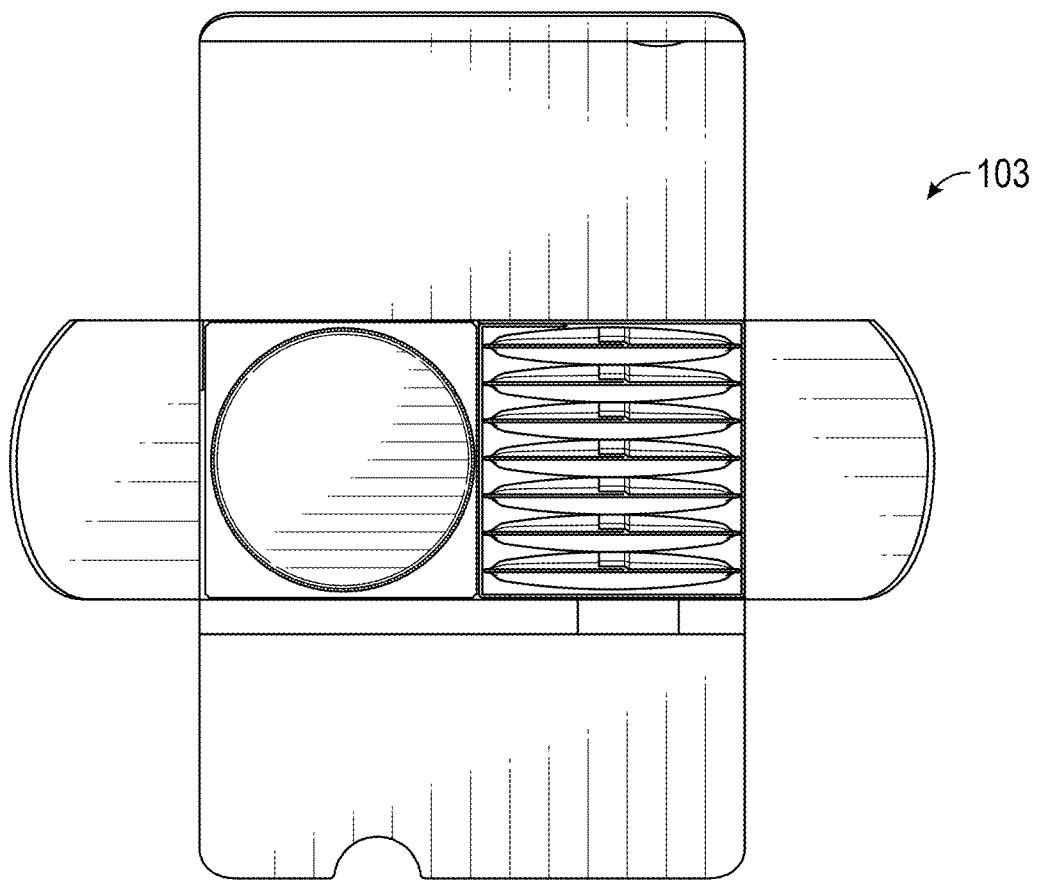

FIG. 132 is a top plan view of FIG. 131.

FIG. 133A, FIG. 133B, FIG. 133C, and FIG. 133D are example instructions for use of the composition in a once-nightly dosing packet and suspension in water using the mixing cup.

Figure 134:
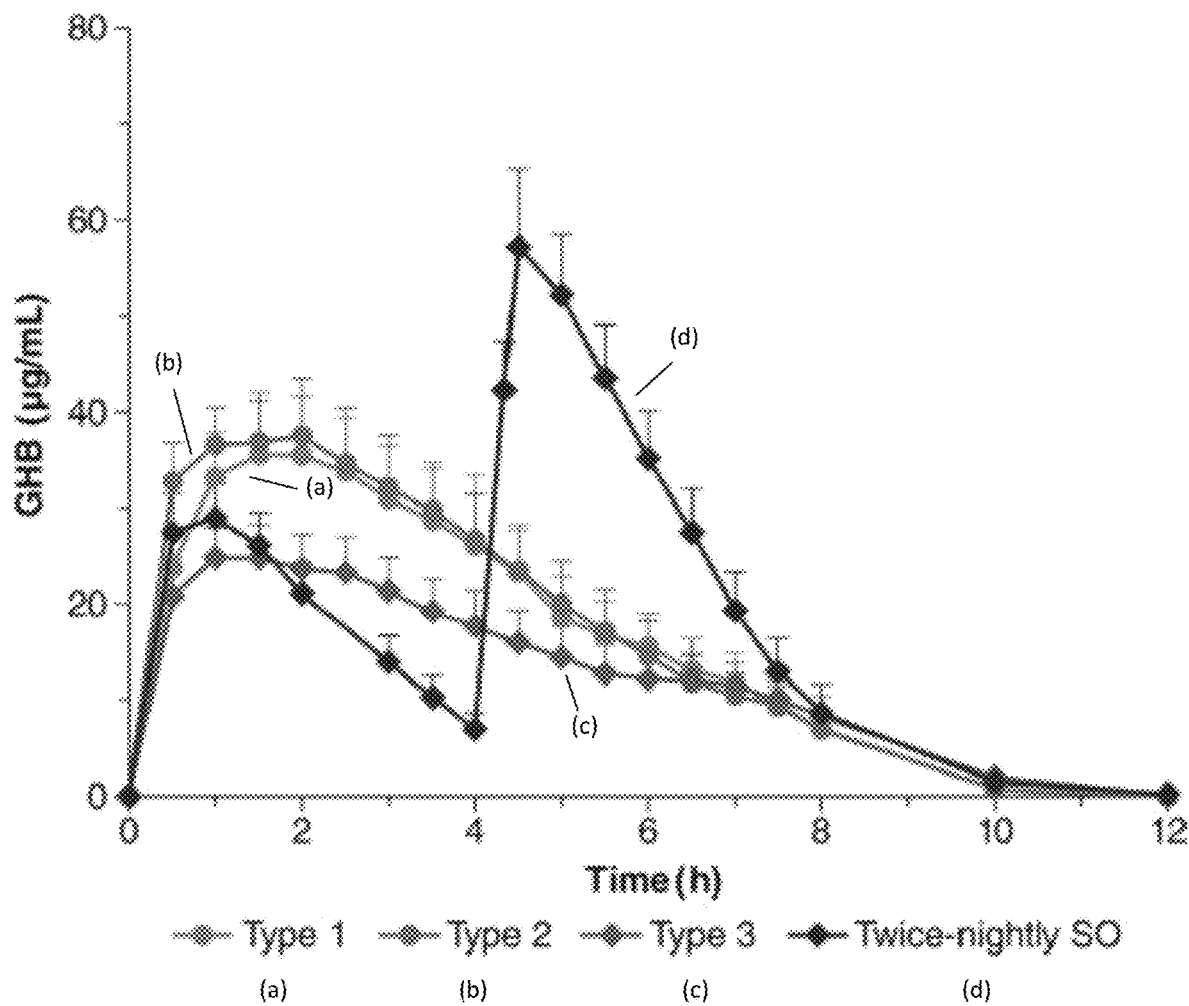

FIG. 134 shows mean plasma concentrations of γ-hydroxybutyrate (GHB) over time after twice-nightly sodium oxybate (SO) or 3 formulations of FT218 in the pilot study. Error bars indicate SEs.

Figure 135:
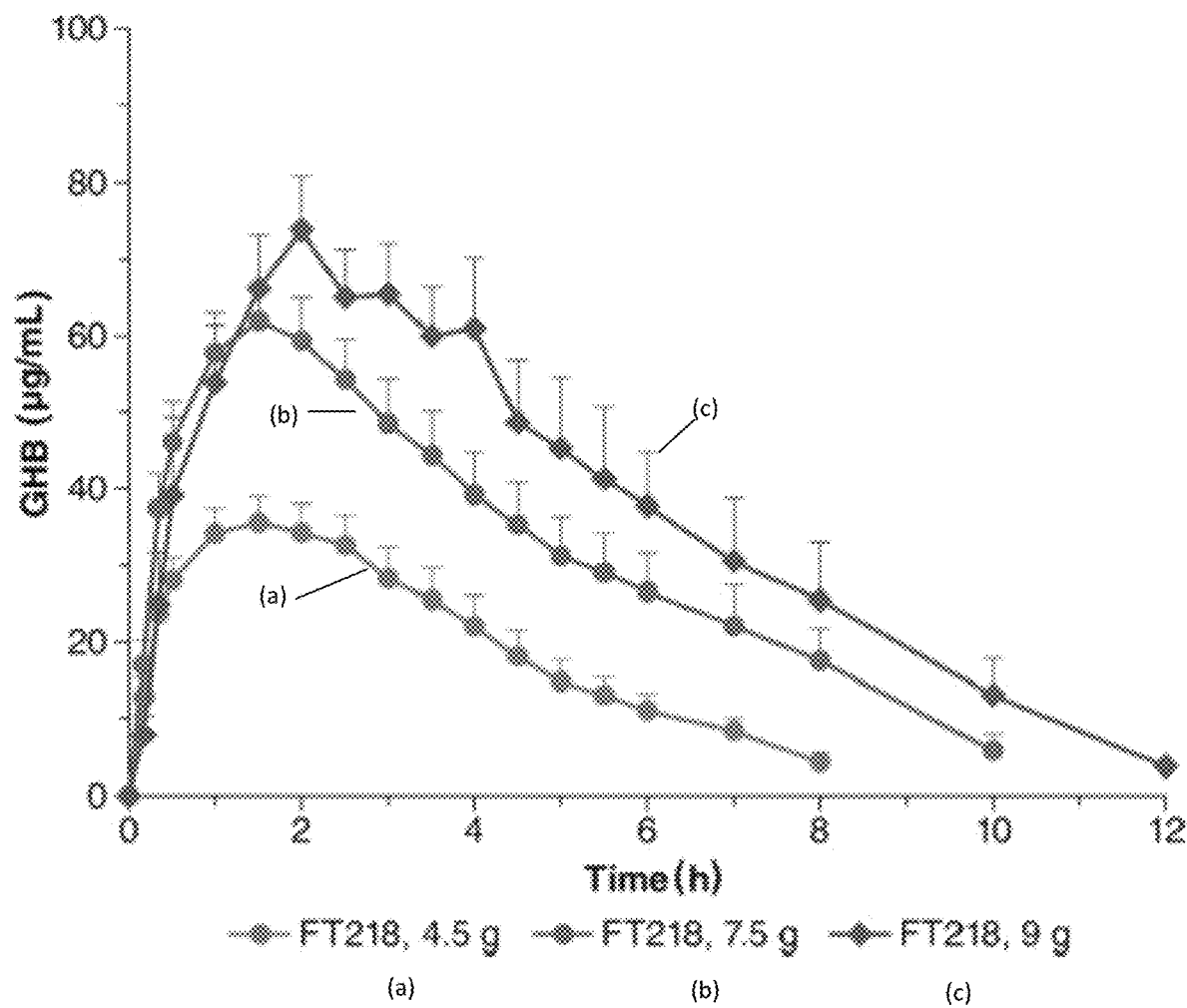

FIG. 135 shows mean plasma concentrations of γ-hydroxybutyrate (GHB) over time after 3 dose levels of FT218 in the dose-proportionality study. Error bars indicate SEs.

Figure 136:
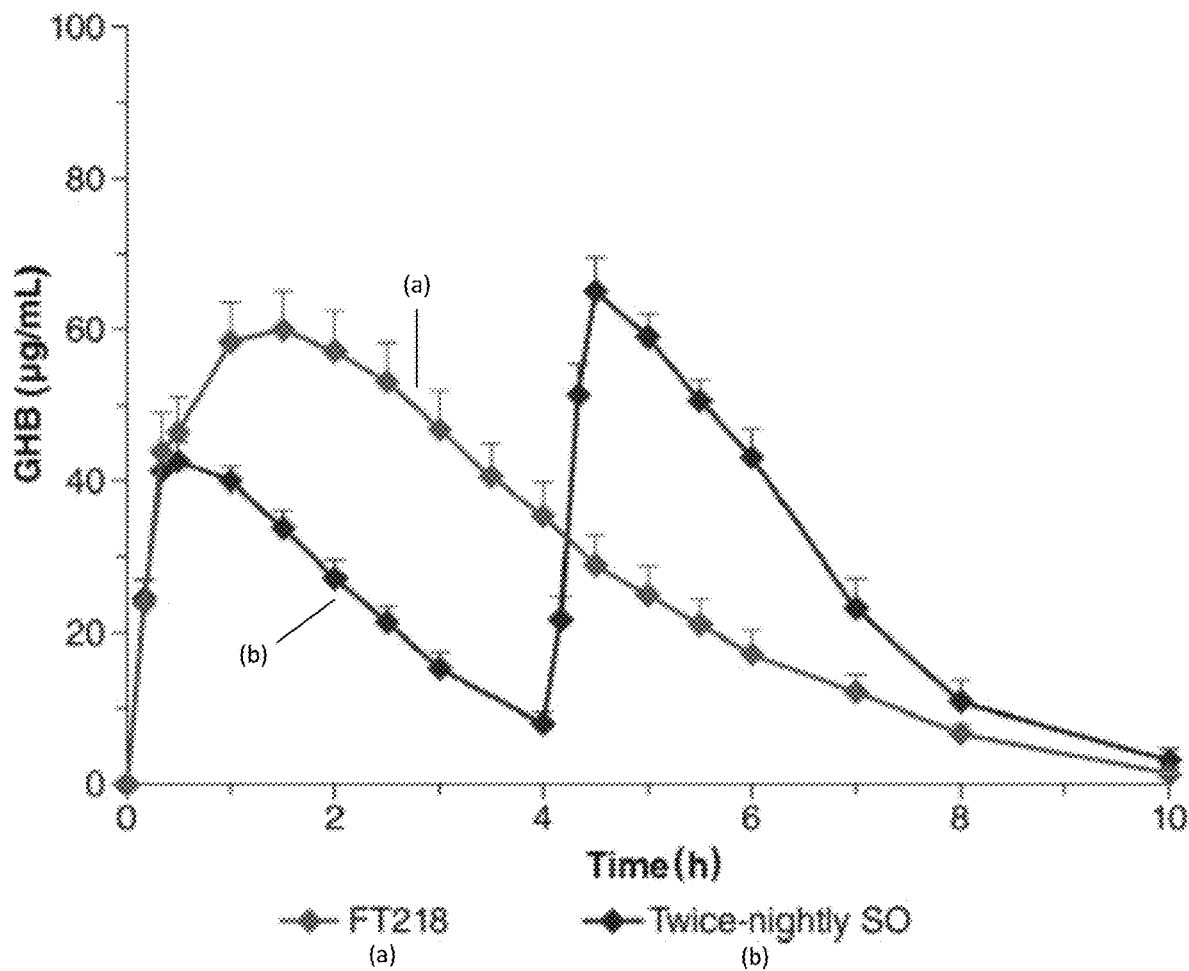

FIG. 136 shows mean plasma concentrations of γ-hydroxybutyrate (GHB) over time after FT218 or twice-nightly sodium oxybate (SO) in the relative bioequivalence study. Error bars indicate SEs.

Figure 137:
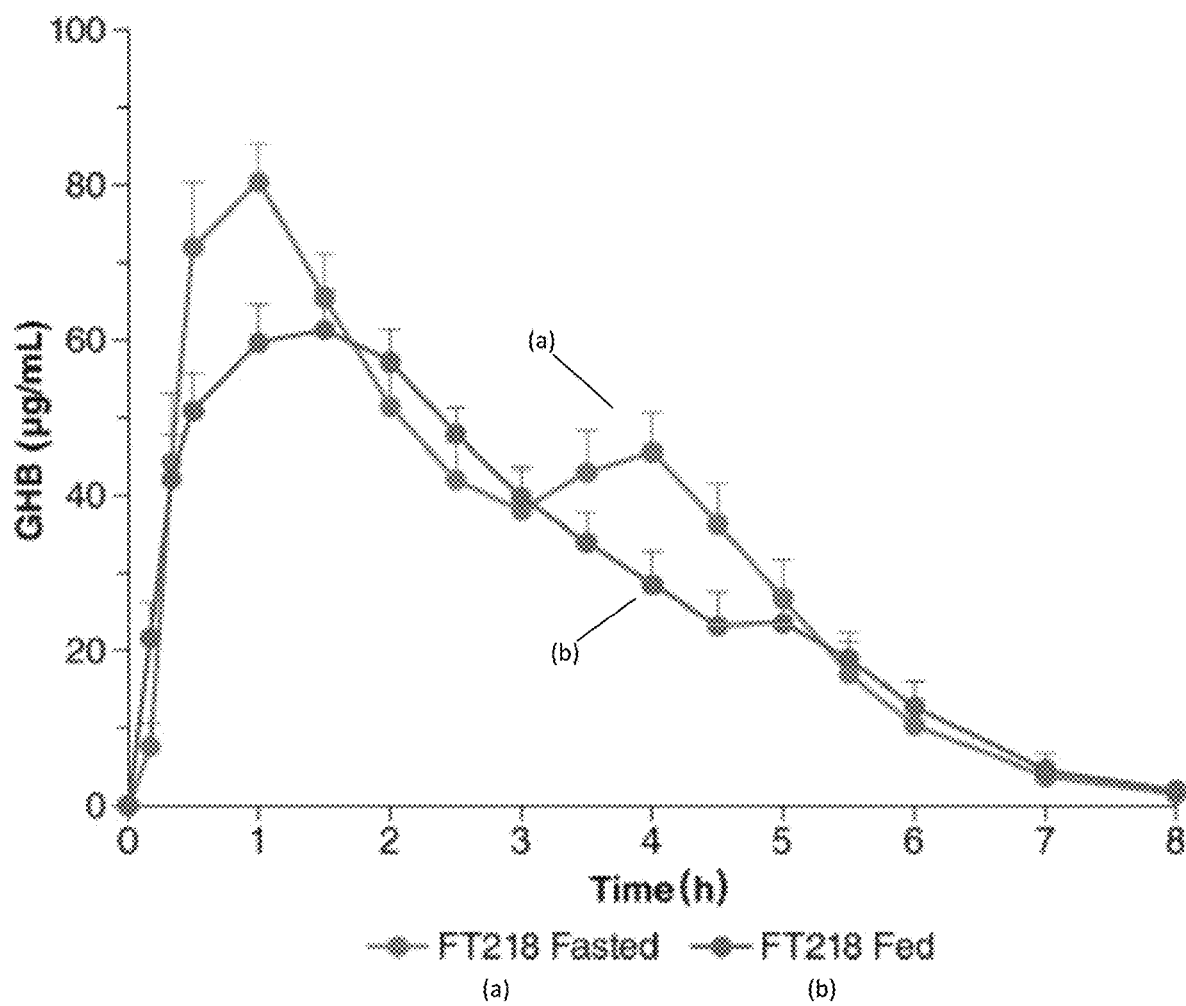

FIG. 137 mean plasma concentrations of γ-hydroxybutyrate (GHB) over time after FT218 administration in fasted or fed participants in the food-effect study. Error bars indicate SEs.

Figure 138A:
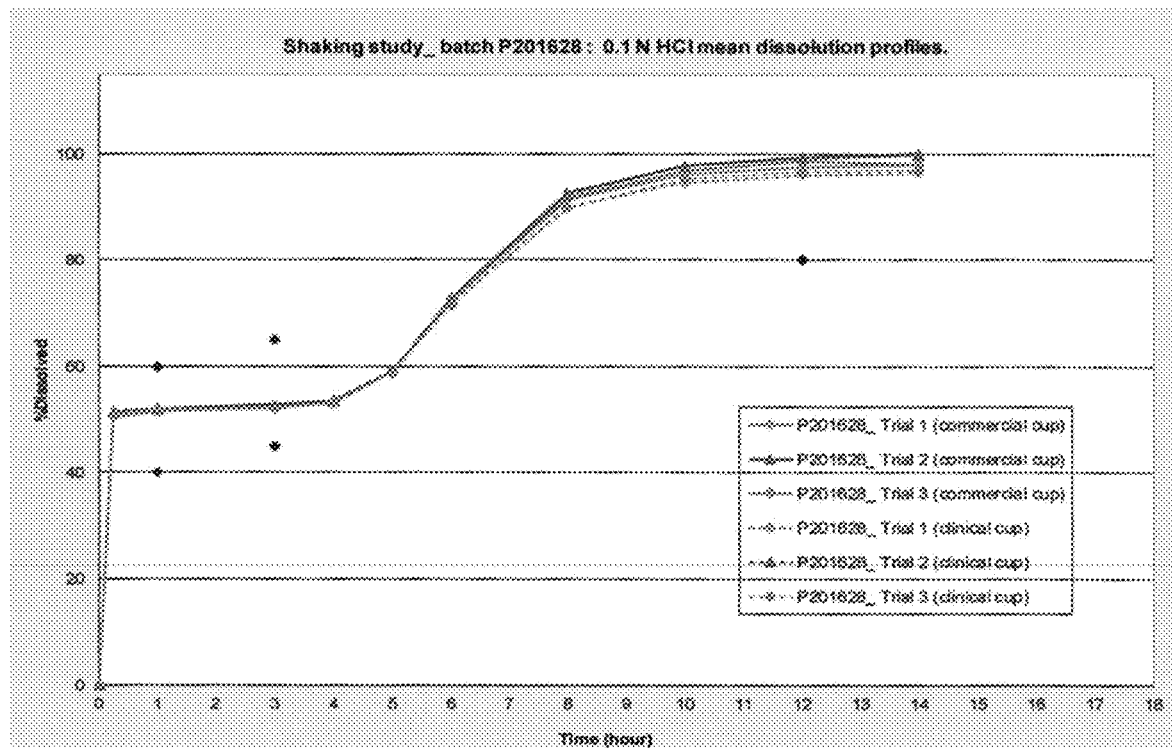

FIG. 138A shows dissolution profiles for Trials 1-3 for 4.5 g FT218 with two different cups.

Figure 138B:
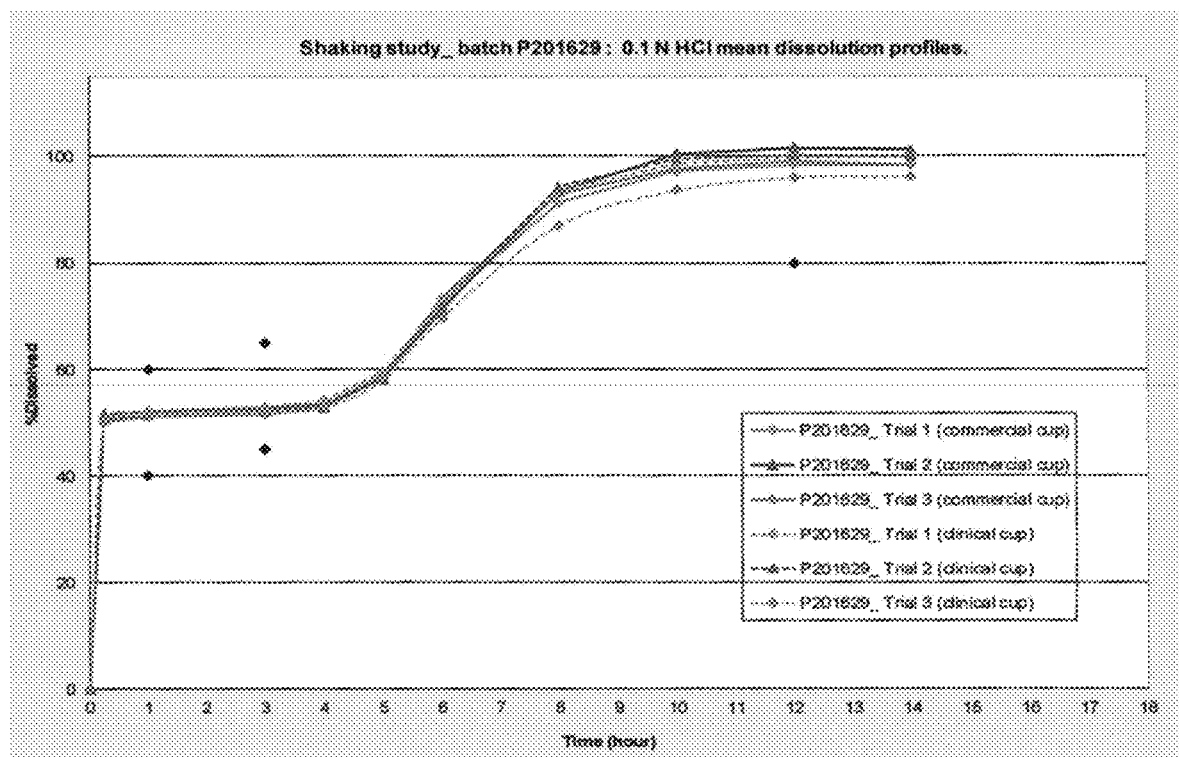

FIG. 138B shows dissolution profiles for Trials 1-3 for 9 g FT218 with two different cups.

Figure 139A:
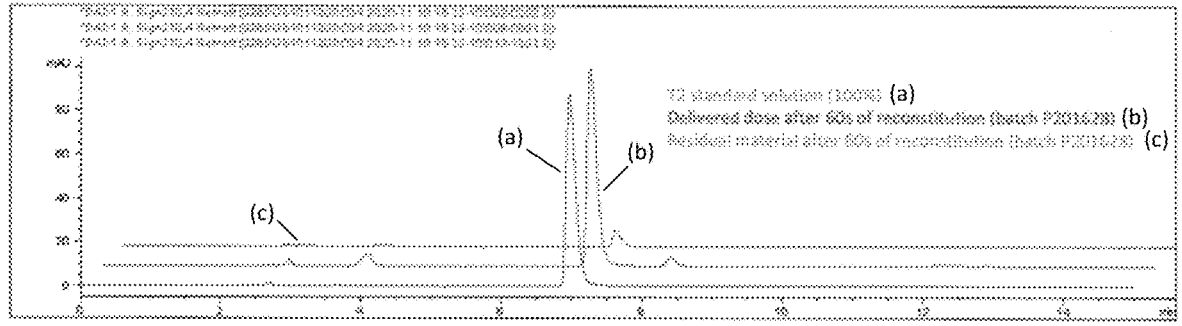
Figure 139B:
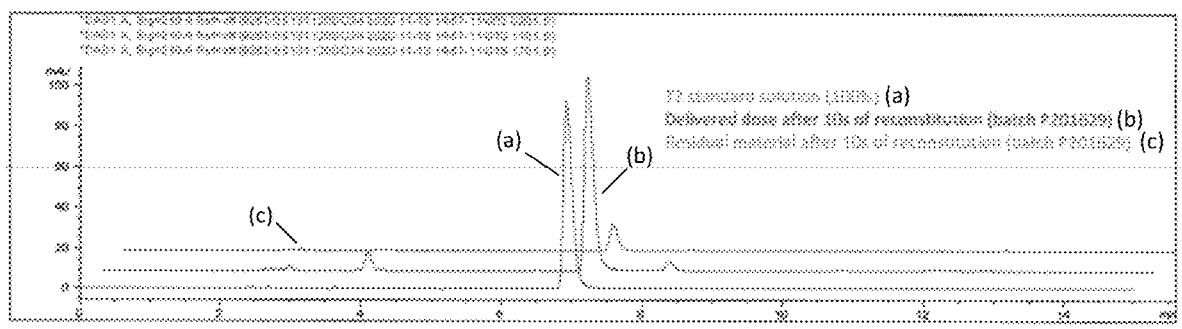

FIG. 139A shows a chromatogram for Trial 1 of the mixing cup assessment and FIG. 139B shows a chromatogram for Trial 2 of the mixing cup assessment.

DETAILED DESCRIPTION OF THE INVENTION

The present invention may be understood more readily by reference to the following detailed description of preferred embodiments of the invention and the Examples included therein.

Definitions and Use of Terms

Wherever an analysis or test is required to understand a given property or characteristic recited herein, it will be understood that the analysis or test is performed in accordance with applicable guidances, draft guidances, regulations and monographs of the United States Food and Drug Administration ("FDA") and United States Pharmacopoeia ("USP") applicable to drug products in the United States in force as of Nov. 1, 2015 unless otherwise specified. Clinical endpoints can be judged with reference to standards adopted by the American Academy of Sleep Medicine, including standards published at C Iber, S Ancoli-Israel, A Chesson, SF Quan. The AASM Manual for the Scoring of Sleep and Associated Events. Westchester, Ill.: American Academy of Sleep Medicine; 2007.

When a pharmacokinetic comparison is made between a formulation described or claimed herein and a reference product, it will be understood that the comparison is preferably performed in a suitable designed cross-over trial, although it will also be understood that a cross-over trial is not required unless specifically stated. It will also be understood that the comparison may be made either directly or indirectly. For example, even if a formulation has not been tested directly against a reference formulation, it may still satisfy a comparison to the reference formulation if it has been tested against a different formulation, and the comparison with the reference formulation may be deduced therefrom.

As used in this specification and in the claims which follow, the singular forms "a," "an" and "the" include plural referents unless the context dictates otherwise. Thus, for example, reference to "an ingredient" includes mixtures of ingredients, reference to "an active pharmaceutical agent" includes more than one active pharmaceutical agent, and the like.

"Bioavailability" means the rate and extent to which the active ingredient or active moiety is absorbed from a drug product and becomes available at the site of action.

"Relative bioavailability" or "Rel BA" or "RBA" means the percentage of mean AUCinf of the tested product relative to the mean AUCinf of the reference product. Unless otherwise specified, relative bioavailability refers to the percentage of the mean AUCinf observed for a full dose of the test product relative to the mean AUCinf observed for two 2-doses of an immediate release liquid solution administered four hours apart.

"Bioequivalence" means the absence of a significant difference in the rate and extent to which the active ingredient or active moiety in pharmaceutical equivalents or pharmaceutical alternatives become available at the site of drug action when administered at the same molar dose under similar conditions in an appropriately designed study.

When ranges are given by specifying the lower end of a range separately from the upper end of the range, it will be understood that the range may be defined by selectively combining any one of the lower end variables with any one of the upper end variables that is mathematically and physically possible. Thus, for example, if a formulation may contain from 1 to 10 weight parts of a particular ingredient, or 2 to 8 parts of a particular ingredient, it will be understood that the formulation may also contain from 2 to 10 parts of the ingredient. In like manner, if a formulation may contain greater than 1 or 2 weight parts of an ingredient and up to 10 or 9 weight parts of the ingredient, it will be understood that the formulation may contain 1-10 weight parts of the ingredient, 2-9 weight parts of the ingredient, etc. unless otherwise specified, the boundaries of the range (lower and upper ends of the range) are included in the claimed range.

In like manner, when various sub-embodiments of a senior (i.e. principal) embodiment are described herein, it will be understood that the sub-embodiments for the senior embodiment may be combined to define another sub-embodiment. Thus, for example, when a principal embodiment includes sub-embodiments 1, 2 and 3, it will be understood that the principal embodiment may be further limited by any one of sub-embodiments 1, 2 and 3, or any combination of sub-embodiments 1, 2 and 3 that is mathematically and physically possible. In like manner, it will be understood that the principal embodiments described herein may be combined in any manner that is mathematically and physically possible, and that the invention extends to such combinations.

When used herein the term "about" or "substantially" or "approximately" will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength, as described in FDA's March 2003 Guidance for Industry on BIOAVAILABILITY AND BIOEQUIVALENCE STUDIES FOR ORALLY ADMINISTERED DRUG PRODUCTS—GENERAL CONSIDERATIONS.

When used herein the term "gamma-hydroxybutyrate" or GHB, unless otherwise specified, refers to the free base of gamma hydroxy-butyrate, a pharmaceutically acceptable salt of gamma-hydroxybutyric acid, and combinations thereof, their hydrates, solvates, complexes or tautomers forms. Gamma-hydroxybutyric acid salts may be selected from the sodium salt of gamma-hydroxybutyric acid or sodium oxybate, the potassium salt of gamma-hydroxybutyric acid, the magnesium salt of gamma-hydroxybutyric acid, the calcium salt of gamma-hydroxybutyric acid, the lithium salt of gamma-hydroxybutyric, the tetra ammonium salt of gamma-hydroxybutyric acid or any other pharmaceutically acceptable salt forms of gamma-hydroxybutyric acid and mixtures thereof.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. The term "formulation" or "composition" refers to the quantitative and qualitative characteristics of a drug product or dosage form prepared in accordance with the current invention.

As used herein the doses and strengths of gamma-hydroxybutyrate are expressed in equivalent-gram (g) weights of sodium oxybate unless stated expressly to the contrary. Thus, when considering a dose of gamma-hydroxybutyrate other than the sodium salt of gamma-hydroxybutyrate, one must convert the recited dose or strength from sodium oxybate to the gamma-hydroxybutyrate under evaluation. Thus, if an embodiment is said to provide a 4.5 g dose of gamma-hydroxybutyrate, because the form of gamma-hydroxybutyrate is not specified, it will be understood that the dose encompasses a 4.5 g dose of sodium oxybate, a 5.1 g dose of potassium gamma-hydroxybutyrate (assuming a 126.09 g/mol MW for sodium oxybate and a 142.20 g/mol MW for potassium gamma-hydroxybutyrate), and a 3.7 g dose of the free base (assuming a 126.09 g/mol MW for sodium oxybate and a 104.1 g/mol MW for the free base of gamma-hydroxybutyrate), or by the weight of any mixture of salts of gamma-hydroxybutyric acid that provides the same amount of GHB as 4.5 g of sodium oxybate.

As used herein "microparticle" means any discreet particle of solid material. The particle may be made of a single material or have a complex structure with core and shells and be made of several materials. The terms "microparticle", "particle", "microspheres" or "pellet" are interchangeable and have the same meaning. Unless otherwise specified, the microparticle has no particular particle size or diameter and is not limited to particles with volume mean diameter D(4,3) below 1 mm.

As used herein, the "volume mean diameter D(4,3)" is calculated according to the following formula:

$$D(4,3) = \Sigma(d_i^4 \cdot n_i) / \Sigma(d_i^3 \cdot n_i)$$

wherein the diameter d of a given particle is the diameter of a hard sphere having the same volume as the volume of that particle.

As used herein, the terms "finished composition", "finished formulation" or "formulation" are interchangeable and designate the modified release formulation of gamma-hydroxybutyrate preferably comprising modified release microparticles of gamma-hydroxybutyrate, immediate release microparticles of gamma-hydroxybutyrate, and any other excipients.

As used herein and in the claims that follow, an "immediate release (IR) portion" of a formulation includes physically discreet portions of a formulation, mechanistically discreet portions of a formulation, and pharmacokinetically discreet portions of a formulation that lend to or support a defined IR pharmacokinetic characteristic. Thus, for example, any formulation that releases active ingredient at the rate and extent required of the immediate release portion of the formulations of the present invention includes an "immediate release portion," even if the immediate release portion is physically integrated in what might otherwise be considered an extended release formulation. Thus, the IR portion may be structurally discreet or structurally indiscreet from (i.e. integrated with) the MR portion. In a preferred embodiment, the IR portion and MR portion are provided as particles, and in an even more preferred sub-embodiment the IR portion and MR portion are provided as particles discreet from each other.

As used here in, "immediate release formulation" or "immediate release portion" refers to a composition that releases at least 80% of its gamma-hydroxybutyrate in 1 hour when tested in a dissolution apparatus 2 according to USP 38 <711> in a 0.1N HCl dissolution medium at a temperature of 37° C. and a paddle speed of 75 rpm.

In like manner, a "modified-release (MR) portion" includes that portion of a formulation or dosage form that lends to or supports a particular MR pharmacokinetic characteristic, regardless of the physical formulation in which the MR portion is integrated. The modified release drug delivery systems are designed to deliver drugs at a specific time or over a period of time after administration, or at a specific location in the body. The USP defines a modified release system as one in which the time course or location of drug release or both, are chosen to accomplish objectives of therapeutic effectiveness or convenience not fulfilled by conventional IR dosage forms. More specifically, MR solid oral dosage forms include extended release (ER) and delayed-release (DR) products. A DR product is one that releases a drug all at once at a time other than promptly after administration. Typically, coatings (e.g., enteric coatings) are used to delay the release of the drug substance until the dosage form has passed through the acidic medium of the stomach. An ER product is formulated to make the drug available over an extended period after ingestion, thus allowing a reduction in dosing frequency compared to a drug presented as a conventional dosage form, e.g. a solution or an immediate release dosage form. For oral applications, the term "extended-release" is usually interchangeable with "sustained-release", "prolonged-release" or "controlled-release".

Traditionally, extended-release systems provided constant drug release to maintain a steady concentration of drug. For some drugs, however, zero-order delivery may not be optimal and more complex and sophisticated systems have been developed to provide multi-phase delivery. One may distinguish among four categories of oral MR delivery systems: (1) delayed-release using enteric coatings, (2) site-specific or timed release (e.g. for colonic delivery), (3) extended-release (e.g., zero-order, first-order, biphasic release, etc.), and (4), programmed release (e.g., pulsatile, delayed extended release, etc.) See Modified Oral Drug Delivery Systems at page 34 in Gibaldi's DRUG DELIVERY SYSTEMS IN PHARMACEUTICAL CARE, AMERICAN SOCIETY OF HEALTH-SYSTEM PHARMACISTS, 2007 and Rational Design of Oral Modified-release Drug Delivery Systems at page 469 in DEVELOPING SOLID ORAL DOSAGE FORMS: PHARMACEUTICAL THEORY AND PRACTICE, Academic Press, Elsevier, 2009. As used herein, "modified release formulation" or "modified release portion" in one embodiment refers to a composition that releases its gamma-hydroxybutyrate according a multiphase delivery that is comprised in the fourth class of MR products, e.g. delayed extended release. As such it differs from the delayed release products that are classified in the first class of MR products.

As used herein the terms "coating", "coating layer," "coating film," "film coating" and like terms are interchangeable and have the same meaning. The terms refer to the coating applied to a particle comprising the gamma-hydroxybutyrate that controls the modified release of the gamma-hydroxybutyrate.

In all pharmacokinetic testing described herein, unless otherwise stated, the dosage form, or the initial dosage form if the dosing regimen calls for more than one administration, is administered approximately two hours after consumption of a standardized dinner consisting of 25.5% fat, 19.6% protein, and 54.9% carbohydrates.

A "similar PK profile" or "comparable bioavailability" means that the mean AUCinf of a test product is from 80% to 125% of the mean AUCinf of a reference product in a suitably designed cross-over trial, and that the mean plasma concentration at 8 hours (C8h) of the test product is from 50% to 130% of the mean plasma concentration at 8 hours (C8h) of the reference product.

Type 1 Narcolepsy (NT1) refers to narcolepsy characterized by excessive daytime sleepiness ("EDS") and cataplexy. Type 2 Narcolepsy (NT2) refers to narcolepsy characterized by excessive daytime sleepiness without cataplexy. A diagnosis of narcolepsy (with or without cataplexy) may be confirmed by one or a combination of (i) an overnight polysomnogram (PSG) and a Multiple Sleep Latency Test (MSLT) performed within the last 2 years, (ii) a full documentary evidence confirming diagnosis from the PSG and MSLT from a sleep laboratory must be made available, (iii) current symptoms of narcolepsy including: current complaint of EDS for the last 3 months (ESS greater than 10), (iv) mean MWT less than 8 minutes, (v) mean number of cataplexy events of 8 per week on baseline Sleep/Cataplexy Diary, and/or (vi) presence of cataplexy for the last 3 months and 28 events per week during screening period.

Unless otherwise specified herein, percentages, ratios and numeric values recited herein are based on weight; averages and means are arithmetic means; all pharmacokinetic measurements based on the measurement of bodily fluids are based on plasma concentrations.

It will be understood, when defining a composition by its pharmacokinetic or dissolution properties herein, that the formulation may in the alternative be defined as "means for" achieving the recited pharmacokinetic or dissolution properties. Thus, a formulation in which the modified release portion releases less than 20% of its gamma-hydroxybutyrate at one hour may instead be defined as a formulation comprising "means for" or "modified release means for" releasing less than 20% of its gamma-hydroxybutyrate at one hour. It will be further understood that the preferred structures for achieving the recited pharmacokinetic or dissolution properties are the structures described in the examples hereof that accomplish the recited pharmacokinetic or dissolution properties.

Discussion of Principal Embodiments

The invention may be described in terms of principal embodiments, which in turn may be recombined to make other principal embodiments, and limited by sub-embodiments to make other principal embodiments.

A first embodiment provides a method of treating cataplexy or excessive daytime sleepiness (EDS) in a patient with narcolepsy, the method comprising: orally administering a dosage of a composition comprising sodium oxybate once per night, wherein the patient experiences fewer adverse reactions as compared to a second patient administered twice-nightly sodium oxybate treatment.

A second embodiment provides a method comprising: orally administering a dosage of a composition comprising sodium oxybate once per night, wherein the patient experiences no adverse reactions.

A third embodiment provides a method comprising: orally administering a dosage of a composition comprising sodium oxybate once per night, wherein the patient experiences less or no obtundation as compared to the twice-nightly sodium oxybate treatment.

A fourth embodiment provides a method comprising: orally administering a dosage of a composition comprising sodium oxybate once per night, wherein the patient experiences less or no clinically significant respiratory depression as compared to the twice-nightly sodium oxybate treatment.

A fifth embodiment provides a method comprising: orally administering a dosage of a composition comprising sodium oxybate once per night, wherein the patient does not have profound CNS depression or severe difficulty breathing at doses of 4.5 g to 9 g sodium oxybate per night.

A sixth embodiment provides a method comprising: orally administering a dosage of a composition comprising sodium oxybate once per night, wherein the patient does not have a clinically significant worsening of respiratory function as measured by apnea/hypopnea index and pulse oximetry at doses of 4.5 g to 9 g sodium oxybate per night.

A seventh embodiment provides a method comprising: orally administering a dosage of a composition comprising sodium oxybate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

An eighth embodiment provides a method comprising: orally administering a dosage of a composition comprising sodium oxybate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

A ninth embodiment provides a method comprising: orally administering a dosage of a composition comprising sodium oxybate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

A tenth embodiment provides a method comprising: orally administering a dosage of a composition comprising sodium oxybate once per night, wherein a peak plasma concentration ($C_{max}$) following administration of one dose is lower than a twice-nightly sodium oxybate treatment. In some aspects, the $C_{max}$ following administration of one 6 g dose is about 65.8 mcg/mL. In other aspects, there is a steady decrease in concentration following a time to peak plasma concentration ($T_{max}$) approximately two hours after dosing. In additional aspects, the $T_{max}$ is about 1.51 hours.

An eleventh embodiment provides a method comprising: orally administering a dosage of a composition comprising sodium oxybate once per night, wherein the dosage of the composition initially administered comprises 4.5 g sodium oxybate. In some aspects, the method further comprises increasing the dosage by 1.5 g per night at weekly intervals to an effective dosage range of 6 g to 9 g per night.

A twelfth embodiment provides a method comprising: orally administering a dosage of a composition comprising sodium oxybate once per night, wherein the composition is a powder for oral suspension. In some aspects, the composition comprises immediate-release and controlled-release granules comprising sodium oxybate and may further comprise microcrystalline cellulose spheres, povidone K30, hydrogenated vegetable oil, methacrylic acid copolymer, malic acid, xanthan gum, hydroxyethyl cellulose, carrageenan, and/or magnesium stearate.

A thirteenth embodiment provides a method comprising: providing the composition in a nightly dose packet of 4.5 g, 6 g, 7.5, g, or 9 g sodium oxybate, wherein the composition is a powder for oral suspension; and orally administering a dosage of a composition comprising sodium oxybate once per night.

A fourteenth embodiment provides a method comprising: providing the composition in a nightly dose packet of 4.5 g, 6 g, 7.5, g, or 9 g sodium oxybate, wherein the composition is a powder for oral suspension; preparing the dosage by suspending the composition from the dose packet in water; and orally administering a dosage of a composition comprising sodium oxybate once per night. In some aspects, the dosage is suspended in approximately 50 mL of water.

A fifteenth embodiment provides a method comprising: orally administering a dosage of a composition comprising sodium oxybate once per night, wherein the dosage is administered without regard for meals.

A sixteenth embodiment provides a method comprising: orally administering a dosage of a composition comprising sodium oxybate once per night, wherein the patient is in bed prior to orally administering the dosage. In some aspects, the patient lays down immediately after administering the dosage.

A seventeenth embodiment provides a method comprising: orally administering a dosage of a composition comprising sodium oxybate once per night, wherein the patient falls asleep within 5 minutes to 15 minutes after administering the dosage.

An eighteenth embodiment provides a method comprising: orally administering a dosage of a composition comprising sodium oxybate once per night and administering single dose of divalproex sodium ER. In some aspects, the dose of divalproex sodium ER is about 1250 mg.

A nineteenth embodiment provides a method comprising: orally administering a dosage of a composition comprising sodium oxybate once per night, wherein the patient is an adult.

A twentieth embodiment provides a method of treating cataplexy or excessive daytime sleepiness (EDS) in a patient with narcolepsy, the method comprising: orally administering a dosage of a composition comprising sodium oxybate once per night, wherein the patient experiences less obtundation as compared to a twice-nightly sodium oxybate treatment.

A twenty first embodiment provides a method comprising: orally administering a dosage of a composition comprising sodium oxybate once per night, wherein the patient experiences no obtundation.

A twenty second embodiment provides a method comprising: orally administering a dosage of a composition comprising sodium oxybate once per night, wherein the patient experiences less or no clinically significant respiratory depression as compared to the twice-nightly sodium oxybate treatment.

A twenty third embodiment provides a method comprising: orally administering a dosage of a composition comprising sodium oxybate once per night, wherein the patient does not have profound CNS depression or severe difficulty breathing at doses of 4.5 g to 9 g sodium oxybate per night.

A twenty fourth embodiment provides a method comprising: orally administering a dosage of a composition comprising sodium oxybate once per night, wherein the patient does not have a clinically significant worsening of respiratory function as measured by apnea/hypopnea index and pulse oximetry at doses of 4.5 g to 9 g sodium oxybate per night.

A twenty fifth embodiment provides a method comprising: orally administering a dosage of a composition comprising sodium oxybate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

A twenty sixth embodiment provides a method comprising: orally administering a dosage of a composition comprising sodium oxybate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

A twenty seventh embodiment provides a method comprising: orally administering a dosage of a composition comprising sodium oxybate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

A twenty ninth embodiment provides a method of treating cataplexy or excessive daytime sleepiness (EDS) in a patient with narcolepsy, the method comprising: orally administering a dosage of a composition comprising sodium oxybate once per night, wherein the patient experiences less respiratory depression as compared to a twice-nightly sodium oxybate treatment.

A thirtieth embodiment provides a method comprising: orally administering a dosage of a composition comprising sodium oxybate once per night, wherein the patient experiences no clinically significant respiratory depression.

A thirty first embodiment provides a method comprising: orally administering a dosage of a composition comprising sodium oxybate once per night, wherein the patient experiences less or no obtundation as compared to the twice-nightly sodium oxybate treatment.

A thirty second embodiment provides a method comprising: orally administering a dosage of a composition comprising sodium oxybate once per night, wherein the patient does not have profound CNS depression or severe difficulty breathing at doses of 4.5 g to 9 g sodium oxybate per night.

A thirty third embodiment provides a method comprising: orally administering a dosage of a composition comprising sodium oxybate once per night, wherein the patient does not have a clinically significant worsening of respiratory function as measured by apnea/hypopnea index and pulse oximetry at doses of 4.5 g to 9 g sodium oxybate per night.

A thirty fourth embodiment provides a method comprising: orally administering a dosage of a composition comprising sodium oxybate once per night, wherein the patient has statistically significant improvement on the Maintenance of Wakefulness Test at dosages of 6 g, 7.5 g, and 9 g as compared to placebo. In some aspects, the patient has a latency to sleep onset about 5 minutes or more than placebo.

A thirty fifth embodiment provides a method comprising: orally administering a dosage of a composition comprising sodium oxybate once per night, wherein the patient has statistically significant improvement on the Clinical Global Impression-Improvement at dosages of 6 g, 7.5 g, and 9 g as compared to placebo. In some aspects, the patient is 5 times or more likely to respond as much or very much improved as compared to placebo.

A thirty sixth embodiment provides a method comprising: orally administering a dosage of a composition comprising sodium oxybate once per night, wherein the patient has statistically significant improvement in mean weekly cataplexy attacks at dosages of 6 g, 7.5 g, and 9 g as compared to placebo. In some aspects, the patient has about 4 or fewer mean cataplexy attacks per week as compared to placebo.

A thirty seventh embodiment provides a modified release formulation of gamma-hydroxybutyrate comprising immediate release and modified release portions, wherein the modified release formulation is suitable for administration only once nightly, without obtundation and clinically significant respiratory depression occurring in adult patients treated with twice-nightly sodium oxybate.

A thirty eighth embodiment provides a modified release formulation of gamma-hydroxybutyrate comprising immediate release and modified release portions, wherein the modified release formulation is suitable for administration only once nightly, with reduced side effects of obtundation and clinically significant respiratory depression occurring in adult patients treated with twice-nightly sodium oxybate.

A thirty ninth embodiment provides a modified release formulation of gamma-hydroxybutyrate comprising immediate release and modified release portions, wherein the immediate release portion comprises gamma-hydroxybutyrate, and the modified release portion comprises gamma-hydroxybutyrate coated with a coating comprising: a polymer carrying free carboxylic groups, and a hydrophobic compound having a melting point equal or greater than 40° C.

Figure 12:
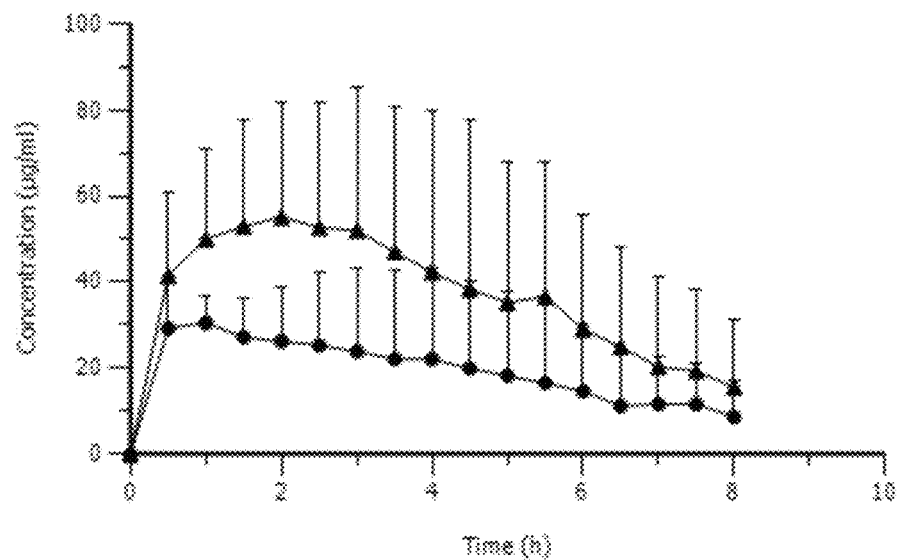
FIG. 12 plots the mean+SD (standard deviation) plasma gamma-hydroxybutyrate concentrations (microgram/mL) versus time after a Single Oral Administration of 4.5 g (• symbols) and 6 g (▲ symbols) of finished composition of Example 1bis in the same 7 subjects tested in vivo according to the methods of Example 3.
Figure 13:
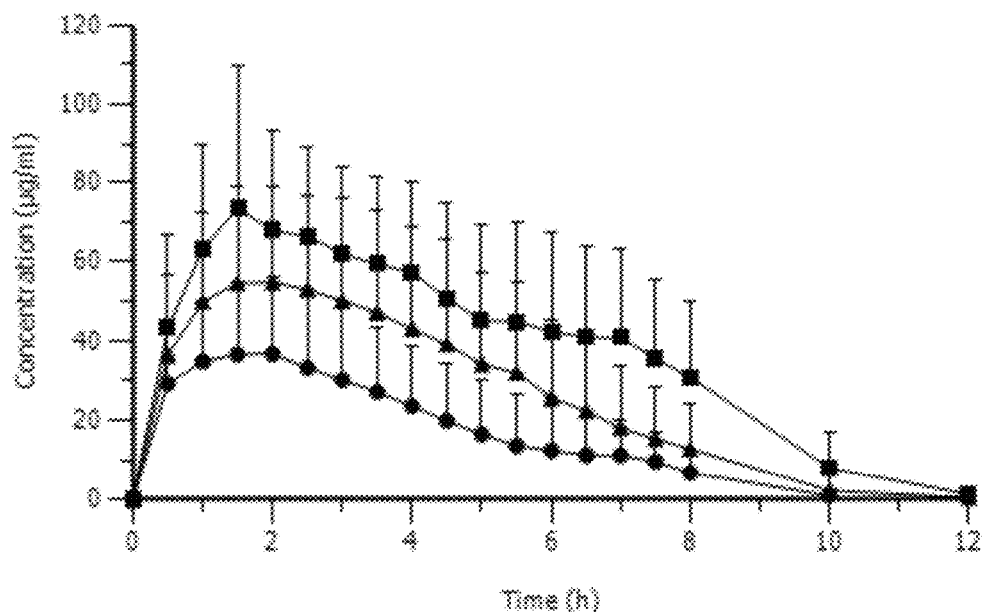
FIG. 13 plots the mean+SD (standard deviation) plasma gamma-hydroxybutyrate concentrations (microgram/mL) versus time of three separate doses of finished composition prepared according to Example 1bis tested in vivo according to the methods of Example 3. Mean time profiles are given for a single oral administration of 4.5 g (N=26) (□), 6.0 g (N=19) (▲) or 7.5 g (■) doses (N=11).

A fortieth embodiment provides a modified release formulation of gamma-hydroxybutyrate comprising immediate release and modified release portions, wherein the formulation yields a plasma concentration versus time curve when administered at a dose of 4.5 g, 6.0 g or 7.5 g approximately two hours after a standardized evening meal substantially as depicted in FIG. 12 or FIG. 13 for the corresponding dose.

Figure 22:
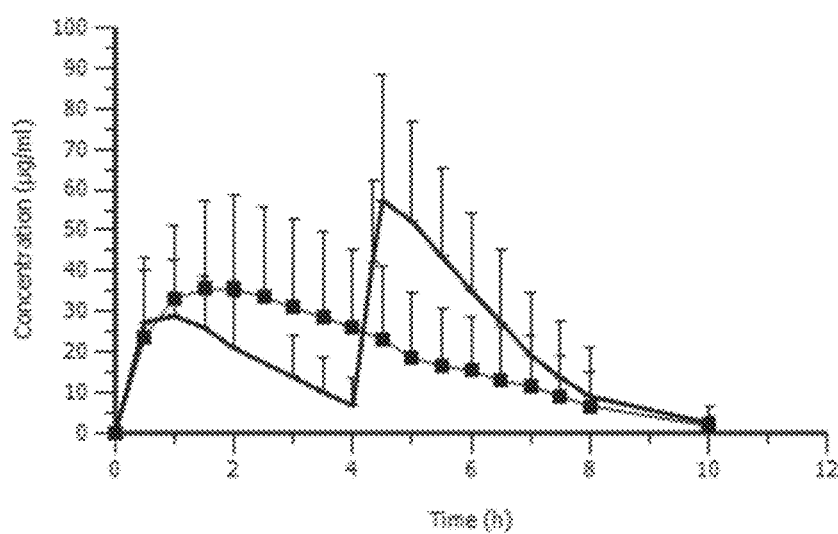
FIG. 22 plots mean plasma gamma-hydroxybutyrate concentration (microgram/mL) time profiles after a Single Dose of 4.5 g (■) of finished composition of Example 4bis, N=15 compared to 2×2.25 g Xyrem® post fed, N=15.

A forty fourth embodiment provides a modified release formulation of gamma-hydroxybutyrate comprising immediate release and modified release portions, wherein the formulation yields a plasma concentration versus time curve when administered at a dose of 4.5 g approximately two hours after a standardized evening meal substantially as depicted in FIG. 22.

Figure 7:
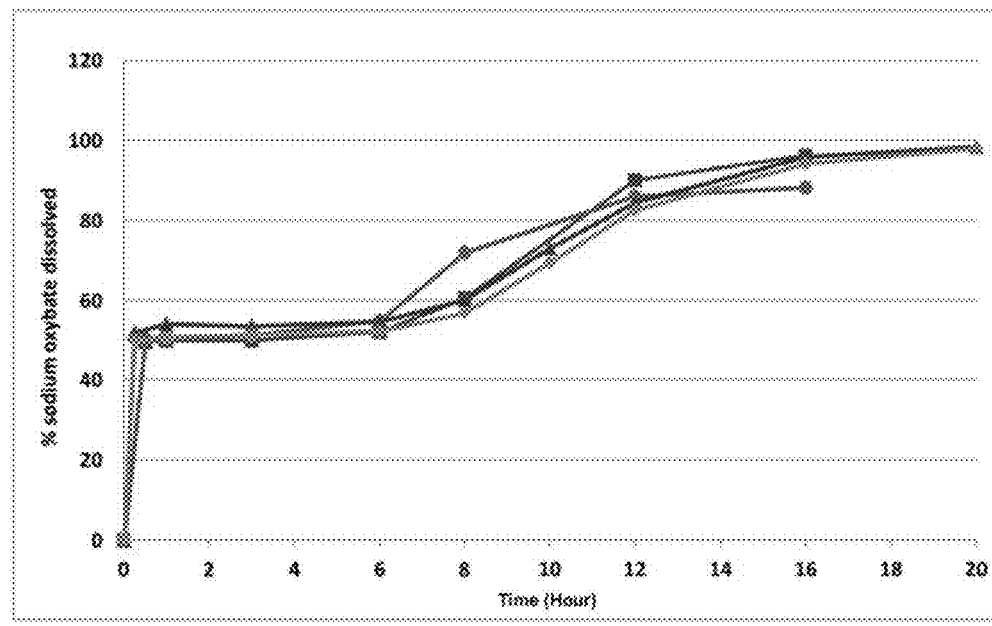
FIG. 7 plots time release dissolution profiles in 0.1N HCl of four separate batches of finished compositions produced in accordance with Example 1 or Example 1bis.
Figure 8:
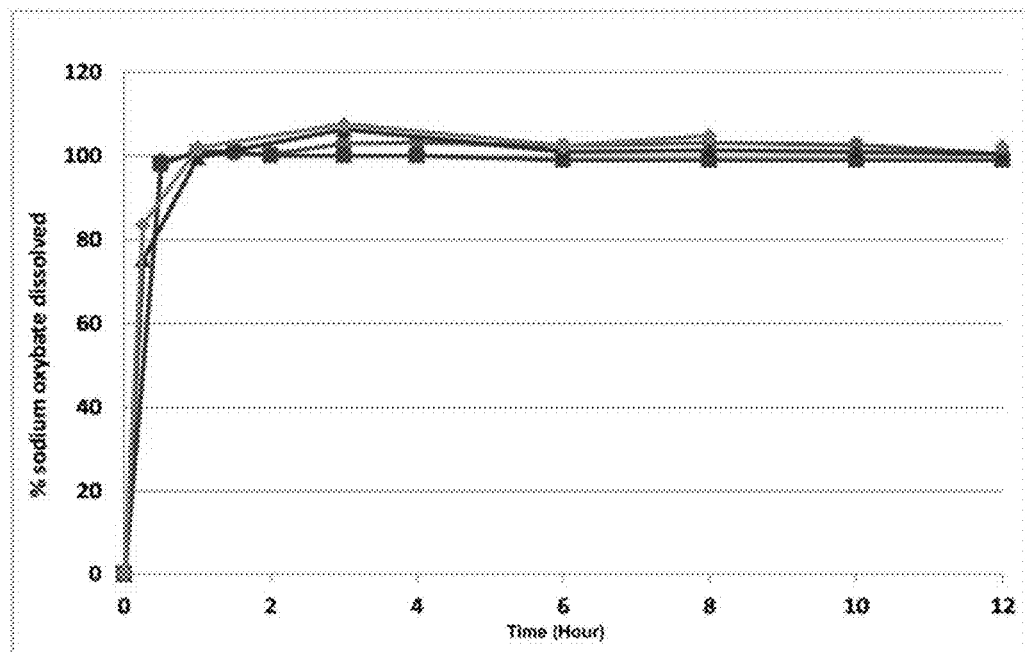
FIG. 8 plots time release dissolution profiles in phosphate buffer pH 6.8 of four separate batches of finished compositions produced in accordance with Example 1 or Example 1bis.

A forty fifth embodiment provides a modified release formulation of gamma-hydroxybutyrate comprising immediate release and modified release portions, wherein the formulation yields a dissolution profile substantially as depicted in FIG. 7 and FIG. 8.

Figure 20:
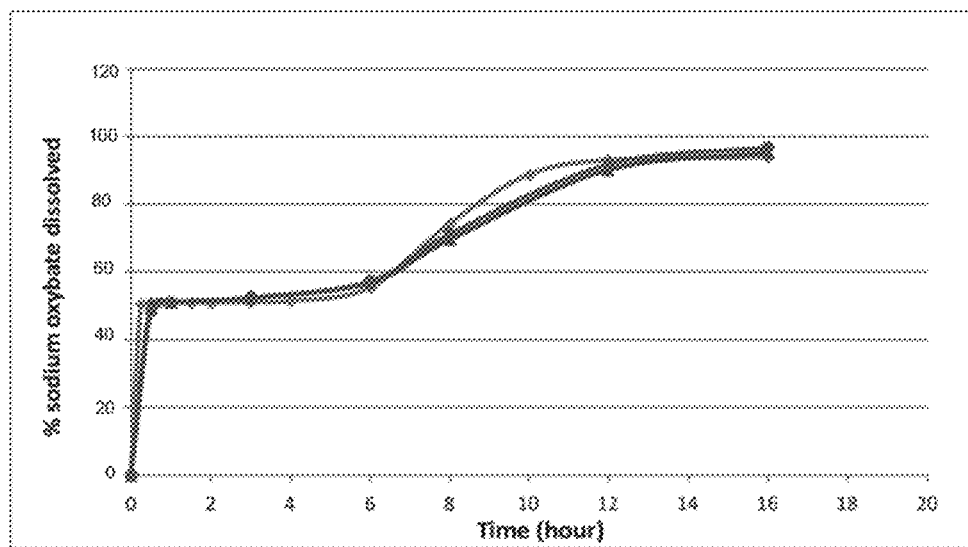
FIG. 20 plots time release dissolution profiles in 0.1N HCl of three separate batches of finished compositions produced in accordance with Example 4 or 4bis.
Figure 21:
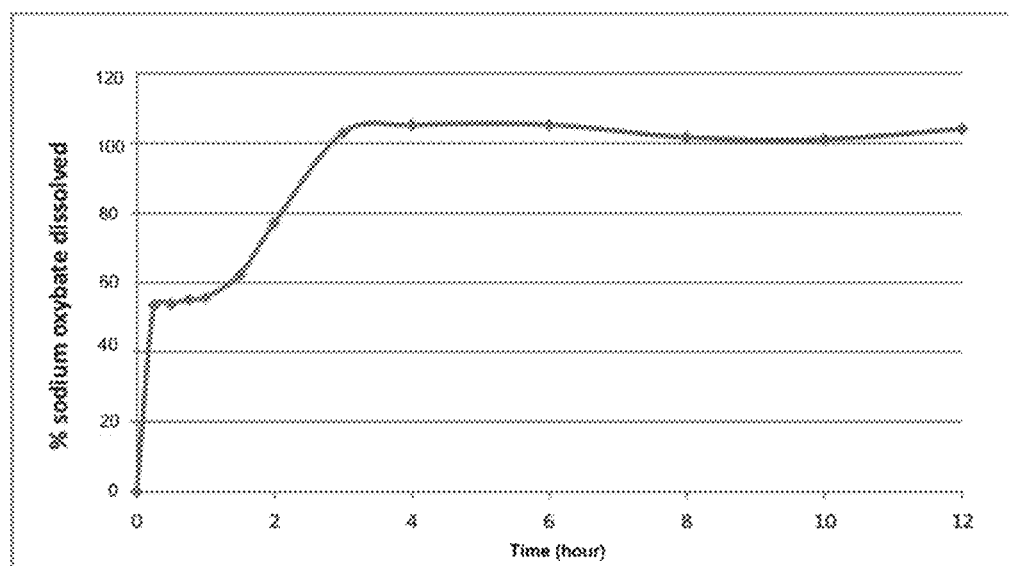
FIG. 21 plots a time release dissolution profile in phosphate buffer pH 6.8 of a finished composition produced in accordance with Example 4.

A forty sixth embodiment provides a modified release formulation of gamma-hydroxybutyrate comprising immediate release and modified release portions, wherein the formulation yields a dissolution profile substantially as depicted in FIG. 20 and FIG. 21.

Figure 3:
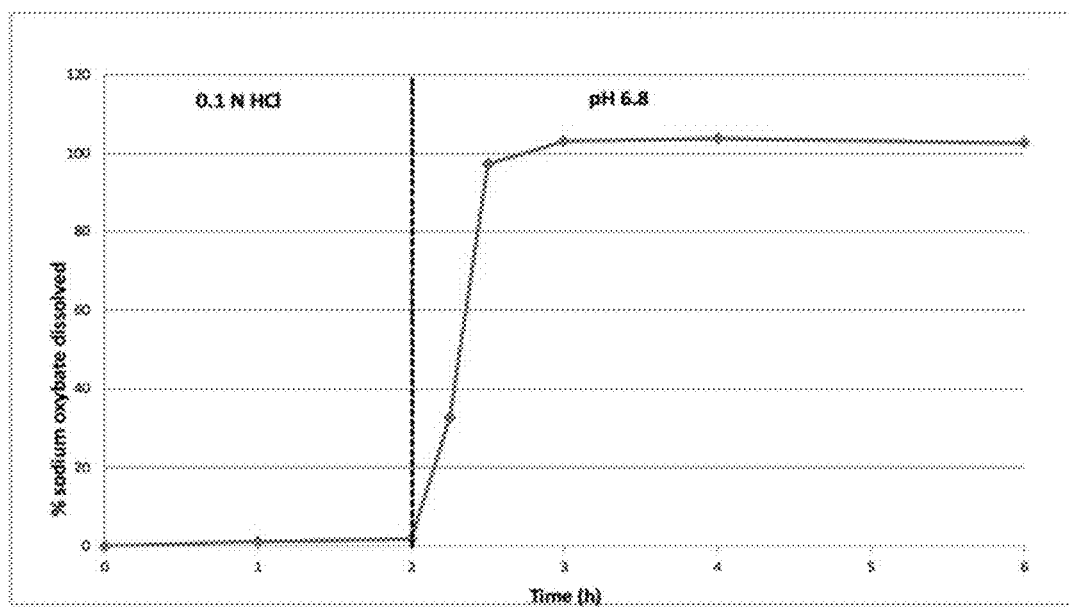
FIG. 3 plots a time release dissolution profile of MR microparticles of gamma-hydroxybutyrate of Example 1 in two sequential dissolution media (0.1 N HCl/phosphate buffer pH 6.8).
Figure 16:
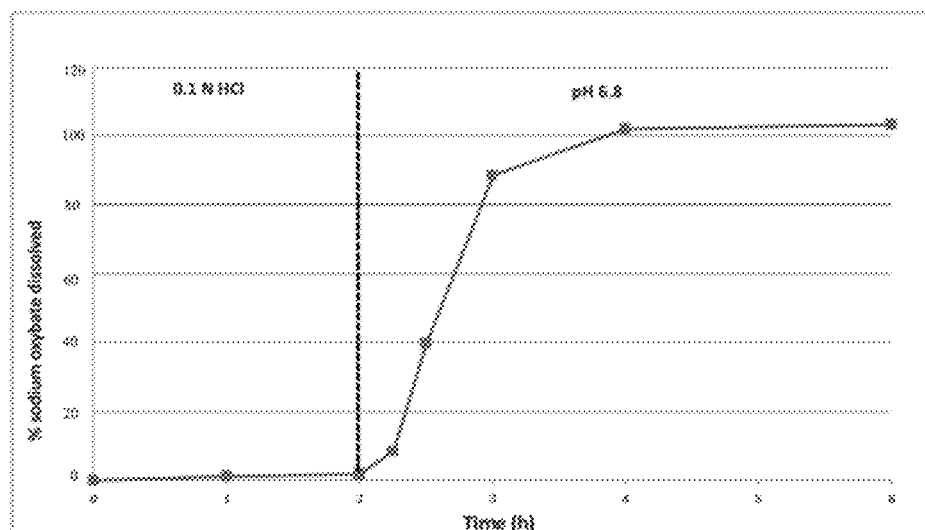
FIG. 16 plots a time release dissolution profile of MR microparticles of gamma-hydroxybutyrate of Example 4 in two sequential dissolution media (0.1 N HCl and phosphate buffer pH 6.8).

A forty seventh embodiment provides a modified release formulation of gamma-hydroxybutyrate comprising immediate release and modified release portions, wherein the modified release portion yields a dissolution profile substantially as depicted in FIG. 3 or FIG. 16.

A forty eighth embodiment provides a modified release formulation of gamma-hydroxybutyrate comprising immediate release and modified release portions, wherein the formulation yields a dissolution profile between the minimum and maximum values depicted in FIG. 25 and FIG. 26.

A forty ninth embodiment provides a modified release formulation of gamma-hydroxybutyrate comprising immediate release and modified release portions, wherein the formulation yields a dissolution profile between the minimum and maximum values depicted in FIG. 27 and FIG. 28.

A fiftieth embodiment provides a modified release formulation of gamma-hydroxybutyrate comprising immediate release and modified release portions, wherein the formulation yields a dissolution profile substantially as shown in any one of FIGS. 29 through 89.

A fifty first embodiment provides a modified release formulation of gamma-hydroxybutyrate comprising immediate release and modified release portions, wherein the formulation yields a plasma concentration versus time curve when administered at a dose of 4.5 g, 7.5 g or 9.0 g approximately two hours after a standardized evening meal substantially as depicted in FIG. 90 for the corresponding dose.

A fifty second embodiment provides a modified release formulation of gamma-hydroxybutyrate comprising immediate release and modified release portions, wherein the formulation yields a dissolution profile between the minimum and maximum values depicted in FIG. 26 and FIG. 28.

A fifty third embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 4.5 g dose achieves a mean $C_{8h}$ of from 4.7 to 9.0 microgram/mL.

A fifty fourth embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 4.5 g dose achieves a mean $C_{8h}$ of from 3.5 to 4.7 microgram/mL.

A fifty fifth embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 6.0 g dose achieves a mean $C_{8h}$ of from 6.3 to 16.7 microgram/mL.

A fifty sixth embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 6.0 g dose achieves a mean $C_{8h}$ of from 7.3 to 15.4 microgram/mL.

A fifty seventh embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 7.5 g dose achieves a mean $C_{8h}$ of from 13.0 to 40.3 microgram/mL.

A fifty eighth embodiment provides a modified release formulation of gamma-hydroxybutyrate comprising immediate release and modified release portions, wherein the formulation is defined based on the concentration of gamma-hydroxybutyrate in the blood stream 8 hours after administration to a patient, and further wherein a 7.5 g dose achieves a mean $C_{8h}$ of from 24.7 to 37.2 microgram/mL.

A fifty ninth embodiment provides a modified release formulation of gamma-hydroxybutyrate comprising immediate release and modified release portions, wherein the formulation is defined based on the time required to reach maximum blood concentration of gamma-hydroxybutyrate to a patient, and further achieves a median $T_{max}$ of 1.25 to 3.25 hours when administered once approximately two hours after a standardized evening meal.

A sixtieth embodiment provides a modified release formulation of gamma-hydroxybutyrate comprising immediate release and modified release portions, wherein the formulation is defined based on the time required to reach maximum blood concentration of gamma-hydroxybutyrate to a patient, and further achieves a median $T_{max}$ of 0.5 to 3.25 hours when administered once approximately two hours after a standardized evening meal.

A sixty first embodiment provides a modified release formulation of gamma-hydroxybutyrate comprising immediate release and modified release portions, wherein the formulation produces a residual drug content in the bloodstream similar to one observed after administration of an equal dose of an immediate release liquid solution of sodium oxybate administered twice nightly.

A sixty second embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation is suitable for administration once-daily, and further wherein the formulation is resistant to alcohol-induced dose dumping.

A sixty third embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

A sixty fourth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

A sixty fifth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

A sixty sixth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and further wherein ethanol concentrations from about 5% to about 20% does not change the dissolution profile.

A sixty seventh embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

A sixty eighth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion provides a modified release profile, and the release rate when measured using a first in vitro dissolution test in the absence of ethanol and the release rate when using a second vitro dissolution test in the presence of about 5% to about 20% ethanol (v/v) are substantially the same, wherein, other than the absence or presence ethanol, the first in vitro dissolution test and the second in vitro dissolution test are the same.

A sixty ninth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm, and further wherein ethanol concentrations from about 5% to about 20% does not change the dissolution profile.

A seventieth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm, and further wherein ethanol concentrations from about 5% to about 20% does not change the dissolution profile.

A seventy first embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a relative bioavailability (RBA) of greater than 80% when compared to an equal dose of an immediate release liquid solution of sodium oxybate administered at $t_0$ and $t_{4h}$ in equally divided doses, when administered approximately two hours after a standardized evening meal.

A seventy second embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 1.25 to 3.25 hours when administered once approximately two hours after a standardized evening meal.

A seventy third embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 0.5 to 3.25 hours when administered once approximately two hours after a standardized evening meal.

A seventy fourth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of about 1.25, 1.5, 1.75, 2, 2.25, 2.5, 2.75, 3, or 3.25 hours when administered once approximately two hours after a standardized evening meal.

A seventy fifth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $AUC_{inf}$ of greater than 300 hr·microgram/mL when administered once approximately two hours after a standardized evening meal. In some aspects, the mean $AUC_{inf}$ is greater than 340 hr·microgram/mL, 375 hr·microgram/mL, or greater than 400 hr·microgram/mL.

A seventy sixth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $C_{max}$ of greater than 70 microgram/mL when administered once approximately two hours after a standardized evening meal.

A seventy seventh embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a mean $AUC_{inf}$ of greater than 80% of the mean $AUC_{inf}$ provided by an equal dose of immediate release liquid solution of sodium oxybate administered at $t_0$ and $t_{4h}$ in equally divided doses approximately two hours after a standardized evening meal, and a mean $C_{8h}$ less than 95% of the mean $C_{8h}$ provided by an equal dose of immediate release liquid solution of sodium oxybate administered at $t_0$ and $t_{4h}$ in equally divided doses approximately two hours after a standardized evening meal.

A seventy eighth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 4.7 to 9.0 microgram/mL when administered once approximately two hours after a standardized evening meal.

A seventy ninth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 3.5 to 4.7 microgram/mL when administered once approximately two hours after a standardized evening meal.

An eightieth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 6.3 to 16.7 microgram/mL when administered once approximately two hours after a standardized evening meal.

An eighty first embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 7.3 to 15.4 microgram/mL when administered once approximately two hours after a standardized evening meal.

An eighty second embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 13.0 to 40.3 microgram/mL when administered once approximately two hours after a standardized evening meal.

An eighty third embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 24.7 to 37.2 microgram/mL when administered once approximately two hours after a standardized evening meal.

An eighty fourth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C.

An eighty fifth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the weight ratio of the hydrophobic compound to the polymer carrying free carboxylic groups is from 0.4 to 4.

An eighty sixth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the pharmaceutically acceptable salt of gamma-hydroxybutyrate comprises a sodium salt of gamma-hydroxybutyric acid, a calcium salt of gammahydroxybutyric acid, a potassium salt of gamma-hydroxybutyric acid, and/or a magnesium salt of gamma-hydroxybutyric acid, and mixtures thereof. In some aspects, the pharmaceutically acceptable salt of gamma-hydroxybutyrate is a calcium salt of gamma-hydroxybutyric acid. In another aspect, the pharmaceutically acceptable salt of comprises calcium and magnesium salt of gamma-hydroxybutyric acid. In yet another aspect, the pharmaceutically acceptable salt of comprises calcium, potassium, and magnesium salt of gamma-hydroxybutyric acid.

An eighty seventh embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising microcrystalline cellulose. In some aspects, the microcrystalline cellulose is present at about 10% w/w-15% w/w.

An eighty eighth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising a layer of hydroxypropyl cellulose.

An eighty ninth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups has a pH-dependent solubility.

A ninetieth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups is selected from the group consisting of (meth)acrylic acid/alkyl (meth)acrylate copolymers, methacrylic acid and methylmethacrylate copolymers, methacrylic acid and ethyl acrylate copolymers, methacrylic acid copolymers type A, B or C, cellulose derivatives carrying free carboxylic groups, preferably cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate, and mixtures thereof.

A ninety first embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the polymer carrying free carboxylic groups comprises a methacrylic acid copolymer. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In additional aspects, the methacrylic acid copolymer comprises poly(methacrylic acid, ethyl acrylate) 1:1.

A ninety second embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the coating is from 10 to 50% of the weight of the modified release portion.

A ninety third embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., further comprising an immediate release portion comprising a pharmaceutically acceptable salt of gamma-hydroxybutyrate. In some aspects, the formulation further comprises xanthan gum, carrageenan gum, gellan gum, guar gum, sodium alginate, calcium alginate, agar, sodium carboxymethyl cellulose, microcrystalline cellulose, hydroxyethyl cellulose, hydroxypropylmethyl cellulose, or mixtures thereof. In at least one aspect, the formulation comprises guar gum. For example, the guar gum is present at 1% to 15% by weight of the formulation.

A ninety fourth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation is a dry particulate formulation or a powdered formulation.

A ninety fifth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation comprises 4.5 g, 6.0 g, 7.5 g, or 9.0 g of gamma-hydroxybutyrate.

A ninety sixth embodiment provides a formulation comprising: a modified release portion comprising: a pharmaceutically acceptable salt of gamma-hydroxybutyrate; and at least one coating on the gamma-hydroxybutyrate comprising: a polymer carrying free carboxylic groups; and a hydrophobic compound having a melting point equal or greater than 40° C., wherein the formulation is suitable to be orally administered once-nightly.

A ninety seventh embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C.

A ninety eighth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the weight ratio of the hydrophobic compound to the methacrylic acid copolymer is from 0.4 to 4.

A ninety ninth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the ratio of gamma-hydroxybutyrate in the immediate release portion and the modified release portion is from 10/90 to 65/35.

A one hundredth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the pharmaceutically acceptable salt of gamma-hydroxybutyrate is selected from a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some aspects, the pharmaceutically acceptable salt of gamma-hydroxybutyrate is a calcium salt of gamma-hydroxybutyric acid.

A one hundred and first embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the microparticles further comprise a layer of hydroxypropyl cellulose.

A one hundred and second embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the methacrylic acid copolymer is selected from the group consisting of (meth)acrylic acid/alkyl (meth)acrylate copolymers, methacrylic acid and methylmethacrylate copolymers, methacrylic acid and ethyl acrylate copolymers, methacrylic acid copolymers type A, B or C, and mixtures thereof. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In at least one aspect, the methacrylic acid copolymers comprise poly(methacrylic acid, ethyl acrylate) 1:1.

A one hundred and third embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the coating is from 10 to 50% of the weight of the microparticles.

A one hundred and fourth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., further comprising xanthan gum, carrageenan gum, gellan gum, guar gum, sodium alginate, calcium alginate, agar, sodium carboxymethyl cellulose, microcrystalline cellulose, hydroxyethyl cellulose, hydroxypropylmethyl cellulose, or mixtures thereof. In some aspects, the formulation comprises guar gum. In at least one aspect, the guar gum is present at 1% to 15% by weight of the formulation.

A one hundred and fifth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation is a dry particulate formulation or a powdered formulation.

A one hundred and sixth embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation comprises 4.5 g, 6.0 g, 7.5 g, or 9.0 g of the pharmaceutically acceptable salt of gamma-hydroxybutyrate.

A one hundred and seventh embodiment provides a formulation of gamma-hydroxybutyrate comprising: an immediate release portion comprising a pharmaceutically acceptable salt of gamma-hydroxybutyrate; a modified release portion comprising: microparticles comprising a pharmaceutically acceptable salt of gamma-hydroxybutyrate; and at least one coating on the microparticles comprising: a methacrylic acid copolymer; and a hydrophobic compound having a melting point equal or greater than 40° C., wherein the formulation is suitable to be orally administered once-daily. In some aspects, the formulation is suitable to be orally administered once-nightly.

A one hundred and eighth embodiment provides a formulation comprising: a modified release portion comprising: microparticles comprising a pharmaceutically acceptable salt of gamma-hydroxybutyrate; and at least one coating on the microparticles comprising a methacrylic acid copolymer.

A one hundred and ninth embodiment provides a formulation comprising: a modified release portion comprising: microparticles comprising a pharmaceutically acceptable salt of gamma-hydroxybutyrate; and at least one coating on the microparticles comprising a methacrylic acid copolymer, wherein the pharmaceutically acceptable salt of gamma-hydroxybutyrate is selected from a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some aspects, the pharmaceutically acceptable salt of gamma-hydroxybutyrate is a calcium salt of gamma-hydroxybutyric acid.

A one hundred and tenth embodiment provides a formulation comprising: a modified release portion comprising: microparticles comprising a pharmaceutically acceptable salt of gamma-hydroxybutyrate; and at least one coating on the microparticles comprising a methacrylic acid copolymer, wherein the microparticles further comprise a layer of hydroxypropyl cellulose.

A one hundred and eleventh embodiment provides a formulation comprising: a modified release portion comprising: microparticles comprising a pharmaceutically acceptable salt of gamma-hydroxybutyrate; and at least one coating on the microparticles comprising a methacrylic acid copolymer, wherein the methacrylic acid copolymer is selected from the group consisting of (meth)acrylic acid/alkyl (meth)acrylate copolymers, methacrylic acid and methylmethacrylate copolymers, methacrylic acid and ethyl acrylate copolymers, methacrylic acid copolymers type A, B or C, and mixtures thereof. In some aspects, the methacrylic acid copolymer is selected from the group consisting of poly (methacrylic acid, methyl methacrylate) 1:1, poly (methacrylic acid, ethyl acrylate) 1:1, poly (methacrylic acid, methyl methacrylate) 1:2, and mixtures thereof. In at least one aspect, the methacrylic acid copolymers comprise poly (methacrylic acid, ethyl acrylate) 1:1.

A one hundred and twelfth embodiment provides a formulation comprising: a modified release portion comprising: microparticles comprising a pharmaceutically acceptable salt of gamma-hydroxybutyrate; and at least one coating on the microparticles comprising a methacrylic acid copolymer, wherein the coating is from 10 to 50% of the weight of the microparticles.

A one hundred and thirteenth embodiment provides a method of treating cataplexy in narcolepsy or excessive daytime sleepiness ("EDS") in narcolepsy, the method comprising administering a formulation of gamma-hydroxybutyrate once-daily.

A one hundred and fourteenth embodiment provides a method of treating cataplexy in narcolepsy or excessive daytime sleepiness ("EDS") in narcolepsy, the method comprising administering a formulation of gamma-hydroxybutyrate once-nightly.

A one hundred and fifteenth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation is suitable for administration once-daily.

A one hundred and sixteenth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm.

A one hundred and seventeenth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the formulation releases from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

A one hundred and eighteenth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm.

A one hundred and nineteenth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

A one hundred and twentieth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the modified release portion releases greater than 80% of its gamma-hydroxybutyrate at three hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

A one hundred and twenty first embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

A one hundred and twenty second embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a relative bioavailability (RBA) of greater than 80% when compared to an equal dose of an immediate release liquid solution of sodium oxybate administered at $t_0$ and $t_{4h}$ in equally divided doses, when administered approximately two hours after a standardized evening meal.

A one hundred and twenty third embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 1.25 to 3.25 hours when administered once approximately two hours after a standardized evening meal.

A one hundred and twenty fourth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of 0.5 to 3.25 hours when administered once approximately two hours after a standardized evening meal.

A one hundred and twenty fifth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a median $T_{max}$ of about 1.25, 1.5, 1.75, 2, 2.25, 2.5, 2.75, 3, or 3.25 hours when administered once approximately two hours after a standardized evening meal.

A one hundred and twenty sixth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $AUC_{inf}$ of greater than 300 hr·microgram/mL when administered once approximately two hours after a standardized evening meal. In some aspects, the mean $AUC_{inf}$ is greater than 340 hr·microgram/mL, greater than 375 hr·microgram/mL, or greater than 400 hr·microgram/mL.

A one hundred and twenty seventh embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose of the formulation achieves a mean $C_{max}$ of greater than 70 microgram/mL when administered once approximately two hours after a standardized evening meal.

A one hundred and twenty eighth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a dose of the formulation achieves a mean $AUC_{inf}$ of greater than 80% of the mean $AUC_{inf}$ provided by an equal dose of immediate release liquid solution of sodium oxybate administered at $t_0$ and $t_{4h}$ in equally divided doses approximately two hours after a standardized evening meal, and a mean $C_{8h}$ less than 95% of the mean $C_{8h}$ provided by an equal dose of immediate release liquid solution of sodium oxybate administered at $t_0$ and $t_{4h}$ in equally divided doses approximately two hours after a standardized evening meal.

A one hundred and twenty ninth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 4.7 to 9.0 microgram/mL when administered once approximately two hours after a standardized evening meal.

A one hundred and thirtieth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 4.5 g dose achieves a mean $C_{8h}$ of from 3.5 to 4.7 microgram/mL when administered once approximately two hours after a standardized evening meal.

A one hundred and thirty first embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 6.3 to 16.7 microgram/mL when administered once approximately two hours after a standardized evening meal.

A one hundred and thirty second embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 6.0 g dose achieves a mean $C_{8h}$ of from 7.3 to 15.4 microgram/mL when administered once approximately two hours after a standardized evening meal.

A one hundred and thirty third embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 13.0 to 40.3 microgram/mL when administered once approximately two hours after a standardized evening meal.

A one hundred and thirty fourth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein a 7.5 g dose achieves a mean $C_{8h}$ of from 24.7 to 37.2 microgram/mL when administered once approximately two hours after a standardized evening meal.

A one hundred and thirty fifth embodiment provides a pharmaceutical formulation comprising: an immediate release portion comprising a pharmaceutically acceptable salt of gamma-hydroxybutyrate; and a modified release portion comprising: microparticles comprising a pharmaceutically acceptable salt of gamma-hydroxybutyrate; and at least one coating on the microparticles comprising: a methacrylic acid polymer; and a hydrophobic compound having a melting point equal or greater than 40° C., wherein the composition produces a residual drug content in the bloodstream similar to one observed after administration of an equal dose of an immediate release liquid solution of sodium oxybate administered twice nightly.

A one hundred and thirty sixth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, and wherein the formulation is suitable for administration once-daily.

A one hundred and thirty seventh embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a mean $AUC_{inf}$ of greater than 80% of the mean $AUC_{inf}$ provided by an equal dose of immediate release liquid solution of sodium oxybate administered at $t_0$ and $t_{4h}$ in equally divided doses approximately two hours after a standardized evening meal. In some aspects, a 7.5 g dose of the formulation achieves a mean $AUC_{inf}$ of greater than 340 hr·microgram/mL, greater than 375 hr·microgram/mL, or greater than 400 hr·microgram/mL.

A one hundred and thirty eighth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median $T_{max}$ of 1.25 to 3.25 hours when administered once approximately two hours after a standardized evening meal.

A one hundred and thirty ninth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median $T_{max}$ of 0.5 to 3.25 hours when administered once approximately two hours after a standardized evening meal.

A one hundred and fortieth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a median $T_{max}$ of about 1.25, 1.5, 1.75, 2, 2.25, 2.5, 2.75, 3, or 3.25 hours when administered once approximately two hours after a standardized evening meal.

A one hundred and forty first embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose of the formulation achieves a mean $C_{max}$ of greater than 70 microgram/mL when administered once approximately two hours after a standardized evening meal.

A one hundred and forty second embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 4.5 g dose achieves a mean $C_{8h}$ of from 4.7 to 9.0 microgram/mL when administered once approximately two hours after a standardized evening meal.

A one hundred and forty third embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 4.5 g dose achieves a mean $C_{8h}$ of from 3.5 to 4.7 microgram/mL when administered once approximately two hours after a standardized evening meal.

A one hundred and forty fourth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 6.0 g dose achieves a mean $C_{8h}$ of from 6.3 to 16.7 microgram/mL when administered once approximately two hours after a standardized evening meal.

A one hundred and forty fifth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 6.0 g dose achieves a mean $C_{8h}$ of from 7.3 to 15.4 microgram/mL when administered once approximately two hours after a standardized evening meal.

A one hundred and forty sixth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose achieves a mean $C_{8h}$ of from 13.0 to 40.3 microgram/mL when administered once approximately two hours after a standardized evening meal.

A one hundred and forty seventh embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a 7.5 g dose achieves a mean $C_{8h}$ of from 24.7 to 37.2 microgram/mL when administered once approximately two hours after a standardized evening meal.

A one hundred and forty eighth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein the 7.5 g dose of the formulation achieves a mean $C_{8h}$ from 50% to 130% of the mean $C_{8h}$ provided by an equal dose of an immediate release liquid solution of sodium oxybate administered at $t_0$ and $t_{4h}$ in equally divided doses approximately two hours after a standardized evening meal. In some aspects, the mean $C_{8h}$ achieved by the formulation is from 60% to 90% of the mean $C_{8h}$ provided by the immediate release liquid solution of sodium oxybate.

A one hundred and forty ninth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein a dose of the formulation achieves a relative bioavailability (RBA) of greater than 80% when compared to an equal dose of an immediate release liquid solution of sodium oxybate administered at $t_0$ and $t_{4h}$ in equally divided doses, when administered approximately two hours after a standardized evening meal.

A one hundred and fiftieth embodiment provides a formulation comprising a pharmaceutically acceptable salt of gamma-hydroxybutyrate in an immediate release portion and a modified release portion, wherein the modified release portion comprises microparticles having at least one coating comprising a methacrylic acid copolymer, wherein the dose is a 4.5 g, 6 g, 7.5 g, or 9 g dose of the formulation.

A one hundred and fifty first embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers.

A one hundred and fifty second embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising ethylcellulose or microcrystalline cellulose.

A one hundred and fifty third embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising cellulose derivatives carrying free carboxylic groups.

A one hundred and fifty fourth embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, further comprising cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate, and mixtures thereof.

A one hundred and fifty fifth embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers comprising Eudragit™ L100, or Eudragit™ L100-55, or Eudragit™ S100.

A one hundred and fifty sixth embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, wherein the coating comprises ethyl acrylate.

A one hundred and fifty seventh embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers comprising poly (methacrylic acid, methyl methacrylate) 1:1, poly (methacrylic acid, ethyl acrylate) 1:1, or poly (methacrylic acid, methyl methacrylate).

A one hundred and fifty eighth embodiment provides a pharmaceutical formulation comprising: particles of gamma-hydroxybutyrate comprising a core and a coating deposited on the core, wherein the coating inhibits the release of gamma-hydroxybutyrate, and wherein the coating comprises a polymer that is selected from methylmethacrylate polymers, wherein the coating comprises a polymer that is selected from methylmethacrylate polymers having a pH-dependent solubility.

A one hundred and fifty ninth embodiment provides a pharmaceutical formulation comprising: particles of gamma-hydroxybutyrate comprising a core and a coating deposited on the core; and immediate release particles that release at least 80% or 90% of its gamma-hydroxybutyrate at 3 hours, 2 hours, 1 hour, 0.5 hours, or 0.25 hours, wherein the coating inhibits the release of gamma-hydroxybutyrate, and wherein the coating comprises a polymer that is selected from methylmethacrylate polymers.

A one hundred and sixtieth embodiment of the present invention provides a modified release formulation of gamma-hydroxybutyrate, preferably comprising immediate release and modified release portions, wherein a 7.5 g dose of the formulation has been shown to achieve a mean $AUC_{inf}$ of greater than 245, 300, 325, 340, 375, 400, 425, or 450 hr×microgram/mL, most preferably greater than 340 hr×microgram/mL.

A one hundred and sixty first principal embodiment of the present invention provides a modified release formulation of gamma-hydroxybutyrate, preferably comprising immediate release and modified release portions, wherein a 7.5 g dose of the formulation has been shown to achieve a mean $AUC_{inf}$ of greater than 245, 265, 285, 300, 315, 325, 340, 350, 375, 400, 425, or 450 hr×microgram/mL, most preferably greater than 340 hr×microgram/mL, and a mean $C_{8h}$ that is from 50% to 130%, from 60% to 130%, from 70% to 130%, from 75% to 125%, from 80% to 125%, from 80 to 120%, from 90% to 110%, from 50% to 95%, from 60% to 90%, most preferably from 60% to 90% or 60% to 130% of the mean $C_{8h}$ provided by an equal dose of an immediate release liquid solution of sodium oxybate (e.g. Xyrem©) administered at $t_0$ and $t_{4h}$ in equally divided doses approximately two hours after a standardized evening meal.

A one hundred and sixty second principal embodiment of the present invention provides a modified release formulation of gamma-hydroxybutyrate, preferably comprising immediate release and modified release portions, wherein the formulation releases (a) at least 80% or 90% of its gamma-hydroxybutyrate at 3 hours, 2 hours, 1 hour, 0.5 hours, or 0.25 hours, preferably 1 hour, when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 10 to 65%, from 15 to 60%, from 20 to 55%, from 25 to 55%, from 30 to 55%, from 35 to 55%, from 40 to 55%, from 40 to 60%, or from 45 to 55%, preferably from 40% to 60%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

A one hundred and sixty third principal embodiment of the present invention provides a modified release formulation of gamma-hydroxybutyrate, comprising immediate release and modified release portions, wherein (a) the formulation releases at least 80% or 90% of its gamma-hydroxybutyrate at 3 hours, 2 hours, 1 hour, 0.5 hours, or 0.25 hours, preferably 1 hour, when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 10 to 65%, from 15 to 60%, from 20 to 55%, from 25 to 55%, from 30 to 55%, from 35 to 55%, from 40 to 55%, from 40 to 60%, or from 45 to 55%, preferably from 40% to 60%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, and (c) the modified release portion preferably releases greater than 80% or 90% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

A one hundred and sixty fourth embodiment of the present invention provides a modified release formulation of gamma-hydroxybutyrate, comprising immediate release and modified release portions, wherein (a) the formulation releases at least 80% or 90% of its gamma-hydroxybutyrate at 3 hours, 2 hours, 1 hour, 0.5 hours, or 0.25 hours, preferably 1 hour, when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 10 to 65%, from 15 to 60%, from 20 to 55%, from 25 to 55%, from 30 to 55%, from 35 to 55%, from 40 to 55%, from 40 to 60%, or from 45 to 55%, preferably from 40% to 60%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60%, 70%, or 80%, preferably greater than 80%, of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

A one hundred and sixty fifth embodiment of the present invention provides a modified release formulation of gamma-hydroxybutyrate, comprising immediate release and modified release portions, wherein (a) a 7.5 g dose of the formulation has been shown to achieve a mean $AUC_{inf}$ of greater than 245, 300, 325, 340, 375, 400, 425, or 450 hr×microgram/mL, preferably 340 hr×microgram/mL, and a mean $C_{8h}$ that is from 50% to 130%, from 60% to 130%, from 70% to 130%, from 75% to 125%, from 80% to 125%, from 80 to 120%, from 90% to 110%, from 50% to 95%, or from 60% to 90%, preferably from 60% to 90% or from 60% to 130%, of the mean $C_{8h}$ provided by an equal dose of an immediate release liquid solution of gamma-hydroxybutyrate (e.g. Xyrem®) administered at $t_0$ and $t_{4h}$ in equally divided doses approximately two hours after a standardized evening meal, and (b) the formulation releases (i) at least 80% or 90% of its gamma-hydroxybutyrate at 3 hours, 2 hours, 1 hour, 0.5 hours, or 0.25 hours, preferably 1 hour, when tested in a dissolution apparatus 2 according to USP 38 <711> in 900 mL of 0.05M monobasic potassium phosphate buffer pH 6.8 at a temperature of 37° C. and a paddle speed of 75 rpm, and (ii) from 10 to 65%, from 15 to 60%, from 20 to 55%, from 25 to 55%, from 30 to 55%, from 35 to 55%, from 40 to 55%, from 40 to 60%, or from 45 to 55%, preferably from 40% to 60%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

A one hundred and sixty sixth embodiment of the present invention provides a modified release formulation of gamma-hydroxybutyrate comprising immediate release and modified release portions, wherein: (a) said immediate release portion releases greater than 80% or 90% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (b) said modified release portion releases less than 20% or 10% of its gamma-hydroxybutyrate at one hour when tested in a dissolution apparatus 2 according to USP 38<711> in 900 mL of 0.1N hydrochloric acid at a temperature of 37° C. and a paddle speed of 75 rpm; and (c) said modified release portion releases greater than 80% or 90% of its gamma-hydroxybutyrate at three hours, two hours or one hour, when tested in a dissolution apparatus 2 according to USP 38 <711> in 900 mL of 0.05M monobasic potassium phosphate buffer pH 6.8 at a temperature of 37° C. and a paddle speed of 75 rpm.

A one hundred and sixty seventh embodiment of the present invention provides a modified release formulation of gamma-hydroxybutyrate comprising immediate release and modified release portions, wherein: (a) said immediate release portion releases greater than 80% or 90% of its gamma-hydroxybutyrate at one hour, two hours, or three hours when tested in a dissolution apparatus 2 according to USP 38 <711> in 900 mL of 0.1N hydrochloric acid at a temperature of 37° C. and a paddle speed of 75 rpm; (b) said modified release portion releases less than 20% or 10% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (c) said modified release portion releases greater than 80% or 90% of its gamma-hydroxybutyrate at three hours, two hours, or one hour, when tested in a dissolution apparatus 2 according to USP 38 <711> in 900 mL of 0.05M monobasic potassium phosphate buffer pH 6.8 at a temperature of 37° C. and a paddle speed of 75 rpm; and (d) said modified release portion releases greater than 80% or 90% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

A one hundred and sixty eighth embodiment of the present invention provides a modified release formulation of gamma-hydroxybutyrate, preferably comprising immediate release and modified release portions, wherein a 4.5 g, 6 g, 7.5 g, and 9 g dose of the formulation has been shown to achieve a relative bioavailability (RBA) of greater than 80%, 85% or 90% when compared to an equal dose of an immediate release liquid solution of sodium oxybate administered at $t_0$ and $t_{4h}$ in equally divided doses, when administered approximately two hours after a standardized evening meal. The relative bioavailability is even higher with larger doses, and with a 6.0 g or 7.5 g or 9.0 g dose is preferably greater than 90, 95 or 100% when compared to an equal dose of an immediate release liquid solution of sodium oxybate administered at to and $t_{4h}$ in equally divided doses, when administered approximately two hours after a standardized evening meal.

A one hundred and sixty ninth embodiment of the present invention provides a modified release formulation of gamma-hydroxybutyrate, wherein a 4.5 g and a 9 g dose of the formulation has been shown to achieve a relative bioavailability (RBA) of greater than 80% when compared to an equal dose of an immediate release liquid solution of sodium oxybate administered at $t_0$ and $t_{4h}$ in equally divided doses, when administered approximately two hours after a standardized evening meal.

A one hundred and seventieth principal embodiment of the present invention provides a modified release formulation of gamma-hydroxybutyrate, preferably comprising immediate release and modified release portions, that yields a plasma concentration versus time curve when administered once nightly at a strength of 4.5 g, 6.0 g, or 7.5 g approximately two hours after a standardized evening meal substantially as depicted in FIG. 12 or FIG. 13 for the corresponding strength.

A one hundred and seventy first principal embodiment of the present invention provides a modified release formulation of gamma-hydroxybutyrate, preferably comprising immediate release and modified release portions, that yields a plasma concentration versus time curve when administered once nightly at a strength of 4.5 g approximately two hours after a standardized evening meal substantially as depicted in FIG. 22.

A one hundred and seventy second principal embodiment of the present invention provides a modified release formulation of gamma-hydroxybutyrate, preferably comprising immediate release and modified release portions, which yields a dissolution profile substantially as depicted in FIG. 7 and FIG. 8.

A one hundred and seventy third principal embodiment of the present invention provides a modified release formulation of gamma-hydroxybutyrate, preferably comprising immediate release and modified release portions, which yields a dissolution profile substantially as depicted in FIG. 20 and FIG. 21.

A one hundred and seventy fourth embodiment of the present invention provides a modified release formulation of gamma-hydroxybutyrate, preferably comprising immediate release and modified release portions that yields a dissolution profile substantially as depicted in FIG. 3 or 16.

A one hundred and seventy fifth embodiment of the invention provides a modified release formulation of gamma-hydroxybutyrate, comprising immediate release and modified release portions that yields a dissolution profile between the minimum and maximum values depicted in FIG. 25 and FIG. 26.

A one hundred and seventy sixth embodiment of the invention provides a modified release formulation of gamma-hydroxybutyrate, comprising immediate release and modified release portions that yields a dissolution profile between the minimum and maximum values depicted in FIG. 27 and FIG. 28.

A one hundred and seventy seventh embodiment of the invention provides a modified release formulation of gamma-hydroxybutyrate yielding a dissolution profile substantially as shown in any one of FIGS. 29 through 89.

A one hundred and seventy eighth embodiment of the present invention provides a modified release formulation of gamma-hydroxybutyrate, preferably comprising immediate release and modified release portions, that yields a plasma concentration versus time curve when administered once nightly at a strength of 4.5 g, 7.5 g or 9.0 g approximately two hours after a standardized evening meal substantially as depicted in FIG. 90 for the corresponding strength.

A one hundred and seventy ninth embodiment of the present invention provides a pharmaceutical composition storage and administration system comprising: at least seven nightly dose packets, each nightly dose packet operable to contain a single once daily dosage of a composition comprising gamma-hydroxybutyrate; one or more packet containers, each packet container operable to receive up to seven nightly dose packets; a mixing cup comprising a lid, a first fill line, and a second fill line; a mixing cup receptacle comprising a cup retaining portion operable to receive the mixing cup; and a carton operable to removably receive the one or more packet containers with up to seven packets in each container and the mixing cup receptacle with the mixing cup.

A one hundred and eightieth embodiment of the present invention provides a pharmaceutical composition storage and administration system, wherein each nightly dose packet contains a once daily dosage of 4.5 g, 6 g, 7.5, g, or 9 g gamma-hydroxybutyrate.

A one hundred and eighty first embodiment of the present invention provides a pharmaceutical composition storage and administration system, wherein the carton is operable to removably receive one packet container with seven nightly dose packets and the mixing cup receptacle with the mixing cup to provide a 7-day supply of the composition.

A one hundred and eighty second embodiment of the present invention provides a pharmaceutical composition storage and administration system, wherein the mixing cup receptacle further comprises a packet portion operable to receive up to two nightly dose packets. In some aspects, the carton is operable to removable receive four packet containers, each with seven nightly dose packets, and the mixing cup receptacle with the mixing cup to provide a 30-day supply of the composition.

A one hundred and eighty third embodiment of the present invention provides a pharmaceutical composition storage and administration system, wherein the first fill line measures about 50 mL and the second fill line measures about 25 mL.

A one hundred and eighty fourth embodiment of the present invention provides a pharmaceutical composition storage and administration system, wherein the mixing cup comprises a bottom and a wall having an inner side operable to intersect with the bottom. In some aspects, the intersection of the inner side of the wall and the bottom is rounded to limit adhesion to the mixing cup. In other aspects, the intersection is not 90 degrees.

A one hundred and eighty fifth embodiment of the present invention provides a method of preparing and administering a pharmaceutical composition to a patient, the method comprising: providing a pharmaceutical composition storage and administration system; removing the lid of the mixing cup and filling the mixing cup with water up to the first fill line; opening one nightly dose packet; emptying the composition from the nightly dose packet into the mixing cup filled with water; replacing the lid of the mixing cup; shaking the mixing cup to form a first suspension of the composition in the water; and administering the first suspension to the patient.

A one hundred and eighty sixth embodiment of the present invention provides a method of preparing and administering a pharmaceutical composition to a patient, the method further comprising: removing the lid of the mixing cup and filling the mixing cup with water up to the second fill line; replacing the lid of the mixing cup; shaking the mixing cup to form a second suspension of any residual composition in the water; and administering the second suspension to the patient.

A one hundred and eighty seventh embodiment of the present invention provides a once-daily modified release formulation of gamma-hydroxybutyrate, wherein the formulation decreases the number of cataplexy attacks (NCA), compared to a dosing regimen consisting of administering the twice-nightly gamma-hydroxybutyrate treatment.

A one hundred and eighty eighth embodiment of the present invention provides a once-daily modified release formulation of gamma-hydroxybutyrate, wherein the formulation produces less confusion, less depressive syndrome, less incontinence, less nausea, or less sleepwalking, compared to a dosing regimen consisting of administering the twice-nightly gamma-hydroxybutyrate treatment.

A one hundred and eighty ninth embodiment of the present invention provides a once-daily modified release formulation of gamma-hydroxybutyrate, wherein the formulation decreases PSG transitions from N/2 to N/3 and REM sleep to wake and N1 sleep, compared to a dosing regimen consisting of administering the twice-nightly gamma-hydroxybutyrate treatment.

A one hundred and ninetieth embodiment of the present invention provides a once-daily modified release formulation of gamma-hydroxybutyrate, wherein the formulation decreases the number of arousals or wakenings obtained from a polysomnogram, compared to a dosing regimen consisting of administering the twice-nightly gamma-hydroxybutyrate treatment.

A one hundred and ninety first embodiment of the present invention provides a once-daily modified release formulation of gamma-hydroxybutyrate, wherein the formulation decreases daytime sleepiness when measured by the Maintenance of Wakefulness Test based on EEG measures of wakefulness, compared to a dosing regimen consisting of administering the twice-nightly gamma-hydroxybutyrate treatment.

A one hundred and ninety second embodiment of the present invention provides a once-daily modified release formulation of gamma-hydroxybutyrate, wherein the formulation decreases the hypnagogic hallucinations or sleep paralysis symptoms in Type 1 narcolepsy patients, compared to a dosing regimen consisting of administering the twice-nightly gamma-hydroxybutyrate treatment.

A one hundred and ninety third embodiment of the present invention provides a once-daily modified release formulation of gamma-hydroxybutyrate, wherein the formulation increases the mean sleep latency compared to a dosing regimen consisting of administering the twice-nightly gamma-hydroxybutyrate treatment.

A one hundred and ninety fourth embodiment of the present invention provides a once-daily modified release formulation of gamma-hydroxybutyrate, wherein the formulation decreases excessive daytime sleepiness (EDS) as measured by patient report via the Epworth Sleepiness Scale (ESS), compared to a dosing regimen consisting of administering the twice-nightly gamma-hydroxybutyrate treatment.

A one hundred and ninety fifth embodiment of the present invention provides a once-daily modified release formulation of gamma-hydroxybutyrate, wherein the formulation improves a Clinical Global Impression (CGI) rating of sleepiness, compared to a dosing regimen consisting of administering the twice-nightly gamma-hydroxybutyrate treatment.

A one hundred and ninety sixth embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in the number of cataplexy attacks (NCA), compared to a patient with a dosing regimen consisting of administering the twice-nightly gamma-hydroxybutyrate treatment.

A one hundred and ninety seventh embodiment of the present invention provides a method of treating cataplexy or excessive daytime sleepiness (EDS) in a patient with narcolepsy by orally administering a dosage of a composition comprising gamma-hydroxybutyrate once per night, wherein the patient has less confusion, less depressive syndrome, less incontinence, less nausea, or less sleepwalking, compared to a patient with a dosing regimen consisting of administering the twice-nightly gamma-hydroxybutyrate treatment.

A one hundred and ninety eighth embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in PSG transitions from N/2 to N/3 and REM sleep to wake and N1 sleep, compared to a patient with a dosing regimen consisting of administering the twice-nightly gamma-hydroxybutyrate treatment.

A one hundred and ninety ninth embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in the number of arousals or wakenings obtained from a polysomnogram, compared to a patient with a dosing regimen consisting of administering the twice-nightly gamma-hydroxybutyrate treatment.

A two hundredth embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in hypnagogic hallucinations or sleep paralysis symptoms in Type 1 narcolepsy patients, compared to a patient with a dosing regimen consisting of administering the twice-nightly gamma-hydroxybutyrate treatment.

A two hundred and first embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in daytime sleepiness when measured by the Maintenance of Wakefulness Test based on EEG measures of wakefulness, compared to a patient administered the twice-nightly gamma-hydroxybutyrate treatment.

A two hundred and second embodiment of the present invention provides a method of treating cataplexy or excessive daytime sleepiness (EDS) in a patient with narcolepsy by orally administering a dosage of a composition comprising gamma-hydroxybutyrate once per night, wherein the patient has a decrease in excessive daytime sleepiness (EDS) as measured by patient report via the Epworth Sleepiness Scale (ESS), compared to a patient administered the twice-nightly gamma-hydroxybutyrate treatment.

A two hundred and third embodiment of the present invention provides a method of treating cataplexy or excessive daytime sleepiness (EDS) in a patient with narcolepsy by orally administering a dosage of a composition comprising gamma-hydroxybutyrate once per night, wherein the patient has an increase in mean sleep latency compared to a patient administered the twice-nightly gamma-hydroxybutyrate treatment.

A two hundred and fourth embodiment of the present invention provides a method of treating cataplexy or excessive daytime sleepiness (EDS) in a patient with narcolepsy by orally administering a dosage of a composition comprising gamma-hydroxybutyrate once per night, wherein the patient improves the Clinical Global Impression-Improvement (CGI) rating of sleepiness, compared to a patient administered the twice-nightly gamma-hydroxybutyrate treatment.

A two hundred and fifth embodiment of the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a plasma GHB concentration maintained throughout the night, and gradual decline of the GHB concentration to lowest levels by 8 to 10 hours after dosing.

A two hundred and sixth embodiment of the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a pharmacokinetic profile that supports once nightly dosing, and eliminates the need for the patient having to wake up in the middle of the night to take a second dose.

A two hundred and seventh embodiment of the present invention provides a method of treating cataplexy or excessive daytime sleepiness (EDS) in a patient with narcolepsy comprising: orally administering a dosage of a composition comprising 4.5-9 g of gamma-hydroxybutyrate once per night, wherein the patient experiences a pharmacokinetic profile that supports once nightly dosing and a full 8 hours of consolidated nocturnal sleep.

A two hundred and eighth embodiment of the present invention provides a method of treating cataplexy or excessive daytime sleepiness (EDS) in a child or adolescent patient with narcolepsy comprising: orally administering a dosage of a composition comprising gamma-hydroxybutyrate once per night, wherein the child or adolescent patient dosage is not calculated based on weight of the patient.

A two hundred and ninth embodiment of the present invention provides a method of treating narcolepsy, cataplexy, or excessive daytime sleepiness in a human patient in need thereof, the method comprising orally administering to the patient a once-nightly dosage of gamma-hydroxybutyrate, wherein the patient has statistically significant improvement on the Maintenance of Wakefulness Test (MWT) at dosages of 4.5 g, 6 g, 7.5 g, and 9 g as compared to placebo.

A two hundred and tenth embodiment of the present invention provides a method of treating narcolepsy, cataplexy, or excessive daytime sleepiness in a human patient in need thereof, the method comprising orally administering to the patient a once-nightly dosage of gamma-hydroxybutyrate, wherein the oral administration of the once-nightly dosage induces the patient to fall asleep within 5 minutes of administration.

A two hundred and eleventh embodiment of the present invention provides a method of treating narcolepsy, cataplexy, or excessive daytime sleepiness in a human patient in need thereof, the method comprising orally administering to the patient a once-nightly dosage of gamma-hydroxybutyrate, wherein the oral administration of the once-nightly dosage induces the patient to fall asleep within 15 minutes of administration.

A two hundred and twelfth embodiment of the present invention provides a method of treating narcolepsy, cataplexy, or excessive daytime sleepiness in a subject comprising administering to the subject a once-nightly dose of gamma-hydroxybutyrate, wherein 2% or fewer subjects administered the once-nightly dose of gamma-hydroxybutyrate experience a confusional state.

A two hundred and thirteenth embodiment of the present invention provides a method of treating narcolepsy, cataplexy, or excessive daytime sleepiness in a subject comprising administering to the subject a once-nightly dose of gamma-hydroxybutyrate, wherein 3% or fewer subjects administered the once-nightly dose of gamma-hydroxybutyrate experience sleepwalking.

A two hundred and thirteenth embodiment of the present invention provides a composition comprising an oral suspension for the treatment of narcolepsy or excessive daytime sleepiness, the suspension comprising a blend of granules for oral suspension in water, the granules comprising gamma-hydroxybutyrate, wherein the oral suspension is administered only once nightly and is effective to induce sleep in a human subject in need thereof for at least six hours, and wherein the composition provides a $C_{max}$ which increases approximately 2-fold, and more than dose proportionally for AUC increasing 2.3-fold, as a total daily dose is doubled from 4.5 g to 9 g.

A two hundred and fourteenth embodiment of the present invention provides a A composition of gamma-hydroxybutyrate comprising immediate release and modified release portions, wherein the immediate release portion comprises particles comprising one or more salts of gamma-hydroxybutyrate and the modified release portion comprises particles comprising one or more salts of gamma-hydroxybutyrate, wherein the particles of the modified release portion are coated with a coating comprising:

a. a polymer carrying free carboxylic groups, and
  b. a hydrophobic compound having a melting point equal or greater than 40° C.,
  c. wherein the composition is suitable for administration only once nightly,
  d. wherein the composition induces sleep for at least 6 consecutive hours, and
  e. provides a $C_{max}$ which increases approximately 2-fold, and more than dose proportionally for AUC increasing 2.3-fold, as a total daily dose is doubled from 4.5 g to 9 g.

In any of these principal embodiments, the formulation is preferably effective to treat narcolepsy Type 1 or Type 2. The formulation is also preferably effective to induce sleep for six to eight, most preferably eight consecutive hours.

In any of these principal embodiments, the formulation preferably comprises immediate release and modified release portions, wherein the modified release portion comprises gamma hydroxybutyrate particles coated by a polymer carrying free carboxylic groups and a hydrophobic compound having a melting point equal or greater than 40° C., and the ratio of gamma-hydroxybutyrate in the immediate release portion and the modified release portion is from 10/90 to 65/35. The polymers comprising free carboxylic groups preferably have a pH dissolution trigger of from 5.5 to 6.97 and are preferably methacrylic acid copolymers having a pH dissolution trigger of from 5.5 to 6.97.

Principal Structural Embodiments

In a first principal structural embodiment, the invention provides a modified release formulation of gamma-hydroxybutyrate comprising immediate release and modified release portions, wherein: (a) the modified release portion comprises coated particles of gamma-hydroxybutyrate; (b) the coating comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35.

In a second principal structural embodiment the invention provides a modified release formulation of gamma-hydroxybutyrate comprising immediate release and modified release portions, a suspending or viscosifying agent, and an acidifying agent, wherein: (a) the modified release portion comprises coated particles of gamma-hydroxybutyrate; (b) the coating comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35.

In a third principal structural embodiment the invention provides a modified release formulation of gamma-hydroxybutyrate comprising immediate release and modified release portions, wherein: (a) the modified release portion comprises coated particles of gamma-hydroxybutyrate; (b) the coating comprises a polymer carrying free carboxylic groups and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In a fourth principal structural embodiment the invention provides a modified release formulation of gamma-hydroxybutyrate comprising immediate release and modified release portions, wherein: (a) the modified release portion comprises coated particles of gamma-hydroxybutyrate; (b) the coating comprises a polymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In a fifth principal structural embodiment the invention provides a modified release formulation of gamma-hydroxybutyrate comprising immediate release and modified release portions, wherein: (a) the modified release portion comprises coated particles of gamma-hydroxybutyrate; (b) the coating comprises a methacrylic acid copolymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35; and (e) the coating is from 10 to 50% of the weight of the particles.

In an additional embodiment, a modified release formulation of gamma-hydroxybutyrate may include immediate release and modified release portions, where the modified release formulation is suitable for administration only once nightly. The formulation may be administered once nightly without obtundation and clinically significant respiratory depression that occurs in adult patients treated with twice-nightly sodium oxybate. The once nightly formulation may result in reduced side effects of obtundation and clinically significant respiratory depression occurring in adult patients treated with twice-nightly sodium oxybate. In these embodiments, the immediate release portion may include gamma-hydroxybutyrate or a pharmaceutically acceptable salt thereof, and the modified release portion may include gamma-hydroxybutyrate or a pharmaceutically acceptable salt thereof coated with a coating comprising: a polymer carrying free carboxylic groups, and a hydrophobic compound having a melting point equal or greater than 40° C.

Discussion of Pharmacokinetic and Dissolution Sub-Embodiments

As mentioned in the definitions section of this document, each of the sub-embodiments may be used to further characterize and limit each of the foregoing principal embodiments. In addition, more than one of the following sub-embodiments may be combined and used to further characterize and limit each of the foregoing principal embodiments, in any manner that is mathematically and physically possible.

In some sub-embodiments, the formulation yields a plasma concentration versus time curve when administered at a dose of 4.5 g, 6.0 g or 7.5 g approximately two hours after a standardized evening meal substantially as depicted in FIG. 12 or FIG. 13 for the corresponding dose.

In additional sub-embodiments, the formulation yields a plasma concentration versus time curve when administered at a dose of 4.5 g approximately two hours after a standardized evening meal substantially as depicted in FIG. 22.

In other sub-embodiments, the formulation yields a dissolution profile substantially as depicted in FIG. 7, FIG. 8, FIG. 20, FIG. 21, and/or FIGS. 29 through 89. The formulation may yield a dissolution profile between the minimum and maximum values depicted in FIG. 25, FIG. 26, FIG. 27, and/or FIG. 28.

In some sub-embodiments, the modified release portion yields a dissolution profile substantially as depicted in FIG. 3 or FIG. 16.

In additional sub-embodiments, the formulation yields a plasma concentration versus time curve when administered at a dose of 4.5 g, 7.5 g or 9.0 g approximately two hours after a standardized evening meal substantially as depicted in FIG. 90 for the corresponding dose.

In other sub-embodiments, the formulation produces a residual drug content in the bloodstream similar to one observed after administration of an equal dose of an immediate release liquid solution of sodium oxybate administered twice nightly.

In various sub-embodiments of the foregoing principal embodiments a 7.5 g dose of the modified release formulation of gamma-hydroxybutyrate may be characterized as having been shown to achieve a mean $AUC_{inf}$ of greater than 245, 265, 285, 300, 315, 325, 340, 350, 375, 400, 425, or 450 hr×microgram/mL when administered once approximately two hours after a standardized evening meal. An upper limit on mean $AUC_{inf}$ for such 7.5 g dose may be set at 500 or 550 hr×microgram/mL.

In additional sub-embodiments of the foregoing principal embodiments a 7.5 g dose of the modified release formulation of gamma-hydroxybutyrate may be characterized as having been shown to achieve a mean $C_{max}$ of greater than 65, 70, 75, 80, 85, or 90 microgram/mL when administered once approximately two hours after a standardized evening meal. An upper limit on mean Cm, for such 7.5 g dose may be set at 125 or 100 microgram/mL. In other embodiments, a 6 g dose of the modified release formulation of gamma-hydroxybutyrate may be characterized as having been shown to achieve a mean $C_{max}$ of greater than 50, 55, 60, 65, 70, 75, or 80 microgram (mcg)/mL when administered once nightly. In at least one embodiment, following oral administration of the formulation of gamma-hydroxybutyrate, the $C_{max}$ of a 6 g dose may be about 65.8 mcg/mL.

In additional sub-embodiments of the forgoing principal embodiments a 7.5 g dose of the modified release formulation of gamma-hydroxybutyrate may be characterized as having been shown to achieve a mean $C_{8h}$ that is from 50% to 130%, from 60% to 130%, from 70 to 130%, from 75% to 125%, from 80% to 125%, from 80 to 120%, or from 90% to 110% of the mean $C_{8h}$ provided by an equal dose of immediate release liquid solution of gamma-hydroxybutyrate administered at $t_0$ and $t_{4h}$ in two equally divided doses, when administered approximately two hours after a standardized evening meal.

In one sub-embodiment, a 7.5 g dose of the formulation has been shown to achieve a mean $AUC_{inf}$ of greater than 340 hr·microgram/mL, and a mean $C_{8h}$ that is from 50% to 130% of the mean $C_{8h}$ provided by an equal dose of immediate release liquid solution of sodium oxybate administered at $t_0$ and $t_{4h}$ in equally divided doses approximately two hours after a standardized evening meal.

Further sub-embodiments may be characterized based on the dissolution properties of the entire (or finished) modified release formulation of gamma-hydroxybutyrate in 0.1N hydrochloric acid dissolution medium. Thus, in additional sub-embodiments the entire modified release formulation of gamma-hydroxybutyrate releases greater than 30%, 35%, 40%, or 45%, and less than 70%, 65%, 60%, or 55%, of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

Further sub-embodiments may be defined based on the dissolution properties of the modified release portion of the formulation of gamma-hydroxybutyrate in a phosphate buffer pH 6.8 dissolution medium. Thus, in additional sub-embodiments the modified release portion releases greater than 80%, 85%, 90%, 95%, 98% or even 99% of its gamma-hydroxybutyrate at 3, 2, 1, 0.5 or 0.25 hours when tested in a dissolution apparatus 2 according to USP 38 <711> in 900 mL of 0.05M monobasic potassium phosphate buffer pH 6.8 at a temperature of 37° C. and a paddle speed of 75 rpm.

Still further embodiments may be defined based on the dissolution properties of the modified release portion of the modified release formulation of gamma-hydroxybutyrate in a 0.1N HCl dissolution medium. Thus, in additional sub-embodiments the modified release portion releases less than 20%, 15%, 10%, 5%, or even 2% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

In additional embodiments, the modified release portion releases less than 20%, 15%, 10%, 5%, or even 2% of its gamma-hydroxybutyrate at one hour and at three hours and more than 30%, 35%, 40%, 45% of its gamma-hydroxybutyrate at ten hours when tested in a dissolution apparatus 2 according to USP 38 <711> in 900 mL of 0.1N hydrochloric acid at a temperature of 37° C. and a paddle speed of 75 rpm.

Further embodiments may be defined based on the dissolution properties of the immediate release portion of the modified release formulation of gamma-hydroxybutyrate in a 0.1N HCl dissolution medium. Thus, in additional sub-embodiments the immediate release portion releases greater than 80%, 85%, 90%, 95%, 98% or even 99% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm.

In another sub-embodiment, the formulation releases (a) at least 80% of its gamma-hydroxybutyrate at three hours when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In another sub-embodiment, the formulation comprises immediate release and modified release portions, and (a) the formulation releases at least 80% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 10% to 65%, of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In another sub-embodiment, the formulation comprises immediate release and modified release portions, and (a) the formulation releases at least 80% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases 10% to 65% of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60% of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

Still further sub-embodiments may be defined based on a pharmacokinetic comparison of the modified release formulation of gamma-hydroxybutyrate to an immediate release solution of gamma-hydroxybutyrate. Therefore, in additional sub-embodiments the modified release formulation of gamma-hydroxybutyrate, preferably in a 4.5 g, 6.0 g, 7.5 g, and 9.0 g dose, has been shown to achieve a relative bioavailability (RBA) of greater than 80%, 85%, 90%, or 95% when compared to an equal dose of an immediate release liquid solution of sodium oxybate administered at $t_0$ and $t_{4h}$ in equally divided doses, when administered approximately two hours after a standardized evening meal.

In additional sub-embodiments of the forgoing principal embodiments the invention provides a modified release formulation of gamma-hydroxybutyrate, preferably comprising immediate release and modified release portions, wherein a 4.5 g and 9 g dose of the formulation has been shown to achieve a relative bioavailability (RBA) of greater than 80%, 85% or 90% when compared to an equal dose of an immediate release liquid solution of sodium oxybate administered at $t_0$ and $t_{4h}$ in equally divided doses, when administered approximately two hours after a standardized evening meal In additional sub-embodiments, a 6.0 g or 7.5 g or 9.0 g dose of the modified release formulation of gamma-hydroxybutyrate has been shown to achieve a relative bioavailability (RBA) of greater than 80%, 85%, 90%, 95% or 100% when compared to an equal dose of an immediate release liquid solution of sodium oxybate administered at $t_0$ and $t_{4h}$ in equally divided doses, when administered approximately two hours after a standardized evening meal. In an example, a 4.5 g, 6.0 g, 7.5 g or 9.0 g dose of the modified release formulation of gamma-hydroxybutyrate has been shown to achieve an absolute bioavailability of about 88%.

The modified release formulations of gamma-hydroxybutyrate of the present invention may also be defined by comparing the area under the concentration/time curve for eight hours to the area under the concentration/time curve calculated to infinity. Thus, in still further sub-embodiments a 4.5 g, 6.0 g, 7.5 g or 9.0 g dose of the modified release formulation of gamma-hydroxybutyrate of the present invention has been shown to achieve a ratio of $AUC_{8h}$ to $AUC_{inf}$ of greater than 0.80, 0.85, 0.90, 0.95 or 0.98 when administered once approximately two hours after a standardized evening meal.

In still further sub-embodiments, the modified release formulations of gamma-hydroxybutyrate are defined based on the concentration of gamma-hydroxybutyrate in the blood stream 8 hours after administration. Therefore, in other sub-embodiments the formulation may be characterized by a 4.5 g dose of the modified release formulation of gamma-hydroxybutyrate that has been shown to achieve a mean $C_{8h}$ of from 3.5 to 4.7, 4.7 to 9.0, from 5.4 to 8.3, from 6.1 to 7.6, from 3.5 to 7.0, or from 4.0 to 5.5 microgram/mL, a 6.0 g dose of the modified release formulation of gamma-hydroxybutyrate has been shown to achieve a mean $C_{8h}$ of from 6.3 to 16.7, from 7.3 to 15.4, from 8.2 to 14.1, from 8.9 to 16.7, from 10.2 to 15.4, or from 11.5 to 14.1 microgram/mL; or a 7.5 g dose of the modified release formulation of gamma-hydroxybutyrate has been shown to achieve a mean $C_{8h}$ of from 13.0 to 40.3, from 16.0 to 26.0, 15.0 to 25.0, from 17.5 to 22.0, from 21.6 to 40.3, from 24.7 to 37.2, or from 27.8 to 34.1 microgram/mL, when administered once approximately two hours after a standardized evening meal.

The modified release formulations of gamma-hydroxybutyrate of the present invention may also be defined by the concentration/time and dissolution curves that they produce when tested according to the examples of the present invention. Therefore, in other sub-embodiments, a 4.5 g, 6.0 g, or 7.5 g dose of the modified release formulation of gamma-hydroxybutyrate of the present invention has been shown to achieve a time/concentration curve substantially as shown in FIGS. 13 (a), (b) and (c) respectively herein. In another principal embodiment or sub-embodiment, the formulation has been shown to achieve a dissolution curve substantially as shown in FIGS. 7 and 8 or FIGS. 20 and 21 herein.

The modified release formulations of gamma-hydroxybutyrate of the present invention may also be defined based on the time required to reach maximum blood concentration of gamma-hydroxybutyrate. Thus, in additional sub-embodiments, the modified release formulation of gamma-hydroxybutyrate has been shown to achieve a median $T_{max}$ of 0.5 to 3.25 hours or 1.25 to 3.25 hours, preferably of about 1.25, 1.5, 1.75, 2, 2.25, 2.5, 2.75, 3, or 3.25 hours when administered once approximately two hours after a standardized evening meal. A lower limit on the median $T_{max}$ in any of the foregoing ranges may alternatively be set at 0.5 or 1.0 hours. In at least one example, the $T_{max}$ of the formulation is about 1.5 hours.

Additional embodiments may be defined by comparing a dose of the modified release formulation of gamma-hydroxybutyrate, administered once nightly, to the same dose of an immediate release liquid solution of sodium oxybate divided in half and administered twice nightly, 4 hours apart. Thus, in another sub-embodiment a 4.5 g, 6.0 g, 7.5 g or 9.0 g dose of the modified release formulation of gamma-hydroxybutyrate has been shown to achieve a median $T_{max}$ within one hundred fifty, one hundred twenty, ninety, sixty or thirty minutes of the median $T_{max}$ of half the dose of an immediate release liquid solution of sodium oxybate, when administered approximately two hours after a standardized evening meal.

In still another sub-embodiment a 4.5 g, 6.0 g, 7.5 g or 9.0 g dose of the modified release formulation of gamma-hydroxybutyrate has been shown to achieve a mean $C_{6h}$ or mean $C_{7h}$ greater than, and a mean $C_{10h}$ less than, the mean $C_{4h}$ of half the dose of an immediate release liquid solution of sodium oxybate, when administered approximately two hours after a standardized evening meal.

Additional embodiments may be defined by comparing the pharmacokinetic profile of a dose of the modified release formulation of gamma-hydroxybutyrate administered once nightly to the same dose of an immediate release liquid solution of sodium oxybate divided in half and administered twice nightly, 4 hours apart. Thus, in another sub-embodiment a modified release formulation of gamma-hydroxybutyrate according to the invention has been shown to achieve a ratio of its mean $C_{3h}$ to the mean $C_{max}$ of the first half dose of the immediate release liquid solution of sodium oxybate from 0.6 to 1.2, preferably from 0.7 to 1.1 and most preferably from 0.8 to 1. In another sub-embodiment, a modified release formulation of gamma-hydroxybutyrate according to the invention has been shown to achieve a ratio of its mean $C_{4h}$ to the mean $C_{max}$ of the first half dose of the immediate release liquid solution of sodium oxybate from 0.5 to 1.1, preferably from 0.6 to 1 and most preferably from 0.7 to 0.9. In another sub-embodiment, a modified release formulation of gamma-hydroxybutyrate according to the invention has been shown to achieve a ratio of its mean $C_{4.5h}$ to the mean $C_{max}$ of the first half dose of the immediate release liquid solution of gamma-hydroxybutyrate from 0.5 to 1, preferably from 0.5 to 0.9 and most preferably from 0.6 to 0.8.

Additional sub-embodiments may be defined by the range of mean blood concentrations of gamma-hydroxybutyrate achieved 3, 4, 4.5 or 5 hours after administration once nightly by a modified release formulation of gamma-hydroxybutyrate according to the invention at the dose of 7.5 g. Thus, in another sub-embodiment, a 7.5 g dose of the modified release formulation of gamma-hydroxybutyrate has been shown to achieve a mean $C_{3h}$ of 43 to 81 microgram/mL, preferably 49 to 75 microgram/mL and more preferably 55 to 69 microgram/mL. In another sub-embodiment, a 7.5 g dose of the modified release formulation of gamma-hydroxybutyrate has been shown to achieve a mean $C_{4h}$ of 40 to 75 microgram/mL, preferably 45 to 69 microgram/mL and more preferably 51 to 64 microgram/mL. In another sub-embodiment, a 7.5 g dose of the modified release formulation of gamma-hydroxybutyrate has been shown to achieve a mean $C_{4.5h}$ of 35 to 67 microgram/mL, preferably 40 to 62 microgram/mL and more preferably 45 to 56 microgram/mL. In another sub-embodiment, a 7.5 g dose of the modified release formulation of gamma-hydroxybutyrate has been shown to achieve a mean $C_{5h}$ of 31 to 59 microgram/mL, preferably 36 to 55 microgram/mL and more preferably 40 to 50 microgram/mL.

In another sub-embodiment, a 7.5 g dose of the formulation has been shown to achieve a mean $AUC_{inf}$ of greater than 300 hr·microgram/mL and a mean $C_{max}$ of greater than 70 microgram/mL when administered once approximately two hours after a standardized evening meal.

In still another sub-embodiment, a 7.5 g dose of the formulation has been shown to achieve a mean $AUC_{inf}$ of greater than 350 hr·microgram/mL and a mean $C_{max}$ of greater than 80 microgram/mL when administered once approximately two hours after a standardized evening meal.

In another sub-embodiment, a 4.5, 6.0, 7.5 and 9.0 g dose of the formulation has been shown to achieve a mean $AUC_{inf}$ of greater than 80% of the mean $AUC_{inf}$ provided by an equal dose of immediate release liquid solution of sodium oxybate administered at $t_0$ and $t_{4h}$ in equally divided doses approximately two hours after a standardized evening meal, and a mean $C_{8h}$ less than 95%, 90 or 85% of the mean $C_{8h}$ provided by an equal dose of immediate release liquid solution of sodium oxybate administered at $t_0$ and $t_{4h}$ in equally divided doses approximately two hours after a standardized evening meal.

Additional embodiments may be defined by comparing the pharmacokinetic profile of a dose of the modified release formulation of gamma-hydroxybutyrate administered once nightly to another dose of an immediate release liquid solution of sodium oxybate divided in half and administered twice nightly, 4 hours apart. Thus, in another sub-embodiment a 7.5 g dose of the modified release formulation of gamma-hydroxybutyrate has been shown to achieve a similar pharmacokinetic profile to the pharmacokinetic profile provided by a 2×4.5 g dose of sodium oxybate as an immediate release liquid solution administered for the first 4.5 g two hours after a standardized evening meal and for the second 4.5 g dose, 4 hours after the first dose. Thus, in another sub-embodiment a modified release formulation of gamma-hydroxybutyrate according to the invention administered at the dose of 7.5 g has been shown to achieve a ratio of its mean $C_{3h}$ to the mean $C_{max}$ of the first 4.5 g dose of the immediate release liquid solution of sodium oxybate from 0.5 to 1.1, preferably from 0.6 to 1 and most preferably from 0.7 to 0.9. In another sub-embodiment, a modified release formulation of gamma-hydroxybutyrate according to the invention has been shown to achieve a ratio of its mean $C_{4h}$ to the mean $C_{max}$ of the first 4.5 g dose of the immediate release liquid solution of sodium oxybate from 0.5 to 1, preferably from 0.6 to 0.9 and most preferably from 0.7 to 0.8. In another sub-embodiment, a modified release formulation of gamma-hydroxybutyrate according to the invention has been shown to achieve a ratio of its mean $C_{4.5h}$ to the mean $C_{max}$ of the 4.5 g dose of the immediate release liquid solution of sodium oxybate from 0.4 to 0.9, preferably from 0.5 to 0.8 and most preferably from 0.6 to 0.7.

The modified release formulation of gamma-hydroxybutyrate administered once nightly at 4.5 and 6 g may have lower overall $C_{max}$ and $C_{8h}$ and similar exposure and variability compared with twice-nightly sodium oxybate. In an embodiment, the modified release formulation of gamma-hydroxybutyrate administered once nightly may have a lower $C_{max}$, lower plasma concentration 8 h after dosing ($C_{8h}$), similar exposure (AUC), and comparable interperson variability to twice-nightly sodium oxybate 4.5 g. In some embodiments, there may be a similar sleep quality and morning alertness between the modified release formulation of gamma-hydroxybutyrate administered once nightly and twice-nightly sodium oxybate. In an embodiment, the modified release formulation of gamma-hydroxybutyrate administered once nightly may have dose proportionality for $C_{max}$ and about dose proportionality for AUC. A 6 g dose of the modified release formulation of gamma-hydroxybutyrate administered once nightly may have a lower $C_{max}$ and $C_{8h}$ than twice-nightly sodium oxybate at 6 g but equivalent AUC and comparable variability. In some embodiments, a 6 g dose of the modified release formulation of gamma-hydroxybutyrate administered once nightly may have a longer $T_{max}$ (1 h later), lower $C_{max}$ (67%), and decreased AUC (86%) in fed versus fasted states. Adverse events with the modified release formulation of gamma-hydroxybutyrate administered once nightly may be mostly mild or moderate in severity, nonserious, and known to be associated with sodium oxybate. Safety profiles of the modified release formulation of gamma-hydroxybutyrate administered once nightly and twice-nightly sodium oxybate at 4.5 and 6 g may be similar.

In direct comparison to twice-nightly sodium oxybate, the modified release formulation of gamma-hydroxybutyrate administered once nightly may have bioequivalent exposure at the 4.5- and 6 g doses. Indirect comparison to twice-nightly sodium oxybate from the published literature suggests that the modified release formulation of gamma-hydroxybutyrate administered once nightly may have a more predictable pharmacokinetic profile with ascending doses (dose-proportional increase in $C_{max}$ and slightly more than dose-proportional increase in $AUC_{inf}$ [e.g. an approximate 2.3-fold increase in plasma GHB concentration with a 2-fold dose increase]). Twice-nightly sodium oxybate treatment produces a 3.7-fold increase in plasma GHB concentration with a 2-fold dose increase, indicating nonlinear clearance and necessitating weight-based dosing in pediatric populations. Moreover, the pharmacokinetic profile of the modified release formulation of gamma-hydroxybutyrate administered once nightly suggests that food may have less of an effect on GHB concentrations, particularly overall exposure, than twice-nightly sodium oxybate. In twice-nightly sodium oxybate, significant differences were observed for $T_{max}$, $C_{max}$, and $AUC_{inf}$ with $C_{max}$ values>2-fold higher in the fasted versus fed states. This difference was reflected by second-dose $T_{max}$ and $C_{max}$ (relatively fasted state at 6 h after eating) being higher than first-dose $T_{max}$ and $C_{max}$ (relatively fed state at 2 h after eating) with twice-nightly SO. The increase in $C_{max}$ observed with the second dose of twice-nightly sodium oxybate (i.e., the relatively fasted state) and associated adverse events could potentially lead some patients to eat during the night before taking their second dose to avoid adverse events associated with high $C_{max}$ further disrupting nocturnal sleep.

The modified release formulation of gamma-hydroxybutyrate administered once nightly eliminates the risks associated with having to wake up in the middle of the night to take the second dose. The modified release formulation of gamma-hydroxybutyrate administered once nightly may also offer other clinical benefits over twice-nightly sodium oxybate in patients with narcolepsy. Once-nightly dosing in itself may have a positive effect on disrupted nocturnal sleep, allowing a full 8 hours of consolidated nocturnal sleep.

A temporal relationship has been observed between incidence of adverse events and $C_{max}$ with twice-nightly sodium oxybate. The single $C_{max}$ with the modified release formulation of gamma-hydroxybutyrate administered once nightly is lower than those of twice-nightly sodium oxybate, which may translate into fewer $C_{max}$-associated adverse events. In some embodiments, 8-hour GHB levels with the modified release formulation of gamma-hydroxybutyrate administered once nightly may be slightly lower than with twice-nightly sodium oxybate, and there may be no observable difference between the modified release formulation of gamma-hydroxybutyrate administered once nightly and twice-nightly sodium oxybate in the "awake following sleep" domain of the LSEQ. In an embodiment, the modified release formulation of gamma-hydroxybutyrate administered once nightly may produce dose proportionality in the GHB concentration. This predictable dosing profile may avoid the weight-based dosing currently needed in children and adolescents treated with twice-nightly sodium oxybate. Pharmacokinetic parameters of the modified release formulation of gamma-hydroxybutyrate administered once nightly may be affected to a lesser extent in relation to food intake compared with those of twice-nightly sodium oxybate. Thus, the modified release formulation of gamma-hydroxybutyrate administered once nightly may also be administered with food or less than 2 hours after eating.

In another sub-embodiment, the modified release formulation of gamma-hydroxybutyrate comprises immediate release and modified release portions, wherein: (a) said immediate release portion releases greater than 80% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; (b) said modified release portion releases less than 20% of its gamma-hydroxybutyrate at one hour when tested in a dissolution apparatus 2 according to USP 38 <711> in 900 mL of 0.1N hydrochloric acid at a temperature of 37° C. and a paddle speed of 75 rpm; and (c) said modified release portion releases greater than 80% of its gamma-hydroxybutyrate at one hour when tested in a dissolution apparatus 2 according to USP 38 <711> in 900 mL of 0.05M monobasic potassium phosphate buffer pH 6.8 at a temperature of 37° C. and a paddle speed of 75 rpm.

In a preferred embodiment, the modified release formulation of gamma-hydroxybutyrate according to the invention achieves an in vitro dissolution profile:

(a) measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being:
  (i) from 40% to 65% at 1 hour,
  (ii) from 40% to 65% at 3 hours,
  (iii) from 47% to 85% at 8 hours,
  (iv) greater or equal to 60% at 10 hours,
  (v) greater or equal to 80% at 16 hours, and
(b) measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being:
  (i) from 43% to 94% at 0.25 hour,
  (ii) greater or equal to 65% at 0.35 hour, and
  (iii) greater or equal to 88% at 1 hour.

In a preferred embodiment, the modified release formulation of gamma-hydroxybutyrate according to the invention achieves an in vitro dissolution profile:
  (a) measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being:
    (i) from 40% to 65% at 1 hour,
    (ii) from 40% to 65% at 3 hours,
    (iii) greater or equal to 47% at 8 hours,
    (iv) greater or equal to 60% at 10 hours,
    (v) greater or equal to 80% at 16 hours, and
  (b) measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being:
    (i) from 43% to 94% at 0.25 hour,
    (ii) greater or equal to 65% at 0.35 hour, and
    (iii) greater or equal to 88% at 1 hour.

In another preferred embodiment, the modified release formulation of gamma-hydroxybutyrate according to the invention achieves an in vitro dissolution profile:
  (a) measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being:
    (i) from 40% to 65% at 1 hour,
    (ii) from 40% to 65% at 3 hours,
    (iii) from 47% to 85% at 8 hours,
    (iv) greater or equal to 60% at 10 hours,
    (v) greater or equal to 80% at 16 hours, and
  (b) measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being:
    (i) from 45% to 67% at 1 hour, and
    (ii) greater or equal to 65% at 3 hours.

In another preferred embodiment, the modified release formulation of gamma-hydroxybutyrate according to the invention achieves an in vitro dissolution profile:
  (a) measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being:
    (i) from 40% to 65% at 1 hour,
    (ii) from 40% to 65% at 3 hours,
    (iii) greater or equal to 47% at 8 hours,
    (iv) greater or equal to 60% at 10 hours,
    (v) greater or equal to 80% at 16 hours, and
  (b) measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being:
    (i) from 45% to 67% at 1 hour, and
    (ii) greater or equal to 65% at 3 hours.

In still another sub-embodiment, the formulation achieves an in vitro dissolution profile: (a) measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being: (i) from 40% to 65% at 1 hour, (ii) from 40% to 65% at 3 hours, (iii) greater than 45% at 8 hours, and (b) measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being: (i) greater than 40% at 0.5 hour, and (ii) greater than 85% at 1 hour.

Alternatively, the formulation may be described as achieving an in vitro dissolution profile measured in a dissolution apparatus 2 according to USP 38 <711> in 900 mL of 0.1N hydrochloric acid at a temperature of 37° C. and a paddle speed of 75 rpm, characterized by the percentage of gamma-hydroxybutyrate dissolved being: (i) from 40% to 65% at 1 hour, (ii) from 40% to 65% at 3 hours, and (iii) greater than 45% at 8 hours.

In another alternative, the formulation may be described as achieving an in vitro dissolution profile measured in a dissolution apparatus 2 according to USP 38 <711> in 900 mL of 0.05M monobasic potassium phosphate buffer pH 6.8 at a temperature of 37° C. and a paddle speed of 75 rpm, characterized by the percentage of gamma-hydroxybutyrate dissolved being: (i) greater than 40% at 0.5 hour, and (ii) greater than 85% at 1 hour.

In some embodiments, the formulation is resistant to alcohol-induced dose dumping. For example, ethanol concentrations from about 5% to about 20% may not change the dissolution profile of the formulation. In additional embodiments, the modified release portion provides a modified release profile, and the release rate when measured using a first in vitro dissolution test in the absence of ethanol and the release rate when using a second vitro dissolution test in the presence of about 5% to about 20% ethanol (v/v) are substantially the same, where, other than the absence or presence ethanol, the first in vitro dissolution test and the second in vitro dissolution test are the same.

Structural Sub-Embodiments

The modified release formulations of gamma-hydroxybutyrate of the present invention may be provided in any dosage form that is suitable for oral administration, including tablets, capsules, liquids, orally dissolving tablets, and the like, but they are preferably provided as dry particulate formulations (i.e. granules, powders, coated particles, microparticles, pellets, microspheres, etc.), in a sachet or other suitable discreet packaging units. A preferred particulate formulation will be mixed with tap water shortly before administration, preferably 30-50 mL. In some embodiments, the formulation is a dry particulate formulation or a powdered formulation. In various embodiments, the formulation is suitable for oral administration once daily, for example, once nightly.

In various embodiments, the formulation may include a pharmaceutically acceptable salt of gamma-hydroxybutyrate selected from a sodium salt of gamma-hydroxybutyric acid, a calcium salt of gamma-hydroxybutyric acid, a potassium salt of gamma-hydroxybutyric acid, and/or a magnesium salt of gamma-hydroxybutyric acid. In some examples, the pharmaceutically acceptable salt of gamma-hydroxybutyrate is a calcium salt of gamma-hydroxybutyric acid.

In one sub-embodiment, the formulation comprises immediate release and modified release portions, wherein: (a) the modified release portion comprises coated microparticles of gamma-hydroxybutyrate; and (b) the ratio of gamma-hydroxybutyrate in the immediate release portion and the modified release portion is from 10/90 to 65/35.

In one sub-embodiment, the formulation comprises immediate release and modified release portions, wherein: (a) the modified release portion comprises coated microparticles of gamma-hydroxybutyrate; and (b) the ratio of gamma-hydroxybutyrate in the immediate release portion and the modified release portion is from 40/60 to 60/40.

In another sub-embodiment, the formulation comprises immediate release and modified release portions, wherein: (a) the modified release portion comprises coated microparticles of gamma-hydroxybutyrate; (b) the coating of said modified release particles of gamma-hydroxybutyrate comprises a polymer carrying free carboxylic groups and a hydrophobic compound having a melting point equal or greater than 40° C.; and (c) the ratio of gamma-hydroxybutyrate in the immediate release portion and the modified release portion is from 10/90 to 65/35 or 40/60 to 60/40.

In another sub-embodiment, the formulation comprises immediate release and modified release portions, wherein: (a) the modified release portion comprises coated microparticles of gamma-hydroxybutyrate; (b) the coating of said modified release particles of gamma-hydroxybutyrate comprises a polymer carrying free carboxylic groups and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35 or 40/60 to 60/40; and (e) the film coating is from 10 to 50% of the weight of the microparticles.

In another sub-embodiment the formulation comprises immediate release and modified release portions, wherein: (a) the modified release portion comprises coated particles of gamma-hydroxybutyrate; (b) the coating of said modified release particles of gamma-hydroxybutyrate comprises a polymer carrying free carboxylic groups having a pH trigger of from 5.5 to 6.97 and a hydrophobic compound having a melting point equal or greater than 40° C.; (c) the weight ratio of the hydrophobic compound to the polymer carrying free carboxylic groups is from 0.4 to 4; (d) the ratio of gamma-hydroxybutyrate in the immediate release portion and the modified release portion is from 10/90 to 65/35 or 40/60 to 60/40; and (e) the coating is from 10 to 50% of the weight of the particles.

In some embodiments, the formulation comprises a modified release portion comprising a pharmaceutically acceptable salt of gamma-hydroxybutyrate and at least one coating on the gamma-hydroxybutyrate, where the coating comprises a polymer carrying free carboxylic groups and a hydrophobic compound having a melting point equal or greater than 40° C. The weight ratio of the hydrophobic compound to the polymer carrying free carboxylic groups may be from 0.4 to 4.

In other embodiments, the formulation may further comprise microcrystalline cellulose. The microcrystalline cellulose may be present at about 10% w/w-15% w/w. In additional embodiments, the formulation may further include a layer of hydroxypropyl cellulose.

In some embodiments, the polymer carrying free carboxylic groups in the coating may have a pH-dependent solubility. In various embodiments, the polymer carrying free carboxylic groups is selected from (meth)acrylic acid/alkyl (meth)acrylate copolymers, methacrylic acid and methylmethacrylate copolymers, methacrylic acid and ethyl acrylate copolymers, methacrylic acid copolymers type A, B or C, cellulose derivatives carrying free carboxylic groups, preferably cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate, and mixtures thereof.

In additional embodiments, the polymer carrying free carboxylic groups comprises a methacrylic acid copolymer. Non-limiting examples of the methacrylic acid copolymer include poly (methacrylic acid, methyl methacrylate) 1:1, poly (methacrylic acid, ethyl acrylate) 1:1, poly (methacrylic acid, methyl methacrylate) 1:2, and mixtures thereof. In additional aspects, the methacrylic acid copolymer comprises poly(methacrylic acid, ethyl acrylate) 1:1.

In some sub-embodiments, the polymer carrying free carboxylic groups comprises from 100% poly (methacrylic acid, ethyl acrylate) 1:1 and 0% poly (methacrylic acid, methylmethacrylate) 1:2 to 2% poly (methacrylic acid, ethyl acrylate) 1:1 and 98% poly (methacrylic acid, methylmethacrylate) 1:2; and the hydrophobic compound comprises hydrogenated vegetable oil.

In an embodiment, the coating comprises from 10 to 50%, 10 to 20%, 20 to 30%, 30 to 40%, or 40 to 50% of the weight of the modified release portion.

In some embodiments, the formulation may further include an immediate release portion comprising a pharmaceutically acceptable salt of gamma-hydroxybutyrate. In an embodiment, the formulation further comprises xanthan gum, carrageenan gum, gellan gum, guar gum, sodium alginate, calcium alginate, agar, sodium carboxymethyl cellulose, microcrystalline cellulose, hydroxyethyl cellulose, hydroxypropylmethyl cellulose, or mixtures thereof. In at least one example, the formulation comprises guar gum. For example, the guar gum may be present at 1% to 15% by weight of the formulation.

In a preferred embodiment, the formulation includes excipients to improve the viscosity and the pourability of the mixture of the particulate formulation with tap water. As such, the particulate formulation comprises, besides the immediate release and modified release particles of gamma-hydroxybutyrate, one or more suspending or viscosifying agents or lubricants.

Preferred suspending or viscosifying agents are chosen from the group consisting of xanthan gum, medium viscosity sodium carboxymethyl cellulose, mixtures of microcrystalline cellulose and sodium carboxymethyl cellulose, mixtures of microcrystalline cellulose and guar gum, medium viscosity hydroxyethyl cellulose, agar, sodium alginate, mixtures of sodium alginate and calcium alginate, gellan gum, carrageenan gum grade iota, kappa or lambda, and medium viscosity hydroxypropylmethyl cellulose.

Medium viscosity sodium carboxymethyl cellulose corresponds to grade of sodium carboxymethyl cellulose whose viscosity, for a 2% solution in water at 25° C., is greater than 200 mPa s and lower than 3100 mPa s.

Medium viscosity hydroxyethyl cellulose corresponds to a grade of hydroxyethyl cellulose whose viscosity, for a 2% solution in water at 25° C., is greater than 250 mPa s and lower than 6500 mPa s. Medium viscosity hydroxypropylmethyl cellulose corresponds to a grade of hydroxypropylmethyl cellulose whose viscosity, for a 2% solution in water at 20° C., is greater than 80 mPa s. and lower than 3800 mPa s.

Preferred suspending or viscosifying agents are xanthan gum, especially Xantural 75™ from Kelco, hydroxyethylcellulose, especially Natrosol 250M™ from Ashland, Kappa carrageenan gum, especially Gelcarin PH812™ from FMC Biopolymer, and lambda carrageenan gum, especially Viscarin PH209™ from FMC Biopolymer.

In a preferred embodiment, the modified release formulation of gamma-hydroxybutyrate comprises from 1 to 15% of viscosifying or suspending agents, preferably from 2 to 10%, more preferably from 2 to 5%, and most preferably from 2 to 3% of the formulation.

In a preferred embodiment, the modified release formulation of gamma-hydroxybutyrate is in the form of a powder that is intended to be dispersed in water prior to administration and further comprises from 1 to 15% of a suspending or viscosifying agent selected from a mixture of xanthan gum, carrageenan gum and hydroxyethylcellulose or xanthan gum and carrageenan gum.

In a preferred embodiment, the modified release formulation of gamma-hydroxybutyrate is in the form of a powder that is intended to be dispersed in water prior to administration and further comprises: from 1.2 to 15% of an acidifying agent selected from malic acid and tartaric acid; and from 1 to 15% of a suspending or viscosifying agent selected from a mixture of xanthan gum, carrageenan gum and hydroxyethylcellulose or xanthan gum and carrageenan gum.

In a most preferred embodiment, the modified release formulation of gamma-hydroxybutyrate comprises about 1% of lambda carrageenan gum or Viscarin PH209™, about 1% of medium viscosity grade of hydroxyethyl cellulose or Natrosol 250M™, and about 0.7% of xanthan gum or Xantural 75™. For a 4.5 g dose unit, these percentages will typically equate to about 50 mg xanthan gum (Xantural 75™), about 75 mg carrageenan gum (Viscarin PH209™) and about 75 mg hydroxyethylcellulose (Natrasol 250M™).

Alternative packages of viscosifying or suspending agents, for a 4.5 g dose, include about 50 mg xanthan gum (Xantural 75™) and about 100 mg carrageenan gum (Gelcarin PH812™), or about 50 mg xanthan gum (Xantural 75™), about 75 mg hydroxyethylcellulose (Natrasol 250M™), and about 75 mg carrageenan gum (Viscarin PH109™).

In a preferred embodiment, the modified release formulation of gamma-hydroxybutyrate further comprises a lubricant or a glidant, besides the immediate release and modified release particles of gamma-hydroxybutyrate. Preferred lubricants and glidants are chosen from the group consisting of salts of stearic acid, in particular magnesium stearate, calcium stearate or zinc stearate, esters of stearic acid, in particular glyceryl monostearate or glyceryl palmitostearate, stearic acid, glycerol behenate, sodium stearyl fumarate, talc, and colloidal silicon dioxide.

The preferred lubricant or glidant is magnesium stearate.

The lubricant or glidant may be used in the particulate formulation in an amount of from 0.1 to 5%. The preferred amount is about 0.5%.

Most preferably, the modified release formulation of gamma-hydroxybutyrate comprises about 0.5% of magnesium stearate.

A preferred modified release formulation of gamma-hydroxybutyrate further comprises an acidifying agent. The acidifying agent helps to ensure that the release profile of the formulation in 0.1N HCl will remain substantially unchanged for at least 15 minutes after mixing, which is approximately the maximum length of time a patient might require before consuming the dose after mixing the formulation with tap water.

In one particular sub-embodiment the formulation is a powder, and further comprising an acidifying agent and a suspending or viscosifying agent, preferably in the weight percentages recited herein.

The preferred acidifying agents are chosen from the group consisting of malic acid, citric acid, tartaric acid, adipic acid, boric acid, maleic acid, phosphoric acid, ascorbic acid, oleic acid, capric acid, caprylic acid, and benzoic acid. In a preferred embodiment, the acidifying agent is present in the formulation from 1.2 to 15%, preferably from 1.2 to 10%, preferably from 1.2 to 5%. Preferred acidifying agents are tartaric acid and malic acid, with malic acid being most preferred.

When tartaric acid is employed, it is preferably employed in an amount of from 1 to 10%, from 2.5 to 7.5%, or about 5%. In a most preferred embodiment, the amount of malic acid in the modified release formulation of gamma-hydroxybutyrate is from 1.2 to 15%, preferably from 1.2 to 10%, preferably from 1.2 to 5%, and most preferably 1.6% or 3.2%.

In a most preferred embodiment, the amount of malic acid in the modified release formulation of gamma hydroxybutyrate is about 1.6%.

The modified release formulation of gamma-hydroxybutyrate preferably includes an immediate release portion and a modified release portion of gamma-hydroxybutyrate, and in a particularly preferred embodiment, the formulation is a particulate formulation that includes a plurality of immediate release gamma-hydroxybutyrate particles and a plurality of modified release gamma-hydroxybutyrate particles. The molar ratio of gamma-hydroxybutyrate in the immediate release and modified release portions preferably ranges from 0.11:1 to 1.86:1, from 0.17:1 to 1.5:1, from 0.25:1 to 1.22:1, from 0.33:1 to 1.22:1, from 0.42:1 to 1.22:1, from 0.53:1 to 1.22:1, from 0.66:1 to 1.22:1, from 0.66:1 to 1.5:1, from 0.8:1 to 1.22:1, and preferably is about 1:1. The molar percentage of gamma-hydroxybutyrate in the immediate release portion relative to the total of gamma-hydroxybutyrate in the formulation preferably ranges from 10% to 65%, from 15 to 60%, from 20 to 55%, from 25 to 55%, from 30 to 55%, from 35 to 55%, from 40 to 55%, from 40 to 60%, or from 45 to 55%, preferably from 40% to 60%. In a preferred embodiment, the molar percentage of the gamma-hydroxybutyrate in the immediate release portion relative to the total of gamma-hydroxybutyrate in the formulation is about 50%. The molar percentage of gamma-hydroxybutyrate in the modified release portion relative to the total of gamma-hydroxybutyrate in the formulation preferably ranges from 90% to 35%, from 85 to 40%, from 80 to 45%, from 75 to 45%, from 70 to 45%, from 65 to 45%, from 60 to 45%, from 60 to 40%, or from 55 to 45%, preferably from 60% to 40%. In a preferred embodiment, the molar ratio of the gamma-hydroxybutyrate in the modified release portion relative to the total of gamma-hydroxybutyrate in the formulation is about 50%. The weight percentage of the IR microparticles relative to the total weight of IR microparticles and MR microparticles, preferably ranges from 7.2% to 58.2%, from 11.0% to 52.9%, from 14.9% to 47.8%, from 18.9% to 47.8%, from 23.1% to 47.8%, from 27.4% to 47.8%, from 31.8% to 47.8%, from 31.8% to 52.9%, or from 36.4% to 47.8%. In other embodiments, the weight percentage of the IR microparticles relative to the total weight of IR microparticles and MR microparticles preferably ranges from 5.9% to 63.2%, from 9.1% to 58.1%, from 12.4% to 53.1%, from 19.9% to 53.1%, from 19.6% to 53.1%, from 23.4% to 53.1%, from 27.4% to 53.1% from 27.4% to 58.1%, preferably from 31.7% to 53.1%.

In a preferred embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to 450 microns and 50% of its sodium oxybate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to 170 microns and 50% of its sodium oxybate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 50% of its sodium oxybate content in immediate-release particles consisting of 80.75% w/w of sodium oxybate, 4.25% w/w of Povidone K30 and 15% of microcrystalline cellulose spheres with a volume mean diameter of about 95 microns to about 450 microns and 50% of its sodium oxybate content in modified release particles consisting of 11.3% w/w of microcrystalline cellulose spheres with a volume mean diameter of about 95 microns to about 450 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

In a preferred embodiment, the finished formulation comprises 50% of its sodium oxybate content in immediate-release particles consisting of 80.75% w/w of sodium oxybate, 4.25% w/w of Povidone™ K30 and 15% of microcrystalline cellulose spheres with a volume mean diameter of about 95 microns to about 170 microns and 50% of its sodium oxybate content in modified release particles consisting of 11.3% w/w of microcrystalline cellulose spheres with a volume mean diameter of about 95 microns to about 170 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

In a preferred embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 16.7% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns, 16.7% of its gamma-hydroxybutyrate content in immediate-release particles consisting of 80.75% w/w of magnesium salt of gamma-hydroxybutyric acid, 4.25% of Povidone K30 and 15% of microcrystalline cellulose spheres with a volume mean diameter of about 95 microns to about 450 microns, 16.7% of its gamma-hydroxybutyrate content in immediate-release particles consisting of 80.75% w/w of calcium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 16.7% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns, 16.7% of its gamma-hydroxybutyrate content in immediate-release particles consisting of 80.75% w/w of magnesium salt of gamma-hydroxybutyric acid, 4.25% w/w of Povidone K30 and 15% of microcrystalline cellulose spheres with a volume mean diameter of about 95 microns to about 170 microns, 16.7% of its gamma-hydroxybutyrate content in immediate-release particles consisting of 80.75% w/w of calcium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 450 microns and 50% of its gamma-hydroxybutyrate content in modified release particles consisting of 10.5% w/w of microcrystalline cellulose spheres with a volume mean diameter of about 95 microns to about 450 microns, layered with 56.5% w/w of calcium salt of gamma-hydroxybutyric acid mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

In a preferred embodiment, the finished formulation comprises 50% of its gamma-hydroxybutyrate content in immediate-release particles consisting of 80.75% w/w of potassium salt of gamma-hydroxybutyric acid, 4.25% w/w of Povidone K30 and 15% of microcrystalline cellulose spheres with a volume mean diameter of about 95 microns to about 170 microns and 50% of its gamma-hydroxybutyrate content in modified release particles consisting of 10.5% w/w of microcrystalline cellulose spheres with a volume mean diameter of about 95 microns to about 170 microns, layered with 56.5% w/w of calcium salt of gamma-hydroxybutyric acid mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent).

Other Characteristics of Immediate Release Portion

The immediate release portion of the formulation may take any form capable of achieving an immediate release of the gamma-hydroxybutyrate when ingested. For example, when the formulation is a particulate formulation, the formulation may include unmodified "raw" gamma-hydroxybutyrate, rapidly dissolving gamma-hydroxybutyrate granules, particles or microparticles comprised of a core covered by a gamma-hydroxybutyrate loaded layer containing a binder such as povidone.

The IR granules or particles of gamma-hydroxybutyrate may be made using any manufacturing process suitable to produce the required particles, including:

agglomeration of the gamma-hydroxybutyrate sprayed preferably in the molten state, such as the Glatt Pro-Cell™ technique, extrusion and spheronization of the gamma-hydroxybutyrate, optionally with one or more physiologically acceptable excipients, wet granulation of the gamma-hydroxybutyrate, optionally with one or more physiologically acceptable excipients, compacting of the gamma-hydroxybutyrate, optionally with one or more physiologically acceptable excipients, granulation and spheronization of the gamma-hydroxybutyrate, optionally with one or more physiologically acceptable excipients, the spheronization being carried out for example in a fluidized bed apparatus equipped with a rotor, in particular using the Glatt CPS™ technique, spraying of the gamma-hydroxybutyrate, optionally with one or more physiologically acceptable excipients, for example in a fluidized bed type apparatus equipped with zig-zag filter, in particular using the Glatt MicroPx™ technique, or spraying, for example in a fluidized bed apparatus optionally equipped with a partition tube or Wurster tube, the gamma-hydroxybutyrate, optionally with one or more physiologically acceptable excipients, in dispersion or in solution in an aqueous or organic solvent on a core.

Preferably, the immediate release portion of the formulation is in the form of microparticles comprising the immediate release gamma-hydroxybutyrate and optional pharmaceutically acceptable excipients. In a preferred embodiment, the immediate release microparticles of gamma-hydroxybutyrate have a volume mean diameter D(4,3) of from 10 to 1000 microns, preferably from 95 to 600 microns, more preferably from 150 to 400 microns. Most preferably their volume mean diameter is about 270 microns.

The preferred immediate release particles of gamma-hydroxybutyrate of the present invention comprises a core and a layer deposited on the core that contains the gamma-hydroxybutyrate. The core may be any particle chosen from the group consisting of:

crystals or spheres of lactose, sucrose (such as Compressuc™ PS from Tereos), microcrystalline cellulose (such as Avicel™ from FMC Biopolymer, Cellet™ from Pharmatrans or Celphere™ from Asahi Kasei), sodium chloride, calcium carbonate (such as Omyapure™ 35 from Omya), sodium hydrogen carbonate, dicalcium phosphate (such as Dicafos™ AC 92-12 from Budenheim) or tricalcium phosphate (such as Tricafos™ SC93-15 from Budenheim);

composite spheres or granules, for example sugar spheres comprising sucrose and starch (such as Suglets™ from NP Pharm), spheres of calcium carbonate and starch (such as Destab™ 90 S Ultra 250 from Particle Dynamics) or spheres of calcium carbonate and maltodextrin (such as Hubercal™ CCG4100 from Huber).

The core may also comprise other particles of pharmaceutically acceptable excipients such as particles of hydroxypropyl cellulose (such as Klucel™ from Aqualon Hercules), guar gum particles (such as Grinsted™ Guar from Danisco), xanthan particles (such as Xantural™ 180 from CP Kelco).

According to a particular embodiment of the invention, the cores are sugar spheres or microcrystalline cellulose spheres, such as Cellets™ 90, Cellets™ 100 or Cellets™ 127 marketed by Pharmatrans, or also Celphere™ CP 203, Celphere™ CP305, Celphere™ SCP 100. Preferably the core is a microcrystalline cellulose sphere. Most preferably the core is a Cellets™ 127 from Pharmatrans.

The core preferably has a mean volume diameter of about 95 to about 450 microns, preferably about 95 to about 170 microns, most preferably about 140 microns.

The layer deposited onto the core comprises the immediate release gamma-hydroxybutyrate. Preferably the layer also comprises a binder, which may be chosen from the group consisting of:

low molecular weight hydroxypropyl cellulose (such as Klucel™ EF from Aqualon-Hercules), low molecular weight hydroxypropyl methylcellulose (or hypromellose) (such as Methocel E3 or E5 from Dow), or low molecular weight methylcellulose (such as Methocel™ A15 from Dow);

low molecular weight polyvinyl pyrrolidone (or povidone) (such as Plasdone K29/32 from ISP or Kollidon 30 from BASF), vinyl pyrrolidone and vinyl acetate copolymer (or copovidone) (such as Plasdone™: S630 from ISP or Kollidon™ VA 64 from BASF);

dextrose, pregelatinized starch, maltodextrin; and mixtures thereof.

Low molecular weight hydroxypropyl cellulose corresponds to grades of hydroxypropyl cellulose having a molecular weight of less than 800,000 g/mol, preferably less than or equal to 400,000 g/mol, and in particular less than or equal to 100,000 g/mol. Low molecular weight hydroxypropyl methylcellulose (or hypromellose) corresponds to grades of hydroxypropyl methylcellulose the solution viscosity of which, for a 2% solution in water and at 20° C., is less than or equal to 1,000 mPa s, preferably less than or equal to 100 mPa s and in particular less than or equal to 15 mPa s. Low molecular weight polyvinyl pyrrolidone (or povidone) corresponds to grades of polyvinyl pyrrolidone having a molecular weight of less than or equal to 1,000,000 g/mol, preferably less than or equal to 800,000 g/mol, and in particular less than or equal to 100,000 g/mol.

Preferably, the binding agent is chosen from low molecular weight polyvinylpyrrolidone or povidone (for example, Plasdone™ K29/32 from ISP), low molecular weight hydroxypropyl cellulose (for example, Klucel™ EF from Aqualon-Hercules), low molecular weight hydroxypropyl methylcellulose or hypromellose (for example, Methocel™ E3 or E5 from Dow) and mixtures thereof.

The preferred binder is povidone K30 or K29/32, especially Plasdone™ K29/32 from ISP. The binder may be present in an amount of 0 to 80%, 0 to 70%, 0 to 60%, 0 to 50%, 0 to 40%, 0 to 30%, 0 to 25%, 0 to 20%, 0 to 15%, 0 to 10%, or from 1 to 9%, most preferably 5% of binder based on the total weight of the immediate release coating.

The preferred amount of binder is 5% of binder over the total mass of gamma-hydroxybutyrate and binder.

The layer deposited on the core may represent at least 10% by weight, and even greater than 20, 25, 30, 35, 40, 45, 50, 55, 60, 65, 70, 75, 80, 85 or 90% by weight of the total weight of the immediate release particle of gamma-hydroxybutyrate. Most preferably, the layer deposited on the core represents about 85% of the weight of the immediate release particle of gamma-hydroxybutyrate.

According to a preferred embodiment, the immediate-release particles comprise 80.75% w/w of gamma-hydroxybutyrate, 4.25% w/w of Povidone K30 and 15% of microcrystalline cellulose spheres.

According to a preferred embodiment, the immediate-release particles comprise 80.75% w/w of gamma-hydroxybutyrate, 4.25% w/w of Povidone K30 and 15% of microcrystalline cellulose spheres with a volume mean diameter of about 95 microns to about 450 microns.

According to a preferred embodiment, the immediate-release particles comprise 80.75% w/w of gamma-hydroxybutyrate, 4.25% w/w of Povidone K30 and 15% of microcrystalline cellulose spheres with a volume mean diameter of about 95 microns to about 170 microns.

According to a preferred embodiment, the immediate-release particles comprise 8.75% w/w of sodium oxybate, 4.25% w/w of Povidone K30 and 15% of microcrystalline cellulose spheres.

According to another preferred embodiment, the immediate-release particles comprise 80.75% w/w of potassium salt of gamma-hydroxybutyric acid, 4.25% w/w of Povidone K30 and 15% of microcrystalline cellulose spheres.

According to another preferred embodiment, the immediate-release particles comprise 80.75% w/w of calcium salt of gamma-hydroxybutyric acid, 4.25% w/w of Povidone K30 and 15% of microcrystalline cellulose spheres.

According to another preferred embodiment, the immediate-release particles comprise 80.75% w/w of magnesium salt of gamma-hydroxybutyric acid, 4.25% w/w of Povidone K30 and 15% of microcrystalline cellulose spheres.

According to another embodiment, the immediate-release particles are manufactured by dissolving the gamma-hydroxybutyrate and the Povidone K30 in a mixture of water/ethanol 40/60 w/w and spraying the resulting solution onto the surface of the microcrystalline cellulose spheres.

Other Characteristics of Modified Release Portion

The modified release portion may be any formulation that provides the desired in vitro dissolution profile of gamma-hydroxybutyrate. The modified release portion is preferably comprised of modified release particles, obtained by coating immediate release particles of gamma-hydroxybutyrate with a coating (or coating film) that inhibits the immediate release of the gamma-hydroxybutyrate. In one sub-embodiment the modified release portion comprises particles comprising: (a) an inert core; (b) a coating; and (c) a layer comprising the gamma hydroxybutyrate interposed between the core and the coating.

In a preferred embodiment, the modified release portion comprises a time-dependent release mechanism and a pH-dependent release mechanism.

In a preferred embodiment, the coating film comprises at least one polymer carrying free carboxylic groups, and at least one hydrophobic compound preferably characterized by a melting point equal or greater than 40° C.

The polymer carrying free carboxylic groups is preferably selected from: (meth)acrylic acid/alkyl (meth)acrylate copolymers or methacrylic acid and methylmethacrylate copolymers or methacrylic acid and ethyl acrylate copolymers or methacrylic acid copolymers type A, B or C, cellulose derivatives carrying free carboxylic groups, preferably cellulose acetate phthalate, cellulose acetate succinate, hydroxypropyl methyl cellulose phthalate, carboxymethylethyl cellulose, cellulose acetate trimellitate, hydroxypropyl methyl cellulose acetate succinate, polyvinyl acetate phthalate, zein, shellac, alginate and mixtures thereof.

In a preferred embodiment, the methacrylic acid copolymers are chosen from the group consisting of poly (meth)acrylic acid, methyl methacrylate) 1:1 or Eudragit™ L100 or equivalent, poly (methacrylic acid, ethyl acrylate) 1:1 or Eudragit™ L00-55 or equivalent and poly (methacrylic acid, methyl methacrylate) 1:2 or Eudragit™ S100 or equivalent.

In another sub-embodiment the coating comprises a polymer carrying free carboxylic groups wherein the free carboxylic groups are substantially ionized at pH 7.5.

The hydrophobic compound with a melting point equal or greater than 40° C. may be selected from the group consisting of hydrogenated vegetable oils, vegetable waxes, wax yellow, wax white, wax microcrystalline, lanolin, anhydrous milk fat, hard fat suppository base, lauroyl macrogol glycerides, polyglyceryl diisostearate, diesters or triesters of glycerol with a fatty acid, and mixtures thereof.

Even more preferably, the hydrophobic compound with a melting point equal or greater than 40° C. is chosen from the group of following products: hydrogenated cottonseed oil, hydrogenated soybean oil, hydrogenated palm oil, glyceryl behenate, hydrogenated castor oil, candellila wax, tristearin, tripalmitin, trimyristin, yellow wax, hard fat or fat that is useful as suppository bases, anhydrous dairy fats, lanolin, glyceryl palmitostearate, glyceryl stearate, lauryl macrogol glycerides, polyglyceryl diisostearate, diethylene glycol monostearate, ethylene glycol monostearate, omega 3 fatty acids, and mixtures thereof. A particularly preferred subgroup of products comprises hydrogenated cottonseed oil, hydrogenated soybean oil, hydrogenated palm oil, glyceryl behenate, hydrogenated castor oil, candellila wax, tristearin, tripalmitin, trimyristin, beeswax, hydrogenated poly-1 decene, carnauba wax, and mixtures thereof.

In practice, and without this being limiting, it is preferable the hydrophobic compound with a melting point equal or greater than 40° C. to be chosen from the group of products sold under the following trademarks: Dynasan™, Cutina™, Hydrobase™, Dub™, Castorwax™, Croduret™, Compritol™, Sterotex™, Lubritab™, Apifil™, Akofine™, Softisan™, Hydrocote™, Livopol™, Super Hartolan™, MGLA™, Corona™, Protalan™, Akosoft™, Akosol™, Cremao™, Massupol™, Novata™, Suppocire™, Wecobee™, Witepsol™, Lanolin™, Jncromega™, Estaram™, Suppoweiss™, Gelucire™, Precirol™, Emulcire™, Plurol diisostéarique™, Geleol™, Hydrine™, Monthyle™, Kahlwax™ and mixtures thereof; and, preferably, from the group of products sold under the following trademarks: Dynasan™ P60, Dynasan™114, Dynasan™116, Dynasan™118, Cutina™ HR, Hydrobase™ 66-68, Dub™ HPH, Compritol™ 888, Sterotex™ NF, Sterotex™ K, Lubritab™, and mixtures thereof.

A particularly suitable coating is composed of a mixture of hydrogenated vegetable oil and a methacrylic acid copolymer. The exact structure and amount of each component, and the amount of coating applied to the particle, controls the release rate and release triggers. Eudragit® methacrylic acid copolymers, namely the methacrylic acid—methyl methacrylate copolymers and the methacrylic acid—ethyl acrylate copolymers, have a pH-dependent solubility: typically, the pH triggering the release of the active ingredient from the microparticles is set by the choice and mixture of appropriate Eudragit® polymers. In the case of gamma hydroxybutyrate modified release microparticles, the theoretical pH triggering the release is preferably from 5.5 to 6.97 or 6.9, more preferably 6.5 up to 6.9. By "pH trigger" is meant the minimum pH above which dissolution of the polymer occurs.

In a particular embodiment, the coating comprises a hydrophobic compound with a melting point equal or greater than 40° C. and a polymer carrying free carboxylic groups are present in a weight ratio from 0.4 or 0.5 to 4, preferably from 0.6 or 0.67 to 2.5, most preferably from 0.6 or 0.67 to 2.33; most preferably about 1.5.

A particularly suitable coating is composed of a mixture of hydrogenated vegetable oil and a methacrylic acid copolymer with a theoretical pH triggering the release from 6.5 up to 6.97 in a weight ratio from 0.4 or 0.5 to 4, preferably from 0.6 or 0.67 to 2.5, most preferably from 0.6 or 0.67 to 2.33; most preferably of about 1.5.

The modified release particles of gamma-hydroxybutyrate preferably have a volume mean diameter of from 100 to 1200 microns, from 100 to 500 microns, from 200 to 800 microns, and preferably of about 320 microns.

The coating may preferably represent 10 to 50%, 15 to 45%, 20 to 40%, or 25 to 35% by weight of the total weight of the coated modified release particles. Preferably, the coating represents 25-30% by weight of the total weight of the modified release particles of gamma-hydroxybutyrate.

In a preferred embodiment, the coating layer of the modified release particles of gamma-hydroxybutyrate is obtained by spraying, in particular in a fluidized bed apparatus, a solution, suspension or dispersion comprising the coating composition as defined previously onto the immediate release particles of gamma-hydroxybutyrate, in particular the immediate release particles of gamma-hydroxybutyrate as previously described. Preferably, the coating is formed by spraying in a fluidized bed equipped with a Wurster or partition tube and according to an upward spray orientation or bottom spray a solution of the coating excipients in hot isopropyl alcohol.

According to a preferred embodiment, the modified release particles of gamma-hydroxybutyrate consist of 10.5% w/w of microcrystalline cellulose spheres with a volume mean diameter of about 95 microns to about 450 microns, layered with 56.5% w/w of gamma-hydroxybutyrate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of gamma-hydroxybutyrate.

According to a preferred embodiment, the modified release particles of gamma-hydroxybutyrate consist of 10.5% w/w of microcrystalline cellulose spheres with a volume mean diameter of about 95 microns to about 170 microns, layered with 56.5% w/w of gamma-hydroxybutyrate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of gamma-hydroxybutyrate.

According to a preferred embodiment, the modified release particles of gamma-hydroxybutyrate consist of 10.5% w/w of microcrystalline cellulose spheres with a volume mean diameter of about 95 microns to about 450 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of sodium oxybate.

According to a preferred embodiment, the modified release particles of gamma-hydroxybutyrate consist of 10.5% w/w of microcrystalline cellulose spheres with a volume mean diameter of about 95 microns to about 170 microns, layered with 56.5% w/w of sodium oxybate mixed with 3% w/w of Povidone™ K30 and finally coated with a coating composition consisting of 18% w/w of hydrogenated vegetable oil (Lubritab™ or equivalent), 4% of methacrylic acid copolymer type C (Eudragit™ L100-55 or equivalent) and 8% of methacrylic acid copolymer type B (Eudragit™ S100 or equivalent), all percentages expressed based on the total weight of the final modified release particles of sodium oxybate.

According to another preferred embodiment, the modified release particles of gamma-hydroxybutyrate consist of 11.3% w/w of microcrystalline cellulose spheres with a volume mean diameter of about 95 microns to about 450 microns, layered with 60.5% w/w of gamma-hydroxybutyrate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another preferred embodiment, the modified release particles of gamma-hydroxybutyrate consist of 11.3% w/w of microcrystalline cellulose spheres with a volume mean diameter of about 95 microns to about 170 microns, layered with 60.5% w/w of gamma-hydroxybutyrate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another preferred embodiment, the modified release particles of gamma-hydroxybutyrate consist of 11.3% w/w of microcrystalline cellulose spheres with a volume mean diameter of about 95 microns to about 450 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

According to another preferred embodiment, the modified release particles of gamma-hydroxybutyrate consist of 11.3% w/w of microcrystalline cellulose spheres with a volume mean diameter of about 95 microns to about 170 microns, layered with 60.5% w/w of sodium oxybate mixed with 3.2% w/w of Povidone™ K30 and finally coated with a coating composition consisting of 15% w/w of hydrogenated vegetable oil (Lubritab™ or equivalent), 0.75% of methacrylic acid copolymer type C (Eudragit™ L100-55 or equivalent) and 9.25% of methacrylic acid copolymer type B (Eudragit™ S100 or equivalent).

Packaging

The modified release formulation of gamma-hydroxybutyrate is preferably supplied in dose packets, sachets, or stick-packs comprising a particulate formulation. The particulate formulation may be a powder for oral suspension. The sachets or dose packets are preferably available in several different doses, comprising gamma-hydroxybutyrate in amounts equivalents to 0.5 g, 1.0 g, 1.5 g, 3.0 g, 4.5 g, 6.0 g, 7.5 g, 9.0 g, 10.5 g and/or 12 g of sodium oxybate. In an embodiment, each nightly dose packet contains a composition comprising a blend of immediate-release and controlled-release granules providing doses of 4.5 g, 6 g, 7.5 g, or 9 g of gamma-hydroxybutyrate. The composition may further include microcrystalline cellulose spheres, povidone K30, hydrogenated vegetable oil, methacrylic acid copolymer, malic acid, xanthan gum, hydroxyethyl cellulose, carrageenan, and/or magnesium stearate. Depending on the dose required, one or more of these packets may be opened, and its contents mixed with tap water to provide the nightly dose of gamma-hydroxybutyrate. Dose packets may contain a single dose of the composition provided in 4.5 g, 6 g, 7.5 g, and 9 g doses. In some embodiments, the dose packet may be mixed with about 1¼ cup water, ⅓ cup water, 1½ cup water, 50 mL water, or 25 mL water. In at least one example, the dose packet is mixed with ⅓ cup water (about 80 mL) to form an oral suspension for administration to the patient. In at least one additional example, the dose packet is mixed with about 50 mL in a mixing cup to form an oral suspension for administration to the patient. The mixing cup may be additionally filled with about 25 mL after administration of the oral suspension to suspend any remaining composition in the mixing cup to form a second oral suspension for administration to the patient. In other examples, only one suspension may be needed to administer the full dosage to the patient. Suspensions may be consumed within 30 minutes.

In some embodiments, nightly dose packets 104 containing the composition may be provided to a patient in a nightly dose packet storage system 100. The nightly dose packet storage system 100 may include into a 30-day supply carton 102 (e.g. FIGS. 91-97) or a 7-day supply carton 103 (e.g. FIG. 129), between 7 and 30 nightly dose packets 104 (e.g. FIGS. 119-125), between one and four nightly dose packet containers 110 (e.g. FIGS. 112-118), a mixing cup 108 (e.g. FIGS. 105-111), and a mixing cup receptacle (e.g. FIGS. 98-104 or 130).

FIGS. 119-125 show example nightly dose packets 104. The nightly dose packets 104 may be child resistant. The nightly dose packet may include a cut or tear line 105 near the upper portion of the nightly dose packet 104. There may be an indicator (e.g. scissors) near the cut line 105 to mark the cut line 105. In some examples, the nightly dose packet 104 may also be operable to be folded longitudinally, perpendicular to the cut line 105, to allow the patient to tear the dose packet without the need for scissors. In this example, the nightly dose packet 104 may include one or more perforations 106 or a portion of weaker material to assist the tearing of the dose packet when folded longitudinally. For example, as seen in FIGS. 119-125, the nightly dose packet 104 may include a gray box to indicate where the perforations 106 are located. A ceramic cylinder may be used to create the perforations that can be torn by hand. Each nightly dose packet may include an expiration date.

As seen in FIGS. 91-132, the sachets or nightly dose packets 104 may be packaged with a mixing cup 108 (e.g. mixing aid or dosing cup) for mixing the composition in the sachet or dose packet 104 with water to for a suspension. The dose packets 104 may be first assembled into a once-nightly dose packet container 110 (e.g. FIGS. 112-118), and then one or more once-nightly dose packet containers 110 may then be assembled into a larger 30-day supply carton 102 (e.g. FIGS. 91-97) or a 7-day supply carton 103 (e.g. FIG. 129). The nightly dose packet container 110 may be operable to hold up to 7 once-nightly dose packets 104. The nightly dose packet container 110 may include a notch 116 to aid in removing the nightly dose packets 104 from the container 110. The nightly dose packet container 110 may be removable from the larger supply carton 102, 103 for the patient's convenience (e.g. moving, traveling, or putting by the patient's bedside) and to allow the patient to track usage (e.g. one container per week). Being able to track usage may be particularly important for patients with memory issues.

In some embodiments, the 30-day or 7-day supply carton include a notch on the top lid/flap to aid in opening the carton. The 30-day or 7-day supply carton 102, 103 may further include an expiration date that matches the expiration date on the dose packets within. In some examples, the 30-day or 7-day supply carton 102, 103 may include a tamper-evident seal. The 30-day or 7-day supply carton 102, 103 may include a tray 112 operable to rest on the top of the nightly dose packet containers 110, the mixing cup receptacle 109, and/or the mixing cup 108. In some embodiments, the tray 112 may be formed by one of four flaps for closing the 30-day or 7-day supply carton 102, 103. In at least one example, the front facing flap of the carton 102, 103 includes a crease to fold the flap inward to form the tray 112 inset from the top of the carton. In some examples, the crease may be about ¾ in from the edge of the carton opening. The tray 112 may be operable to rest on the top of one or more dose packet containers 110, mixing cup receptacle 109, and/or mixing cup 108. The tray 112 may be operable to hold instructions for use for the formulation or any other relevant material. In some embodiments, the front facing flap may further include a cutout portion between the crease and the edge of the carton opening. The cutout may align with the notch on the top lid/flap when all flaps are folded to close the carton to aid in opening the carton via the notch.

In some embodiments, the mixing cup 108 (e.g. FIGS. 105-111) may be assembled into a mixing cup receptacle 109 (e.g. FIGS. 98-104), which may then be assembled into the larger 30-day or 7-day supply cartons 102, 103 (e.g. FIGS. 126-132). The mixing cup receptacle 109 may include a cup retaining portion 111 operable for holding the mixing cup 108. The mixing cup receptacle 109 may further include a packet portion 113 for holding up to two once-nightly dose packets (e.g. FIGS. 126-128) or only hold the mixing cup (e.g. FIGS. 130-132). In some examples, the cup retaining portion 111 may include a platform to elevate the mixing cup within the mixing cup receptacle 109. The platform may be formed from a back wall of the mixing cup receptacle 109 such that the back wall is folded in to the cup retaining portion 111.

In some embodiments, the mixing cup 108 may have a child-resistant cap. In other embodiments, the mixing cup 108 may have a quarter turn lid. In various embodiments, the mixing cup 108 may be pre-marked with fill lines for the water, such that the patient does not have to measure the amount of water to mix with the dose packet. For example, the mixing cup 108 may include a first fill line 114 for measuring a first portion of water to mix and suspend the composition in a nightly dose packet 104. The mixing cup 108 may further include at least one additional marking for measuring additional water for suspending any remnant composition remaining in the pre-marked mixing cup after administration of the suspension to the patient. The patient may further administer the suspension of the additional water with the remnant composition to ensure that the patient receives the full dosage of the composition. For example, the mixing cup 108 may include a second fill line 115 for measuring a second portion of water to mix any remnant composition in the mixing cup 108. In some examples, the first fill line 114 may indicate about 50 mL and the second fill line 115 may indicate about 25 mL. In other examples, the first line 114 may mark about ⅓ cup. As illustrated in FIGS. 105-109, the first fill line 114 may be an "A" fill line and the second fill line 115 may be a "B" fill line. In some examples, the "A" and "B" fill lines may be on two sides of the mixing cup.

In some embodiments, the mixing cup 108 include a resin and a polymer additive to prevent cracking when dropped while also having a clarity to see liquids (e.g. water) in the mixing cup at the fill lines. For example, the mixing cup may be made of polypropylene and a propylene elastomer additive. In some examples, the propylene elastomer additive may be composed of isotactic propylene repeat units with random ethylene distribution (e.g. Vistamaxx™ Performance Polymer). The mixing cup may include up to 30% of the polymer additive. In some examples, the mixing cup may be resistant to cracking when dropped from about 18 inches to about 6 feet.

In some embodiments, the inner wall of the mixing cup may be rounded at the point where the inner wall meets the bottom of the mixing cup. Stated another way, the intersection of the wall and the bottom of the mixing cup may not be a 90 degree angle. Having a rounded or non-90 degree intersection may limit adhesion of the composition to the cup. For example, less residual of the composition may be left in the cup after administering the first suspension (i.e. the composition in the daily dosage packet mixed with water to the first fill line) as compared to a cup with a 90 degree angle between the wall and bottom of the mixing cup. Therefore, there may be less composition remaining in the cup to mix with water filled to the second fill line.

Figure 133A:
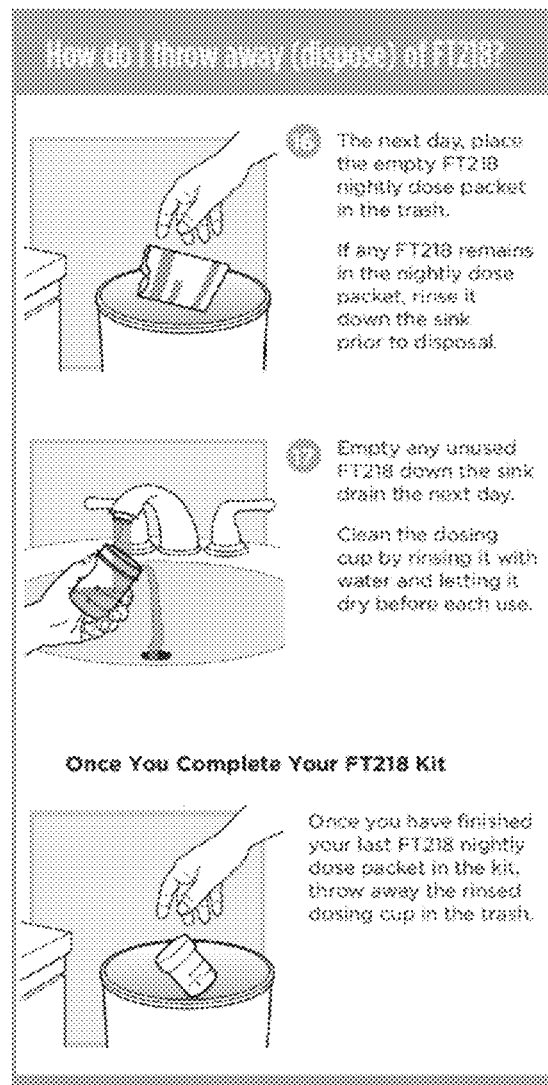
Figure 133C:
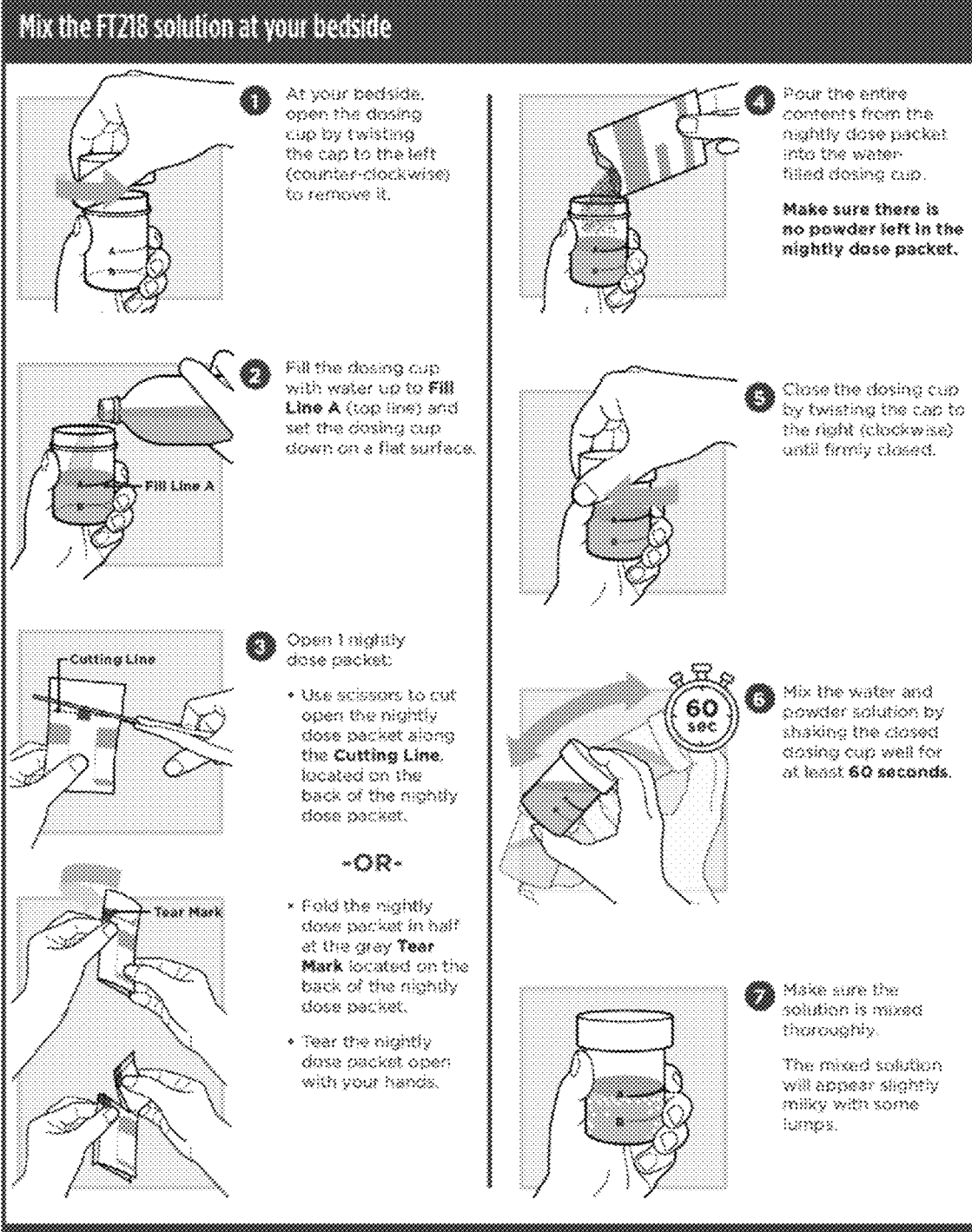
Figure 133D:
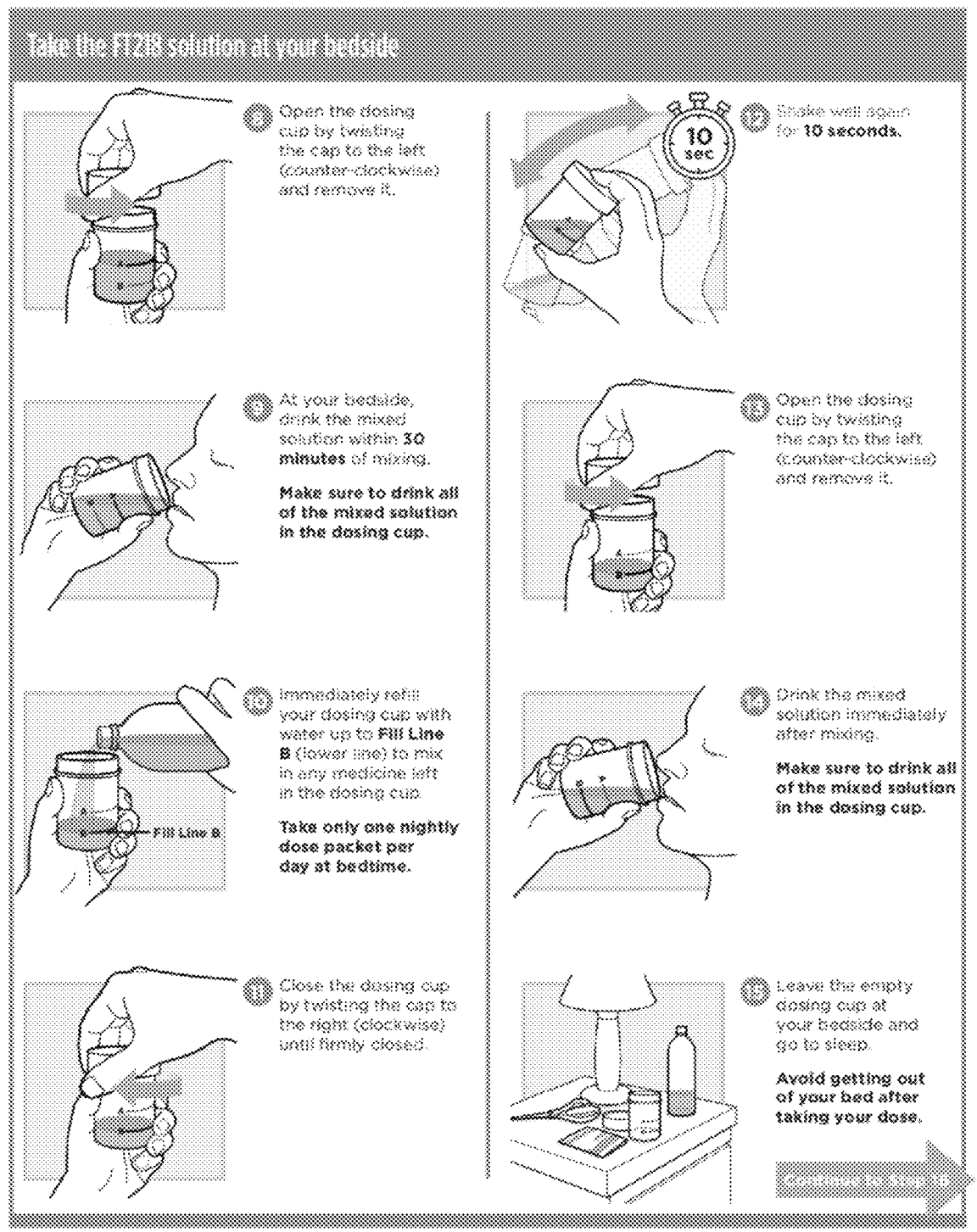

FIGS. 133A-133D are example instructions for use of the composition in a nightly dosing packet and suspension in water using the mixing cup. As shown in FIG. 133C, a method of preparing the formulation may include, but is not limited to, opening the mixing cup by twisting the cap to the left (counter-clockwise) to remove it, filling the mixing cup with water up to fill line A (top line) and setting the mixing cup down on a flat surface, opening 1 once-nightly dose packet by folding the once-nightly dose packet in half at the gray tear mark located on the back of the nightly dose packet and tearing the once-nightly dose packet open or using scissors to cut open the nightly dose packet along the cutting line, located on the back of the nightly dose packet, pouring the entire contents from the once-nightly dose packet into the water filled mixing cup making sure that there is no powder left in the once-nightly dose packet, closing the mixing cup by twisting the cap to the right (clockwise) until firmly closed, mixing the water and powder solution by shaking the closed mixing cup well for at least 60 seconds, and/or making sure the solution is mixed thoroughly, where the mixed solution may appear slightly milky with some lumps. As shown in FIG. 133D, a method of taking the formulation in solution form may include, but is not limited to, opening the mixing cup by twisting the cap to the left (counter-clockwise) and removing it, drinking the mixed solution within 30 minutes of mixing, making sure to drink all of the mixed solution in the mixing cup, immediately refilling the mixing cup with water up to fill line B (lower line) to mix any composition left in the mixing cup, closing the mixing cup by twisting the cap to the right (clockwise) until firmly closed, shaking the mixing cup well for 10 seconds, opening the mixing cup by twisting the cap to the left (counter-clockwise) and removing it, drinking the mixed solution immediately after mixing, making sure to drink all of the mixed solution in the mixing cup, and/or leaving the empty mixing cup at the patient's bedside and going to sleep. The patient may avoid getting out of bed after taking the dose.

Methods of Treatment

The invention further provides a method of treating a disorder treatable with a pharmaceutically acceptable salt of gamma-hydroxybutyrate in a human subject in need thereof comprising orally administering a single nighttime daily dose to said human amounts of gamma-hydroxybutyrate equivalent to from 3.0 to 12.0 g of gamma-hydroxybutyrate or a salt thereof in the formulation of the present invention. In some embodiments, the gamma-hydroxybutyrate salt may be a calcium salt, a sodium salt, a potassium salt, and/or a magnesium salt of gamma-hydroxybutyric acid. The invention further provides methods of treating narcolepsy, types 1 and/or 2, by orally administering at bedtime a therapeutically effective amount of a gamma-hydroxybutyrate formulation characterized by the novel gamma-hydroxybutyrate pharmacokinetics or dissolution properties of the present invention. The formulation is suitable to be administered once daily. In some examples, the formulation is suitable to be administered once nightly. The modified release formulation of the present invention is effective to treat narcolepsy Type 1 or Type 2, wherein said treatment of narcolepsy is defined as reducing excessive daytime sleepiness or reducing the frequency of cataplectic attacks. The therapeutically effective amount preferably comprises equivalents from 3.0 to 12.0 g of gamma-hydroxybutyrate, more preferably from 4.5 to 9.0 g of gamma-hydroxybutyrate, and most preferably 4.5, 6.0, 7.5 or 9.0 g of gamma-hydroxybutyrate. The dosage of gamma-hydroxybutyrate may be up-titrated to a suitable effective dosage for the patient. In some embodiments, the dosage of the composition initially administered may be 4.5 g gamma-hydroxybutyrate. The dosage may then be increased by about 1.5 g per night at weekly intervals to an effective dosage range of 6 g to 9 g per night. The dosage may be up-titrated at a rate appropriate for the patient. Once the desired effective dosage is reached, the dosage may remain stable.

The effectiveness of the once daily treatment may be measured by one or any combination of the following criteria:

Fewer adverse reactions/effects as compared to a patient administered twice-nightly sodium oxybate No adverse reactions/effects Less or no obtundation as compared to the twice-nightly sodium oxybate treatment Less of no clinically significant respiratory depression as compared to the twice-nightly sodium oxybate treatment No profound CNS depression or severe difficulty breathing No clinically significant worsening of respiratory function as measured by apnea/hyponea index and pulse oximetry Increase the mean sleep latency, preferably as determined on the Maintenance of Wakefulness Test (MWT)

Statistically significant improvement on the MWT at dosages of 6 g, 7.5 g, and 9 g as compared to placebo Latency to sleep onset of about 5 minutes or more than placebo Improve the Clinical Global Impression (CGI) rating of sleepiness Statistically significant improvement on CGI at dosages of 6 g, 7.5 g, and 9 g as compared to placebo 5 times or more likely to respond as much or very much improved on CGI-Improvement as compared to placebo Decrease the number of cataplexy attacks (NCA) preferably determined from the cataplexy frequency item in the Sleep and Symptoms Daily Diary Statistically significant improvement in mean weekly cataplexy attacks at dosages of 6 g, 7.5 g, and 9 g as compared to placebo 4 or fewer mean cataplexy attacks per week as compared to placebo Decrease the disturbed nocturnal sleep (DNS), the disturbed nocturnal events or the adverse respiratory events preferably as determined by polysomnographic (PSG) measures of sleep fragmentation Decrease the excessive daytime sleepiness (EDS) preferably as measured by patient report via the Epworth Sleepiness Scale (ESS)

Decrease the daytime sleepiness as measured by the Maintenance of Wakefulness Test based on EEG measures of wakefulness Decrease PSG transitions from N/2 to N/3 and REM sleep to wake and N1 sleep (as determined by C Iber, S Ancoli-Israel, A Chesson, SF Quan. *The AASM Manual for the Scoring of Sleep and Associated Events.* Westchester, Ill.: American Academy of Sleep Medicine; 2007).

Decrease the number of arousals or wakenings, preferably obtained from a PSG as defined by the American Academy of Sleep Medicine Improve the sleep quality, preferably obtained from one or more of (i) the Sleep and Symptom Daily Diary, (ii) Visual Analog Scale (VAS) for sleep quality and sleep diary, and (iii) VAS for the refreshing nature of sleep Decrease the Hypnagogic Hallucinations (HH) or sleep paralysis (SP) symptoms in NT1 narcolepsy patients, preferably as measured by the Sleep and Symptom Daily Diary Contraindication for patients with hepatic impairment Obtundation may refer to a dulled or reduced level of alertness or consciousness, such that a patient that is obtunded may have a more depressed level of consciousness and may not be fully aroused. In some examples, obtundation may be measured based on a level of consciousness using scales such as but not limited to the Grady Coma Scale or the Glasgow Coma Scale. Respiratory depression may refer to slow or ineffective breathing. Central nervous system (CNS) depression may refer to a decreased breathing rate, decreased heart rate, and/or loss of consciousness. In various embodiments, "clinically significant" may mean having an effect on the patient's daily life. In various embodiments, "statistically significant" may refer to $p<0.05$.

The Maintenance of Wakefulness Test measures a patient's ability to remain awake during soporific circumstances through a daytime polysomnographic procedure. In some examples, the MWT may be quantified by latency to sleep onset measured in minutes. CGI may refer to an assessment of a clinician's view of the patient's global functioning prior to and after initiating a medication. CGI-Improvement may be used to compare the patient's clinical condition to the one week prior to initiating the medication using a 7-point scale (e.g. 1=very much improved; 2=much improved; 3=minimally improved; 4=no change from baseline; 5=minimally worse; 6=much worse; 7=very much worse).

In various embodiments, the method of treating cataplexy or excessive daytime sleepiness (EDS) in a patient with narcolepsy includes orally administering a dosage of a composition comprising sodium oxybate once per night. In some embodiments, the patient is an adult. A peak plasma concentration ($C_{max}$) following administration of one dose of the composition may be lower than a twice-nightly sodium oxybate treatment. For example, the $C_{max}$ following administration of one 6 g dose may be about 65.8 mcg/mL. There may be a steady decrease in concentration following a time to peak plasma concentration ($T_{max}$) approximately two hours after dosing. For example, the $T_{max}$ may be about 1.51 hours.

In some embodiments, the composition may be provided in a pre-measured dosage packet for administration. In an embodiment, the composition may be provided as a powder for oral suspension. The powder composition may include immediate-release and controlled-release granules of sodium oxybate. In some examples, the composition may further include microcrystalline cellulose spheres, povidone K30, hydrogenated vegetable oil, methacrylic acid copolymer, malic acid, xanthan gum, hydroxyethyl cellulose, carrageenan, and/or magnesium stearate. In various embodiments, the method may include providing the powder composition in a nightly dose packet of 4.5 g, 6 g, 7.5 g, or 9 g sodium oxybate. The method may further include preparing the dosage of the composition by suspending the composition from the dose packet in water. For example, the dose packet may be suspended in approximately ⅓ cup water (approximately 80 mL) or about 50 mL. In some embodiments, the patient may be provided with a pre-marked mixing cup for measuring the water and mixing the dose packet and water. In additional embodiments, the pre-marked mixing cup may further include at least one additional marking for measuring additional water for suspending any remnant composition remaining in the pre-marked mixing cup after administration of the suspension of the dose packet in the water. The patient may further administer the additional water with the remnant composition to ensure that the patient receives the full dosage of the composition.

In various embodiments, the dosage is administered without regard for meals. For example, the composition may be administered immediately after eating, up to 2 hours after eating a meal, or more than 2 hours after eating a meal. The meal may be an evening meal. In at least one embodiment, the composition is prepared and administered prior to bedtime. The patient may be in bed prior to orally administering the dosage and may lie down immediately after dosing as the composition may cause the patient to fall asleep abruptly without first feeling drowsy. Patients may fall asleep within 5 minutes of taking the composition, within 15 minutes of taking the composition, within 30 minutes of taking the composition, within 1 hour of taking the composition, within 1.5 hours of taking the composition, or within 2 hours of taking the composition. The time it takes any individual patient to fall asleep may vary from night to night. Patients may remain in bed following ingestion of the composition.

In some embodiments, the composition may be co-administered with a single dose of divalproex sodium ER. In some examples, the dose of divalproex sodium ER may be about 1250 mg.

In a preferred embodiment, the treatment of the present invention is superior, as measured by any one or combination of the foregoing criteria, to an equal dose administered twice nightly of an immediate release liquid solution of sodium oxybate, with the second dose administered 4 hours after the first dose. The invention further provides a method of treatment of narcolepsy Type 1 or Type 2 wherein, compared to a dosing regimen consisting of administering half the dose at $t_0$ and another half of the dose at $t_{4h}$ of an immediate release liquid solution of sodium oxybate, a single bedtime daily dose administration of a therapeutically effective amount of the formulation of the invention has been shown to produce less confusion, less depressive syndrome, less incontinence, less nausea or less sleepwalking.

Dose-Proportionality

In one additional embodiment, the present invention provides a composition comprising an oral suspension for the treatment of narcolepsy or excessive daytime sleepiness, the suspension comprising a blend of granules for oral suspension in water, the granules comprising gamma-hydroxybutyrate, wherein the oral suspension is administered only once nightly and is effective to induce sleep in a human subject in need thereof for at least six hours, and wherein the composition provides a $C_{max}$ which increases approximately 2-fold, and more than dose proportionally for AUC increasing 2.3-fold, as a total daily dose is doubled from 4.5 g to 9 g. In some examples, the oral suspension is effective to induce sleep in a human subject in need thereof for at least six hours, at least seven hours, or at least eight hours. The granules comprising gamma-hydroxybutyrate may include any formulation of gamma-hydroxybutyrate described herein.

In some aspects, the composition may include an amount of gamma-hydroxybutyrate that provides the same amount of gamma-hydroxybutyrate as 3.7 g, 5.0 g, 6.2 g, or 7.4 g of sodium oxybate.

In some aspects, the composition further includes about 80 mL of water. The water temperature may be 50° C. or less. The composition may be consumed within 30 minutes of mixing with water.

In some aspects, the granules may include carrageenan, hydrogenated vegetable oil, hydroxyethyl cellulose, magnesium stearate, malic acid, methacrylic acid copolymer, microcrystalline cellulose, povidone, xanthan gum, and combinations thereof.

In some additional aspects, the granules for oral suspension in water may be packaged in a once-nightly dose packet. The composition may be provided in single dose packets that include 3.0 g, 4.5 g, 6 g, 7.5 g, or 9 g of gamma-hydroxybutyrate. The single dose packets may be provided as a total of 7 or 30 single dose packets per package.

In still further aspects, the composition may be provided with a prepackaged mixing cup.

The composition may be suspended in about one-third of a cup of water prior to administration. The composition may be taken at least 2 hours after eating.

In one additional embodiment, the present invention provides a composition of gamma-hydroxybutyrate comprising immediate release and modified release portions, wherein the immediate release portion comprises particles comprising one or more salts of gamma-hydroxybutyrate and the modified release portion comprises particles comprising one or more salts of gamma-hydroxybutyrate, wherein the particles of the modified release portion are coated with a coating comprising:

a. a polymer carrying free carboxylic groups, and b. a hydrophobic compound having a melting point equal or greater than 40° C., c. wherein the composition is suitable for administration only once nightly, d. wherein the composition induces sleep for at least 6 consecutive hours, and e. provides a $C_{max}$ which increases approximately 2-fold, and more than dose proportionally for AUC increasing 2.3-fold, as a total daily dose is doubled from 4.5 g to 9 g.

In some aspects, the amount of gamma-hydroxybutyrate in the immediate release portion may be equal to the amount of gamma-hydroxybutyrate in the modified release portion. In other aspects, the ratio of gamma-hydroxybutyrate in the immediate release portion and the modified release portion may be from 10/90 to 65/35. In some exemplary embodiments, the ratio of gamma-hydroxybutyrate in the immediate release portion and the modified release portion is from 40/60 to 60/40. The compositon may include an amount of gamma-hydroxybutyrate that provides the same amount of gamma-hydroxybutyrate as 3.7 g, 5.0 g, 6.2 g, or 7.4 g of sodium oxybate.

The polymer carrying free carboxylic acid groups may have a pH trigger from 5.5 to 6.97. The free carboxylic acid groups may be ionized at pH 7.5.

The granules may further include hydroxyethyl cellulose, malic acid, methacrylic acid copolymer, microcrystalline cellulose, and povidone.

The granules may further include carrageenan, hydrogenated vegetable oil, hydroxyethyl cellulose, malic acid, methacrylic acic copolymer, microcrystalline cellulose, povidone, and xanthan gum.

In some aspects, the composition may be in an amount effective to treat narcolepsy Type 1 or Type 2, wherein said treatment of narcolepsy includes reducing excessive daytime sleepiness, reducing the frequency of cataplectic attacks, or a combination thereof.

In some aspects, the composition may be in an amount effective to induce sleep for at least eight hours.

In some aspects, the particles comprising the gamma-hydroxybutyrate in the immediate release portion and the modified release portion have a mean diameter from 10 to 1000 microns, and the particles of gamma-hydroxybutyrate in the modified release portion have a mean diameter from 100 to 1200 microns. In some examples, the particles comprising gamma-hydroxybutyrate in the immediate release portion have a mean diameter from 150 to 400 microns, and the particles of gamma-hydroxybutyrate in the modified release portion have a mean diameter from 200 to 800 microns.

The granules for oral suspension in water may be packaged in a once-nightly dose packet. The composition may be provided in single dose packets comprising 3.0 g, 4.5 g, 6 g, 7.5 g, or 9 g of gamma-hydroxybutyrate. The single dose packets may be provided as a total of 7 or 30 single dose packets.

In some additional aspects, the composition may have preferred qualities as compared to a twice-nightly sodium oxybate compoisiton. The composition may have a lower risk of causing a confusional state in a patient as compared to a twice-nightly sodium oxybate composition. The composition may have a 50% lower risk of causing a confusional state in a patient as compared to a twice-nightly sodium oxybate composition.

Ideopathic Hypersomnia and Exessive Daytime Sleepiness Symptoms

In one additional embodiment, the present invention provides a method of treating narcolepsy, cataplexy, or excessive daytime sleepiness in a subject comprising administering to the subject a once-nightly dose of gamma-hydroxybutyrate, wherein 2% or fewer subjects administered the once-nightly dose of gamma-hydroxybutyrate experience a confusional state. For example, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0% of subjects administered the once-nightly dose of gamma-hydroxybutyrate may experience a confusional state. The once-nightly dosage of gamma-hydroxybutyrate may be any formulation of gamma-hydroxybutyrate described herein.

In some aspects, the subject may have a reduction in symptoms related to narcolepsy, cataplexy, or excessive daytime sleepiness. For example, the subject may have a decreased risk of falls or headaches. The subject may have a decreased risk of car and work accidents. The subject may have a decreased risk of work-related errors or lack of energy. The subject may have a decreased risk of irritability or mood problems. The subject may have a decreased risk of gastrointestinal, cardiovascular, or metabolic disorders. The subject may have a decreased risk of drug or alcohol abuse. The subject may have a decreased risk of one or more of the sleep deprivation side effects selected form the group consisting of lack of alertness, irritation, memory lapses, lack of focus, difficulty retaining new concepts, difficulty making decisions, slower reaction times, and combinations thereof. The subject may have a decreased risk of developing diabetes, obesity, and heart disease associated with long-term sleep deprivation.

In another embodiment, the present invention provides a method of treating narcolepsy, cataplexy, or excessive daytime sleepiness in a subject comprising administering to the subject a once-nightly dose of gamma-hydroxybutyrate, wherein 3% or fewer subjects administered the once-nightly dose of gamma-hydroxybutyrate experience sleepwalking. For example, 3%, 2.99%, 2.88%, 2.7%, 2.6%, 2.50%, 2.4%, 2.30%, 2.2%, 2.10%, 2%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0% of subjects administered the once-nightly dose of gamma-hydroxybutyrate may experience sleepwalking. The once-nightly dosage of gamma-hydroxybutyrate may be any formulation of gamma-hydroxybutyrate described herein.

In some aspects, the sleepwalking may be a parasomnia that occurs during non-REM sleep.

Maintenance of Wakefulness Test

In one additional embodiment, the invention provides a method of treating narcolepsy, cataplexy, or excessive daytime sleepiness in a human patient in need thereof, the method comprising orally administering to the patient a once-nightly dosage of gamma-hydroxybutyrate, wherein the patient has statistically significant improvement on the Maintenance of Wakefulness Test (MWT) at dosages of 4.5 g, 6 g, 7.5 g, and 9 g as compared to placebo. The once-nightly dosage of gamma-hydroxybutyrate may be any formulation of gamma-hydroxybutyrate described herein. The MWT may measure latency to sleep onset in minutes averaged over five sessions at 2-hour intervals following nocturnal polysomnography.

In some aspects, the patient may have a latency to sleep onset about 5 minutes or more than placebo. The sleep latency may be determined as the number of minutes a patient remains awake during the MWT.

In some additional aspects, the patient may have a reduction in weekly cataplexy attacks. The patient may have an average total reduction in weekly cataplexy attacks from about 4.00 to about 7.00 as compared to placebo. For example, the patient may have an average total reduction in weekly cataplexy attacks from about 4.00, 4.10, 4.20, 4.30, 4.40, 4.50, 4.60, 4.70, 4.80, 4.90, 5.00, 5.10, 5.20, 5.30, 5.40, 5.50, 5.60, 5.70, 5.80, 5.90, 6.00, 6.10, 6.20, 6.30, 6.40, 6.50, 6.60, 6.70, 6.80, 6.90, or about 7.00. In an exemplary embodiment, the patient has an average total reduction in weekly cataplexy attacks from 4.83 to 6.65 as compared to placebo.

In further aspects, the patient may have an average improvement from 4.00 minutes to 7.00 minutes in the change form baseline in the MWT as compared to placebo. For example, the patient may have an average improvement of about 4.00, 4.10, 4.20, 4.30, 4.40, 4.50, 4.60, 4.70, 4.80, 4.90, 5.00, 5.10, 5.20, 5.30, 5.40, 5.50, 5.60, 5.70, 5.80, 5.90, 6.00, 6.10, 6.20, 6.30, 6.40, 6.50, 6.60, 6.70, 6.80, 6.90, or about 7.00 minutes from baseline in the MWT as compared to placebo. In an exemplary embodiment, the patient has an average improvement from 4.98 minutes to 6.21 minutes in the change from baseline in MWT as compared to placebo.

In still further aspects, the patient may be on concomitant stimulant use. The stimulants used may include slriamfetol, pitolisant, methylphenidate, modafinil, dextroamphetamine, amphetamine, armodafinil, lisdexamfetamine, and other CNS stimulants known in the art and combinations thereof.

In addition to the results obtained from the MWT, the patient may also have a change of being much improved or very much improved in a Clinical Global Impression-Improvement (CGI-I) score. In an exemplary embodiment, the patient has a 42.1 to 77.0% chance of being much improved or very much improved in a CGI-I score.

In another embodiment, the invention provides a method of treating narcolepsy, cataplexy, or excessive daytime sleepiness in a human patient in need thereof, the method comprising orally administering to the patient a once-nightly dosage of gamma-hydroxybutyrate, wherein the oral administration of the once-nightly dosage induces the patient to fall asleep within 5 minutes of administration. The once-nightly dosage of gamma-hydroxybutyrate may be any formulation of gamma-hydroxybutyrate described herein.

In another embodiment, the invention provides a method of treating narcolepsy, cataplexy, or excessive daytime sleepiness in a human patient in need thereof, the method comprising orally administering to the patient a once-nightly dosage of gamma-hydroxybutyrate, wherein the oral administration of the once-nightly dosage induces the patient to fall asleep within 15 minutes of administration. The once-nightly dosage of gamma-hydroxybutyrate may be any formulation of gamma-hydroxybutyrate described herein.

Additional Embodiments

In one additional embodiment, the invention provides a modified release formulation of gamma-hydroxybutyrate, preferably comprising immediate release and modified release portions, wherein the formulation releases (a) at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 10% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In a second additional embodiment, the invention provides a modified release formulation of gamma-hydroxybutyrate, comprising immediate release and modified release portions, wherein (a) the formulation releases at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 10% to 65% of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a third additional embodiment, the invention provides a modified release formulation of gamma-hydroxybutyrate, comprising immediate release and modified release portions, wherein (a) the formulation releases at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases 10% to 65%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60% of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a fourth additional embodiment, the invention provides a modified release formulation of gamma-hydroxybutyrate, preferably comprising immediate release and modified release portions, wherein the formulation releases (a) at least 80% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 40% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In a fifth additional embodiment, the invention provides a modified release formulation of gamma-hydroxybutyrate, comprising immediate release and modified release portions, wherein (a) the formulation releases at least 80% of its gamma-hydroxybutyrate at 3 hour 3 when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 40% to 65% of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a sixth additional embodiment, the invention provides a modified release formulation of gamma-hydroxybutyrate, comprising immediate release and modified release portions, wherein (a) the formulation releases at least 80% of its gamma-hydroxybutyrate at 3 hours when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases 40% to 65%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60% of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a seventh additional embodiment, the invention provides a modified release formulation of gamma-hydroxybutyrate, preferably comprising immediate release and modified release portions, wherein the formulation releases (a) at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, and (b) from 40% to 65%, of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm.

In an eighth additional embodiment, the invention provides a modified release formulation of gamma-hydroxybutyrate, comprising immediate release and modified release portions, wherein (a) the formulation releases at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases from 40% to 65% of its gamma-hydroxybutyrate at one hour and three hours when tested in a dissolution apparatus 2 according to USP 38 <711> in 900 mL of 0.1N hydrochloric acid at a temperature of 37° C. and a paddle speed of 75 rpm, and (c) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

In a ninth additional embodiment, the invention provides a modified release formulation of gamma-hydroxybutyrate, comprising immediate release and modified release portions, wherein (a) the formulation releases at least 80% of its gamma-hydroxybutyrate at 1 hour when tested in a dissolution apparatus 2 according to USP 38 <711> in 900 mL of 0.05M monobasic potassium phosphate buffer pH 6.8 at a temperature of 37° C. and a paddle speed of 75 rpm, (b) the formulation releases 40 to 65%, of its gamma-hydroxybutyrate at one hour and at three hours when tested in a dissolution apparatus 2 according to USP 38 <711> in 900 mL of 0.1N hydrochloric acid at a temperature of 37° C. and a paddle speed of 75 rpm, (c) the formulation releases greater than 60% of its gamma-hydroxybutyrate at 10 hours when tested in a dissolution apparatus 2 according to USP 38 <711> in 900 mL of 0.1N hydrochloric acid at a temperature of 37° C. and a paddle speed of 75 rpm, and (d) the modified release portion releases greater than 80% of its gamma-hydroxybutyrate at 3 hours in a dissolution test started in 750 mL of 0.1N hydrochloric acid for 2 hours then switched to 950 mL 0.05M monobasic potassium phosphate buffer adjusted to pH 6.8 at a temperature of 37° C. and a paddle speed of 75 rpm.

EXAMPLES

Example 1. Formulations

Figure 1A:
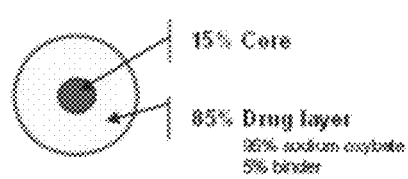
FIG. 1A depicts the qualitative and quantitative structure of the immediate release (IR) microparticles of gamma-hydroxybutyrate of Example 1.
Figure 1B:
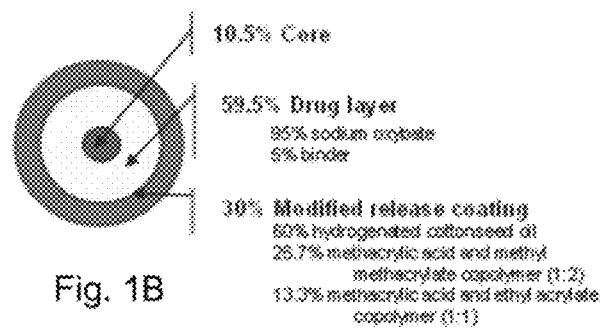
FIG. 1B depicts the qualitative and quantitative structure of the modified release (MR) microparticles of gamma-hydroxybutyrate of Example 1.

Tables 1a-1d provide the qualitative and quantitative compositions of sodium oxybate IR microparticles, MR microparticles, and mixtures of IR and MR microparticles. The physical structure of the microparticles showing the qualitative and quantitative composition of the IR and MR microparticles is depicted in FIGS. 1A and 1B, respectively.

Briefly, sodium oxybate immediate release (IR) microparticles were prepared as follows: 1615.0 g of sodium oxybate and 85.0 g of polyvinylpyrrolidone (Povidone K30-Plasdone™ K29/32 from ISP) were solubilized in 1894.3 g of absolute ethyl alcohol and 1262.9 g of water. The solution was entirely sprayed onto 300 g of microcrystalline cellulose spheres (Cellets™ 127) in a fluid bed spray coater apparatus. IR Microparticles with volume mean diameter of about 270 microns were obtained.

Sodium oxybate modified release (MR) microparticles were prepared as follows: 22.8 g of methacrylic acid copolymer Type C (Eudragit™ L100-55), 45.8 g of methacrylic acid copolymer Type B (Eudragit™ S100), 102.9 g of hydrogenated cottonseed oil (Lubritab™), were dissolved in 1542.9 g of isopropanol at 78° C. The solution was sprayed entirely onto 400.0 g of the sodium oxybate IR microparticles described above in a fluid bed spray coater apparatus with an inlet temperature of 48° C., spraying rate around 11 g per min and atomization pressure of 1.3 bar. MR microparticles were dried for two hours with inlet temperature set to 56° C. MR microparticles with mean volume diameter of about 320 microns were obtained.

The finished composition, which contains a 50:50 mixture of MR and IR microparticles calculated on their sodium oxybate content, was prepared as follows: 353.36 g of the above IR microparticles, 504.80 g of the above MR microparticles, 14.27 g of malic acid (D/L malic acid), 6.34 g of xanthan gum (Xantural™ 75 from Kelco), 9.51 g of carrageenan gum (Viscarin™ PH209 from FMC Biopolymer), 9.51 g of hydroxyethylcellulose (Natrosol™ 250M from Ashland) and 4.51 g of magnesium stearate were mixed. Individual samples of 7.11 g (corresponding to a 4.5 g dose of sodium oxybate with half of the dose as immediate-release fraction and half of the dose as modified release fraction) were weighed.

TABLE 1a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |

TABLE 1a-continued

Composition of IR Microparticles

| Component | Function | Quantity per 2.25 g dose (g) |
|---|---|---|
| Ethyl alcohol | Solvent | Eliminated during processing |
| Purified water | Solvent | Eliminated during processing |
| Total | | 2.786 |

TABLE 1b

Composition of MR Microparticles

| Component | Function | Quantity per 4.5 g dose (g) |
|---|---|---|
| IR Microparticles | Core of MR microparticles | 2.786 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Isopropyl alcohol | Solvent | Eliminated during processing |
| Total | | 3.981 |

TABLE 1c

Qualitative Finished Composition

| Component | Function | Quantity per 4.5 g dose (g) |
|---|---|---|
| MR microparticles | Modified release fraction of sodium oxybate | 3.981 |
| IR microparticles | Immediate release fraction of sodium oxybate | 2.786 |
| Malic acid | Acidifying agent | 0.113 |
| Xanthan gum | Suspending agent | 0.050 |
| Hydroxyethyl-cellulose | Suspending agent | 0.075 |
| Carrageenan gum | Suspending agent | 0.075 |
| Magnesium stearate | Lubricant | 0.036 |
| Total | | 7.116 |

TABLE 1d

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Malic acid | Acidifying agent | 0.113 |
| Xanthan gum | Suspending agent | 0.050 |

TABLE 1d-continued

Quantitative finished composition

| Component | Function | Quantity per 4.5 g dose (g) |
|---|---|---|
| Hydroxyethylcellulose | Suspending agent | 0.075 |
| Carrageenan gum | Suspending agent | 0.075 |
| Magnesium stearate | Lubricant | 0.036 |
| Total | | 7.116 |

Example 1Bis: Alternative Formulation

An alternative formulation to the formulation described in example 1 is described in Example 1bis.

Sodium oxybate immediate release (IR) microparticles were prepared by coating the IR microparticles described in example 1 with a top coat layer. Microparticles were prepared as follows: 170.0 of hydroxypropyl cellulose (Klucel™ EF Pharm from Hercules) were solubilized in 4080.0 g of acetone. The solution was entirely sprayed onto 1530.0 g of the IR microparticles of Example 1 in a fluid bed spray coater apparatus. IR Microparticles with volume mean diameter of about 298 microns were obtained (see Table 1bis-a).

Sodium oxybate modified release (MR) microparticles were prepared as described in example 1 (see Table 1b).

The finished composition, which contains a 50:50 mixture of MR and IR microparticles based on their sodium oxybate content, was prepared as follows: 412.22 g of the above IR microparticles, 530.00 g of the above MR microparticles, 29.96 g of malic acid (D/L malic acid), 4.96 g of xanthan gum (Xantural™ 75 from Kelco), 4.96 g of colloidal silicon dioxide (Aerosil™ 200 from Degussa) and 9.92 g of magnesium stearate were mixed. Individual samples of 7.45 g (corresponding to a 4.5 g dose of sodium oxybate with half of the dose in an immediate-release fraction and half of the dose in a modified release fraction) were weighed (see Table 1bis-b and 1bis-c).

TABLE 1bis-a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |
| Hydroxypropyl cellulose | Top coat | 0.310 |
| Ethyl alcohol | Solvent | Eliminated during processing |
| Purified water | Solvent | Eliminated during processing |
| Acetone | Solvent | Eliminated during processing |
| Total | | 3.096 |

TABLE 1bis-b

Qualitative Finished Composition

| Component | Function | Quantity per 4.5 g dose (g) |
|---|---|---|
| MR microparticles | Modified release fraction of sodium oxybate | 3.981 |
| IR microparticles | Immediate release fraction of sodium oxybate | 3.096 |
| Malic acid | Acidifying agent | 0.225 |
| Xanthan gum | Suspending agent | 0.037 |
| Colloidal silicon dioxide | Gliding agent | 0.037 |
| Magnesium stearate | Lubricant | 0.075 |
| Total | | 7.451 |

TABLE 1bis-c

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydroxypropyl cellulose | Top coat | 0.310 |
| Hydrogenated Vegetable Oil | Coating excipient | 0.716 |
| Methacrylic acid Copolymer Type C | Coating excipient | 0.159 |
| Methacrylic acid Copolymer Type B | Coating excipient | 0.318 |
| Malic acid | Acidifying agent | 0.225 |
| Xanthan gum | Suspending agent | 0.037 |
| Colloidal silicon dioxide | Gliding agent | 0.037 |
| Magnesium stearate | Lubricant | 0.075 |
| Total | | 7.451 |

Compared to the finished composition described in example 1, this alternative composition has the following characteristics: same MR microparticles, same IR microparticles but with a top coat, increased amount of malic acid, only one suspending agent (xanthan gum) and presence of a glidant.

Finished compositions from Example 1 and 1bis exhibit substantially the same in-vitro dissolution profiles (see FIGS. 7 and 8).

Figure 2:
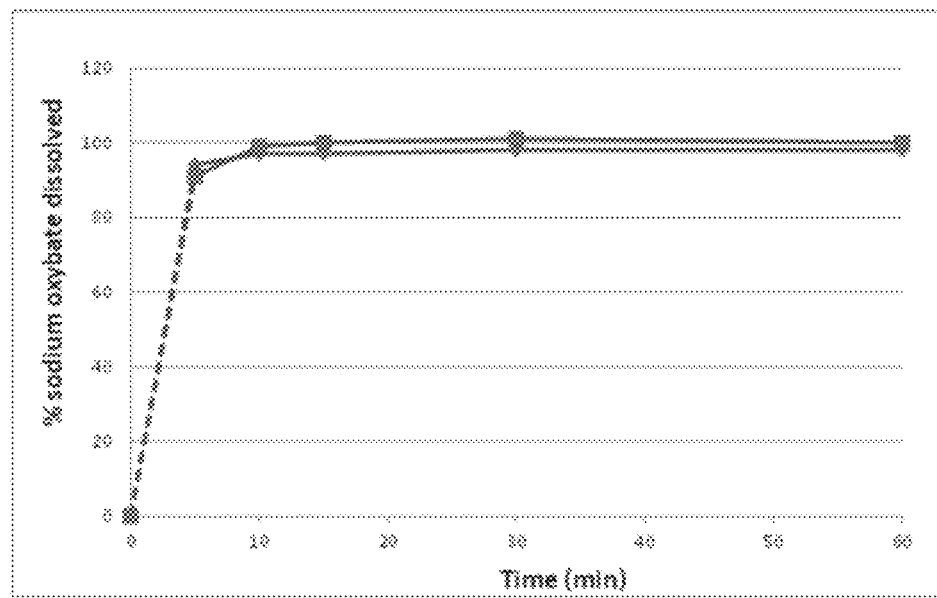
FIG. 2 plots a time release dissolution profile of IR microparticles of gamma-hydroxybutyrate of Example 1 (♦) and 1bis (■) in a 0.1N HCl dissolution medium.

Example 2: In Vitro Release Profiles of IR, MR and Finished Compositions of Formulations of Examples 1 and 1Bis Dissolution Testing of IR Microparticles The dissolution profile of 2786 mg of IR microparticles of Example 1, corresponding to 2250 mg of sodium oxybate per vessel, was determined in 0.1N HCl dissolution medium using a USP apparatus 2. Dissolution medium temperature was maintained at 37.0±0.5° C., and the rotating paddle speed was set at 100 rpm. The release profile of the IR microparticles is shown in FIG. 2 and Table 2a. All the sodium oxybate was released at 1 hour.

TABLE 2a

Percent Sodium Oxybate Released in 0.1N HCl for IR microparticles of sodium oxybate prepared according to Example 1

| Time (min) | % released |
|---|---|
| 0 | 0 |
| 5 | 94 |
| 10 | 97 |
| 15 | 97 |
| 30 | 98 |
| 60 | 98 |

Dissolution Testing of IR Microparticles from Example 1Bis

The dissolution profile of 3096 mg of IR microparticles of Example 1bis, corresponding to 2250 mg of sodium oxybate per vessel, was determined in 0.1N HCl dissolution medium using a USP apparatus 2. Dissolution medium temperature was maintained at 37.0±0.5° C., and the rotating paddle speed was set at 100 rpm. The release profile of the IR microparticles is shown in FIG. 2 and Table 2b. All the sodium oxybate was released at 1 hour.

TABLE 2b

Percent Sodium Oxybate Released in 0.1N HCl for IR microparticles of sodium oxybate prepared according Example 1bis

| Time (min) | % Released |
|---|---|
| 0 | 0 |
| 5 | 91 |
| 10 | 99 |
| 15 | 100 |
| 30 | 101 |
| 60 | 100 |

Dissolution Testing of MR Microparticles from Example 1—Protocol (2 h 0.1N HCl/Phosphate Buffer pH 6.8)

49.1 g of MR microparticles from Example 1 were mixed with 0.5 g of magnesium stearate (from Peter Graven) and 0.25 g of colloidal silicon dioxide (Aerosil™ 200 from Evonik). The dissolution profile of 4040 mg of the mixture which corresponds to 2250 mg of sodium oxybate per vessel was determined using the USP apparatus 2. Dissolution medium temperature was maintained at 37.0±0.5° C., and the rotating paddle speed was set at 75 rpm.

After 2 hours in 750 mL of 0.1N HCl medium, 6.5 g of monobasic potassium phosphate was added to the dissolution vessel. pH and volume were then respectively adjusted to 6.8 and 950 mL, as needed by the addition of NaOH and water. The potassium phosphate concentration was equal to 0.05 M in the dissolution medium after pH and volume adjustment.

The release profile of the MR microparticles is shown in FIG. 3 and Table 2c. The sodium oxybate was not released in the 0.1N HCl dissolution medium during two hours. After the switch to pH 6.8 dissolution medium, all the sodium oxybate was released within 30 minutes.

TABLE 2c

Percent Sodium Oxybate Released in two
sequential dissolution media (0.1 HCl for
2 hours, then phosphate buffer pH 6.8) for
MR microparticles of sodium
oxybate prepared according to Example 1

| Time (h) | % released |
|---|---|
| 0 | 0 |
| 1 | 1 |
| 2 | 2 |
| 2.25 | 33 |
| 2.5 | 97 |
| 3 | 103 |
| 4 | 104 |
| 6 | 103 |

Figure 4:
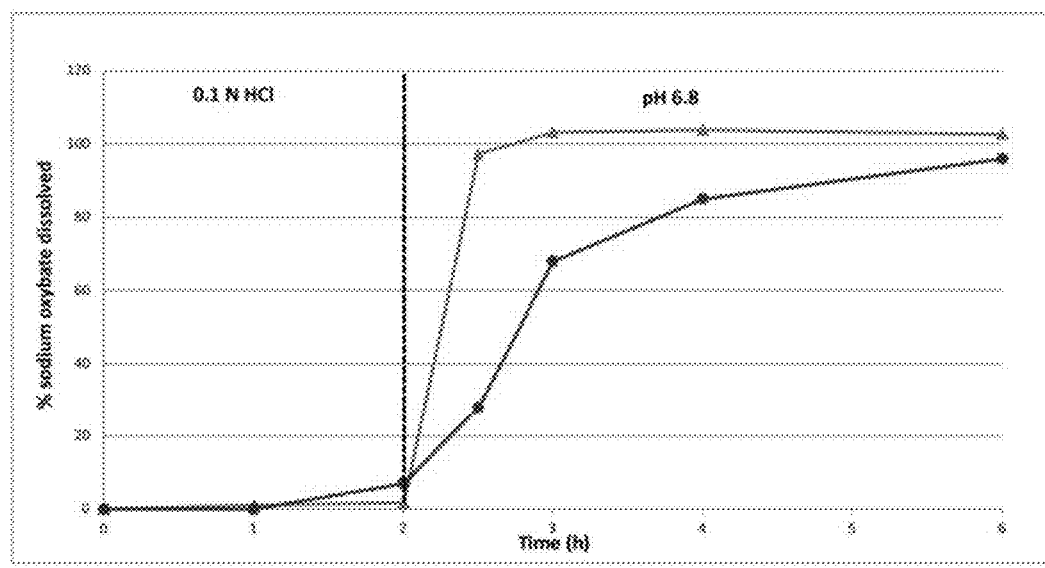
FIG. 4 plots a time release dissolution profile of MR microparticles (▲ symbols) of Example 1 in two sequential dissolution media (0.1 N HCl/phosphate buffer pH 6.8), overlaid against dissolution profile described in FIG. 3 of U.S. Pat. No. 8,193,211 (• symbols).

FIG. 4 overlays the dissolution profile of the MR microparticles of Example 1 with the dissolution profile for MR microparticles reported in Supernus U.S. Pat. No. 8,193,211, FIG. 3. It shows that the dissolution profiles are different and that the MR microparticles according to the present invention release greater than 80% of their sodium oxybate at 3 hours, whereas the MR microparticles described in Supernus U.S. Pat. No. 8,193,211, FIG. 3 do not and exhibit a much slower release profile.

Figure 5:
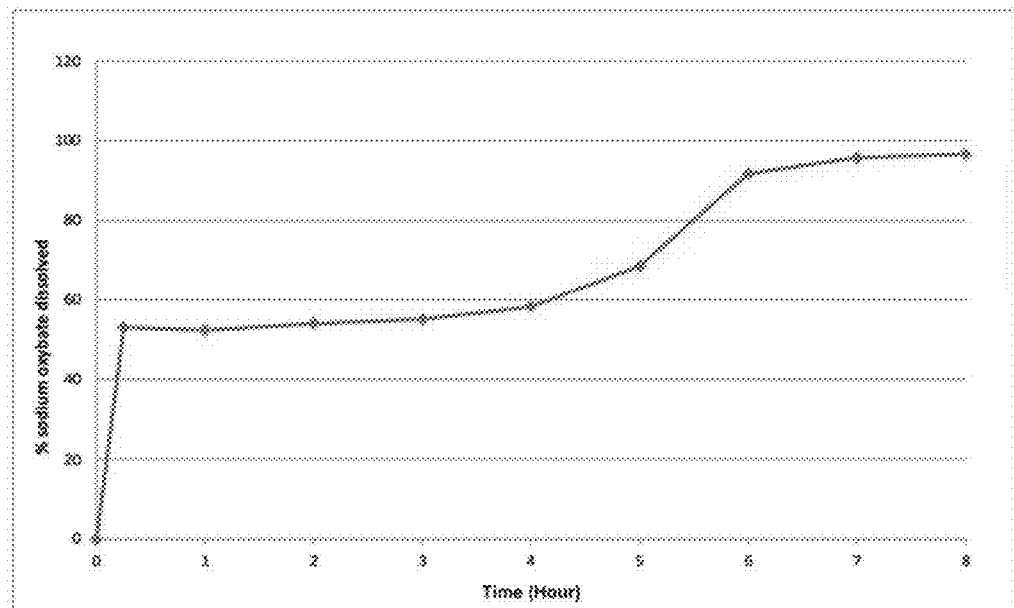
FIG. 5 plots a time release dissolution profile of the finished formulation of Example 1 in deionized water.

Dissolution Testing of Finished Composition According to Example 1 in Deionized Water The dissolution profile of the quantity equivalent to 4.5 g sodium oxybate of the finished composition according Example 1 was determined in 900 mL of deionized water using the USP apparatus 2. The dissolution medium was maintained at 37.0±0.5° C. and the rotating paddle speed was fixed at 50 rpm. The release profile is shown in FIG. 5 and Table 2d. The IR fraction of sodium oxybate was solubilized in 15 minutes. The release of sodium oxybate from the modified-release fraction started after approximately 4 hours with 90% of the total dose released at 6 hours.

TABLE 2d

Percent Sodium Oxybate Released in deionized
water for finished composition of sodium
oxybate prepared according to Example 1

| Time (h) | % released |
|---|---|
| 0 | 0 |
| 0.25 | 53 |
| 1 | 52 |
| 2 | 54 |
| 3 | 55 |
| 4 | 58 |
| 5 | 69 |
| 6 | 92 |
| 7 | 96 |
| 8 | 97 |

Figure 6:
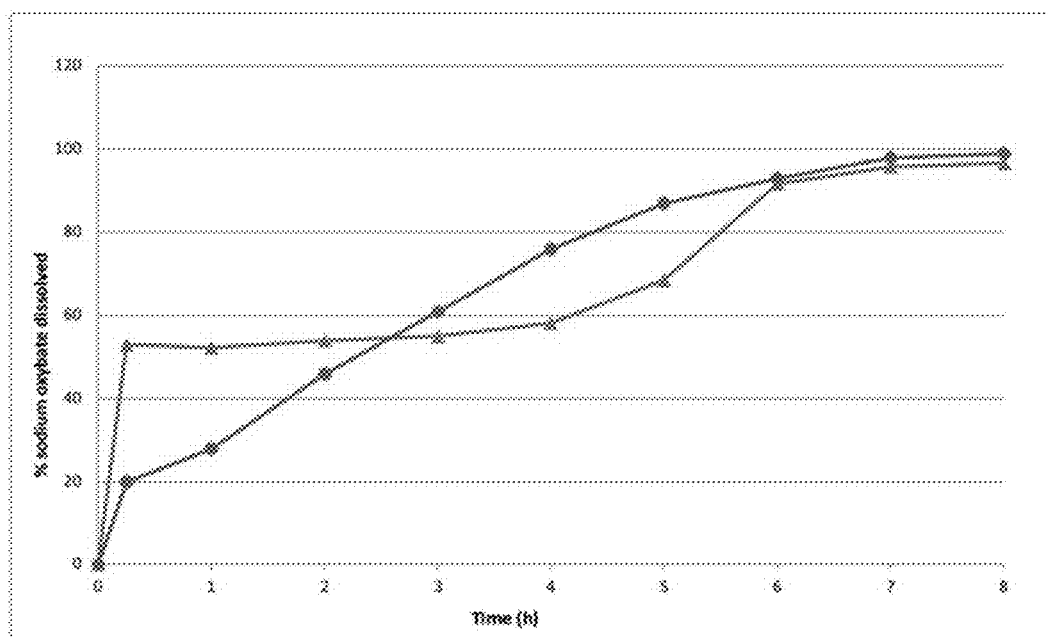
FIG. 6 plots a time release dissolution profile of the finished composition of Example 1 in deionized water (▲ symbols), overlaid against dissolution profile described in FIG. 2 of USP 2012/0076865 (• symbols).

An overlay of the release profile of the finished formulation of Example 1 versus that reported in USP 2012/0076865 FIG. 2 is shown in FIG. 6. It shows that the dissolution profiles are different. The formulation described in USP 2012/0076865 FIG. 2 does not exhibit a lag phase after the dissolution of the immediate release part.

Release Testing of Different Batches of MR Microparticles and Finished Dosage Forms In vitro release profiles obtained in 900 mL of 0.1N HCl dissolution medium for different batches of modified release (MR) microparticles prepared according to Example 1 are described below in Table 2e. The dissolution profile of 4040 mg of microparticles corresponding to 2250 mg of sodium oxybate per vessel is determined using the USP apparatus 2. Dissolution medium temperature was maintained at 37.0±0.5° C., and the rotating paddle speed was set at 100 rpm.

TABLE 2e

Percent Sodium Oxybate Released
in 0.1N HCl Dissolution Medium from
different manufacturing lots of MR Particles of Example 1

| Time | Lot 1 | Lot 2 | Lot 3 | Lot 4 | Lot 5 | Lot 6 | Lot 7 | Lot 8 |
|---|---|---|---|---|---|---|---|---|
| 0.25 | 2.22 | 0.62 | 0.42 | 0.86 | 0.56 | 1.03 | 0.69 | 0.26 |
| 1.0 | 2.59 | 1.14 | 1.23 | 1.48 | 0.96 | 2.15 | 1.43 | 0.97 |
| 2.00 | 3.07 | 1.71 | 2.09 | 1.94 | 1.36 | 3.16 | 2.17 | 1.39 |
| 3 | 3.55 | 2.31 | 2.75 | 2.29 | 1.76 | 4.08 | 2.82 | 1.80 |
| 4.0 | 4.23 | 3.03 | 3.53 | 2.75 | 2.18 | 4.92 | 3.50 | 2.31 |
| 6 | 7.99 | 7.68 | 8.69 | 5.33 | 3.78 | 7.52 | 5.70 | 8.10 |
| 8.0 | 37.44 | 33.84 | 33.84 | 26.20 | 17.00 | 21.59 | 21.02 | 37.27 |
| 10 | 77.09 | 69.85 | 65.51 | 61.77 | 49.89 | 50.98 | 53.48 | 67.64 |
| 12 | 91.26 | 85.72 | 84.25 | 83.55 | 77.65 | 75.68 | 78.00 | 82.66 |
| 16 | 96.15 | 90.48 | 95.35 | 97.34 | 96.94 | 95.19 | 96.17 | 90.35 |

In vitro release profiles obtained in 0.1N HCl for three batches of finished composition comprising IR (50% w/w sodium oxybate dose) and MR microparticles (50% w/w sodium oxybate dose), prepared as described in Example 1, are provided in Table 2f. The sodium oxybate dose per vessel was 4.5 g, 6 g and 7.5 g respectively and dissolution was determined in 900 mL of 0.1N HCl dissolution medium using the USP apparatus 2. The dissolution medium was maintained at 37.0±0.5° C. and the rotating paddle speed was fixed at 100 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 2f

Percent Sodium Oxybate Released in 0.1N HCl Dissolution
Medium for three batches of finished composition prepared
according to Example 1

| Time (hour) | Batch 1 | Batch 2 | Batch 3 |
|---|---|---|---|
| 0.5 | 50 | 49 | 50 |
| 1 | 50 | 50 | 50 |
| 3 | 50 | 50 | 50 |
| 6 | 52 | 52 | 53 |
| 8 | 61 | 64 | 63 |
| 12 | 90 | 93 | 97 |
| 16 | 96 | 94 | 95 |

FIG. 7 and Table 2g depict dissolution profiles determined using a USP apparatus 2 in a 900 mL in 0.1N HCl dissolution medium of four finished compositions, two prepared according to Example 1 and two prepared according to Example 1bis. The dissolution medium was maintained at 37.0±0.5° C. and the rotating paddle speed was fixed at 100 rpm. It shows that the composition according to the invention releases from 10 to 65% of its sodium oxybate at 1 and 3 hours and releases greater than 60% at 10 hours.

TABLE 2g

Percent Sodium Oxybate Released in 0.1N HCl Dissolution Medium for four batches of finished compositions, two prepared according to Example 1 and two prepared according to Example 1bis

| Time (hour) | Example 1bis | Example 1bis | Example 1 | Example 1 |
|---|---|---|---|---|
| 0 | 0 | 0 | 0 | 0 |
| 0.25 | Nd | Nd | 52 | 50 |
| 0.5 | 51 | 50 | Nd | Nd |
| 1 | 51 | 50 | 54 | 51 |
| 3 | 51 | 50 | 54 | 52 |
| 6 | 55 | 52 | 55 | 53 |
| 8 | 72 | 61 | 60 | 57 |
| 10 | Nd | Nd | 73 | 70 |
| 12 | 86 | 90 | 85 | 83 |
| 16 | 88 | 96 | 96 | 94 |
| 20 | Nd | Nd | 99 | 98 |

Nd: not determined

FIG. 8 and Table 2h depict dissolution profiles determined using a USP apparatus 2 in a 900 mL phosphate buffer pH 6.8 dissolution medium for four finished compositions prepared according to Example 1 or 1bis. The dissolution medium was maintained at 37.0±0.5° C. and the rotating paddle speed was fixed at 100 rpm. It shows that the composition according to the invention releases more than 80% of its sodium oxybate at 3 hours.

TABLE 2h

Percent Sodium Oxybate Released in phosphate buffer pH 6.8 Dissolution Medium for four batches of finished compositions, two prepared according to Example 1 and two prepared according to Example 1bis

| Time (hour) | Example 1bis | Example 1bis | Example 1 | Example 1 |
|---|---|---|---|---|
| 0 | 0 | 0 | 0 | 0 |
| 0.25 | Nd | Nd | 75 | 84 |
| 0.5 | 99 | 98 | Nd | Nd |
| 1 | 101 | 101 | 100 | 102 |
| 1.5 | 101 | 101 | 106 | 108 |
| 2 | 100 | 100 | Nd | Nd |
| 3 | 103 | 100 | Nd | Nd |
| 4 | 103 | 100 | Nd | Nd |
| 6 | 102 | 99 | 101 | 102 |
| 8 | 103 | 99 | 101 | 105 |
| 10 | 103 | 99 | 101 | Nd |
| 12 | 101 | 99 | 101 | 102 |
| 16 | Nd | Nd | 100 | 101 |
| 20 | Nd | Nd | 99 | 98 |

Nd: not determined

Figure 9:
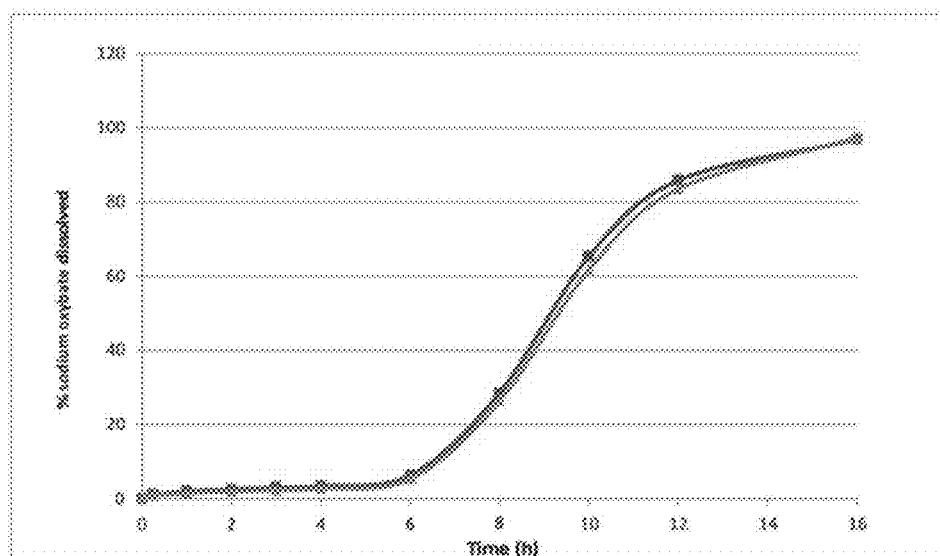
FIG. 9 plots time release dissolution profiles in 0.1N HCl of MR microparticles of gamma-hydroxybutyrate produced in accordance with Example 1 at 75 rpm (■ symbols) and 100 rpm (▲ symbols).

Release Testing of MR Microparticles and Finished Compositions—Effect of Paddle Speed:

FIG. 9 and Table 2i depict dissolution profiles in 0.1N HCl of a batch of MR microparticles prepared according to Example 1. The dissolution profile of 4040 mg of microparticles corresponding to 2250 mg of sodium oxybate per vessel was determined using the USP apparatus 2. The dissolution medium temperature was maintained at 37.0±0.5° C., and the rotating paddle speed was set at 75 or 100 rpm.

TABLE 2i

Percent Sodium Oxybate Released in 0.1N HCl Dissolution Medium for MR microparticles prepared according to Example 1

| Time (hour) | 75 rpm | 100 rpm |
|---|---|---|
| 0 | 0 | 0 |
| 0.25 | 1 | 1 |
| 1 | 2 | 1 |
| 2 | 2 | 2 |
| 3 | 3 | 2 |
| 4 | 3 | 3 |
| 6 | 6 | 5 |
| 8 | 28 | 26 |
| 10 | 65 | 62 |
| 12 | 86 | 84 |
| 16 | 97 | 97 |

Figure 10:
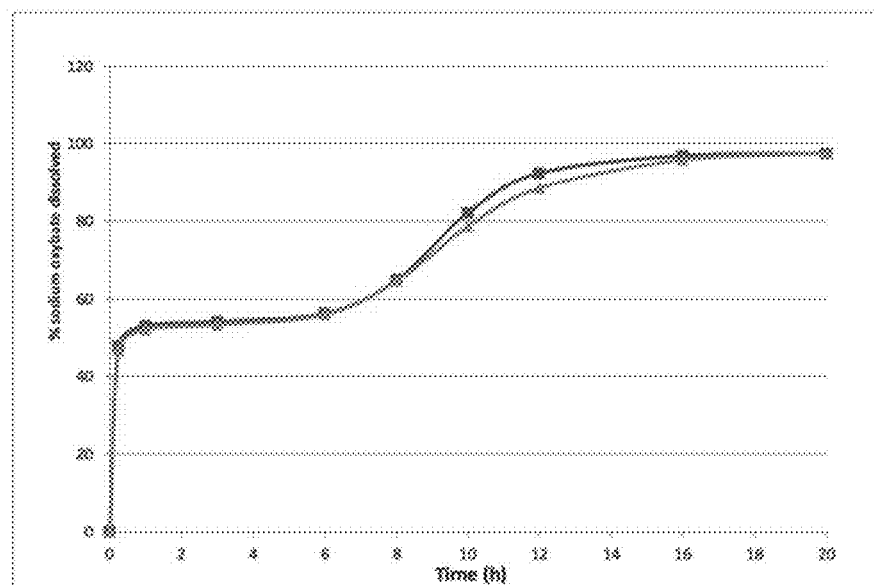
FIG. 10 plots time release dissolution profiles in 0.1N HCl of finished composition produced in accordance with Example 1 performed with paddle rotation speed set at 75 rpm (■ symbols) and 100 rpm (▲ symbols).

FIG. 10 and Table 2j depict dissolution profiles in 0.1N HCl of a finished composition prepared according to Example 1. The dose per vessel was 4.5 g and dissolution was determined in 900 mL of dissolution medium using the USP apparatus 2. The dissolution medium temperature was maintained at 37.0±0.5° C. and the rotating paddle speed was set at 75 or 100 rpm.

Single dose units were poured in a container containing 50 mL of tap water. After 5 minutes, the suspension was poured in the dissolution vessel containing 840 mL of 0.1N HCl medium. 10 mL of water were used to rinse the container and were added to the dissolution vessel.

TABLE 2j

Percent Sodium Oxybate Released in 0.1N HCl Dissolution Medium for finished composition prepared according to Example 1

| Time (hour) | 75 rpm | 100 rpm |
|---|---|---|
| 0 | 0 | 0 |
| 0,25 | 48 | 47 |
| 1 | 53 | 52 |
| 3 | 54 | 53 |
| 6 | 56 | 56 |
| 8 | 65 | 65 |
| 10 | 82 | 79 |
| 12 | 92 | 89 |
| 16 | 97 | 96 |
| 20 | 98 | 98 |

Example 3. In Vivo Pharmacokinetic Study of Finished Composition According to Example 1Bis Pharmacokinetic testing was undertaken in vivo in healthy human volunteers according to the principles described in FDA's March 2003 Guidance for Industry on BIOAVAILABILITY AND BIOEQUIVALENCE STUDIES FOR ORALLY ADMINISTERED DRUG PRODUCTS—GENERAL CONSIDERATIONS. All testing was performed in subjects two hours after eating a standardized dinner. Xyrem® doses were administered in two equipotent doses four hours apart. All other tested doses were manufactured as described in Example 1bis. The standardized dinner consisted of 25.5% fat, 19.6% protein, and 54.9% carbohydrates.

Figure 11:
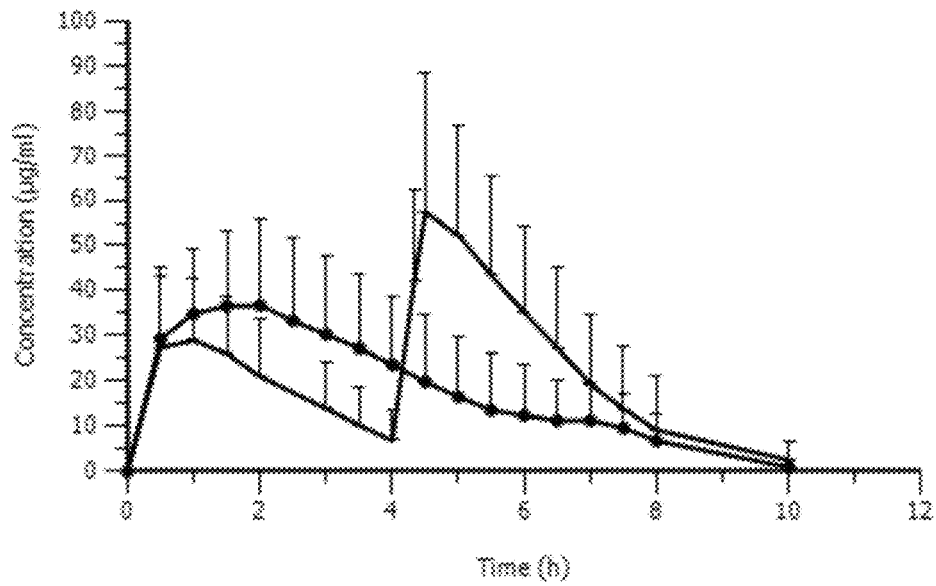
FIG. 11 plots the mean+SD (standard deviation) plasma gamma-hydroxybutyrate concentrations (microgram/mL) versus time for two different modified release formulations of gamma-hydroxybutyrate tested in vivo according to the methods of Example 3. Time profiles are given for a 4.5 g dose of the finished composition of Example 1bis administered once (• symbols) (N=26) and a 4.5 g dose of Xyrem® administered in two divided doses (- symbols) (N=15).

The finished composition of Example 1bis given as a 4.5 g once-nightly dose rather than a standard Xyrem® dosing twice (2×2.25 g) nightly 4 hours apart, produced a dramatically different pharmacokinetic profile than Xyrem® as shown in FIG. 11. As summarized below (Tables 3a and 3b), 4.5 g nighttime doses of finished composition of the invention equivalent to twice-nightly doses of Xyrem® (2×2.25 g) provided somewhat less total exposure to sodium oxybate with a later median Tmax than the initial Xyrem® dose. The relative bioavailability was about 88%. Composition according to the invention avoids the high second-dose peak concentration of Xyrem® and therefore does not exhibit the substantial between-dose fluctuations in concentration, while achieving a comparable mean C8h.

The pharmacokinetic profile of a single 6 g dose of finished composition produced according to Example 1bis was also tested and found to have a similar pharmacokinetic profile as the 4.5 g dose. FIG. 12 provides a pharmacokinetic profile comparison of a single 4.5 g or 6 g dose of finished composition according to Example 1bis in the same 7 subjects. The pharmacokinetic profile for a 7.5 g dose of finished formulation produced according to Example 1bis was also obtained. FIG. 13 and Table 3c provide data on a single 4.5 g, 6 g and 7.5 g dose, showing effects on Tmax, Cmax, C8h, AUC8h and AUCinf related to dose strength. The 7.5 g dose achieved a mean C8h equal to about 31 microgram/mL which represents approximately 128.5% of the C8h obtained for Xyrem® dosed 2×3.75 g which was extrapolated to be approximately 24.07 microgram/mL from published data. The 7.5 g dose achieved a ratio of AUC8h to AUCinf of about 0.89, whereas the ratio was 0.83 and 0.93 for the 4.5 g and 6 g doses respectively.

TABLE 3a

Pharmacokinetic Parameters of finished composition of Example 1bis vs. Xyrem®

| | Mean Cmax (µg/mL) (% CV) | Mean AUCinf (h*µg/mL) | Median Tmax (hour) (min-max) |
|---|---|---|---|
| Finished composition of Example 1bis 4.5 g | 44.35 (38) | 188.88 (44) | 1.5 (0.5-4) |
| Xyrem® 2 × 2.25 g | 1st dose: 33.41 (41) 2nd dose: 65.91 (40) | 214.32 (48) | 1st dose: 1.00 (0.5-2) 2nd dose: 4.50 (4.33-6.5) |

TABLE 3b

Mean plasma concentration of gamma-hydroxybutyrate (microgram/mL) versus time of finished composition of Example 1bis and Xyrem®

| Time (hour) | Finished composition Example 1bis 4.5 g (2 h after meal) pooled mean (N = 26) | Finished composition Example 1bis 6.0 g (2 h after meal) pooled mean (N = 19) | Finished composition Example 1bis 7.5 g (2 h after meal) (N = 11) | Xyrem® (2 × 2.25 g) part 1 (N = 15) |
|---|---|---|---|---|
| 0 | 0.00 | 0.00 | 0.00 | 0.00 |
| 0.5 | 29.31 | 36.44 | 43.19 | 27.44 |
| 1 | 34.93 | 49.97 | 63.32 | 28.97 |
| 1.5 | 36.63 | 54.66 | 73.40 | 26.12 |
| 2 | 36.78 | 54.82 | 67.96 | 21.11 |
| 2.5 | 33.35 | 53.05 | 66.59 | NA |
| 3 | 30.28 | 50.25 | 62.13 | 13.93 |
| 3.5 | 27.30 | 47.22 | 59.45 | 10.25 |
| 4 | 23.66 | 43.06 | 57.40 | 6.92 |
| 4.5 | 19.89 | 39.13 | 50.85 | 57.33 |
| 5 | 16.55 | 34.28 | 45.09 | 52.27 |
| 5.5 | 13.62 | 32.11 | 44.94 | 43.55 |
| 6 | 12.40 | 25.84 | 42.36 | 35.20 |
| 6.5 | 11.25 | 22.36 | 41.02 | 27.44 |
| 7 | 11.27 | 18.07 | 40.76 | 19.36 |
| 7.5 | 9.65 | 15.41 | 35.83 | 13.88 |
| 8 | 6.86 | 12.80 | 30.94 | 9.24 |
| 10 | 1.08 | 2.38 | 7.99 | 2.64 |
| 12 | NC | 0.52 | 1.47 | NC |

NC: Not Calulated

TABLE 3c

Pharmacokinetic Parameters of 4.5 g, 6 g, and 7.5 g of finished composition produced according to Example 1bis

| Finished composition according to Example 1bis | Mean Cmax (μg/mL) (% CV) | Mean $AUC_{inf}$ (h*μg/mL) (% CV) | Mean $AUC_{8h}$ (h*μg/mL) (% CV) | Median $T_{max}$ (h) (min-max) | Mean $C_{8h}$ (μg/mL) (% CV) |
|---|---|---|---|---|---|
| 4.5 g | 44.35 (38) | 188.88 (47) | 174.68 (48) | 1.5 (0.5-4) | 6.86 (84) |
| 6 g | 65.46 (35) | 307.34 (48) | 290.97 (47) | 3 (0.5-5.5) | 12.8 (82) |
| 7.5 g | 88.21 (30) | 454.99 (34) | 404.88 (31) | 2 (0.5-6) | 30.94 (34) |

Figure 14:
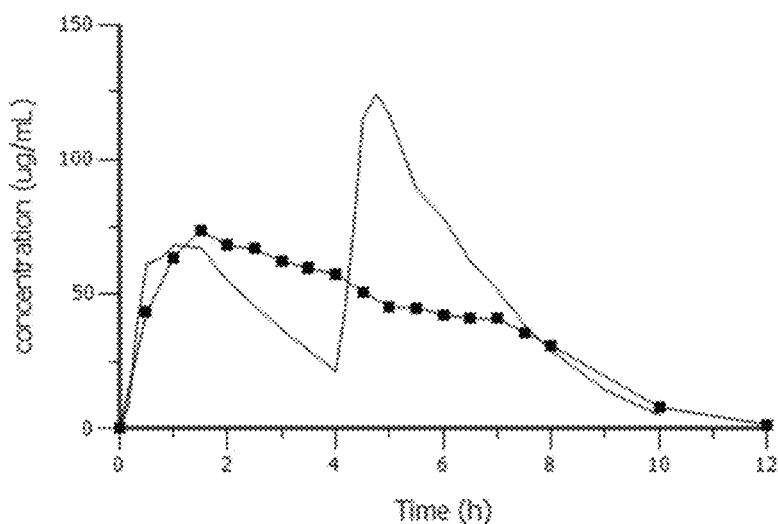
FIG. 14 plots the mean plasma gamma-hydroxybutyrate Concentrations (microgram/mL) of a Single dose of 7.5 g (■) of finished composition prepared according to Example 1bis compared to 2×4.5 g Xyrem® post-fed (Source NDA 21-196 review).

FIG. 14 and table 3d compare the pharmacokinetic parameters AUCinf and C8h obtained for 7.5 g of a finished composition according to Example 1bis to the same parameters calculated for 2×4.5 g, i.e. 9 g total dose of Xyrem®. The data show that a 7.5 g dose of a formulation according to the invention given once nightly exhibits a similar PK profile to 9 g of Xyrem® given in two separate equal doses.

TABLE 3d

Pharmacokinetic Parameters of 7.5 g of finished composition produced according to Example 1bis compared to 2 × 4.5 g of Xyrem ®

| | Mean $C_{8h}$ (ug/mL) | Mean $AUC_{inf}$ (ug/mL*h) | Ratio (%) $AUC_{inf}$ composition to $AUC_{inf}$ Xyrem ® | Ratio (%) $C_{8h}$ composition to $C_{8h}$ Xyrem ® |
|---|---|---|---|---|
| Xyrem ® 2 × 4.5 g | 28.9 | 518 | NA | NA |
| Finished composition according to Example 1bis 7.5 g | 30.9 | 455 | 88% | 107% |

Example 4. Alternative Formulation

Figure 15A:
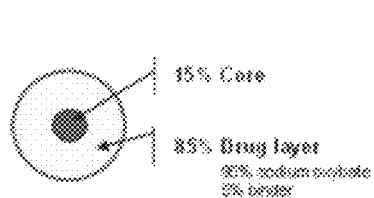
FIG. 15A depicts the qualitative and quantitative structure of the immediate release (IR) microparticles of gamma-hydroxybutyrate of Example 4.
Figure 15B:
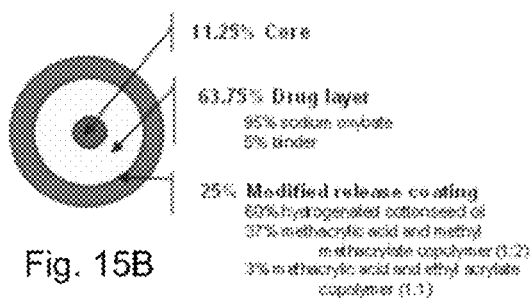
FIG. 15B depicts the qualitative and quantitative structure of the modified release (MR) microparticles of gamma-hydroxybutyrate of Example 4.

Tables 4a-4d provide the qualitative and quantitative compositions of IR microparticles, MR microparticles, and mixtures of IR and MR microparticles. The physical structure of the microparticles showing the qualitative and quantitative composition of the IR and MR microparticles is depicted in FIGS. 15A and 15B, respectively.

Briefly, sodium oxybate immediate release (IR) microparticle were prepared as follows: 1615.0 g of Sodium Oxybate and 85.0 g of polyvinylpyrrolidone (Povidone K30-Plasdone™ K29/32 from ISP) were solubilized in 1894.3 g of absolute ethyl alcohol and 1262.9 g of water. The solution was entirely sprayed onto 300 g of microcrystalline cellulose spheres (Cellets™ 127) in a fluid bed spray coater apparatus. IR microparticles with volume mean diameter of about 270 microns were obtained.

Sodium oxybate modified release (MR) microparticles were prepared as follows: 4.0 g of Methacrylic acid copolymer Type C (Eudragit™ L100-55), 49.3 g of Methacrylic acid copolymer Type B (Eudragit™ S100), 80 g of Hydrogenated cottonseed oil (Lubritab™), were dissolved in 1200.0 g of isopropanol at 78° C. The solution was sprayed entirely on 400.0 g of IR microparticles prepared above in a fluid bed spray coater apparatus with an inlet temperature 48° C., spraying rate around 11 g per min and atomization pressure 1.3 bar. MR microparticles were dried for two hours with inlet temperature set to 56° C. MR microparticles with volume mean diameter of about 330 microns were obtained.

The finished composition, which contained a 50:50 mixture of MR and IR microparticles calculated on their sodium oxybate content, was prepared as follows: 27.86 g of IR microparticles, 37.15 g of MR microparticles, 1.13 g of malic acid (D/L malic acid), 0.50 g of xanthan gum (Xantural™ 75 from Kelco), 0.75 g of carrageenan gum (Viscarin™ PH209 from FMC Biopolymer), 0.75 g of hydroxyethylcellulose (Natrosol™ 250M from Ashland) and 0.34 g of magnesium stearate were mixed. Individual samples of 6.85 g (corresponding to a 4.5 g sodium oxybate dose with half of the dose as immediate-release fraction and half of the dose as modified release fraction) were weighed.

TABLE 4a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |
| Ethyl alcohol | Solvent | Eliminated during processing |
| Purified water | Solvent | Eliminated during processing |
| Total | | 2.786 |

TABLE 4b

Composition of MR Microparticles

| Component | Function | Quantity per 2.25 g dose (g) |
|---|---|---|
| IR Microparticles | Core of MR Microparticles | 2.786 |
| Hydrogenated Vegetable Oil | Coating excipient | 0.557 |
| Methacrylic acid Copolymer Type C | Coating excipient | 0.028 |

TABLE 4b-continued

Composition of MR Microparticles

| Component | Function | Quantity per 2.25 g dose (g) |
|---|---|---|
| Methacrylic acid Copolymer Type B | Coating excipient | 0.344 |
| Isopropyl alcohol | Solvent | Eliminated during processing |
| Total | | 3.715 |

TABLE 4c

Qualitative Finished Composition

| Component | Function | Quantity per 4.5 g dose (g) |
|---|---|---|
| MR microparticles | Modified release fraction of sodium oxybate | 3.715 |
| IR microparticles | Immediate release fraction of sodium oxybate | 2.786 |
| Malic acid | Acidifying agent | 0.113 |
| Xanthan gum | Suspending agent | 0.050 |
| Hydroxy ethylcellulose | Suspending agent | 0.075 |
| Carrageenan gum | Suspending agent | 0.075 |
| Magnesium stearate | Lubricant | 0.034 |
| Total | | 6.848 |

TABLE 4d

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydrogenated Vegetable Oil | Coating excipient | 0.557 |
| Methacrylic acid Copolymer Type C | Coating excipient | 0.028 |
| Methacrylic acid Copolymer Type B | Coating excipient | 0.344 |
| Malic acid | Acidifying agent | 0.113 |
| Xanthan gum | Suspending agent | 0.050 |
| Hydroxy ethylcellulose | Suspending agent | 0.075 |
| Carrageenan gum | Suspending agent | 0.075 |
| Magnesium stearate | Lubricant | 0.034 |
| Total | | 6.848 |

Example 4Bis

An alternative formulation to example 4 is described in example 4bis. Sodium oxybate immediate release (IR) microparticles were prepared by coating the IR microparticles described in example 4 with a top coat layer. IR Microparticles were prepared as follows: 170.0 of hydroxypropyl cellulose (Klucel™ EF Pharm from Hercules) were solubilized in 4080.0 g of acetone. The solution was entirely sprayed onto 1530.0 g of the IR microparticles of Example 4 in a fluid bed spray coater apparatus. IR Microparticles with volume mean diameter of about 298 microns were obtained (see Table 4bis-a).

Sodium oxybate modified release (MR) microparticles were prepared as described in example 4 (see Table 4b).

The finished composition, which contains a 50:50 mixture of MR and IR microparticles calculated based on sodium oxybate content, was prepared as follows: 424.99 g of the above IR microparticles, 509.98 g of the above MR microparticles, 30.89 g of malic acid (D/L malic acid), 4.93 g of xanthan gum (Xantural™ 75 from Kelco), 4.93 g of colloidal silicon dioxide (Aerosil™ 200 from Degussa) and 9.86 g of magnesium stearate were mixed. Individual samples of 7.18 g (corresponding to a 4.5 g dose of sodium oxybate with half of the dose as an immediate-release fraction and half of the dose as a modified release fraction) were weighed. (see Tables 4bis-b and 4bis-c).

TABLE 4bis-a

Composition of IR Microparticles

| Component | Function | Quantity per 2.25 g dose (g) |
|---|---|---|
| Sodium oxybate | Drug substance | 2.25 |
| Microcrystalline cellulose spheres | Core | 0.418 |
| Povidone K30 | Binder and excipient in diffusion coating | 0.118 |
| Hydroxypropyl cellulose | Top coat | 0.310 |
| Ethyl alcohol | Solvent | Eliminated during processing |
| Purified water | Solvent | Eliminated during processing |
| Acetone | Solvent | Eliminated during processing |
| Total | | 3.096 |

TABLE 4bis-b

Qualitative Finished Composition

| Component | Function | Quantity per 4.5 g dose (g) |
|---|---|---|
| MR microparticles | Modified release fraction of sodium oxybate | 3.715 |
| IR microparticles | Immediate release fraction of sodium oxybate | 3.096 |
| Malic acid | Acidifying agent | 0.225 |
| Xanthan gum | Suspending agent | 0.036 |
| Colloidal silicon dioxide | Gliding agent | 0.036 |
| Magnesium stearate | Lubricant | 0.072 |
| Total | | 7.180 |

TABLE 4bis-c

Quantitative finished composition

| Component | Function | Quantity per 4.5 g dose (g) |
|---|---|---|
| Sodium oxybate | Drug substance | 4.5 |
| Microcrystalline cellulose spheres | Core | 0.836 |
| Povidone K30 | Binder | 0.237 |
| Hydroxypropyl cellulose | Top coat | 0.310 |
| Hydrogenated Vegetable Oil | Coating excipient | 0.557 |
| Methacrylic acid Copolymer Type C | Coating excipient | 0.028 |
| Methacrylic acid Copolymer Type B | Coating excipient | 0.344 |
| Malic acid | Acidifying agent | 0.225 |
| Xanthan gum | Suspending agent | 0.036 |
| Colloidal silicon dioxide | Gliding agent | 0.036 |
| Magnesium stearate | Lubricant | 0.072 |
| Total | | 7.180 |

Compared to the finished composition described in example 4, this alternative composition has the following characteristics: same MR microparticles, same IR microparticles but with a top coat, increased amount of malic acid, only one suspending agent (xanthan gum) and presence of a glidant.

Example 5 In Vitro Release Profiles of IR, MR and Finished Compositions of Formulation of Example 4 and 4Bis Dissolution Testing of MR Microparticles from Example 4—Protocol (2 h 0.1N HCl/Phosphate Buffer pH 6.8)

49.1 g of MR microparticles from Example 4 were mixed with 0.5 g of magnesium stearate (from Peter Greven) and 0.25 g of colloidal silicon dioxide (Aerosil™ 200 from Evonik).

The dissolution profile of 3770 mg of the mixture which correspond to 2250 mg of sodium oxybate per vessel was determined using the USP apparatus 2. Dissolution medium temperature was maintained at 37.0±0.5° C., and the rotating paddle speed was set at 75 rpm.

After 2 hours in 750 mL of 0.1N HCl dissolution medium, 6.5 g of monobasic potassium phosphate was added in the dissolution vessel. pH and volume were then respectively adjusted to 6.8 and 950 mL. The potassium phosphate concentration was equal to 0.05 M in the dissolution medium after pH and volume adjustment. The release profile is shown in FIG. 16 and Table 5a.

TABLE 5a

Percent Sodium Oxybate Released in two sequential dissolution media (0.1N HCl for two hours, then phosphate buffer pH 6.8) for MR microparticles of sodium oxybate prepared according to Example 4

| Time (h) | % sodium oxybate dissolved |
|---|---|
| 0 | 0 |
| 1 | 1 |
| 2 | 2 |
| 2,25 | 9 |
| 2,5 | 40 |
| 3 | 89 |
| 4 | 102 |
| 6 | 103 |

Figure 17:
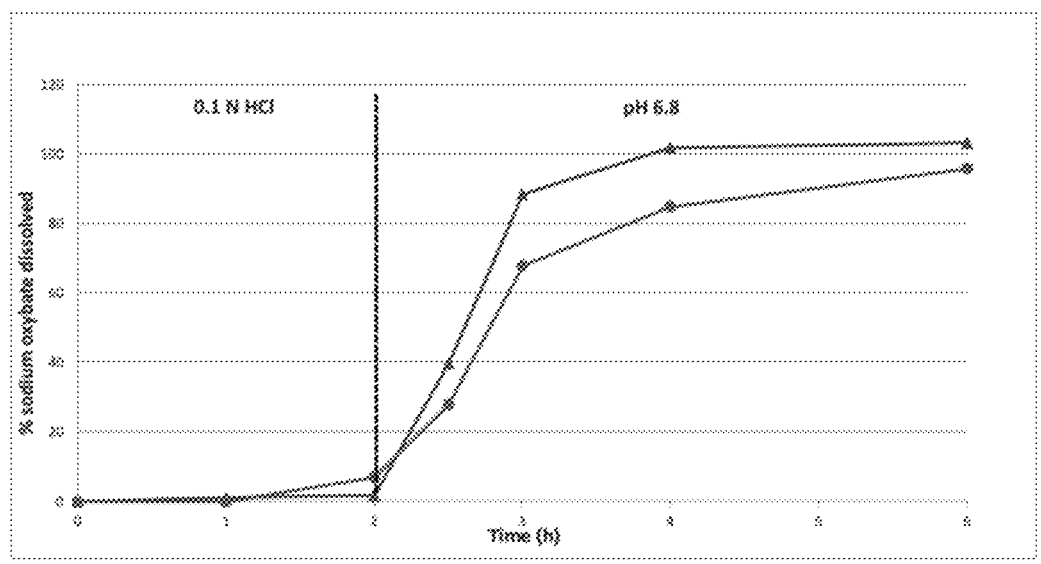
FIG. 17 plots a time release dissolution profile of MR microparticles (▲ symbols) of Example 4 in two sequential dissolution media (0.1 N HCl and phosphate buffer pH 6.8), overlaid against dissolution profile described in FIG. 3 of U.S. Pat. No. 8,193,211 (• symbols).

The sodium oxybate was not released in the 0.1N HCl medium during two hours. After the switch at pH 6.8, 40% of the API was released after 30 minutes and 90% of API after 1 hour. FIG. 17 overlays the dissolution profile of the MR microparticles of Example 4 with the dissolution profile for MR microparticles reported in Supernus U.S. Pat. No. 8,193,211, FIG. 3. It shows that the dissolution profiles are different and especially that the MR microparticles according to the invention release greater than 80% of its sodium oxybate at 3 hours, whereas the MR microparticles described in Supernus U.S. Pat. No. 8,193,211, FIG. 3 do not and exhibit a much slower releasing profile.

Figure 18:
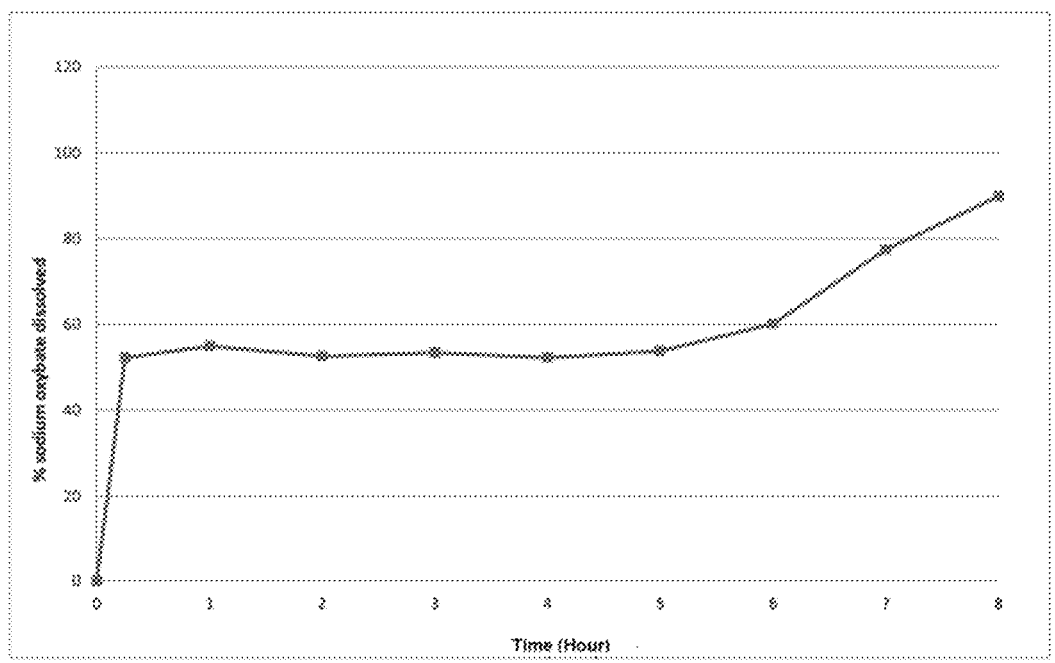
FIG. 18 plots a time release dissolution profile of the finished composition of Example 4 in deionized water.

Dissolution Testing of Finished Composition According to Example 4 in Deionized Water:

The dissolution profile of the quantity equivalent to 4.5 g of sodium oxybate of the finished composition of the Example 4 was determined in 900 mL of deionized water using the USP apparatus 2. The dissolution medium was maintained at 37.0±0.5° C. and the rotating paddle speed was set at 50 rpm. The release profile of is shown in FIG. 18 and Table 5b.

TABLE 5b

Percent Sodium Oxybate Released in deionized water for finished composition of sodium oxybate prepared according to Example 4

| Time (hour) | Example 4 |
|---|---|
| 0 | 0 |
| 0,25 | 52 |
| 1 | 55 |
| 2 | 53 |
| 3 | 54 |
| 4 | 52 |
| 5 | 54 |
| 6 | 60 |
| 7 | 78 |
| 8 | 90 |

The IR fraction of sodium oxybate was solubilized in 15 minutes. The release of sodium oxybate from the modified release fraction started after 5 hours with 90% of the total dose released at 8 hours.

Figure 19:
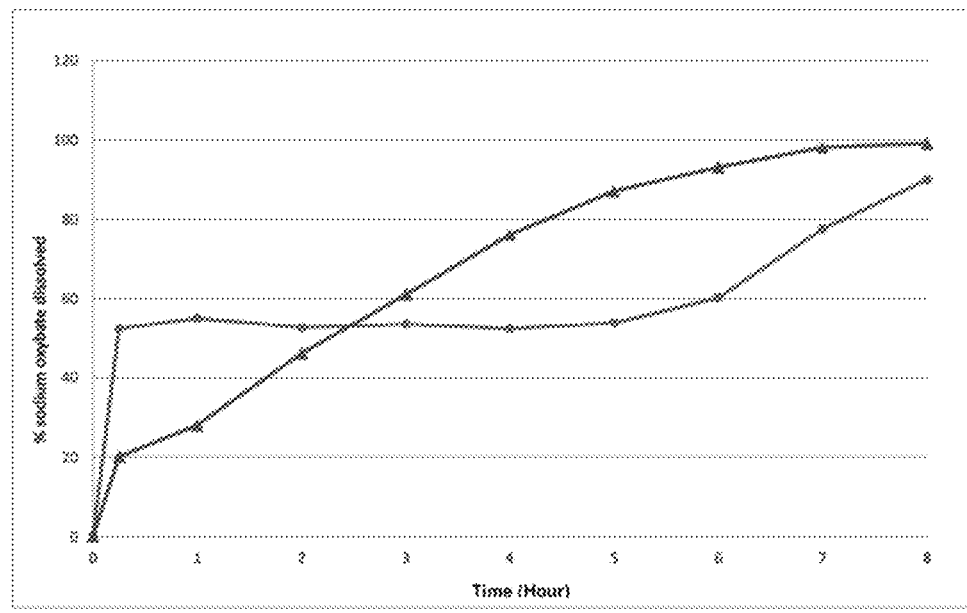
FIG. 19 plots a time release dissolution profile of the finished composition of Example 4 in deionized water (• symbols), overlaid against dissolution profile described in FIG. 2 of USP 2012/0076865 (▲ symbols).

An overlay of the release profile of the finished composition of the Example 4 versus that reported in USP 2012/0076865 FIG. 2 is shown in FIG. 19. It shows that the dissolution profiles are different. The formulation described in USP 2012/0076865 FIG. 2 does not exhibit a lag phase after the dissolution of the immediate release part.

FIG. 20 and Table 5c depict dissolution profiles determined using a USP apparatus 2 in a 900 mL in 0.1N HCl dissolution medium of three finished compositions prepared according to Example 4bis. The dissolution medium was maintained at 37.0±0.5° C. and the rotating paddle speed was fixed at 100 rpm. It shows that the composition according to the invention releases from 10 to 65% of its sodium oxybate at 1 and 3 hours and releases greater than 60% at 10 hours.

TABLE 5c

Percent Sodium Oxybate Released in 0.1 N HCl Dissolution Medium for three batches of finished composition prepared according to Example 4bis

| Time (Hour) | Batch 1 | Batch 2 | Batch 3 |
|---|---|---|---|
| 0 | 0 | 0 | 0 |
| 0,25 | 50 | Nd | Nd |
| 0,5 | 51 | 50 | 49 |
| 0,75 | 51 | Nd | Nd |
| 1 | 51 | 51 | 51 |
| 1,5 | 51 | Nd | Nd |
| 2 | 51 | Nd | Nd |
| 3 | 51 | 52 | 53 |
| 4 | 51 | Nd | Nd |
| 6 | 55 | 57 | 57 |
| 8 | 74 | 70 | 71 |
| 10 | 89 | Nd | Nd |
| 12 | 93 | 90 | 92 |
| 16 | 94 | 95 | 97 |

NTA = not determined

FIG. 21 and Table 5d depict dissolution profile determined using a USP apparatus 2 in a 900 mL phosphate buffer pH 6.8 dissolution medium for a finished composition prepared according to Example 4bis. The dissolution medium was maintained at 37.0±0.5° C. and the rotating paddle speed was set at 100 rpm. It shows that the composition according to the invention releases more than 80% of its sodium oxybate at 3 hours.

TABLE 5d

Percent Sodium Oxybate Released in phosphate buffer pH 6.8 Dissolution Medium for finished composition prepared according to Example 4bis

| Time (Hour) | Example 4bis |
| --- | --- |
| 0 | 0 |
| 0.25 | 54 |
| 0.5 | 54 |
| 0.75 | 55 |
| 1.0 | 56 |
| 1.5 | 63 |
| 2 | 77 |
| 3 | 103 |
| 4 | 105 |
| 6 | 105 |
| 8 | 102 |
| 10 | 101 |
| 12 | 104 |
| 16 | 100 |

Example 6. In Vivo Pharmacokinetic Study of Finished Composition According to Example 4Bis Pharmacokinetic testing was undertaken in vivo in healthy human volunteers according to the principles described in FDA's March 2003 Guidance for Industry on BIOAVAILABILITY AND BIOEQUIVALENCE STUDIES FOR ORALLY ADMINISTERED DRUG PRODUCTS—GENERAL CONSIDERATIONS. All testing was performed in subjects two hours after eating a standardized dinner. Xyrem® doses were administered in two equipotent doses four hours apart. All other tested doses were manufactured as described in Example 4bis. The standardized dinner consisted of 25.5% fat, 19.6% protein, and 54.9% carbohydrates.

The finished composition of Example 4bis given as a 4.5 g once-nightly dose rather than a standard Xyrem® dosing twice (2×2.25 g) nightly 4 hours apart, produced a dramatically different pharmacokinetic profile than Xyrem® as shown in FIG. 22. As summarized below (Tables 6a and 6b), 4.5 g nighttime doses of finished composition of the invention equivalent to twice-nightly doses of Xyrem® (2×2.25 g) provided somewhat less total exposure to sodium oxybate with a later median Tmax than the initial Xyrem® dose. The relative bioavailability was about 88%. Composition according to the invention avoids the high second-dose peak concentration of Xyrem® and therefore does not exhibit the substantial between-dose fluctuations in concentration, while achieving a comparable mean C8h.

TABLE 6a

Pharmacokinetic Parameters of finished composition of Example 4bis vs. Xyrem ®

| | Mean $C_{max}$ (µg/mL) (% CV) | Mean $AUC_{inf}$ (h * µg/mL) (% CV) | Mean $AUC_{8h}$ (h * µg/mL) (% CV) | Median $T_{max}$ (hour) (min-max) | Mean $C_{8h}$ (µg/mL)( % CV) |
| --- | --- | --- | --- | --- | --- |
| Finished composition of Example 4bis 4.5 g | 43.47 (49) | 188.96 (57) | 179.69 (57) | 2 (0.5-7) | 6.85 (118) |
| Xyrem ® 2 × 2.25 g | 1st dose: 33.41 (41) 2nd dose: 65.91 (40) | 214.32 (48) | 202.78 (46) | 1st dose: 1.0 (0.5-2) 2nd dose: 4.5 (4.33-6.5) | 9.24 (127) |

TABLE 6b

Mean plasma concentration of gamma-hydroxybutyrate (microgram/mL) versus time of finished composition of Example 4bis and Xyrem ®

| Time (hour) | Finished composition Example 4bis 4.5 g (2 h after meal) (N = 15) | Xyrem ® (2 × 2.25 g) (N = 15) |
| --- | --- | --- |
| 0 | 0.00 | 0.00 |
| 0.5 | 23.80 | 27.44 |
| 1 | 33.26 | 28.97 |
| 1.5 | 35.60 | 26.12 |
| 2 | 35.57 | 21.11 |
| 2.5 | 33.81 | 13.93 |
| 3 | 30.96 | 10.25 |
| 3.5 | 28.73 | 6.92 |
| 4 | 26.06 | 42.32 |
| 4.5 | 23.27 | 57.33 |
| 5 | 18.68 | 52.27 |
| 5.5 | 16.67 | 43.55 |
| 6 | 15.55 | 35.20 |
| 6.5 | 13.07 | 27.44 |
| 7 | 11.75 | 19.36 |
| 7.5 | 9.20 | 13.88 |
| 8 | 6.85 | 9.24 |
| 10 | 1.94 | 2.64 |
| 12 | NC | NC |

NC: Not Calculated

The 4.5 g dose achieved a mean C8h equal to about 6.85 microgram/mL which represents approximately 74.1% of the C8h obtained for Xyrem® dosed 2×2.25 g. The ratio of AUC8h to AUCinf was about 0.89.

Figure 23A:
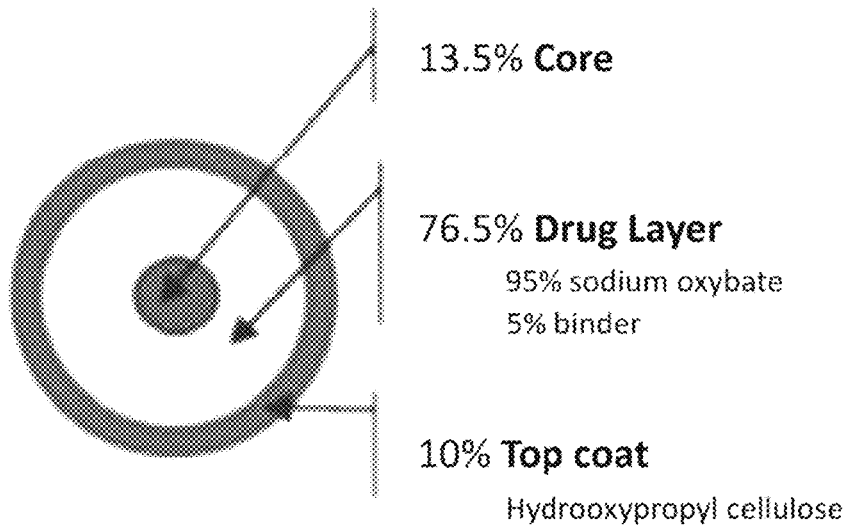
FIG. 23A depicts the qualitative and quantitative structure of the immediate release (IR) microparticles of gamma-hydroxybutyrate of Example 7.
Figure 23B:
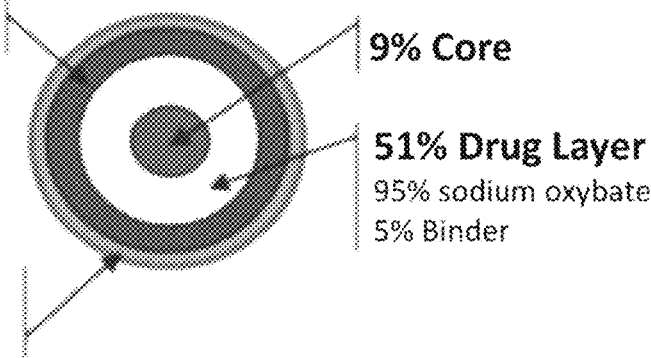
FIG. 23B depicts the qualitative and quantitative structure of the modified release (MR) microparticles of gamma-hydroxybutyrate of Example 7.

Example 7. In Vitro and In Vivo Pharmacokinetic Study of a Comparative Formulation A formulation having an in vitro dissolution profile comparable to the formulation reported in FIG. 3 of U.S. Pat. No. 8,193,211 was prepared to confirm the in vitro/in vivo correlations reported herein. Tables 7a-7c provide the qualitative and quantitative compositions of the MR microparticles, and mixtures of IR and MR microparticles. The physical structure of the microparticles showing the qualitative and quantitative composition of the IR and MR microparticles is depicted in FIGS. 23A and 23B, respectively.

Briefly, sodium oxybate immediate release (IR) microparticles were prepared according to Example 1bis. Sodium oxybate modified release (MR) microparticles were prepared in two steps:

Step 1: 106.7 g of water insoluble polymer Ethylcellulose (Ethocel™ 20 Premium), 10.7 g of polyvinylpyrrolidone (Plasdone™ K30 from ISP), 10.7 g of castor oil (from Olvea) and 5.3 g of Polyoxyl 40 Hydrogenated Castor Oil (Kolliphor RH40 from BASF), were dissolved in a mixture of 828.0 g of acetone, 552.0 g of isopropanol and 153.3 g of water. The solution was sprayed entirely on 400.0 g of immediate release microparticles of sodium oxybate prepared above in a fluid bed spray coater apparatus Glatt G.P.C.G.1.1 with inlet temperature 57° C., spraying rate around 14.5 g per min and atomization pressure 2.5 bar. Microparticles with volume mean diameter of about 310 microns were obtained.

Step 2: 15.0 g of Methacrylic acid copolymer Type C (Eudragit™ L100-55 from Evonik), 30.0 g of Methacrylic acid copolymer Type B (Eudragit™ S100 from Evonik), 67.5 g of Hydrogenated cottonseed oil (Lubritab™), were dissolved in 1012.5 g of isopropanol at 78° C. The solution was sprayed entirely on 450.0 g of the above prepared microparticles in a fluid bed spray coater apparatus with an inlet temperature 47° C., spraying rate around 10.5 g per min and atomization pressure 1.3 bar. MR microparticles were dried for two hours with inlet temperature set to 56° C. MR Microparticles with volume mean diameter of 335 microns were obtained.

The finished composition, which contains a 60:40 mixture of MR and IR microparticles calculated based on their sodium oxybate content, was prepared as follows: 326.69 g of the above IR microparticles, 735.04 g of the above MR microparticles, 23.74 g of malic acid (D/L malic acid), 5.54 g of xanthan gum (Xantural™ 75 from Kelco), 5.54 g of colloidal silicon dioxide (Aerosil™ 200 from Degussa) and 11.08 g of magnesium stearate were mixed. Individual samples of 8.40 g (corresponding to a 4.5 g dose of sodium oxybate with 40% of the dose as immediate-release fraction and 60% of the dose as modified release fraction) were weighed.

TABLE 7a

Composition of MR Microparticles

| Component | Function | Quantity per 2.25 g dose (g) |
| --- | --- | --- |
| IR Microparticles | Core of MR Microparticles | 2.786 |
| Ethylcellulose 20 | Coating excipient | 0.743 |
| Povidone K30 | Coating excipient | 0.074 |
| Polyoxyl 40 Hydrogenated Castor Oil | Coating excipient | 0.037 |
| Castor oil | Coating excipient | 0.074 |
| Hydrogenated Vegetable Oil | Coating excipient | 0.557 |
| Methacrylic acid Copolymer Type C | Coating excipient | 0.124 |
| Methacrylic acid Copolymer Type B | Coating excipient | 0.248 |
| Ethyl alcohol | Solvent | Eliminated during processing |
| Acetone | Solvent | Eliminated during processing |
| Water | Solvent | Eliminated during processing |
| Isopropyl alcohol | Solvent | Eliminated during processing |
| Total | | 4.644 |

TABLE 7b

Qualitative Composition of Finished Composition

| Component | Function | Quantity per 4.5 g dose (g) |
| --- | --- | --- |
| MR microparticles | Modified release fraction of sodium oxybate | 5.573 |
| IR microparticles | Immediate release fraction of sodium oxybate | 2.477 |
| Malic acid | Acidifying agent | 0.180 |
| Xanthan gum | Suspending agent | 0.042 |
| Colloidal silicon dioxide | Gliding agent | 0.042 |
| Magnesium stearate | Lubricant | 0.084 |
| Total | | 8.398 |

TABLE 7c

Quantitative Composition of Finished Composition

| Component | Function | Quantity per 4.5 g dose (g) |
| --- | --- | --- |
| Sodium oxybate | Drug substance | 4.5 |
| Microcrystalline cellulose spheres | Core | 0.836 |
| Povidone K30 | der and coating excipient | 0.326 |
| Hydroxypropyl cellulose | Top coat | 0.248 |
| Ethylcellulose 20 | Coating excipient | 0.892 |
| Polyoxyl 40 Hydrogenated Castor Oil | Coating excipient | 0.045 |
| Castor oil | Coating excipient | 0.089 |
| Hydrogenated Vegetable Oil | Coating excipient | 0.669 |
| Methacrylic acid Copolymer Type C | Coating excipient | 0.149 |
| Methacrylic acid Copolymer Type B | Coating excipient | 0.297 |
| Malic acid | Acidifying agent | 0.180 |
| Xanthan gum | Suspending agent | 0.042 |
| Colloidal silicon dioxide | Gliding agent | 0.042 |
| Magnesium stearate | Lubricant | 0.084 |
| Total | | 8.398 |

Figure 24:
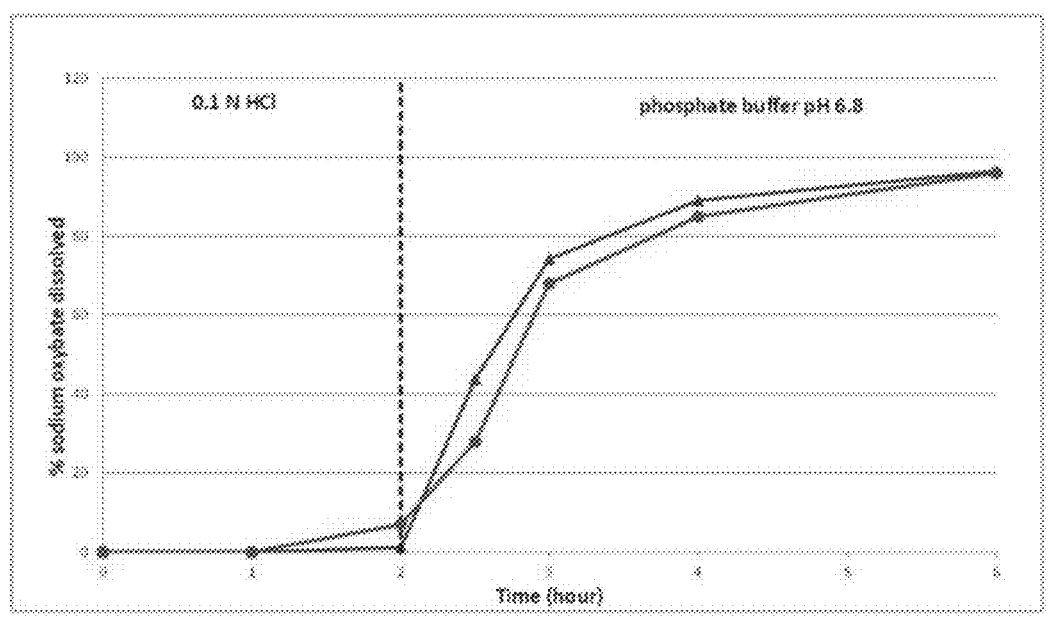
FIG. 24 plots a time release dissolution profile of MR microparticles of gamma-hydroxybutyrate of Example 7 (▲ symbols) in two sequential dissolution media (0.1 N HCl and phosphate buffer pH 6.8), overlaid against dissolution profile described in FIG. 3 of U.S. Pat. No. 8,193,211 (• symbols).

The dissolution profile obtained for the MR microparticles in two sequential dissolution media (0.1N HCl for 2 hours then phosphate buffer pH 6.8) is shown in FIG. 24 and Table 7d. These data show that the dissolution profile of the MR microparticles produced according the comparative Example 7 was quite similar to the dissolution profile of FIG. 3 from U.S. Pat. No. 8,193,211. In particular, the MR microparticles according to the comparative Example 7 do not release more than 80% of its sodium oxybate at 3 hours.

TABLE 7d

Dissolution profile obtained for the MR microparticles of Example 7 in two sequential dissolution media (0.1N HCl for 2 hours then phosphate buffer pH 6.8)

| Time (hour) | Example 7 |
| --- | --- |
| 0 | 0 |
| 1 | 0 |
| 2 | 1 |
| 2.25 | 5 |
| 2.5 | 44 |
| 3 | 74 |
| 64 | 89 |
| 6 | 96 |

The finished composition of Comparative Example 7 was tested in the same pharmacokinetic study than the finished composition of Example 1 and 4. As summarized below (Tables 7e), 4.5 g nighttime dose of finished composition of the comparative Example 7 compared to twice-nightly doses of Xyrem® (2×2.25 g) provided much less total exposure to sodium oxybate with a relative bioavailability of 67%.

TABLE 7e

Pharmacokinetic Parameters of finished composition of Comparative Example 7 vs. Xyrem ®

| | Mean $C_{max}$ (μg/mL) (% CV) | Mean $AUC_{inf}$ (h * μg/mL) (% CV) | Median $T_{max}$ (hour) (min-max) | Mean $C_{8h}$ (μg/mL) (% CV) |
|---|---|---|---|---|
| Finished composition of Comparative Example 7 4.5 g | 28.99 (45) | 143.90 (53) | 1.5 (0.5-8) | 7.79 (82) |
| Xyrem ® 2 × 2.25 g | 1st dose: 33.41 (41) 2nd dose: 65.91 (40) | 214.32 (48) | 1st dose: 1.0 (0.5-2) 2nd dose: 4.5 (4.33-6.5) | 9.24 (127) |

TABLE 7f

Mean plasma concentration (microgram/mL) of gamma-hydroxybutyrate versus time of finished composition of Comparative Example 7 and Xyrem ®

| Time (hour) | Comparative Example 7 @ 4.5 g (2 h after meal) pooled mean (N = 27) | Comparative Example 7 @ 6.0 g (2 h after meal) pooled mean (N = 18) | Comparative Example 7 @ 7.5 g (2 h after meal) (N = 12) | Xyrem ® (2 × 2.25 g) part I (N = 15) |
|---|---|---|---|---|
| 0 | 0.00 | 0.00 | 0.00 | 0.00 |
| 0.5 | 18.84 | 25.54 | 31.40 | 27.44 |
| 1 | 23.93 | 35.80 | 46.78 | 28.97 |
| 1.5 | 24.31 | 38.59 | 58.29 | 26.12 |
| 2 | 24.32 | 40.78 | 57.47 | 21.11 |
| 2.5 | 23.10 | 38.03 | 52.25 | 13.93 |
| 3 | 20.05 | 35.76 | 49.00 | 10.25 |
| 3.5 | 17.47 | 33.99 | 45.66 | 6.92 |
| 4 | 16.48 | 30.47 | 40.52 | 0.00 |
| 4.5 | 15.44 | 26.87 | 37.70 | 57.33 |
| 5 | 14.10 | 25.59 | 36.82 | 52.27 |
| 5.5 | 12.60 | 24.63 | 35.93 | 43.55 |
| 6 | 11.68 | 23.90 | 34.47 | 35.20 |
| 6.5 | 11.45 | 23.98 | 31.60 | 27.44 |
| 7 | 10.64 | 20.94 | 31.89 | 19.36 |
| 7.5 | 9.35 | 17.93 | 29.69 | 13.88 |
| 8 | 7.79 | 14.36 | 25.80 | 9.24 |
| 10 | 1.98 | 3.71 | 11.00 | 2.64 |
| 12 | 0.59 | 0.78 | 3.63 | NC |

NC: not calculated

The pharmacokinetic profiles of single 6 g and 7.5 g doses of the finished composition produced according to comparative Example 7 were also generated. Table 7g provides data on a single 4.5 g, 6 g and 7.5 g dose, showing effects on Cmax, C8h, AUC8h and AUCinf related to dose strength.

TABLE 7g

Pharmacokinetic Parameters of 4.5 g, 6 g, and 7.5 g of finished composition produced according Comparative Example 7

| Finished composition Comparative of Example 7 | Mean $C_{max}$ (μg/mL) (% CV) | Mean $AUC_{inf}$ (h* μg/mL) (% CV) | Mean $AUC_{8h}$ (h * μg/mL) (% CV) | Median $T_{max}$ (min-max) (h) (% CV) | Mean $C_{8h}$ (μg/mL) (% CV) |
|---|---|---|---|---|---|
| 4.5 g | 28.98 (45) | 143.90 (53) | 128.83 (55) | 1.5 (0.5-8) | 7.79 (82) |
| 6 g | 45.64 (35) | 248.24 (47) | 225.00 (47) | 2 (0.5-6.5) | 14.36 (77) |
| 7.5 g | 63.31 (33) | 379.83 (54) | 316.18 (48) | 1.75 (1-4.5) | 25.80 (74) |

Example 8. Alternative Formulations

Example 8.1: Modified Release Formulation of Gamma-Hydroxybutyrate Comprising Immediate Release Microparticles of Potassium Salt of Gamma-Hydroxybutyric Acid and Modified Release Microparticles of Sodium Salt of Gamma-Hydroxybutyric Acid (Sodium Oxybate)

Immediate release (IR) microparticles of potassium salt of gamma-hydroxybutyric acid may be prepared as follows: 1615.0 g of potassium salt of gamma-hydroxybutyric acid and 85.0 g of polyvinylpyrrolidone (Povidone K30-Plasdone™ K29/32 from ISP) are solubilized in 1894.3 g of absolute ethyl alcohol and 1262.9 g of water. The solution is entirely sprayed onto 300 g of microcrystalline cellulose spheres (Cellets™ 127) in a fluid bed spray coater apparatus.

Immediate release (IR) microparticles of sodium salt of gamma-hydroxybutyric acid were prepared as follows: 1615.0 g of sodium salt of gamma-hydroxybutyric acid and 85.0 g of polyvinylpyrrolidone (Povidone K30—Plasdone K29/32 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans Sanaq) in a fluid bed spray coater apparatus.

Sodium oxybate modified release (MR) microparticles are prepared as follows: 22.8 g of methacrylic acid copolymer Type C (Eudragit™ L100-55), 45.8 g of methacrylic acid copolymer Type B (Eudragit™ S100), 102.9 g of hydrogenated cottonseed oil (Lubritab™), are dissolved in 1542.9 g of isopropanol at 78° C. The solution is sprayed entirely onto 400.0 g of the sodium oxybate IR microparticles described above in a fluid bed spray coater apparatus with an inlet temperature of 48° C., spraying rate around 11 g per min and atomization pressure of 1.3 bar. MR microparticles are dried for two hours with inlet temperature set to 56° C. MR microparticles with mean volume diameter of about 320 microns were obtained.

The finished formulation, which contains a 50:50 mixture of MR and IR microparticles calculated on their gamma-hydroxybutyrate content, may be prepared as follows: 398.51 g of the above IR microparticles, 504.80 g of the above MR microparticles, 16.09 g of D/L malic acid, 6.34 g of xanthan gum (Xantural™ 75 from Kelco), 9.51 g of carrageenan gum (Viscarin™ PH209 from FMC Biopolymer), 9.51 g of hydroxyethylcellulose (Natrosol™ 250M from Ashland) and 4.75 g of magnesium stearate were mixed. Individual samples of 7.49 g of the mixture (amount equivalent to a 4.5 g dose of sodium oxybate with half of the dose as immediate-release fraction and half of the dose as modified release fraction) were weighed.

TABLE 8a

Composition of IR Microparticles of gamma-hydroxybutyrate of example 8.1

| Component | Function | Quantity per 2.25 g dose (g) |
| --- | --- | --- |
| Potassium salt of hydroxybutyric acid | Drug substance | 2.537 |
| Microcrystalline cellulose spheres | Core | 0.471 |
| Povidone K30 | Binder and excipient in diffusion coating | 0.134 |
| Ethyl alcohol | Solvent | Eliminated during processing |
| Purified water | Solvent | Eliminated during processing |
| Total | | 3.142 |

TABLE 8b

Composition of MR Microparticles of gamma-hydroxybutyrate of example 8.1

| Component | Function | Quantity per 2.25 g dose (g) |
| --- | --- | --- |
| Sodium oxybate | Drug substance | 2.25 |
| Povidone K30 | Binder | 0.118 |
| Microcrystalline cellulose spheres | Core | 0.419 |
| Hydrogenated Vegetable Oil | Coating excipient | 0.717 |
| Methacrylic acid Copolymer Type C | Coating excipient | 0.159 |
| Methacrylic acid Copolymer Type B | Coating excipient | 0.318 |
| Ethyl alcohol | Solvent | Eliminated during processing |
| Acetone | Solvent | Eliminated during processing |

TABLE 8b-continued

Composition of MR Microparticles of gamma-hydroxybutyrate of example 8.1

| Component | Function | Quantity per 2.25 g dose (g) |
| --- | --- | --- |
| Water | Solvent | Eliminated during processing |
| Isopropyl alcohol | Solvent | Eliminated during processing |
| Total | | 3.981 |

TABLE 8c

Qualitative Composition of Finished Formulation of Example 8.1

| Component | Function | Quantity per 4.5 g dose (g) |
| --- | --- | --- |
| MR microparticles | Modified release fraction of sodium oxybate | 3.981 |
| IR microparticles | Immediate release fraction of potassium salt of gamma-hydroxybutyric acid | 3.142 |
| Malic acid | Acidifying agent | 0.127 |
| Xanthan gum | Suspending agent | 0.050 |
| Hydroxy ethylcellulose | Suspending agent | 0.075 |
| Carrageenan gum | Suspending agent | 0.075 |
| Magnesium stearate | Lubricant | 0.037 |
| Total | | 7.487 |

TABLE 8d

Quantitative Composition of Finished Formulation of Example 8.1

| Component | Function | Quantity per 4.5 g dose (g) |
| --- | --- | --- |
| Sodium oxybate | Drug substance | 2.25 |
| Potassium salt of gamma-hydroxybutyric acid | Drug substance | 2.537 |
| Microcrystalline cellulose spheres | Core | 0.890 |
| Povidone K30 | Binder | 0.252 |
| Hydrogenated Vegetable Oil | Coating excipient | 0.717 |
| Methacrylic acid Copolymer Type C | Coating excipient | 0.159 |
| Methacrylic acid Copolymer Type B | Coating excipient | 0.318 |
| Malic acid | Acidifying agent | 0.127 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.037 |
| Total | | 7.487 |

Example 8.2: Modified Release Formulation of Gamma-Hydroxybutyrate Comprising Immediate Release Microparticles of Potassium Salt of Gamma-Hydroxybutyric Acid, Immediate Release Microparticles of Magnesium Salt of Gamma-Hydroxybutyric Acid, Immediate Release Microparticles of Calcium Salt of Gamma-Hydroxybutyric Acid and Modified Release Microparticles of Sodium Salt of Gamma-Hydroxybutyric Acid (Sodium Oxybate)

Immediate release (IR) microparticles of potassium salt of gamma-hydroxybutyric acid are prepared according to example 8.1.

Immediate release (IR) microparticles of magnesium salt of gamma-hydroxybutyric acid or calcium salt of gamma-hydroxybutyric acid may be prepared using the same manufacturing process by replacing the potassium salt of gamma-hydroxybutyric acid by the same weight of respectively magnesium salt of gamma-hydroxybutyric acid or calcium salt of gamma-hydroxybutyric acid.

Sodium oxybate modified release (MR) microparticles are prepared according to example 8.1.

The finished formulation, which contains a 50:50 mixture of MR and IR microparticles calculated on their gamma-hydroxybutyrate content, may be prepared as follows. 132.84 g of the IR microparticles of potassium salt of gamma-hydroxybutyric acid, 215.32 g of the IR microparticles of magnesium salt of gamma-hydroxybutyric acid, 230.05 g of the IR microparticles of calcium salt of gamma-hydroxybutyric acid, 504.80 g of the MR microparticles of sodium oxybate, 23.35 g of D/L malic acid, 6.34 g of xanthan gum (Xantural™ 75 from Kelco), 9.51 g of carrageenan gum (Viscarin™ PH209 from FMC Biopolymer), 9.51 g of hydroxyethylcellulose (Natrosol™ 250M from Ashland) and 5.69 g of magnesium stearate were mixed. Individual samples of 8.96 g of the mixture (amount equivalent to a 4.5 g dose of sodium oxybate with half of the dose as immediate-release fraction and half of the dose as modified release fraction) were weighed.

TABLE 8e

Qualitative Composition of Finished Formulation of Example 8.2

| Component | Function | Quantity per 4.5 g dose (g) |
| --- | --- | --- |
| MR microparticles | Modified release fraction of sodium oxybate | 3.981 |
| IR microparticles | Immediate release fraction of potassium salt of gamma-hydroxybutyric acid + immediate release fraction of magnesium salt of gamma-hydroxybutyric acid + immediate release fraction of calcium salt of gamma-hydroxybutyric acid | 4.559 |
| Malic acid | Acidifying agent | 0.184 |
| Xanthan gum | Suspending agent | 0.050 |
| Hydroxy-ethylcellulose | Suspending agent | 0.075 |
| Carrageenan gum | Suspending agent | 0.075 |
| Magnesium stearate | Lubricant | 0.045 |
| Total | | 8.97 |

TABLE 8f

Quantitative Composition of Finished Formulation of Example 8.2

| Component | Function | Quantity per 4.5 g dose (g) |
| --- | --- | --- |
| Sodium oxybate | Drug substance | 2.25 |
| Potassium salt of gamma-hydroxybutyric acid | Drug substance | 0.84 |
| Magnesium salt of gamma-hydroxybutyric acid | Drug substance | 1.37 |
| Calcium salt of gamma-hydroxybutyric acid | Drug substance | 1.46 |
| Microcrystalline cellulose spheres | Core | 1.102 |
| Povidone K30 | Binder | 0.312 |
| Hydrogenated Vegetable Oil | Coating excipient | 0.717 |
| Methacrylic acid Copolymer Type C | Coating excipient | 0.159 |
| Methacrylic acid Copolymer Type B | Coating excipient | 0.318 |
| Malic acid | Acidifying agent | 0.184 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.045 |
| Total | | 8.96 |

Example 8.3: Modified Release Formulation of Gamma-Hydroxybutyrate Comprising Immediate Release Microparticles of Potassium Salt of Gamma-Hydroxybutyric Acid and Modified Release Microparticles of Calcium Salt of Gamma-Hydroxybutyric Acid Immediate release (IR) microparticles of potassium salt of gamma-hydroxybutyric acid are prepared according to example 8.1.

Immediate release (IR) microparticles of calcium salt of gamma-hydroxybutyric acid may be prepared using the manufacturing process described in example 8.1 for immediate release (IR) microparticles of potassium salt of gamma-hydroxybutyric acid by replacing the potassium salt of gamma-hydroxybutyric acid by the same weight of calcium salt of gamma-hydroxybutyric acid. These Immediate release (IR) microparticles of calcium salt of gamma-hydroxybutyric acid are used to manufacture modified release (MR) microparticles of calcium salt of gamma-hydroxybutyric acid as follows: 22.8 g of methacrylic acid copolymer Type C (Eudragit™ L100-55), 45.8 g of methacrylic acid copolymer Type B (Eudragit™ S100), 102.9 g of hydrogenated cottonseed oil (Lubritab™), are dissolved in 1542.9 g of isopropanol at 78° C. The solution is sprayed entirely onto 400.0 g of the immediate release microparticles of calcium salt of gamma-hydroxybutyric acid described above in a fluid bed spray coater apparatus with an inlet temperature of 48° C., spraying rate around 11 g per min and atomization pressure of 1.3 bar. MR microparticles are dried for two hours with inlet temperature set to 56° C.

The finished formulation, which contains a 50:50 mixture of MR and IR microparticles calculated on their gamma-hydroxybutyrate content, may be prepared as follows: 398.53 g of the IR microparticles of potassium salt of gamma-hydroxybutyric acid, 492.87 g of the MR microparticles of sodium oxybate, 16.10 g of D/L malic acid, 6.34 g of xanthan gum (Xantural™ 75 from Kelco), 9.51 g of carrageenan gum (Viscarin™ PH209 from FMC Biopolymer), 9.51 g of hydroxyethylcellulose (Natrosol™ 250M from Ashland) and 4.69 g of magnesium stearate were mixed. Individual samples of 7.39 g of the mixture (amount equivalent to a 4.5 g dose of sodium oxybate with half of the dose as immediate-release fraction and half of the dose as modified release fraction) were weighed.

TABLE 8g

Qualitative Composition of Finished Formulation of Example 8.3

| Component | Function | Quantity per 4.5 g dose (g) |
|---|---|---|
| MR microparticles | Modified release fraction of calcium salt of gamma-hydroxybutyric acid | 3.887 |
| IR microparticles | Immediate release fraction of potassium salt of gamma-hydroxybutyric acid | 3.143 |
| Malic acid | Acidifying agent | 0.127 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.037 |
| Total | | 7.39 |

TABLE 8h

Quantitative Composition of Finished Formulation of Example 8.3

| Component | Function | Quantity per 4.5 g dose (g) |
|---|---|---|
| Potassium salt of gamma-hydroxybutyric acid | Drug substance | 2.54 |
| Calcium salt of gamma-hydroxybutyric acid | Drug substance | 2.19 |
| Microcrystalline cellulose spheres | Core | 0.880 |
| Povidone K30 | Binder | 0.249 |
| Hydrogenated Vegetable Oil | Coating excipient | 0.700 |
| Methacrylic acid Copolymer Type C | Coating excipient | 0.155 |
| Methacrylic acid Copolymer Type B | Coating excipient | 0.311 |
| Malic acid | Acidifying agent | 0.127 |
| Xanthan gum | Suspending agent | 0.050 |

TABLE 8h-continued

Quantitative Composition of Finished Formulation of Example 8.3

| Component | Function | Quantity per 4.5 g dose (g) |
|---|---|---|
| Hydroxyethylcellulose | Suspending agent | 0.075 |
| Carrageenan gum | Suspending agent | 0.075 |
| Magnesium stearate | Lubricant | 0.037 |
| Total | | 7.39 |

Example 9: Alternative Formulations with Differing Concentrations of Acidic Agents Different prototypes were developed to evaluate the effect of acidic agent on the dissolution stability of the formulation dispersed in water. Experimental data with 0.8%, 1.6% and 15% malic acid are detailed below.

Example 9.1: 1.6% Malic Acid

IR particles were prepared as follows: 1615.0 g of Sodium Oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 268 microns were obtained.

MR coated particles were prepared as follows: 39.9 g of Methacrylic acid copolymer Type C (Eudragit™ L100-55 from Evonik), 80.1 g of Methacrylic acid copolymer Type B (Eudragit™ S100 from Evonik), 180.0 g of Hydrogenated cottonseed oil (Lubritab™ from JRS), were dissolved in 2700.0 g of isopropanol at 78° C. The solution was sprayed entirely on 700.0 g of IR particles in a fluid bed spray coater apparatus Glatt™ G.P.C.G.1.1 with inlet temperature 49° C., spraying rate around 11.6 g per min and atomization pressure 1.6 bar. MR microparticles were dried for 2 hours with inlet temperature set to 56° C. Sodium oxybate MR coated particles with mean diameter of 324 microns were obtained.

The finished composition, which contains a 50:50 mixture of MR and IR particles calculated on their sodium oxybate content, was prepared as follows: 655.1 g of the above IR particles, 936.4 g of the above MR particles, 26.5 g of Malic acid (D/L malic acid regular from Bartek), 11.7 g of xanthan gum (Xantural™ 75 from CP Kelco), 17.6 g of carrageenan gum (Viscarin™ PH209 from FMC Biopolymer), 17.6 g of hydroxyethylcellulose (Natrosol™ 250M from Ashland) and 8.2 g of magnesium stearate (from Peter Greven) were mixed in a Roue-Roehn mixer. Individual doses of 7.11 g (corresponding to a 4.5 g dose with half of the dose as immediate-release fraction and half of the dose as modified release fraction) were weighed.

FIG. 29 and Table 9a below depict dissolution profiles determined in 0.1N HCl using a USP apparatus 2. The dissolution medium was maintained at 37.0±0.5° C. and the rotating paddle speed was fixed at 75 rpm. Single dose units were poured in a container containing 50 mL of tap water. After 5 and 15 minutes, the suspension was poured in the dissolution vessel containing 840 mL of 0.1N HCl dissolution medium. 10 mL of water were used to rinse the container and were added to the dissolution vessel.

TABLE 9a

| Time (h) | % dissolved 5 min reconstitution time | % dissolved 15 min reconstitution time |
|---|---|---|
| 0 | 0 | 0 |
| 0,25 | 47 | 48 |
| 1 | 53 | 52 |
| 3 | 53 | 53 |
| 6 | 55 | 54 |
| 8 | 59 | 60 |
| 10 | 74 | 77 |
| 12 | 87 | 88 |
| 16 | 96 | 97 |
| 20 | 97 | 98 |

Example 9.2: 0.8% Malic Acid

IR particles were prepared as follows: 1615.0 g of Sodium Oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 273 microns were obtained.

MR coated particles were prepared as follows: 39.9 g of Methacrylic acid copolymer Type C (Eudragit™ L100-55 from Evonik), 80.1 g of Methacrylic acid copolymer Type B (Eudragit™ S100 from Evonik), 180.0 g of Hydrogenated cottonseed oil (Lubritab™ from JRS), were dissolved in 2700.0 g of isopropanol at 78° C. The solution was sprayed entirely on 700.0 g of IR particles in a fluid bed spray coater apparatus Glatt™ G.P.C.G.1.1 with inlet temperature 47° C., spraying rate around 10.7 g per min and atomization pressure 1.6 bar. MR microparticles were dried for 2 hours with inlet temperature set to 60° C. Sodium oxybate MR coated particles with mean diameter of 309 microns were obtained.

The finished composition, which contains a 50:50 mixture of MR and IR particles calculated on their sodium oxybate content, was prepared as follows: 100.0 g of the above IR particles, 142.9 g of the above MR particles, 2.0 g of Malic acid (D/L malic acid regular from Bartek), 1.2 g of xanthan gum (Xantural™ 75 from CP Kelco), 1.2 g of hydrophilic fumed silica (Aerosil™ 200 from Degussa) and 2.5 g of magnesium stearate (from Peter Greven) were mixed in a Roue-Roehn mixer. Individual doses of 6.93 g (corresponding to a 4.5 g dose with half of the dose as immediate-release fraction and half of the dose as modified release fraction) were weighed.

FIG. 30 and Table 9b below depict dissolution profiles determined in 0.1N HCl using a USP apparatus 2. The dissolution medium was maintained at 37.0±0.5° C. and the rotating paddle speed was fixed at 75 rpm. Single dose units were poured in a container containing 50 mL of tap water. After 5 and 15 minutes, the suspension was poured in the dissolution vessel containing 840 mL of 0.1N HCl dissolution medium. 10 mL of water were used to rinse the container and were added to the dissolution vessel.

TABLE 9b

| Time (h) | % dissolved 5 min reconstitution time | % dissolved 15 min reconstitution time |
|---|---|---|
| 0 | 0 | 0 |
| 0,25 | 51 | 51 |
| 1 | 51 | 52 |
| 3 | 51 | 53 |
| 6 | 52 | 62 |
| 8 | 60 | 86 |
| 10 | 77 | 96 |
| 12 | 90 | 98 |
| 16 | 98 | 98 |

Example 9.3: 15% Malic Acid

IR particles were prepared as follows: 1615.0 g of Sodium Oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 255 microns were obtained.

MR coated particles were prepared as follows: 22.8 g of Methacrylic acid copolymer Type C (Eudragit™ L100-55 from Evonik), 45.8 g of Methacrylic acid copolymer Type B (Eudragit™ S100 from Evonik), 102.9 g of Hydrogenated cottonseed oil (Lubritab™ from JRS), were dissolved in 1544.8 g of isopropanol at 78° C. The solution was sprayed entirely on 400.0 g of IR particles in a fluid bed spray coater apparatus Glatt™ G.P.C.G.1.1 with inlet temperature 49° C., spraying rate around 12.0 g per min and atomization pressure 1.3 bar. MR microparticles were dried for 2 hours with inlet temperature set to 56° C. Sodium oxybate MR coated particles with mean diameter of 298 microns were obtained.

The finished composition, which contains a 50:50 mixture of MR and IR particles calculated on their sodium oxybate content, was prepared as follows: 36.2 g of the above IR particles, 51.8 g of the above MR particles, 16.1 g of Malic acid (D/L malic acid regular from Bartek), 0.7 g of xanthan gum (Xantural™ 75 from CP Kelco), 1.0 g of carrageenan gum (Viscarin™ PH209 from FMC Biopolymer), 1.0 g of hydroxyethylcellulose (Natrosol™ 250M from Ashland) and 0.6 g of magnesium stearate (from Peter Greven) were mixed in a Roue-Roehn mixer. Individual doses of 8.25 g (corresponding to a 4.5 g dose with half of the dose as immediate-release fraction and half of the dose as modified release fraction) were weighed.

FIG. 31 and Table 9c below depict dissolution profiles determined in 0.1N HCl using a USP apparatus 2. The dissolution medium was maintained at 37.0±0.5° C. and the rotating paddle speed was fixed at 75 rpm. Single dose units were poured in a container containing 50 mL of tap water. After 5 and 15 minutes, the suspension was poured in the dissolution vessel containing 840 mL of 0.1N HCl dissolution medium. 10 mL of water were used to rinse the container and were added to the dissolution vessel.

TABLE 9c

| Time (h) | % dissolved 5 min reconstitution time | % dissolved 15 min reconstitution time |
|---|---|---|
| 0 | 0 | 0 |
| 0,25 | 48 | 49 |
| 1 | 51 | 51 |
| 3 | 51 | 51 |

TABLE 9c-continued

| Time (h) | % dissolved 5 min reconstitution time | % dissolved 15 min reconstitution time |
|---|---|---|
| 4 | 51 | 51 |
| 6 | 52 | 51 |
| 8 | 56 | 56 |
| 10 | 71 | 71 |
| 12 | 86 | 85 |
| 16 | 97 | 96 |
| 20 | 99 | 98 |

Example 10. Alternative Formulations

Suspending agents are present in the formulation to limit microparticles settling after reconstitution. Without suspending agents, microparticles starts settling as soon as shaking stops. In presence of the suspending agents, full microparticles settling does not occur in less than 1 minute. The following data illustrates the good pourability of the suspension assessed by the high recovery of sodium oxybate content in the dissolution test:

IR particles were prepared as follows: 1615.0 g of sodium oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 271 microns were obtained.

MR coated particles were prepared as follows: 39.9 g of methacrylic acid copolymer type C (Eudragit™ L100-55 from Evonik), 80.1 g of methacrylic acid copolymer type B (Eudragit™ S100 from Evonik), 180.0 g of hydrogenated cottonseed oil (Lubritab™ from JRS), were dissolved in 2700.0 g of isopropanol at 78° C. The solution was sprayed entirely on 700.0 g of sodium oxybate IR particles in a fluid bed spray coater apparatus Glatt™ G.P.C.G.1.1 with inlet temperature 48° C., spraying rate around 11.5 g per min and atomization pressure 1.6 bar. MR coated particles were dried for 2 hours with inlet temperature set to 56° C. MR particles of sodium oxybate with mean diameter of 321 microns were obtained.

The finished composition, which contains a 50:50 mixture of MR and IR sodium oxybate particles calculated on their sodium oxybate content, was prepared as follows: 634.0 g of the above IR particles, 907.6 g of the above MR particles, 25.7 g of malic acid (D/L malic acid regular from Bartek), 11.4 g of xanthan gum (Xantural™ 75 from CP Kelco), 17.1 g of carrageenan gum (Viscarin™ PH209 from FMC Biopolymer), 17.1 g of hydroxyethylcellulose (Natrosol™ 250M from Ashland) and 8.1 g of magnesium stearate (from Peter Greven) were mixed in a Roue-Roehn mixer. Individual doses of 14.20 g (corresponding to a 9 g dose with half of the dose as immediate-release fraction and half of the dose as modified release fraction) were weighed.

FIG. 32 and Table 10a below depict dissolution profiles of 9 g doses determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel. Dissolution profile was determined with and without rinsing step.

TABLE 10a

| Time (h) | with rinsing | without rinsing |
|---|---|---|
| 0 | 0 | 0 |
| 0,25 | 47 | 46 |
| 1 | 51 | 51 |
| 3 | 53 | 52 |
| 6,0 | 54 | 53 |
| 8 | 61 | 60 |
| 10 | 77 | 74 |
| 12 | 91 | 88 |
| 16 | 98 | 95 |
| 20 | 98 | 96 |

Example 11. Alternative Formulations with a Different Ratio of IR and MR Fractions Different prototypes were prepared and evaluated to determine the effect of MI/MR ratio.

Example 11a: 15% IR/85% IR with MR pH*6.5 Microparticles

IR particles were prepared as follows: 1615.0 g of Sodium Oxybate and 85.0 g of water soluble polymer polyvinylpyrrolidone (Povidone—Plasdone™ K30 from ISP) were solubilized in 1896.2 g of absolute ethyl alcohol and 1264.4 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 275 microns were obtained.

MR coated particles were prepared as follows: 22.8 g of Methacrylic acid copolymer Type C (Eudragit™ L100-55 from Evonik), 45.8 g of Methacrylic acid copolymer Type B (Eudragit™ S100 from Evonik), 102.9 g of Hydrogenated cottonseed oil (Lubritab™ from JRS), were dissolved in 1543.1 g of isopropanol at 78° C. The solution was sprayed entirely on 400.0 g of IR particles in a fluid bed spray coater apparatus Glatt™ G.P.C.G.1.1 with inlet temperature 47° C., spraying rate around 10.8 g per min and atomization pressure 1.3 bar. MR microparticles were dried for 2 hours with inlet temperature set to 56° C. Sodium oxybate MR coated particles with mean diameter of 330 microns were obtained.

17.1 g of MR microparticles were mixed with 0.09 g of magnesium stearate (from Peter Greven). The dissolution profile of 4000 mg of the mixture which correspond to 2250 mg of sodium oxybate per vessel was determined in 900 ml of 0.1N HCl and pH 6.8 phosphate buffer (0.05M monobasic potassium phosphate solution—pH adjusted to 6.8 with 5N NaOH) using the USP apparatus 2. Dissolution medium temperature was maintained at 37.0±0.5° C., and the rotating paddle speed was set at 75 rpm. The release profiles are shown in FIG. 33, Table 11a, and Table 11b.

TABLE 11a

| Dissolution data - 0.1N HCl | |
|---|---|
| Time (hour) | % dissolved |
| 0 | 0,0 |
| 0,25 | 1 |
| 1 | 1 |
| 3 | 2 |

TABLE 11a-continued

Dissolution data - 0.1N HCl

| Time (hour) | % dissolved |
|---|---|
| 4 | 3 |
| 6 | 6 |
| 8 | 24 |
| 10 | 59 |
| 12 | 83 |
| 16 | 95 |
| 20 | 97 |

TABLE 11b

Dissolution data - 50 mM phosphate buffer pH 6.8

| Time (hour) | % dissolved |
|---|---|
| 0 | 0 |
| 0,25 | 18 |
| 0,5 | 80 |
| 0,75 | 97 |
| 1 | 97 |
| 2 | 97 |

The qualitative composition of 4.5 g dose units comprising 15% of the dose as IR fraction and 85% of the dose as MR fraction is described in Table 11c.

TABLE 11c

| Component | Function | Quantity per 4.5 g dose (g) |
|---|---|---|
| MR microparticles | Modified release fraction of sodium oxybate | 6.767 |
| IR microparticles | Immediate release fraction of sodium oxybate | 0.836 |
| Malic acid | Acidifying agent | 0.034 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.039 |
| Total | | 7.876 |

The finished composition, which contains a 85:15 mixture of MR and IR particles calculated on their sodium oxybate content, may be prepared as follows: 100.0 g of the above IR particles, 809.5 g of the above MR particles, 4.0 g of malic acid (D/L malic acid regular from Bartek), 6.0 g of xanthan gum (Xantural™ 75 from CP Kelco), 9.0 g of carrageenan gum (Viscarin™ PH209 from FMC Biopolymer), 9.0 g of hydroxyethylcellulose (Natrosol™ 250M from Ashland) and 4.7 g of magnesium stearate (from Peter Greven) were mixed in a Roue-Roehn mixer. Individual doses of 7.88 g (corresponding to a 4.5 g dose with 15% of the dose as immediate-release fraction and 85% of the dose as modified release fraction) were weighed.

After reconstitution with 50 ml of tap water and a rinsing volume of 10 ml of tap water, the finished composition will display the dissolution profiles in FIGS. 34 and 35 and Tables 11d and 11e in 840 ml of 0.1N HCl and in pH6.8 phosphate buffer (0.05M monobasic potassium phosphate solution—pH adjusted to 6.8 with 5N NaOH) using a USP apparatus 2, at 37.0±0.5° C. and the rotating paddle speed at 75 rpm.

TABLE 11d

| Time (hour) | % dissolved |
|---|---|
| 0 | 0,0 |
| 0,25 | 16 |
| 1 | 16 |
| 3 | 17 |
| 4 | 17 |
| 6 | 20 |
| 8 | 35 |
| 10 | 65 |
| 12 | 85 |
| 16 | 96 |

TABLE 11e

| Time (hour) | % dissolved |
|---|---|
| 0 | 0 |
| 0,25 | 30 |
| 0,5 | 83 |
| 0,75 | 97 |
| 1 | 98 |
| 2 | 98 |

Example 11b 30% IR/70% MR with MR pH*6.2 Microparticles

IR particles were prepared as follows: 1615.1 g of sodium oxybate and 85.0 g of water soluble polymer polyvinylpyrrolidone (Povidone—Plasdone™ K30 from ISP) were solubilized in 1903.2 g of absolute ethyl alcohol and 1267.1 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 268 microns were obtained.

MR coated particles were prepared as follows: 36.6 g of Methacrylic acid copolymer Type C (Eudragit™ L100-55 from Evonik), 32.1 g of methacrylic acid copolymer type B (Eudragit™ S100 from Evonik), 103.0 g of hydrogenated cottonseed oil (Lubritab™ from JRS), were dissolved in 1543.5 g of isopropanol at 78° C. The solution was sprayed entirely on 400.0 g of IR particles in a fluid bed spray coater apparatus Glatt™ G.P.C.G.1.1 with inlet temperature 48° C., spraying rate around 12.0 g per min and atomization pressure 1.3 bar. MR particles were dried for 2 hours with inlet temperature set to 56° C. Sodium oxybate MR coated particles with mean diameter of 323 microns were obtained.

17.0 g of sodium oxybate MR particles were mixed with 0.09 g of magnesium stearate (from Peter Greven). The dissolution profile of 4050 mg of the mixture which correspond to 2280 mg of sodium oxybate per vessel was determined in 900 ml of 0.1N HCl dissolution medium using the USP apparatus 2. Dissolution medium temperature was maintained at 37.0±0.5° C., and the rotating paddle speed was set at 75 rpm. The release profile in 0.1N HCl is shown in FIG. 36 and Table 11f.

TABLE 11f

| Time (hour) | % dissolved |
|---|---|
| 0,0 | 0 |
| 0,3 | 1 |
| 1,0 | 3 |
| 3,0 | 4 |
| 4,0 | 4 |

TABLE 11f-continued

| Time (hour) | % dissolved |
|---|---|
| 6,0 | 8 |
| 8,0 | 40 |
| 10,0 | 81 |
| 12,0 | 95 |
| 16,0 | 100 |
| 20,0 | 99 |

The finished composition, which contains a 70:30 mixture of MR and IR sodium oxybate particles calculated on their sodium oxybate content, was prepared as follows: 92.1 g of the above IR particles, 306.5 g of the above MR particles, 7.5 g of malic acid (D/L malic acid regular from Bartek), 2.8 g of xanthan gum (Xantural™ 75 from CP Kelco), 4.1 g of carrageenan gum (Viscarin™ PH209 from FMC Biopolymer), 4.1 g of hydroxyethylcellulose (Natrosol™ 250M from Ashland) and 2.0 g of magnesium stearate (from Peter Greven) were mixed in a Roue-Roehn mixer. Individual doses of 7.62 g (corresponding to a 4.5 g dose with 30% of the dose as immediate-release fraction and 70% of the dose as modified release fraction) were weighed.

FIGS. 37 and 38 and Tables 11g and 11h below depict dissolution profiles determined using a USP apparatus 2 in 0.1N HCl and pH 6.8 phosphate buffer (0.05M monobasic potassium phosphate solution—pH adjusted to 6.8 with 5N NaOH). The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of dissolution medium. 10 mL of water were used to rinse the container and were added to the dissolution vessel.

TABLE 11g

| Time (hour) | % dissolved in 0.1N HCl |
|---|---|
| 0,0 | 0,0 |
| 0,3 | 29 |
| 1,0 | 31 |
| 3,0 | 32 |
| 4,0 | 32 |
| 6,0 | 35 |
| 8,0 | 70 |
| 10,0 | 94 |
| 12,0 | 99 |
| 16,0 | 99 |

TABLE 11h

| Time (h) | % dissolved in pH 6.8 phosphate buffer |
|---|---|
| 0 | 0 |
| 0,25 | 64 |
| 0,5 | 87 |
| 1 | 100 |
| 2 | 100 |
| 3 | 102 |

Example 11c: 65% IR/35% MR with MR pH*6.5 Microparticles

IR particles were prepared as follows: 1615.0 g of sodium oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 270 microns were obtained.

MR coated particles were prepared as follows: 22.8 g of methacrylic acid copolymer type C (Eudragit™ L100-55 from Evonik), 45.8 g of methacrylic acid copolymer type B (Eudragit™ S100 from Evonik), 102.9 g of hydrogenated cottonseed oil (Lubritab™ from JRS), were dissolved in 1543.1 g of isopropanol at 78° C. The solution was sprayed entirely on 400.0 g of IR particles in a fluid bed spray coater apparatus Glatt™ G.P.C.G.1.1 with inlet temperature 47° C., spraying rate around 10.8 g per min and atomization pressure 1.3 bar. MR coated particles were dried for 2 hours with inlet temperature set to 56° C. Sodium oxybate MR coated particles with mean diameter of 330 microns were obtained.

Refer to the Example 11a for the dissolution profile of the MR microparticles. The qualitative composition of 4.5 g dose units comprising 65% of the dose as IR fraction and 35% of the dose as MR fraction is described in Table 11i.

TABLE 11i

| Component | Function | Quantity per 4.5 g dose (g) |
|---|---|---|
| MR microparticles | Modified release fraction of sodium oxybate | 2.786 |
| IR microparticles | Immediate release fraction of sodium oxybate | 3.622 |
| Malic acid | Acidifying agent | 0.110 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.034 |
| Total | | 6.752 |

The finished composition, which contains a 85:15 mixture of sodium oxybate MR and IR particles calculated on their sodium oxybate content, may be prepared as follows: 100.0 g of the above IR particles, 76.9 g of the above MR coated particles, 3.0 g of Malic acid (D/L malic acid regular from Bartek), 1.4 g of xanthan gum (Xantural™ 75 from CP Kelco), 2.1 g of carrageenan gum (Viscarin™ PH209 from FMC Biopolymer), 2.1 g of hydroxyethylcellulose (Natrosol™ 250M from Ashland) and 0.9 g of magnesium stearate (from Peter Greven) were mixed in a Roue-Roehn mixer. Individual doses of 6.75 g (corresponding to a 4.5 g dose with 65% of the dose as immediate-release fraction and 35% of the dose as modified release fraction) were weighed.

Dissolution profile: After reconstitution with 50 ml tap water and rinsing with 10 ml of tap water, the finished composition will display the dissolution profiles in FIGS. 39 and 40 and Tables 11j and 11k in 840 ml of 0.1N HCl and in pH 6.8 phosphate buffer (0.05M monobasic potassium phosphate solution—pH adjusted to 6.8 with 5N NaOH) using a USP apparatus 2, at 37.0±0.5° C. and the rotating paddle speed at 75 rpm.

TABLE 11j

| Time (hour) | % dissolved in 0.1N HCl |
|---|---|
| 0 | 0,0 |
| 0.25 | 65 |
| 1 | 65 |
| 3 | 66 |
| 4 | 66 |

TABLE 11j-continued

| Time (hour) | % dissolved in 0.1N HCl |
| --- | --- |
| 6 | 67 |
| 8 | 73 |
| 10 | 86 |
| 12 | 94 |
| 16 | 98 |
| 20 | 99 |

TABLE 11k

| Time (hour) | % dissolved in pH 6.8 phosphate buffer |
| --- | --- |
| 0 | 0 |
| 0.25 | 71 |
| 0.5 | 93 |
| 0.75 | 99 |
| 1 | 99 |
| 2 | 99 |

Example 12: Alternative Formulations with IR Fraction Obtained Using Different Manufacturing Processes Prototype formulations were developed to test the impact of different manufacturing processes on the dissolution of the formulations.

Example 12a: IR Portion=Raw Sodium Oxybate

IR particles to serve as cores of the MR coated microparticles were prepared as follows: 1615.0 g of sodium oxybate and 85.0 g of water soluble polymer polyvinylpyrroli done (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 256 microns were obtained.

MR coated particles were prepared as follows: 22.8 g of methacrylic acid copolymer type C (Eudragit™ L100-55 from Evonik), 45.8 g of methacrylic acid copolymer type B (Eudragit™ S100 from Evonik), 102.9 g of hydrogenated cottonseed oil (Lubritab™ from JRS), were dissolved in 1542.9 g of isopropanol at 78° C. The solution was sprayed entirely on 400.0 g of IR particles in a fluid bed spray coater apparatus Glatt™ G.P.C.G.1.1 with inlet temperature 48° C., spraying rate around 10 g per min and atomization pressure 1.3 bar. MR particles were dried for 2 hours with inlet temperature set to 56° C. Sodium oxybate MR coated particles with mean diameter of 308 microns were obtained.

25.2 g of MR microparticles were mixed with 0.26 g of magnesium stearate (from Peter Greven) and 0.13 g of colloidal silicon dioxide (Aerosil™ 200 from Evonik). The dissolution profile of 4000 mg of the mixture which correspond to 2250 mg of sodium oxybate per vessel was determined in 900 ml of 0.1N HCl dissolution medium using the USP apparatus 2. Dissolution medium temperature was maintained at 37.0±0.5° C., and the rotating paddle speed was set at 75 rpm. The release profile in 0.1N HCl is shown in FIG. 41 and Table 12a.

TABLE 12a

| Time (hour) | % dissolved |
| --- | --- |
| 0 | 0 |
| 0.25 | 1 |
| 1 | 1 |
| 3 | 2 |
| 4 | 3 |
| 6 | 14 |
| 8 | 40 |
| 10 | 65 |
| 12 | 78 |
| 16 | 89 |

The finished composition, which contains a 50:50 mixture of sodium oxybate MR coated particles and raw sodium oxybate as IR fraction calculated on their sodium oxybate content, was prepared as follows: 36 g of raw sodium oxybate, 63.7 g of the above MR coated particles, 1.8 g of malic acid (D/L malic acid regular from Bartek), 1.6 g of xanthan gum (Xantural™ 75 from CP Kelco), 2.4 g of carrageenan gum (Viscarin™ PH209 from FMC Biopolymer), 0.047 g of an apple aroma and 0.3 g of hydrophilic fumed silica (Aerosil 200 from Degussa) were mixed in a Roue-Roehn mixer. Individual doses of 6.66 g (corresponding to a 4.5 g dose with half of the dose as raw sodium oxybate as IR fraction and half of the dose as modified release fraction) were weighed.

FIG. 42 and Table 12b below depict dissolution profiles determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 12b

| Time (hour) | % dissolved |
| --- | --- |
| 0 | 0 |
| 0.25 | 50 |
| 1 | 52 |
| 4 | 55 |
| 6 | 57 |
| 8 | 70 |
| 10 | 82 |
| 12 | 87 |
| 16 | 93 |

Considering that the 0.1N HCl dissolution profile of the MR coated particles is similar to the MR microparticles from examples 1 and 1bis, the dissolution profile in pH 6.8 phosphate buffer of the finished composition is expected to be similar to the profile depicted in FIG. 8, insofar as the MR particles are similar and only the nature of the immediate-release fraction was changed.

Example 12b: IR=Microparticles Obtained by Extrusion-Spheronization

IR particles were prepared as follows: 97 g of sodium oxybate and 3 g of water soluble polymer polyvinylpyrrolidone (Povidone—Plasdone™ K30 from ISP) were mixed with 7.5 g of water. The mixture was extruded through a 400-micron mesh and spheronized at 1500 rpm for 1.5 min in an extruder-spheronizer Fuji-Paudal MG-55. After drying for 4 hours at 45° C. in a ventilated oven, microparticles were sieved between 150 microns and 500 microns.

MR coated particles were prepared as described in Example 14.

The finished composition, which contains a 50:50 mixture of MR and IR sodium oxybate particles calculated on their sodium oxybate content, was prepared as follows: 67.4 g of the above IR particles obtained by extrusion-spheronization, 115.6 g of the above MR coated particles, 3.3 g of malic acid (D/L malic acid regular from Bartek), 0.9 g of xanthan gum (Xantural™ 75 from CP Kelco), 0.9 g of hydrophilic fumed silica (Aerosil 200 from Degussa) and 1.9 g of magnesium stearate (from Peter Greven) were mixed in a Roue-Roehn mixer. Individual doses of 6.54 g (corresponding to a 4.5 g dose with half of the dose as immediate-release fraction and half of the dose as modified release fraction) were weighed.

FIG. 43 and Table 12c below depict dissolution profiles determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 12c

| Time (hour) | % dissolved in 0.1N HCl |
| --- | --- |
| 0 | 0 |
| 0.25 | 51 |
| 1 | 53 |
| 4 | 54 |
| 6 | 54 |
| 8 | 56 |
| 10 | 65 |
| 12 | 79 |
| 16 | 92 |

Based on the dissolution profile of the MR coated particles in pH 6.8 phosphate buffer, finished compositions are expected to have the dissolution profile in pH 6.8 phosphate buffer given in Table 12d and FIG. 44.

TABLE 12d

| Time (h) | % dissolved in pH 6.8 phosphate buffer |
| --- | --- |
| 0 | 0 |
| 0.25 | 55 |
| 0.50 | 97 |
| 1 | 101 |
| 1.5 | 102 |
| 2 | 101 |
| 3 | 101 |

Example 13. Alternative Formulation without Binder

IR particles were prepared as follows: 1700.0 g of Sodium Oxybate are solubilized in 1899.4 g of absolute ethyl alcohol and 1261.3 g of water. The solution is entirely sprayed onto 300 g of microcrystalline cellulose spheres (Cellets 127 from Pharmatrans) in a fluid bed spray coater apparatus GPCG1.1. Sodium oxybate IR particles with mean diameter of 244 microns are obtained.

MR coated particles were prepared as follows: 17.1 g of methacrylic acid copolymer type C (Eudragit L100-55 from Evonik), 34.3 g of methacrylic acid copolymer type B (Eudragit S100 from Evonik), and 77.1 g of hydrogenated cottonseed oil (Lubritab from JRS), are dissolved in 1157.9 g of isopropanol at 78° C. The solution is sprayed entirely on 300.0 g of IR particles prepared above in a fluid bed spray coater apparatus Glatt G.P.C.G.1.1 with inlet temperature 48° C., spraying rate around 10.7 g per min and atomization pressure 1.3 bar. MR microparticles were dried for 2 hours with inlet temperature set to 56° C. Sodium oxybate MR coated particles with mean diameter of 289 microns are obtained.

25.3 g of MR coated microparticles were mixed with 0.12 g of magnesium stearate (from Peter Greven). The dissolution profile of 4000 mg of the mixture which correspond to 2368 mg of sodium oxybate per vessel was determined in 900 ml of 0.1N HCl and pH 6.8 phosphate buffer (0.05M monobasic potassium phosphate solution with pH adjusted to 6.8 with 5N NaOH) using the USP apparatus 2. Dissolution medium temperature was maintained at 37.0±0.5° C., and the rotating paddle speed was set at 75 rpm. The release profiles are shown below in FIG. 45 and Tables 13a and 13b.

TABLE 13a

Dissolution data - 0.1N HCl

| Time (h) | % dissolved |
| --- | --- |
| 0 | 0 |
| 0.25 | 0 |
| 1 | 0 |
| 3 | 1 |
| 4 | 3 |
| 6 | 29 |
| 8 | 50 |
| 10 | 69 |
| 12 | 82 |
| 16 | 97 |
| 20 | 102 |

TABLE 13b

Dissolution data - 50 mM pH 6.8 phosphate buffer

| Time (h) | % dissolved |
| --- | --- |
| 0 | 0 |
| 0.25 | 5 |
| 1 | 102 |
| 3 | 106 |

The qualitative composition of 4.5 g dose units comprising 50% of the dose as IR fraction and 50% of the dose as MR fraction is described in Table 13c.

TABLE 13c

| Component | Function | Quantity per 4.5 g dose (g) |
| --- | --- | --- |
| MR microparticles | Modified release fraction of sodium oxybate | 3.841 |
| IR microparticles | Immediate release fraction of sodium oxybate | 2.647 |
| Malic acid | Acidifying agent | 0.113 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.034 |
| Total | | 6.835 |

After reconstitution with 50 ml of tap water and rinsing with 10 ml of tap water, the finished composition is expected to provide the following dissolution profiles in FIGS. 46 and 47 and Tables 13d and B3e in 840 ml of 0.1N HCl and pH6.8 phosphate buffer (0.05M monobasic potassium phosphate solution with pH adjusted to 6.8 with 5N NaOH) using a USP apparatus 2, at 37.0±0.5° C. and the rotating paddle speed at 75 rpm.

TABLE 13d

| Time (h) | % dissolved in 0.1N HCl |
|---|---|
| 0.0 | 0 |
| 0.3 | 50 |
| 1.0 | 50 |
| 3.0 | 50 |
| 4.0 | 52 |
| 6.0 | 64 |
| 8.0 | 75 |
| 10.0 | 84 |
| 12.0 | 91 |
| 16.0 | 98 |
| 20.0 | 101 |

TABLE 13e

| Time (h) | % dissolved in pH 6.8 buffer |
|---|---|
| 0 | 0 |
| 0.25 | 53 |
| 1.0 | 101 |
| 3 | 103 |

Example 14. MR Particles with Larger Core Size (160 Microns)

Different prototypes were also developed to evaluate the impact of the core size on the dissolution of the formulation.

IR particles were prepared as follows: 1615.0 g of sodium oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 100 from Pharmatrans) (D[4,3]=160 microns) in a fluid bed spray coater apparatus GPCG1.1. Sodium oxybate IR particles with mean diameter of 310 microns were obtained.

MR coated particles were prepared as follows: 25.7 g of methacrylic acid copolymer type C (Eudragit™ L100-55 from Evonik), 51.5 g of methacrylic acid copolymer type B (Eudragit™ S100 from Evonik), 115.7 g of hydrogenated cottonseed oil (Lubritab™ from JRS), were dissolved in 1735.7 g of isopropanol at 78° C. The solution was sprayed entirely on 450.0 g of IR particles in a fluid bed spray coater apparatus Glatt™ G.P.C.G.1.1 with inlet temperature 47° C., spraying rate around 9.6 g per min and atomization pressure 1.6 bar. MR particles were dried for 2 hours with inlet temperature set to 56° C. Sodium oxybate MR coated particles with mean diameter of 370 microns were obtained.

49.3 g of sodium oxybate MR particles were mixed with 0.52 g of magnesium stearate (from Peter Greven) and 0.26 g of colloidal silicon dioxide (Aerosil™ 200 from Evonik). The dissolution profile of 4000 mg of the mixture which correspond to 2250 mg of sodium oxybate per vessel was determined using the USP apparatus 2 in 900 ml of 0.1N HCl medium and pH 6.8 phosphate buffer (0.05M monobasic potassium phosphate solution—pH adjusted to 6.8 with 5N NaOH). Dissolution medium temperature was maintained at 37.0±0.5° C., and the rotating paddle speed was set at 100 rpm. The release profile in 0.1N HCl and pH 6.8 phosphate buffer is shown below in FIG. 48 and Tables 14a and 14b.

TABLE 14a

Dissolution data - 0.1N HCl

| Time (h) | % dissolved |
|---|---|
| 0 | 0 |
| 0.25 | 0 |
| 1 | 1 |
| 3 | 2 |
| 6 | 3 |
| 8 | 7 |
| 10 | 18 |
| 12 | 37 |
| 16 | 75 |

TABLE 14b

Dissolution data - 50 mM pH 6.8 phosphate buffer

| Time (h) | % dissolved |
|---|---|
| 0 | 0 |
| 0.25 | 9 |
| 0.5 | 95 |
| 1 | 101 |
| 3 | 101 |

The qualitative composition of 4.5 g dose units comprising 50% of the dose as IR fraction and 50% of the dose as MR fraction is described in Table 14c.

TABLE 14c

| Component | Function | Quantity per 4.5 g dose (g) |
|---|---|---|
| MR microparticles | Modified release fraction of sodium oxybate | 2.786 |
| IR microparticles | Immediate release fraction of sodium oxybate | 3.981 |
| Malic acid | Acidifying agent | 0.113 |
| Xanthan gum | Suspending agent | 0.050 |
| Hydroxyethylcellulose | Suspending agent | 0.075 |
| Carrageenan gum | Suspending agent | 0.075 |
| Magnesium stearate | Lubricant | 0.037 |
| Total | | 7.115 |

After reconstitution with 50 ml of tap water and rinsing with 10 ml of tap water, the finished composition is expected to provide the dissolution profiles in FIGS. 49 and 50 and Table 14d and 14e in 840 ml of 0.1N HCl and in pH6.8 phosphate buffer (0.05M monobasic potassium phosphate solution with pH adjusted to 6.8 with 5N NaOH) using a USP apparatus 2, at 37.0±0.5° C. and the rotating paddle speed at 75 rpm.

TABLE 14d

| Time (hour) | % dissolved in 0.1N HCl |
|---|---|
| 0 | 0 |
| 0.25 | 50 |
| 1 | 51 |
| 4 | 51 |

TABLE 14d-continued

| Time (hour) | % dissolved in 0.1N HCl |
|---|---|
| 6 | 52 |
| 8 | 53 |
| 10 | 59 |
| 12 | 69 |
| 16 | 87 |

TABLE 14e

| Time (hour) | % dissolved in pH 6.8 buffer |
|---|---|
| 0 | 0 |
| 0.25 | 55 |
| 1 | 101 |
| 3 | 101 |

Example 15. MR Microparticles with Different Ratios of Lubritab™ and Eudragit™

Different prototypes were developed to evaluate the effect of the ratio between Lubritab™ and Eudragit™ on the formulation.

Example 15a: 30% Lubritab™; Cellets™ 127; Coating Level=35%

IR particles were prepared as follows: 1615.0 g of Sodium Oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 100 from Pharmatrans) in a fluid bed spray coater apparatus GPCG1.1. Sodium oxybate IR particles with mean diameter of 272 microns were obtained.

MR coated particles were prepared as follows: 50.2 g of Methacrylic acid copolymer Type C (Eudragit™ L100-55 from Evonik), 100.6 g of Methacrylic acid copolymer Type B (Eudragit™ S100 from Evonik), 64.6 g of Hydrogenated cottonseed oil (Lubritab™ from JRS), were dissolved in 1943.5 g of isopropanol at 78° C. The solution was sprayed entirely on 400.0 g of IR particles in a fluid bed spray coater apparatus Glatt™ G.P.C.G.1.1 with inlet temperature 48° C., spraying rate around 11.0 g per min and atomization pressure 1.3 bar. MR microparticles were dried for 2 hours with inlet temperature set to 56° C. Sodium oxybate MR coated particles with mean diameter of 403 microns were obtained.

17.9 g of sodium oxybate MR microparticles were mixed with 0.1 g of magnesium stearate (from Peter Greven). The dissolution profile of 4308 mg of the mixture which corresponds to 2250 mg of sodium oxybate per vessel was determined using the USP apparatus 2 in 900 ml of 0.1N HCl medium. Dissolution medium temperature was maintained at 37.0±0.5° C., and the rotating paddle speed was set at 75 rpm. The release profile is shown in FIG. 51 and Table 15a.

TABLE 15a

| Time (h) | % dissolved in 0.1N HCl |
|---|---|
| 0 | 0 |
| 0.25 | 3 |
| 1 | 5 |

TABLE 15a-continued

| Time (h) | % dissolved in 0.1N HCl |
|---|---|
| 3 | 69 |
| 4 | 96 |
| 6 | 101 |
| 8 | 102 |
| 10 | 102 |

Alternative MR coated particles of sodium oxybate were prepared according to the above manufacturing protocol with the coating level adjusted to 50% instead of 35%. The dissolution profile of the alternative sodium oxybate MR particles was determined using the same protocol as above. The 0.1N HCl dissolution profile is shown in FIG. 52 and Table 15b.

TABLE 15b

| Time (h) | % dissolved |
|---|---|
| 0 | 0 |
| 0.25 | 1 |
| 1 | 1 |
| 3 | 36 |
| 4 | 67 |
| 6 | 95 |
| 8 | 98 |
| 10 | 98 |

The finished composition, which contains a 50:50 mixture of MR and IR sodium oxybate particles calculated on their sodium oxybate content, was prepared as follows. 153.3 g of the above IR microparticles, 235.8 g of the above sodium oxybate MR microparticles with a coating level of 30%, 6.2 g of malic acid (D/L malic acid regular from Bartek), 2.7 g of xanthan gum (Xantural™ 75 from CP Kelco), 4.1 g of carrageenan gum (Viscarin™ PH109 from FMC Biopolymer), 4.1 g of hydroxyethylcellulose (Natrosol™ 250M from Ashland) and 2.0 g of magnesium stearate (from Peter Greven) were mixed in a Roue-Roehn mixer. Individual doses of 7.42 g (corresponding to a 4.5 g dose with half of the dose as immediate-release fraction and half of the dose as modified release fraction) were weighed.

FIG. 53 and Table 15c below depict dissolution profiles determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 15c

| Time (hour) | % dissolved |
|---|---|
| 0 | 0 |
| 0.25 | 45 |
| 1 | 52 |
| 2 | 92 |
| 3 | 94 |
| 4 | 97 |
| 6 | 97 |
| 8 | 97 |
| 10 | 96 |

Example 15b: Celphere™ CP203 as Neutral Cores and Coating Level=35%

IR particles were prepared as follows: 665.0 g of Sodium Oxybate and 35.0 g of water soluble polymer polyvinylpyrrolidone (Povidone—Plasdone™ K30 from ISP) were solubilized in 781.2 g of absolute ethyl alcohol and 521.6 g of water. The solution was entirely sprayed onto 300 g of microcrystalline cellulose spheres (Celphere™ CP203 from Asahi Kasei—mean diameter D[4,3]=250 microns) in a fluid bed spray coater apparatus GPCG1.1. Sodium oxybate IR particles with mean diameter of 398 microns were obtained.

MR coated particles were prepared as follows: 37.6 g of Methacrylic acid copolymer Type C (Eudragit™ L100-55 from Evonik), 75.4 g of Methacrylic acid copolymer Type B (Eudragit™ S100 from Evonik), 48.5 g of Hydrogenated cottonseed oil (Lubritab™ from JRS), were dissolved in 1458.0 g of isopropanol at 78° C. The solution was sprayed entirely on 300.0 g of IR particles in a fluid bed spray coater apparatus Glatt™ G.P.C.G.1.1 with inlet temperature 48° C., spraying rate around 11.7 g per min and atomization pressure 1.6 bar. MR microparticles were dried for 2 hours with inlet temperature set to 56° C. Sodium oxybate MR coated particles with mean diameter of 491 microns were obtained.

17.0 g of MR microparticles were mixed with 0.08 g of magnesium stearate (from Peter Greven). The dissolution profile of 5210 mg of the mixture which corresponds to 2250 mg of sodium oxybate per vessel was determined using the USP apparatus 2 in 900 ml of 0.1N HCl medium and in pH 6.8 phosphate buffer (0.05M monobasic potassium phosphate solution—pH adjusted to 6.8 with 5N NaOH). Dissolution medium temperature was maintained at 37.0±0.5° C., and the rotating paddle speed was set at 75 rpm. The release profile is shown in FIG. 54 and Tables 15d and 15e.

TABLE 15d

| Dissolution data - 0.1N HCl | |
|---|---|
| Time (hour) | % dissolved |
| 0 | 0 |
| 0.25 | 3 |
| 1 | 3 |
| 3 | 45 |
| 4 | 77 |
| 6 | 96 |
| 8 | 98 |
| 10 | 98 |

TABLE 15e

| Dissolution data - 50 mM pH 6.8 phosphate buffer | |
|---|---|
| Time (h) | % dissolved |
| 0 | 0 |
| 0.25 | 1 |
| 0.5 | 22 |
| 0.75 | 87 |
| 1 | 98 |
| 2 | 97 |

The qualitative composition of 4.5 g dose units comprising 5000 of the dose as IR fraction and 50% of the dose as MR fraction is described in Table 15f.

TABLE 15f

| Component | Function | Quantity per 4.5 g dose (g) |
|---|---|---|
| MR microparticles | Modified release fraction of sodium oxybate | 5.205 |
| IR microparticles | Immediate release fraction of sodium oxybate | 3.383 |
| Malic acid | Acidifying agent | 0.113 |
| Xanthan gum | Suspending agent | 0.050 |
| Hydroxyethylcellulo | Suspending agent | 0.075 |
| Carrageenan gum | Suspending agent | 0.075 |
| Magnesium stearate | Lubricant | 0.045 |
| Total | | 8.946 |

After reconstitution, the finished composition is expected to exhibit the dissolution profiles in FIGS. 55 and 56 and Tables 15g and 15h in 0.1N HCl and in pH6.8 phosphate buffer (0.05M monobasic potassium phosphate solution with pH adjusted to 6.8 with 5N NaOH) using a USP apparatus 2, at 37.0±0.5° C. and the rotating paddle speed at 75 rpm.

TABLE 15g

| Time (h) | % dissolved in 0.1N HCl |
|---|---|
| 0 | 0 |
| 0.25 | 51 |
| 1 | 51 |
| 3 | 73 |
| 4 | 88 |
| 6 | 98 |
| 8 | 99 |
| 10 | 99 |

TABLE 15h

| Time (h) | % dissolved in pH 6.8 buffer |
|---|---|
| 0 | 0 |
| 0.25 | 50 |
| 0.5 | 61 |
| 0.75 | 93 |
| 1 | 99 |
| 2 | 99 |

Example 15c: 40% Lubritab™ (Coating Level=40%)

IR pellets were prepared as follows: 1615.0 g of Sodium Oxybate and 85.0 g of water soluble polymer polyvinylpyrrolidone (Povidone—Plasdone™ K30 from ISP) were solubilized in 1903.2 g of absolute ethyl alcohol and 1267.1 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 268 microns were obtained.

MR coated particles were prepared as follows: 40.6 g of Methacrylic acid copolymer Type C (Eudragit™ L100-55 from Evonik), 80.1 g of Methacrylic acid copolymer Type B (Eudragit™ S100 from Evonik), 80.5 g of Hydrogenated cottonseed oil (Lubritab™ from JRS), were dissolved in 1799.4 g of isopropanol at 78° C. The solution was sprayed entirely on 300.0 g of IR particles in a fluid bed spray coater apparatus Glatt™ G.P.C.G.1.1 with inlet temperature 48° C., spraying rate around 10.5 g per min and atomization pressure 1.3 bar. MR microparticles were dried for 2 hours with inlet temperature set to 56° C. Sodium oxybate MR coated particles with mean diameter of 348 microns were obtained.

20.0 g of MR coated particles were mixed with 0.1 g of magnesium stearate (from Peter Greven). The dissolution profile of 4700 mg of the mixture which corresponds to 2250 mg of sodium oxybate per vessel was determined using the USP apparatus 2 in 900 ml of 0.1N HCl medium. Dissolution medium temperature was maintained at 37.0±0.5° C., and the rotating paddle speed was set at 75 rpm. The release profile is shown in FIG. 57 and Table 15i.

TABLE 15i

| Time (h) | % dissolved in 0.1N HCl |
| --- | --- |
| 0 | 0 |
| 0.25 | 0 |
| 1 | 0 |
| 3 | 1 |
| 4 | 8 |
| 6 | 52 |
| 8 | 84 |
| 10 | 95 |
| 12 | 97 |
| 16 | 98 |

The finished composition, which contains a 50:50 mixture of MR and IR particles calculated on their sodium oxybate content, was prepared as follows: 156.0 g of the above IR particles, 260.0 g of the above MR coated particles, 6.3 g of malic acid (D/L malic acid regular from Bartek), 2.8 g of xanthan gum (Xantural™ 75 from CP Kelco), 4.2 g of carrageenan gum (Viscarin™ PH209 from FMC Biopolymer), 4.2 g of hydroxyethylcellulose (Natrosol™ 250M from Ashland) and 2.2 g of magnesium stearate (from Peter Greven) were mixed in a Roue-Roehn mixer. Individual doses of 7.78 g (corresponding to a 4.5 g dose with half of the dose as immediate-release fraction and half of the dose as modified release fraction) were weighed.

FIGS. 58 and 59 and Tables 15j and 15k below depict dissolution profiles determined in 0.1N HCl and pH 6.8 buffer (0.05M monobasic potassium phosphate solution with pH adjusted to 6.8 with 5N NaOH) using a USP apparatus 2. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 15j

| Time (h) | % dissolved in 0.1N HCl |
| --- | --- |
| 0 | 0 |
| 0.25 | 48 |
| 1 | 52 |
| 3 | 52 |
| 4 | 62 |
| 6 | 89 |
| 8 | 96 |
| 10 | 97 |
| 12 | 98 |
| 16 | 98 |
| 20 | 97 |

TABLE 15k

| Time (h) | % dissolved in pH 6.8 buffer |
| --- | --- |
| 0 | 0 |
| 0.25 | 49 |
| 0.5 | 85 |
| 1 | 91 |
| 2 | 96 |
| 3 | 104 |

Example 15d: 70% Lubritab™ (Coating Level 25%)

IR particles were prepared as follows: 1615.1 g of Sodium Oxybate and 85.0 g of water soluble polymer polyvinylpyrrolidone (Povidone—Plasdone™ K30 from ISP) were solubilized in 1894.4 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 272 microns were obtained.

MR coated particles were prepared as follows: 13.3 g of Methacrylic acid copolymer Type C (Eudragit™ L100-55 from Evonik), 26.8 g of Methacrylic acid copolymer Type B (Eudragit™ S100 from Evonik), 93.3 g of Hydrogenated cottonseed oil (Lubritab™ from JRS), were dissolved in 1200.3 g of isopropanol at 78° C. The solution was sprayed entirely on 400.0 g of IR particles in a fluid bed spray coater apparatus Glatt™ G.P.C.G.1.1 with inlet temperature 48° C., spraying rate around 10.6 g per min and atomization pressure 1.3 bar. MR microparticles were dried for 2 hours with inlet temperature set to 56° C. Sodium oxybate MR coated particles with mean diameter of 313 microns were obtained.

17.0 g of MR coated particles were mixed with 0.06 g of magnesium stearate (from Peter Greven). The dissolution profile of 3750 mg of the mixture which corresponds to 2250 mg of sodium oxybate per vessel was determined using the USP apparatus 2 in 900 ml of 0.1N HCl medium and pH6.8 phosphate buffer (0.05M monobasic potassium phosphate solution—pH adjusted to 6.8 with 5N NaOH). Dissolution medium temperature was maintained at 37.0±0.5° C., and the rotating paddle speed was set at 75 rpm. The release profile is shown in FIG. 60 and Tables 15l and 15m.

TABLE 15l

Dissolution profile in 0.1N HCl

| Time (h) | % dissolved |
| --- | --- |
| 0 | 0.0 |
| 0.25 | 5 |
| 1 | 4 |
| 3 | 5 |
| 4 | 5 |
| 6 | 8 |
| 8 | 33 |
| 10 | 78 |
| 12 | 98 |
| 16 | 103 |

TABLE 15M

Dissolution profile in 50 mM pH 6.8 phosphate buffer

| Time (h) | % dissolved |
|---|---|
| 0 | 0.0 |
| 0.25 | 1 |
| 0.5 | 45 |
| 1 | 97 |
| 2 | 108 |
| 3 | 114 |

The finished composition, which contains a 50:50 mixture of MR and IR particles calculated on their sodium oxybate content, was prepared as follows: 153.3 g of the above IR particles, 204.3 g of the above MR coated particles, 6.2 g of Malic acid (D/L malic acid regular from Bartek), 2.7 g of xanthan gum (Xantural™ 75 from CP Kelco), 4.1 g of carrageenan gum (Viscarin™ PH209 from FMC Biopolymer), 4.1 g of hydroxyethylcellulose (Natrosol™ 250M from Ashland) and 1.9 g of magnesium stearate (from Peter Greven) were mixed in a Roue-Roehn mixer. Individual doses of 6.85 g (corresponding to a 4.5 g dose with half of the dose as immediate-release fraction and half of the dose as modified release fraction) were weighed.

FIGS. 61 and Table 15n depict the dissolution profiles determined in 0.1N HCl using a USP apparatus 2. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 15n

| Time (h) | % dissolved |
|---|---|
| 0 | 0 |
| 0,25 | 48 |
| 1 | 52 |
| 3 | 52 |
| 4 | 52 |
| 6 | 55 |
| 8 | 76 |
| 10 | 95 |
| 12 | 100 |
| 16 | 100 |
| 20 | 100 |

Based on the dissolution profile of the MR coated particles in pH 6.8 phosphate buffer, single dose units are expected to have the dissolution profile in pH6.8 buffer shown in FIG. 62 and in Table 15o.

TABLE 15o

| Time (h) | % dissolved in pH 6.8 buffer |
|---|---|
| 0 | 0,0 |
| 0,25 | 51 |
| 0,5 | 72 |
| 1 | 99 |
| 2 | 104 |
| 3 | 107 |

Example 16. Evaluation of Different Hydrophobic Compounds in the Coating

Prototypes with different hydrophobic coatings were prepared and evaluated to determine the effect of coating type on the dissolution of the formulations.

Example 16a: Glyceryl Dibehenate (Compritol™ ATO888)

IR particles were prepared as follows: 1615.0 g of Sodium Oxybate and 85.0 g of water soluble polymer polyvinylpyrrolidone (Povidone—Plasdone™ K30 from ISP) were solubilized in 1903.2 g of absolute ethyl alcohol and 1267.1 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 268 microns were obtained.

MR coated particles were prepared as follows: 22.9 g of Methacrylic acid copolymer Type C (Eudragit™ L100-55 from Evonik), 45.8 g of Methacrylic acid copolymer Type B (Eudragit™ S100 from Evonik), 102.9 g of glyceryl dibehenate (Compritol™ ATO 888 from Gattefossé), were dissolved in 1371.8 g of isopropanol at 78° C. The solution was sprayed entirely on 400.0 g of IR particles in a fluid bed spray coater apparatus Glatt™ G.P.C.G.1.1 with inlet temperature 48° C., spraying rate around 11.7 g per min and atomization pressure 1.6 bar. MR microparticles were dried for 2 hours with inlet temperature set to 56° C. Sodium oxybate MR coated particles with mean diameter of 322 microns were obtained.

17.0 g of MR coated particles were mixed with 0.1 g of magnesium stearate (from Peter Greven). The dissolution profile of 4000 mg of the mixture which corresponds to 2250 mg of sodium oxybate per vessel was determined using the USP apparatus 2 in 900 ml of 0.1N HCl medium and in pH 6.8 phosphate buffer (0.05M monobasic potassium phosphate solution—pH adjusted to 6.8 with 5N NaOH). Dissolution medium temperature was maintained at 37.0±0.5° C., and the rotating paddle speed was set at 75 rpm. The release profile is shown in FIG. 63 and Tables 16a and 16b.

TABLE 16a

Dissolution profile - 0.1N HCl

| Time (h) | % dissolved |
|---|---|
| 0 | 0 |
| 0,25 | 0 |
| 1 | 1 |
| 3 | 3 |
| 4 | 6 |
| 6 | 31 |
| 8 | 67 |
| 10 | 90 |
| 12 | 98 |
| 16 | 100 |

TABLE 16b

Dissolution profile - 50 mM pH 6.8 phosphate buffer

| Time (h) | % dissolved |
|---|---|
| 0 | 0 |
| 0,25 | 1 |

TABLE 16b-continued

Dissolution profile - 50 mM pH 6.8 phosphate buffer

| Time (h) | % dissolved |
|---|---|
| 1 | 102 |
| 3 | 105 |

The finished composition, which contains a 50:50 mixture of MR and IR particles calculated on their sodium oxybate content, was prepared as follows: 181.1 g of the above IR particles, 258.7 g of the above MR coated particles, 7.3 g of Malic acid (D/L malic acid regular from Bartek), 3.3 g of xanthan gum (Xantural™ 75 from CP Kelco), 4.9 g of carrageenan gum (Viscarin™ PH209 from FMC Biopolymer), 4.9 g of hydroxyethylcellulose (Natrosol™ 250M from Ashland) and 2.3 g of magnesium stearate (from Peter Greven) were mixed in a Roue-Roehn mixer. Individual doses of 7.12 g (corresponding to a 4.5 g dose with half of the dose as immediate-release fraction and half of the dose as modified release fraction) were weighed.

FIGS. 64 and Table 16c depict dissolution profiles determined in 0.1N HCl using a USP apparatus 2. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 16c

| Time (hour) | % dissolved in 0.1N HCl |
|---|---|
| 0 | 0 |
| 0,25 | 46 |
| 1 | 50 |
| 3 | 51 |
| 4 | 56 |
| 6 | 78 |
| 8 | 92 |
| 10 | 96 |
| 12 | 97 |
| 16 | 96 |

Based on the dissolution profile of the MR microparticles alone in pH 6.8 phosphate buffer, single dose units are expected to have the dissolution profile at pH6.8 shown in FIG. 65 and in Table 16d.

TABLE 16d

| Time (hour) | % dissolved in pH 6.8 buffer |
|---|---|
| 0 | 0 |
| 0,25 | 50 |
| 1 | 101 |
| 3 | 102 |

Example 16b: 60% Candelilla Wax with Coating Level of 20%

IR particles were prepared as follows: 1615.1 g of Sodium Oxybate and 85.0 g of water soluble polymer polyvinylpyrrolidone (Povidone—Plasdone™ K30 from ISP) were solubilized in 1894.4 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 255 microns were obtained.

MR coated particles were prepared as follows: 13.3 g of Methacrylic acid copolymer Type C (Eudragit™ L100-55 from Evonik), 26.7 g of Methacrylic acid copolymer Type B (Eudragit™ S100 from Evonik), 60.0 g of candelilla wax (Kahlwax™ 2039L from Brenntag), were dissolved in 902.2 g of isopropanol at 78° C. The solution was sprayed entirely on 400.0 g of IR particles in a fluid bed spray coater apparatus Glatt™ G.P.C.G.1.1 with inlet temperature 48° C., spraying rate around 12.8 g per min and atomization pressure 1.3 bar. MR microparticles were dried for 2 hours with inlet temperature set to 56° C. Sodium oxybate MR coated particles with mean diameter of 289 microns were obtained.

21.2 g of MR microparticles were mixed with 0.11 g of magnesium stearate (from Peter Greven). The dissolution profile of 4000 mg of the mixture which corresponds to 2570 mg of sodium oxybate per vessel was determined using the USP apparatus 2 in 900 ml of 0.1N HCl medium and in pH 6.8 phosphate buffer (0.05M monobasic potassium phosphate solution—pH adjusted to 6.8 with 5N NaOH). Dissolution medium temperature was maintained at 37.0±0.5° C., and the rotating paddle speed was set at 75 rpm. The release profiles are shown below in FIG. 66 and Tables 16e and 16f.

TABLE 16e

Dissolution profile - 0.1N HCl

| Time (h) | % dissolved |
|---|---|
| 0 | 0 |
| 0,25 | 0 |
| 1 | 0 |
| 3 | 0 |
| 4 | 1 |
| 6 | 2 |
| 8 | 2 |
| 10 | 2 |
| 12 | 2 |
| 16 | 3 |
| 20 | 4 |

TABLE 16f

Dissolution profile - 50 mM pH 6.8 phosphate buffer

| Time (h) | % dissolved |
|---|---|
| 0 | 0 |
| 0,25 | 0 |
| 0,5 | 10 |
| 0,75 | 62 |
| 1 | 89 |
| 2 | 101 |

The qualitative composition of 4.5 g dose units comprising 50% of the dose as IR fraction and 50% of the dose as MR fraction is described in Table 16g.

TABLE 16g

| Component | Function | Quantity per 4.5 g dose (g) |
|---|---|---|
| MR microparticles | Modified release fraction of sodium oxybate | 3.483 |
| IR microparticles | Immediate release fraction of sodium oxybate | 2.786 |
| Malic acid | Acidifying agent | 0.113 |
| Xanthan gum | Suspending agent | 0.050 |
| Hydroxy ethylcellulose | Suspending agent | 0.075 |
| Carrageenan gum | Suspending agent | 0.075 |
| Magnesium stearate | Lubricant | 0.033 |
| Total | | 6.615 |

The finished composition, which contains a 50:50 mixture of MR and IR particles calculated on their sodium oxybate content, may be prepared as follows: 200.0 g of the above IR particles, 250.0 g of the above MR coated particles, 8.1 g of Malic acid (D/L malic acid regular from Bartek), 3.6 g of xanthan gum (Xantural™ 75 from CP Kelco), 5.4 g of carrageenan gum (Viscarin™ PH209 from FMC Biopolymer), 5.4 g of hydroxyethylcellulose (Natrosol™ 250M from Ashland) and 2.4 g of magnesium stearate (from Peter Greven) were mixed in a Roue-Roehn mixer. Individual doses of 6.61 g (corresponding to a 4.5 g dose with half of the dose as immediate-release fraction and half of the dose as modified release fraction) were weighed. After reconstitution, the finished composition is expected to provide the dissolution profiles in FIGS. 67 and 68 and Tables 16h and 16i in 0.1N HCl and in pH6.8 phosphate buffer (0.05M monobasic potassium phosphate solution with pH adjusted to 6.8 with 5N NaOH) using a USP apparatus 2, at 37.0±0.5° C. and the rotating paddle speed at 75 rpm.

TABLE 16h

| Time (hour) | % dissolved in 0.1N HCl |
|---|---|
| 0 | 0 |
| 0,25 | 50 |
| 1 | 50 |
| 3 | 50 |
| 4 | 50 |
| 6 | 51 |
| 8 | 51 |
| 10 | 51 |
| 12 | 51 |
| 16 | 52 |
| 20 | 52 |

TABLE 16i

| Time (hour) | % dissolved in pH 6.8 buffer |
|---|---|
| 0 | 0 |
| 0,25 | 50 |
| 0,5 | 55 |
| 0,75 | 81 |
| 1 | 94 |
| 2 | 100 |

Example 16c: 40% Candelilla Wax (Coating Level=20%)

IR particles were prepared as follows: 1615.1 g of Sodium Oxybate and 85.0 g of water soluble polymer polyvinylpyrrolidone (Povidone—Plasdone™ K30 from ISP) were solubilized in 1894.4 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 270 microns were obtained.

MR coated particles were prepared as follows: 20.0 g of Methacrylic acid copolymer Type C (Eudragit™ L100-55 from Evonik), 40.0 g of Methacrylic acid copolymer Type B (Eudragit™ S100 from Evonik), 40.0 g of candelilla wax (Kahlwax™ 2039L from Brenntag), were dissolved in 904.0 g of isopropanol at 78° C. The solution was sprayed entirely on 400.0 g of IR particles in a fluid bed spray coater apparatus Glatt™ G.P.C.G.1.1 with inlet temperature 48° C., spraying rate around 10.9 g per min and atomization pressure 1.3 bar. MR microparticles were dried for 2 hours with inlet temperature set to 56° C. Sodium oxybate MR coated particles with mean diameter of 302 microns were obtained.

17.0 g of MR microparticles were mixed with 0.08 g of magnesium stearate (from Peter Greven). The dissolution profile of 3500 mg of the mixture which corresponds to 2250 mg of sodium oxybate per vessel was determined using the USP apparatus 2 in 900 ml of 0.1N HCl medium and pH 6.8 phosphate buffer (0.05M monobasic potassium phosphate solution—pH adjusted to 6.8 with 5N NaOH) is given in FIG. 69 and Tables 16j and 16k. Dissolution medium temperature was maintained at 37.0±0.5° C., and the rotating paddle speed was set at 75 rpm.

TABLE 16j

| Dissolution profile in 0.1N HCl | |
|---|---|
| Time (h) | % dissolved |
| 0 | 0 |
| 0,25 | 0 |
| 1 | 3 |
| 3 | 6 |
| 4 | 8 |
| 6 | 9 |
| 8 | 15 |
| 10 | 37 |
| 12 | 70 |
| 16 | 97 |
| 20 | 100 |

TABLE 16k

| Dissolution profile in 50 mM pH 6.8 phosphate buffer | |
|---|---|
| Time (h) | % dissolved |
| 0 | 0 |
| 0,25 | 24 |
| 0,5 | 86 |
| 0,75 | 99 |
| 1 | 100 |
| 2 | 100 |

The qualitative composition of 4.5 g dose units comprising 50% of the dose as IR fraction and 50% of the dose as MR fraction is described in Table 16l.

TABLE 16l

| Component | Function | Quantity per 4.5 g dose (g) |
|---|---|---|
| MR microparticles | Modified release fraction of sodium oxybate | 3.483 |
| IR microparticles | Immediate release fraction of sodium oxybate | 2.786 |
| Malic acid | Acidifying agent | 0.113 |
| Xanthan gum | Suspending agent | 0.050 |
| Hydroxy ethylcellulose | Suspending agent | 0.075 |
| Carrageenan gum | Suspending agent | 0.075 |
| Magnesium stearate | Lubricant | 0.033 |
| Total | | 6.615 |

The finished composition, which contains a 50:50 mixture of MR and IR particles calculated on their sodium oxybate content, was prepared as follows: 122.7 g of the above IR particles, 153.2 g of the above MR coated particles, 5.0 g of malic acid (D/L malic acid regular from Bartek), 2.2 g of xanthan gum (Xantural™ 75 from CP Kelco), 3.3 g of carrageenan gum (Viscarin™ PH209 from FMC Biopolymer), 3.3 g of hydroxyethylcellulose (Natrosol™ 250M from Ashland) and 1.5 g of magnesium stearate (from Peter Greven) were mixed in a Roue-Roehn mixer. Individual doses of 6.62 g (corresponding to a 4.5 g dose with half of the dose as immediate-release fraction and half of the dose as modified release fraction) were weighed.

FIGS. 70 and Table 16m depict dissolution profiles determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 16m

| Time (hour) | % dissolved in 0.1N HCl |
|---|---|
| 0 | 0 |
| 0,25 | 47 |
| 1 | 51 |
| 3 | 51 |
| 4 | 52 |
| 6 | 52 |
| 8 | 55 |
| 10 | 72 |
| 12 | 89 |
| 16 | 97 |

Based on the dissolution profile of the MR coated particles in pH6.8 phosphate buffer, 4.5 g single dose units of the finished compositions are expected to provide the dissolution profile in pH 6.8 phosphate buffer shown in FIG. 71 and in Table 16n.

TABLE 16n

| Time (h) | % dissolved in pH 6.8 buffer |
|---|---|
| 0 | 0 |
| 0.25 | 62 |
| 0.5 | 93 |
| 0.75 | 99 |
| 1 | 100 |
| 2 | 100 |

Example 16d—60% Cetyl Alcohol (Kolliwax™ CA)

IR particles were prepared as follows: 1615.1 g of Sodium Oxybate and 85.0 g of water soluble polymer polyvinylpyrrolidone (Povidone—Plasdone™ K30 from ISP) were solubilized in 1898.7 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 272 microns were obtained.

MR coated particles were prepared as follows: 22.8 g of methacrylic acid copolymer Type C (Eudragit™ L100-55 from Evonik), 45.8 g of Methacrylic acid copolymer Type B (Eudragit™ S100 from Evonik), 102.9 g of cetyl alcohol (Kolliwax™ CA from BASF), were dissolved in 1472.5 g of isopropanol and 77.7 g of water at room temperature. The solution was sprayed entirely on 400.0 g of IR particles in a fluid bed spray coater apparatus Glatt™ G.P.C.G.1.1 with inlet temperature 48° C., spraying rate around 14.5 g per min and atomization pressure 2.5 bar. Sodium oxybate MR coated particles with mean diameter of 315 microns were obtained.

16.4 g of MR microparticles were mixed with 0.08 g of magnesium stearate (from Peter Greven). The dissolution profile of 4000 mg of the mixture which corresponds to 2250 mg of sodium oxybate per vessel was determined using the USP apparatus 2 in 900 ml of 0.1N HCl medium is given in FIG. 72 and Table 16o. Dissolution medium temperature was maintained at 37.0±0.5° C., and the rotating paddle speed was set at 75 rpm.

TABLE 16o

| Time (h) | % dissolved in 0.1N HCl |
|---|---|
| 0 | 0 |
| 0.25 | 13 |
| 1 | 84 |
| 3 | 103 |
| 4 | 103 |
| 6 | 103 |
| 8 | 103 |
| 10 | 104 |
| 12 | 104 |
| 16 | 103 |
| 20 | 102 |

Example 17. Effect of Eudragit™ Selection in the Coating of the MR Microparticles Further prototypes were developed and evaluate to determine the effect of the Eudragit™ selected on the dissolution of the MR microparticles.

Example 17a 100% Eudragit™ S100

IR particles were prepared as follows: 1615.0 g of Sodium Oxybate and 85.0 g of water soluble polymer polyvinylpyrrolidone (Povidone—Plasdone™ K30 from ISP) were solubilized in 1894.3 g of absolute ethyl alcohol and 1262.9 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 285 microns were obtained.

Sodium oxybate IR seal-coated particles were prepared by coating the IR particles described above with a seal-coat layer: 170.0 g of hydroxypropylcellulose (Klucel™ EF Pharm from Hercules) were solubilized in 4080.0 g of acetone. The solution was entirely sprayed onto 1530.0 g of the above IR particles in a fluid bed spray coater apparatus. Sodium oxybate IR particles with volume mean diameter of about 298 microns were obtained.

MR coated particles were prepared as follows: 100.0 g of Methacrylic acid copolymer Type B (Eudragit™ S100 from Evonik), 150.0 g of Hydrogenated cottonseed oil (Lubritab™ from JRS), were dissolved in 2250.0 g of isopropanol at 78° C. The solution was sprayed entirely on 750.0 g of the above IR particles in a fluid bed spray coater apparatus Glatt™ G.P.C.G.1.1 with inlet temperature 48° C., spraying rate around 12.0 g per min and atomization pressure 1.6 bar. MR microparticles were dried for 2 hours with inlet temperature set to 56° C. Sodium oxybate MR coated particles with mean diameter of 307 microns were obtained.

The dissolution profile of 2100 mg of the mixture which corresponds to 1253 mg of sodium oxybate per vessel was determined using the USP apparatus 2 in 500 ml of 0.1N HCl medium is reported in FIG. 73 and Table 17a. Dissolution medium temperature was maintained at 37.0±0.5° C., and the rotating paddle speed was set at 100 rpm.

TABLE 17a

| Time (h) | % dissolved |
|---|---|
| 0 | 0 |
| 0.25 | 0 |
| 1 | 1 |
| 3 | 3 |
| 4 | 4 |
| 6 | 9 |
| 8 | 30 |
| 10 | 60 |
| 12 | 81 |
| 16 | 92 |

The finished composition, which contains a 50:50 mixture of MR and IR particles calculated on their sodium oxybate content, was prepared as follows: 425.0 g of the above IR seal-coated particles, 510.0 g of the above MR coated particles, 30.9 g of malic acid (D/L malic acid regular from Bartek), 4.9 g of xanthan gum (Xantural™ 180 from CP Kelco), 4.9 g of Aerosil™ 200 (amorphous anhydrous colloidal silicon dioxide from Evonik) and 9.9 g of magnesium stearate (from Peter Greven) were mixed in a Roue-Roehn mixer. Individual doses of 7.18 g (corresponding to a 4.5 g dose with half of the dose as immediate-release fraction and half of the dose as modified release fraction) were weighed.

FIG. 74 and Table 17b below depict dissolution profiles determined using a USP apparatus 2 in 0.1N HCl. The dissolution medium was maintained at 37.0±0.5° C. and the rotating paddle speed was fixed at 100 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 17b

| Time (hour) | % dissolved in 0.1N HCl |
|---|---|
| 0 | 0 |
| 0.25 | 50 |
| 1 | 50 |
| 3 | 50 |
| 4 | 51 |
| 6 | 55 |
| 8 | 67 |
| 10 | 84 |
| 12 | 91 |
| 16 | 94 |

FIG. 75 and Table 17c depict the dissolution profile determined using a USP apparatus 2 in phosphate buffer pH 6.8 (0.05M monobasic potassium phosphate solution—pH adjusted to 6.8 with 5N NaOH). The dissolution medium was maintained at 37.0±0.5° C. and the rotating paddle speed was fixed at 100 rpm. Single dose units were poured in a container containing 50 mL of tap water. After 5 minutes, the suspension was poured in the dissolution vessel containing 840 mL of pH 6.8 dissolution medium. 10 mL of water were used to rinse the container and were added to the dissolution vessel.

TABLE 17c

| Time (hour) | % dissolved |
|---|---|
| 0 | 0 |
| 0.25 | 50 |
| 1 | 51 |
| 3 | 54 |
| 4 | 56 |
| 6 | 93 |
| 8 | 99 |
| 10 | 100 |
| 12 | 100 |
| 16 | 97 |

Example 17b 100% Eudragit™ L100-55

IR particles were prepared as follows: 1615.0 g of Sodium Oxybate and 85.1 g of water soluble polymer polyvinylpyrrolidone (Povidone—Plasdone™ K30 from ISP) were solubilized in 1896.2 g of absolute ethyl alcohol and 1264.4 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 275 microns were obtained.

MR coated particles were prepared as follows: 68.7 g of Methacrylic acid copolymer Type C (Eudragit™ L100-55 from Evonik), 102.9 g of hydrogenated cottonseed oil (Lubritab™ from JRS), were dissolved in 1543.2 g of isopropanol at 78° C. The solution was sprayed entirely on 400.0 g of IR particles in a fluid bed spray coater apparatus Glatt™ G.P.C.G.1.1 with inlet temperature 46° C., spraying rate around 12.7 g per min and atomization pressure 1.3 bar. MR microparticles were dried for 2 hours with inlet temperature set to 56° C. Sodium oxybate MR coated particles with mean diameter of 328 microns were obtained.

17.0 g of MR microparticles were mixed with 0.09 g of magnesium stearate (from Peter Greven). The dissolution profile in of 4000 mg of the mixture which corresponds to 2250 mg of sodium oxybate per vessel was determined using the USP apparatus 2 in 900 ml of 0.1N HCl medium and in pH 6.8 phosphate buffer (0.05M monobasic potassium phosphate solution—pH adjusted to 6.8 with 5N NaOH) is given in FIG. 76 and Tables 17d and 17e. Dissolution medium temperature was maintained at 37.0±0.5° C., and the rotating paddle speed was set at 100 rpm.

TABLE 17d

Dissolution profile in 0.1N HCl

| Time (h) | % dissolved |
| --- | --- |
| 0 | 0 |
| 0.25 | 0 |
| 1 | 2 |
| 3 | 3 |
| 4 | 6 |
| 6 | 53 |
| 8 | 95 |
| 10 | 99 |
| 12 | 99 |
| 16 | 99 |
| 20 | 99 |

TABLE 17e

Dissolution profile in 50 mM pH 6.8 phosphate buffer

| Time (h) | % dissolved |
| --- | --- |
| 0 | 0 |
| 0.25 | 21 |
| 0.5 | 99 |
| 0.75 | 103 |
| 1 | 103 |
| 2 | 103 |

The finished composition, which contains a 50:50 mixture of MR and IR particles calculated on their sodium oxybate content, was prepared as follows: 153.3 g of the above IR particles, 219.0 g of the above MR coated particles, 6.2 g of malic acid (D/L malic acid regular from Bartek), 2.8 g of xanthan gum (Xantural™ 75 from CP Kelco), 4.1 g of carrageenan gum (Viscarin™ PH209 from FMC Biopolymer), 4.1 g of hydroxyethylcellulose (Natrosol™ 250M from Ashland) and 1.9 g of magnesium stearate (from Peter Greven) were mixed in a Roue-Roehn mixer. Individual doses of 7.12 g (corresponding to a 4.5 g dose with half of the dose as immediate-release fraction and half of the dose as modified release fraction) were weighed.

FIG. 77 and Table 17f depict dissolution profiles determined using a USP apparatus 2 in 0.1N HCL. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 17f

| Time (hour) | % dissolved |
| --- | --- |
| 0 | 0 |
| 0.25 | 46 |
| 1 | 51 |
| 3 | 52 |
| 4 | 59 |
| 6 | 94 |
| 8 | 98 |
| 10 | 98 |
| 12 | 98 |
| 16 | 98 |

Based on the dissolution profile of the MR coated particles in pH6.8 phosphate buffer, 4.5 g single dose units of the finished compositions are expected to provide the dissolution profile in pH 6.8 phosphate buffer in FIG. 78 and Table 17g.

TABLE 17g

| Time (h) | % dissolved in pH 6.8 buffer |
| --- | --- |
| 0 | 0 |
| 0.25 | 61 |
| 0.5 | 99 |
| 0.75 | 101 |
| 1 | 101 |
| 2 | 101 |

Example 17c Mixture Eudragit™ L100-S100 (50-50)

IR particles were prepared as follows: 1615.0 g of Sodium Oxybate and 85.0 g of water soluble polymer polyvinylpyrrolidone (Povidone—Plasdone™ K30 from ISP) were solubilized in 1903.2 g of absolute ethyl alcohol and 1267.1 g of water. The solution was entirely sprayed onto 300 g of microcrystalline cellulose spheres (Cellets™ 127 from Pharmatrans) in a fluid bed spray coater apparatus GPCG1.1. Sodium oxybate IR particles with mean diameter of 268 microns were obtained.

MR coated particles were prepared as follows: 34.3 g of Methacrylic acid copolymer Type A (Eudragit™ L100 from Evonik), 34.3 g of Methacrylic acid copolymer Type B (Eudragit™ S100 from Evonik), 102.9 g of Hydrogenated cottonseed oil (Lubritab™ from JRS), were dissolved in 1543.0 g of isopropanol at 78° C. The solution was sprayed entirely on 400.0 g of IR particles in a fluid bed spray coater apparatus Glatt™ G.P.C.G.1.1 with inlet temperature 48° C., spraying rate around 11.8 g per min and atomization pressure 1.3 bar. MR microparticles were dried for 2 hours with inlet temperature set to 56° C. Sodium oxybate MR coated particles with mean diameter of 316 microns were obtained.

24.0 g of MR microparticles were mixed with 0.12 g of magnesium stearate (from Peter Greven). The dissolution profile of 4050 mg of the mixture which corresponds to 2280 mg of sodium oxybate per vessel was determined using the USP apparatus 2 in 900 ml of 0.1N HCl medium and in pH 6.8 phosphate buffer (0.05M monobasic potassium phosphate solution—pH adjusted to 6.8 with 5N NaOH) is given in FIG. 79 and Tables 17h and 17i. Dissolution medium temperature was maintained at 37.0±0.5° C., and the rotating paddle speed was set at 100 rpm.

TABLE 17h

Dissolution profile in 0.1N HCl

| Time (h) | % dissolved |
|---|---|
| 0 | 0 |
| 0.25 | 0 |
| 1 | 2 |
| 3 | 2 |
| 4 | 3 |
| 6 | 7 |
| 8 | 31 |
| 10 | 62 |
| 12 | 83 |
| 16 | 98 |
| 20 | 100 |

TABLE 17i

Dissolution profile in 50 mM pH 6.8 phosphate buffer

| Time (h) | % dissolved |
|---|---|
| 0 | 0 |
| 0.25 | 2 |
| 0.5 | 5 |
| 0.75 | 13 |
| 1 | 47 |
| 2 | 101 |

The finished composition, which contains a 50:50 mixture of MR and IR particles calculated on their sodium oxybate content, was prepared as follows: 223.0 g of the above IR particles, 318.4 g of the above MR coated particles, 11.2 g of malic acid (D/L malic acid regular from Bartek), 4.0 g of xanthan gum (Xantural™ 75 from CP Kelco), 6.0 g of carrageenan gum (Viscarin™ PH209 from FMC Biopolymer), 6.0 g of hydroxyethylcellulose (Natrosol™ 250M from Ashland) and 2.9 g of magnesium stearate (from Peter Greven) were mixed in a Roue-Roehn mixer. Individual doses of 7.14 g (corresponding to a 4.5 g dose with half of the dose as immediate-release fraction and half of the dose as modified release fraction) were weighed.

FIG. 80 and Table 17j depict dissolution profiles determined using a USP apparatus 2 in 0.1N HCl. The dissolution medium was maintained at 37.0±0.5° C. and the rotating paddle speed was fixed at 75 rpm. Single dose units were poured in a container containing 50 mL of tap water. After 5 minutes, the suspension was poured in the dissolution vessel containing 840 mL of 0.1N HCl dissolution medium. 10 mL of water were used to rinse the container and were added to the dissolution vessel.

TABLE 17j

| Time (hour) | % dissolved |
|---|---|
| 0 | 0 |
| 0.25 | 47 |
| 1 | 51 |
| 3 | 51 |
| 6 | 59 |
| 8 | 80 |
| 10 | 92 |
| 12 | 96 |
| 16 | 97 |

Based on the dissolution profile of the MR coated particles in pH6.8 phosphate buffer, 4.5 g single dose units of the finished composition are expected to have the dissolution profile in pH 6.8 phosphate buffer given in FIG. 81 and Table 17k.

TABLE 17k

| Time (h) | % dissolved in pH 6.8 buffer |
|---|---|
| 0 | 0 |
| 0.25 | 51 |
| 0.5 | 53 |
| 0.75 | 56 |
| 1 | 73 |
| 2 | 100 |

Example 18: In Vivo Pharmacokinetic Study of Finished Composition According to Example 1 (Dose Escalating Study)

Pharmacokinetic testing was undertaken in vivo in healthy human volunteers. Pharmacokinetic parameters were normalized by the dose. To assess the dose-proportionality, log-transformed dose-normalized PK parameters were pairwise compared according to the statistical methodology described in FDA's 2013 Draft Guidance entitled BIOEQUIVALENCE STUDIES WITH PHARMACOKINETIC ENDPOINTS FOR DRUGS SUBMITTED UNDER AN ANDA (2013). All testing was performed in subjects two hours after eating a standardized dinner. A test product with finished composition of Example 1 and manufactured at larger scale was administered in sequential ascending doses, 4.5 g, 7.5 g and 9 g, one week apart. The tested samples were manufactured as described in Table 1c for 4.5 g and quantities were homothetically adjusted for the other strengths. The dissolution profiles of the MR portions of the test product are presented in FIGS. 86 and 87. The dissolution profiles of the test product are presented in FIGS. 88 and 89. The individual concentrations of gamma-hydroxybutyrate and derived PK parameters are summarized below (Tables 18a and 18b) and in FIG. 90.

TABLE 18a

Pharmacokinetic Parameters of 4.5 g, 7.5 g, and 9 g

| Finished composition of test product | Mean $C_{max}$ (µg/mL) (% CV) | Mean $AUC_{inf}$ (µg/mL * h) (% CV) | Mean $AUC_{8h}$ (µg/mL * h) (% CV) | Median $T_{max}$ (hour) (min-max) | Mean $C_{8h}$ (µg/mL) (% CV) |
|---|---|---|---|---|---|
| 4.5 g | 42.9 (37) | 191 (50) | 174 (55) | 1.71 (0.333-4) | 4.76 (105) |
| 7.5 g | 72.0 (32) | 357 (48) | 320 (46) | 1.5 (0.333-7) | 19.7 (101) |
| 9.0 g | 84.5 (34) | 443 (46) | 379 (41) | 2 (0.5-4) | 25.5 (97) |

AUC and $C_{max}$ values increased more than dose-proportionally with increasing doses of gamma-hydroxybutyrate formulated as the test product.

TABLE 18b

Mean plasma concentration of gamma-hydroxybutyrate (microgram/mL) versus time of finished composition of test product

| Time (hr) | Test product 4.5 g (2 h after meal) (N = 20) | Test product 7.5 g (2 h after meal) (N = 20) | Test product 9 g (2 h after meal) (N = 12) |
|---|---|---|---|
| 0 | 0.00 | 0.00 | 0.00 |
| 0.167 | 12.5 | 17.7 | 9.34 |
| 0.333 | 23.4 | 39.0 | 32.7 |
| 0.5 | 28.1 | 48.4 | 47.5 |
| 1 | 34.7 | 59.8 | 60.9 |
| 1.5 | 36.7 | 63.8 | 71.6 |
| 2 | 35.7 | 61.6 | 79.3 |
| 2.5 | 34.7 | 56.0 | 64.9 |
| 3 | 29.8 | 50.1 | 65.3 |
| 3.5 | 26.9 | 46.0 | 60.0 |
| 4 | 23.5 | 40.9 | 60.8 |
| 4.5 | 20.1 | 36.6 | 48.8 |
| 5 | 17.3 | 32.7 | 45.3 |
| 5.5 | 15.4 | 30.8 | 41.3 |
| 6 | 13.4 | 28.7 | 37.6 |
| 7 | 9.66 | 24.7 | 30.5 |
| 8 | 4.76 | 19.7 | 25.5 |
| 10 | 0.727 | 6.97 | 13.0 |
| 12 | 0.211 | 1.35 | 5.13 |
| 14 | NC | 0.392 | 0.820 |

NC: Not Calculated

Table 18c compares the pharmacokinetic parameters AUCinf and C8h obtained for 4.5 g of the test product to the same parameters calculated 2×2.25 g, i.e. 4.5 g total dose of Xyrem®.

TABLE 18c

Comparison to 4.5 g divided dose of Xyrem ®

| | Mean $C_{8h}$ (µg/mL) | Ratio (%) $C_{8h}$ composition to $C_{8h}$ Xyrem ® | Mean $AUC_{inf}$ (µg/mL * h) | Ratio (%) $AUC_{inf}$ composition to $AUC_{inf}$ Xyrem ® |
|---|---|---|---|---|
| Xyrem ® 2 × 2.25 g * | 9.24 | NA | 214 | NA |
| Test product 4.5 g | 4.76 | 52% | 191 | 89% |

* data from the pilot PK study of example 3

Table 18d compares the pharmacokinetic parameters AUCinf and C8h obtained for 7.5 g of the test product to the same parameters calculated 2×3.75 g, i.e. 7.5 g total dose of Xyrem®.

TABLE 18d

Comparison to 7.5 g divided dose of Xyrem ®

| | Mean $C_{8h}$ (µg/mL) | Ratio (%) $C_{8h}$ composition to $C_{8h}$ Xyrem ® | Mean $AUC_{inf}$ (µg/mL * h) | Ratio (%) $AUC_{inf}$ composition to $AUC_{inf}$ Xyrem ® |
|---|---|---|---|---|
| Xyrem ® 2 × 3.75 g (extrapolation from 2 × 4.5 g *) | 24.1 | NA | 432 | NA |
| Test product 7.5 g | 19.7 | 82% | 357 | 83% |

* based on data from NDA #21-196

Table 18e compares the pharmacokinetic parameters $AUC_{inf}$ and $C_{8h}$ obtained for 7.5 g and 9 g of the test product to the same parameters calculated for 2×4.5 g, i.e. 9 g total dose of Xyrem®.

TABLE 18e

Comparison to 9 g divided dose of Xyrem ®

| | Mean $C_{8h}$ (µg/mL) | Ratio (%) $C_{8h}$ composition to $C_{8h}$ Xyrem ® | Mean $AUC_{inf}$ (µg/mL * h) | Ratio (%) $AUC_{inf}$ composition to $AUC_{inf}$ Xyrem ® |
|---|---|---|---|---|
| Xyrem ® 2 × 4.5 g * | 28.9 | NA | 518 | NA |
| Test product 7.5 g | 19.7 | 68% | 357 | 69% |
| Test product 9 g | 25.5 | 88% | 443 | 86% |

* data from NDA #21-196

For the finished composition administered at 4.5 g, mean $C_{6h}$, mean $C_{7h}$ are greater than, and mean $C_{10h}$ are less than, the mean $C_{4h}$ of the dose of Xyrem®. In addition, the ratio $C_{3h}/C_{max}$(Xyrem®) is 1.03. The ratio $C_{4h}/C_{max}$(Xyrem®) is 0.81. The ratio $C_{4.5h}/C_{max}$(Xyrem®) is 0.69.

For the finished composition administered at 7.5 g, mean $C_{6h}$, mean $C_{7h}$ are greater than, and mean $C_{10h}$ are less than, the mean $C_{4h}$ of the dose of Xyrem®. In addition, the ratio $C_{3h}/C_{max}$(Xyrem®) is 0.77. The ratio $C_{4h}/C_{max}$(Xyrem®) is 0.63. The ratio $C_{4.5h}/C_{max}$(Xyrem®) is 0.57.

For the finished composition administered at 9 g, mean $C_{6h}$, mean $C_{7h}$ are greater than, and mean $C_{10h}$ are less than, the mean $C_{4h}$ of the dose of Xyrem®. In addition, the ratio $C_{3h}/C_{max}$(Xyrem®) is 0.84. The ratio $C_{4h}/C_{max}$(Xyrem®) is 0.78. The ratio $C_{4.5h}/C_{max}$(Xyrem®) is 0.63.

For the finished composition administered at 7.5 g compared to Xyrem® at 2×4.5 g, i.e. total dose of 9 g, the ratio $C_{3h}/C_{max}$(Xyrem®) is 0.65. The ratio $C_{4h}/C_{max}$(Xyrem®) is 0.53. The ratio $C_{4.5h}/C_{max}$(Xyrem®) is 0.47.

Example 19: Clinical Study of Composition According to Example 1

The efficacy of the composition according to Example 1 (FT218) for the treatment of cataplexy or excessive daytime sleepiness (EDS) in adults with narcolepsy was established based on a double-blind, randomized, placebo-controlled, two arm multi-center study to assess the efficacy and safety of a once nightly administration of FT218 in patients with narcolepsy. In some instances, FT218 may be referred to as LUMRYZ.

A total of 212 subjects were randomized to the active or placebo arm in a 1:1 ratio. The study was divided into four sequential study periods and incorporates dose titration to stabilized dose administration of FT218 (4.5 g, 6 g, 7.5 g, and 9 g). There was a three-week screening period, a 13-week treatment period including up-titration over a period of eight weeks and five weeks of stable dosing at 9 g/night, and a one-week follow-up period. The up-titration included dosing at 4.5 g for week 1, dosing at 6 g for weeks 2-3, dosing at 7.5 g for weeks 4-8, and dosing at 9 g for weels 9-13. Stable dosing at 9 g/night means the dosing did not change once the 9 g dose was given. Patients could be on concomitant stimulant use as long as it was stable for 3 weeks prior to study start.

The three co-primary endpoints were the Maintenance of Wakefulness Test (MWT), Clinical Global Impression-Improvement (CGI-I) and mean change in weekly cataplexy attacks. The Epworth Sleepiness Scale (ESS) was a secondary endpoint in the study. Other measures include the number of arousals determined by PSG, the Visual analogue scale (VAS), number of hypnogogic hallucination, and number of sleep paralysis. The results of these endpoints may be found in Tables 19a-19i.

The Maintenance of Wakefulness Test measures latency to sleep onset (in minutes) averaged over five sessions at 2-hour intervals following nocturnal polysomnography. For each test session, patients were instructed to remain awake for as long as possible during 30-minute test sessions, and sleep latency was determined as the number of minutes patients could remain awake. The overall score was the mean sleep latency for the 5 sessions. The Clinical Global Impression-Improvement was evaluated on a 7-point scale, centered at No Change and ranging from Very Much Worse to Very Much Improved. Patients were rated by evaluators who based their assessments on the severity of narcolepsy at Baseline.

ESS total score is defined as the sum of the eight item scores, or the sum of the available item scores and imputed item scores (as the average of the available ones) if one or two item scores are missing. If more than two of the eight item scores have missing results, ESS score will be assigned as missing. Higher total scores indicate a greater tendency to sleepiness. Baseline is defined as the last assessment at Visit 2. Arousals are the number of transient arousals on the nocturnal polysomnogram (PSG) as defined by the American Academy of Sleep Medicine Scoring Guidelines for the PSG. Visual analogue scale (VAS) was part of the Sleep and Symptom Daily Diary with two categories, i.e. sleep quality and refreshing nature of sleep. Each category is a 1-100 scale with 1 indicating "did not sleep" or "not refreshed", and 100 indicating "slept very well" or "refreshed", respectively. VAS is the mean of the responses to the quality of sleep question averaged over the past 14 days preceding the test day. Number of Hypnogogic Hallucination (HH) was collected via the Sleep and Symptom Daily Diary. Averaged quantity of HH and/or their log transformed data, whichever gives minimal AIC was used in this MMRM analysis. Number of Sleep Paralysis (SP) is collected via the Sleep and Symptom Daily Diary. Averaged quantity of SP and/or their log transformed data, whichever gives minimal AIC will be used in this MMRM analysis. Averaged quantity was calculated as the number of events averaged over the 14 days preceding the test day. If a week had less than 3 days of Diary entries, data (both the score and count of days) collected of that week would be considered invalid and excluded from analyses. Baseline is calculated as the mean of the past 14 days preceding Visit 2.

Demographic and mean Baseline characteristics were similar for the FT218 and placebo groups. A total of 76% were NT1 patients and 24% were NT2 patients. Mean age was 31.2 years and 68% was female. Approximately 63% patients were on concomitant stimulant use. The mean MWT at Baseline was 5 minutes for the FT218 group and 4.7 minutes for the placebo group. The mean number of cataplexy attacks per week at Baseline was 18.9 in the FT218 group and 19.8 in the placebo group. For the three co-primary endpoints, statistically significant improvement was seen on the Maintenance of Wakefulness Test, Clinical Global Impression-Improvement and mean weekly cataplexy attacks for the 6 g (Week 3), 7.5 g (Week 8) and 9 g (Week 13) dose of FT218 compared to the placebo group (see Tables 19a, 19b, and 19c). Results (MWT and CGI-I) were consistent between NT1 and NT2 patients as well as patients on stimulants compared to those not on stimulants.

TABLE 19a

Change from Baseline in the Maintenance of Wakefulness Test (in minutes)

| Dose | Treatment Group (N) | Change from Baseline (SE) | Difference from Placebo [95% CI] | p-value |
|---|---|---|---|---|
| 6 g (Week 3) | FT218 (87) | 8.08 (0.75) | 4.98 [2.90;7.05] | <0.001 |
|  | Placebo (88) | 3.10 (0.74) |  |  |
| 7.5 g (Week 8) | FT218 (76) | 9.55 (0.86) | 6.21 [3.84;8.58] | <0.001 |
|  | Placebo (78) | 3.34 (0.84) |  |  |
| 9 g (Week 13) | FT218 (68) | 10.82 (0.96) | 6.13 [3.52,8.75] | <0.001 |
|  | Placebo (78) | 4.69 (0.92) |  |  |

Mean (SD) MWT at Baseline was 4.99 (3.15) minutes for the FT218 group and 4.73 (2.58) minutes for the placebo group.

TABLE 19b

Proportion of Patients with a Very Much or Much Improved Clinical Global Impression-Improvement

| Dose | Treatment Group (N) | Percentage of Responders (Much or Very Much Improved) | Odds Ratio [95% CI] | p-value |
|---|---|---|---|---|
| 6 g (Week 3) | FT218 (87) | 40.1 | 10.29 [3.93;26.92] | <0.001 |
|  | Placebo (87) | 6.1 | — | — |
| 7.5 g (Week 8) | FT218 (75) | 62.6 | 5.67 [2.82;11.40] | <0.001 |
|  | Placebo (81) | 22.8 | — | — |
| 9 g (Week 13) | FT218 (69) | 72.0 | 5.56 [2.76;11.23] | <0.001 |
|  | Placebo (79) | 31.6 | — | — |

TABLE 19c

Change from Baseline in the Mean Cataplexy Attacks Per Week

| Dose | Treatment Group (N) | Change from Baseline (SE) | Difference from Placebo [95% CI] | p-value |
|---|---|---|---|---|
| 6 g (Week 3) | FT218 (55) | −7.42 (0.79) | −4.83 [−7.03;−2.62] | <0.001 |
| | Placebo (62) | −2.59 (0.79) | — | — |
| 7.5 g (Week 8) | FT218 (66) | −9.98 (0.88) | −6.23 [−8.74;−3.80] | <0.001 |
| | Placebo (69) | −3.71 (0.88) | — | — |
| 9 g (Week 13) | FT218 (73) | −11.51 (0.96) | −6.65 [−9.32;−3.98] | <0.001 |
| | Placebo (72) | −4.86 (0.945) | — | — |

Mean (SD) number of cataplexy attacks per week at Baseline was 18.93 (8.70) in the FT218 group and 19.82 (8.87) in the placebo group.

TABLE 19d

Change from Baseline in the Mean Disturbed Nocturnal Sleep (DNS) measured by polysomnography (PSG)

| Dose | Treatment Group (N) | Change from Baseline (SE) | Difference from Placebo [95% CI] | p-value |
|---|---|---|---|---|
| 6 g (Week 3) | FT218 (88) | −9.7 (1.82) | −11.00 [−16.07;−5.93] | <0.001 |
| | Placebo (88) | 1.31 (1.81) | — | — |
| 7.5 g (Week 8) | FT218 (76) | −15.00 (2.32) | −17.70 [−24.12;−11.28] | <0.001 |
| | Placebo (79) | 2.70 (2.28) | — | — |
| 9 g (Week 13) | FT218 (69) | −20.54 (2.19) | −22.63 [−28.60;−16.66] | <0.001 |
| | Placebo (78) | 2.09 (2.09) | — | — |

Mean (SD) disturbed nocturnal sleep (DNS) measured by PSG at Baseline was 60.1 (23.37) in the FT218 group and 60.3 (21.77) in the placebo group.

TABLE 19e

Change from Baseline in the Epworth Sleepiness Scale (ESS)

| Dose | Treatment Group (N) | Change from Baseline (SE) | Difference from Placebo [95% CI] | p-value |
|---|---|---|---|---|
| 6 g (Week 3) | FT218 (93) | −3.48 (0.42) | −2.06 [−3.23;−0.89] | <0.001 |
| | Placebo (91) | −1.42 (0.42) | — | — |
| 7.5 g (Week 8) | FT218 (83) | −5.34 (0.54) | −3.16 [−4.67;−1.64] | <0.001 |
| | Placebo (85) | −2.18 (0.54) | — | — |
| 9 g (Week 13) | FT218 (73) | −6.52 (0.58) | −3.86 [−5.47;−2.26] | <0.001 |
| | Placebo (80) | −2.66 (0.57) | — | — |

Mean (SD) Epworth Sleepiness Scale (ESS) at Baseline was 16.6 (3.84) in the FT218 group and 17.5 (4.04) in the placebo group.

TABLE 19f

Change from Baseline in the Number of Arousals Determined by PSG

| Dose | Treatment Group (N) | Change from Baseline (SE) | Difference from Placebo [95% CI] | p-value |
|---|---|---|---|---|
| 6 g (Week 3) | FT218 (88) | −31.32 (3.45) | −11.29 [−20.89;−1.69] | <0.001 |
| | Placebo (88) | −20.03 (3.44) | — | — |
| 7.5 g (Week 8) | FT218 (76) | −39.16 (3.83) | −19.41 [−30.00;−8.82] | <0.001 |
| | Placebo (79) | −19.75 (3.76) | — | — |
| 9 g (Week 13) | FT218 (69) | −39.39 (4.15) | −23.68 [−35.01;−12.35] | <0.001 |
| | Placebo (78) | −15.71 (3.96) | — | — |

Mean (SD) number of arousals determined by PSG at Baseline was 81.8 (43.68) in the FT218 group and 77.2 (38.13) in the placebo group.

TABLE 19g

Change from Baseline in the Visual Analogue Scale (VAS) for Sleep Quality

| Dose | Treatment Group (N) | Change from Baseline (SE) | Difference from Placebo [95% CI] | p-value |
|---|---|---|---|---|
| 6 g (Week 3) | FT218 (97) | 11.94 (1.11) | 6.95 [3.84;10.06] | <0.001 |
| | Placebo (93) | 4.99 (1.12) | — | — |
| 7.5 g (Week 8) | FT218 (83) | 18.83 (1.40) | 9.87 [5.98;13.76] | <0.001 |
| | Placebo (85) | 8.96 (1.39) | — | — |
| 9 g (Week 13) | FT218 (73) | 21.40 (1.66) | 10.41 [5.82;15.01] | <0.001 |
| | Placebo (79) | 10.98 (1.63) | — | — |

Mean (SD) visual analogue scale for sleep quality at Baseline was 53.78 (20.85) in the FT218 group and 55.94 (22.62) in the placebo group.

TABLE 19h

Change from Baseline in the Number of Hypnogogic Hallucination (HH)

| Dose | Treatment Group (N) | Change from Baseline (SE) | Difference from Placebo [95% CI] | p-value |
|---|---|---|---|---|
| 6 g (Week 3) | FT218 (73) | −0.12 (0.02) | −0.014 [−0.08;0.05] | <0.001 |
| | Placebo (72) | −0.11 (0.02) | — | — |
| 7.5 g (Week 8) | FT218 (62) | −0.21 (0.03) | −0.08 [−0.17;0.01] | <0.001 |
| | Placebo (65) | −0.13 (0.03) | — | — |
| 9 g (Week 13) | FT218 (54) | −0.24 (0.04) | −0.07 [−0.17;0.04] | <0.001 |
| | Placebo (62) | −0.17 (0.04) | — | — |

Mean (SD) number of hypnogogic hallucinations at Baseline was 0.45 (0.40) in the FT218 group and 0.52 (0.41) in the placebo group.

TABLE 19i

Change from Baseline in the Number of Sleep Paralysis (SP)

| Dose | Treatment Group (N) | Change from Baseline (SE) | Difference from Placebo [95% CI] | p-value |
|---|---|---|---|---|
| 6 g (Week 3) | FT218 (73) | −0.28 (0.06) | −0.19 [−0.37;−0.01] | <0.001 |
| | Placebo (72) | −0.09 (0.06) | — | — |
| 7.5 g (Week 8) | FT218 (62) | −0.42 (0.07) | −0.22 [−0.41;−0.04] | <0.001 |
| | Placebo (65) | −0.20 (0.07) | — | — |
| 9 g (Week 13) | FT218 (54) | −0.43 (0.08) | −0.23 [−0.45;−0.014] | <0.001 |
| | Placebo (62) | −0.19 (0.08) | — | — |

Mean (SD) number of sleep paralysis at Baseline was 0.67 (0.95) in the FT218 group and 0.94 (1.38) in the placebo group.

Example 20: Pharmacokinetics of FT218 Embodiment

A pilot study, dose-proportionality study, relative bioavailability study, and food-effect study were conducted. Individuals eligible for study enrollment were men or women (white/non-Hispanic or Latino) 18-65 years of age who weighed 60 kg with a body mass index of 18e28 kg/m2 and were considered healthy by comprehensive clinical assessment (detailed medical history and complete physical examination). All participants had normal supine blood pressure and heart rate, ECG findings, laboratory parameters, and dietary habits and were nonsmokers (or able to abstain from smoking during the clinical inpatient period). Women were required to be nonpregnant and nonlactating, and all participants had to use adequate forms of contraception if sexually active. Specific exclusion criteria across studies included succinic semialdehyde dehydrogenase deficiency, sleep apnea, suicidal ideation, migraine, symptomatic hypotension, asymptomatic postural hypotension, use of renal or hepatic-clearing medication within 30 days of study start, use of vitamins (such as St. John's wort) within 21 days of study start, positive drug screen result, or alcohol use. All participants provided written informed consent for participation, and studies were approved by the local institutional review board or independent ethics committee. Studies were performed in accordance with the Declaration of Helsinki.

In each of the four studies, at each sampling time point, 4-6 mL of blood was drawn (via indwelling intravenous catheter or direct venipuncture) in a heparinized tube and centrifuged at 1500 g for 5 min at 4 C within 30 min of blood draw. At least 2 mL of the top layer of plasma was transferred into 2 prelabeled polypropylene tubes, each containing at least 1000 mL of plasma and frozen at −70° C. (+/−15° C.) within 2 h. Blood samples were sent for analysis to Eurofins/ADME Bioanalyses. Concentrations of GHB in sodium heparinized human plasma were assayed according to an analytical method validated by Eurofins/ADME Bioanalyses. The method involves a liquideliquid extraction followed by LC-MS/MS with a calibration range of 0.2 mg/mL as the lower limit of quantitation to 150 mg/mL as the upper limit of quantitation. Quality control principles were applied throughout the performance of the studies. All study samples were analyzed with analytical runs that complied with acceptance ranges for the quality control samples. Frozen quality control samples at 3 times the lower limit of quantitation (0.6 mg/mL), 0.5 times the upper limit of quantitation (75 mg/mL), and 0.8 times the upper limit of quantitation (120 mg/mL) GHB concentration levels were used. The quality control concentration levels covered the study sample concentration range of 0.204-143 mg/mL. Incurred sample reanalysis was approximately 98%, met the acceptance criteria, and indicated the robustness of the analytical method. Pharmacokinetic parameters were calculated using noncompartmental analysis with Kinetica software or WinNonlin software.

Evaluated pharmacokinetic parameters were estimated from the plasma concentration time data for plasma GHB and included $C_{max}$, $t_{max}$, concentration 8 h after administration ($C_{8h}$), $AUC_{0-8}$, $AUC_{inf}$, and $AUC_{0-t}$). AUC was calculated using log-transformed data (logarithmic trapezoid method). In the pilot study, pharmacodynamic effects were explored using the Leeds Sleep Evaluation Questionnaire (LSEQ; getting to sleep, quality of sleep, awake following sleep, behavior following wakening) and actigraphy (sleep time >8 h).

Safety evaluations included AE reporting, physical examination, and monitoring of vital signs and clinical laboratory values. It was prespecified that participants who vomited after study drug intake were excluded from the primary analysis.

Statistical analyses were performed using SAS statistical software. Descriptive statistics with no formal statistical analysis were used for safety parameters, general analysis of pharmacokinetic parameters in all studies, and LSEQ scores and actigraphy in the pilot study. Variability of concentrations of FT218 and twice-nightly SO were compared in terms of SD. Bioequivalence was analyzed using the two 1-sided test procedure on log-transformed data for $C_{max}$, $AUC_{0-t}$, and $AUC_{inf}$ and was defined as 90% CIs for ratios of geometric means falling within the 80%-125% range.

Dose proportionality was assessed using the power model with slope estimate and 90% CI for dosenormalized pharmacokinetic data. Sensitivity analyses were performed using ANOVA on log-transformed normalized data.

Pilot Study

The pilot study was a randomized, open-label, crossover study to evaluate the pharmacokinetic properties, safety profile, and tolerability of 3 formulations of FT218 (prototypes 1, 2, and 3) compared with twice-nightly sodium oxybate (SO). Participants were randomized 1:1:1:1 to a single 4.5-g dose of each formulation of FT218 or 4.5 g twice-nightly SO (given as two 2.25-g doses 4 h apart) in 4 different sequential orders separated by a washout period of 3 days.

The pilot study included 16 participants (8 men and 8 women), with a mean (SD) age of 39.5 (11.9) years. There were no study discontinuations due to adverse events (AEs).

In the pilot study, for FT218 treatment, blood samples were collected from all participants before dosing and at 30 min and 1, 1.5, 2, 2.5, 3, 3.5, 4, 4.5, 5, 5.5, 6, 6.5, 7, 7.5, 8, 10, and 12 h after dosing. For twice-nightly SO treatment, the same time points were used for the first dose (omitting the 2.5-hour collection), with an additional collection 20 min after the second dose (at 4 h 20 min).

Each of the 3 FT218 formulations exhibited an extended-release profile with $t_{max}$ at approximately 2 h, followed by a gradual decline in plasma GHB concentration (Table 20a and FIG. 134). $C_{max}$ for the 3 FT218 formulations was lower than the global $C_{max}$ of twice-nightly SO (mean [SE] $C_{max}$ was 43 [6] µg/mL for prototype 1, 46 [5] µg/mL for prototype 2, 30 [4] µg/mL for prototype 3, and 66 [7] µg/mL for twice-nightly SO). Mean (SE) $AUC_{inf}$ was 189 (28) h*mg/mL for prototype 1, 210 (28) h*µg/mL for prototype 2, 153 (22) h*mg/mL for prototype 3, and 214 (27) h*µg/mL for twice-nightly SO. $C_{8h}$ values were numerically lower for the 3 FT218 formulations (mean [SE] prototype 1, 6.85 [2.1]; prototype 2, 7.40 [1.6]; prototype 3, 8.33 [1.9] µg/mL) relative to twice-nightly SO (mean [SE], 9.24 [3.2] µg/mL).

TABLE 20a

Pharmacokinetic properties in the pilot study

| | FT218 4.5 g | | | Twice-Nightly |
| --- | --- | --- | --- | --- |
| Parameter | Type 1 (n = 12) | Type 2 (n = 12z0) | Type 3 (n = 12) | SO 4.5 g (n = 12) |
| $C_{max}$, mean (SE), µg/mL | 43 (6) | 46 (5) | 30 (4) | 66 (7) |
| $AUC_{inf}$, mean (SE), h * µg/mL | 189 (28) | 210 (28) | 153 (22) | 214 (27) |
| $C_{8h}$, mean (SE), µg/mL | 6.85 (2.09) | 7.40 (1.63) | 8.33 (1.93) | 9.24 (3.15) |

Prototype 2 was selected for further optimization and used in the remainder of the studies because it exhibited pharmacokinetic characteristics closest to the desired target profile, with higher $C_{max}$ compared with other prototypes and $AUC_{inf}$ comparable to that of twice-nightly SO. For each LSEQ domain and sleep time >8 h, there appeared to be no clinically meaningful differences between the FT218 prototypes and twice-nightly SO.

Four participants reported a total of 5 Aes. All AEs were mild to moderate in severity, with no SAEs or AEs leading to study discontinuation. AEs were comparable between the 3 prototypes of FT218 and twice-nightly SO.

Dose-Proportionality Study

The dose-proportionality study was an open-label, single-dose, 3-sequential period study to assess the pharmacokinetic properties, safety profile, and tolerability of single dose FT218 (optimized prototype selected from the pilot study) 4.5, 7.5, and 9 g, and to estimate dose proportionality. Participants received 3 separate single doses of FT218 (without titration) in a sequential order of 4.5, 7.5, and 9 g with a minimum 7-day washout period between doses.

The dose-proportionality study included 20 individuals (12 men and 8 women), with a mean (SD) age of 45.5 (12.5) years. All participants completed the 4.5- and 7.5-g periods of the study, and 12 of 20 participants (60.0%) completed the 9-g period. The study was stopped by the sponsor after a serious AE (SAE) of somnolence in 1 individual (described below) after 12 participants were given the 9-g dose level without titration. One individual was withdrawn owing to a positive drug screen.

In the dose-proportionality study, blood samples were collected before dosing; at 10, 20, and 30 min after dosing; and at 1, 1.5, 2, 2.5, 3, 3.5, 4, 4.5, 5, 5.5, 6, 7, 8, 10, 12, and 14 h after dosing.

At all 3 doses of FT218, mean pharmacokinetic properties exhibited similar overall profiles (Table 20b and FIG. 135). The $t_{max}$ was reached after approximately 1.5-2 h followed by a gradual decline in GHB concentration. Mean (SD) $C_{max}$ increased with increasing doses of FT218 (42.9 [15.8] µg/mL at 4.5 g, 72.0 [23.3] µg/mL at 7.5 g, and 84.5 [28.6] µg/mL at 9 g). Similarly, mean (SD) $AUC_{inf}$ increased with increasing doses of FT218 (191 [94.7]h*µg/mL at 4.5 g, 358 [170] h*µg/mL at 7.5 g, and 443 [202] h*µg/mL at 9 g). Mean (SD) $C_{8h}$ also increased with increasing doses of FT218 (4.8 [5.01] µg/mL at 4.5 g, 19.7 [19.9] µg/mL at 7.5 g, and 25.5 [24.8] µg/mL at 9 g). Moreover, the variability of the concentrations was similar.

TABLE 20b

Pharmacokinetic properties in the dose-proportionality study

| Parameter | FT218 4.5 g (n = 20) | FT218 7.5 g (n = 20) | FT218 9 g (n = 11) |
|---|---|---|---|
| $T_{max}$, median (range), h | 1.71 (0.33-4) | 1.5 (0.33-7) | 2 (0.5-4) |
| $C_{max}$, mean (SD), µg/mL [CV] | 42.9 (15.8) [37] | 72.0 (23.3) [32] | 84.5 (28.6) [34] |
| $AUC_{inf}$, mean (SD), h * µg/mL [CV] | 191 (94.7) [50] | 358 (170) [48] | 443 (202) [46] |
| $AUC_{0-8}$, mean (SD), h * µg/mL [CV] | 174 (96.3) [55] | 320 (148) [46] | 379 (154) [41] |
| $C_{8h}$, mean (SD), µg/mL [CV] | 4.76 (5.01) [37] | 19.7 (19.9) [101] | 25.5 (24.8) [97] |

Using the power method, the estimated slope of $C_{max}$ was 1.02 (90% CI, 0.76-1.28), indicating dose proportionality, and the estimated slope of $AUC_{inf}$ was 1.34 (90% CI, 1.19-1.48), which indicated that dose-dependent increase in $AUC_{inf}$ was slightly more than proportional. These results were consistent with ANOVA sensitivity analyses.

Thirteen participants (65%) reported a total of 31 AEs. The incidence of AEs increased with increasing doses. Eight AEs (mainly headache [n=5/8]) were experienced by 7 of 20 participants (35%) during the 4.5-g period, 7 AEs (mainly gastrointestinal disorders [n=4/7]) were experienced by 4 of 20 participants (20%) during the 7.5-g period; and 16 AEs (mainly gastrointestinal disorders [n=8/16]) were experienced by 6 of 12 participants (50%) during the 9-g period. One of these, a nervous system disorder (sedation), was an SAE. This SAE was most likely a result of treatment at 9 g without subsequent continuous titration through the lower doses of FT218; however, even without titration, AEs at the 9-g dose only occurred in 50% of participants and were mainly mild to moderate in severity. All AEs were resolved before the end of the study.

Relative Bioavailability Study

The relative bioavailability study was a randomized, open-label, crossover study to evaluate the relative bioavailability of FT218 compared with twice-nightly SO. Participants were randomized 1:1 to a single dose of 6 g FT218 or 6 g twice-nightly SO (given as two 3-g doses 4 h apart) with a washout period of ≥3 days between treatments. For the pilot, doseproportionality, and relative bioavailability studies, FT218 or the first dose of twice-nightly SO was administered at approximately 9:00 PM, 2 h after a standardized dinner (1251 kcal, 19.6 g of protein, 25.5 g of fat, and 54.9 g of carbohydrate).

The relative bioavailability study included 28 individuals (10 men and 18 women), with a mean (SD) age of 27 (9) years. Overall, 26 of 28 participants completed both study phases per protocol, and the remaining 2 participants withdrew prematurely owing to AEs.

In the relative bioavailability study, for FT218 treatment, blood samples were collected from all participants before dosing; at 10, 20, and 30 min after dosing; and at 1, 1.5, 2, 2.5, 3, 3.5, 4, 4.5, 5, 5.5, 6, 7, 8, 10, 12, and 14 h after dosing. The same time points were used in reference to the first dose of twice-nightly SO, omitting the 3.5-hour collection; there were 2 additional collections at 10 and 20 min after the second dose of twice-nightly SO (at 4 h, 10 min, and at 4 h 20 min).

Once-nightly FT218 6 g had equivalent exposure with a lower overall $C_{max}$ than twice-nightly SO at a total dose of 6 g (Table 20c and FIG. 136). Mean (SE) $AUC_{inf}$ of FT218 6 g (273 [27] h*µg/mL) met bioequivalence criteria compared with $AUC_{inf}$ of twice-nightly SO 6 g (259 [22] h*µg/mL). Mean (SE) $C_{max}$ of FT218 6 g (64.6 [5] µg/mL) was lower (below bioequivalence criteria) than overall $C_{max}$ of twice-nightly SO 6 g (70.9 [4] µg/mL). Mean (SE) $AUC_{0-8}$ of FT218 6 g (267 [27] h*µg/mL) also met bioequivalence criteria compared with $AUC_{0-8}$ of twice-nightly SO 6 g (248 [18] h*µg/mL). Mean (SE) $C_{8h}$ for FT218 6 g (6.6 [1]µg/mL) was lower (below equivalence criteria) than $C_{8h}$ of twice-nightly SO 6 g (10.7 [3]µg/mL). Interpatient variability between the 2 treatments was similar for all pharmacokinetic parameters.

TABLE 20c

Pharmacokinetic properties in the relative bioavailability study

| Parameter | FT218 6 g (n = 26) | Twice-Nightly SO 6 g (First Dose) (n = 27) |
|---|---|---|
| $T_{max}$, median (range), h | 1.50 (0.3-3.5) | 0.05 (0.3-2.0) |
| $C_{max}$, mean (SD), µg/mL [CV] | 64.6 (5) [40] | 70.9 (4) [28] |
| $AUC_{inf}$, mean (SD), h * µg/mL [CV] | 273 (27) [51] | 259 (22) [44] |
| $AUC_{0-8}$, mean (SD), h * µg/mL [CV] | 267 (27) [51] | 248 (18) [39] |
| $C_{8h}$, mean (SD), µg/mL [CV] | 6.6 (1) [108] | 10.7 (3) [145] |

The incidence and types of AEs were similar between the FT218 and twice-nightly SO groups, and most were known SO-related AEs. The most common AE during both treatments was somnolence, and all AEs were mild or moderate in severity. There were no SAEs during the study. Two participants withdrew from the study after experiencing AEs, including 1 event of nausea after FT218 treatment and 1 event of flulike symptoms after twice-nightly SO treatment.

Food-Effect Study

The food-effect study was an open-label, 2-period, crossover, single-dose study to assess the effect of food on the pharmacokinetic properties of single-dose FT218 6 g. Participants were randomized 1:1 to single-dose FT218 6 g after a 10-hour overnight fast (fasted state) or 30 min after a standardized, high-fat breakfast (fed state; 50% total content of meal consisting of fat and 800e1000 kcal, of which 150 kcal was derived from protein, 250 kcal derived from carbohydrate, and 500-600 kcal derived from fat) with a minimum 3-day washout between study periods. For all studies, FT218 was administered orally as a powder reconstituted as a suspension in 50-70 mL of water. Twice-nightly SO was administered orally as a 500-mg/mL solution diluted in 60 mL of water in divided doses given 4 h apart. All treatments were administered under investigator supervision and were followed by a hospitalization period of 16-36 h.

The food-effect study included 16 individuals (10 men and 6 women), with a mean (SD) age of 32 (13) years. A total of 15 of 16 participants completed the study per protocol. One individual discontinued participation in the study because of vomiting after receiving FT218 in the fasted state. Two individuals were also excluded from the pharmacokinetic analysis set because of vomiting.

In the food-effect study, during the fed and fasted study periods, blood samples were collected before dosing; at 10, 20, and 30 min after dosing; and at 1, 1.5, 2, 2.5, 3, 3.5, 4, 4.5, 5, 5.5, 6, 7, 8, 10, 12, and 14 h after dosing.

FT218 had lower $C_{max}$ in the fed versus the fasted state, and exposure met bioequivalence criteria (Table 20d and FIG. 137). Mean $t_{max}$ was 1 h longer in the fed versus the fasted state (1.5 vs 0.5 h). Mean (SE) $C_{max}$ in the fed state (64.0 [5] µg/mL) was lower than in the fasted state (90.5 [4] µg/mL) and was below the bioequivalence 80%-125% no-effect boundaries (mean fed:fasted ratio, 66.7%; 90% CI, 58.2%-76.5%). Mean (SE) $AUC_{inf}$ the fasted state (267 [24] h*µg/mL) was slightly higher than in the fed state (242 [24] h*µg/mL), but the 90% CIs were within the 80%-125% no-effect boundaries for bioequivalence (mean fed:fasted ratio, 86.1%; 90% CI, 80.0%-92.7%).

TABLE 20d

Pharmacokinetic properties in the food effect study

| | FT218 6 g | |
|---|---|---|
| Parameter | Fed (n = 14) | Fasted (n = 13) |
| $T_{max}$, median (range), h | 1.50 (0.5-2.5) | 0.53 (0.33-1) |
| $C_{max}$, mean (SD), µg/mL [CV] | 64.0 (5) [27.3] | 90.5 (4) [17.5] |
| $AUC_{inf}$, mean (SD), h*µg/mL [CV] | 242 (24) [36.5] | 267 (24) [32] |
| $AUC_{0-8}$, mean (SD), h*µg/mL [CV] | 239 (23) [35.5] | 266 (23) [31.2] |
| $C_{8h}$, mean (SD), µg/mL [CV] | 2.09(1) [150.5] | 1.43 (1) [142.7] |

The frequency of AEs was higher in the fasted versus the fed state (58 AEs in all 16 participants [100%, with 54 potentially related to study treatment] in the fasted state and 32 AEs in 13 participants [86.7%, 31 potentially related to study treatment] in the fed state). This finding was primarily driven by an increase in gastrointestinal disorders (37.5% in the fasted state vs 13.3% in the fed state; most commonly nausea and vomiting) and nervous system disorders (all participants in the fasted state vs 80.0% in the fed state; most commonly somnolence and dizziness). All events were mild or moderate in severity, and no SAEs were reported.

Example 21: Labeling for FT218 Embodiment

Warning: Central Nervous System (CNS) Depression and Abuse and Misuse.

Central Nervous System Depression

Sodium oxybate is a CNS depressant. In clinical trials at recommended doses, obtundation and clinically significant respiratory depression occurred in adult patients treated with twice-nightly sodium oxybate (i.e., Xyrem). Many patients who received sodium oxybate during clinical trials in narcolepsy were receiving central nervous system stimulants.

Abuse and Misuse

Sodium oxybate is the sodium salt of gamma-hydroxybutyrate (GHB). Abuse or misuse of illicit GHB, either alone or in combination with other CNS depressants, may be associated with CNS adverse reactions, including seizure, respiratory depression, decreases in the level of consciousness, coma, and death.

Because of the risks of CNS depression and abuse and misuse, FT218 may be available only through a restricted program under a Risk Evaluation and Mitigation Strategy (REMS) called the FT218 REMS Program using certified pharmacies. Prescribers and patients must enroll in the program.

Indications and Usage

FT218 is indicated for the treatment of cataplexy or excessive daytime sleepiness (EDS) in adults with narcolepsy.

Dosage and Administration

Dosing Information

The recommended starting dosage is 4.5 grams (g) per night administered orally. Increase the dosage by 1.5 g per night at weekly intervals to the effective dosage range of 6 g to 9 g per night orally. The dosage may be gradually titrated based on efficacy and tolerability. Doses higher than 9 g per night may not have been studied and may not ordinarily be administered.

Important Administration Instructions

FT218 is taken as a single dose at bedtime. Prepare the dose of FT218 prior to bedtime. Prior to ingestion, each dose of FT218 should be suspended in approximately ⅓ cup (approximately 80 mL) of water in the mixing cup provided.

FT218 may be given without regard for meals.

Patients should take FT218 while in bed and lie down immediately after dosing as FT218 may cause them to fall asleep abruptly without first feeling drowsy. Patients may often fall asleep within 5 minutes of taking FT218, and will usually fall asleep within 15 minutes, though the time it takes any individual patient to fall asleep may vary from night to night. Rarely, patients may take up to 2 hours to fall asleep. Patients may remain in bed following ingestion of FT218.

Switching Patients from Twice-Nightly Sodium Oxybate

Patients who are currently being treated with twice-nightly sodium oxybate may be switched to FT218 at the nearest equivalent dose (g per night), e.g., 7.5 g sodium oxybate divided into two 3.75 g doses per night to 7.5 g FT218 once per night.

Dosage Forms and Strengths

FT218 is a white to off-white powder for oral suspension provided in nightly dose packets of 4.5 g, 6 g, 7.5 g, or 9 g.

Contraindications

FT218 is contraindicated for use in:
- combination with sedative hypnotic agents.
- combination with alcohol.
- patients with succinic semialdehyde dehydrogenase deficiency.
- patients with hepatic impairment.

Warnings and Precautions

Central Nervous System Depression

The active ingredient in FT218, sodium oxybate, is a central nervous system (CNS) depressant. In adult clinical trials at recommended doses, obtundation and clinically significant respiratory depression occurred in patients treated with twice-nightly sodium oxybate (i.e., Xyrem). FT218 is contraindicated in combination with alcohol and sedative hypnotics. The concurrent use of FT218 with other CNS depressants, including but not limited to opioid analgesics, benzodiazepines, sedating antidepressants or antipsychotics, sedating anti-epileptic drugs, general anesthetics, muscle relaxants, and/or illicit CNS depressants, may increase the risk of respiratory depression, hypotension, profound sedation, syncope, and death. If use of these CNS depressants in combination with FT218 is required, dose reduction or discontinuation of one or more CNS depressants (including FT218) may be considered. In addition, if short-term use of an opioid (e.g., post- or perioperative) is required, interruption of treatment with FT218 may be considered. Consumption of alcohol while taking FT218 may result in a more rapid release of the dose of sodium oxybate.

Healthcare providers should caution patients about operating hazardous machinery, including automobiles or airplanes, until they are reasonably certain that FT218 does not affect them adversely (e.g., impair judgment, thinking, or motor skills). Patients should not engage in hazardous occupations or activities requiring complete mental alertness or motor coordination, such as operating machinery or a motor vehicle or flying an airplane, for at least 6 hours after taking FT218. Patients should be queried about CNS depression-related events upon initiation of FT218 therapy and periodically thereafter. FT218 is available only through a restricted program under a REMS.

Abuse and Misuse

FT218 is a Schedule III controlled substance. The active ingredient of FT218, sodium oxybate or gamma-hydroxybutyrate (GHB), is a Schedule I controlled substance. Abuse of illicit GHB, either alone or in combination with other CNS depressants, is associated with CNS adverse reactions, including seizure, respiratory depression, decreases in the level of consciousness, coma, and death. The rapid onset of sedation, coupled with the amnestic features of FT218, particularly when combined with alcohol, has proven to be dangerous for the voluntary and involuntary user (e.g., assault victim). Because illicit use and abuse of GHB have been reported, physicians should carefully evaluate patients for a history of drug abuse and follow such patients closely, observing them for signs of misuse or abuse of GHB (e.g., increase in size or frequency of dosing, drug-seeking behavior, feigned cataplexy).

FT218 REMS Program

Because of the risks of central nervous system depression and abuse/misuse, FT218 is available only through the FT218 REMS Program. Required components of the FT218 REMS Program are:
- FT218 is only dispensed through certified specialty pharmacies.
- Healthcare providers who prescribe FT218 must complete the enrollment forms and comply with the requirements.
- Pharmacists must complete the enrollment forms and comply with the requirements.
- To receive FT218, patients must understand the risks and benefits of FT218.

Respiratory Depression and Sleep-Disordered Breathing

FT218 may impair respiratory drive, especially in patients with compromised respiratory function. In overdoses, life-threatening respiratory depression has been reported. In an adult study assessing the respiratory-depressant effects of twice-nightly sodium oxybate at doses up to 9 g per night in 21 patients with narcolepsy, no dose-related changes in oxygen saturation were demonstrated in the group as a whole. One of the four patients with preexisting, moderate-to-severe sleep apnea had significant worsening of the apnea/hypopnea index during treatment.

In an adult study assessing the effects of twice-nightly sodium oxybate 9 g per night in 50 patients with obstructive sleep apnea, twice-nightly sodium oxybate did not increase the severity of sleep-disordered breathing and did not adversely affect the average duration and severity of oxygen desaturation overall. However, there was a significant increase in the number of central apneas in patients taking twice-nightly sodium oxybate, and clinically significant oxygen desaturation (55%) was measured in three patients (6%) after administration, with one patient with-drawing from the study and two continuing after single brief instances of desaturation. Prescribers should be aware that increased central apneas and clinically relevant desaturation events have been observed with twice-nightly administration in adult patients.

In adult clinical trials in 128 patients with narcolepsy administered twice-nightly sodium oxybate, two subjects had profound CNS depression, which resolved after supportive respiratory intervention. Two other patients discontinued twice-nightly sodium oxybate because of severe difficulty breathing and an increase in obstructive sleep apnea. There were no cases of profound CNS depression or severe difficulty breathing in adult clinical trials in 212 patients with narcolepsy administered FT218; there was one patient with worsening sleep apnea in both the FT218 and placebo-treated groups. In two controlled trials assessing PSG measures in adult patients with narcolepsy administered twice-nightly sodium oxybate, 40 of 477 patients were included with a baseline apnea/hypopnea index of 16 to 67 events per hour, indicative of mild to severe sleep-disordered breathing. None of the 40 patients had a clinically significant worsening of respiratory function as measured by apnea/hypopnea index and pulse oximetry at doses of 4.5 g to 9 g per night. In adult clinical trials of FT218 in patients with narcolepsy, no sub-jects with apnea/hypopnea indexes greater than 15 were allowed to enroll. Prescribers should be aware that sleep-related breathing disorders tend to be more prevalent in obese patients, in men, in postmenopausal women not on hormone replacement therapy and among patients with narcolepsy.

Depression and Suicidality

In an adult clinical trial in patients with narcolepsy (n=212) administered FT218, there were no suicide attempts and one patient developed suicidal ideation at the 9 g dose. In adult clinical trials in patients with narcolepsy (n=781) administered twice-nightly sodium oxybate, there were two suicides and two attempted suicides in patients treated with twice-nightly sodium oxybate, including three patients with a previous history of depressive psychiatric disorder. Of the two suicides, one patient used twice-nightly sodium oxybate in conjunction with other drugs. Twice-nightly sodium oxybate was not involved in the second suicide. Adverse reactions of depression were reported by 7% of 781 patients treated with twice-nightly sodium oxybate, with four patients (<1%) discontinuing because of depression. In most cases, no change in twice-nightly sodium oxybate treatment was required.

In a controlled trial in adults with narcolepsy administered FT218 (n=212) where patients were titrated from 4.5 g to 9 g per night, the incidences of depression were 0 at 4.5 g, 1 (1%) at 6 g, 1 (1.1%) at 7.5 g and 1 (1.3%) at 9 g. In a controlled adult trial, with patients randomized to fixed doses of 3 g, 6 g, or 9 g per night twice-nightly sodium oxybate or placebo, there was a single event of depression at the 3 g per night dose. In another adult controlled trial, with patients titrated from an initial 4.5 g per night starting dose of twice-nightly sodium oxybate, the incidences of depression were 1 (1.7%), 1 (1.5%), 2 (3.2%), and 2 (3.6%) for the placebo, 4.5 g, 6 g, and 9 g per night doses, respectively. The emergence of depression in patients treated with FT218 requires careful and immediate evaluation. Patients with a previous history of a depressive illness and/or suicide attempt should be monitored carefully for the emergence of depressive symptoms while taking FT218.

Other Behavioral or Psychiatric Adverse Reactions

During adult clinical trials in patients with narcolepsy administered FT218, 2% of 107 patients treated with FT218 experienced a confusional state. During adult clinical trials in patients with narcolepsy administered twice-nightly sodium oxybate, 3% of 781 patients treated with twice-nightly sodium oxybate experienced confusion, with incidence generally increasing with dose. No patients treated with FT218 discontinued treatment because of confusion. Less than 1% of patients discontinued the twice-nightly sodium oxybate because of confusion. Confusion was reported at all recommended doses from 6 g to 9 g per night. In a controlled trial in adults where patients were randomized to twice-nightly sodium oxybate in fixed total daily doses of 3 g, 6 g, or 9 g per night or placebo, a dose-response relationship for confusion was demonstrated, with 17% of patients at 9 g per night experiencing confusion. In all cases in that controlled trial, the confusion resolved soon after termination of treatment. In one trial, where twice-nightly sodium oxybate was titrated from an initial 4.5 g per night dose, there was a single event of confusion in one patient at the 9 g per night dose. In the majority of cases in all adult clinical trials in patients with narcolepsy administered twice-nightly sodium oxybate, confusion resolved either soon after termination of dosing or with continued treatment.

Anxiety occurred in 7.5% of 107 patients treated with FT218 in the adult trial in patients with narcolepsy. In the study, 16.5% of narcolepsy patients had anxiety at study entry. Anxiety occurred in 5.8% of the 874 patients receiving twice-nightly sodium oxybate in adult clinical trials in another population. Other psychiatric reactions reported in adult clinical trials in patients with narcolepsy administered FT218 included irritability, emotional disorder, panic attack, agitation, delirium, and obsessive thoughts. Other neuropsychiatric reactions reported in adult clinical trials in patients with narcolepsy administered twice-nightly sodium oxybate and the post-marketing setting for twice-nightly sodium oxybate included hallucinations, paranoia, psychosis, aggression, and agitation. The emergence or increase in the occurrence of behavioral or psychiatric events in adult patients taking FT218 should be carefully monitored.

Parasomnias

Sleepwalking, defined as confused behavior occurring at night and at times associated with wandering was reported in 3% of 107 patients with narcolepsy treated with FT218. No patients treated with FT218 discontinued due to sleepwalking. Sleepwalking was reported in 6% of 781 patients with narcolepsy treated with twice-nightly sodium oxybate in adult controlled and long-term open-label studies, with <1% of patients discontinuing due to sleepwalking. Rates of sleepwalking were similar for patients taking placebo and patients taking twice-nightly sodium oxybate in controlled trials. It is unclear if some or all of the reported sleepwalking episodes correspond to true somnambulism, which is a parasomnia occurring during non-REM sleep, or to any other specific medical disorder. Five instances of sleepwalking with potential injury or significant injury were reported during a clinical trial of twice-nightly sodium oxybate in patients with narcolepsy. Parasomnias, including sleepwalking, also have been reported in the postmarketing experience with twice-nightly sodium oxybate. Therefore, episodes of sleepwalking should be fully evaluated and appropriate interventions considered.

Use in Patients Sensitive to High Sodium Intake

FT218 has a high salt content. In patients sensitive to salt intake (e.g., those with heart failure, hypertension, or renal impairment), consider the amount of daily sodium intake in each dose of FT218. Table 21 provides the approximate sodium content per FT218 dose.

TABLE 21

Approximate Sodium Content per Total Nightly Dose of FT218 (g = grams)

| FT218 Dose | Sodium Content/Total Nightly Exposure |
| --- | --- |
| 4.5 g per night | 820 mg |
| 6 g per night | 1094 mg |
| 7.5 g per night | 1367 mg |
| 9 g per night | 1641 mg |

Adverse Reactions

The following clinically significant adverse reactions appear in other sections of the labeling:

CNS depression

Abuse and Misuse

Respiratory Depression and Sleep-Disordered Breathing

Depression and Suicidality

Other Behavioral or Psychiatric Adverse Reactions

Parasomnias

Use in Patients Sensitive to High Sodium Intake

Clinical Trial Experience

Because clinical trials are conducted under widely varying conditions, adverse reaction rates observed in the clinical trials of a drug cannot be directly compared to rates in the clinical trials of another drug and may not reflect the rates observed in clinical practice.

Adult Patients

FT218 was studied in one placebo-controlled trial (Study 1) in 212 patients with narcolepsy (107 subjects treated with FT218 and 105 with placebo).

Most Common Adverse Reactions:

The most common adverse reactions (incidence>50 and greater than placebo) reported for all doses of FT218 combined were nausea, dizziness, enuresis, headache, decreased appetite, vomiting, and anxiety.

Adverse Reactions Occurring at an Incidence of 2% or Greater:

Table 22 lists adverse reactions occurring in 2% or more of FT218-treated patients on any individual dose and at a rate greater than placebo-treated patients in Study 1.

Adverse Reactions Leading to Treatment Discontinuation:

Of the 212 patients with narcolepsy treated with FT218, 15.9% discontinued because of adverse reactions compared to 1.900 of patients receiving placebo. For FT218, 5.6% of patients discontinued due to adverse reactions on 4.5 g, 4.1% on 6 g, 4.5% on 7.5 g and 3.9% on 9 g dose.

TABLE 22

Adverse reactions occurring in 2% or more of FT218-treated patients on any individual dose and for which the rate for FT218-treated patients exceeds the rate for placebo-treated patients in Study 1.

| System Organ Class/ Adverse Reaction | Week 1 | | Weeks 2-3 | | Weeks 4-8 | | Weeks 9-13 | |
|---|---|---|---|---|---|---|---|---|
| | Placebo (N = 107) | FT218 4.5 g (N = 105) | Placebo (N = 97) | FT218 6 g (N = 102) | Placebo (N = 88) | FT218 7.5 g (N = 88) | Placebo (N = 77) | FT218 9 g (N = 80) |
| Gastrointestinal Disorders | | | | | | | | |
| Vomiting | 1 | 3 | 1 | 3 | 0 | 6 | 0 | 5 |
| Nausea | 1 | 6 | 2 | 8 | 0 | 7 | 1 | 1 |
| Investigations | | | | | | | | |
| Weight Decreased | 0 | 1 | 0 | 0 | 0 | 0 | 0 | 4 |
| Metabolism and Nutritional Disorders | | | | | | | | |
| Decreased Appetite | 0 | 4 | 0 | 4 | 0 | 3 | 0 | 3 |
| Nervous System Disorders | | | | | | | | |
| Dizziness | 0 | 6 | 0 | 4 | 0 | 6 | 0 | 5 |
| Somnolence | 1 | 0 | 0 | 1 | 0 | 2 | 1 | 4 |
| Headache | 4 | 8 | 1 | 5 | 1 | 6 | 0 | 1 |
| Psychiatric Disorders | | | | | | | | |
| Enuresis | 0 | 2 | 0 | 4 | 0 | 9 | 0 | 9 |
| Anxiety | 0 | 3 | 0 | 1 | 1 | 3 | 0 | 1 |
| Somnambulism | 0 | 1 | 0 | 2 | 0 | 0 | 0 | 0 |

Adverse Reactions Leading to Treatment Discontinuation:

Of the 212 patients with narcolepsy treated with FT218, 15.9% discontinued because of adverse reactions compared to 1.9% of patients receiving placebo. For FT218, 5.6% of patients discontinued due to adverse reactions on 4.5 g, 4.1% on 6 g, 4.5% on 7.5 g and 3.9% on 9 g dose.

Dose-Response Information

In clinical trials in adult patients with narcolepsy, a dose-response relationship was observed for enuresis.

Postmarketing Experience

The following adverse reactions have been identified during post approval use of twice-nightly sodium oxybate. Because these reactions are reported voluntarily from a population of uncertain size, it is not always possible to reliably estimate their frequency or establish a causal relation-ship to drug exposure: arthralgia, decreased appetite, fall, fluid retention, hangover, headache, hypersensitivity, hyper-tension, memory impairment, nocturia, panic attack, vision blurred, and weight decreased. The sudden onset of sleep in patients taking twice-nightly sodium oxybate, including in a standing position or while rising from bed, has led to falls complicated by injuries, in some cases requiring hospitalization.

Drug Interactions

Alcohol, Sedative Hypnotics, and CNS Depressants

FT218 is contraindicated for use in combination with alcohol or sedative hypnotics. Use of other CNS depressants may potentiate the CNS-depressant effects of FT218. Consumption of alcohol while taking FT218 may result in a more rapid release of the dose of sodium oxybate.

Use in Specific Populations

Pregnancy Risk Summary

There are no adequate data on the developmental risk associated with the use of sodium oxybate in pregnant women. Oral administration of sodium oxybate to pregnant rats (150, 350, or 1,000 mg/kg/day) or rabbits (300, 600, or 1,200 mg/kg/day) throughout organogenesis produced no clear evidence of developmental toxicity; however, oral administration to rats throughout pregnancy and lactation resulted in increased stillbirths and decreased offspring postnatal viability and growth, at a clinically relevant dose. In the U.S. general population, the estimated background risk of major birth defects and miscarriage in clinically recognized pregnancies is 24% and 15-20%, respectively. The background risk of major birth defects and miscarriage for the indicated population is unknown.

Clinical Considerations for Labor or Delivery

FT218 has not been studied in labor or delivery. In obstetric anesthesia using an injectable formulation of sodium oxybate, newborns had stable cardiovascular and respiratory measures but were very sleepy, causing a slight decrease in Apgar scores. There was a fall in the rate of uterine contractions 20 minutes after injection. Placental transfer is rapid and gamma-hydroxybutyrate (GHB) has been detected in newborns at delivery after intravenous administration of GHB to mothers. Subsequent effects of sodium oxybate on later growth, development, and maturation in humans are unknown.

Animal Data

Oral administration of sodium oxybate to pregnant rats (150, 350, or 1,000 mg/kg/day) or rabbits (300, 600, or 1,200 mg/kg/day) throughout organogenesis produced no clear evidence of developmental toxicity. The highest doses tested in rats and rabbits were approximately 1 and 3 times, respectively, the maximum recommended human dose (MRHD) of 9 g per night on a body surface area (mg/m$^2$) basis. Oral administration of sodium oxybate (150, 350, or 1,000 mg/kg/day) to rats throughout pregnancy and lactation resulted in increased stillbirths and decreased offspring postnatal viability and body weight gain at the highest dose tested. The no-effect dose for pre- and post-natal developmental toxicity in rats is less than the MRHD on a mg/m$^2$ basis.

Lactation Risk Summary

GHB is excreted in human milk after oral administration of sodium oxybate. There is insufficient information on the risk to a breastfed infant, and there is insufficient information on milk production in nursing mothers. The developmental and health benefits of breastfeeding should be considered along with the mother's clinical need for FT218 and any potential adverse effects on the breastfed infant from FT218 or from the underlying maternal condition.

Pediatric Use

The safety and effectiveness of FT218 in the treatment of cataplexy or excessive daytime sleepiness in pediatric patients have not been established.

Geriatric Use

Clinical studies of FT218 in patients with narcolepsy did not include sufficient numbers of subjects age 65 years and older to determine whether they respond differently from younger subjects. In controlled trials of twice-nightly sodium oxybate in another population, 39 (5%) of 874 patients were 65 years or older. Discontinuations of treatment due to adverse reactions were increased in the elderly compared to younger adults (21% v. 19%). Frequency of headaches was markedly increased in the elderly (39% v. 19%). The most common adverse reactions were similar in both age categories. In general, dose selection for an elderly patient should be cautious, usually starting at the low end of the dosing range, reflecting the greater frequency of decreased hepatic, renal, or cardiac function, and of concomitant disease or other drug therapy.

Hepatic Impairment

Because of an increase in exposure to FT218, FT218 should not be administered to patients with liver impairment.

Drug Abuse and Dependence

Controlled Substance

FT218 is a Schedule III controlled substance under the Federal Controlled Substances Act. Non-medical use of FT218 could lead to penalties assessed under the higher Schedule I controls.

Abuse

FT218 (sodium oxybate), the sodium salt of GHB, produces dose-dependent central nervous system effects, including hypnotic and positive subjective reinforcing effects. The onset of effect is rapid, enhancing its potential for abuse or misuse.

Drug abuse is the intentional non-therapeutic use of a drug product or substance, even once, for its desirable psychological or physiological effects. Misuse is the intentional use, for therapeutic purposes of a drug by an individual in a way other than prescribed by a health care provider or for whom it was not prescribed. Drug misuse and abuse may occur with or without progression to addiction. Drug addiction is a cluster of behavioral, cognitive, and physiological phenomena that may include a strong desire to take the drug, difficulties in controlling drug use (e.g., continuing drug use despite harmful consequences, giving a higher priority to drug use than other activities and obligations), and possible tolerance or physical dependence.

The rapid onset of sedation, coupled with the amnestic features of GHB, particularly when combined with alcohol, has proven to be dangerous for the voluntary and involuntary user (e.g., assault victim).

Illicit GHB is abused in social settings. Some of the doses estimated to be abused are in a similar dosage range to that used for treatment of patients with cataplexy. GHB has some commonalities with ethanol over a limited dose range, and some cross tolerance with ethanol has been reported as well. Cases of severe dependence and craving for GHB have been reported when the drug is taken around the clock. Patterns of abuse indicative of dependence include: 1) the use of increasingly large doses, 2) increased frequency of use, and 3) continued use despite adverse consequences.

Because illicit use and abuse of GHB have been reported, physicians should carefully evaluate patients for a history of drug abuse and follow such patients closely, observing them for signs of misuse or abuse of GHB (e.g., increase in size or frequency of dosing, drug-seeking behavior, feigned cataplexy). Dispose of FT218 according to state and federal regulations. It is safe to dispose of FT218 down the sanitary sewer.

Dependence

Physical dependence is a state that develops as a result of physiological adaptation in response to repeated drug use, manifested by withdrawal signs and symptoms after abrupt discontinuation or a significant dose reduction of a drug. There have been case reports of withdrawal, ranging from mild to severe, following discontinuation of illicit use of GHB at frequent repeated doses (18 g to 250 g per day) in excess of the recommended dosage range. Signs and symptoms of GHB withdrawal following abrupt discontinuation included insomnia, restlessness, anxiety, psychosis, lethargy, nausea, tremor, sweating, muscle cramps, tachycardia, headache, dizziness, rebound fatigue and sleepiness, confusion, and, particularly in the case of severe withdrawal, visual hallucinations, agitation, and delirium. These symptoms generally abated in 3 to 14 days. In cases of severe withdrawal, hospitalization may be required. The discontinuation effects of FT218 have not been systematically evaluated in controlled clinical trials. In the clinical trial experience with FT218, there were no reported reactions occurring following abrupt discontinuation of FT218. In the clinical trial experience with twice-nightly sodium oxybate in narcolepsy/cataplexy patients at recommended doses, two patients reported anxiety and one reported insomnia following abrupt discontinuation at the termination of the clinical trial; in the two patients with anxiety, the frequency of cataplexy had increased markedly at the same time.

Tolerance

Tolerance is a physiological state characterized by a reduced response to a drug after repeated administration (i.e., a higher dose of a drug is required to product the same effect that was once obtained at a lower dose). Tolerance to FT218 has not been systematically studied in controlled clinical trials. There have been some case reports of symptoms of tolerance developing after illicit use at dosages far in excess of the recommended FT218 dosage regimen. Clinical studies of twice-nightly sodium oxybate in the treatment of alcohol withdrawal suggest a potential cross-tolerance with alcohol. The safety and effectiveness of FT218 in the treatment of alcohol withdrawal have not been established.

Overdosage

Human Experience

Information regarding overdose with FT218 is derived largely from reports in the medical literature that describe symptoms and signs in individuals who have ingested GHB illicitly. In these circumstances the co-ingestion of other drugs and alcohol was common, and may have influenced the presentation and severity of clinical manifestations of overdose. There were no cases of overdose in adult clinical trials of FT218. In adult clinical trials of twice-nightly sodium oxybate, two cases of overdose with sodium oxybate were reported. In the first case, an estimated dose of 150 g, more than 15 times the maximum recommended dose, caused a patient to be unresponsive with brief periods of apnea and to be incontinent of urine and feces. This individual recovered without sequelae. In the second case, death was reported following a multiple drug overdose consisting of sodium oxybate and numerous other drugs.

Signs and Symptoms

Information about signs and symptoms associated with overdosage with FT218 derives from reports of illicit use of GHB. Patient presentation following overdose is influenced by the dose ingested, the time since ingestion, the co-ingestion of other drugs and alcohol, and the fed or fasted state. Patients have exhibited varying degrees of depressed consciousness that may fluctuate rapidly between a confusional, agitated combative state with ataxia and coma. Emesis (even when obtunded), diaphoresis, headache, and impaired psychomotor skills have been observed. No typical pupillary changes have been described to assist in diagnosis; pupillary reactivity to light is maintained. Blurred vision has been reported. An increasing depth of coma has been observed at higher doses. Myoclonus and tonic-clonic seizures have been reported. Respiration may be unaffected or compromised in rate and depth. Cheyne-Stokes respiration and apnea have been observed. Bradycardia and hypothermia may accompany unconsciousness, as well as muscular hypotonia, but tendon reflexes remain intact.

Recommended Treatment of Overdose

General symptomatic and supportive care should be instituted immediately, and gastric decontamination may be considered if coingestants are suspected. Because emesis may occur in the presence of obtundation, appropriate posture (left lateral recumbent position) and protection of the airway by intubation may be warranted. Although the gag reflex may be absent in deeply comatose patients, even unconscious patients may become combative to intubation, and rapid-sequence induction (without the use of sedative) should be considered. Vital signs and consciousness should be closely monitored. The bradycardia reported with GHB overdose has been responsive to atropine intravenous administration. No reversal of the central depressant effects of FT218 can be expected from naloxone or flumazenil administration. The use of hemodialysis and other forms of extracorporeal drug removal have not been studied in GHB overdose. However, due to the rapid metabolism of sodium oxybate, these measures are not warranted.

Poison Control Center

As with the management of all cases of drug overdosage, the possibility of multiple drug ingestion should be considered. The healthcare provider is encouraged to collect urine and blood samples for routine toxicologic screening, and to consult with a regional poison control center (1-800-222-1222) for current treatment recommendations.

Description

Sodium oxybate, a CNS depressant, is the active ingredient in FT218. The chemical name for sodium oxybate is sodium 4-hydroxybutyrate. The molecular formula is $C_4H_7NaO_3$, and the molecular weight is 126.09 g/mole. The chemical structure is:

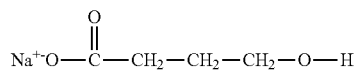

Sodium oxybate is white to off-white solid powder. Each nightly dose packet contains a blend of immediate-release and controlled-release granules of FT218 providing doses of 4.5 g, 6 g, 7.5 g, or 9 g of sodium oxybate. The inactive ingredients are microcrystalline cellulose spheres, povidone K30, hydrogenated vegetable oil, methacrylic acid copolymer, malic acid, xanthan gum, hydroxyethyl cellulose, carrageenan, and magnesium stearate.

Clinical Pharmacology

Mechanism of Action

FT218 is a CNS depressant. The mechanism of action of FT218 in the treatment of narcolepsy is unknown. Sodium oxybate is the sodium salt of gamma-hydroxybutyrate (GHB), an endogenous compound and metabolite of the neurotransmitter GABA. It is hypothesized that the therapeutic effects of FT218 on cataplexy and excessive daytime sleepiness are mediated through $GABA_B$ actions at noradrenergic and dopaminergic neurons, as well as at thalamo-cortical neurons.

Pharmacokinetics

Following oral administration of twice-nightly sodium oxybate, GHB is absorbed rapidly across the clinical dose range, with an absolute bioavailability of about 88%. Following oral administration of FT218, the peak plasma concentrations ($C_{max}$) following administration of one 6 g dose was 65.8 mcg/mL and the time to peak plasma concentration ($T_{max}$) was 1.51 hours. Following oral administration of FT218, the plasma levels of GHB increased dose-proportionally, with blood levels increasing 2-fold as total daily dose is doubled from 4.5 g to 9 g.

Effect of Food

The AUC data from a food-effect study involving administration of FT218 to healthy volunteers under fasting conditions and with a high-fat meal indicated that exposure to the drug is not affected by food. Although administration of FT218 immediately after a high-fat meal resulted in delayed absorption (average $T_{max}$ increased from 0.53 hr to 1.5 hr) and a reduction in $C_{max}$ of GHB by a mean of 33.3%, these changes are not clinically relevant. Therefore, FT218 may be taken without regard to meals.

Effect of Ethanol

An in vitro ethanol interaction demonstrated that >90% of an administered dose of FT218 may be released within 1 hour, if administered at the same time as alcohol is ingested.

Distribution

GHB is a hydrophilic compound with an apparent volume of distribution averaging 190 mL/kg to 384 mL/kg. At GHB concentrations ranging from 3 mcg/mL to 300 mcg/mL, less than 1% is bound to plasma proteins.

Elimination and Metabolism

Animal studies indicate that metabolism is the major elimination pathway for GHB, producing carbon dioxide and water via the tricarboxylic acid (Krebs) cycle and secondarily by beta-oxidation. The primary pathway involves a cytosolic NADP+-linked enzyme, GHB dehydrogenase, that catalyzes the conversion of GHB to succinic semialdehyde, which is then biotransformed to succinic acid by the enzyme succinic semialdehyde dehydrogenase. Succinic acid enters the Krebs cycle where it is metabolized to carbon dioxide and water. A second mitochondrial oxidoreductase enzyme, a transhydrogenase, also catalyzes the conversion to succinic semialdehyde in the presence of α-ketoglutarate. An alternate pathway of biotransformation involves β-oxidation via 3,4-dihydroxybutyrate to carbon dioxide and water. No active metabolites have been identified.

Excretion

The clearance of GHB is almost entirely by biotransformation to carbon dioxide, which is then eliminated by expiration. On average, less than 5% of unchanged drug appears in human urine within 6 to 8 hours after dosing. Fecal excretion is negligible. GHB has an elimination half-life of 0.5 to 1 hour.

Specific Populations

Geriatric Patients

There is limited experience with FT218 in the elderly. Results from a pharmacokinetic study of twice-nightly sodium oxybate (n=20) in another studied population indicate that the pharmacokinetic characteristics of GHB are consistent among younger (age 48 to 64 years) and older (age 65 to 75 years) adults.

Pediatric Patients

The pharmacokinetics of sodium oxybate in patients younger than 18 years of age have not been studied.

Male and Female Patients

In a study of 18 female and 18 male healthy adult volunteers, no gender differences were detected in the pharmacokinetics of GHB following a single twice nightly sodium oxybate oral dose of 4.5 g.

Racial or Ethnic Groups

There are insufficient data to evaluate any pharmacokinetic differences among races Patients with Renal Impairment No pharmacokinetic study in patients with renal impairment has been conducted.

Patients with Hepatic Impairment

The pharmacokinetics of GHB in 16 cirrhotic patients, half without ascites (Child's Class A) and half with ascites (Child's Class C), were compared to the kinetics in 8 subjects with normal hepatic function after a single sodium oxybate oral dose of 25 mg/kg. AUC values were double in the cirrhotic patients, with apparent oral clearance reduced from 9.1 mL/min/kg in healthy adults to and 4.1 mL/min/kg in Class A and Class C patients, respectively. Elimination half-life was significantly longer in Class C and Class A patients than in control patients (mean $t_{1/2}$ of 59 and 32 minutes, respectively, versus 22 minutes in control patients). FT218 should not be administered to patients with liver impairment.

Drug Interaction Studies

Studies in vitro with pooled human liver microsomes indicate that sodium oxybate does not significantly inhibit the activities of the human isoenzymes CYP1A2, CYP2C9, CYP2C19, CYP2D6, CYP2E1, or CYP3A up to the concentration of 3 mM (378 mcg/mL), a level considerably higher than levels achieved with recommended doses.

Drug interaction studies in healthy adults (age 18 to 50 years) were conducted with FT218 and divalproex sodium:

Divalproex sodium: Co-administration of a single dose of FT218 (6 g) with a single dose of divalproex sodium ER (1250 mg) resulted in comparable systemic exposure to GHB as shown by plasma $C_{max}$ and AUC values. Co-administration did not appear to affect the pharmacokinetics of divalproex sodium and no dose adjustment is recommended for concomitant administration with FT218 based on this pharmacokinetic observation.

Drug interaction studies in healthy adults (age 18 to 50 years) were conducted with twice-nightly sodium oxybate and diclofenac and ibuprofen:

Diclofenac: Co-administration of sodium oxybate (6 g per day as two equal doses of 3 grams dosed four hours apart) with diclofenac (50 mg/dose twice per day) showed no significant differences in systemic exposure to GHB. Co-administration did not appear to affect the pharmacokinetics of diclofenac.

Ibuprofen: Co-administration of sodium oxybate (6 g per day as two equal doses of 3 grams dosed four hours apart) with ibuprofen (800 mg/dose four times per day also dosed four hours apart) resulted in comparable systemic exposure to GHB as shown by plasma $C_{max}$ and AUC values. Co-administration did not affect the pharmacokinetics of ibuprofen.

Drug interaction studies in healthy adults demonstrated no pharmacokinetic interactions be-tween twice-nightly sodium oxybate and protriptyline hydrochloride, zolpidem tartrate, and modafinil. Also, there were no pharmacokinetic interactions with the alcohol dehydrogenase inhibitor fomepizole. However, pharmacodynamic interactions with these drugs cannot be ruled out. Alteration of gastric pH with omeprazole produced no significant change in the pharmacokinetics of GHB. In addition, drug interaction studies in healthy adults demonstrated no pharmacokinetic or clinically significant pharmacodynamic interactions between twice-nightly sodium oxybate and duloxetine HCl.

Nonclinical Toxicology

Carcinogenesis

Administration of sodium oxybate to rats at oral doses of up to 1,000 mg/kg/day for 83 (males) or 104 (females) weeks resulted in no increase in tumors. Plasma exposure (AUC) at the highest dose tested was 2 times that in humans at the maximum recommended human dose (MRHD) of 9 g per night.

The results of 2-year carcinogenicity studies in mouse and rat with gamma-butyrolactone, a compound that is metabolized to sodium oxybate in vivo, showed no clear evidence of carcinogenic activity. The plasma AUCs of sodium oxybate achieved at the highest doses tested in these studies were less than that in humans at the MRHD.

Mutagenesis

Sodium oxybate was negative in the in vitro bacterial gene mutation assay, an in vitro chromosomal aberration assay in mammalian cells, and in an in vivo rat micronucleus assay.

Impairment of Fertility

Oral administration of sodium oxybate (150, 350, or 1,000 mg/kg/day) to male and female rats prior to and throughout mating and continuing in females through early gestation resulted in no adverse effects on fertility. The highest dose tested is approximately equal to the MRHD on a mg/m² basis.

Clinical Studies

The efficacy of FT218 for the treatment of cataplexy or excessive daytime sleepiness (EDS) in adults with narcolepsy has been established based on a double-blind, randomized, placebo-controlled, two arm multi-center study to assess the efficacy and safety of a once nightly administration of FT218 in patients with narcolepsy (Study 1).

A total of 212 subjects were randomized to the active or placebo arm in a 1:1 ratio. The study is divided into four sequential study periods and incorporates dose titration to stabilized dose administration of FT218 (4.5 g, 6 g, 7.5 g, and 9 g). There was a three-week screening period, a 13-week treatment period including up-titration over a period of eight weeks and five weeks of stable dosing at 9 g/night, and a one-week follow-up period. Patients could be on concomitant stimulant use as long as it was stable for 3 weeks prior to study start.

The three co-primary endpoints were the Maintenance of Wakefulness Test (MWT), Clinical Global Impression-Improvement (CGI-I) and mean change in weekly cataplexy attacks. The Epworth Sleepiness Scale was a secondary endpoint in the study. The Maintenance of Wakefulness Test measures latency to sleep onset (in minutes) averaged over five sessions at 2-hour intervals following nocturnal polysomnography. For each test session, patients were instructed to remain awake for as long as possible during 30-minute test sessions, and sleep latency was determined as the number of minutes patients could remain awake. The overall score is the mean sleep latency for the 5 sessions. The Clinical Global Impression-Improvement is evaluated on a 7-point scale, centered at No Change and ranging from Very Much Worse to Very Much Improved. Patients were rated by evaluators who based their assessments on the se-verity of narcolepsy at Baseline.

Demographic and mean Baseline characteristics were similar for the FT218 and placebo groups. A total of 76% were NT1 patients and 24% were NT2 patients. Mean age was 31.2 years and 68% was female. Approximately 63% patients were on concomitant stimulant use. The mean MWT at Baseline was 5 minutes for the FT218 group and 4.7 minutes for the placebo group. The mean number of cataplexy attacks per week at Baseline was 18.9 in the FT218 group and 19.8 in the placebo group. For the three coprimary endpoints, statistically significant improvement was seen on the Maintenance of Wakefulness Test, Clinical Global Impression-Improvement and mean weekly cataplexy attacks for the 6 g (Week 3), 7.5 g (Week 8) and 9 g (Week 13) dose of FT218 compared to the placebo group (see Table 23, Table 24 and Table 25). Results (MWT and CGI-I) were consistent between NT1 and NT2 patients as well as patients on stimulants compared to those not on stimulants.

TABLE 23

Change from Baseline in the Maintenance of Wakefulness Test (in minutes)

| Dose | Treatment Group (N) | Change from Baseline (SE) | Difference from Placebo [95% CI] | p-value |
|---|---|---|---|---|
| 6 g (Week 3) | FT218 (87) | 8.08 (0.75) | 4.98 [2.90;7.05] | <0.001 |
|  | Placebo (88) | 3.10 (0.74) |  |  |
| 7.5 g (Week 8) | FT218 (76) | 9.55 (0.86) | 6.21 [3.84;8.58] | <0.001 |
|  | Placebo (78) | 3.34 (0.84) |  |  |
| 9 g (Week 13) | FT218 (68) | 10.82 (0.96) | 6.13 [3.52,8.75] | <0.001 |
|  | Placebo (78) | 4.690.92) |  |  |

Mean (SD) MWT at Baseline was 4.99 (3.15) minutes for the FT218 group and 4.73 (2.58) minutes for the placebo group.

TABLE 24

Proportion of Patients with a Very Much or Much Improved Clinical Global Impression-Improvement

| Dose | Treatment Group (N) | Percentage of Responders (Much or Very Much Improved) | Odds Ratio [95% CI] | p-value |
|---|---|---|---|---|
| 6 g (Week 3) | FT218 (87) | 40.1 | 10.29 [3.93;26.92] | <0.001 |
|  | Placebo (87) | 6.1 |  |  |
| 7.5 g (Week 8) | FT218 (75) | 62.6 | 5.67 [2.82;11.40] | <0.001 |
|  | Placebo (81) | 22.8 |  |  |
| 9 g (Week 13) | FT218 (69) | 72.0 | 5.56 [2.76;11.23] | <0.001 |
|  | Placebo (79) | 31.6 |  |  |

TABLE 25

Change from Baseline in the Mean Cataplexy Attacks Per Week

| Dose | Treatment Group (N) | Change from Baseline (SE) | Difference from Placebo [95% CI] | p-value |
|---|---|---|---|---|
| 6 g (Week 3) | FT218 (55) | −7.42 (0.79) | −4.83 [−7.03; −2.62] | <0.001 |
|  | Placebo (62) | −2.59 (0.79) | — | — |
| 7.5 g (Week 8) | FT218 (66) | −9.98 (0.88) | −6.23 [−8.74; −3.80] | <0.001 |
|  | Placebo (69) | −3.71 (0.88) | — | — |
| 9 g (Week 13) | FT218 (73) | −11.51 (0.96) | −6.65 [−9.32; −3.98] | <0.001 |
|  | Placebo (72) | −4.86 (0.945) | — | — |

Mean (SD) number of cataplexy attacks per week at Baseline was 18.93 (8.70) in the FT218 group and 19.82 (8.87) in the placebo group How Supplied/Storage and Handling How Supplied FT218 is a blend of white to off-white granules for oral suspension in water. Each prescription includes nightly dose packets of FT218 with a mixing cup.

Dose packets contain a single dose of FT218 provided in 4.5 g, 6 g, 7.5 g, and 9 g doses.

Storage

Keep out of reach of children. FT218 should be stored at 25° C. (77° F.); excursions permitted to 15° to 30° C. (59° to 86° F.) (see USP Controlled Room Temperature). Suspensions should be consumed within 30 minutes.

Handling and Disposal

FT218 is a Schedule III drug under the Controlled Substances Act. FT218 should be handled according to state and federal regulations. It is safe to dispose of FT218 down the sanitary sewer.

Patient Counseling Information

Advise the patient and/or caregiver to read the FDA-approved patient labeling (Medication Guide and Instructions for Use).

Central Nervous System Depression

Inform patients and/or caregivers that FT218 can cause central nervous system depression, including respiratory depression, hypotension, profound sedation, syncope, and death. Instruct patients to not engage in activities requiring mental alertness or motor coordination, including operating hazardous machinery, for at least 6 hours after taking FT218. Instruct patients and/or their caregivers to inform their healthcare providers of all the medications they take.

Abuse and Misuse

Inform patients and/or caregivers that the active ingredient of FT218 is gamma-hydroxybutyrate (GHB), which is associated with serious adverse reactions with illicit use and abuse.

FT218 REMS Program

Inform patients that FT218 is available only through the FT218 REMS Program. The contents of the FT218 Medication Guide and educational materials are reviewed with every patient before initiating treatment with FT218.

Patients must read and understand the materials in the FT218 REMS Program prior to initiating treatment. Inform the patient that they should be seen by the prescriber frequently to review dose titration, symptom response, and adverse reactions; a follow-up of every three months is recommended.

Discuss safe and proper use of FT218 and dosing information with patients prior to the initiation of treatment.

Instruct patients to store FT218 nightly dose packets and FT218 doses in a secure place, out of the reach of children and pets.

Alcohol or Sedative Hypnotics

Advise patients and/or caregivers that alcohol and other sedative hypnotics should not be taken with FT218.

Sedation

Inform patients and/or caregivers that the patient is likely to fall asleep quickly after taking FT218 (often within 5 and usually within 15 minutes), but the time it takes to fall asleep can vary from night to night. The sudden onset of sleep, including in a standing position or while rising from bed, has led to falls complicated by injuries, in some cases requiring hospitalization. Instruct patients that they should remain in bed following ingestion of their dose.

Respiratory Depression and Sleep-Disordered Breathing

Inform patients that FT218 may impair respiratory drive, especially in patients with compromised respiratory function, and may cause apnea.

Depression and Suicidality

Instruct patients to contact a healthcare provider immediately if they develop depressed mood, markedly diminished interest or pleasure in usual activities, significant change in weight and/or appetite, psychomotor agitation or retardation, increased fatigue, feelings of guilt or worthlessness, slowed thinking or impaired concentration, or suicidal ideation.

Other Behavioral or Psychiatric Adverse Reactions

Inform patients that FT218 can cause behavioral or psychiatric adverse reactions, including confusion, anxiety, and psychosis. Instruct them to notify their healthcare provider if any of these types of symptoms occur.

Sleepwalking

Instruct patients that FT218 has been associated with sleepwalking and other behaviors during sleep, and to contact their healthcare provider if this occurs.

Sodium Intake

Instruct patients that FT218 contains a significant amount of sodium and patients who are sensitive to sodium intake (e.g., those with heart failure, hypertension, or renal impairment) should limit their sodium intake.

Medication Guide FT218 (sodium oxybate) extended-release oral suspension, CIII

Read this Medication Guide carefully before you start taking FT218 and each time you get a refill. There may be new information. This information does not take the place of talking to your doctor about your medical condition or treatment.

What is the Most Important Information I should Know about FT218?

FT218 is a central nervous system (CNS) depressant. Taking FT218 with other CNS depressants such as medicines used to make you fall asleep, including opioid analgesics, benzodiazepines, sedating antidepressants, antipsychotics, sedating anti-epileptic medicines, general anesthetics, muscle relaxants, alcohol, or street drugs, may cause serious medical problems, including:
  trouble breathing (respiratory depression)
  low blood pressure (hypotension)
  changes in alertness (drowsiness)
  dizziness (syncope)
  death Ask your doctor if you are not sure if you are taking a medicine listed above.

FT218 is a federal controlled substance (CIII). The active ingredient of FT218 is a form of gamma-hydroxybutyrate (GHB) that is also a federal controlled substance (CI). Abuse of illegal GHB, either alone or with other CNS depressants may cause serious medical problems, including:
  seizure
  trouble breathing (respiratory depression)
  changes in alertness (drossiness)
  coma
  death Call your doctor right away if you have any of these serious side effects.

Anyone who takes FT218 should not do anything that requires them to be fully awake or is dangerous, including driving a car, using heavy machinery, or flying an airplane, for at least 6 hours after taking FT218. Those activities should not be done until you know how FT218 affects you. Keep FT218 in a safe place to prevent abuse and misuse. Selling or giving away FT218 may harm others, and is against the law. Tell your doctor if you have ever abused or been dependent on alcohol, prescription medicines, or street drugs.

Because of the risk of CNS depression, abuse, and misuse, FT218 is available only by prescription and filled through certified pharmacies in the FT218 REMS Program. You must be enrolled in the FT218 REMS Program to receive FT218. Before you receive FT218, your doctor or pharmacist will make sure that you understand how to use FT218 safely and effectively. If you have any questions about FT218, ask your doctor or call the FT218 REMS Program.

What is FT218?

FT218 is a prescription medicine used to treat the following symptoms in people with narcolepsy:
  sudden onset of weak or paralyzed muscles (cataplexy)
  excessive daytime sleepiness (EDS)

It is not known if FT218 is safe and effective in people less than 18 years of age.

Do not take FT218 if you:
  take other sleep medicines or sedatives (medicines that cause sleepiness)
  drink alcohol
  have a rare problem called succinic semialdehyde dehydrogenase deficiency Before taking FT218, tell your doctor about all medical conditions, including if you:
  have a history of drug abuse.
  have short periods of not breathing while sleeping (sleep apnea)
  snore, have trouble breathing, or have lung problems. You may have a higher chance of having serious breathing problems when taking FT218.
  have or had depression or have tried to harm yourself or themselves. You should be watched carefully for new symptoms of depression.
  have or had behavior or other psychiatric problems such as:
    anxiety
    seeing or hearing things that are not real (hallucinations)
    feeling more suspicious (paranoia)
    being out of touch with reality (psychosis)
    acting aggressive
    agitation
  have liver problems
  are on a salt-restricted diet. FT218 contains a lot of sodium (salt) and may not be right for you.
  have high blood pressure
  have heart failure
  have kidney problems are pregnant or plan to become pregnant. It is not known if FT218 can harm your unborn baby.

are breastfeeding or plan to breastfeed. FT218 passes into breast milk. You and your doctor should decide if you will take FT218 or breastfeed.

Tell your doctor about all the medicines you take, including prescription and over-the-counter medicines, vitamins, and herbal supplements. Especially, tell your doctor if you take other medicines to help you sleep (sedatives). Know the medicines you take. Keep a list of them to show your doctor and pharmacist when you get a new medicine.

How should I Take FT218?

Read the Instructions for Use at the end of this Medication Guide for detailed instructions on how to take FT218. Take FT218 exactly as your doctor tells you to take it. FT218 can cause physical dependence and craving for the medicine when it is not taken as directed. Never change the FT218 dose without talking to your doctor.

FT218 can cause sleep very quickly without feeling drowsy. Some people fall asleep within 5 minutes and most fall asleep within 15 minutes. The time it takes to fall asleep might be different from night to night. Falling asleep quickly, including while standing or while getting up from the bed, has led to falls with injuries that have required some people to be hospitalized. If you take too much FT218, call your doctor or go to the nearest hospital emergency room right away.

What are the Possible Side Effects of FT218?

FT218 may cause serious side effects, including:

See "What is the most important information I should know about FT218?"

breathing problems, including:
  slower breathing
  trouble breathing
  short periods of not breathing while sleeping (sleep apnea). People who already have breathing or lung problems have a higher chance of having breathing problems when they use FT218.

mental health problems, including:
  confusion
  seeing or hearing things that are not real (hallucinations)
  unusual or disturbing thoughts (abnormal thinking)
  feeling anxious or upset
  depression
  thoughts of killing yourself or trying to kill yourself
  increased tiredness
  feelings of guilt or worthlessness
  difficulty concentrating Call your doctor right away if you have symptoms of mental health problems.

sleepwalking. Sleepwalking can cause injuries. Call your doctor if you start sleepwalking. Your doctor should check you.

The most common side effects of FT218 include:
nausea
dizziness
bedwetting
headache
decreased appetite
vomiting
anxiety Side effects may increase when taking higher doses of FT218.

These are not all the possible side effects of FT218. For more information, ask your doctor or pharmacist. Call your doctor for medical advice about side effects. You may report side effects to FDA at 1-800-FDA-1088.

How should I store FT218?

Store FT218 in the original nightly dose packets prior to mixing with water. After mixing with water, store FT218 in the mixing cup provided in each kit. Store FT218 at room between 68° F. to 77° F. (20° C. to 25° C.). FT218 suspension may be consumed within 30 minutes of preparation. When you have finished using the FT218 nightly dose packet, dispose of it in the trash. FT218 comes in a child-resistant package. Keep FT218 and all medicines out of the reach of children and pets.

General Information about the Safe and Effective Use of FT218.

Medicines are sometimes prescribed for purposes other than those listed in a Medication Guide. Do not use FT218 for a condition for which it was not prescribed. Do not give FT218 to other people, even if they have the same symptoms. It may harm them. You can ask your pharmacist or doctor for information about FT218 that is written for health professionals.

What are the Ingredients in FT218?

Active ingredients: sodium oxybate. Additional ingredients: microcrystalline cellulose spheres, povidone K30, hydrogenated vegetable oil, methacrylic acid copolymer, malic acid, xanthan gum, hydroxyethyl cellulose, carrageenan, magnesium stearate.

Example 22: Mixing Cup Assessment

The design of the mixing cup (e.g. mixing aid) was assessed for impact on shaking and reconstitution of the composition, any residual material, and resistance to breakage in a drop test.

Shaking Study

The following tests were performed to assess the impact of the new clear mixing aid with "A" (50 mL) and "B" (25 mL) volume markers and white cap (i.e. commercial mixing aid) on the shaking and reconstitution step of the sodium oxybate ER oral suspension (FT218). The mixing aid was compared to reconstitution of the sodium oxybate ER suspension prepared in a 110 mL Dram Amber mixing aid with a white cap (i.e. clinical mixing aid).

The protocol used for preparing the suspension in either mixing aid was as follows:
  Add half of the total content of the mixing aid with water (about 50 mL)
  Pour the content of a 4.5 g or 9 g dose unit in the mixing aid
  Close the mixing aid and shake vigorously
  Introduce the content of the mixing aid in the dissolution vessel
  Add about ¼ of the volume of the mixing aid with water (about 25 mL)
  Close the mixing aid and shake vigorously
  Introduce the content of the mixing aid in the dissolution vessel The purpose of this study was to demonstrate that different shaking times have no effect on the dissolution of FT218 formulations in either the clinical or commercial mixing aid and very minimal residual drug is left if the second rinsing step is omitted. This impact was evaluated by: visual observation (picture of the mixing aid after the rinsing step); calculating the weight of the residual suspension material after executing the rinsing step; and comparison of the 0.1N HCl dissolution profiles generated in each condition.

Reconstitution protocol and introduction of the suspension in the dissolution vessel included the following steps:
Weigh the mixing aid before use;
Add about 50 mL of tap water (volume marker A)
Pour the content of a 4.5 or 9 g dose sachet,
Close the mixing aid and shake vigorously (duration 1),
Pour the content of the mixing aid in the dissolution vessel
Add ¼ of the volume of the mixing aid (about 25 mL) with tap water (volume marker B)
Close the mixing aid and shake vigorously (duration 2)
Pour the content of the mixing aid in the dissolution vessel
Take a picture of remaining material in the mixing aid;
Weigh the mixing aid after use and calculate the remaining quantity of suspension in the mixing aid
Three trials, each with different durations for mixing were performed according to Table 26 below.

TABLE 26

Mixing Durations

| Trial | Duration 1 (reconstitution step) | Duration 2 (rinsing step) |
|---|---|---|
| Trial 1 | 60 s | 10 s |
| Trial 2 | 30 s | 5 s |
| Trail 3 | 10 s | 5 s |

Table 27 shows the results of Trail 1, Table 28 shows the results of Trial 2, and Table 29 shows the results of Trial 3 for a 4.5 g dose of FT218.

TABLE 27

Mixing Aid and Residual Suspension Weight for Trial 1

| | Commercial mixing aid | | Clinical mixing aid | |
|---|---|---|---|---|
| Empty mixing aid | 20.7521 g | 20.7556 g | 20.6472 g | 20.9528 g |
| Mixing aid after rinsing | 20.9353 g | 20.873 g | 21.3992 g | 21.9166 g |
| Residual suspension material | 0.1832 g | 0.1174 g | 0.7520 g | 0.9638 g |

TABLE 28

Mixing Aid and Residual Suspension Weight for Trial 2

| | Commercial mixing aid | | Clinical mixing aid | |
|---|---|---|---|---|
| Empty mixing aid | 20.771 g | 20.7553 g | 20.7478 g | 20.825 g |
| Mixing aid after rinsing | 20.9129 g | 20.8727 g | 21.4482 g | 21.4718 g |
| Residual suspension material | 0.1419 g | 0.1174 g | 0.7004 g | 0.6468 g |

TABLE 29

Mixing Aid and Residual Suspension Weight for Trial 3

| | Commercial mixing aid | | Clinical mixing aid | |
|---|---|---|---|---|
| Empty mixing aid | 20.7798 g | 20.7622 g | 20.6482 g | 20.5647 g |
| Mixing aid after rinsing | 20.9313 g | 20.848 g | 21.2636 g | 21.3438 g |
| Residual suspension material | 0.1515 g | 0.0858 g | 0.6154 g | 0.7791 g |

FIG. 138A shows dissolution profiles for Trials 1-3 for 4.5 g with the two different cups. The dissolution test used paddle apparatus USP II, in 1800 mL of pH 6.8 and/or 0.1 N HCl medium and an RP-HPLC assay with spectrophotometric detection of collected samples. The HPLC assay includes an external calibration using standard solutions of sodium oxybate (GHB) and/or gamma-butyrolactone (GBL). For the sodium oxybate for ER oral suspension in 0.1N HCl medium, 40%<T1 hour<60% dissolved, 45%<T3 hours<65% dissolved, and T12 hours>80% dissolved.

In a first step, the result of the analysis was initially expressed in g/L as the assayed sodium oxybate concentration using the GHB calibration slope and as the assayed gamma-butyrolactone concentration using the GBL calibration slope. The assayed gamma-butyrolactone concentration was then converted in GHB taking into account the molecular mass of both compounds ("GBL equivalent GHB"). In a second step, the sum of both concentrations was adjusted with the volume of dissolution vessel before the sampling and converted in % of dissolved sodium oxybate. For this example, the result, expressed in % dissolved, was the mean of 2 determinations.

Table 30 shows the results of Trail 1, Table 31 shows the results of Trial 2, and Table 32 shows the results of Trial 3 for a 9 g dose of FT218. FIG. 138B shows dissolution profiles for Trials 1-3 for 9 g with the two different cups.

TABLE 30

Mixing Aid and Residual Suspension Weight for Trial 1

| | Commercial mixing aid | | Clinical mixing aid | |
|---|---|---|---|---|
| Empty mixing aid | 20.6412 g | 20.7386 g | 20.7414 g | 20.7925 g |
| Mixing aid after rinsing | 20.9772 g | 20.8566 g | 21.3499 g | 21.3597 g |
| Residual suspension material | 0.2360 g | 0.1180 g | 0.6085 g | 0.5672 g |

TABLE 31

Mixing Aid and Residual Suspension Weight for Trial 2

| | Commercial mixing aid | | Clinical mixing aid | |
|---|---|---|---|---|
| Empty mixing aid | 20.7441 g | 20.7386 g | 20.9105 g | 20.8712 g |
| Mixing aid after rinsing | 20.8882 g | 20.9354 g | 21.5980 g | 21.7062 g |
| Residual suspension material | 0.1441 g | 0.1968 g | 0.6875 g | 0.8350 g |

TABLE 32

Mixing Aid and Residual Suspension Weight for Trial 3

| | Commercial mixing aid | | Clinical mixing aid | |
|---|---|---|---|---|
| Empty mixing aid | 20.7797 g | 20.752 g | 20.6974 g | 20.7965 g |
| Mixing aid after rinsing | 20.8823 g | 20.9073 g | 21.3399 g | 21.6625 g |
| Residual suspension material | 0.1026 g | 0.1553 g | 0.6425 g | 0.8660 g |

Visual inspection showed a difference between the two types of mixing aids. The quantity of residual material was visually higher in the amber clinical mixing aid than in colorless commercial mixing aid. The mass of residual material after the rinsing step confirmed this observation with masses of no more than 0.2 g with the colorless commercial mixing aid and the residual masses ranging from 0.6 to 1.0 g for the clinical mixing aid. The amount of remaining suspension did not depend on the amount of sample introduced into the mixing aid (about 7.1 g for the drug product dosed at 4.5 g and 14.2 g for the drug product dosed at 9.0 g), nor on the stirring time tested, but on the type of mixing aid: the presence of additive in commercial mixing aid reduces the amount of product left in the mixing aid.

In terms of dissolution, all individual and mean dissolution data comply with the specifications. Mean dissolution profiles could be considered as similar and superimposable whatever the shaking time and the type of mixing aid (or amount of residual sample not introduced in the vessel) but individual profiles seems to be more heterogeneous for the trial 3 i.e. for the shortest shaking time (duration 1) and particularly for the drug product dosed at 9.0 g.

The reconstitution protocol and assay of the suspension and residual material in the commercial mixing aid by HPLC included the following steps:

Add about 50 mL of tap water in the mixing aid (volume marker A)

Pour the content of a 4.5 or 9 g dose unit

Close the mixing aid and shake vigorously (duration 1)

Pour the content of the mixing aid in a 500 mL volumetric flask and perform the assay of the delivered dose.

Rinse the mixing aid with diluent several times to ensure that all the drug is removed and place into a separate 100 mL volumetric flask.

Determine the residual drug according to the HPLC assay.

The assay consisted of a solid-liquid extraction in mobile phase and methanol and of an RP-HPLC assay with spectrophotometric detection at 210 nm. The Agilent HPLC system D034, fitted with a refrigerated auto-sampler and auto-injector, a DAD UV detector containing a cell with a 10 mm optical path-length, and a column temperature regulation system, was used. Duration 1 for Trial 1 was 60 s and duration 1 for Trial 2 was 10 s. Table 33 shows the results of Trial 1 and Table 34 shows the results of Trial 2. FIG. 139A shows a chromatogram for Trial 1 and FIG. 139B shows a chromatogram for Trial 2.

TABLE 33

Sodium oxybate content in % respect to the label claim after 60s of reconstitution

| Trial 1 | Label Claim dose 4.5 g | Label Claim dose 9 g |
|---|---|---|
| | % delivered dose after 60 s shaking | |
| % respect to label claim | 100.13255 | 100.81816 |
| | 99.31198 | 101.02804 |
| Mean value (%) | 99.7 | 100.9 |
| | % residual material in the mixing aid | |
| % respect to label claim | 1.15476 | 1.72903 |
| | 1.08915 | 1.43801 |
| Mean value (%) | 1.1 | 1.6 |

TABLE 34

Sodium oxybate content in % respect to the label claim after 10s of reconstitution

| Trial 2 | Label Claim dose 4.5 g | Label Claim dose 9 g |
|---|---|---|
| | % delivered dose after 10 s shaking | |
| % respect to label claim | 97.89911 | 99.45515 |
| | 99.44576 | 100.60717 |
| Mean value (%) | 98.7 | 100 |
| | % residual material in the mixing aid | |
| % respect to label claim | 1.45817 | 0.95056 |
| | 0.72853 | 1.03431 |
| Mean value (%) | 1.1 | 1.0 |

In terms of delivered dose, individual and mean data range from 97.9 to 100.8% and comply with specifications of from 90.0 to 110.0 of the label claim. The residual drug left in the mixing aid if the second rinsing step is omitted, ranges from 1.0 to 1.6% of the label claim. This amount of residual material does not depend on the amount of sample introduced into the mixing aid (about 7.1 g for the drug product dosed at 4.5 g and 14.2 g for the drug product dosed at 9.0 g), nor on the stirring time tested.

Quality Testing 30 mixing aids were filled to the "A" line with water. An adapter in a torque wrench and clamp was used to torque the cap on the cup 10 in/lbs+2 in/lbs. The mixing aids were then dropped from 18 inches onto a hard floor surface. No cracks, breaks, or leaks were observed in any of the mixing aids.

30 mixing aids were filled to the "A" line with water. An adapter in a torque wrench and clamp was used to torque the cap on the cup 10 in/lbs+2 in/lbs. The mixing aids were then shaken by hand for 1 minute. No leaks were observed.

Throughout this application, various publications are referenced. The disclosures of these publications in their entireties are hereby incorporated by reference into this application in order to more fully describe the state of the art to which this invention pertains. It will be apparent to those skilled in the art that various modifications and variations may be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Example 23: Labeling for Additional FT218 Embodiment

Warning: Central Nervous System (CNS) Depression and Abuse and Misuse

Central Nervous System Depression

FT218 (sodium oxybate) is a CNS depressant. In clinical trials at recommended doses, obtundation and clinically significant respiratory depression occurred in adult patients treated with twice-nightly sodium oxybate. Many patients who received sodium oxybate during clinical trials in narcolepsy were receiving central nervous system stimulants.

Abuse and Misuse

FT218 (sodium oxybate) is the sodium salt of gamma-hydroxybutyrate (GHB). Abuse or misuse of illicit GHB, either alone or in combination with other CNS depressants, is associated with CNS adverse reactions, including seizure, respiratory depression, decreases in the level of consciousness, coma, and death [see Warnings and Precautions (5.2)].

Because of the risks of CNS depression and abuse and misuse, FT218 is available only through a restricted program under a Risk Evaluation and Mitigation Strategy (REMS) called the FT218 REMS.INDICATIONS AND USAGE FT218 is indicated for the treatment of cataplexy or excessive daytime sleepiness (EDS) in adults with narcolepsy.

Dosage and Administration

Dosing Information

The recommended starting dosage is 4.5 grams (g) once per night administered orally. Increase the dosage by 1.5 g per night at weekly intervals to the effective dosage range of 6 g to 9 g once per night orally. The dosage may be gradually titrated based on efficacy and tolerability. Doses higher than 9 g per night have not been studied and should not ordinarily be administered.

Important Administration Instructions

FT218 is taken orally as a single dose at bedtime. Prepare the dose of FT218 prior to bedtime. Prior to ingestion, each dose of FT218 should be suspended in approximately ⅓ cup (approximately 80 mL) of water in the dosing cup provided. Do not use hot water. After mixing, consume FT218 within 30 minutes.

Take FT218 at least 2 hours after eating.

Patients should take FT218 while in bed and lie down immediately after dosing as FT218 may cause them to fall asleep abruptly without first feeling drowsy. Patients will often fall asleep within 5 minutes of taking FT218, and will usually fall asleep within 15 minutes, though the time it takes any individual patient to fall asleep may vary from night to night. Rarely, patients may take up to 2 hours to fall asleep. Patients should remain in bed following ingestion of FT218.

Dosage Forms and Strengths

For extended-release oral suspension: FT218 is a white to off-white powder provided in packets of 4.5 g, 6 g, 7.5 g, or 9 g of sodium oxybate.

Contraindications

FT218 is contraindicated for use in:
combination with sedative hypnotics
combination with alcohol
patients with succinic semialdehyde dehydrogenase deficiency Postmarketing Experience The following adverse reactions have been identified during postapproval use of sodium oxybate. Because these reactions are reported voluntarily from a population of uncertain size, it is not always possible to reliably estimate their frequency or establish a causal relationship to drug exposure:

Arthralgia, decreased appetite, fall*, fluid retention, hangover, headache, hypersensitivity, hypertension, memory impairment, nocturia, panic attack, vision blurred, and weight decreased. *The sudden onset of sleep in patients taking sodium oxybate, including in a standing position or while rising from bed, has led to falls complicated by injuries, in some cases requiring hospitalization.

Drug Interactions

Alcohol, Sedative Hypnotics, and CNS Depressants

FT218 is contraindicated for use in combination with alcohol or sedative hypnotics. Use of other CNS depressants may potentiate the CNS-depressant effects of FT218 [see Warnings and Precautions (5.1)]. Consumption of alcohol while taking FT218 may result in a more rapid release of the dose of sodium oxybate.

Divalproex Sodium

FT218, like other oxybate products, may have a pharmacodynamic interaction that could increase the risk of certain adverse reactions. Appropriate dosage adjustments of LYMRYZ cannot be made with the dosage strengths available; however, if concomitant use of FT218 and divalproex sodium is warranted, prescribers are advised to monitor patient response closely and adjust dosage accordingly.

Use in Specific Populations

Pregnancy

Risk Summary

There are no adequate data on the developmental risk associated with the use of sodium oxybate in pregnant women. Oral administration of sodium oxybate to pregnant rats (150, 350, or 1,000 mg/kg/day) or rabbits (300, 600, or 1,200 mg/kg/day) throughout organogenesis produced no clear evidence of developmental toxicity; however, oral administration to rats throughout pregnancy and lactation resulted in increased stillbirths and decreased offspring postnatal viability and growth, at a clinically relevant dose [see Data].

In the U.S. general population, the estimated background risk of major birth defects and miscarriage in clinically recognized pregnancies is 24% and 15-20%, respectively. The background risk of major birth defects and miscarriage for the indicated population is unknown.

Clinical Considerations

Labor or Delivery

FT218 has not been studied in labor or delivery. In obstetric anesthesia using an injectable formulation of sodium oxybate, newborns had stable cardiovascular and respiratory measures but were very sleepy, causing a slight decrease in Apgar scores. There was a fall in the rate of uterine contractions 20 minutes after injection. Placental transfer is rapid and gamma-hydroxybutyrate (GHB) has been detected in newborns at delivery after intravenous administration of GHB to mothers. Subsequent effects of sodium oxybate on later growth, development, and maturation in humans are unknown.

Data

Animal Data

Oral administration of sodium oxybate to pregnant rats (150, 350, or 1,000 mg/kg/day) or rabbits (300, 600, or 1,200 mg/kg/day) throughout organogenesis produced no clear evidence of developmental toxicity. The highest doses tested in rats and rabbits were approximately 1 and 3 times, respectively, the maximum recommended human dose (MRHD) of 9 g per night on a body surface area (mg/m2) basis.

Oral administration of sodium oxybate (150, 350, or 1,000 mg/kg/day) to rats throughout pregnancy and lactation resulted in increased stillbirths and decreased offspring postnatal viability and body weight gain at the highest dose tested. The no-effect dose for pre- and post-natal developmental toxicity in rats is less than the MRHD on a mg/m2 basis.

Lactation

Risk Summary

GHB is excreted in human milk after oral administration of sodium oxybate. There is insufficient information on the risk to a breastfed infant, and there is insufficient information on milk production in nursing mothers. The developmental and health benefits of breastfeeding should be considered along with the mother's clinical need for FT218 and any potential adverse effects on the breastfed infant from FT218 or from the underlying maternal condition.

Geriatric Use

Clinical studies of FT218 or twice-nightly sodium oxybate in patients with narcolepsy did not include sufficient numbers of subjects age 65 years and older to determine whether they respond differently from younger subjects. In controlled trials of twice-nightly sodium oxybate in another population, 39 (5%) of 874 patients were 65 years or older. Discontinuations of treatment due to adverse reactions were increased in the elderly compared to younger adults (21% vs. 19%). Frequency of headaches was markedly increased in the elderly (39% vs. 19%). The most common adverse reactions were similar in both age categories. In general, dose selection for an elderly patient should be cautious, usually starting at the low end of the dosing range, reflecting the greater frequency of decreased hepatic, renal, or cardiac function, and of concomitant disease or other drug therapy.

Hepatic Impairment

Because of an increase in exposure to FT218, FT218 should not be initiated in patients with hepatic impairment because appropriate dosage adjustments for initiation of LYMRYZ cannot be made with the available dosage strengths [see Clinical Pharmacology (12.3)]. Patients with hepatic impairment who have been titrated to a maintenance dosage of another oxybate product can be switched to FT218 if the appropriate dosage strength is available.

Drug Abuse and Dependence

Controlled Substance

FT218 is a Schedule III controlled substance under the Federal Controlled Substances Act. Non-medical use of FT218 could lead to penalties assessed under the higher Schedule I controls.

Abuse

FT218 (sodium oxybate), the sodium salt of GHB, produces dose-dependent central nervous system effects, including hypnotic and positive subjective reinforcing effects. The onset of effect is rapid, enhancing its potential for abuse or misuse.

Drug abuse is the intentional non-therapeutic use of a drug product or substance, even once, for its desirable psychological or physiological effects. Misuse is the intentional use, for therapeutic purposes of a drug by an individual in a way other than prescribed by a health care provider or for whom it was not prescribed. Drug misuse and abuse may occur with or without progression to addiction. Drug addiction is a cluster of behavioral, cognitive, and physiological phenomena that may include a strong desire to take the drug, difficulties in controlling drug use (e.g., continuing drug use despite harmful consequences, giving a higher priority to drug use than other activities and obligations), and possible tolerance or physical dependence.

The rapid onset of sedation, coupled with the amnestic features of GHB, particularly when combined with alcohol, has proven to be dangerous for the voluntary and involuntary user (e.g., assault victim).

Illicit GHB is abused in social settings primarily by young adults. Some of the doses estimated to be abused are in a similar dosage range to that used for treatment of patients with cataplexy. GHB has some commonalities with ethanol over a limited dose range, and some cross tolerance with ethanol has been reported as well. Cases of severe dependence and craving for GHB have been reported when the drug is taken around the clock. Patterns of abuse indicative of dependence include: 1) the use of increasingly large doses, 2) increased frequency of use, and 3) continued use despite adverse consequences.

Because illicit use and abuse of GHB have been reported, physicians should carefully evaluate patients for a history of drug abuse and follow such patients closely, observing them for signs of misuse or abuse of GHB (e.g., increase in size or frequency of dosing, drug-seeking behavior, feigned cataplexy). Dispose of FT218 according to state and federal regulations. It is safe to dispose of FT218 down the sanitary sewer.

Dependence

Physical dependence is a state that develops as a result of physiological adaptation in response to repeated drug use, manifested by withdrawal signs and symptoms after abrupt discontinuation or a significant dose reduction of a drug. There have been case reports of withdrawal, ranging from mild to severe, following discontinuation of illicit use of GHB at frequent repeated doses (18 g to 250 g per day) in excess of the recommended dosage range. Signs and symptoms of GHB withdrawal following abrupt discontinuation included insomnia, restlessness, anxiety, psychosis, lethargy, nausea, tremor, sweating, muscle cramps, tachycardia, headache, dizziness, rebound fatigue and sleepiness, confusion, and, particularly in the case of severe withdrawal, visual hallucinations, agitation, and delirium. These symptoms generally abated in 3 to 14 days. In cases of severe withdrawal, hospitalization may be required. The discontinuation effects of FT218 have not been systematically evaluated in controlled clinical trials. In the clinical trial experience with twice-nightly sodium oxybate in narcolepsy/cataplexy patients at recommended doses, two patients reported anxiety and one reported insomnia following abrupt discontinuation at the termination of the clinical trial; in the two patients with anxiety, the frequency of cataplexy had increased markedly at the same time.

Tolerance

Tolerance is a physiological state characterized by a reduced response to a drug after repeated administration (i.e., a higher dose of a drug is required to product the same effect that was once obtained at a lower dose). Tolerance to FT218 has not been systematically studied in controlled clinical trials. There have been some case reports of symptoms of tolerance developing after illicit use at dosages far in excess of the recommended FT218 dosage regimen. Clinical studies of twice-nightly sodium oxybate in the treatment of alcohol withdrawal suggest a potential cross-tolerance with alcohol. The safety and effectiveness of FT218 in the treatment of alcohol withdrawal have not been established.

Overdosage

Human Experience

Information regarding overdose with FT218 is derived largely from reports in the medical literature that describe symptoms and signs in individuals who have ingested GHB illicitly. In these circumstances, the co-ingestion of other drugs and alcohol was common and may have influenced the presentation and severity of clinical manifestations of overdose.

In adult clinical trials of twice-nightly sodium oxybate, two cases of overdose with sodium oxybate were reported. In the first case, an estimated dose of 150 g, more than 15 times the maximum recommended dose, caused a patient to be unresponsive with brief periods of apnea and to be incontinent of urine and feces. This individual recovered without sequelae. In the second case, death was reported following a multiple drug overdose consisting of sodium oxybate and numerous other drugs.

Signs and Symptoms

Information about signs and symptoms associated with overdosage with FT218 derives from reports of illicit use of GHB. Patient presentation following overdose is influenced by the dose ingested, the time since ingestion, the co-ingestion of other drugs and alcohol, and the fed or fasted state. Patients have exhibited varying degrees of depressed consciousness that may fluctuate rapidly between a confusional, agitated combative state with ataxia and coma. Emesis (even when obtunded), diaphoresis, headache, and impaired psychomotor skills have been observed. No typical pupillary changes have been described to assist in diagnosis; pupillary reactivity to light is maintained. Blurred vision has been reported. An increasing depth of coma has been observed at higher doses. Myoclonus and tonic-clonic seizures have been reported.

Respiration may be unaffected or compromised in rate and depth. Cheyne-Stokes respiration and apnea have been observed. Bradycardia and hypothermia may accompany unconsciousness, as well as muscular hypotonia, but tendon reflexes remain intact.

Recommended Treatment of Overdose

General symptomatic and supportive care should be instituted immediately, and gastric decontamination may be considered if co-ingestants are suspected. Because emesis may occur in the presence of obtundation, appropriate posture (left lateral recumbent position) and protection of the airway by intubation may be warranted. Although the gag reflex may be absent in deeply comatose patients, even unconscious patients may become combative to intubation, and rapid-sequence induction (without the use of sedative) should be considered. Vital signs and consciousness should be closely monitored. The bradycardia reported with GHB overdose has been responsive to atropine intravenous administration. No reversal of the central depressant effects of FT218 can be expected from naloxone or flumazenil administration. The use of hemodialysis and other forms of extracorporeal drug removal have not been studied in GHB overdose. However, due to the rapid metabolism of sodium oxybate, these measures are not warranted.

Poison Control Center

As with the management of all cases of drug overdosage, the possibility of multiple drug ingestion should be considered. The healthcare provider is encouraged to collect urine and blood samples for routine toxicologic screening, and to consult with a regional poison control center (1-800-222-1222) for current treatment recommendations.

Description

Sodium oxybate, a CNS depressant, is the active ingredient in FT218 for extended-release oral suspension. The chemical name for sodium oxybate is sodium 4-hydroxybutyrate. The molecular formula is $C_4H_7NaO_3$, and the molecular weight is 126.09 g/mole. The chemical structure is:

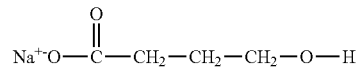

Sodium oxybate is a white to off-white solid powder.

Each single dose packet of FT218 contains 4.5 g, 6 g, 7.5 g, or 9 g of sodium oxybate, equivalent to 3.7 g, 5.0 g, 6.2 g, or 7.4 g of oxybate, respectively. The inactive ingredients are carrageenan, hydrogenated vegetable oil, hydroxyethyl cellulose, magnesium stearate, malic acid, methacrylic acid copolymer, microcrystalline cellulose, povidone, and xanthan gum.

Clinical Pharmacology

Mechanism of Action

FT218 is a CNS depressant. The mechanism of action of FT218 in the treatment of narcolepsy is unknown. Sodium oxybate is the sodium salt of gamma-hydroxybutyrate (GHB), an endogenous compound and metabolite of the neurotransmitter GABA. It is hypothesized that the therapeutic effects of FT218 on cataplexy and excessive daytime sleepiness are mediated through GABAB actions at noradrenergic and dopaminergic neurons, as well as at thalamo-cortical neurons.

Pharmacokinetics

Absorption

Following oral administration of twice-nightly sodium oxybate, GHB is absorbed rapidly across the clinical dose range, with an absolute bioavailability of about 88%. Following oral administration of FT218, the peak plasma concentrations ($C_{max}$) following administration of one 6 g dose was 66 mcg/mL, and the time to peak plasma concentration ($T_{max}$) was 1.5 hours. Following oral administration of FT218, the plasma levels of GHB increased more than dose-proportionally, with $C_{max}$ increasing approximately 2-fold, and AUC increasing 2.3-fold, as total daily dose is doubled from 4.5 g to 9 g.

Effect of Food

Administration of FT218 immediately after a high-fat meal resulted in a mean reduction in $C_{max}$ and AUC of GHB by 33% and 16%, respectively, and average $T_{max}$ increased from 0.5 hr to 1.5 hr.

Effect of Ethanol

An in vitro study showed alcohol-induced dose-dumping of sodium oxybate from extended-release oral suspension at 1 hour, and increase of drug release to approximately 60% at 2 hours in the presence of 20% alcohol. Effects of 5% and 10% alcohol on drug release were not significant up to 14 hours. No in vivo data on the effect of alcohol on drug exposure are available.

Effect of Water Temperature

An in vitro dissolution study showed that FT218 mixed with hot water (90° C.) resulted in a dose-dumping phenomenon for the release of sodium oxybate, whereas warm water (50° C.) did not significantly affect the drug release from the extended-release suspension.

Distribution

GHB is a hydrophilic compound with an apparent volume of distribution averaging 190 mL/kg to 384 mL/kg. At GHB concentrations ranging from 3 mcg/mL to 300 mcg/mL, less than 1% is bound to plasma proteins.

Elimination

Metabolism

Animal studies indicate that metabolism is the major elimination pathway for GHB, producing carbon dioxide and water via the tricarboxylic acid (Krebs) cycle, and secondarily by beta-oxidation. The primary pathway involves a cytosolic NADP+-linked enzyme, GHB dehydrogenase, which catalyzes the conversion of GHB to succinic semialdehyde, which is then biotransformed to succinic acid by the enzyme succinic semialdehyde dehydrogenase. Succinic acid enters the Krebs cycle where it is metabolized to carbon dioxide and water. A second mitochondrial oxidoreductase enzyme, a transhydrogenase, also catalyzes the conversion to succinic semialdehyde in the presence of α-ketoglutarate. An alternate pathway of biotransformation involves β-oxidation via 3,4-dihydroxybutyrate to carbon dioxide and water. No active metabolites have been identified.

Excretion

The clearance of GHB is almost entirely by biotransformation to carbon dioxide, which is then eliminated by expiration. On average, less than 5% of unchanged drug appears in human urine within 6 to 8 hours after dosing. Fecal excretion is negligible. GHB has an elimination half-life of 0.5 to 1 hour.

Specific Population

Geriatric Patients

There is limited experience with FT218 in the elderly. Results from a pharmacokinetic study of twice-nightly sodium oxybate (n=20) in another studied population indicate that the pharmacokinetic characteristics of GHB are consistent among younger (age 48 to 64 years) and older (age 65 to 75 years) adults.

Pediatric Patients

The pharmacokinetics of FT218 in patients younger than 18 years of age have not been studied.

Male and Female Patients

In a study of 18 female and 18 male healthy adult volunteers, no gender differences were detected in the pharmacokinetics of GHB following a twice-nightly oral dose of sodium oxybate 4.5 g.

Racial or Ethnic Groups

There are insufficient data to evaluate any pharmacokinetic differences among races.

Patients with Renal Impairment

No pharmacokinetic study in patients with renal impairment has been conducted.

Patients with Hepatic Impairment

The pharmacokinetics of GHB in 16 cirrhotic patients, half without ascites (Child's Class A) and half with ascites (Child's Class C), were compared to the kinetics in 8 subjects with normal hepatic function, after a single sodium oxybate oral dose of 25 mg/kg. AUC values were double in the cirrhotic patients, with apparent oral clearance reduced from 9.1 mL/min/kg in healthy adults to 4.5 and 4.1 mL/min/kg in Class A and Class C patients, respectively. Elimination half-life was significantly longer in Class C and Class A patients than in control patients (mean $t_{1/2}$ of 59 and 32 minutes, respectively, versus 22 minutes in control patients). FT218 should not be initiated in patients with liver impairment.

Drug Interaction Studies

Studies in vitro with pooled human liver microsomes indicate that sodium oxybate does not significantly inhibit the activities of the human isoenzymes CYP1A2, CYP2C9, CYP2C19, CYP2D6, CYP2E1, or CYP3A, up to the concentration of 3 mM (378 mcg/mL), a level considerably higher than levels achieved with recommended doses.

Drug interaction studies in healthy adults (age 18 to 50 years) were conducted with FT218 and divalproex sodium:

Divalproex sodium: Co-administration of a single dose of FT218 (6 g) with divalproex sodium ER at steady state resulted in comparable systemic exposure to GHB, as shown by plasma $C_{max}$ and AUC values. A single dose of FT218 (6 g) did not appear to affect the pharmacokinetics of divalproex sodium. However, a potential pharmacodynamic interaction between FT218 and divalproex sodium cannot be ruled out.

Drug interaction studies in healthy adults (age 18 to 50 years) were conducted with twice-nightly sodium oxybate and diclofenac and ibuprofen:

Diclofenac: Co-administration of sodium oxybate (6 g per day as two equal doses of 3 grams dosed four hours apart) with diclofenac (50 mg/dose twice per day) showed no significant differences in systemic exposure to GHB. Co-administration did not appear to affect the pharmacokinetics of diclofenac.

Ibuprofen: Co-administration of sodium oxybate (6 g per day as two equal doses of 3 grams dosed four hours apart) with ibuprofen (800 mg/dose four times per day also dosed four hours apart) resulted in comparable systemic exposure to GHB as shown by plasma $C_{max}$ and AUC values. Co-administration did not affect the pharmacokinetics of ibuprofen.

Drug interaction studies in healthy adults demonstrated no pharmacokinetic interactions between twice-nightly sodium oxybate and protriptyline hydrochloride, zolpidem tartrate, and modafinil. Also, there were no pharmacokinetic interactions with the alcohol dehydrogenase inhibitor fomepizole. However, pharmacodynamic interactions with these drugs cannot be ruled out. Alteration of gastric pH with omeprazole produced no significant change in the pharmacokinetics of GHB. In addition, drug interaction studies in healthy adults demonstrated no pharmacokinetic or clinically significant pharmacodynamic interactions between twice-nightly sodium oxybate and duloxetine HCl.

Nonclinical Toxicology

Carcinogenesis, Mutagenesis, Impairment of Fertility

Carcinogenesis

Administration of sodium oxybate to rats at oral doses of up to 1,000 mg/kg/day for 83 (males) or 104 (females) weeks resulted in no increase in tumors. Plasma exposure (AUC) at the highest dose tested was 2 times that in humans at the maximum recommended human dose (MRHD) of 9 g per night.

The results of 2-year carcinogenicity studies in mouse and rat with gamma-butyrolactone, a compound that is metabolized to sodium oxybate in vivo, showed no clear evidence of carcinogenic activity. The plasma AUCs of sodium oxybate achieved at the highest doses tested in these studies were less than that in humans at the MRHD.

Mutagenesis

Sodium oxybate was negative in the in vitro bacterial gene mutation assay, an in vitro chromosomal aberration assay in mammalian cells, and in an in vivo rat micronucleus assay.

Impairment of Fertility

Oral administration of sodium oxybate (150, 350, or 1,000 mg/kg/day) to male and female rats prior to and throughout mating and continuing in females through early gestation resulted in no adverse effects on fertility. The highest dose tested is approximately equal to the MRHD on a mg/m2 basis.

How Supplied/Storage and Handling

How Supplied

FT218 is a blend of white to off-white granules for extended-release oral suspension in water. Each carton contains either 7 or 30 packets of FT218, a dosing cup, Prescribing Information, Instructions for Use, and Medication Guide.

Dose packets contain a single dose of FT218 provided in 4.5 g, 6 g, 7.5 g, and 9 g doses.

| Strength | Package Size | NDC Number |
| --- | --- | --- |
| 4.5 g | 7 packets | NDC XXXXX-XXX-XX |
| | 30 packets | NDC XXXXX-XXX-XX |
| 6 g | 7 packets | NDC XXXXX-XXX-XX |
| | 30 packets | NDC XXXXX-XXX-XX |
| 7.5 g | 7 packets | NDC XXXXX-XXX-XX |
| | 30 packets | NDC XXXXX-XXX-XX |
| 9 g | 7 packets | NDC XXXXX-XXX-XX |
| | 30 packets | NDC XXXXX-XXX-XX |

Storage

Keep out of reach of children.

FT218 should be stored at 20° C. to 25° C. (68° F. to 77° F.); excursions permitted to 15° C. to 30° C. (59° F. to 86° F.) (see USP Controlled Room Temperature).

Suspensions should be consumed within 30 minutes.

Handling and Disposal

FT218 is a Schedule III drug under the Controlled Substances Act. FT218 should be handled according to state and federal regulations. It is safe to dispose of FT218 down the sanitary sewer.

Patient Counseling Information

Advise the patient to read the FDA-approved patient labeling (Medication Guide and Instructions for Use).

Central Nervous System Depression

Inform patients that FT218 can cause central nervous system depression, including respiratory depression, hypotension, profound sedation, syncope, and death. Instruct patients to not engage in activities requiring mental alertness or motor coordination, including operating hazardous machinery, for at least 6 hours after taking FT218. Instruct patients to inform their healthcare providers of all the medications they take.

Abuse and Misuse

Inform patients that the active ingredient of FT218 is gamma-hydroxybutyrate (GHB), which is associated with serious adverse reactions with illicit use and abuse.

FT218 Rems

FT218 is available only through a restricted program called the FT218 REMS. Inform the patient of the following notable requirements:

FT218 is dispensed only by pharmacies that are specially certified

FT218 will be dispensed and shipped only to patients who are enrolled in the FT218 REMS FT218 is available only from certified pharmacies participating in the program. Therefore, provide patients with the telephone number and website for information on how to obtain the product.

Alcohol or Sedative Hypnotics

Advise patients that alcohol and other sedative hypnotics should not be taken with FT218 [see Warnings and Precautions (5.1)].

Sedation

Inform patients that they are likely to fall asleep quickly after taking FT218 (often within 5 and usually within 15 minutes), but the time it takes to fall asleep can vary from night to night. The sudden onset of sleep, including in a standing position or while rising from bed, has led to falls complicated by injuries, in some cases requiring hospitalization. Instruct patients that they should remain in bed following ingestion of their dose.

Food Effects on FT218

Inform patients that FT218 should be taken at least 2 hours after eating.

Respiratory Depression and Sleep-Disordered Breathing

Inform patients that FT218 may impair respiratory drive, especially in patients with compromised respiratory function, and may cause apnea.

Depression and Suicidality

Instruct patients to contact a healthcare provider immediately if they develop depressed mood, markedly diminished interest or pleasure in usual activities, significant change in weight and/or appetite, psychomotor agitation or retardation, increased fatigue, feelings of guilt or worthlessness, slowed thinking or impaired concentration, or suicidal ideation.

Other Behavioral or Psychiatric Adverse Reactions

Inform patients that FT218 can cause behavioral or psychiatric adverse reactions, including confusion, anxiety, and psychosis. Instruct them to notify their healthcare provider if any of these types of symptoms occur.

Sleepwalking

Instruct patients that FT218 has been associated with sleepwalking and other behaviors during sleep, and to contact their healthcare provider if this occurs.

Sodium Intake

Instruct patients that FT218 contains a significant amount of sodium and patients who are sensitive to sodium intake (e.g., those with heart failure, hypertension, or renal impairment) should limit their sodium intake.

What is claimed is:

1. A method of treating cataplexy or excessive daytime sleepiness in a human subject with narcolepsy, the method comprising:
    administering to the subject a single daily dose of a gamma-hydroxybutyrate formulation comprising an immediate-release portion and a modified-release portion,
    wherein the single daily dose comprises an amount of gamma-hydroxybutyrate equivalent to 3.0 g, 4.5 g, 6 g, 7.5 g, or 9 g of sodium oxybate,
    wherein the administering occurs at bedtime, and
    wherein 2% or fewer subjects administered the formulation experience a confusional state.

2. The method of claim 1, wherein the subject has a decreased risk of falls or headaches.

3. The method of claim 1, wherein the subject has a decreased risk of car and work accidents.

4. The method of claim 1, wherein the subject has a decreased risk of work-related errors or lack of energy.

5. The method of claim 1, wherein the subject has a decreased risk of irritability or mood problems.

6. The method of claim 1, wherein the subject has a decreased risk of gastrointestinal, cardiovascular, or metabolic disorders.

7. The method of claim 1, wherein the subject has a decreased risk of drug or alcohol abuse.

8. The method of claim 1, wherein the subject has a decreased risk of one or more of the sleep deprivation side effects selected from the group consisting of lack of alertness, irritation, memory lapses, lack of focus, difficulty retaining new concepts, difficulty making decisions, slower reaction times, and combinations thereof.

9. The method of claim 1, where the subject has a decreased risk of developing diabetes, obesity, and heart disease associated with long-term sleep deprivation.

10. A method of treating cataplexy or excessive daytime sleepiness in a human subject with narcolepsy, the method comprising:
- administering to the subject a single daily dose of a gamma-hydroxybutyrate formulation comprising an immediate-release portion and a modified-release portion,
- wherein the single daily dose comprises an amount of gamma-hydroxybutyrate equivalent to 3.7 g, 5.0 g, 6.2 g, or 7.4 g of oxybate,
- wherein the administering occurs at bedtime, and
- wherein 3% or fewer subjects administered the formulation experience sleepwalking.

11. The method of claim 10, wherein the sleepwalking is a parasomnia that occurs during non-REM sleep.

* * * * *